(12) United States Patent
Kerns et al.

(10) Patent No.: US 8,063,071 B2
(45) Date of Patent: Nov. 22, 2011

(54) CHEMICAL COMPOUNDS

(75) Inventors: Jeffrey K. Kerns, King of Prussia, PA (US); Qi Jin, King of Prussia, PA (US); Michael Lindenmuth, King of Prussia, PA (US); Sonia M Thomas, King of Prussia, PA (US); Katherine L. Widdowson, King of Prussia, PA (US)

(73) Assignee: GlaxoSmithKline, LLC, Philadelphia, PA (US)

( * ) Notice: Subject to any disclaimer, the term of this patent is extended or adjusted under 35 U.S.C. 154(b) by 607 days.

(21) Appl. No.: 11/931,189

(22) Filed: Oct. 31, 2007

(65) Prior Publication Data

US 2009/0143372 A1 Jun. 4, 2009

(51) Int. Cl.
*A61K 31/445* (2006.01)
*C07D 401/04* (2006.01)

(52) U.S. Cl. ........................... 514/323; 546/201
(58) Field of Classification Search ............ None
See application file for complete search history.

(56) References Cited

U.S. PATENT DOCUMENTS

| | | | |
|---|---|---|---|
| 4,775,761 | A | 10/1988 | Strupczewski |
| 5,026,856 | A | 6/1991 | Yatsunami et al. |
| 5,254,473 | A | 10/1993 | Patel |
| 5,256,673 | A | 10/1993 | Böttcher et al. |
| 5,330,986 | A | 7/1994 | Shutske |
| 6,245,799 | B1 | 6/2001 | Asselin et al. |
| 6,358,994 | B1 | 3/2002 | Fritz et al. |
| 6,509,340 | B1 | 1/2003 | Van Amsterdam et al. |
| 6,589,954 | B1 | 7/2003 | Mavunkel et al. |
| 6,919,335 | B2 | 7/2005 | Iwanowicz et al. |
| 2002/0103229 | A1 | 8/2002 | Bhagwat et al. ......... 514/338 |
| 2002/0147189 | A1 | 10/2002 | Cai et al. |
| 2002/0161004 | A1 | 10/2002 | Browner et al. |
| 2003/0022898 | A1 | 1/2003 | Burke et al. |
| 2005/0153966 | A1 | 7/2005 | Gangloff et al. |
| 2005/0165086 | A1 | 7/2005 | Callahan et al. |
| 2006/0116419 | A1 | 6/2006 | Callahan et al. |
| 2006/0062058 | A1 | 12/2006 | Kerns |
| 2007/0254873 | A1 | 11/2007 | Kerns et al. |
| 2007/0281933 | A1 | 12/2007 | Kerns et al. |
| 2008/0146606 | A1 | 6/2008 | Bamborough et al. |
| 2008/0242685 | A1 | 10/2008 | Kerns et al. |
| 2008/0262040 | A1 | 10/2008 | Callahan et al. |
| 2008/0269291 | A1 | 10/2008 | Kerns et al. |
| 2008/0293802 | A1 | 11/2008 | Kerns et al. |
| 2009/0030014 | A1 | 1/2009 | Kugimiya et al. |
| 2009/0143372 | A1 | 6/2009 | Kerns et al. |
| 2010/0130468 | A1 | 5/2010 | Busch-Petersen et al. |
| 2010/0179139 | A1 | 7/2010 | Bamborough et al. |

FOREIGN PATENT DOCUMENTS

| | | |
|---|---|---|
| DE | 3342632 | 6/1985 |
| DE | 19500689 | 7/1996 |
| DE | 19807993 | 9/1999 |
| DE | 19928424 | 12/2000 |
| DE | 10112151 | 9/2002 |
| DE | 10259244 | 7/2004 |
| EP | 279263 | 8/1993 |
| EP | 0556949 A2 | 8/1993 |
| EP | 610134 | 8/1994 |
| EP | 416609 | 1/1997 |
| EP | 0812826 | 12/1997 |
| EP | 1077213 | 2/2001 |
| EP | 1134221 | 9/2001 |
| EP | 1209158 | 5/2002 |
| JP | A-60-132980 | 7/1985 |
| JP | A-2002-533333 | 10/2002 |
| WO | WO94/21627 | 9/1994 |
| WO | WO 94/21627 | 9/1994 |
| WO | WO94/21630 | 9/1994 |
| WO | WO96/40115 | 12/1996 |
| WO | WO97/44319 | 11/1997 |
| WO | WO98/06715 | 2/1998 |
| WO | WO98/28292 | 7/1998 |
| WO | WO99/43652 | 2/1999 |

(Continued)

OTHER PUBLICATIONS

Wermuth, C.G., *The Practice of Medicinal Chemistry*, Academic Press, pp. 203-214 (1996).

(Continued)

*Primary Examiner* — Zinna Northington Davis
(74) *Attorney, Agent, or Firm* — Nora L. Stein; Theodore R. Furman

(57) ABSTRACT

The invention is directed to novel indole carboxamide derivatives. Specifically, the invention is directed to compounds according to formula I:

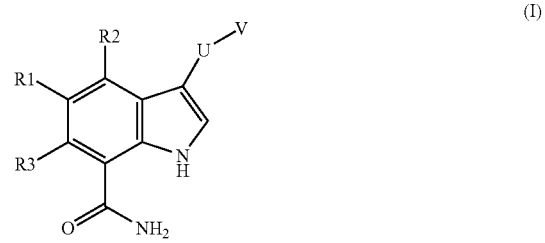

where R1, R2, R3, U and V are defined below and to pharmaceutically acceptable salts thereof.

The compounds of the invention are inhibitors of IKK2 and can be useful in the treatment of disorders associated with inappropriate IKK2 (also known as IKKβ) activity, such as rheumatoid arthritis, asthma, and COPD (chronic obstructive pulmonary disease). Accordingly, the invention is further directed to pharmaceutical compositions comprising a compound of the invention. The invention is still further directed to methods of inhibiting IKK2 activity and treatment of disorders associated therewith using a compound of the invention or a pharmaceutical composition comprising a compound of the invention.

7 Claims, No Drawings

FOREIGN PATENT DOCUMENTS

| | | |
|---|---|---|
| WO | WO99/17773 | 4/1999 |
| WO | WO00/00487 | 1/2000 |
| WO | WO01/00610 | 1/2001 |
| WO | WO01/30774 | 5/2001 |
| WO | WO01/34598 | 5/2001 |
| WO | WO 01/83472 | 5/2001 |
| WO | WO01/58890 | 8/2001 |
| WO | WO01/68648 | 9/2001 |
| WO | WO01/83472 | 11/2001 |
| WO | WO01/87298 | 11/2001 |
| WO | WO01/98290 | 12/2001 |
| WO | WO02/14317 | 2/2002 |
| WO | WO02/16353 | 2/2002 |
| WO | WO 02/16353 | 2/2002 |
| WO | WO02/24679 | 3/2002 |
| WO | WO02/24693 | 3/2002 |
| WO | WO02/28860 | 3/2002 |
| WO | WO02/30353 | 4/2002 |
| WO | WO02/30423 | 4/2002 |
| WO | WO02/41843 | 5/2002 |
| WO | WO02/44153 | 6/2002 |
| WO | WO02/46171 | 6/2002 |
| WO | WO02/051837 | 7/2002 |
| WO | WO02/060386 | 8/2002 |
| WO | WO02/094265 | 11/2002 |
| WO | WO02/094322 | 11/2002 |
| WO | WO02/094813 | 11/2002 |
| WO | WO03/007076 | 1/2003 |
| WO | WO03/010158 | 2/2003 |
| WO | WO03/010163 | 2/2003 |
| WO | WO03/022898 | 3/2003 |
| WO | WO03/024935 | 3/2003 |
| WO | WO03/024936 | 3/2003 |
| WO | WO03/027075 | 4/2003 |
| WO | WO 03/035625 | 5/2003 |
| WO | WO03/037664 | 5/2003 |
| WO | WO 03/037886 | 5/2003 |
| WO | WO03/037886 | 5/2003 |
| WO | WO03/068193 A | 8/2003 |
| WO | WO03/084959 | 10/2003 |
| WO | WO03/087087 | 10/2003 |
| WO | WO03/095430 | 11/2003 |
| WO | WO03/101987 | 12/2003 |
| WO | WO03/103661 | 12/2003 |
| WO | WO03/104218 | 12/2003 |
| WO | WO2004/019935 | 3/2004 |
| WO | WO2004/022553 | 3/2004 |
| WO | WO2004/024730 | 3/2004 |
| WO | WO2004/024732 | 3/2004 |
| WO | WO2004/024736 | 3/2004 |
| WO | WO2004/047760 | 6/2004 |
| WO | WO2004/075846 | 9/2004 |
| WO | WO 2004/089913 | 10/2004 |
| WO | WO2004/089913 | 10/2004 |
| WO | WO2004/106293 | 12/2004 |
| WO | WO2005/012283 | 2/2005 |
| WO | WO2005/035527 | 4/2005 |
| WO | WO2005/035537 | 4/2005 |
| WO | WO 2005/067923 | 7/2005 |
| WO | WO2005/067923 | 7/2005 |
| WO | WO 2006/002434 | 1/2006 |
| WO | WO2006/002434 | 1/2006 |
| WO | WO 2006/034317 | 3/2006 |
| WO | WO2006/034317 | 3/2006 |
| WO | WO2006/106326 | 10/2006 |
| WO | WO2007/005534 | 1/2007 |
| WO | WO2007/010964 | 1/2007 |
| WO | WO2007/114848 | 10/2007 |
| WO | WO2009/112473 | 9/2009 |
| WO | WO2010/102968 | 9/2010 |
| WO | WO2010/106016 | 9/2010 |

OTHER PUBLICATIONS

U.S. Appl. No. 10/597,154, filed Jul. 13, 2006, Baldwin et al.
U.S. Appl. No. 11/570,060, filed Dec. 5, 2006, Jeffrey K. Kerns.
U.S. Appl. No. 11/575,416, filed Mar. 16, 2007, Kerns et al.
U.S. Appl. No. 12/532,773, filed Mar. 20, 2008, Jeffrey K. Kerns.
Aupperle et al., "NF-κB Regulation by IκB Kinase in Primary Fibroblast-Like Synoviocytes" *J. Immunology* (1999) 163:427-433.
Aupperle et al., "NF-κB Regulation by IκB Kinase-2 in Rheumatoid Arthritis Synoviocytes" *J. Immunology* (2001) 166:31496-31501.
Breton et al., "The Natural Product Hymenialdisine Inhibits Interleukin-8 Production in U937 Cells by Inhibition of Nuclear Factor-κB" *JPET* (1997) 282(1):459-466.
Burke et al., "BMS-345541 Is a Highly Selective Inhibitor of IκB Kinase That Binds at an Allosteric Site of the Enzyme and Blocks NF-κB-dependent Transcription in Mice" *J. Biol Chem.* (2003) 278:1450-1456.
Guttridge et al., "NF-κB-Induced Loss of *MyoD* Messenger RNA: Possible Role in Muscle Decay and Cachexia" *Science* (2000) 289:2363-2365.
Murata et al., "Discovery of novel and selective IKK-β serine-threonine protein kinase inhibitors. Part 1." *Bioorg. Med. Chem. Letter* (2003) 13:913-198.
Murata et al., "Synthesis and structure—activity relationships of novel IKK-β inhibitors. Part 2: Improvement of in vitro activity" *Bioorg. Med. Chem. Letter* (2004) 14(15):4013-4017 and "Synthesis and structure—activity relationships of novel IKK-β inhibitors. Part 3: Orally active anti-inflammatory agents," *Bioorg. Med. Chem. Letter* (2004) 14(15):4019-4022.
Peet et al., "IκB Kinases α and β Show a Random Sequential Kinetic Mechanism and Are Inhibited by Staurosporine and Quercetin" *J. Biol. Chem.* (1999) 274:32655-32661.
Pierce, et al., "Novel Inhibitors of Cytokine-induced IκBα Phosphorylation and Endothelial Cell Adhesion Molecule Expression Show Anti-inflammatory Effects *in Vivo*" *J. Biol. Chem.* (1997) 272:21096-21103.
Roshak, et al., "Inhibition of NFκB-Mediated Interleukin-1[62]-Stimulated Prostaglandin $E_2$ formation by the Marine Natural Product Hymenialdisine" *JPET* (1997) 283(2):955-961.
Roshak, et al., "Manipulation of Distinct NFκB Proteins Alters Interleukin-1β-induced Human Rheumatoid Synovial Fibroblast Prostaglandin $E_2$ Formation" *J. Biol. Chem.* (1996) 271:31496-31501.
Sullivan et al., "2-Chloro-4-(trifluoromethyl)pyrimidine-5-*N*-(3',5'-bis(trifluoromethyl)phenyl)-carboxamide: A Potent Inhibitor of NF-κB- and AP-1-Mediated Gene Expression Identified Using Solution-Phase Combinatorial Chemistry" *J. Med. Chem.* (1998) 41:413-419.
Tak et al., "Inhibitor of nuclear factor κB kinase [62] is a key regulator of synovial inflammation" *Arthritis and Rheumatism* (2001) 44(8):1897-1907.
Wahl et al., "Sulfasalazine: a potent and specific inhibitor of nuclear factor kappa B" *J. Clin. Invest.* (1998) 101(5):1163-1174.
Wisniewski et al., "Assay for IκB Kinases Using an *in Vivo* Biotinylated IκB Protein Substrate" *Analytical Biochem.* (1999) 274:220-228.
Abstract No. 98323-88-7 (Sep. 29, 1985).
U.S. Appl. No. 12/093,750, filed May 15, 2008, Kerns et al.
U.S. Appl. No. 12/096,397, filed Jun. 6, 2008, Kerns et al.
U.S. Appl. No. 12/532,773, filed Sep. 23, 2009, Busch-Petersen et al.
C. G. Wermuth. *The Practice of Medicinal Chemistry*, Academic Press, pp. 203-214 (1996).
Restriction Requirement dated May 20, 2009 in U.S. Appl. No. 10/597,154.
Official Action dated Oct. 27, 2009 in U.S. Appl. No. 10/597,154.
Final Action dated Jul. 15, 2010 in U.S. Appl. No. 10/597,154.
Restriction Requirement dated Dec. 15, 2009 in U.S. Appl. No. 11/570,060.
Official Action dated May 20, 2010 in U.S. Appl. No. 11/570,060.
Final Action dated May 14, 2009 in U.S. Appl. No. 11/575,416.
Official Action dated Jan. 4, 2010 in U.S. Appl. No. 11/575,416.
Notice of Allowance dated Nov. 12, 2010 in U.S. Appl. No. 11/575,416.
Restriction Requirement dated Aug. 10, 2010 in U.S. Appl. No. 12/093,750.
Aupperles. J. Immunology 2001; 166: 2705-11.
Pharmaceutical Research, 1986, vol. 3, No. 6, 318.
Protecting Groups in organic Synthesis; TW Green, PG M Wuts, John Wiley & Sons, 1991.

Stereochemistry of Organic Compounds, TW Green, P. G M Wuts, E L ELeil, S H Wile, L N Mander, Wiley-Interscience, 1994.
Micallef., et al.: "Brominated isoindolines: Precursors to functionalised nitroxides", Journal of the Chemical Society; Perkin 2, (001), 65 and 72, 1999.

Baxter, Bioorg. Med. Chem. Lett., 14, 2817-2822 (2004).
Miller, et al: "3,5-Disubstituted-indole-7-carboxamides: The Discovery of a novel series of potent, selective inhibitors of IKK-β". Bioorganic & Medicine Chemistry Letters 21 (2011) 2255-2258.
CA 143:172 754 (Baldwin), Jul. 2005.

CHEMICAL COMPOUNDS

FIELD OF THE INVENTION

The invention is directed to certain indole carboxamide compounds, which are inhibitors of kinase activity. More specifically, the compounds are IKK2 inhibitors. These compounds are useful in the treatment of disorders associated with inappropriate IKK2 (also known as IKKβ) activity, in particular in the treatment and prevention of disorders mediated by IKK2 mechanisms including inflammatory and tissue repair disorders. Such disorders include rheumatoid arthritis, asthma, and COPD (chronic obstructive pulmonary disease).

BACKGROUND OF THE INVENTION

An important large family of enzymes is the protein kinase enzyme family. Currently, there are about 500 different known protein kinases. However, because three to four percent of the human genome is a code for the formation of protein kinases, there may be many thousands of distinct and separate kinases in the human body. Protein kinases serve to catalyze the phosphorylation of an amino acid side chain in various proteins by the transfer of the γ-phosphate of the ATP-$Mg^{2+}$ complex to said amino acid side chain. These enzymes control the majority of the signaling processes inside cells, thereby governing cell function, growth, differentiation and destruction (apoptosis) through reversible phosphorylation of the hydroxyl groups of serine, threonine and tyrosine residues in proteins. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity. Due to their physiological relevance, variety and ubiquitousness, protein kinases have become one of the most important and widely studied family of enzymes in biochemical and medical research.

The protein kinase family of enzymes is typically classified into two main subfamilies: Protein Tyrosine Kinases and Protein Serine/Threonine Kinases, based on the amino acid residue they phosphorylate. The serine/threonine kinases (PSTK), includes cyclic AMP- and cyclic GMP-dependent protein kinases, calcium and phospholipid dependent protein kinase, calcium- and calmodulin-dependent protein kinases, casein kinases, cell division cycle protein kinases and others. These kinases are usually cytoplasmic or associated with the particulate fractions of cells, possibly by anchoring proteins. Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are important targets for drug design. The tyrosine kinases phosphorylate tyrosine residues. Tyrosine kinases play an equally important role in cell regulation. These kinases include several receptors for molecules such as growth factors and hormones, including epidermal growth factor, insulin receptor, platelet derived growth factor receptor and others. Studies have indicated that many tyrosine kinases are transmembrane proteins with their receptor domains located on the outside of the cell and their kinase domains on the inside. Much work is also under progress to identify modulators of tyrosine kinases as well.

Nuclear factor κB (NF-κB) belongs to a family of closely related dimeric transcription factor complexes composed of various combinations of the Rel/NF-κB family of polypeptides. The family consists of five individual gene products in mammals, RelA (p65), NF-κB1 (p50/p105), NF-κB2 (p49/p100), c-Rel, and RelB, all of which can form hetero- or homodimers. These proteins share a highly homologous 300 amino acid "Rel homology domain" which contains the DNA binding and dimerization domains. At the extreme C-terminus of the Rel homology domain is a nuclear translocation sequence important in the transport of NF-κB from the cytoplasm to the nucleus. In addition, p65 and cRel possess potent transactivation domains at their C-terminal ends.

The activity of NF-κB is regulated by its interaction with a member of the inhibitor IκB family of proteins. This interaction effectively blocks the nuclear localization sequence on the NF-κB proteins, thus preventing migration of the dimer to the nucleus. A wide variety of stimuli activate NF-κB through what are likely to be multiple signal transduction pathways. Included are bacterial products (LPS), some viruses (HIV-1, HTLV-1), inflammatory cytokines (TNFα, IL-1), environmental and oxidative stress and DNA damaging agents. Apparently common to all stimuli however, is the phosphorylation and subsequent degradation of IκB. IκB is phosphorylated on two N-terminal serines by the recently identified IκB kinases (IKK-α and IKK-β). IKK-β is also known as IKK2. Site-directed mutagenesis studies indicate that these phosphorylations are critical for the subsequent activation of NF-κB in that once phosphorylated the protein is flagged for degradation via the ubiquitin-proteasome pathway. Free from IκB, the active NF-κB complexes are able to translocate to the nucleus where they bind in a selective manner to preferred gene-specific enhancer sequences. Included in the genes regulated by NF-κB are a number of cytokines and chemokines, cell adhesion molecules, acute phase proteins, immunoregulatory proteins, eicosanoid metabolizing enzymes and anti-apoptotic genes.

It is well-known that NF-κB plays a key role in the regulated expression of a large number of pro-inflammatory mediators including cytokines such as TNF, IL-1β, IL-6 and IL-8, cell adhesion molecules, such as ICAM and VCAM, and inducible nitric oxide synthase (iNOS). Such mediators are known to play a role in the recruitment of leukocytes at sites of inflammation and in the case of iNOS, may lead to organ destruction in some inflammatory and autoimmune diseases.

The importance of NF-κB in inflammatory disorders is further strengthened by studies of airway inflammation including asthma, in which NF-κB has been shown to be activated. This activation may underlie the increased cytokine production and leukocyte infiltration characteristic of these disorders. In addition, inhaled steroids are known to reduce airway hyperresponsiveness and suppress the inflammatory response in asthmatic airways. In light of the recent findings with regard to glucocorticoid inhibition of NF-κB, one may speculate that these effects are mediated through an inhibition of NF-κB.

Further evidence for a role of NF-κB in inflammatory disorders comes from studies of rheumatoid synovium. Although NF-κB is normally present as an inactive cytoplasmic complex, recent immunohistochemical studies have indicated that NF-κB is present in the nuclei, and hence active, in the cells comprising rheumatoid synovium. Furthermore, NF-κB has been shown to be activated in human synovial cells in response to stimulation with TNF-α or IL-1β. Such a distribution may be the underlying mechanism for the increased cytokine and eicosanoid production characteristic of this tissue. See Roshak, A. K., et al., *J. Biol. Chem.*, 271, 31496-31501 (1996). Expression of IKK-β has been shown in synoviocytes of rheumatoid arthritis patients and gene transfer studies have demonstrated the central role of IKK-β in stimulated inflammatory mediator production in these cells. See Aupperele et al. *J. Immunology* 1999. 163:427-433 and Aupperle et al. *J. Immunology* 2001; 166:2705-11. More recently, the intra-articular administration of a wild type IKK-β adenoviral construct was shown to cause paw swelling while intra-articular administration of dominant-negative IKKβ inhibited adjuvant-induced arthritis in rat. See Tak et al. *Arthritis and Rheumatism* 2001, 44:1897-1907.

The NF-κB/Rel and IκB proteins are also likely to play a key role in neoplastic transformation and metastasis. Family members are associated with cell transformation in vitro and in vivo as a result of overexpression, gene amplification, gene rearrangements or translocations. In addition, rearrangement and/or amplification of the genes encoding these proteins are seen in 20-25% of certain human lymphoid tumors. Further, NF-κB is activated by oncogenic ras, the most common defect in human tumors and blockade of NF-κB activation inhibits ras mediated cell transformation. In addition, a role for NF-κB in the regulation of apoptosis has been reported strengthening the role of this transcription factor in the regulation of tumor cell proliferation. TNF, ionizing radiation and DNA damaging agents have all been shown to activate NF-κB which in turn leads to the upregulated expression of several anti-apoptotic proteins. Conversely, inhibition of NF-κB has been shown to enhance apoptotic-killing by these agents in several tumor cell types. As this likely represents a major mechanism of tumor cell resistance to chemotherapy, inhibitors of NF-κB activation may be useful chemotherapeutic agents as either single agents or adjunct therapy. Recent reports have implicated NF-κB as an inhibitor of skeletal cell differentiation as well as a regulator of cytokine-induced muscle wasting (Guttridge et al. *Science;* 2000; 289: 2363-2365.) further supporting the potential of NFκB inhibitors as novel cancer therapies.

Several NF-κB inhibitors are described in C. Wahl, et al. *J. Clin. Invest.* 101(5), 1163-1174 (1998), R. W. Sullivan, et al. *J. Med. Chem.* 41, 413-419 (1998), J. W. Pierce, et al. *J. Biol. Chem.* 272, 21096-21103 (1997).

The marine natural product hymenialdisine is known to inhibit NF-κB. Roshak, A., et al., *JPET,* 283, 955-961 (1997). Breton, J. J and Chabot-Fletcher, M. C., *JPET,* 282, 459-466 (1997).

Additionally, patent applications have been filed on aminothiophene inhibitors of the IKK2, see Callahan, et al., WO 2002030353; Baxter, et al., WO 2001058890, Faull, et al., WO 2003010158; Griffiths, et al., WO2003010163; Fancelli, et al., WO 200198290; Granetto, et al., WO 2003037886; imidazole inhibitors of IKK2, see Callahan, et al., WO 200230423; anilinophenylpyrimidine inhibitors of IKK2, see Kois, et al., WO 2002046171; β-carboline inhibitors of IKK2, see Ritzeler, et al, WO 2001068648, Ritzeler, et al., EP 1134221; Nielsch, et al. DE 19807993; Ritzeler, et al., EP 1209158; indole inhibitors of IKK2, see Ritzeler, et al., WO 2001030774; benzimidazole inhibitors of the IKK2, see Ritzeler, et al., DE 19928424; Ritzeler et al, WO 2001000610; Ritzeler, et al., WO 2004022553; aminopyridine inhibitors of IKK2, see Lowinger, et al, WO 2002024679; Murata, et al, WO 2002024693; Murata, et al., WO 2002044153; aminopyrimidine inhibitors of IKK2, see Bollbuck, et al., WO 2004089913; pyrazole inhibitors of IKK2, see Bergmanis, et al., WO 2003024935; Metz, et al., WO 2003024936; Geng et al., WO 2003027075; Stealey, et al., WO 2003035625; Xu, et al., WO 200307076; Lennon, et al., WO 2003095430; pyrazinone inhibitors of IKK2, see Boys, et al., WO 2005035527; pyrazolaquinazoline inhibitors of IKK2, see Beaulieu, et al., WO 2002028860; Burke et al, WO 2002060386; Burke, et al. US 20030022898; thiophene tricyclic inhibitors of IKK2, see Belema, et al., WO 2003084959; pyrazolopurine inhibitors of IKK2, see Qiu, et al., WO 2004075846; oxazolo and thiazolo pyridine inhibitors of IKK2, see Pitts, et al., WO 2004106293; quinoline inhibitors of IKK2, Browner, et al., WO2002041843, Browner, et al., US 20020161004 and pyridylcyanoguanidine inhibitors of IKK2, see Bjorkling, et al., WO 2002094813, Binderup et al, WO 2002094322 and Madsen, et al., WO 200294265; thienopyridine inhibitors of IKK2, see Cywin, et al., WO 2003103661; Liu, et al., WO 2005035537; benzothiophene inhibitors of IKK2, see Chen et al., WO 2005012283. The natural products staurosporine, quercetin, K252a and K252b have been shown to be IKK2 inhibitors, see Peet, G. W. and Li, J. J. *Biol. Chem.,* 274, 32655-32661 (1999) and Wisniewski, D., et al., *Analytical Biochem.* 274, 220-228 (1999). Synthetic inhibitors of IKK2 have also been described, see Burke, et al. *J. Biol. Chem.,* 278, 1450-1456 (2003), Murata, et al., *Bioorg. Med. Chem. Lett.,* 13, 913-198 (2003), Murata, et al., *Bioorg. Med. Chem. Lett.,* 14, 4013-4017 (2004), and Murata, et al., *Bioorg. Med. Chem. Lett.,* 14, 4019-4022 (2004) have described IKK2 inhibitors.

Thus, attempts have been made to prepare compounds that inhibit IKK2 activity and a number of such compounds have been disclosed in the art. However, in view of the number of pathological responses that are mediated by IKK2, there remains a continuing need for inhibitors of IKK2 which can be used in the treatment of a variety of conditions.

The present inventors have discovered novel indole carboxamide compounds, which are inhibitors of kinase activity, in particular inappropriate IKK2 activity. Such indole carboxamide derivatives are therefore useful in the treatment of disorders associated with inappropriate kinase, in particular inappropriate IKK2 activity in particular in the treatment and prevention of disease states mediated by IKK2 mechanisms including inflammatory and tissue repair disorders, particularly rheumatoid arthritis, inflammatory bowel disease, asthma and COPD (chronic obstructive pulmonary disease); osteoarthritis, osteoporosis and fibrotic diseases; dermatosis, including psoriasis, atopic dermatitis and ultraviolet radiation (UV)-induced skin damage; autoimmune diseases including systemic lupus eythematosus, multiple sclerosis, psoriatic arthritis, alkylosing spondylitis, tissue and organ rejection, Alzheimer's disease, stroke, atherosclerosis, restonosis, diabetes, glomerulonephritis, cancer, including Hodgkins disease, cachexia, inflammation associated with infection and certain viral infections, including acquired immune deficiency syndrome (AIDS), adult respiratory distress syndrome, and Ataxia Telangiestasia.

SUMMARY OF THE INVENTION

The invention is directed to novel indole carboxamide derivatives. Specifically, the invention is directed to compounds according to formula (I):

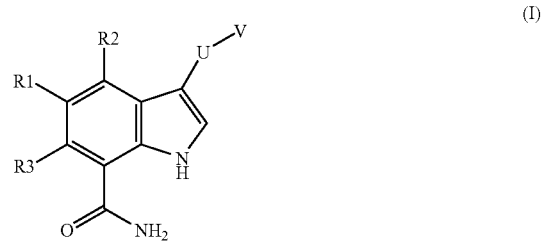

where R1, R2, R3, U and V are defined below and to pharmaceutically acceptable salts thereof.

The compounds of the invention are inhibitors of IKK2 and can be useful in the treatment of disorders associated with inappropriate IKK2 (also known as IKKβ) activity, such as rheumatoid arthritis, asthma, and COPD (chronic obstructive pulmonary disease). Accordingly, the invention is further directed to pharmaceutical compositions comprising a compound of the invention. The invention is still further directed to methods of inhibiting IKK2 activity and treatment of disorders associated therewith using a compound of the invention or a pharmaceutical composition comprising a compound of the invention.

DETAILED DESCRIPTION OF THE INVENTION

The invention is directed to compounds according to formula (I):

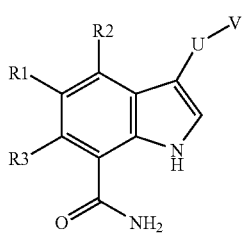

where R1 is the group —XYZ or

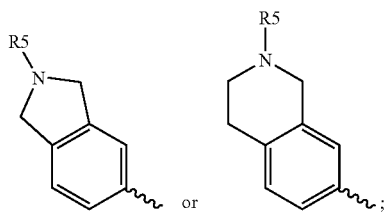

X is phenyl, heteroaryl, 1,2,3,4-tetrahydronaphthalenyl, or 2,3-dihydro-1H-indenyl,
  where said phenyl, heteroaryl, 1,2,3,4-tetrahydronaphthalenyl, and 2,3-dihydro-1H-indenyl are optionally substituted with one or two substituents each independently selected from the following:
  1) halo,
  2) nitro,
  3) cyano,
  4) —NR7R8,
  5) $C_1$-$C_6$-alkyl,
  6) CHO,
  7) $CONH_2$, and
  8) —OR4,
    where said $C_1$-$C_6$-alkyl is optionally substituted with one —NR4R5 group;
Y is a bond or $C_1$-$C_6$ alkylene,
  where $C_1$-$C_6$ alkylene is optionally substituted with one or two substituents each independently selected from the following:
  1) $C_1$-$C_3$-alkyl optionally substituted by one OR4 group,
  2) $C_3$-$C_7$-cycloalkyl,
  3) methoxy,
  4) hydroxy, and
  5) heteroaryl;

Z is —NR4R5 or heterocycloalkyl,
  where said heterocycloalkyl is optionally substituted with one or two substituents each independently selected from the following:
  1) $C_1$-$C_6$-alkyl optionally substituted by one OR4 or one heterocycloalkyl group,
  2) $C_3$-$C_7$-cycloalkyl,
  3) methoxy,
  4) —$CONH_2$
  5) hydroxy,
  6) heteroaryl,
  7) $CF_3$,
  8) phenyl,
  9) heterocycloalkyl, and
  10) $N(CH_3)_2$;
R2 is selected from
  1) H,
  2) fluoro, and
  3) chloro;
R3 is selected from
  1) H,
  2) fluoro, and
  3) chloro;
R4 is selected from
  1) H and
  2) $C_1$-$C_6$-alkyl,
    where said $C_1$-$C_6$-alkyl is optionally substituted with one hydroxy or one methoxy group;
R5 is selected from
  1) H,
  2) $C_5$-$C_6$-heterocycloalkyl,
  3) —$CO_2$Et,
  4) $C_1$-$C_6$-alkoxy,
  5) $C_3$-$C_7$-cycloalkyl,
  6) $C_1$-$C_6$-alkyl,
  7) —$SO_2$R10, and
  8) —C(O)R10.
    where said $C_3$-$C_7$-cycloalkyl and $C_1$-$C_6$-alkyl are optionally substituted with one to three substituents selected from R6;
each R6 is independently selected from
  1) —NR7R8,
  2) —$SO_2$R7,
  3) —$CONH_2$,
  4) —$CF_3$,
  5) —CN,
  6) —$CO_2$R7,
  7) —$OCH_2CH_2$OR7,
  8) —SR5,
  9) C3-C4 alkenyl,
  10) OH,
  11) $C_1$-$C_6$-alkoxy,
  12) heteroaryl,
  13) $C_3$-$C_7$-cycloalkyl,
  14) phenyl,
  15) heterocycloalkyl, and
  16) halo,
    where said heteroaryl, cycloalkyl, phenyl and heterocycloalkyl are optionally substituted with one to two substituents selected from R9;
R7 is selected from
  1) H,
  2) $C_1$-$C_3$-alkyl, and
  3) phenyl;
R8 is selected from
  1) H,
  2) $C_1$-$C_3$-alkyl, and
  3) —C(O)R4;

each R9 is independently selected from
1) hydroxy,
2) —OMe,
3) nitro,
4) $C_1$-$C_6$-alkyl,
5) $NH_2$,
6) halo,
7) $CF_3$,
8) $C_1$-$C_6$-alkoxy, and
9) CN;
R10 is selected from
1) H,
2) $C_1$-$C_6$-alkyl,
3) phenyl,
4) $C_3$-$C_7$-cycloalkyl,
5) heteroaryl,
6) $C_1$-$C_6$-heteroaryl, and
7) heterocycloalkyl,
where said $C_1$-$C_6$-alkyl is optionally substituted with one or two substituents each independently selected from $C_3$-$C_7$-cycloalkyl and —S—R7; where said heterocycloalkyl is optionally substituted with one —C(O)R7 group; and where said phenyl, heteroaryl and $C_1$-$C_6$-heteroaryl are optionally substituted with one to two substituents selected from R11;
each R11 is independently selected from
1) H,
2) $C_1$-$C_6$-alkyl, and
3) halo;
U is a bond, $C_1$-$C_6$ alkylene or $C_2$-$C_6$ alkenylene;
V is phenyl, 5 or 6 membered heteroaryl, 5-7 membered heterocycloalkyl, $C_5$-$C_7$ cycloalkyl, or $C_5$-$C_7$ cycloalkenyl, each of which is substituted by —N(R7)S(O)$_m$R12, —S(O)$_m$N(R7)R12, —S(O)$_m$R12, or —C(O)R12;
m is 1 or 2; and
R12 is $C_1$-$C_6$-alkyl, $C_3$-$C_7$ cycloalkyl, $C_1$-$C_6$-alkyl-$C_3$-$C_7$cycloalkyl, or $C_1$-$C_6$-alkyl-phenyl; or a pharmaceutically acceptable salt thereof.

One embodiment of the present invention is a compound according to formula (I):
where R1 is the group —XYZ;
X is phenyl or heteroaryl,
where said phenyl and heteroaryl are optionally substituted with one or two substituents each independently selected from the following:
1) halo,
2) nitro,
3) cyano,
4) —NR7R8,
5) $C_1$-$C_6$-alkyl,
6) CHO,
7) $CONH_2$, and
8) —OR4,
where said $C_1$-$C_6$-alkyl is optionally substituted with one —NR4R5 group;
Y is a bond or $C_1$-$C_6$ alkylene,
where $C_1$-$C_6$ alkylene is optionally substituted with one or two substituents each independently selected from the following:
1) $C_1$-$C_3$-alkyl optionally substituted by one OR4 group,
2) $C_3$-$C_7$-cycloalkyl,
3) methoxy,
4) hydroxy, and
5) heteroaryl;
Z is —NR4R5 or heterocycloalkyl,
where said heterocycloalkyl is optionally substituted with one or two substituents each independently selected from the following:
1) $C_1$-$C_6$-alkyl optionally substituted by one OR4 group,
2) $C_3$-$C_7$-cycloalkyl,
3) methoxy,
4) hydroxy, and
5) heteroaryl;
R2 is selected from
1) H,
2) fluoro, and
3) chloro;
R3 is selected from
1) H,
2) fluoro, and
3) chloro;
R4 is selected from
1) H and
2) $C_1$-$C_6$-alkyl,
where said $C_1$-$C_6$-alkyl is optionally substituted with one hydroxy or one methoxy group;
R5 is selected from
1) H,
2) $C_1$-$C_6$-alkoxy,
3) $C_3$-$C_7$-cycloalkyl,
4) $C_1$-$C_6$-alkyl,
5) —$SO_2$R10, and
6) —C(O)R10,
where said $C_3$-$C_7$-cycloalkyl and $C_1$-$C_6$-alkyl are optionally substituted with one to three substituents selected from R6;
each R6 is independently selected from
1) —NR7R8,
2) —$SO_2$R7,
3) OH,
4) methoxy,
5) heteroaryl,
6) $C_3$-$C_7$-cycloalkyl,
7) phenyl,
8) heterocycloalkyl, and
9) halo,
where said heteroaryl, cycloalkyl, phenyl and heterocycloalkyl are optionally substituted with one to two substituents selected from R9;
R7 is selected from
1) H and
2) $C_1$-$C_3$-alkyl;
R8 is selected from
1) H and
2) $C_1$-$C_3$-alkyl;
each R9 is independently selected from
1) hydroxy,
2) nitro,
3) $C_1$-$C_6$-alkyl,
4) $NH_2$,
5) halo,
6) $CF_3$,
7) $C_1$-$C_6$-alkoxy, and
8) CN;
R10 is selected from
1) H,
2) $C_1$-$C_6$-alkyl,
3) phenyl,
4) $C_3$-$C_7$-cycloalkyl, and
5) heteroaryl,
where said $C_1$-$C_6$-alkyl is optionally substituted with one or two substituents each independently selected from C$_3$-C$_7$-cycloalkyl and —S—R7; where said heterocycloalkyl is optionally substituted with one —C(O)R7 group; and where said phenyl and heteroaryl are optionally substituted with one to two substituents selected from R11;
each R11 is independently selected from
1) H,
2) C$_1$-C$_6$-alkyl, and
3) halo;
U is a bond, C$_1$-C$_6$ alkylene or C$_2$-C$_6$ alkenylene;
V is phenyl, 5 or 6 membered heteroaryl, 5-7 membered heterocycloalkyl, C$_5$-C$_7$ cycloalkyl, or C$_5$-C$_7$ cycloalkenyl, each of which is substituted by —N(R7)S(O)$_m$R12, —S(O)$_m$N(R7)R12, —S(O)$_m$R12, or —C(O)R12;
m is 1 or 2; and
R12 is C$_1$-C$_6$-alkyl, C$_3$-C$_7$ cycloalkyl, C$_1$-C$_6$-alkyl-C$_3$-C$_7$cycloalkyl, or C$_1$-C$_6$-alkyl-phenyl; or a pharmaceutically acceptable salt thereof.

Another embodiment of the present invention is a compound according to formula (I):
where R1 is the group —XYZ or

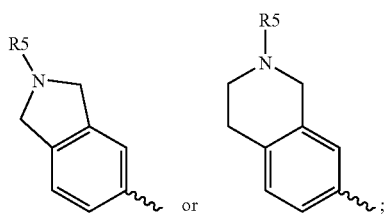

X is phenyl, heteroaryl, 1,2,3,4-tetrahydronaphthalenyl, or 2,3-dihydro-1H-indenyl;
Y is a bond or C$_1$-C$_6$ alkylene;
Z is —NR4R5 or heterocycloalkyl,
where said heterocycloalkyl is optionally substituted with one or two substituents each independently selected from the following:
1) C$_1$-C$_6$-alkyl optionally substituted by one OR4 or one heterocycloalkyl group,
2) C$_3$-C$_7$-cycloalkyl,
3) methoxy,
4) —CONH$_2$
5) hydroxy,
6) heteroaryl;
7) CF$_3$,
8) phenyl,
9) heterocycloalkyl, and
10) N(CH$_3$)$_2$;
R2 is H;
R3 is H;
R4 is selected from
1) H and
2) C$_1$-C$_6$-alkyl,
where said C$_1$-C$_6$-alkyl is optionally substituted with one hydroxy or one methoxy group;
R5 is selected from
1) H,
2) C$_5$-C$_6$-heterocycloalkyl,
3) —CO$_2$Et,
4) C$_1$-C$_6$-alkoxy,
5) C$_3$-C$_7$-cycloalkyl,
6) C$_1$-C$_6$-alkyl,
7) —SO$_2$R10, and
8) —C(O)R10, where said C$_3$-C$_7$-cycloalkyl and C$_1$-C$_6$-alkyl are optionally substituted with one to three substituents selected from R6;
each R6 is independently selected from
1) —NR7R8,
2) —SO$_2$R7,
3) —CONH$_2$,
4) —CF$_3$,
5) —CN,
6) —CO$_2$R7,
7) —OCH$_2$CH$_2$OR7,
8) —SR5,
9) C3-C4 alkenyl,
10) OH,
11) C$_1$-C$_6$-alkoxy,
12) heteroaryl,
13) C$_3$-C$_7$-cycloalkyl,
14) phenyl,
15) heterocycloalkyl, and
16) halo,
where said heteroaryl, cycloalkyl, phenyl and heterocycloalkyl are optionally substituted with one to two substituents selected from R9;
R7 is selected from
1) H,
2) C$_1$-C$_3$-alkyl, and
3) phenyl;
R8 is selected from
1) H,
2) C$_1$-C$_3$-alkyl, and
3) —C(O)R4;
each R9 is independently selected from
1) hydroxy,
2) —OMe
3) nitro,
4) C$_1$-C$_6$-alkyl,
5) NH$_2$,
6) halo,
7) CF$_3$,
8) C$_1$-C$_6$-alkoxy, and
9) CN;
R10 is selected from
1) H,
2) C$_1$-C$_6$-alkyl,
3) phenyl,
4) C$_3$-C$_7$-cycloalkyl,
5) heteroaryl,
6) C$_1$-C$_6$-heteroaryl, and
7) heterocycloalkyl,
where said C$_1$-C$_6$-alkyl is optionally substituted with one or two substituents each independently selected from C$_3$-C$_7$-cycloalkyl and —S—R7; where said heterocycloalkyl is optionally substituted with one —C(O)R7 group; and where said phenyl, heteroaryl and C$_1$-C$_6$-heteroaryl are optionally substituted with one to two substituents selected from R11;
each R11 is independently selected from
1) H,
2) C$_1$-C$_6$-alkyl, and
3) halo;
U is a bond;
V is a 5-7 membered heterocycloalkyl substituted by —S(O)$_m$R12;
m is 1 or 2; and
R12 is C$_1$-C$_6$-alkyl; or a pharmaceutically acceptable salt thereof.

Another embodiment of the present invention is a compound according to formula (I):
where R1 is the group —XYZ;
X is phenyl or heteroaryl;
Y is a bond or $C_1$-$C_6$ alkylene;
Z is —NR4R5 or heterocycloalkyl,
  where said heterocycloalkyl is optionally substituted with one or two substituents each independently selected from the following:
    1) $C_1$-$C_6$-alkyl optionally substituted by one OR4 group,
    2) $C_3$-$C_7$-cycloalkyl,
    3) methoxy,
    4) hydroxy, and
    5) heteroaryl;
R2 is H;
R3 is H;
R4 is selected from
  1) H and
  2) $C_1$-$C_6$-alkyl,
    where said $C_1$-$C_6$-alkyl is optionally substituted with one hydroxy or one methoxy group;
R5 is selected from
  1) H,
  2) $C_1$-$C_6$-alkoxy,
  3) $C_3$-$C_7$-cycloalkyl,
  4) $C_1$-$C_6$-alkyl,
  5) —SO$_2$R10, and
  6) —C(O)R10,
    where said $C_3$-$C_7$-cycloalkyl and $C_1$-$C_6$-alkyl are optionally substituted with one to three substituents selected from R6;
each R6 is independently selected from
  1) NR7R8,
  2) SO$_2$R7,
  3) OH,
  4) methoxy,
  5) heteroaryl,
  6) $C_3$-$C_7$-cycloalkyl,
  7) phenyl,
  8) heterocycloalkyl, and
  9) halo,
    where said heteroaryl, cycloalkyl, phenyl and heterocycloalkyl are optionally substituted with one to two substituents selected from R9;
R7 is selected from
  1) H and
  2) $C_1$-$C_3$-alkyl;
R8 is selected from
  1) H and
  2) $C_1$-$C_3$-alkyl;
each R9 is independently selected from
  1) hydroxy,
  2) nitro,
  3) $C_1$-$C_6$-alkyl,
  4) NH$_2$,
  5) halo,
  6) CF$_3$,
  7) $C_1$-$C_6$-alkoxy, and
  8) CN;
R10 is selected from
  1) H,
  2) $C_1$-$C_6$-alkyl,
  3) phenyl,
  4) $C_3$-$C_7$-cycloalkyl, and
  5) heteroaryl,
    where said $C_1$-$C_6$-alkyl is optionally substituted with one or two substituents each independently selected from
    $C_3$-$C_7$-cycloalkyl and —S—R7; where said heterocycloalkyl is optionally substituted with one —C(O)R7 group; and where said phenyl and heteroaryl are optionally substituted with one to two substituents selected from R11;
each R11 is independently selected from
  1) H,
  2) $C_1$-$C_6$-alkyl, and
  3) halo;
U is a bond;
V is a 5-7 membered heterocycloalkyl substituted by —S(O)$_m$R12;
m is 1 or 2; and
R12 is $C_1$-$C_6$-alkyl; or a pharmaceutically acceptable salt thereof.

Another embodiment of the present invention is a compound of formula (I) where:
where R1 is the group —XYZ;
X is 2- or 3-thiophenyl;
Y is a bond or $C_1$-$C_4$ alkylene;
Z is —NR4R5 or heterocycloalkyl,
  1) $C_1$-$C_6$-alkyl optionally substituted by one OR4 or one heterocycloalkyl group,
  2) $C_3$-$C_7$-cycloalkyl,
  3) methoxy,
  4) —CONH$_2$,
  5) hydroxy,
  6) heteroaryl;
  7) CF$_3$,
  8) phenyl,
  9) heterocycloalkyl, and
  10) N(CH$_3$)$_2$;
R2 is H;
R3 is H;
R4 is selected from
  1) H and
  2) $C_1$-$C_6$-alkyl,
    where said $C_1$-$C_6$-alkyl is optionally substituted with one hydroxy or one methoxy group;
R5 is selected from
  1) $C_3$-$C_7$-cycloalkyl,
  2) $C_1$-$C_6$-alkyl,
    where said $C_3$-$C_7$-cycloalkyl and $C_1$-$C_6$-alkyl are optionally substituted with one to three substituents selected from R6;
each R6 is independently selected from
  1) —NR7R8,
  2) —CONH$_2$,
  3) —CN,
  4) —OCH$_2$CH$_2$OR7,
  5) C3-C4 alkenyl,
  6) OH,
  7) $C_1$-$C_6$-alkoxy,
  8) heteroaryl,
  9) $C_3$-$C_7$-cycloalkyl,
  10) phenyl,
  11) heterocycloalkyl, and
  12) halo,
    where said heteroaryl, cycloalkyl, phenyl and heterocycloalkyl are optionally substituted with one to two substituents selected from R9;
R7 is selected from
  1) H,
  2) $C_1$-$C_3$-alkyl, and
  3) phenyl;

R8 is selected from
1) H,
2) $C_1$-$C_3$-alkyl, and
3) —C(O)R4;
each R9 is independently selected from
1) $C_1$-$C_6$-alkyl;
U is a bond;
V is 4-piperidinyl substituted by —S(O)$_2$R12; and
R12 is ethyl or isopropyl; or a pharmaceutically acceptable salt thereof.

Another embodiment of the present invention is a compound according to formula (I) where the group U-V is

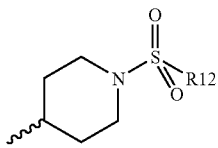

and R12 is ethyl or isopropyl.

Another embodiment of the present invention is a compound of formula (II)

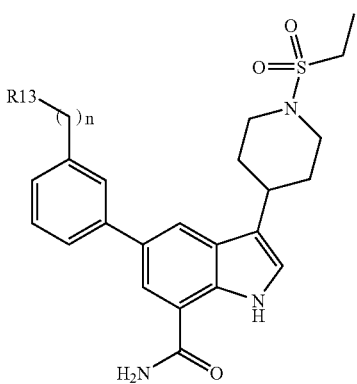

where R13 is —NR14R15 or heterocycloalkyl
where said heterocycloalkyl is optionally substituted with one or two substituents selected from the following:
1) $C_1$-$C_6$-alkyl optionally substituted by one OR14 group,
2) hydroxy,
3) methoxy, and
4) heteroaryl;
R14 is selected from
1) H and
2) $C_1$-$C_6$-alkyl,
where said $C_1$-$C_6$-alkyl is optionally substituted with one hydroxyl or one methoxy group;
R15 is selected from
1) H,
2) methoxy,
3) $C_3$-$C_7$ cycloalkyl, and
4) $C_1$-$C_6$-alkyl,
where said $C_3$-$C_7$cycloalkyl and $C_1$-$C_6$-alkyl are optionally substituted with one to three substituents selected from R16;
each R16 is independently selected from
1) —NR17R18,
2) —SO$_2$R17,
3) OH,
4) methoxy
5) heteroaryl,
6) $C_3$-$C_7$cycloalkyl,
7) phenyl, and
8) heterocycloalkyl,
where said heteroaryl, cycloalkyl, phenyl and heterocycloalkyl are optionally substituted with one to three substituents selected from R19;
R17 is selected from
1) H and
2) $C_1$-$C_3$-alkyl;
R18 is selected from
1) H and
2) $C_1$-$C_3$-alkyl;
R19 is selected from
1) hydroxy,
2) nitro,
3) $C_1$-$C_6$-alkyl,
4) NH$_2$,
5) halo,
6) CF$_3$, and
7) $C_1$-$C_6$-alkoxy; and
n is 1 to 3; or a pharmaceutically acceptable salt thereof.

Specific examples of compounds of the present invention include the following:
3-[1-(ethylsulfonyl)-4-piperidinyl]-5-[3-(1-piperidinylmethyl)phenyl]-1H-indole-7-carboxamide;
3-[1-(ethylsulfonyl)-4-piperidinyl]-5-[3-(1-piperazinylmethyl)phenyl]-1H-indole-7-carboxamide;
3-[1-(ethylsulfonyl)-4-piperidinyl]-5-[3-(4-morpholinylmethyl)phenyl]-1H-indole-7-carboxamide;
3-[1-(ethylsulfonyl)-4-piperidinyl]-5-[3-({methyl[2-(methylsulfonyl)ethyl]amino}methyl)phenyl]-1H-indole-7-carboxamide;
5-(3-{[[2-(dimethylamino)ethyl](methyl)amino]methyl}phenyl)-3-[1-(ethylsulfonyl)-4-piperidinyl]-1H-indole-7-carboxamide;
3-[1-(ethylsulfonyl)-4-piperidinyl]-5-{3-[(4-{2-[(2-hydroxyethyl)oxy]ethyl}-1-piperazinyl)methyl]phenyl}-1H-indole-7-carboxamide;
3-[1-(ethylsulfonyl)-4-piperidinyl]-5-(3-{[3-(hydroxymethyl)-1-piperidinyl]methyl}phenyl)-1H-indole-7-carboxamide;
5-[3-({bis[2-(methyloxy)ethyl]amino}methyl)phenyl]-3-[1-(ethylsulfonyl)-4-piperidinyl]-1H-indole-7-carboxamide;
5-{3-[(2,6-dimethyl-4-morpholinyl)methyl]phenyl}-3-[1-(ethylsulfonyl)-4-piperidinyl]-1H-indole-7-carboxamide;
3-[1-(ethylsulfonyl)-4-piperidinyl]-5-(3-{[2-(1,3-thiazol-2-yl)-1-pyrrolidinyl]methyl}phenyl)-1H-indole-7-carboxamide;
3-[1-(ethylsulfonyl)-4-piperidinyl]-5-(3-{[2-(2-thienyl)-1-pyrrolidinyl]methyl}phenyl)-1H-indole-7-carboxamide;
3-[1-(ethylsulfonyl)-4-piperidinyl]-5-(3-{[(2-hydroxy-2-phenylethyl)(methyl)amino]methyl}phenyl)-1H-indole-7-carboxamide;
5-(3-{[ethyl(methyl)amino]methyl}phenyl)-3-[1-(ethylsulfonyl)-4-piperidinyl]-1H-indole-7-carboxamide;
5-[3-(aminomethyl)phenyl]-3-[1-(ethylsulfonyl)-4-piperidinyl]-1H-indole-7-carboxamide;
5-{3-[(cyclopentylamino)methyl]phenyl}-3-[1-(ethylsulfonyl)-4-piperidinyl]-1H-indole-7-carboxamide;
5-[3-({[(3,4-dihydroxyphenyl)methyl]amino}methyl)phenyl]-3-[1-(ethylsulfonyl)-4-piperidinyl]-1H-indole-7-carboxamide;
3-[1-(ethylsulfonyl)-4-piperidinyl]-5-(3-{[(2-thienylmethyl)amino]methyl}phenyl)-1H-indole-7-carboxamide;

3-[1-(ethylsulfonyl)-4-piperidinyl]-5-[3-({[(2S)-2-(hydroxymethyl)-3-methylbutyl]amino}methyl)phenyl]-1H-indole-7-carboxamide;

3-[1-(ethylsulfonyl)-4-piperidinyl]-5-(3-{[(2-hydroxy-1-methylethyl)amino]methyl}phenyl)-1H-indole-7-carboxamide;

3-[1-(ethylsulfonyl)-4-piperidinyl]-5-(3-{[(trans-4-hydroxycyclohexyl)amino]methyl}phenyl)-1H-indole-7-carboxamide;

3-[1-(ethylsulfonyl)-4-piperidinyl]-5-{3-[({[1-(1-piperidinyl)cyclohexyl]methyl}amino)methyl]phenyl}-1H-indole-7-carboxamide;

3-[1-(ethylsulfonyl)-4-piperidinyl]-5-[3-({[(2S)-2-hydroxypropyl]amino}methyl)phenyl]-1H-indole-7-carboxamide;

5-{3-[(ethylamino)methyl]phenyl}-3-[1-(ethylsulfonyl)-4-piperidinyl]-1H-indole-7-carboxamide;

3-[1-(ethylsulfonyl)-4-piperidinyl]-5-{3-[(propylamino)methyl]phenyl}-1H-indole-7-carboxamide;

3-[1-(ethylsulfonyl)-4-piperidinyl]-5-(3-{[(1-methylethyl)amino]methyl}phenyl)-1H-indole-7-carboxamide;

5-(3-{[(1-ethylpropyl)amino]methyl}phenyl)-3-[1-(ethylsulfonyl)-4-piperidinyl]-1H-indole-7-carboxamide;

3-[1-(ethylsulfonyl)-4-piperidinyl]-5-[3-(1-piperidinylmethyl)phenyl]-1H-indole-7-carboxamide;

3-[1-(ethylsulfonyl)-4-piperidinyl]-5-[4-(1-piperidinylmethyl)phenyl]-1H-indole-7-carboxamide;

3-[1-(ethylsulfonyl)-4-piperidinyl]-5-{3-[(methylamino)methyl]phenyl}-1H-indole-7-carboxamide;

3-[1-(ethylsulfonyl)-4-piperidinyl]-5-[4-(4-morpholinylmethyl)phenyl]-1H-indole-7-carboxamide;

5-[4-(aminomethyl)phenyl]-3-[1-(ethylsulfonyl)-4-piperidinyl]-1H-indole-7-carboxamide;

3-[1-(ethylsulfonyl)-4-piperidinyl]-5-[3-(4-morpholinylmethyl)phenyl]-1H-indole-7-carboxamide;

5-{3-[(cyclopropylamino)methyl]phenyl}-3-[1-(ethylsulfonyl)-4-piperidinyl]-1H-indole-7-carboxamide;

5-{3-[(cyclobutylamino)methyl]phenyl}-3-[1-(ethylsulfonyl)-4-piperidinyl]-1H-indole-7-carboxamide;

3-(1-{[3-(dimethylamino)propyl]sulfonyl}-4-piperidinyl)-5-[4-(1-piperidinylmethyl)phenyl]-1H-indole-7-carboxamide;

3-[1-(ethylsulfonyl)-4-piperidinyl]-5-{3-[(2-methylpropyl)amino]-2,3-dihydro-1H-inden-5-yl}-1H-indole-7-carboxamide;

3-[1-(ethylsulfonyl)-4-piperidinyl]-5-{8-[(2-methylpropyl)amino]-5,6,7,8-tetrahydro-2-naphthalenyl}-1H-indole-7-carboxamide;

5-(5-{[(2-cyanoethyl)amino]methyl}-2-fluorophenyl)-3-[1-(ethylsulfonyl)-4-piperidinyl]-1H-indole-7-carboxamide;

3-[1-(ethylsulfonyl)-4-piperidinyl]-5-(2-fluoro-5-{[(2,2,2-trifluoroethyl)amino]methyl}phenyl)-1H-indole-7-carboxamide;

3-[1-(ethylsulfonyl)-4-piperidinyl]-5-(1,2,3,4-tetrahydro-7-isoquinolinyl)-1H-indole-7-carboxamide;

3-[1-(ethylsulfonyl)-4-piperidinyl]-5-(3-{[(2,2,2-trifluoroethyl)amino]methyl}phenyl)-1H-indole-7-carboxamide;

5-(3-{[(2-amino-2-oxoethyl)(methyl)amino]methyl}phenyl)-3-[1-(ethylsulfonyl)-4-piperidinyl]-1H-indole-7-carboxamide;

3-[1-(ethylsulfonyl)-4-piperidinyl]-5-(2-{[(2,2,2-trifluoroethyl)amino]methyl}-1,3-thiazol-4-yl)-1H-indole-7-carboxamide;

5-(3-cyano-5-{[(2,2,2-trifluoroethyl)amino]methyl}phenyl)-3-[1-(ethylsulfonyl)-4-piperidinyl]-1H-indole-7-carboxamide;

3-[1-(ethylsulfonyl)-4-piperidinyl]-5-(5-{[methyl(1-methyl-4-piperidinyl)amino]methyl}-3-thienyl)-1H-indole-7-carboxamide;

5-(5-{[(2-cyanoethyl)(methyl)amino]methyl}-3-thienyl)-3-[1-(ethylsulfonyl)-4-piperidinyl]-1H-indole-7-carboxamide;

5-(5-{[(2-amino-2-oxoethyl)(methyl)amino]methyl}-3-thienyl)-3-[1-(ethylsulfonyl)-4-piperidinyl]-1H-indole-7-carboxamide;

3-[1-(ethylsulfonyl)-4-piperidinyl]-5-[5-({methyl[2-(phenylsulfonyl)ethyl]amino}methyl)-3-thienyl]-1H-indole-7-carboxamide;

3-[1-(ethylsulfonyl)-4-piperidinyl]-5-{5-[(2-phenyl-1-pyrrolidinyl)methyl]-3-thienyl}-1H-indole-7-carboxamide;

3-[1-(ethylsulfonyl)-4-piperidinyl]-5-(5-{[2-(1-piperidinylmethyl)-1-pyrrolidinyl]methyl}-3-thienyl)-1H-indole-7-carboxamide;

5-(5-{[(2R)-2-(aminocarbonyl)-1-pyrrolidinyl]methyl}-3-thienyl)-3-[1-(ethylsulfonyl)-4-piperidinyl]-1H-indole-7-carboxamide;

5-(5-{[(2S)-2-(dimethylamino)-1-pyrrolidinyl]methyl}-3-thienyl)-3-[1-(ethylsulfonyl)-4-piperidinyl]-1H-indole-7-carboxamide;

5-(1-{2-[4-(dimethylamino)-1-piperidinyl]ethyl}-1H-pyrazol-4-yl)-3-[1-(ethylsulfonyl)-4-piperidinyl]-1H-indole-7-carboxamide;

5-[3-[(dimethylamino)methyl]-4,5-bis(methyloxy)phenyl]-3-[1-(ethylsulfonyl)-4-piperidinyl]-1H-indole-7-carboxamide;

5-[3,4-bis(methyloxy)-5-(4-morpholinylmethyl)phenyl]-3-[1-(ethylsulfonyl)-4-piperidinyl]-1H-indole-7-carboxamide;

3-[1-(ethylsulfonyl)-4-piperidinyl]-5-[3-{[(1-methylethyl)amino]methyl}-4,5-bis(methyloxy)phenyl]-1H-indole-7-carboxamide;

3-[1-(ethylsulfonyl)-4-piperidinyl]-5-[3-{[(1-methylethyl)amino]methyl}-4,5-bis(methyloxy)phenyl]-1H-indole-7-carboxamide;

5-[3-[(2,2-dimethylpropyl)amino]methyl-4,5-bis(methyloxy)phenyl]-3-[1-(ethylsulfonyl)-4-piperidinyl]-1H-indole-7-carboxamide;

3-[1-(ethylsulfonyl)-4-piperidinyl]-5-[3-{[(2-hydroxyethyl)(methyl)amino]methyl}-4,5-bis(methyloxy)phenyl]-1H-indole-7-carboxamide;

5-[3,4-bis(methyloxy)-5-(1-pyrrolidinylmethyl)phenyl]-3-[1-(ethylsulfonyl)-4-piperidinyl]-1H-indole-7-carboxamide;

5-{4-[(dimethylamino)methyl]-2,3-dihydro-1-benzofuran-6-yl}-3-[1-(ethylsulfonyl)-4-piperidinyl]-1H-indole-7-carboxamide;

3-[1-(ethylsulfonyl)-4-piperidinyl]-5-(4-{[(1-methylethyl)amino]methyl}-2,3-dihydro-1-benzofuran-6-yl)-1H-indole-7-carboxamide;

3-[1-(ethylsulfonyl)-4-piperidinyl]-5-[4-(4-morpholinylmethyl)-2,3-dihydro-1-benzofuran-6-yl]-1H-indole-7-carboxamide;

3-[1-(ethylsulfonyl)-4-piperidinyl]-5-[5-({[1-methyl-2-(methyloxy)ethyl]amino}methyl)-2-thienyl]-1H-indole-7-carboxamide;

5-(5-{[(2-cyanoethyl)amino]methyl}-3-pyridinyl)-3-[1-(ethylsulfonyl)-4-piperidinyl]-1H-indole-7-carboxamide;

3-[1-(ethylsulfonyl)-4-piperidinyl]-5-(5-{[(2,2,2-trifluoroethyl)amino]methyl}-3-pyridinyl)-1H-indole-7-carboxamide;

5-{3-[(dimethylamino)methyl]phenyl}-3-[1-(ethylsulfonyl)-4-piperidinyl]-1H-indole-7-carboxamide;

5-(5-{[ethyl(methyl)amino]methyl}-3-thienyl)-3-[1-(ethylsulfonyl)-4-piperidinyl]-1H-indole-7-carboxamide;

5-(5-{[[2-(diethylamino)ethyl](methyl)amino]methyl}-3-thienyl)-3-[1-(ethylsulfonyl)-4-piperidinyl]-1H-indole-7-carboxamide;

5-(5-{[butyl(methyl)amino]methyl}-3-thienyl)-3-[1-(ethylsulfonyl)-4-piperidinyl]-1H-indole-7-carboxamide;

3-[1-(ethylsulfonyl)-4-piperidinyl]-5-(5-{[methyl(propyl)amino]methyl}-3-thienyl)-1H-indole-7-carboxamide;

5-(5-{[[2-(dimethylamino)ethyl](methyl)amino]methyl}-3-thienyl)-3-[1-(ethylsulfonyl)-4-piperidinyl]-1H-indole-7-carboxamide;

5-(5-{[[3-(dimethylamino)propyl](methyl)amino]methyl}-3-thienyl)-3-[1-(ethylsulfonyl)-4-piperidinyl]-1H-indole-7-carboxamide;

5-(5-{[cyclopentyl(methyl)amino]methyl}-3-thienyl)-3-[1-(ethylsulfonyl)-4-piperidinyl]-1H-indole-7-carboxamide;

3-[1-(ethylsulfonyl)-4-piperidinyl]-5-(5-{[methyl(pentyl)amino]methyl}-3-thienyl)-1H-indole-7-carboxamide;

3-[1-(ethylsulfonyl)-4-piperidinyl]-5-(5-{[methyl(2-methylpropyl)amino]methyl}-3-thienyl)-1H-indole-7-carboxamide;

3-[1-(ethylsulfonyl)-4-piperidinyl]-5-(5-{[methyl(phenylmethyl)amino]methyl}-3-thienyl)-1H-indole-7-carboxamide;

3-[1-(ethylsulfonyl)-4-piperidinyl]-5-(5-{[(2-hydroxyethyl)(methyl)amino]methyl}-3-thienyl)-1H-indole-7-carboxamide;

3-[1-(ethylsulfonyl)-4-piperidinyl]-5-[5-({methyl[2-(2-pyridinyl)ethyl]amino}methyl)-3-thienyl]-1H-indole-7-carboxamide;

3-[1-(ethylsulfonyl)-4-piperidinyl]-5-(5-{[(2-furanylmethyl)(methyl)amino]methyl}-3-thienyl)-1H-indole-7-carboxamide;

3-[1-(ethylsulfonyl)-4-piperidinyl]-5-(5-{[methyl(4-pyridinylmethyl)amino]methyl}-3-thienyl)-1H-indole-7-carboxamide;

3-[1-(ethylsulfonyl)-4-piperidinyl]-5-{5-[(methyl{[1-(1-methylethyl)-3-pyrrolidinyl]methyl}amino)methyl]-3-thienyl}-1H-indole-7-carboxamide;

3-[1-(ethylsulfonyl)-4-piperidinyl]-5-(5-{[methyl(2-thienylmethyl)amino]methyl}-3-thienyl)-1H-indole-7-carboxamide;

3-[1-(ethylsulfonyl)-4-piperidinyl]-5-[5-({methyl[1-(2-thienyl)ethyl]amino}methyl)-3-thienyl]-1H-indole-7-carboxamide;

3-[1-(ethylsulfonyl)-4-piperidinyl]-5-(5-{[methyl(3-thienylmethyl)amino]methyl}-3-thienyl)-1H-indole-7-carboxamide;

3-[1-(ethylsulfonyl)-4-piperidinyl]-5-(5-{[methyl(tetrahydro-2H-pyran-4-ylmethyl)amino]methyl}-3-thienyl)-1H-indole-7-carboxamide; trifluoroacetate 3-[1-(ethylsulfonyl)-4-piperidinyl]-5-(5-{[methyl(3-pyridinylmethyl)amino]methyl}-3-thienyl)-1H-indole-7-carboxamide; trifluoroacetate 3-[1-(ethylsulfonyl)-4-piperidinyl]-5-(5-{[methyl(4-pyrimidinylmethyl)amino]methyl}-3-thienyl)-1H-indole-7-carboxamide;

3-[1-(ethylsulfonyl)-4-piperidinyl]-5-[5-({methyl[2-(methyloxy)ethyl]amino}methyl)-3-thienyl]-1H-indole-7-carboxamide;

5-{3-[(dimethylamino)methyl]phenyl}-3-[1-(ethylsulfonyl)-4-piperidinyl]-1H-indole-7-carboxamide;

3-[1-(ethylsulfonyl)-4-piperidinyl]-5-(5-{[methyl(1-methylethyl)amino]methyl}-3-thienyl)-1H-indole-7-carboxamide;

3-[1-(ethylsulfonyl)-4-piperidinyl]-5-{5-[(2-propyl-1-pyrrolidinyl)methyl]-3-thienyl}-1H-indole-7-carboxamide;

3-[1-(ethylsulfonyl)-4-piperidinyl]-5-(5-{[2-(3-pyridinyl)-1-pyrrolidinyl]methyl}-3-thienyl)-1H-indole-7-carboxamide;

5-(5-{[2-(1,1-dimethylethyl)-1-pyrrolidinyl]methyl}-3-thienyl)-3-[1-(ethylsulfonyl)-4-piperidinyl]-1H-indole-7-carboxamide;

5-{5-[(2-ethyl-1-pyrrolidinyl)methyl]-3-thienyl}-3-[1-(ethylsulfonyl)-4-piperidinyl]-1H-indole-7-carboxamide;

3-[1-(ethylsulfonyl)-4-piperidinyl]-5-(5-{[2-(2-methylpropyl)-1-pyrrolidinyl]methyl}-3-thienyl)-1H-indole-7-carboxamide;

3-[1-(ethylsulfonyl)-4-piperidinyl]-5-(5-{[2-(1-methylethyl)-1-pyrrolidinyl]methyl}-3-thienyl)-1H-indole-7-carboxamide;

3-[1-(ethylsulfonyl)-4-piperidinyl]-5-[5-({(2S)-2-[(methyloxy)methyl]-1-pyrrolidinyl}methyl)-3-thienyl]-1H-indole-7-carboxamide;

5-(5-{[cyclohexyl(methyl)amino]methyl}-3-thienyl)-3-[1-(ethylsulfonyl)-4-piperidinyl]-1H-indole-7-carboxamide;

3-[1-(ethylsulfonyl)-4-piperidinyl]-5-(5-{[2-(2-methylpropyl)-1-pyrrolidinyl]methyl}-3-thienyl)-1H-indole-7-carboxamide;

5-(5-{[ethyl(methyl)amino]methyl}-3-thienyl)-3-[1-(ethylsulfonyl)-4-piperidinyl]-1H-indole-7-carboxamide;

3-[1-(ethylsulfonyl)-4-piperidinyl]-5-(5-{[methyl(propyl)amino]methyl}-3-thienyl)-1H-indole-7-carboxamide;

3-{1-[(1-methylethyl)sulfonyl]-4-piperidinyl}-5-(5-{[methyl(propyl)amino]methyl}-3-thienyl)-1H-indole-7-carboxamide;

5-(5-{[ethyl(methyl)amino]methyl}-3-thienyl)-3-{1-[(1-methylethyl)sulfonyl]-4-piperidinyl}-1H-indole-7-carboxamide;

3-{1-[(1-methylethyl)sulfonyl]-4-piperidinyl}-5-[5-({methyl[2-(methyloxy)ethyl]amino}methyl)-3-thienyl]-1H-indole-7-carboxamide;

3-[1-(ethylsulfonyl)-4-piperidinyl]-5-{5-[(methylamino)methyl]-2-thienyl}-1H-indole-7-carboxamide;

3-[1-(ethylsulfonyl)-4-piperidinyl]-5-{5-[(2-methyl-1-pyrrolidinyl)methyl]-3-thienyl}-1H-indole-7-carboxamide;

3-[1-(ethylsulfonyl)-4-piperidinyl]-5-(5-{[(2-methylpropyl)amino]methyl}-3-thienyl)-1H-indole-7-carboxamide;

3-[1-(ethylsulfonyl)-4-piperidinyl]-5-{-5-[(propylamino)methyl]-3-thienyl}-1H-indole-7-carboxamide;

5-{5-[(diethylamino)methyl]-3-thienyl}-3-[1-(ethylsulfonyl)-4-piperidinyl]-1H-indole-7-carboxamide;

5-(5-{[(2R,5R)-2,5-dimethyl-1-pyrrolidinyl]methyl}-3-thienyl)-3-[1-(ethylsulfonyl)-4-piperidinyl]-1H-indole-7-carboxamide;

5-{5-[(cyclopropylamino)methyl]-3-thienyl}-3-[1-(ethylsulfonyl)-4-piperidinyl]-1H-indole-7-carboxamide;

5-{5-[(cyclobutylamino)methyl]-3-thienyl}-3-[1-(ethylsulfonyl)-4-piperidinyl]-1H-indole-7-carboxamide;

5-{5-[(dimethylamino)methyl]-3-thienyl}-3-[1-(ethylsulfonyl)-4-piperidinyl]-1H-indole-7-carboxamide;

5-(5-{[(cyclopentylmethyl)amino]methyl}-3-thienyl)-3-[1-(ethylsulfonyl)-4-piperidinyl]-1H-indole-7-carboxamide;

5-[5-({[(1R)-1,2-dimethylpropyl]amino}methyl)-3-thienyl]-3-[1-(ethylsulfonyl)-4-piperidinyl]-1H-indole-7-carboxamide;

5-{5-[(cyclopentylamino)methyl]-3-thienyl}-3-[1-(ethylsulfonyl)-4-piperidinyl]-1H-indole-7-carboxamide;

5-(5-{[(cyclopropylmethyl)amino]methyl}-3-thienyl)-3-[1-(ethylsulfonyl)-4-piperidinyl]-1H-indole-7-carboxamide;

5-[5-({[(1S)-1,2-dimethylpropyl]amino}methyl)-3-thienyl]-3-[1-(ethylsulfonyl)-4-piperidinyl]-1H-indole-7-carboxamide;
5-(5-{[(2,2-dimethylpropyl)amino]methyl}-3-thienyl)-3-[1-(ethylsulfonyl)-4-piperidinyl]-1H-indole-7-carboxamide;
3-[1-(ethylsulfonyl)-4-piperidinyl]-5-(5-{[(phenylmethyl)amino]methyl}-3-thienyl)-1H-indole-7-carboxamide;
3-[1-(ethylsulfonyl)-4-piperidinyl]-5-[5-({[(2S)-tetrahydro-2-furanylmethyl]amino}methyl)-3-thienyl]-1H-indole-7-carboxamide;
3-[1-(ethylsulfonyl)-4-piperidinyl]-5-(5-{[(tetrahydro-2H-pyran-4-ylmethyl)amino]methyl}-3-thienyl)-1H-indole-7-carboxamide;
5-{5-[(butylamino)methyl]-3-thienyl}-3-[1-(ethylsulfonyl)-4-piperidinyl]-1H-indole-7-carboxamide;
3-[1-(ethylsulfonyl)-4-piperidinyl]-5-[5-({[(2R)-tetrahydro-2-furanylmethyl]amino}methyl)-3-thienyl]-1H-indole-7-carboxamide;
3-[1-(ethylsulfonyl)-4-piperidinyl]-5-[5-({(2S)-2-[(methyloxy)methyl]-1-pyrrolidinyl}methyl)-3-thienyl]-1H-indole-7-carboxamide;
3-[1-(ethylsulfonyl)-4-piperidinyl]-5-[5-({(2R)-2-[(methyloxy)methyl]-1-pyrrolidinyl}methyl)-3-thienyl]-1H-indole-7-carboxamide;
3-[1-(ethylsulfonyl)-4-piperidinyl]-5-{4-[2-(methylamino)ethyl]phenyl}-1H-indole-7-carboxamide;
3-[1-(ethylsulfonyl)-4-piperidinyl]-5-{4-[2-(propylamino)ethyl]phenyl}-1H-indole-7-carboxamide;
5-{4-[2-(ethylamino)ethyl]phenyl}-3-[1-(ethylsulfonyl)-4-piperidinyl]-1H-indole-7-carboxamide;
5-{4-[({[1-(1,1-dimethylethyl)-3-methyl-1H-pyrazol-5-yl]carbonyl}amino)methyl]phenyl}-3-[1-(ethylsulfonyl)-4-piperidinyl]-1H-indole-7-carboxamide;
3-[1-(ethylsulfonyl)-4-piperidinyl]-5-(4-{[(4-pyridinylcarbonyl)amino]methyl}phenyl)-1H-indole-7-carboxamide;
5-(4-{[(cyclopentylcarbonyl)amino]methyl}phenyl)-3-[1-(ethylsulfonyl)-4-piperidinyl]-1H-indole-7-carboxamide;
3-[1-(ethylsulfonyl)-4-piperidinyl]-5-(4-{[(2-furanylcarbonyl)amino]methyl}phenyl)-1H-indole-7-carboxamide;
5-{4-[2-(acetylamino)ethyl]phenyl}-3-[1-(ethylsulfonyl)-4-piperidinyl]-1H-indole-7-carboxamide;
3-[1-(ethylsulfonyl)-4-piperidinyl]-5-(4-{2-[(methylsulfonyl)amino]ethyl}phenyl)-1H-indole-7-carboxamide;
5-(4-{2-[(cyclobutylcarbonyl)amino]ethyl}phenyl)-3-[1-(ethylsulfonyl)-4-piperidinyl]-1H-indole-7-carboxamide;
5-(4-{2-[(cyclohexylcarbonyl)amino]ethyl}phenyl)-3-[1-(ethylsulfonyl)-4-piperidinyl]-1H-indole-7-carboxamide;
3-[1-(ethylsulfonyl)-4-piperidinyl]-5-(3-{2-[(methylsulfonyl)amino]ethyl}phenyl)-1H-indole-7-carboxamide;
5-(3-{2-[(cyclohexylcarbonyl)amino]ethyl}phenyl)-3-[1-(ethylsulfonyl)-4-piperidinyl]-1H-indole-7-carboxamide;
3-[1-(ethylsulfonyl)-4-piperidinyl]-5-[6-(1-piperazinyl)-3-pyridinyl]-1H-indole-7-carboxamide trifluoroacetate;
5-[6-(4-ethyl-1-piperazinyl)-3-pyridinyl]-3-[1-(ethylsulfonyl)-4-piperidinyl]-1H-indole-7-carboxamide;
3-[1-(ethylsulfonyl)-4-piperidinyl]-5-[4-(1-piperidinylmethyl)phenyl]-1H-indole-7-carboxamide;
3-[1-(ethylsulfonyl)-4-piperidinyl]-5-[3-(1-piperidinylmethyl)phenyl]-1H-indole-7-carboxamide;
3-[1-(ethylsulfonyl)-4-piperidinyl]-5-{4-[(methylamino)methyl]phenyl}-1H-indole-7-carboxamide;
3-[1-(ethylsulfonyl)-4-piperidinyl]-5-(4-{[(1-methylethyl)amino]methyl}phenyl)-1H-indole-7-carboxamide;
3-[1-(ethylsulfonyl)-4-piperidinyl]-5-{4-[(propylamino)methyl]phenyl}-1H-indole-7-carboxamide;
5-(4-{[(1-ethylpropyl)amino]methyl}phenyl)-3-[1-(ethylsulfonyl)-4-piperidinyl]-1H-indole-7-carboxamide;
5-{4-[(cyclopentylamino)methyl]phenyl}-3-[1-(ethylsulfonyl)-4-piperidinyl]-1H-indole-7-carboxamide;
5-{4-[(cyclobutylamino)methyl]phenyl}-3-[1-(ethylsulfonyl)-4-piperidinyl]-1H-indole-7-carboxamide;
5-{4-[(ethylamino)methyl]phenyl}-3-[1-(ethylsulfonyl)-4-piperidinyl]-1H-indole-7-carboxamide;
5-{4-[(dimethylamino)methyl]phenyl}-3-[1-(ethylsulfonyl)-4-piperidinyl]-1H-indole-7-carboxamide;
5-{4-[(diethylamino)methyl]phenyl}-3-[1-(ethylsulfonyl)-4-piperidinyl]-1H-indole-7-carboxamide;
3-[1-(ethylsulfonyl)-4-piperidinyl]-5-[4-(4-morpholinylmethyl)phenyl]-1H-indole-7-carboxamide;
3-[1-(ethylsulfonyl)-4-piperidinyl]-5-[4-(1-pyrrolidinylmethyl)phenyl]-1H-indole-7-carboxamide;
3-[1-(ethylsulfonyl)-4-piperidinyl]-5-[4-({[(1S)-2-hydroxy-1-methylethyl]amino}methyl)phenyl]-1H-indole-7-carboxamide;
3-[1-(ethylsulfonyl)-4-piperidinyl]-5-[4-({[(1R)-2-hydroxy-1-methylethyl]amino}methyl)phenyl]-1H-indole-7-carboxamide;
3-[1-(ethylsulfonyl)-4-piperidinyl]-5-[4-({[(2R)-2-hydroxypropyl]amino}methyl)phenyl]-1H-indole-7-carboxamide;
3-[1-(ethylsulfonyl)-4-piperidinyl]-5-[4-({[2-hydroxy-1-(hydroxymethyl)ethyl]amino}methyl)phenyl]-1H-indole-7-carboxamide;
3-[1-(ethylsulfonyl)-4-piperidinyl]-5-(3-{[(1-methylbutyl)amino]methyl}phenyl)-1H-indole-7-carboxamide;
3-[1-(ethylsulfonyl)-4-piperidinyl]-5-[3-({[(1R)-1-methylpropyl]amino}methyl)phenyl]-1H-indole-7-carboxamide;
3-[1-(ethylsulfonyl)-4-piperidinyl]-5-(3-{[(2-methylpropyl)amino]methyl}phenyl)-1H-indole-7-carboxamide;
3-[1-(ethylsulfonyl)-4-piperidinyl]-5-[3-({[(1S)-1-methylpropyl]amino}methyl)phenyl]-1H-indole-7-carboxamide;
5-{4-[(acetylamino)methyl]phenyl}-3-[1-(ethylsulfonyl)-4-piperidinyl]-1H-indole-7-carboxamide;
3-[1-(ethylsulfonyl)-4-piperidinyl]-5-{4-[(propanoylamino)methyl]phenyl}-1H-indole-7-carboxamide;
5-(4-{[(cyclopropylcarbonyl)amino]methyl}phenyl)-3-[1-(ethylsulfonyl)-4-piperidinyl]-1H-indole-7-carboxamide;
5-(4-{[(cyclobutylcarbonyl)amino]methyl}phenyl)-3-[1-(ethylsulfonyl)-4-piperidinyl]-1H-indole-7-carboxamide;
3-[1-(ethylsulfonyl)-4-piperidinyl]-5-(4-{[(2-thienylacetyl)amino]methyl}phenyl)-1H-indole-7-carboxamide;
5-[4-({[(1S)-1,2-dimethylpropyl]amino}methyl)phenyl]-3-[1-(ethylsulfonyl)-4-piperidinyl]-1H-indole-7-carboxamide;
5-{4-[(butanoylamino)methyl]phenyl}-3-[1-(ethylsulfonyl)-4-piperidinyl]-1H-indole-7-carboxamide;
3-[1-(ethylsulfonyl)-4-piperidinyl]-5-(4-{[(2-methylpropanoyl)amino]methyl}phenyl)-1H-indole-7-carboxamide
3-[1-(ethylsulfonyl)-4-piperidinyl]-5-(4-{[(3-methylbutanoyl)amino]methyl}phenyl)-1H-indole-7-carboxamide;
3-[1-(ethylsulfonyl)-4-piperidinyl]-5-(4-{[(methylsulfonyl)amino]methyl}phenyl)-1H-indole-7-carboxamide;
5-[3-({[(1R)-1,2-dimethylpropyl]amino}methyl)phenyl]-3-[1-(ethylsulfonyl)-4-piperidinyl]-1H-indole-7-carboxamide;
5-(4-{[(ethylsulfonyl)amino]methyl}phenyl)-3-[1-(ethylsulfonyl)-4-piperidinyl]-1H-indole-7-carboxamide;
5-(4-{[(butylsulfonyl)amino]methyl}phenyl)-3-[1-(ethylsulfonyl)-4-piperidinyl]-1H-indole-7-carboxamide;
3-[1-(ethylsulfonyl)-4-piperidinyl]-5-[4-({[(1-methylethyl)sulfonyl]amino}methyl)phenyl]-1H-indole-7-carboxamide;

5-(6-amino-2-pyridinyl)-3-[1-(ethylsulfonyl)-4-piperidinyl]-1H-indole-7-carboxamide;
3-[1-(ethylsulfonyl)-4-piperidinyl]-5-[3-(1H-pyrazol-1-yl)phenyl]-1H-indole-7-carboxamide;
5-[4-(dimethylamino)phenyl-3-[1-(ethylsulfonyl)-4-piperidinyl]-1H-indole-7-carboxamide;
5-(3-aminophenyl)-3-[1-(ethylsulfonyl)-4-piperidinyl]-1H-indole-7-carboxamide;
3-[1-(ethylsulfonyl)-4-piperidinyl]-5-{5-[(2-methyl-1-pyrrolidinyl)methyl]-2-thienyl}-1H-indole-7-carboxamide;
5-{5-[(ethylamino)methyl]-2-thienyl}-3-[1-(ethylsulfonyl)-4-piperidinyl]-1H-indole-7-carboxamide;
3-[1-(ethylsulfonyl)-4-piperidinyl]-5-(5-{[(1-methylethyl)amino]methyl}-2-thienyl)-1H-indole-7-carboxamide;
5-{5-[(cyclopropylamino)methyl]-2-thienyl}-3-[1-(ethylsulfonyl)-4-piperidinyl]-1H-indole-7-carboxamide;
5-(5-{[(2,2-dimethylpropyl)amino]methyl}-2-thienyl)-3-[1-(ethylsulfonyl)-4-piperidinyl]-1H-indole-7-carboxamide;
5-(5-{[(cyclopropylmethyl)amino]methyl}-2-thienyl)-3-[1-(ethylsulfonyl)-4-piperidinyl]-1H-indole-7-carboxamide;
5-(5-{[(cyclopropylmethyl)amino]methyl}-3-pyridinyl)-3-[1-(ethylsulfonyl)-4-piperidinyl]-1H-indole-7-carboxamide;
3-[1-(ethylsulfonyl)-4-piperidinyl]-5-[5-({[2-(methyloxy)ethyl]amino}methyl)-3-pyridinyl]-1H-indole-7-carboxamide;
3-[1-(ethylsulfonyl)-4-piperidinyl]-5-[5-({[3-(methyloxy)propyl]amino}methyl)-3-pyridinyl]-1H-indole-7-carboxamide;
3-[1-(ethylsulfonyl)-4-piperidinyl]-5-[5-(4-morpholinylmethyl)-3-pyridinyl]-1H-indole-7-carboxamide;
5-{5-[(ethylamino)methyl]-3-pyridinyl}-3-[1-(ethylsulfonyl)-4-piperidinyl]-1H-indole-7-carboxamide;
5-{5-[(dimethylamino)methyl]-3-pyridinyl}-3-[1-(ethylsulfonyl)-4-piperidinyl]-1H-indole-7-carboxamide;
3-[1-(ethylsulfonyl)-4-piperidinyl]-5-{5-[(2-methyl-1-pyrrolidinyl)methyl]-3-pyridinyl}-1H-indole-7-carboxamide;
3-[1-(ethylsulfonyl)-4-piperidinyl]-5-(5-{[(2-methylpropyl)amino]methyl}-3-pyridinyl)-1H-indole-7-carboxamide;
5-(5-{[(2,2-dimethylpropyl)amino]methyl}-3-pyridinyl)-3-[1-(ethylsulfonyl)-4-piperidinyl]-1H-indole-7-carboxamide;
3-[1-(ethylsulfonyl)-4-piperidinyl]-5-(5-{[(2-methylbutyl)amino]methyl}-2-thienyl)-1H-indole-7-carboxamide;
5-[5-({[(1R)-1,2-dimethylpropyl]amino}methyl)-2-thienyl]-3-[1-(ethylsulfonyl)-4-piperidinyl]-1H-indole-7-carboxamide;
3-[1-(ethylsulfonyl)-4-piperidinyl]-5-{5-[(pentylamino)methyl]-2-thienyl}-1H-indole-7-carboxamide;
3-[1-(ethylsulfonyl)-4-piperidinyl]-5-[5-({[(2S)-2-methylbutyl]amino}methyl)-2-thienyl]-1H-indole-7-carboxamide;
3-[1-(ethylsulfonyl)-4-piperidinyl]-5-(5-{[(1-methylbutyl)amino]methyl}-2-thienyl)-1H-indole-7-carboxamide;
5-{5-[(butylamino)methyl]-2-thienyl}-3-[1-(ethylsulfonyl)-4-piperidinyl]-1H-indole-7-carboxamide;
3-[1-(ethylsulfonyl)-4-piperidinyl]-5-[5-({[2-(methyloxy)ethyl]amino}methyl)-2-thienyl]-1H-indole-7-carboxamide;
5-{5-[(cyclopentylamino)methyl]-2-thienyl}-3-[1-(ethylsulfonyl)-4-piperidinyl]-1H-indole-7-carboxamide;
3-[1-(ethylsulfonyl)-4-piperidinyl]-5-(5-{[(3-methylbutyl)amino]methyl}-2-thienyl)-1H-indole-7-carboxamide;
3-[1-(ethylsulfonyl)-4-piperidinyl]-5-(5-{[(1-methylethyl)amino]methyl}-3-pyridinyl)-1H-indole-7-carboxamide;
5-(5-{[(2-ethylbutyl)amino]methyl}-2-thienyl)-3-[1-(ethylsulfonyl)-4-piperidinyl]-1H-indole-7-carboxamide;
5-[5-({[3-(ethyloxy)propyl]amino}methyl)-2-thienyl]-3-[1-(ethylsulfonyl)-4-piperidinyl]-1H-indole-7-carboxamide;
3-[1-(ethylsulfonyl)-4-piperidinyl]-5-[5-({[3-(methyloxy)propyl]amino}methyl)-2-thienyl]-1H-indole-7-carboxamide;
5-(5-{[(cyclohexylmethyl)amino]methyl}-2-thienyl)-3-[1-(ethylsulfonyl)-4-piperidinyl]-1H-indole-7-carboxamide;
3-[1-(ethylsulfonyl)-4-piperidinyl]-5-{5-[({3-[(1-methylethyl)oxy]propyl}amino)methyl]-2-thienyl}-1H-indole-7-carboxamide;
5-[5-({[2-(ethyloxy)ethyl]amino}methyl)-2-thienyl]-3-[1-(ethylsulfonyl)-4-piperidinyl]-1H-indole-7-carboxamide;
3-[1-(ethylsulfonyl)-4-piperidinyl]-5-[5-({[3-(propyloxy)propyl]amino}methyl)-2-thienyl]-1H-indole-7-carboxamide;
5-(5-{[(3,3-dimethylbutyl)amino]methyl}-2-thienyl)-3-[1-(ethylsulfonyl)-4-piperidinyl]-1H-indole-7-carboxamide;
3-[1-(ethylsulfonyl)-4-piperidinyl]-5-[5-({[(1S)-1,2,2-trimethylpropyl]amino}methyl)-2-thienyl]-1H-indole-7-carboxamide;
3-[1-(ethylsulfonyl)-4-piperidinyl]-5-{5-[(hexylamino)methyl]-2-thienyl}-1H-indole-7-carboxamide;
3-[1-(ethylsulfonyl)-4-piperidinyl]-5-{4-[(methylsulfonyl)amino]phenyl}-1H-indole-7-carboxamide;
5-[2-(dimethylamino)-4-pyridinyl]-3-[1-(ethylsulfonyl)-4-piperidinyl]-1H-indole-7-carboxamide;
3-[1-(ethylsulfonyl)-4-piperidinyl]-5-[2-(1-pyrrolidinyl)-4-pyridinyl]-1H-indole-7-carboxamide;
3-[1-(ethylsulfonyl)-4-piperidinyl]-5-[2-(4-morpholinyl)-4-pyridinyl]-1H-indole-7-carboxamide;
3-[1-(ethylsulfonyl)-4-piperidinyl]-5-{2-[(2-methylpropyl)amino]-4-pyridinyl}-1H-indole-7-carboxamide;
5-{2-[(2,2-dimethylpropyl)amino]-4-pyridinyl}-3-[1-(ethylsulfonyl)-4-piperidinyl]-1H-indole-7-carboxamide;
3-[1-(ethylsulfonyl)-4-piperidinyl]-5-[2-(propylamino)-4-pyridinyl]-1H-indole-7-carboxamide;
3-[1-(ethylsulfonyl)-4-piperidinyl]-5-{4-[(methylamino)methyl]-2-thienyl}-1H-indole-7-carboxamide;
3-[1-(ethylsulfonyl)-4-piperidinyl]-5-[4-(1-pyrrolidinylmethyl)-2-thienyl]-1H-indole-7-carboxamide;
3-[1-(ethylsulfonyl)-4-piperidinyl]-5-(4-{[(2-methylpropyl)amino]methyl}-2-thienyl)-1H-indole-7-carboxamide;
5-{4-[(dimethylamino)methyl]-2-thienyl}-3-[1-(ethylsulfonyl)-4-piperidinyl]-1H-indole-7-carboxamide;
3-[1-(ethylsulfonyl)-4-piperidinyl]-5-{5-[(1S)-1-(1-pyrrolidinyl)ethyl]-3-thienyl}-1H-indole-7-carboxamide;
3-[1-(ethylsulfonyl)-4-piperidinyl]-5-{5-[(1R)-1-(1-pyrrolidinyl)ethyl]-3-thienyl}-1H-indole-7-carboxamide;
3-[1-(ethylsulfonyl)-4-piperidinyl]-5-[4-({[3-(methyloxy)propyl]amino}methyl)-2-thienyl]-1H-indole-7-carboxamide;
3-[1-(ethylsulfonyl)-4-piperidinyl]-5-[4-({(2S)-2-[(methyloxy)methyl]-1-pyrrolidinyl}methyl)-2-thienyl]-1H-indole-7-carboxamide;
5-(4-{[(2R,5R)-2,5-dimethyl-1-pyrrolidinyl]methyl}-2-thienyl)-3-[1-(ethylsulfonyl)-4-piperidinyl]-1H-indole-7-carboxamide;
3-[1-(ethylsulfonyl)-4-piperidinyl]-5-(5-{[(2S)-2-methyl-1-pyrrolidinyl]methyl}-3-thienyl)-1H-indole-7-carboxamide;
3-[1-(ethylsulfonyl)-4-piperidinyl]-5-(5-{[(2R)-2-methyl-1-pyrrolidinyl]methyl}-3-thienyl)-1H-indole-7-carboxamide;
3-[1-(ethylsulfonyl)-4-piperidinyl]-5-{5-[1-(1-pyrrolidinyl)propyl]-3-thienyl}-1H-indole-7-carboxamide;

5-{5-[(dimethylamino)methyl]-3-thienyl}-3-{1-[(1-methylethyl)sulfonyl]-4-piperidinyl}-1H-indole-7-carboxamide;
5-[5-(aminomethyl)-3-thienyl]-3-[1-(ethylsulfonyl)-4-piperidinyl]-1H-indole-7-carboxamide;
3-[1-(ethylsulfonyl)-4-piperidinyl]-5-(5-{2-[(2-methylpropyl)amino]ethyl}-3-thienyl)-1H-indole-7-carboxamide;
5-{5-[2-(dimethylamino)ethyl]-3-thienyl}-3-[1-(ethylsulfonyl)-4-piperidinyl]-1H-indole-7-carboxamide;
3-[1-(ethylsulfonyl)-4-piperidinyl]-5-[6-(1-pyrrolidinyl)-3-pyridinyl]-1H-indole-7-carboxamide;
5-{6-[ethyl(methyl)amino]-3-pyridinyl}-3-[1-(ethylsulfonyl)-4-piperidinyl]-1H-indole-7-carboxamide;
5-[6-(dimethylamino)-3-pyridinyl]-3-[1-(ethylsulfonyl)-4-piperidinyl]-1H-indole-7-carboxamide;
3-[1-(ethylsulfonyl)-4-piperidinyl]-5-[6-(propylamino)-3-pyridinyl]-1H-indole-7-carboxamide;
3-[1-(ethylsulfonyl)-4-piperidinyl]-5-{6-[(1-methylethyl)amino]-3-pyridinyl}-1H-indole-7-carboxamide;
3-[1-(ethylsulfonyl)-4-piperidinyl]-5-[6-(4-morpholinyl)-3-pyridinyl]-1H-indole-7-carboxamide;
3-[1-(ethylsulfonyl)-4-piperidinyl]-5-{5-[(methylamino)methyl]-3-thienyl}-1H-indole-7-carboxamide;
3-[1-(ethylsulfonyl)-4-piperidinyl]-5-(5-{[(1-methylethyl)amino]methyl}-3-thienyl)-1H-indole-7-carboxamide;
3-[1-(ethylsulfonyl)-4-piperidinyl]-5-[5-(1-pyrrolidinylmethyl)-3-thienyl]-1H-indole-7-carboxamide;
5-{5-[(ethylamino)methyl]-3-thienyl}-3-[1-(ethylsulfonyl)-4-piperidinyl]-1H-indole-7-carboxamide;
3-[1-(ethylsulfonyl)-4-piperidinyl]-5-[5-({[(1R)-2-hydroxy-1-methylethyl]amino}methyl)-3-thienyl]-1H-indole-7-carboxamide;
3-[1-(ethylsulfonyl)-4-piperidinyl]-5-[5-(1-piperidinylmethyl)-3-thienyl]-1H-indole-7-carboxamide;
3-[1-(ethylsulfonyl)-4-piperidinyl]-5-[5-(4-morpholinylmethyl)-3-thienyl]-1H-indole-7-carboxamide;
3-[1-(ethylsulfonyl)-4-piperidinyl]-5-{5-[(methylamino)methyl]-3-furanyl}-1H-indole-7-carboxamide;
3-[1-(ethylsulfonyl)-4-piperidinyl]-5-{5-[1-(1-pyrrolidinyl)ethyl]-3-thienyl}-1H-indole-7-carboxamide;
3-[1-(ethylsulfonyl)-4-piperidinyl]-5-[5-(1-pyrrolidinylmethyl)-2-thienyl]-1H-indole-7-carboxamide;
5-{5-[(dimethylamino)methyl]-2-thienyl}-3-[1-(ethylsulfonyl)-4-piperidinyl]-1H-indole-7-carboxamide;
3-[1-(ethylsulfonyl)-4-piperidinyl]-5-{5-[(propylamino)methyl]-2-thienyl}-1H-indole-7-carboxamide;
5-{5-[(diethylamino)methyl]-2-thienyl}-3-[1-(ethylsulfonyl)-4-piperidinyl]-1H-indole-7-carboxamide;
3-[1-(ethylsulfonyl)-4-piperidinyl]-5-(5-{[(2-methylpropyl)amino]methyl}-2-thienyl)-1H-indole-7-carboxamide;
5-(5-{[(2,2-dimethylpropyl)amino]methyl}-3-furanyl)-3-[1-(ethylsulfonyl)-4-piperidinyl]-1H-indole-7-carboxamide;
3-[1-(ethylsulfonyl)-4-piperidinyl]-5-(5-{[(2-methylpropyl)amino]methyl}-3-furanyl)-1H-indole-7-carboxamide;
5-(5-{[(cyclopentylmethyl)amino]methyl}-3-furanyl)-3-[1-(ethylsulfonyl)-4-piperidinyl]-1H-indole-7-carboxamide;
3-[1-(ethylsulfonyl)-4-piperidinyl]-5-[5-(1-pyrrolidinylmethyl)-3-furanyl]-1H-indole-7-carboxamide;
5-{5-[(diethylamino)methyl]-3-furanyl}-3-[1-(ethylsulfonyl)-4-piperidinyl]-1H-indole-7-carboxamide;
3-[1-(ethylsulfonyl)-4-piperidinyl]-5-[5-(1-pyrrolidinylmethyl)-1,3-thiazol-2-yl]-1H-indole-7-carboxamide;
3-[1-(ethylsulfonyl)-4-piperidinyl]-5-{5-[2-methyl-1-(1-pyrrolidinyl)propyl]-3-thienyl}-1H-indole-7-carboxamide;
3-[1-(ethylsulfonyl)-4-piperidinyl]-5-[4-(1-pyrrolidinylmethyl)-1,3-thiazol-2-yl]-1H-indole-7-carboxamide;
5-{1-[2-(dimethylamino)ethyl]-1H-pyrazol-4-yl}-3-[1-(ethylsulfonyl)-4-piperidinyl]-1H-indole-7-carboxamide;
3-[1-(ethylsulfonyl)-4-piperidinyl]-5-{1-[2-(1-pyrrolidinyl)ethyl]-1H-pyrazol-4-yl}-1H-indole-7-carboxamide;
3-[1-(ethylsulfonyl)-4-piperidinyl]-5-{1-[2-(4-morpholinyl)ethyl]-1H-pyrazol-4-yl}-1H-indole-7-carboxamide;
3-[1-(ethylsulfonyl)-4-piperidinyl]-5-(1-{2-[(2-hydroxyethyl)amino]ethyl}-1H-pyrazol-4-yl)-1H-indole-7-carboxamide;
5-{1-[2-(butylamino)ethyl]-1H-pyrazol-4-yl}-3-[1-(ethylsulfonyl)-4-piperidinyl]-1H-indole-7-carboxamide;
5-{1-[2-(cyclobutylamino)ethyl]-1H-pyrazol-4-yl}-3-[1-(ethylsulfonyl)-4-piperidinyl]-1H-indole-7-carboxamide;
5-[1-(2-{[2-(diethylamino)ethyl]amino}ethyl)-1H-pyrazol-4-yl]-3-[1-(ethylsulfonyl)-4-piperidinyl]-1H-indole-7-carboxamide;
3-[1-(ethylsulfonyl)-4-piperidinyl]-5-(1-{2-[(1-methylethyl)amino]ethyl}-1H-pyrazol-4-yl)-1H-indole-7-carboxamide;
3-[1-(ethylsulfonyl)-4-piperidinyl]-5-(1-{2-[(2-methylpropyl)amino]ethyl}-1H-pyrazol-4-yl)-1H-indole-7-carboxamide;
5-(1-{2-[(cyclopentylmethyl)amino]ethyl}-1H-pyrazol-4-yl)-3-[1-(ethylsulfonyl)-4-piperidinyl]-1H-indole-7-carboxamide;
3-[1-(ethylsulfonyl)-4-piperidinyl]-5-[4-(methyloxy)-3-(1-pyrrolidinylmethyl)phenyl]-1H-indole-7-carboxamide;
5-[3-[(dimethylamino)methyl]-4-(methyloxy)phenyl]-3-[1-(ethylsulfonyl)-4-piperidinyl]-1H-indole-7-carboxamide;
3-[1-(ethylsulfonyl)-4-piperidinyl]-5-[4-(methyloxy)-3-(4-morpholinylmethyl)phenyl]-1H-indole-7-carboxamide;
3-[1-(ethylsulfonyl)-4-piperidinyl]-5-[3-{[(1-methylethyl)amino]methyl}-4-(methyloxy)phenyl]-1H-indole-7-carboxamide;
3-[1-(ethylsulfonyl)-4-piperidinyl]-5-[3-[(methylamino)methyl]-4-(methyloxy)phenyl]-1H-indole-7-carboxamide;
5-[3-{[(2,2-dimethylpropyl)amino]methyl}-4-(methyloxy)phenyl]-3-[1-(ethylsulfonyl)-4-piperidinyl]-1H-indole-7-carboxamide;
3-[1-(ethylsulfonyl)-4-piperidinyl]-5-(1-{2-[(2-hydroxyethyl)(methyl)amino]ethyl}-1H-pyrazol-4-yl)-1H-indole-7-carboxamide;
3-[1-(ethylsulfonyl)-4-piperidinyl]-5-{4-fluoro-3-[(methylamino)methyl]phenyl}-1H-indole-7-carboxamide;
5-{3,5-bis[(methylamino)methyl]phenyl}-3-[1-(ethylsulfonyl)-4-piperidinyl]-1H-indole-7-carboxamide;
5-{3-[(ethylamino)methyl]-4-fluorophenyl}-3-[1-(ethylsulfonyl)-4-piperidinyl]-1H-indole-7-carboxamide;
3-[1-(ethylsulfonyl)-4-piperidinyl]-5-[4-fluoro-3-({[2-hydroxy-1-(hydroxymethyl)ethyl]amino}methyl)phenyl]-1H-indole-7-carboxamide;
3-[1-(ethylsulfonyl)-4-piperidinyl]-5-[4-fluoro-3-({[(1S)-2-hydroxy-1-methylethyl]amino}methyl)phenyl]-1H-indole-7-carboxamide;
5-{3-[(cyclopropylamino)methyl]-4-fluorophenyl}-3-[1-(ethylsulfonyl)-4-piperidinyl]-1H-indole-7-carboxamide;
5-{3-[(cyclobutylamino)methyl]-4-fluorophenyl}-3-[1-(ethylsulfonyl)-4-piperidinyl]-1H-indole-7-carboxamide;
3-[1-(ethylsulfonyl)-4-piperidinyl]-5-[3-(1-pyrrolidinylmethyl)phenyl]-1H-indole-7-carboxamide;
5-{3,5-bis[(ethylamino)methyl]phenyl}-3-[1-(ethylsulfonyl)-4-piperidinyl]-1H-indole-7-carboxamide;
5-{3,5-bis[(dimethylamino)methyl]phenyl}-3-[1-(ethylsulfonyl)-4-piperidinyl]-1H-indole-7-carboxamide;
3-[1-(ethylsulfonyl)-4-piperidinyl]-5-[3-(2-piperidinyl)phenyl]-1H-indole-7-carboxamide;

5-{3-[1-(ethylamino)ethyl]phenyl}-3-[1-(ethylsulfonyl)-4-piperidinyl]-1H-indole-7-carboxamide;
5-{3-[1-(dimethylamino)ethyl]phenyl}-3-[1-(ethylsulfonyl)-4-piperidinyl]-1H-indole-7-carboxamide;
3-[1-(ethylsulfonyl)-4-piperidinyl]-5-{3-fluoro-5-[(methylamino)methyl]phenyl}-1H-indole-7-carboxamide;
5-{3-[(ethylamino)methyl]-5-fluorophenyl}-3-[1-(ethylsulfonyl)-4-piperidinyl]-1H-indole-7-carboxamide;
3-[1-(ethylsulfonyl)-4-piperidinyl]-5-{3-fluoro-5-[(propylamino)methyl]phenyl}-1H-indole-7-carboxamide;
3-[1-(ethylsulfonyl)-4-piperidinyl]-5-(3-fluoro-5-{[(1-methylethyl)amino]methyl}phenyl)-1H-indole-7-carboxamide;
3-[1-(ethylsulfonyl)-4-piperidinyl]-5-(3-fluoro-5-{[(2-methylpropyl)amino]methyl}phenyl)-1H-indole-7-carboxamide;
5-{3-[(cyclobutylamino)methyl]-5-fluorophenyl}-3-[1-(ethylsulfonyl)-4-piperidinyl]-1H-indole-7-carboxamide;
5-{3-[(dimethylamino)methyl]-5-fluorophenyl}-3-[1-(ethylsulfonyl)-4-piperidinyl]-1H-indole-7-carboxamide;
3-[1-(ethylsulfonyl)-4-piperidinyl]-5-[3-fluoro-5-(1-pyrrolidinylmethyl)phenyl]-1H-indole-7-carboxamide;
3-[1-(ethylsulfonyl)-4-piperidinyl]-5-[3-fluoro-5-(4-morpholinylmethyl)phenyl]-1H-indole-7-carboxamide;
3-[1-(ethylsulfonyl)-4-piperidinyl]-5-[3-fluoro-5-(1-piperidinylmethyl)phenyl]-1H-indole-7-carboxamide;
3-[1-(ethylsulfonyl)-4-piperidinyl]-5-{3-[1-(methylamino)ethyl]phenyl}-1H-indole-7-carboxamide;
3-[1-(ethylsulfonyl)-4-piperidinyl]-5-(3-{1-[(1-methylethyl)amino]ethyl}phenyl)-1H-indole-7-carboxamide;
3-[1-(ethylsulfonyl)-4-piperidinyl]-5-(3-{1-[(2-methylpropyl)amino]ethyl}phenyl)-1H-indole-7-carboxamide;
5-{3-[1-(cyclobutylamino)ethyl]phenyl}-3-[1-(ethylsulfonyl)-4-piperidinyl]-1H-indole-7-carboxamide;
3-[1-(ethylsulfonyl)-4-piperidinyl]-5-{3-[1-(1-pyrrolidinyl)ethyl]phenyl}-1H-indole-7-carboxamide;
3-[1-(ethylsulfonyl)-4-piperidinyl]-5-[3-(3-thiomorpholinyl)phenyl]-1H-indole-7-carboxamide;
3-[1-(ethylsulfonyl)-4-piperidinyl]-5-[5-(2-piperazinyl)-2-thienyl]-1H-indole-7-carboxamide;
3-[1-(ethylsulfonyl)-4-piperidinyl]-5-[4-(2-piperazinyl)phenyl]-1H-indole-7-carboxamide;
3-[1-(ethylsulfonyl)-4-piperidinyl]-5-[3-(2-piperazinyl)phenyl]-1H-indole-7-carboxamide;
3-[1-(ethylsulfonyl)-4-piperidinyl]-5-[6-(4-morpholinyl)-3-pyridazinyl]-1H-indole-7-carboxamide;
3-[1-(ethylsulfonyl)-4-piperidinyl]-5-[6-(1-pyrrolidinyl)-3-pyridazinyl]-1H-indole-7-carboxamide;
3-[1-(ethylsulfonyl)-4-piperidinyl]-5-{2-[(methylamino)methyl]phenyl}-1H-indole-7-carboxamide;
3-[1-(ethylsulfonyl)-4-piperidinyl]-5-(3-{[(2-thienylmethyl)amino]methyl}phenyl)-1H-indole-7-carboxamide;
3-[1-(ethylsulfonyl)-4-piperidinyl]-5-[3-({[(5-methyl-2-furanyl)methyl]amino}methyl)phenyl]-1H-indole-7-carboxamide;
3-[1-(ethylsulfonyl)-4-piperidinyl]-5-[3-({[(2R)-tetrahydro-2-furanylmethyl]amino}methyl)phenyl]-1H-indole-7-carboxamide;
3-[1-(ethylsulfonyl)-4-piperidinyl]-5-[3-({[(2S)-tetrahydro-2-furanylmethyl]amino}methyl)phenyl]-1H-indole-7-carboxamide;
5-(3-{[(2,2-dimethylpropyl)amino]methyl}phenyl)-3-[1-(ethylsulfonyl)-4-piperidinyl]-1H-indole-7-carboxamide;
3-[1-(ethylsulfonyl)-4-piperidinyl]-5-(3-{[(2-methylbutyl)amino]methyl}phenyl)-1H-indole-7-carboxamide;
3-[1-(ethylsulfonyl)-4-piperidinyl]-5-[3-({[(2S)-2-methylbutyl]amino}methyl)phenyl]-1H-indole-7-carboxamide;
3-[1-(ethylsulfonyl)-4-piperidinyl]-5-[3-({[(1R)-1,2,2-trimethylpropyl]amino}methyl)phenyl]-1H-indole-7-carboxamide;
3-[1-(ethylsulfonyl)-4-piperidinyl]-5-[3-fluoro-5-({[(2S)-tetrahydro-2-furanylmethyl]amino}methyl)phenyl]-1H-indole-7-carboxamide;
3-[1-(ethylsulfonyl)-4-piperidinyl]-5-[3-fluoro-5-({[(2R)-tetrahydro-2-furanylmethyl]amino}methyl)phenyl]-1H-indole-7-carboxamide;
5-[3-({[(1S)-1,2-dimethylpropyl]amino}methyl)-5-fluorophenyl]-3-[1-(ethylsulfonyl)-4-piperidinyl]-1H-indole-7-carboxamide;
5-[3-({[(1R)-1,2-dimethylpropyl]amino}methyl)-5-fluorophenyl]-3-[1-(ethylsulfonyl)-4-piperidinyl]-1H-indole-7-carboxamide;
3-[1-(ethylsulfonyl)-4-piperidinyl]-5-(3-fluoro-5-{[(1-methylpropyl)amino]methyl}phenyl)-1H-indole-7-carboxamide;
3-[1-(ethylsulfonyl)-4-piperidinyl]-5-[3-fluoro-5-({[(1S)-1,2,2-trimethylpropyl]amino}methyl)phenyl]-1H-indole-7-carboxamide;
3-[1-(ethylsulfonyl)-4-piperidinyl]-5-[3-fluoro-5-({[(2S)-2-methylbutyl]amino}methyl)phenyl]-1H-indole-7-carboxamide;
3-[1-(ethylsulfonyl)-4-piperidinyl]-5-(3-fluoro-5-{[(2-methylbutyl)amino]methyl}phenyl)-1H-indole-7-carboxamide;
3-[1-(ethylsulfonyl)-4-piperidinyl]-5-[3-fluoro-5-({[(1R)-1,2,2-trimethylpropyl]amino}methyl)phenyl]-1H-indole-7-carboxamide;
5-(3-{[(2,2-dimethylpropyl)amino]methyl}-5-fluorophenyl)-3-[1-(ethylsulfonyl)-4-piperidinyl]-1H-indole-7-carboxamide;
5-(3-{[(cyclopropylmethyl)amino]methyl}-5-fluorophenyl)-3-[1-(ethylsulfonyl)-4-piperidinyl]-1H-indole-7-carboxamide;
5-(3-{[(cyclopentylmethyl)amino]methyl}-5-fluorophenyl)-3-[1-(ethylsulfonyl)-4-piperidinyl]-1H-indole-7-carboxamide;
3-[1-(ethylsulfonyl)-4-piperidinyl]-5-(3-fluoro-5-{[(tetrahydro-2H-pyran-4-ylmethyl)amino]methyl}phenyl)-1H-indole-7-carboxamide;
3-[1-(ethylsulfonyl)-4-piperidinyl]-5-(3-fluoro-5-{[(2-thienylmethyl)amino]methyl}phenyl)-1H-indole-7-carboxamide;
3-[1-(ethylsulfonyl)-4-piperidinyl]-5-[3-fluoro-5-({[2-(methyloxy)ethyl]amino}methyl)phenyl]-1H-indole-7-carboxamide;
3-[1-(ethylsulfonyl)-4-piperidinyl]-5-[3-fluoro-5-({[3-(methyloxy)propyl]amino}methyl)phenyl]-1H-indole-7-carboxamide;
3-[1-(ethylsulfonyl)-4-piperidinyl]-5-(3-fluoro-5-{[(2-furanylmethyl)amino]methyl}phenyl)-1H-indole-7-carboxamide;
3-[1-(ethylsulfonyl)-4-piperidinyl]-5-(3-fluoro-5-{[(3-methylbutyl)amino]methyl}phenyl)-1H-indole-7-carboxamide;
3-[1-(ethylsulfonyl)-4-piperidinyl]-5-[3-fluoro-5-({[(5-methyl-2-furanyl)methyl]amino}methyl)phenyl]-1H-indole-7-carboxamide;
3-[1-(ethylsulfonyl)-4-piperidinyl]-5-(3-{[(2-methylpropyl)amino]methyl}phenyl)-1H-indole-7-carboxamide;
3-[1-(ethylsulfonyl)-4-piperidinyl]-5-[3-(2-pyrrolidinyl)phenyl]-1H-indole-7-carboxamide;
3-[1-(ethylsulfonyl)-4-piperidinyl]-5-{2-fluoro-5-[(methylamino)methyl]phenyl}-1H-indole-7-carboxamide;

3-[1-(ethylsulfonyl)-4-piperidinyl]-5-{2-fluoro-5-[(propylamino)methyl]phenyl}-1H-indole-7-carboxamide;

3-[1-(ethylsulfonyl)-4-piperidinyl]-5-(2-fluoro-5-{[(2-methylpropyl)amino]methyl}phenyl)-1H-indole-7-carboxamide;

5-(5-{[(2,2-dimethylpropyl)amino]methyl}-2-fluorophenyl)-3-[1-(ethylsulfonyl)-4-piperidinyl]-1H-indole-7-carboxamide;

5-[5-({[(1S)-1,2-dimethylpropyl]amino}methyl)-2-fluorophenyl]-3-[1-(ethylsulfonyl)-4-piperidinyl]-1H-indole-7-carboxamide;

5-[5-({[(1R)-1,2-dimethylpropyl]amino}methyl)-2-fluorophenyl]-3-[1-(ethylsulfonyl)-4-piperidinyl]-1H-indole-7-carboxamide;

5-(5-{[(cyclopropylmethyl)amino]methyl}-2-fluorophenyl)-3-[1-(ethylsulfonyl)-4-piperidinyl]-1H-indole-7-carboxamide;

3-[1-(ethylsulfonyl)-4-piperidinyl]-5-[2-fluoro-5-(1-pyrrolidinylmethyl)phenyl]-1H-indole-7-carboxamide;

3-[1-(ethylsulfonyl)-4-piperidinyl]-5-[2-fluoro-5-(4-morpholinylmethyl)phenyl]-1H-indole-7-carboxamide;

3-[1-(ethylsulfonyl)-4-piperidinyl]-5-[2-fluoro-5-({[2-(methyloxy)ethyl]amino}methyl)phenyl]-1H-indole-7-carboxamide;

3-[1-(ethylsulfonyl)-4-piperidinyl]-5-[2-fluoro-5-({[3-(methyloxy)propyl]amino}methyl)phenyl]-1H-indole-7-carboxamide;

3-[1-(ethylsulfonyl)-4-piperidinyl]-5-[3-(1-methyl-2-pyrrolidinyl)phenyl]-1H-indole-7-carboxamide;

3-[1-(ethylsulfonyl)-4-piperidinyl]-5-(3-{2-[(2-methylpropyl)amino]ethyl}phenyl)-1H-indole-7-carboxamide;

5-{3-[2-(ethylamino)ethyl]phenyl}-3-[1-(ethylsulfonyl)-4-piperidinyl]-1H-indole-7-carboxamide;

3-[1-(ethylsulfonyl)-4-piperidinyl]-5-{3-[2-(propylamino)ethyl]phenyl}-1H-indole-7-carboxamide;

5-{3-[2-(dimethylamino)ethyl]phenyl}-3-[1-(ethylsulfonyl)-4-piperidinyl]-1H-indole-7-carboxamide;

5-{3-[2-(dipropylamino)ethyl]phenyl}-3-[1-(ethylsulfonyl)-4-piperidinyl]-1H-indole-7-carboxamide;

5-[3-({[2-(3,5-dimethyl-1H-pyrazol-1-yl)ethyl]amino}methyl)phenyl]-3-[1-(ethylsulfonyl)-4-piperidinyl]-1H-indole-7-carboxamide;

3-[1-(ethylsulfonyl)-4-piperidinyl]-5-[2-(4-morpholinylmethyl)-1,3-thiazol-4-yl]-1H-indole-7-carboxamide;

3-[1-(ethylsulfonyl)-4-piperidinyl]-5-(2-{[(2-methylpropyl)amino]methyl}-1,3-thiazol-4-yl)-1H-indole-7-carboxamide;

3-[1-(ethylsulfonyl)-4-piperidinyl]-5-[2-(1-pyrrolidinylmethyl)-1,3-thiazol-4-yl]-1H-indole-7-carboxamide;

3-[1-(ethylsulfonyl)-4-piperidinyl]-5-[2-(1-piperidinylmethyl)-1,3-thiazol-4-yl]-1H-indole-7-carboxamide;

5-{2-[(dimethylamino)methyl]-1,3-thiazol-4-yl}-3-[1-(ethylsulfonyl)-4-piperidinyl]-1H-indole-7-carboxamide;

5-(2-{[ethyl(methyl)amino]methyl}-1,3-thiazol-4-yl)-3-[1-(ethylsulfonyl)-4-piperidinyl]-1H-indole-7-carboxamide;

5-(3-cyano-5-{[(2-methylpropyl)amino]methyl}phenyl)-3-[1-(ethylsulfonyl)-4-piperidinyl]-1H-indole-7-carboxamide;

5-{3-cyano-5-[(dimethylamino)methyl]phenyl}-3-[1-(ethylsulfonyl)-4-piperidinyl]-1H-indole-7-carboxamide;

3-[1-(ethylsulfonyl)-4-piperidinyl]-5-{3-[(methylsulfonyl)amino]phenyl}-1H-indole-7-carboxamide;

5-[4-(acetylamino)phenyl]-3-[1-(ethylsulfonyl)-4-piperidinyl]-1H-indole-7-carboxamide;

5-[3-(acetylamino)phenyl]-3-[1-(ethylsulfonyl)-4-piperidinyl]-1H-indole-7-carboxamide;

3-[1-(ethylsulfonyl)-4-piperidinyl]-5-[3-(4-morpholinylmethyl)phenyl]-1H-indole-7-carboxamide;

5-{3-[(acetylamino)methyl]phenyl}-3-[1-(ethylsulfonyl)-4-piperidinyl]-1H-indole-7-carboxamide;

3-[1-(ethylsulfonyl)-4-piperidinyl]-5-(3-{[(methylsulfonyl)amino]methyl}phenyl)-1H-indole-7-carboxamide;

5-{3-[(butanoylamino)methyl]phenyl}-3-[1-(ethylsulfonyl)-4-piperidinyl]-1H-indole-7-carboxamide;

3-[1-(ethylsulfonyl)-4-piperidinyl]-5-[3-({[(4-fluorophenyl)carbonyl]amino}methyl)phenyl]-1H-indole-7-carboxamide;

3-[1-(ethylsulfonyl)-4-piperidinyl]-5-(3-{[(2-methylpropanoyl)amino]methyl}phenyl)-1H-indole-7-carboxamide;

3-[1-(ethylsulfonyl)-4-piperidinyl]-5-(3-{[(2-furanylcarbonyl)amino]methyl}phenyl)-1H-indole-7-carboxamide;

5-(3-{[(cyclopentylcarbonyl)amino]methyl}phenyl)-3-[1-(ethylsulfonyl)-4-piperidinyl]-1H-indole-7-carboxamide 3-[1-(ethylsulfonyl)-4-piperidinyl]-5-{3-[(pentanoylamino)methyl]phenyl}-1H-indole-7-carboxamide;

5-(3-{[(2-ethylbutanoyl)amino]methyl}phenyl)-3-[1-(ethylsulfonyl)-4-piperidinyl]-1H-indole-7-carboxamide;

5-(3-{[(1-benzothien-2-ylcarbonyl)amino]methyl}phenyl)-3-[1-(ethylsulfonyl)-4-piperidinyl]-1H-indole-7-carboxamide;

5-[3-({[(1-acetyl-4-piperidinyl)carbonyl]amino}methyl)phenyl]-3-[1-(ethylsulfonyl)-4-piperidinyl]-1H-indole-7-carboxamide;

3-[1-(ethylsulfonyl)-4-piperidinyl]-5-[3-({[(1-methyl-1H-pyrrol-2-yl)carbonyl]amino}methyl)phenyl]-1H-indole-7-carboxamide;

3-[1-(ethylsulfonyl)-4-piperidinyl]-5-(3-{[(3-methyl-2-butenoyl)amino]methyl}phenyl)-1H-indole-7-carboxamide;

3-[1-(ethylsulfonyl)-4-piperidinyl]-5-{3-[(heptanoylamino)methyl]phenyl}-1H-indole-7-carboxamide;

3-[1-(ethylsulfonyl)-4-piperidinyl]-5-{3-[(octanoylamino)methyl]phenyl}-1H-indole-7-carboxamide;

3-[1-(ethylsulfonyl)-4-piperidinyl]-5-(3-{[(2-methylpentanoyl)amino]methyl}phenyl)-1H-indole-7-carboxamide;

3-[1-(ethylsulfonyl)-4-piperidinyl]-5-(3-{[(3-methylbutanoyl)amino]methyl}phenyl)-1H-indole-7-carboxamide;

3-[1-(ethylsulfonyl)-4-piperidinyl]-5-(3-{[(2-thienylacetyl)amino]methyl}phenyl)-1H-indole-7-carboxamide;

3-[1-(ethylsulfonyl)-4-piperidinyl]-5-{3-[(hexanoylamino)methyl]phenyl}-1H-indole-7-carboxamide;

3-[1-(ethylsulfonyl)-4-piperidinyl]-5-(3-{[(2-methylbutanoyl)amino]methyl}phenyl)-1H-indole-7-carboxamide;

5-(3-{[(cyclobutylcarbonyl)amino]methyl}phenyl)-3-[1-(ethylsulfonyl)-4-piperidinyl]-1H-indole-7-carboxamide;

5-(3-{[(cyclopropylcarbonyl)amino]methyl}phenyl)-3-[1-(ethylsulfonyl)-4-piperidinyl]-1H-indole-7-carboxamide;

3-[1-(ethylsulfonyl)-4-piperidinyl]-5-{3-[(propanoylamino)methyl]phenyl}-1H-indole-7-carboxamide;

5-(3-{[(cyclopentylacetyl)amino]methyl}phenyl)-3-[1-(ethylsulfonyl)-4-piperidinyl]-1H-indole-7-carboxamide;

3-[1-(ethylsulfonyl)-4-piperidinyl]-5-[3-({[3-(methylthio)propanoyl]amino}methyl)phenyl]-1H-indole-7-carboxamide;

3-[1-(ethylsulfonyl)-4-piperidinyl]-5-[3-({[(1-methylethyl)sulfonyl]amino}methyl)phenyl]-1H-indole-7-carboxamide;

5-(3-{[(cyclopropylsulfonyl)amino]methyl}phenyl)-3-[1-(ethylsulfonyl)-4-piperidinyl]-1H-indole-7-carboxamide;

5-[3-({[(2,5-dichlorophenyl)sulfonyl]amino}methyl)phenyl]-3-[1-(ethylsulfonyl)-4-piperidinyl]-1H-indole-7-carboxamide;

5-[3-({[(4-bromophenyl)sulfonyl]amino}methyl)phenyl]-3-[1-(ethylsulfonyl)-4-piperidinyl]-1H-indole-7-carboxamide;
5-[3-({[(4-chlorophenyl)sulfonyl]amino}methyl)phenyl]-3-[1-(ethylsulfonyl)-4-piperidinyl]-1H-indole-7-carboxamide;
3-[1-(ethylsulfonyl)-4-piperidinyl]-5-[3-({[(3-fluorophenyl)sulfonyl]amino}methyl)phenyl]-1H-indole-7-carboxamide;
5-[3-({[(2-chlorophenyl)sulfonyl]amino}methyl)phenyl]-3-[1-(ethylsulfonyl)-4-piperidinyl]-1H-indole-7-carboxamide;
5-[3-({[(2,5-dichloro-3-thienyl)sulfonyl]amino}methyl)phenyl]-3-[1-(ethylsulfonyl)-4-piperidinyl]-1H-indole-7-carboxamide;
5-[3-({[(2-chloro-6-methylphenyl)sulfonyl]amino}methyl)phenyl]-3-[1-(ethylsulfonyl)-4-piperidinyl]-1H-indole-7-carboxamide;
3-[1-(ethylsulfonyl)-4-piperidinyl]-5-[3-({[(5-fluoro-2-methylphenyl)sulfonyl]amino}methyl)phenyl]-1H-indole-7-carboxamide;
5-[3-({[(1,2-dimethyl-1H-imidazol-4-yl)sulfonyl]amino}methyl)phenyl]-3-[1-(ethylsulfonyl)-4-piperidinyl]-1H-indole-7-carboxamide;
3-[1-(ethylsulfonyl)-4-piperidinyl]-5-(3-{[(propylsulfonyl)amino]methyl}phenyl)-1H-indole-7-carboxamide;
5-(3-{[(butylsulfonyl)amino]methyl}phenyl)-3-[1-(ethylsulfonyl)-4-piperidinyl]-1H-indole-7-carboxamide;
3-[1-(ethylsulfonyl)-4-piperidinyl]-5-(3-{[(phenylsulfonyl)amino]methyl}phenyl)-1H-indole-7-carboxamide;
3-[1-(ethylsulfonyl)-4-piperidinyl]-5-[3-({[(4-fluorophenyl)sulfonyl]amino}methyl)phenyl]-1H-indole-7-carboxamide;
5-[3-({[(4-bromo-2-ethylphenyl)sulfonyl]amino}methyl)phenyl]-3-[1-(ethylsulfonyl)-4-piperidinyl]-1H-indole-7-carboxamide;
5-(3-{[(1-benzothien-3-ylsulfonyl)amino]methyl}phenyl)-3-[1-(ethylsulfonyl)-4-piperidinyl]-1H-indole-7-carboxamide;
5-{3-[({[4-(1,1-dimethylethyl)phenyl]sulfonyl}amino)methyl]phenyl}-3-[1-(ethylsulfonyl)-4-piperidinyl]-1H-indole-7-carboxamide;
5-[3-({[(3,4-difluorophenyl)sulfonyl]amino}methyl)phenyl]-3-[1-(ethylsulfonyl)-4-piperidinyl]-1H-indole-7-carboxamide;
5-(3-{[(ethylsulfonyl)amino]methyl}phenyl)-3-[1-(ethylsulfonyl)-4-piperidinyl]-1H-indole-7-carboxamide;
5-(3-{[(2,1,3-benzoxadiazol-4-ylsulfonyl)amino]methyl}phenyl)-3-[1-(ethylsulfonyl)-4-piperidinyl]-1H-indole-7-carboxamide;
3-[1-(ethylsulfonyl)-4-piperidinyl]-5-(3-{[(tetrahydro-3-furanylcarbonyl)amino]methyl}phenyl)-1H-indole-7-carboxamide;
5-{4-[(cyclopentylsulfonyl)amino]phenyl}-3-[1-(ethylsulfonyl)-4-piperidinyl]-1H-indole-7-carboxamide;
3-[1-(ethylsulfonyl)-4-piperidinyl]-5-[4-(4-methyl-2-oxo-1-piperazinyl)phenyl]-1H-indole-7-carboxamide;
5-[6-(4-acetyl-1-piperazinyl)-3-pyridinyl]-3-[1-(ethylsulfonyl)-4-piperidinyl]-1H-indole-7-carboxamide;
3-[1-(ethylsulfonyl)-4-piperidinyl]-5-(4-{[(methyloxy)amino]methyl}phenyl)-1H-indole-7-carboxamide;
3-[1-(ethylsulfonyl)-4-piperidinyl]-5-(3-{[(methyloxy)amino]methyl}phenyl)-1H-indole-7-carboxamide;
3-[1-(ethylsulfonyl)-4-piperidinyl]-5-(5-{[4-(1-pyrrolidinyl)-1-piperidinyl]methyl}-3-thienyl)-1H-indole-7-carboxamide;
3-[1-(ethylsulfonyl)-4-piperidinyl]-5-(5-{[(2S)-2-(trifluoromethyl)-1-pyrrolidinyl]methyl}-3-thienyl)-1H-indole-7-carboxamide;
5-(5-{[(2R)-2-(hydroxymethyl)-1-pyrrolidinyl]methyl}-3-thienyl)-3-{1-[(1-methylethyl)sulfonyl]-4-piperidinyl}-1H-indole-7-carboxamide;
5-(5-{[(3S)-3-hydroxy-1-pyrrolidinyl]methyl}-3-thienyl)-3-{1-[(1-methylethyl)sulfonyl]-4-piperidinyl}-1H-indole-7-carboxamide;
5-(5-{[cyclopentyl(methyl)amino]methyl}-3-thienyl)-3-{1-[(1-methylethyl)sulfonyl]-4-piperidinyl}-1H-indole-7-carboxamide;
5-(5-{[(2-hydroxyethyl)(methyl)amino]methyl}-3-thienyl)-3-{1-[(1-methylethyl)sulfonyl]-4-piperidinyl}-1H-indole-7-carboxamide;
5-(5-{[(2-amino-2-oxoethyl)(methyl)amino]methyl}-3-thienyl)-3-{1-[(1-methylethyl)sulfonyl]-4-piperidinyl}-1H-indole-7-carboxamide;
3-[1-(ethylsulfonyl)-4-piperidinyl]-5-(5-{[methyl(2-propen-1-yl)amino]methyl}-3-thienyl)-1H-indole-7-carboxamide;
5-(5-{[[(3,5-dimethyl-1H-pyrazol-4-yl)methyl](methyl)amino]methyl}-3-thienyl)-3-[1-(ethylsulfonyl)-4-piperidinyl]-1H-indole-7-carboxamide;
5-(5-{[(cyanomethyl)(methyl)amino]methyl}-3-thienyl)-3-[1-(ethylsulfonyl)-4-piperidinyl]-1H-indole-7-carboxamide;
3-[1-(ethylsulfonyl)-4-piperidinyl]-5-(5-{[methyl(1-methylpropyl)amino]methyl}-3-thienyl)-1H-indole-7-carboxamide;
5-(5-{[[2-(ethyloxy)ethyl](methyl)amino]methyl}-3-thienyl)-3-[1-(ethylsulfonyl)-4-piperidinyl]-1H-indole-7-carboxamide;
5-(5-{[cyclobutyl(methyl)amino]methyl}-3-thienyl)-3-[1-(ethylsulfonyl)-4-piperidinyl]-1H-indole-7-carboxamide;
3-[1-(ethylsulfonyl)-4-piperidinyl]-5-[5-({2-[(methyloxy)methyl]-1-pyrrolidinyl}methyl)-3-thienyl]-1H-indole-7-carboxamide;
5-(5-{[(1,1-dimethylethyl)(methyl)amino]methyl}-3-thienyl)-3-[1-(ethylsulfonyl)-4-piperidinyl]-1H-indole-7-carboxamide;
3-[1-(ethylsulfonyl)-4-piperidinyl]-5-(5-{[3-(trifluoromethyl)-1-piperidinyl]methyl}-3-thienyl)-1H-indole-7-carboxamide;
3-[1-(ethylsulfonyl)-4-piperidinyl]-5-(5-{[[(1S)-2-hydroxy-1-methylethyl](methyl)amino]methyl}-3-thienyl)-1H-indole-7-carboxamide;
5-(5-{[(cyclopropylmethyl)(methyl)amino]methyl}-3-thienyl)-3-[1-(ethylsulfonyl)-4-piperidinyl]-1H-indole-7-carboxamide;
5-(5-{[[2-(acetylamino)ethyl](methyl)amino]methyl}-3-thienyl)-3-[1-(ethylsulfonyl)-4-piperidinyl]-1H-indole-7-carboxamide;
3-[1-(ethylsulfonyl)-4-piperidinyl]-5-(5-{[[(1R,2R)-2-hydroxycyclopentyl](methyl)amino]methyl}-3-thienyl)-1H-indole-7-carboxamide;
5-(5-{[(1,1-dimethylpropyl)(methyl)amino]methyl}-3-thienyl)-3-[1-(ethylsulfonyl)-4-piperidinyl]-1H-indole-7-carboxamide;
3-[1-(ethylsulfonyl)-4-piperidinyl]-5-(5-{[[(2S)-2-hydroxypropyl](methyl)amino]methyl}-3-thienyl)-1H-indole-7-carboxamide;
3-[1-(ethylsulfonyl)-4-piperidinyl]-5-[5-({methyl[(2R)-tetrahydro-2-furanylmethyl]amino}methyl)-3-thienyl]-1H-indole-7-carboxamide;

3-[1-(ethylsulfonyl)-4-piperidinyl]-5-(5-{[{2-[(2-hydroxyethyl)oxy]ethyl}(methyl)amino]methyl}-3-thienyl)-1H-indole-7-carboxamide;

3-[1-(ethylsulfonyl)-4-piperidinyl]-5-[5-(1-{methyl[2-(methyloxy)ethyl]amino}ethyl)-3-thienyl]-1H-indole-7-carboxamide;

3-[1-(ethylsulfonyl)-4-piperidinyl]-5-(5-{1-[methyl(propyl)amino]ethyl}-3-thienyl)-1H-indole-7-carboxamide;

3-[1-(ethylsulfonyl)-4-piperidinyl]-5-(5-{[[(1S)-2-hydroxy-1-methylethyl](methyl)amino]methyl}-3-thienyl)-1H-indole-7-carboxamide; and 5-(5-{[(1,1-dioxidotetrahydro-3-thienyl)(methyl)amino]methyl}-3-thienyl)-3-[1-(ethylsulfonyl)-4-piperidinyl]-1H-indole-7-carboxamide; or a pharmaceutically acceptable salt thereof.

TERMS AND DEFINITIONS

"Alkyl" refers to a saturated hydrocarbon chain having the specified number of member atoms. For example, $C_1$-$C_6$ alkyl refers to an alkyl group having from 1 to 6 member atoms. Alkyl groups may be optionally substituted with one or more substituents as defined herein. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

"Alkylene" when used alone or in forming other groups (such as the $C_1$-$C_6$ alkylene-heteroaryl, $C_1$-$C_6$ alkylene-heterocycloalkyl, $C_1$-$C_6$ alkylene-$C_4$-$C_7$cycloalkyl, and $C_1$-$C_6$ alkylene-$C_5$-$C_7$cycloalkenyl groups) refers to a saturated divalent hydrocarbon chain having the specified number of member atoms. For example, $C_1$-$C_6$ alkylene refers to an alkylene group having from 1 to 6 member atoms. Alkylene groups may be optionally substituted with one or more substituents as defined herein. Alkylene groups may be straight or branched. Representative branched alkylene groups have one, two, or three branches. Alkylene includes methylene, ethylene, propylene (n-propylene and isopropylene), butylene (n-butylene, isobutylene, and t-butylene), pentylene (n-pentylene, isopentylene, and neopentylene), and hexylene.

"Alkenyl" refers to an unsaturated hydrocarbon chain having the specified number of member atoms and having one or more carbon-carbon double bond within the chain. For example, $C_2$-$C_6$ alkenyl refers to an alkenyl group having from 2 to 6 member atoms. In certain embodiments alkenyl groups have one carbon-carbon double bond within the chain. In other embodiments, alkenyl groups have more than one carbon-carbon double bond within the chain. Alkenyl groups may be optionally substituted with one or more substituents as defined herein. Alkenyl groups may be straight or branched. Representative branched alkenyl groups have one, two, or three branches. Alkenyl includes ethylenyl, propenyl, butenyl, pentenyl, and hexenyl.

"Alkenylene" refers to an unsaturated divalent hydrocarbon chain having the specified number of member atoms and having one or more carbon-carbon double bond within the chain. For example, $C_2$-$C_6$ alkenylene refers to an alkenylene group having from 2 to 6 member atoms. In certain embodiments alkenylene groups have one carbon-carbon double bond within the chain. In other embodiments, alkenylene groups have more than one carbon-carbon double bond within the chain. Alkenylene groups may be optionally substituted with one or more substituents as defined herein. Alkenylene groups may be straight or branched. Representative branched alkenylene groups have one, two, or three branches. Alkenyl includes ethylenylene, propenylene, butenylene, pentenylene, and hexenylene.

"Alkynylene" refers to an unsaturated divalent hydrocarbon chain having the specified number of member atoms and having one or more carbon-carbon triple bond within the chain. For example, $C_2$-$C_6$ alkynylene refers to an alkynylene group having from 2 to 6 member atoms. In certain embodiments alkynylene groups have one carbon-carbon triple bond within the chain. In other embodiments, alkynylene groups have more than one carbon-carbon triple bond within the chain. For the sake of clarity, unsaturated divalent hydrocarbon chains having one or more carbon-carbon triple bond within the chain and one or more carbon-carbon double bond within the chain are alkynylene groups. Alkynylene groups may be optionally substituted with one or more substituents as defined herein. Alkynylene groups may be straight or branched. Representative branched alkynylene groups have one, two, or three branches. Alkynyl includes ethylynylene, propynylene, butynylene, pentynylene, and hexynylene.

"Aryl" refers to an aromatic hydrocarbon ring. Aryl groups are monocyclic ring systems or bicyclic ring systems. Monocyclic aryl ring refers to phenyl. Bicyclic aryl rings refer to napthyl and rings wherein phenyl is fused to a cycloalkyl or cycloalkenyl ring having 5, 6, or 7 member atoms. Aryl groups may be optionally substituted with one or more substituents as defined herein.

"Cycloalkyl" refers to a saturated hydrocarbon ring having the specified number of member atoms. Cycloalkyl groups are monocyclic ring systems. For example, $C_3$-$C_6$ cycloalkyl refers to a cycloalkyl group having from 3 to 6 member atoms. Cycloalkyl groups may be optionally substituted with one or more substituents as defined herein. Cycloalkyl includes cyclopropyl, cyclobutyl, cyclopentyl, and cyclohexyl.

"Cycloalkenyl" refers to an unsaturated hydrocarbon ring having the specified number of member atoms and having a carbon-carbon double bond within the ring. For example, $C_3$-$C_6$ cycloalkenyl refers to a cycloalkenyl group having from 3 to 6 member atoms. In certain embodiments cycloalkenyl groups have one carbon-carbon double bond within the ring. In other embodiments, cycloalkenyl groups have more than one carbon-carbon double bond within the ring. However, cycloalkenyl rings are not aromatic. Cycloalkenyl groups are monocyclic ring systems. Cycloalkenyl groups may be optionally substituted with one or more substituents as defined herein. Cycloalkenyl includes cyclopropenyl, cyclobutenyl, cyclopentenyl, and cyclohexenyl.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" (or "half-lives") refers to the time required for half of a quantity of a substance to be converted to another chemically distinct specie in vitro or in vivo.

"Halo" refers to the halogen radical fluoro, chloro, bromo, or iodo.

"Haloalkyl" refers to an alkyl group wherein at least one hydrogen atom attached to a member atom within the alkyl group is replaced with halo. Haloalkyl includes trifluoromethyl.

"Heteroaryl" refers to an aromatic ring containing from 1 to 4 heteroatoms as member atoms in the ring. Heteroaryl groups containing more than one heteroatom may contain different heteroatoms. Heteroaryl groups may be optionally substituted with one or more substituents as defined herein. Heteroaryl groups are monocyclic ring systems or are fused, spiro, or bridged bicyclic ring systems. Monocyclic heteroaryl rings have 5 or 6 member atoms. Bicyclic heteroaryl rings have from 7 to 11 member atoms. Bicyclic heteroaryl rings include those rings wherein phenyl and a monocyclic heterocycloalkyl ring are attached forming a fused, spiro, or bridged bicyclic ring system, and those rings wherein a monocyclic heteroaryl ring and a monocyclic cycloalkyl, cycloalkenyl, heterocycloalkyl, or heteroaryl ring are attached forming a fused, spiro, or bridged bicyclic ring system. Heteroaryl includes pyrrolyl, pyrazolyl, imidazolyl, oxazolyl, isoxazolyl, thiazolyl, isothiazolyl, furanyl, furazanyl, thienyl, triazolyl, pyridinyl, pyrimidinyl, pyridazinyl, pyrazinyl, triazinyl, tetrazinyl, indolyl, isoindolyl, indolizinyl, indazolyl, purinyl, quinolinyl, isoquinolinyl, quinoxalinyl, quinazolinyl, pteridinyl, cinnolinyl, benzimidazolyl, benopyranyl, benzoxazolyl, benzofuranyl, isobenzofuranyl, benzothiazolyl, benzothienyl, furopyridinyl, and napthyridinyl.

"Heteroatom" refers to a nitrogen, sulphur, or oxygen atom.

"Heterocycloalkyl" refers to a saturated or unsaturated ring containing from 1 to 4 heteroatoms as member atoms in the ring. However, heterocycloalkyl rings are not aromatic. Heterocycloalkyl groups containing more than one heteroatom may contain different heteroatoms. Heterocycloalkyl groups may be optionally substituted with one or more substituents as defined herein. Heterocycloalkyl groups are monocyclic ring systems having from 4 to 7 member atoms. In certain embodiments, heterocycloalkyl is saturated. In other embodiments, heterocycloalkyl is unsaturated but not aromatic. Heterocycloalkyl includes pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, 1,3-dioxolanyl, 1,3-dioxanyl, 1,4-dioxanyl, 1,3-oxathiolanyl, 1,3-oxathianyl, 1,3-dithianyl, and azetidinyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as alkyl, alkenyl, alkynyl, aryl, cycloalkyl, cycloalkenyl, heterocycloalkyl, or heteroaryl, may be unsubstituted or substituted with one or more substituents as defined herein. "Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams); mg (milligrams);
L (liters); mL (milliliters);
μL (microliters); psi (pounds per square inch);
M (molar); mM (millimolar);
i. v. (intravenous); Hz (Hertz);
MHz (megahertz); mol (moles);
mmol (millimoles); rt (room temperature);
min (minutes); h (hours);
mp (melting point); TLC (thin layer chromatography);
$T_r$ (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); AcOEt (ethyl acetate);
DME (1,2-dimethoxyethane); DCM (dichloromethane);
DCE (dichloroethane); DMF (N,N-dimethylformamide);
DMPU (N,N'-dimethylpropyleneurea); CDI (1,1-carbonyldiimidazole);
IBCF (isobutyl chloroformate); HOAc (acetic acid);
HOSu (N-hydroxysuccinimide); HOBT (1-hydroxybenzotriazole);
mCPBA (meta-chloroperbenzoic acid;
EDC (1-[3-dimethylamino) propyl]-3-ethylcarbodiimide hydrochloride);
BOC (tert-butyloxycarbonyl); FMOC (9-fluorenylmethoxycarbonyl);
DCC (dicyclohexylcarbodiimide); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); BSA (bovine serum albumin);
ATP (adenosine triphosphate); HRP (horseradish peroxidase);
DMEM (Dulbecco's modified Eagle medium);
HPLC (high pressure liquid chromatography);
BOP (bis(2-oxo-3-oxazolidinyl)phosphinic chloride);
TBAF (tetra-n-butylammonium fluoride);
HBTU (O-Benzotriazole-1-yl-N,N,N',N'-tetramethyluroniumhexafluoro phosphate);
HEPES (4-(2-hydroxyethyl)-1-piperazine ethane sulfonic acid);
DPPA (diphenylphosphoryl azide);
$fHNO_3$ (fuming $HNO_3$);
EDTA (ethylenediaminetetraacetic acid);

TMEDA (N,N,N',N'-tetramethyl-1,2-ethanediamine);
NBS (N-bromosuccinimide);
HATU (O-(7azabenzobenzotriazol-1-yl)-N,N,N',N'-tetramethyluronium hexafluorophosphate);
DIPEA (diisopropylethylamine);
Imes (1,3-Bis(2,4,6-trimethylphenyl)imidazolium chloride);
dppf (1,1'-bis(diphenylphosphino)ferrocene);
MDAP (Mass Directed AutoPrep);
$CH_3CN$ (acetonitrile);
EtOAc (ethyl acetate);
and NIS (N-iodsuccinimide).

All references to ether are to diethyl ether and brine refers to a saturated aqueous solution of NaCl.

The compounds according to formulae I-II may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in formulae I-II, or in any chemical structure illustrated herein, is not specified the structure is intended to encompass any stereoisomer and all mixtures thereof. Thus, compounds according to formulae I-II containing one or more chiral center may be used as racemic mixtures, enantiomerically enriched mixtures, or as enantiomerically pure individual stereoisomers.

Individual stereoisomers of a compound according to formulae I-II which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to formulae I-II may also contain double bonds or other centers of geometric asymmetry. Where the stereochemistry of a center of geometric asymmetry present in formulae I-II, or in any chemical structure illustrated herein, is not specified, the structure is intended to encompass the trans (E) geometric isomer, the cis (Z) geometric isomer, and all mixtures thereof.

Likewise, all tautomeric forms are also included in formulae I-II whether such tautomers exist in equilibrium or predominately in one form.

The skilled artisan will appreciate that pharmaceutically-acceptable salts of the compounds according to formulae I-II may be prepared. Indeed, in certain embodiments of the invention, pharmaceutically-acceptable salts of the compounds according to formulae I-II may be preferred over the respective free base or free acid because such salts impart greater stability or solubility to the molecule thereby facilitating formulation into a dosage form. Accordingly, the invention is further directed to pharmaceutically-acceptable salts of the compounds according to formulae I-II.

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

In certain embodiments, compounds according to formulae I-II may contain an acidic functional group. Suitable pharmaceutically-acceptable salts include salts of such acidic functional groups. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to formulae I-II may contain a basic functional group and are therefore capable of forming pharmaceutically-acceptable acid addition salts by treatment with a suitable acid. Suitable acids include pharmaceutically-acceptable inorganic acids and pharmaceutically-acceptable organic acids. Representative pharmaceutically-acceptable acid addition salts include hydrochloride, hydrobromide, nitrate, methylnitrate, sulfate, bisulfate, sulfamate, phosphate, acetate, trifluoroacetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

As used herein, the term "compounds of the invention" means both the compounds according to formulae I-II and the pharmaceutically-acceptable salts thereof.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs.

Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

Compound Preparation

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Examples section.

Compounds of formulae I and II can be prepared, for example, according to Schemes 1, 2, and 3 depicted below:

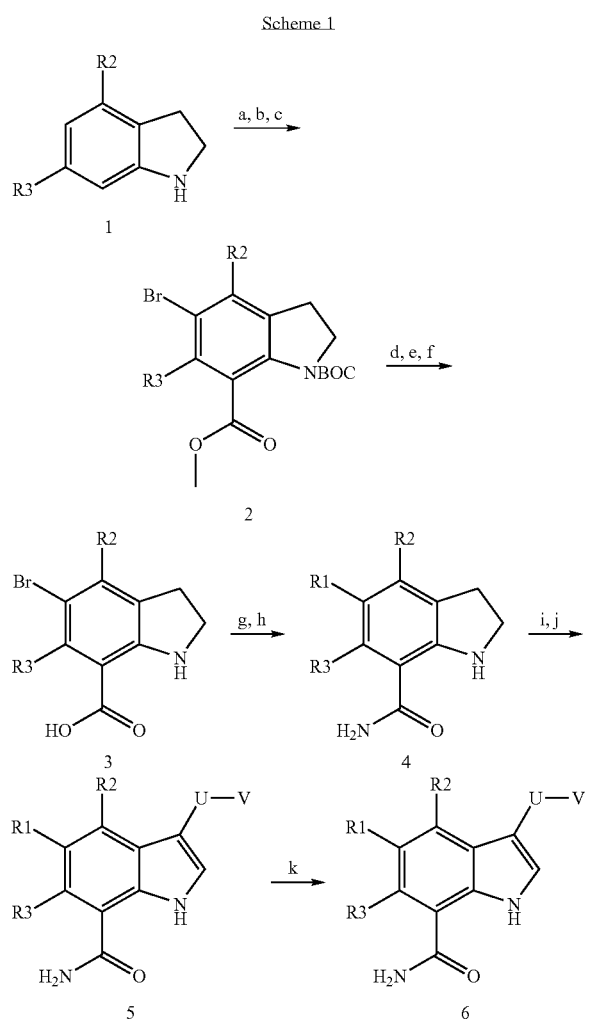

Conditions: a) (BOC)$_2$O, THF; b) s-BuLi, ClCO$_2$Me, TMEDA, Et$_2$O; c) N-bromosuccinimide, Methylene chloride; d) TFA; e) MnO$_2$, THF; f) LiOH, MeOH, water; g) R1B(OR)$_2$, Imes-HCl, Pd(OAc)$_2$, Dioxane/water; h) HATU, NH$_3$, DMF; i) RCHO (or) RC(O)R', NaOMe, MeOH; j) Pd(OH)$_2$, H$_2$, HOAc, EtOH; k) R4Cl, TEA, Methylene chloride (or) (R4)$_2$O, DMAP, Methylene chloride Scheme 1 represents a general scheme for the preparation of compounds according to formulae I and II wherein R2 and R3 are H, F, or Cl, U is a bond or C$_1$-C$_6$ alkylene or C$_2$-C$_6$ alkenylene and V is C5-C7 cycloalkyl or C5-C7 cycloalkenyl or heterocycloalkyl or heterocycloalkenyl. Scheme 1 also represents a general scheme for the preparation of compounds according to formulae I and II wherein U is C$_1$-C$_6$ alkylene or C$_2$-C$_6$ alkenylene and V is aryl, or heteroaryl. In Scheme 1, R1 is defined above unless defined otherwise. The indoline 1 depicted as starting material is commercially available. Reaction conditions are as described above in the scheme; however, the skilled artisan will appreciate that certain modifications in the reaction conditions and/or reagents used are possible.

Treatment of indoline 1 with di-tertbutyl dicarbonate in a suitable solvent such as THF or methylene chloride produces the desired BOC protected product. Further transformation to the desired bromide 2 can be accomplished via lithiation using sec-butyllithium in the presence of TMEDA and quenching with methyl chloroformate followed by bromination with N-bromosuccinimide. Treatment of bromide 2 with trifluoroacetic acid followed by oxidation of the resulting indoline to the indole with manganese dioxide and subsequent hydrolysis of the methyl ester to the acid yields the desired carboxylic acid 3. Installation of the substituent R1 can be accomplished via a transition metal mediated coupling using an appropriate catalyst and coupling partner. As an example of such a transformation, for the case in Scheme 1 condition "g", a Suzuki cross-coupling reaction can be completed using a boronic ester or acid in the presence of Pd(OAc)$_2$, Imes-HCl, and Cs$_2$CO$_3$ in 1,4-dioxane and water. Preparation of the primary carboxamide 4 can be completed via reaction of the carboxylic acid with ammonia in the presence of HATU. Conversion of 4 to 5 incorporating the group U-V is performed via reaction with the appropriate aldehyde or ketone precursor to U-V. This transformation can be completed under either basic or acidic conditions. For the case where the group U-V is fully saturated, a subsequent reduction of the intermediate product will produce the desired product 5. As an example of such a reduction, for the case in Scheme 1 condition "j", a hydrogenation reaction in the presence of Pd(OH)$_2$ completes the transformation to 5. In the case where U-V and/or R1 contains a suitable protecting group, removal of the protecting group under the appropriate conditions and further transformation to other products may be accomplished. Subsequent transformation of the amine function of the group U-V to either the sulfonamide or amide of R4 can be performed with the appropriate sulfonyl or acid chloride or acid anhydride of R4. It will be appreciated by the skilled artisan that upon conversion to either the sulfonamide or amide of R4 the resulting product may require further elaboration to R4. This can include but is not limited to suitable protecting and functional group manipulations and reactions with amines/alcohols R5.

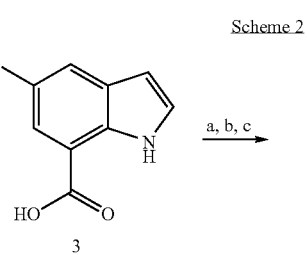

Scheme 2

-continued

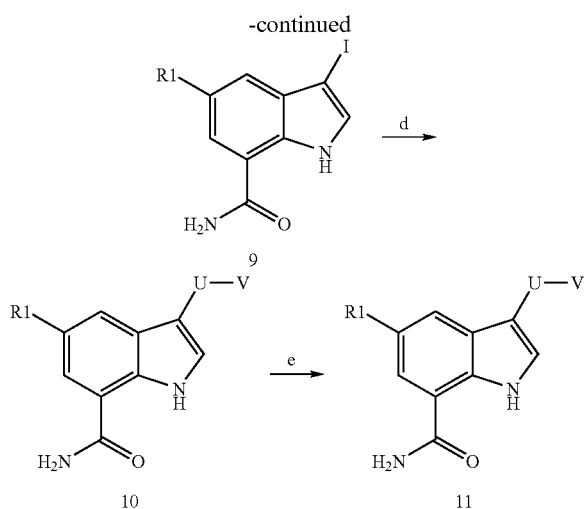

Conditions: a) R1B(OR)$_2$, Imes-HCl, Pd(OAc)$_2$, dioxane/water; b) HATU, NH$_3$, DMF; c) N-iodosuccinimide, Methylene chloride; d) VUB(OR)$_2$, Pd(PPh$_3$)$_4$, Cs$_2$CO$_3$, 1,4-dioxane, water; e) R$_2$Cl, TEA, Methylene chloride (or) (R$_2$)$_2$O, DMAP, Methylene chloride Scheme 2 represents a general scheme for the preparation of compounds according to formulae I and II wherein U is a bond and V is aryl or heteroaryl. In Scheme 2, R1 is defined above unless defined otherwise. The indolecarboxylic acid 3 depicted as starting material is obtained as described in Scheme 1. Reaction conditions are as described above in the scheme; however, the skilled artisan will appreciate that certain modifications in the reaction conditions and/or reagents used are possible.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

Methods of Use

The compounds of the invention are inhibitors of IKK2. These compounds can be useful in the treatment of disorders wherein the underlying pathology is (at least in part) attributable to inappropriate IKK2 (also known as IKKβ) activity such as rheumatoid arthritis, inflammatory bowel disease, asthma, and COPD (chronic obstructive pulmonary disease). "Inappropriate IKK2 activity" refers to any IKK2 activity that deviates from the normal IKK2 activity expected in a particular patient. Inappropriate IKK2 activity may take the form of, for instance, an abnormal increase in activity, or an aberration in the timing and or control of IKK2 activity. Such inappropriate activity may result then, for example, from overexpression or mutation of the protein kinase leading to inappropriate or uncontrolled activation. Accordingly, in another aspect the invention is directed to methods of treating such disorders.

Such disorders include inflammatory and tissue repair disorders, particularly rheumatoid arthritis, inflammatory bowel disease, asthma and COPD (chronic obstructive pulmonary disease); osteoarthritis, osteoporosis and fibrotic diseases; dermatosis, including psoriasis, atopic dermatitis and ultraviolet radiation (UV)-induced skin damage; autoimmune diseases including systemic lupus eythematosus, multiple sclerosis, psoriatic arthritis, alkylosing spondylitis, tissue and organ rejection, Alzheimer's disease, stroke, atherosclerosis, restonosis, diabetes, glomerulonephritis, cancer, including Hodgkins disease, cachexia, inflammation associated with infection and certain viral infections, including acquired immune deficiency syndrome (AIDS), adult respiratory distress syndrome, and Ataxia Telangiestasia.

The methods of treatment of the invention comprise administering a safe and effective amount of a compound according to formulae I-II or a pharmaceutically-acceptable salt thereof to a patient in need thereof. Individual embodiments of the invention include methods of treating any one of the above-mentioned disorders by administering a safe and effective amount of a compound according to formulae I-II or a pharmaceutically-acceptable salt thereof to a patient in need thereof.

As used herein, "treat" in reference to a disorder means: (1) to ameliorate or prevent the disorder or one or more of the biological manifestations of the disorder, (2) to interfere with (a) one or more points in the biological cascade that leads to or is responsible for the disorder or (b) one or more of the biological manifestations of the disorder, (3) to alleviate one or more of the symptoms or effects associated with the disorder, or (4) to slow the progression of the disorder or one or more of the biological manifestations of the disorder.

As indicated above, "treatment" of a disorder includes prevention of the disorder. The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration range from 0.001 mg to 50 mg per kg of total body weight.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

The invention also provides a compound of the invention for use in medical therapy, and particularly in the treatment of disorders mediated by IKK2 activity. Thus, in a further aspect, the invention is directed to the use of a compound according to formulae I-II or a pharmaceutically-acceptable salt thereof in the preparation of a medicament for the treatment of a disorder characterized by inappropriate IKK2 activity.

Particular disorders characterised by inappropriate IKK2 activity include inflammatory and tissue repair disorders, particularly rheumatoid arthritis, inflammatory bowel disease, asthma and COPD (chronic obstructive pulmonary disease); osteoarthritis, osteoporosis and fibrotic diseases; dermatosis, including psoriasis, atopic dermatitis and ultraviolet radiation (UV)-induced skin damage; autoimmune diseases including systemic lupus eythematosus, multiple sclerosis, psoriatic arthritis, alkylosing spondylitis, tissue and organ rejection, Alzheimer's disease, stroke, atherosclerosis, restenosis, diabetes, glomerulonephritis, cancer, including Hodgkins disease, cachexia, inflammation associated with infection and certain viral infections, including acquired immune deficiency syndrome (AIDS), adult respiratory distress syndrome, and Ataxia Telangiestasia as a result of inhibition of the protein kinase IKK2.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically may contain, for example, from 0.5 mg to 1 g, or from 1 mg to 700 mg, or from 5 mg to 100 mg of a compound of the invention.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in Remington's *Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of the invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of the invention. Syrups can be prepared by dissolving the compound of the invention in a suitably flavored aqueous solution, while elixirs are prepared through the use of a non-toxic alcoholic vehicle. Suspensions can be formulated by dispersing the compound of the invention in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

In another aspect, the invention is directed to a dosage form adapted for administration to a patient by inhalation. For example, the compound of the invention may be inhaled into the lungs as a dry powder, an aerosol, a suspension, or a solution.

Dry powder compositions for delivery to the lung by inhalation typically comprise a compound of the invention as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides.

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 20 µg-10 mg of the compound of the invention.

Aerosols may be formed by suspending or dissolving a compound of the invention in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA- 152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of the invention will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Suspensions and solutions comprising a compound of the invention may also be administered to a patient via a nebulizer. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The compound of the invention may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions may be applied as a topical ointment or cream. When formulated in an ointment, the compound of the invention may be employed with either a paraffinic or a water-miscible ointment base. Alternatively, the compound of the invention may be formulated in a cream with an oil-in-water cream base or a water-in-oil base.

Pharmaceutical compositions adapted for nasal administration wherein the carrier is a solid include a coarse powder having a particle size for example in the range 20 to 500 microns which is administered by rapid inhalation through the nasal passage from a container of the powder held close up to the nose. Suitable compositions wherein the carrier is a liquid, for administration as a nasal spray or as nasal drops, include aqueous or oil solutions of the compound of the invention.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

$^1$H NMR spectra were recorded on a Brucker DPX400, a Brucker DPX250, a Brucker AC400, or a Varian Inova 400. Chemical shifts are expressed in parts per million (ppm, δ units). Splitting patterns describe apparent multiplicities and are designated as s (singlet), d (doublet), t (triplet), q (quartet), quint (quintet), m (multiplet), br (broad).

Low-resolution mass spectra (MS) were recorded on a JOEL JMS-AX505HA, JOEL SX-102, or a SCIEX-APIiii spectrometer; LC-MS were recorded on Waters ZQ or PE Sciex Single Quadrupole LC/MS API-150 spectrometers.

Preparative HPLC refers to methods where the material was purified by high performance liquid chromatography on a HPLC ABZ+5 μm column (10 cm×21.2 mm i.d.) with 0.1% formic acid in water and 0.05% formic acid in acetonitrile utilising gradient elution at a flow rate of 8 ml/min and UV detection at 254 nM.

Unless otherwise stated, silica flash column chromatography and Combiflash refers to the purification of material using Redisep™ pre-packed silica flash columns on an ISCO sq16x machine with the stated solvent systems.

Reverse phase HPLC method A refers to methods where the materials were purified by high performance liquid chromatography on an HPLC S-5 μm column (75×30 mm i.d.) utilizing gradient elution with the stated solvent systems and UV detection at 254 nm.

Reverse phase HPLC method B refers to methods where the materials was purified by high performance liquid chromatography on a HPLC Luna C18 (2) 100A column (50×21.2 mm i.d.) utilizing gradient elution with the stated solvent system and UV detection at 254 nm.

| LC-MS Experimental Conditions for PE Sciex Single Quadrupole LC/MS API-150: Liquid Chromatograph: |
| --- |
| System: Shimadzu LC system with SCL-10A Controller and dual UV detector |
| Autosampler: Leap CTC with a Valco six port injector |
| Column: Aquasil/Aquasil (C18 40 × 1 mm) |
| Inj. Volume (μL): 2.0 |
| Solvent A: H2O, 0.02% TFA |
| Solvent B: MeCN, 0.018% TFA |
| Gradient: linear |
| Channel A: UV 214 nm |
| Channel B: ELS |

| Step | Time (min) | Dura. (min) | Flow (μL/min) | Sol. A | Sol. B |
| --- | --- | --- | --- | --- | --- |
| 0 | 0.00 | 0.00 | 300.00 | 95.00 | 5.00 |
| 1 | 0.00 | 0.01 | 300.00 | 95.00 | 5.00 |
| 2 | 0.01 | 3.20 | 300.00 | 10.00 | 90.00 |
| 3 | 3.21 | 1.00 | 300.00 | 10.00 | 90.00 |
| 4 | 4.21 | 0.10 | 300.00 | 95.00 | 5.00 |
| 5 | 4.31 | 0.40 | 300.00 | 95.00 | 5.00 |

Mass Spectrometer: PE Sciex Single Quadrupole LC/MS API-150
Polarity: Positive
Acquisition mode: Profile Intermediates Intermediate 1: 1,1-dimethylethyl 2,3-dihydro-1H-indole-1-carboxylate

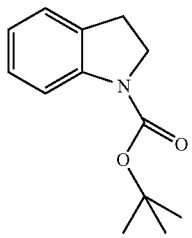

Indoline (10 g, 84 mmol) was dissolved in tetrahydrofuran (100 mL) and di-tert-butylcarbonate (22 g, 0.1 mol) was added. The mixture was left stirring for 16 hours at room temperature under an inert nitrogen atmosphere. The tetrahydrofuran was removed in vacuo and the crude product purified by vacuum distillation to give the title compound (15.1 g) as a clear pale pink oil that crystallised upon standing (temperature: 160-162° C., pressure 1-0.1 mm Hg).

1H NMR (400 MHz, DMSO-D6) δ ppm 1.50 (s, 9H) 3.04 (t, J=8.7 Hz, 2H) 3.89 (t, J=8.8 Hz, 2H) 6.91 (td, J=7.3, 0.8 Hz, 1H) 7.13 (t, J=7.5 Hz, 1H) 7.18 (d, J=7.3 Hz, 1H) 7.5-7.8 (bs, 1H) r.t. 3.44 min.

Intermediate 2: 1-(1,1-dimethylethyl) 7-methyl 2,3-dihydro-1H-indole-1,7-dicarboxylate

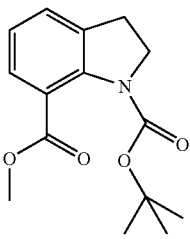

1,1-dimethylethyl 2,3-dihydro-1H-indole-1-carboxylate (5 g, 22.8 mmol) and N,N,N',N'-tetramethyl-1,2-ethanediamine (4.6 mL, 30.5 mmol) was dissolved in dry diethyl ether (300 mL) and cooled to −78° C. in an acetone/dry ice bath. Sec-butyl lithium (1.4 M solution in cyclohexanes, 17.6 mL, 24.6 mmol) was added dropwise over 10 minutes and the reaction left stirring for 90 minutes at this temperature. Methyl chloroformate (8.8 mL, 10.8 g, 0.1 mol) was added to the mixture and the reaction was allowed to warm up to room temperature over 1 hour. Water was added carefully to the mixture and the organic layer separated and washed 3 times with more water. The organic layer was dried over magnesium sulfate, filtered and concentrated in vacuo to give the title compound (4.91 g) as a gummy yellow solid.

1H NMR (400 MHz, DMSO-D6) δ ppm 1.44 (s, 9H) 3.06 (t, J=8.2 Hz, 2H) 3.69 (s, 3H) 4.02 (t, J=8.3 Hz, 2H) 7.06 (t, J=7.5 Hz, 1H) 7.35 (d, J=7.5 Hz, 1H) 7.39 (dd, J=7.4, 1.1 Hz, 1H) MS m/z 278 (M+1)+ r.t. 3.18 min.

Intermediate 3: 1-(1,1-dimethylethyl) 7-methyl 5-bromo-2,3-dihydro-1H-indole-1,7-dicarboxylate

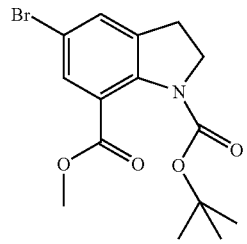

1-(1,1-dimethylethyl) 7-methyl 2,3-dihydro-1H-indole-1, 7-dicarboxylate (3.1 g, 11.2 mmol) and N-bromosuccinimide (2.0 g, 11.2 mmol) were dissolved in dry dichloromethane (100 mL) and stirred under a nitrogen atmosphere at room temperature for 16 hours. The reaction was partitioned with sodium hydroxide solution (2 M), separated and washed with more sodium hydroxide solution. The organic layer was dried over magnesium sulfate and concentrated in vacuo to give the title compound as a gummy red solid (3.55 g).

1H NMR (400 MHz, DMSO-D6) δ ppm 1.41 (s, 9H) 3.09 (t, J=8.3 Hz, 2H) 3.70 (s, 3H) 4.02 (t, J=8.3 Hz, 2H) 7.46 (s, 1H) 7.60 (s, 1H) MS m/z 356/358 (1:1 ratio) (M+1)+ r.t. 3.52 min.

Intermediate 4: methyl 5-bromo-2,3-dihydro-1H-indole-7-carboxylate

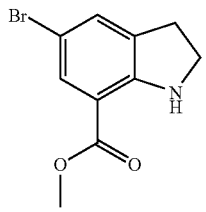

1-(1,1-dimethylethyl) 7-methyl 5-bromo-2,3-dihydro-1H-indole-1,7-dicarboxylate (9 g, 25 mmol) was dissolved in trifluoroacetic acid (6 mL) and stirred at room temperature for 16 hours. Dichloromethane and sodium hydroxide solution (2 M) were added and the organic layer washed twice with sodium hydroxide solution until the aqueous layer pH>7. The organic layer was then concentrated in vacuo to give the title compound as a brown solid (6.5 g).

1H NMR (400 MHz, DMSO-D6) δ ppm 2.99 (t, J=8.5 Hz, 2H) 3.61 (t, J=8.4 Hz, 2H) 3.78 (s, 3H) 6.72 (s, 1H) 7.28 (d, J=1 Hz, 1H) 7.46 (d, J=2 Hz, 1H) MS m/z 256/258 (1:1 ratio) (M+1)$^+$ r.t. 3.32 min.

Intermediate 5: methyl 5-bromo-1H-indole-7-carboxylate

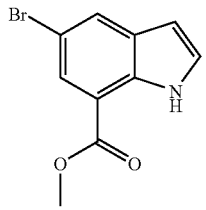

Methyl 5-bromo-2,3-dihydro-1H-indole-7-carboxylate (6.5 g, 25 mmol) was dissolved in tetrahydrofuran (100 mL). Activated manganese dioxide (5 µm particle size, 22 g, 0.25 mol) was added and the mixture stirred at room temperature for 16 hours. A further 22 g of activated manganese dioxide was added and the reaction stirred for 96 hours. The reaction was then filtered through celite and concentrated in vacuo to give the title compound (5.1 g) as a beige solid.

1H NMR (400 MHz, DMSO-D6) δ ppm 3.94 (s, 3H) 6.58 (d, J=3 Hz, 1H) 7.48 (d, J=3 Hz, 1H) 7.8 (d, J=2 Hz, 1H) 8.07 (d, J=1.8 Hz, 1H) 11.39 (bs, 1H) MS m/z 252/254 (1:1 ratio) (M−1) r.t. 3.41 min.

Intermediate 6: 5-bromo-1H-indole-7-carboxylic acid

5-bromo-1H-indole-7-carboxylate (5 g, 19.7 mmol) was dissolved in methanol (200 mL) and a solution of lithium hydroxide (0.99 g, 41 mmol) in water (10 mL) was added. The mixture was heated at reflux for 50 hours. The methanol was removed in vacuo and the residue diluted with aqueous hydrochloric acid (2 M). The resulting precipitate was filtered off and dried in a heated vacuum pistol to give the title compound as a beige solid (4.7 g).

1H NMR (400 MHz, DMSO-D6) δ ppm 6.54 (dd, J=2.0, 3.2 Hz, 1H) 7.42 (t, J=2.8 Hz, 1H) 7.77 (d, J=2 Hz, 1H) 8.03 (d, J=1.8 Hz, 1H) 11.27 (s, 1H) 13.1-13.7 (bs, 1H) MS m/z 238/240 (1:1 ratio) (M−1) r.t. 3.41 min.

Intermediate 7: 5-bromo-1H-indole-7-carboxamide

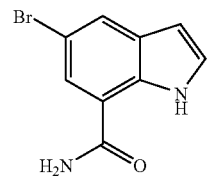

To a solution of 5-bromo-1H-indole-7-carboxylic acid (10.0 g, 42 mmol) in CH$_2$Cl$_2$ (100 mL) at room temperature, EDC (9.66 g, 50.4 mmol), HOBt (6.81 g, 50.4 mmol) and NH$_3$ (2.0 M in MeOH, 84 mL, 168 mmol) were added. The reaction mixture was stirred at room temperature for 16 hours. The solvent was evaporated and the residue partitioned between ethyl acetate (100 mL) and water (100 mL). The water layer was extracted with ethyl acetate (100 mL×2) and the combined organic phase was dried over MgSO$_4$ and concentrated to give the crude product (10 g, 98%). This crude product was used directly in the next step without further purification.

LC/MS: m/z 240.0 (M+H), 1.95 min.

Intermediate 8: 1,1-dimethylethyl 4-[7-(aminocarbonyl)-5-bromo-1H-indol-3-yl]-3,6-dihydro-1(2H)-pyridinecarboxylate

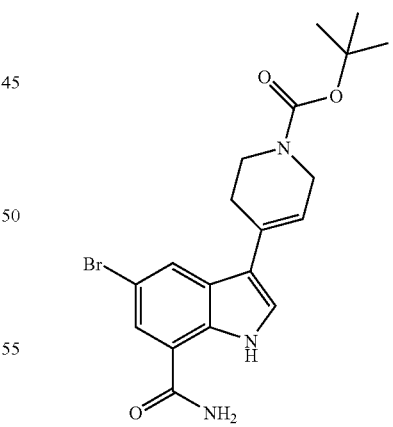

To a solution of 5-bromo-1H-indole-7-carboxamide (10 g, 41.84 mmol) in methanol (5 mL), 1,1-dimethylethyl 4-oxo-1-piperidinecarboxylate (684 mg, 3.42 mmol) and sodium methoxide (0.5 M in THF, 13.7 mL, 6.84 mmol) were added. The reaction mixture was stirred at reflux temperature for 16 hours. All solvent was evaporated under reduced pressure. The residue was partitioned between ethyl acetate (100 mL) and water (100 mL). The combined organic phase was dried over MgSO₄ and concentrated under reduced pressure, and purified by flash column chromatography (ethyl acetate/hexanes, 1/1) to give the desired product (7.4 g, 43
LC/MS: m/z 420.0 (M+H), 2.35 min.

Intermediate 9: 1,1-dimethylethyl 4-[7-(aminocarbonyl)-5-bromo-1H-indol-3-yl]-1-piperidine carboxylate

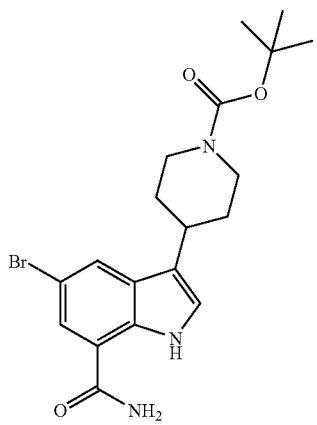

To a solution of 1,1-dimethylethyl 4-[7-(aminocarbonyl)-5-bromo-1H-indol-3-yl]-3,6-dihydro-1(2H)-pyridinecarboxylate (7.41 g, 17.64 mmol) in ethanol (600 mL), platinum oxide (200 mg, 5%) was added. The reaction mixture was hydrogenated under an atmosphere of H₂ for 16 hours. The resulting mixture was filtered through celite and the filtrate was concentrated. The resulting residue was purified by flash column chromatography (Ethyl acetate/hexanes, 1:4 to 2:1 v/v) to give the desired product (3.6 g, 48%).
LC-MS: m/z 422.0 (M+H), 2.25 min.

Intermediate 10:
5-bromo-3-(4-piperidinyl)-1H-indole-7-carboxamide

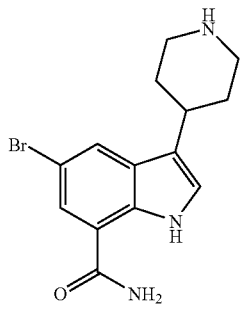

To a solution of 1,1-dimethylethyl 4-[7-(aminocarbonyl)-5-bromo-1H-indol-3-yl]-1-piperidinecarboxylate (1.56 g, 3.7 mmol) in methanol (10 mL), HCl in dioxane (4M, 35.5 mL) was added. The reaction mixture was stirred at room temperature for 2 hours. The solvent was evaporated under reduced pressure and the resulting residue was partitioned between ethyl acetate (50 mL) and 5% of aqueous NaOH (50 mL). The aqueous layer was washed with ethyl acetate (2×50 mL) and the combined organic phases were dried with MgSO₄ and concentrated under reduced pressure to give the desired product (685 mg, 58%), which was used in the next step without further purification.
LC-MS: m/z 322.0 (M+H), 1.45 min.

Intermediate 11: 5-bromo-3-[1-(ethanesulfonyl)-4-piperidinyl]-1H-indole-7-carboxamide

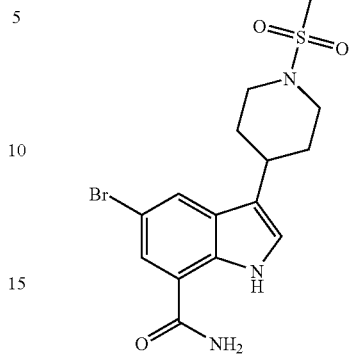

Ethanesulfonyl chloride (4.5 mL, 47.4 mmol) was added dropwise to a solution of 5-bromo-3-(4-piperidinyl)-1H-indole-7-carboxamide hydrochloride (8.49 g, 23.7 mmol) and triethylamine (13.2 mL, 94.7 mmol) in DMF (80 mL) at 0° C. (bath temperature). The reaction mixture was stirred at 0° C. for 45 min. and was then poured into a 2:1 mixture of EtOAc/H₂O (300 mL). The resulting precipitate was filtered off, washed with EtOAc (2×50 mL), and set aside. The EtOAc/H₂O bilayer was separated, and the aqueous layer was extracted with EtOAc (2×100 mL). The combined organic layers were washed with saturated NaCl (1×100 mL), dried (MgSO₄), filtered, and concentrated under reduced pressure. The crude product was combined with the precipitate isolated above and washed with MeOH (1×10 mL) to give 8.19 g of the title compound (83%).

Alternatively, the title compound may be prepared as follows:

To 5-bromo-3-(4-piperidinyl)-1H-indole-7-carboxamide (900 mg, 2.8 mmol) in CH₂Cl₂ (100 mL) at 0° C., ethanesulfonyl chloride (0.8 mg, 8.4 mmol) and triethylamine (1.6 mL, 11.2 mmol) were added. The reaction mixture was stirred at 0° C. for 30 min., after which time the mixture was partitioned between CH₂Cl₂ and water. The aqueous phase was extracted with CH₂Cl₂ (50 mL×2) and the combined organic phase dried over MgSO₄ and concentrated under reduced pressure. The resulting residue was purified by solid phase extraction on a 500 mg aminopropyl column (International Sorbent Technologies) eluting with chloroform (30 mL×2) and ethyl acetate (50 mL) to give 800 mg of the title compound (69%).
LC/MS: m/z 414.0 (M+H), 2.2 min.

Intermediate 12: 3-[1-(ethylsulfonyl)-4-piperidinyl]-5-[3-(hydroxymethyl)phenyl]-1H-indole-7-carboxamide

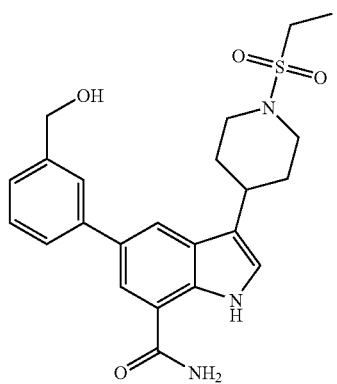

To a solution of 5-bromo-3-[1-(ethylsulfonyl)-4-piperidinyl]-1H-indole-7-carboxamide (20.0 mg, 0.048 mmol), K₃PO₄ (21.0 mg, 0.096 mmol) and [3-(hydroxymethyl)phenyl]boronic acid (30.0 mg, 0.193 mmol) in dioxane/H₂O (2 mL/0.7 mL) was bubbled argon for 5 minutes prior to addition of Pd(PPh₃)₄ (5.0 mg, 0.0048 mmol). The reaction mixture was heated in a microwave reactor (Smith synthesizer) for 20 minutes at 160° C. The solvent was evaporated, and the residue was partitioned between ethyl acetate and water. The organic layer was washed with brine (10 mL), dried over MgSO₄, concentrated, and purified by reverse phase HPLC method A (water/CH₃CN, 0.1% TFA 10-90%) to give the title compound (9.7 mg, 46%).

1H NMR (400 MHz, DMSO-D6) δ ppm 1.25 (t, J=7.2 Hz, 3H), 1.65 (m, 2H), 2.02 (m, 2H), 2.99 (m, 7H), 3.71 (m, 2H), 7.16 (s, 1H), 7.42 (m, 3H), 7.77 (m, 2H), 8.02 (m, 2H), 8.22 (m, 1H), 10.91 (s, 1H).

LC/MS: m/z 442.4 (M+H), r.t: 1.73 min.

Intermediate 13: 3-[1-(ethylsulfonyl)-4-piperidinyl]-5-(3-formylphenyl)-1H-indole-7-carboxamide

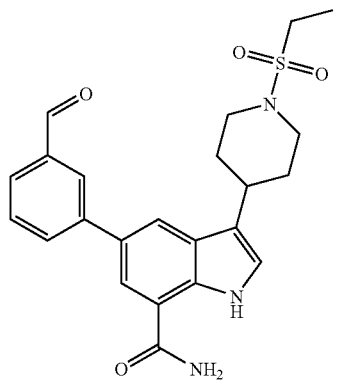

To a solution of 3-[1-(ethylsulfonyl)-4-piperidinyl]-5-[3-(hydroxymethyl)phenyl]-1H-indole-7-carboxamide (52.0 mg, 0.120 mmol) in THF (10 mL), MnO₂ (360.0 mg, 3.5 mmol) was added at ambient temperature. The resulting suspension was stirred overnight, filtered through celite, and the solid rinsed with THF (3×10 mL). The filtrate was concentrated to give the title compound (51.0 mg, 98%) which was used in the next step without purification.

LC/MS: m/z 440.4 (M+H), r.t: 1.97 min.

Intermediate 14: 3-[1-(ethylsulfonyl)-4-piperidinyl]-5-[4-(hydroxymethyl)phenyl]-1H-indole-7-carboxamide

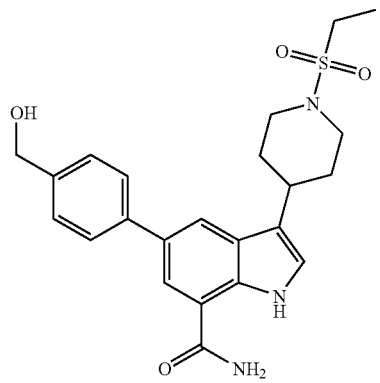

To a solution of 5-bromo-3-[1-(ethylsulfonyl)-4-piperidinyl]-1H-indole-7-carboxamide (20.0 mg, 0.048 mmol), K₃PO₄ (21.0 mg, 0.096 mmol) and [4-(hydroxymethyl)phenyl]boronic acid (30.0 mg, 0.193 mmol) in dioxane/H₂O (2 mL/0.7 mL) was bubbled argon for 5 minutes prior to addition of Pd(PPh₃)₄ (5.0 mg, 0.0048 mmol). The reaction mixture was heated in a microwave reactor (Smith synthesizer) for 20 minutes at 160° C. The solvent was evaporated, and the residue was partitioned between ethyl acetate and water. The organic layer was washed with brine (10 mL), dried over MgSO₄, filtered, concentrated, and purified by reverse phase HPLC method A (water/CH₃CN, 0.1% TFA 10-90%) to give the title compound (6.4 mg, 30%).

LC/MS: m/z 442.4 (M+H), r.t: 1.78 min.

Intermediate 15: 3-[1-(ethylsulfonyl)-4-piperidinyl]-5-(4-formylphenyl)-1H-indole-7-carboxamide

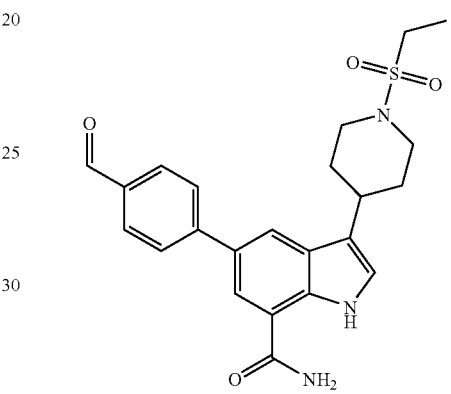

To a solution of 3-[1-(ethylsulfonyl)-4-piperidinyl]-5-[4-(hydroxymethyl)phenyl]-1H-indole-7-carboxamide (25 mg, 0.058 mmol) in THF (5 mL), MnO₂ (160.0 mg, 1.73 mmol) was added at ambient temperature. The resulting suspension was stirred overnight, filtered through celite, and the solid rinsed with THF (3×10 mL). The filtrate was concentrated to give the title compound (15 mg, 58%) which was used in the next step without purification.

LC/MS: m/z 440.4 (M+H), r.t: 2.02 min.

Intermediate 16: 3-[1-(ethylsulfonyl)-4-piperidinyl]-5-(4,4,5,5-tetramethyl-1,3,2-dioxaborolan-2-yl)-1H-indole-7-carboxamide

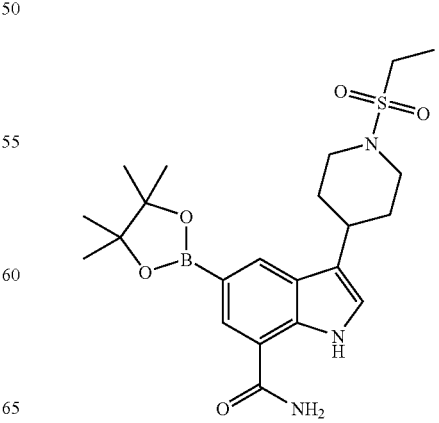

To a solution of 5-bromo-3-[1-(ethylsulfonyl)-4-piperidinyl]-1H-indole-7-carboxamide (1.0 g, 2.42 mmol), Bis(pinacolato)diborane (2.45 g, 9.66 mmol) and potassium carbonate (2.10 g, 21.8 mmol) in DME (15.0 mL) was added Pd$_2$Cl$_2$(dppf) after degassing for 5 min. The mixture was then heated in the microwave at 130° C. for 11000 sec. Reaction mixture was then diluted with EtOAc (300 mL) and H$_2$O (100 mL) and solid was filtered. The organic layer was then washed with H$_2$O (3×80 mL) and brine. Organic layer was dried over MgSO$_4$ and concentrated. DCM (40 mL) was then added to remove any by-product to afford 2.4 g of the title compound.
LC/MS: m/z 462.3 (M+H), r.t: 2.03 min.

Intermediate 17: 3-[1-(ethylsulfonyl)-4-piperidinyl]-5-(5-formyl-2-thienyl)-1H-indole-7-carboxamide

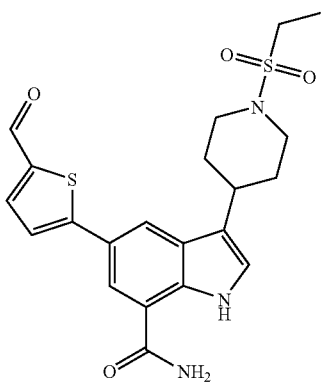

To a solution of 5-bromo-3-[1-(ethylsulfonyl)-4-piperidinyl]-1H-indole-7-carboxamide (200 mg, 0.49 mmol) in dioxane (4.5 mL) and H$_2$O (1.5 mL) was added [5-(hydroxymethyl)-2-thienyl]boronic acid (232 mg, 1.47 mmol), potassium carbonate (406 mg, 2.94 mmol) and tetrakis(triphenylphosphine)palladium (0) (57 mg, 0.049 mmol). Reaction was run in the microwave at 150° C. for 20 min. Aqueous work-up with EtOAc/H$_2$O gave 447 mg of 3-[1-(ethylsulfonyl)-4-piperidinyl]-5-[5-(hydroxymethyl)-2-thienyl]-1H-indole-7-carboxamide.

To a solution of 3-[1-(ethylsulfonyl)-4-piperidinyl]-5-[5-(hydroxymethyl)-2-thienyl]-1H-indole-7-carboxamide (200 mg, 0.46 mmol) in THF (5.0 mL) was added MnO$_2$ (1.21 g, 13.9 mmol). The mixture was stirred at room temperature for 3 h. Filtration of reaction mixture thru celite afforded 100 mg of the title compound (48.8%)
LC/MS: m/z 446.2 (M+H), r.t: 2.27 min.

Intermediate 18: 3-[1-(ethylsulfonyl)-4-piperidinyl]-5-(4-formyl-2-thienyl)-1H-indole-7-carboxamide

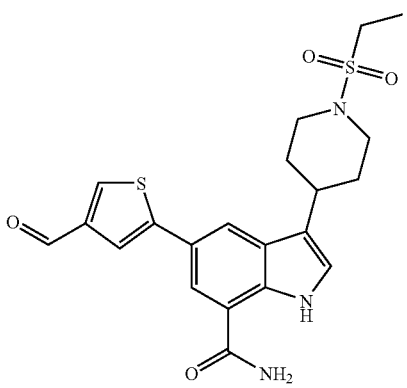

To a solution of 3-thiophenecarbaldehyde (3.0 g, 26.8 mmol) in DCM (54 mL) was added aluminum trichloride (8.37 g, 63 mmol) at 0° C. The reaction was then heated to reflux and bromine (1.6 mL, 30.28 mmol) was added dropwise. After addition, the reaction mixture was stirred at reflux for 4 h. After cooling to room temperature, cold H$_2$O (100 mL) was added and extracted with DCM (2×100 mL). The combined organic layer was washed with NaHCO3 and dried. It was purified by flash chromatography to give 3.62 g of 5-bromo-3-thiophenecarbaldehyde (71%).

To a solution of 5-bromo-3-thiophenecarbaldehyde (250 mg, 1.29 mmol) in dioxane (4.5 mL) and H$_2$O (1.5 mL) was added 3-[1-(ethylsulfonyl)-4-piperidinyl]-5-(4,4,5,5-tetramethyl-1,3,2-dioxaborolan-2-yl)-1H-indole-7-carboxamide (200 mg, 0.43 mmol), potassium carbonate (250 mg, 2.58 mmol) and tetrakis(triphenylphosphine)palladium (0) (56 mg, 0.049 mmol). The reaction was run in the microwave at 150° C. for 20 min. It was then treated with EtOAc and H$_2$O to obtain the crude product. This was then treated with MeOH (10 mL) and the solid was filtered and collected to give 310 mg of the desired title compound.
LC/MS: m/z 446.4 (M+H), r.t: 1.94 min.

Intermediate 19: 3-[1-(ethylsulfonyl)-4-piperidinyl]-5-(5-formyl-3-thienyl)-1H-indole-7-carboxamide

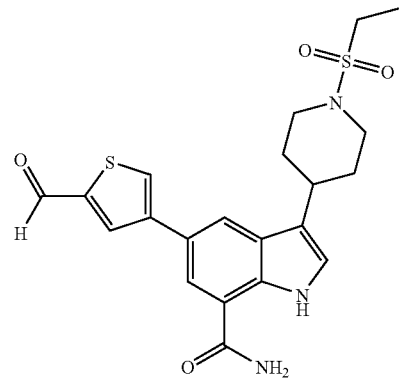

To a solution of 4-bromo-2-thiophenecarbaldehyde (1.0 g, 4.48 mmol) in DME (16 mL) was added Bis(pinacolato)diborane (1.48 g, 5.82 mmol), KOAc (1.14 g, 5.11 mmol) and Pd$_2$Cl$_2$(dppf) (106 mg, 0.448 mmol). The reaction was run in the microwave at 150° C. for 20 min. The solvent was concentrated and an aqueous work-up was performed using EtOAc and H$_2$O. The compound was purified by flash chromatography using hexanes and EtOAc to give 1.8 g of 4-(4,4,5,5-tetramethyl-1,3,2-dioxaborolan-2-yl)-2-thiophenecarbaldehyde.

To a solution of 5-bromo-3-[1-(ethylsulfonyl)-4-piperidinyl]-1H-indole-7-carboxamide (909 mg, 2.2 mmol) in dioxane (7.5 mL) and H$_2$O (2.5 mL) was added 4-(4,4,5,5-tetramethyl-1,3,2-dioxaborolan-2-yl)-2-thiophenecarbaldehyde (1.57 g, 6.6 mmol), potassium carbonate (1.82 g, 13.2 mmol), and tetrakis(triphenylphospine)palladium (0) (30 mg, 0.22 mmol). The reaction was heated in the microwave at 150° C. for 20 min. The mixture was then concentrated to dryness. EtOAc (50 mL) was added to the residue and washed with brine. The precipitate which formed between the water and organic layer was filtered and collected as a brown solid to give 874 mg of the title compound (89%).
LC/MS: m/z 446.4 (M+H), r.t: 1.93 min.

Intermediate 20: 5-Bromoisoindoline

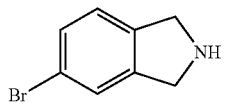

In a dried 50 mL two necked round-bottom flask equipped with an addition funnel and CaCl₂ drying tube was placed 2.0 g (13.6 mmol) of phthalimide. The flask was then cooled to 0° C. in a salt and ice bath. An ice cold mixture of concentrated sulfuric acid and fuming nitric acid (1:1 v/v) 8 mL was gradually added with constant stirring. The mixture was then stirred for 30 min. at 0° C. and allowed to slowly warm to room temperature with stirring over a period of 1 h. The reaction mixture was then poured into ice. The resulting solid product was filtered and dried to give 1.6 g (61.3%) of 5-nitro-1H-isoindole-1,3(2H)-dione as a yellow colour solid.

To a solution of 5-nitro-1H-isoindole-1,3(2H)-dione (1.0 g, 5.2 mmol) in dry THF (15 mL) was added 10% Pd/C (0.2 g). The mixture was hydrogenated at 30-40 psi for 17 h. The catalyst was filtered, and the filtrate was evaporated under vacuo to give 0.5 g (59.3%) of 5-amino-1H-isoindole-1,3 (2H)-dione as a yellow colour solid.

To a stirred solution of 5-amino-1H-isoindole-1,3(2H)-dione (1.0 g, 6.2 mmol) dissolved in sulfuric acid solution (2 mL of Con. H₂SO₄ in 7.5 mL of H₂O) at 0° C., was added ice cold sodium nitrite solution (0.8 g in 2 mL of H₂O) dropwise. After 45 min of stirring at 0° C., CuBr (3.4 g, 23.7 mmol) and HBr[48%] (13.6 mL, 4 vol. w.r.t. CuBr) were added at the same temperature. The resulting mixture was stirred at 80° C. for 8 h then poured into crushed ice. Filtered the solid, washed with ice cold water and dried thoroughly to give 0.6 g (43.0%) of 5-bromo-1H-isoindole-1,3(2H)-dione as a brown colour solid.

In a dried 500 mL three necked round bottom flask equipped with a reflux condenser and addition funnel was taken BH₃-THF (160 mL) solution with dry THF (50 mL). The mixture was cooled to 0° C. To this cold solution 5-bromo-1H-isoindole-1,3(2H)-dione (8.0 g, 35.4 mmol) in dry THF (100 mL) was added gradually and allowed to warm to room temperature. After 10 min at room temperature the mixture was refluxed for 16 h. The reaction mixture was then cooled to 0° C. and quenched with methanol. (Caution: vigorous foaming will occur). 20-30 mL of 2N HCL was added and refluxed the mixture for 1 h. Cooled the mixture and basified with NaOH solution and extracted with ethyl acetate. Combined organic extracts were washed with water, saturated NaCl solution, dried over Na₂SO₄ and concentrated under vacuo. To the crude product in MeOH (150 mL), Et₃N (12 mL) and di-tert-butyl dicarbonate (13.8 g, 63.23 mmol) were added and stirred at room temperature for 16 h. The reaction mixture was then concentrated under vacuo. The crude product was diluted with CH₂Cl₂ (200 mL), washed with water, saturated NaCl solution, and dried over Na₂SO₄. Crude product was purified by column chromatography using 20% ethyl acetate in hexanes as eluant to afford a colourless solid. To this dioxane-HCl was added at room temperature and stirred for 10 min, the solid obtained was then filtered and dried to give 3.0 g (42.8%) of 5-bromoisoindoline hydrochloride salt as an ash colour solid.

Intermediate 21: 5-bromo-3-(4-piperidinyl)-1H-indole-7-carboxamide hydrochloride

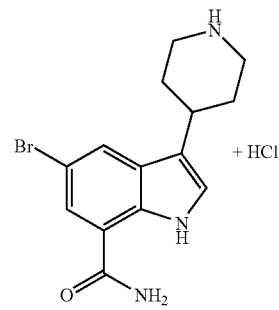

A 4M solution of HCl in dioxane (194 mL) was added to a solution of 1,1-dimethylethyl 4-[7-(aminocarbonyl)-5-bromo-1H-indol-3-yl]-1-piperidinecarboxylate (10 g, 23.7 mmol) in methanol (50 mL). The reaction mixture was stirred at room temperature for 4 hours, and the solvent was evaporated under reduced pressure to give the title compound (9.5 g), which was used in the next step without further purification.

LC-MS: m/z 322.4 (M+H), 1.40 min.

Intermediate 22: 5-bromo-3-{1-[(1-methylethyl)sulfonyl]-4-piperidinyl}-1H-indole-7-carboxamide

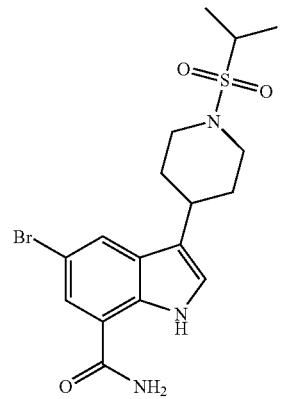

Triethylamine (2.6 mL, 18.7 mmol) was added to a solution of 5-bromo-3-(4-piperidinyl)-1H-indole-7-carboxamide hydrochloride in DMF (15 mL) at 0° C. The mixture was stirred at room temperature for 10 min, and 2-propanesulfonyl chloride (1.04 mL, 9.32 mmol) was added. Stirring continued for another 30 min, and the reaction mixture was diluted with 1:1 EtOAc/H₂O (200 mL). The layers were separated, and the aqueous layer was extracted with EtOAc (2×50 mL). The combined organic layers were washed with saturated NaCl (1×100 mL), dried (MgSO₄), and concentrated under reduced pressure. The crude product was washed with MeOH (2×10 mL) to give the title compound (1.5 g, 75%).

LC/MS: m/z 427.8 (M+H), 1.98 min.

Intermediate 23: 5-(5-formyl-3-thienyl)-3-{1-[(1-methylethyl)sulfonyl]-4-piperidinyl}-1H-indole-7-carboxamide

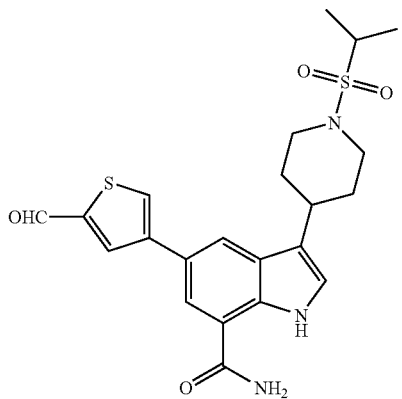

The boronate ester used to make the title compound was prepared in 6 separate equal batches according to the following procedure: To a solution of 4-bromo-2-thiophenecarbaldehyde (1.0 g, 4.48 mmol) in DME (20 mL) was added bis(pinacolato)diborane (1.48 g, 5.82 mmol), KOAc (1.14 g, 5.11 mmol) and $Pd_2Cl_2(dppf)$ (106 mg, 0.448 mmol). The reactions were run in a Smith microwave at 150° C. for 20 min. The 6 reactions were pooled and concentrated under reduced pressure. The residue was taken up in EtOAc (200 mL) and $H_2O$ (50 mL). The layers were separated, the organic layer was washed with saturated NaCl (1×50 mL), dried ($Na_2SO_4$), and concentrated under reduced pressure. The crude product was purified by flash chromatography eluting with hexanes/EtOAc to give 4-(4,4,5,5-tetramethyl-1,3,2-dioxaborolan-2-yl)-2-thiophenecarbaldehyde (5 g, 78%).

A solution of 5-bromo-3-{1-[(1-methylethyl)sulfonyl]-4-piperidinyl}-1H-indole-7-carboxamide (428 mg, 1 mmol), 4-(4,4,5,5-tetramethyl-1,3,2-dioxaborolan-2-yl)-2-thiophenecarbaldehyde (960 mg, 4 mmol), $Cs_2CO_3$ (800 mg, 2.46 mmol), and $Pd(PPh_3)_4$ (100 mg, 0.0865 mmol) were heated in a Smith microwave at 160° C. for 20 min. The reaction mixture was filtered and concentrated under reduced pressure. The crude product was washed with MeOH (1×5 mL) to give the title compound (395 mg, 86%).

LC/MS: m/z 460.4 (M+H), 1.98 min.

EXAMPLES

Example 1

3-[1-(ethylsulfonyl)-4-piperidinyl]-5-[3-(1-piperidinylmethyl)phenyl]-1H-indole-7-carboxamide

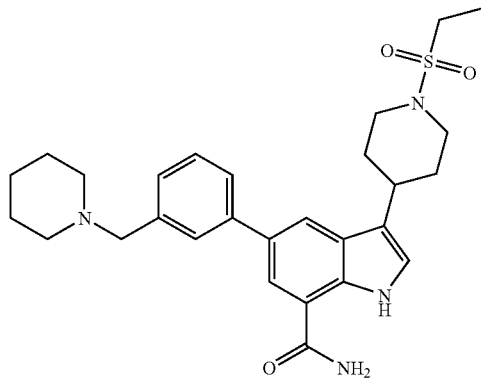

To a solution of 3-[1-(ethylsulfonyl)-4-piperidinyl]-5-(3-formylphenyl)-1H-indole-7-carboxamide (15.0 mg, 0.034 mmol) in DCM (2 mL) was added piperidine (4.0 ul, 0.04 mmol). The reaction solution was stirred at ambient temperature for 1 hr prior to addition of $NaBH(OAc)_3$ (23.0 mg, 0.109 mmol). The resulting mixture was stirred overnight at ambient temperature after which time the solvent was removed under reduced pressure. The resulting residue was dissolved in 1.2 mL DMSO and all undissolved solid was filtered off. This DMSO solution of crude product was purified by reverse phase HPLC ($H_2O/CH_3CN$, 0.1% TFA 10-90%) to give the title compound (8.8 mg, 50.5%).

LC/MS: m/z 509.4 (M+H), r.t: 1.87 min.

Example 2

3-[1-(ethylsulfonyl)-4-piperidinyl]-5-[3-(1-piperazinylmethyl)phenyl]-1H-indole-7-carboxamide

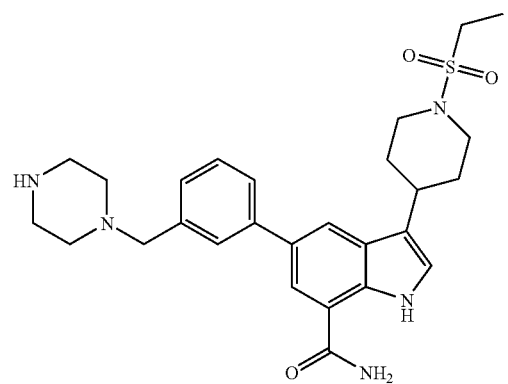

Following the general procedure of example 1, 3-[1-(ethylsulfonyl)-4-piperidinyl]-5-(3-formylphenyl)-1H-indole-7-carboxamide (15.0 mg, 0.034 mmol), piperazine (3.5 mg, 0.04 mmol) and $NaBH(OAc)_3$ (23.0 mg, 0.102 mmol) were reacted to give the title compound (3.4 mg, 19.7%).

LC/MS: m/z 510.2 (M+H), r.t: 1.43 min.

Example 3

3-[1-(ethylsulfonyl)-4-piperidinyl]-5-[3-(4-morpholinylmethyl)phenyl]-1H-indole-7-carboxamide

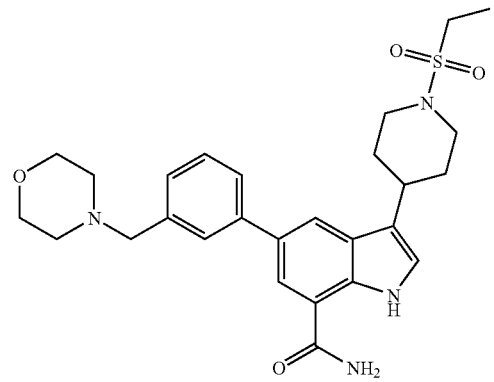

Following the general procedure of example 1, 3-[1-(ethylsulfonyl)-4-piperidinyl]-5-(3-formylphenyl)-1H-indole-7-carboxamide (15.0 mg, 0.034 mmol), morpholine (3.5 ul, 0.04 mmol) and NaBH(OAc)₃ (23.0 mg, 0.102 mmol) were reacted to give the title compound (7.5 mg, 43%).

LC/MS: m/z 511.2 (M+H), r.t: 1.58 min.

Alternatively, example 3 may be prepared as follows:

To a solution of 3-[1-(ethylsulfonyl)-4-piperidinyl]-5-(3-formylphenyl)-1H-indole-7-carboxamide (20 mg, 0.046 mmol) in dichloromethane (1.5 mL) and methanol (1.5 mL) was added morpholine (0.070 mL, 0.276 mmol) and 1 drop of acetic acid. This mixture was stirred for 2 h at room temperature and then sodium borohydride (11 mg, 0.276 mmol) was added. After 30 min the mixture was poured onto an SCX cartridge (5.0 g), and EtOAc (10.0 mL) and MeOH (10.0 mL) were used to flush the cartridge. A 2 M solution of NH₃/MeOH (10.0 mL) was used to elute the product and was then concentrated. The residue was dissolved in dimethyl sulfoxide (1.0 mL) and purified by Gilson Preparatory HPLC to give the title compound (17.6 mg, 75%).

Example 4

3-[1-(ethylsulfonyl)-4-piperidinyl]-5-[3-({methyl[2-(methylsulfonyl)ethyl]amino}methyl)phenyl]-1H-indole-7-carboxamide

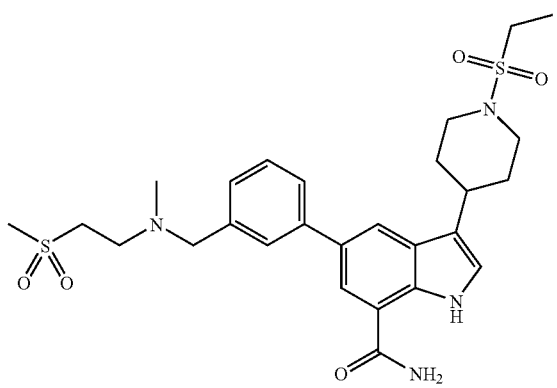

Following the general procedure of example 1, 3-[1-(ethylsulfonyl)-4-piperidinyl]-5-(3-formylphenyl)-1H-indole-7-carboxamide (42.0 mg, 0.096 mmol), N-methyl-2-(methylsulfonyl)ethanamine (12.0 mg, 0.087 mmol) and NaBH(OAc)₃ (58.0 mg, 0.261 mmol) were reacted to give the title compound (15.1 mg, 28.0%).

LC/MS: m/z 561.2 (M+H), r.t: 1.58 min.

Example 5

5-(3-{[[2-(dimethylamino)ethyl](methyl)amino]methyl}phenyl)-3-[1-(ethylsulfonyl)-4-piperidinyl]-1H-indole-7-carboxamide

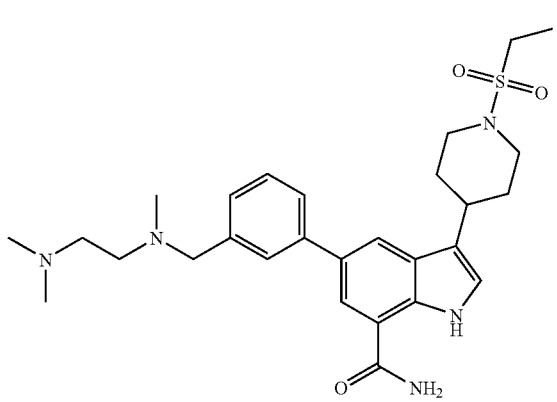

To a solution of 3-[1-(ethylsulfonyl)-4-piperidinyl]-5-(3-formylphenyl)-1H-indole-7-carboxamide (45.0 mg, 0.101 mmol) in DCM (2 mL) was added N,N,N'-trimethyl-1,2-ethanediamine (116 ul, 0.90 mmol). The reaction solution was stirred at ambient temperature for 1 hr prior to addition of NaBH(OAc)₃ (69 mg, 0.326 mmol). The resulting mixture was stirred overnight at ambient temperature, and additional NaBH(OAc)₃ (128 mg, 0.606 mmol) was added. The reaction was stirred for another 2 h, after which time the solvent was removed under reduced pressure. The crude product was purified by reverse phase HPLC (water/CH₃CN, 0.1% TFA 10-90%) to give the title compound (16.0 mg, 29.6%).

LC/MS: m/z 526.8 (M+H), r.t: 1.28 min.

Example 6

3-[1-(ethylsulfonyl)-4-piperidinyl]-5-{3-[(4-{2-[(2-hydroxyethyl)oxy]ethyl}-1-Piperazinyl)methyl]phenyl}-1H-indole-7-carboxamide

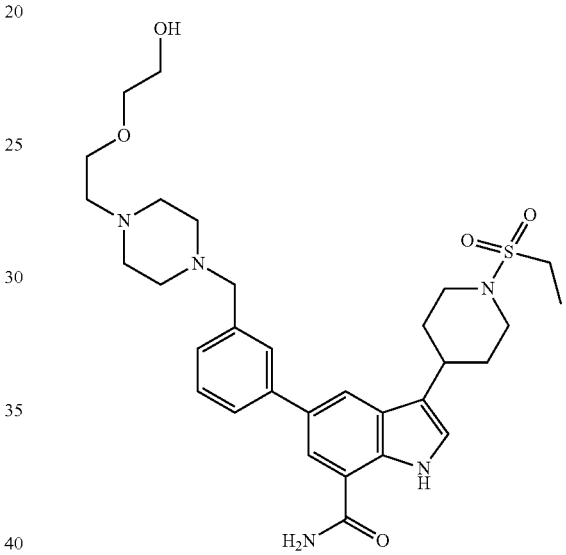

Following the general procedure of example 1, 3-[1-(ethylsulfonyl)-4-piperidinyl]-5-(3-formylphenyl)-1H-indole-7-carboxamide (50.0 mg, 0.112 mmol), 2-{[2-(1-piperazinyl)ethyl]oxy}ethanol (150 mg, 0.87 mmol) and NaBH(OAc)₃ (58.0 mg, 0.303 mmol) were reacted to give the title compound (16.7 mg, 25%).

LC/MS: m/z 598.4 (M+H), r.t: 1.48 min.

Example 7

3-[1-(ethylsulfonyl)-4-piperidinyl]-5-(3-{[3-(hydroxymethyl)-1-piperidinyl]methyl}phenyl)-1H-indole-7-carboxamide

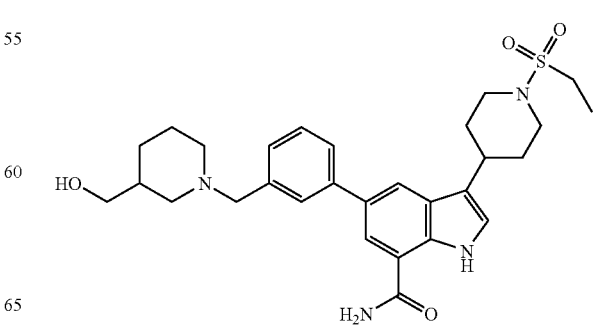

Following the general procedure of example 1, 3-[1-(ethylsulfonyl)-4-piperidinyl]-5-(3-formylphenyl)-1H-indole-7-carboxamide (50.0 mg, 0.112 mmol), 3-piperidinylmethanol (98.9 mg, 0.86 mmol) and NaBH(OAc)₃ (58.0 mg, 0.303 mmol) were reacted to give the title compound (10.2 mg, 17%).

LC/MS: m/z 539.4 (M+H), r.t: 1.52 min.

Example 8

5-[3-({bis[2-(methyloxy)ethyl]amino}methyl)phenyl]-3-[1-(ethylsulfonyl)-4-piperidinyl]-1H-indole-7-carboxamide

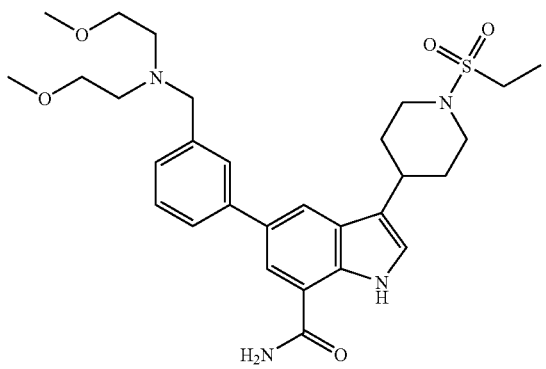

Following the general procedure of example 1, 3-[1-(ethylsulfonyl)-4-piperidinyl]-5-(3-formylphenyl)-1H-indole-7-carboxamide (50.0 mg, 0.112 mmol), 2-(methyloxy)-N-[2-(methyloxy)ethyl]ethanamine (114.3 mg, 0.86 mmol) and NaBH(OAc)₃ (58.0 mg, 0.303 mmol) were reacted to give the title compound (10.5 mg, 16%).

LC/MS: m/z 557.6 (M+H), r.t: 1.62 min.

Example 9

5-{3-[(2,6-dimethyl-4-morpholinyl)methyl]phenyl}-3-[1-(ethylsulfonyl)-4-piperidinyl]-1H-indole-7-carboxamide

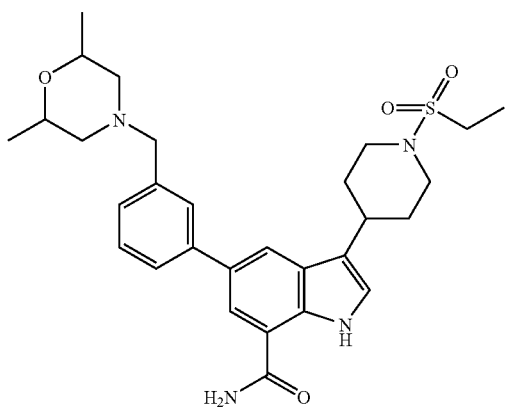

Following the general procedure of example 1, 3-[1-(ethylsulfonyl)-4-piperidinyl]-5-(3-formylphenyl)-1H-indole-7-carboxamide (50.0 mg, 0.112 mmol), 2,6-dimethylmorpholine (98.9 mg, 0.86 mmol) and NaBH(OAc)₃ (58.0 mg, 0.303 mmol) were reacted to give the title compound (19.6 mg, 32%).

LC/MS: m/z 539.2 (M+H), r.t: 1.75 min.

Example 10

3-[1-(ethylsulfonyl)-4-piperidinyl]-5-(3-{[2-(1,3-thiazol-2-yl)-1-pyrrolidinyl]methyl}phenyl)-1H-indole-7-carboxamide

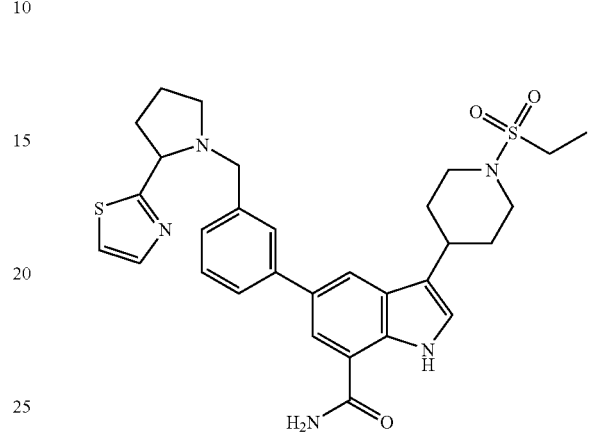

Following the general procedure of example 1, 3-[1-(ethylsulfonyl)-4-piperidinyl]-5-(3-formylphenyl)-1H-indole-7-carboxamide (50.0 mg, 0.112 mmol), 2-(2-pyrrolidinyl)-1,3-thiazole (132.4 mg, 0.86 mmol) and NaBH(OAc)₃ (58.0 mg, 0.303 mmol) were reacted to give the title compound (20.0 mg, 30.4%).

LC/MS: m/z 578.6 (M+H), r.t: 1.57 min.

Example 11

3-[1-(ethylsulfonyl)-4-piperidinyl]-5-(3-{[2-(2-thienyl)-1-pyrrolidinyl]methyl}phenyl)-1H-indole-7-carboxamide

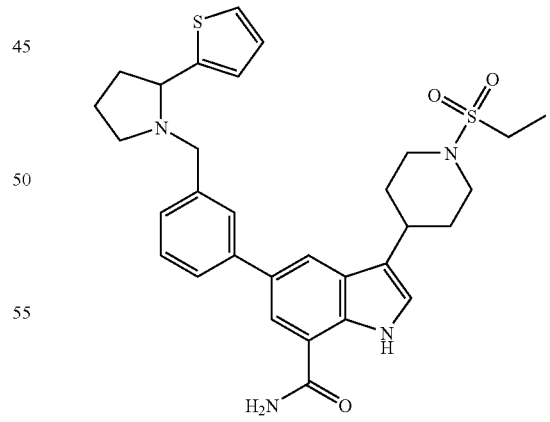

Following the general procedure of example 1, 3-[1-(ethylsulfonyl)-4-piperidinyl]-5-(3-formylphenyl)-1H-indole-7-carboxamide (50.0 mg, 0.112 mmol), 2-(2-thienyl)pyrrolidine (132.4 mg, 0.86 mmol) and NaBH(OAc)₃ (58.0 mg, 0.303 mmol) were reacted to give the title compound (20.0 mg, 30.4%).

LC/MS: m/z 577.4 (M+H), r.t: 1.78 min.

Example 12

3-[1-(ethylsulfonyl)-4-piperidinyl]-5-(3-{[(2-hydroxy-2-phenylethyl)-(methyl)amino]methyl}phenyl)-1H-indole-7-carboxamide

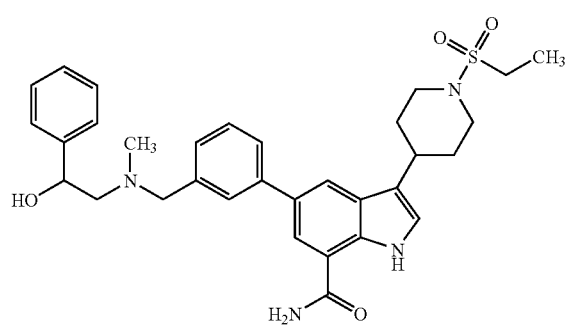

Following the general procedure of example 1, 3-[1-(ethylsulfonyl)-4-piperidinyl]-5-(3-formylphenyl)-1H-indole-7-carboxamide (50.0 mg, 0.112 mmol), 2-(methylamino)-1-phenylethanol (129.9 mg, 0.86 mmol) and NaBH(OAc)$_3$ (58.0 mg, 0.303 mmol) were reacted to give the title compound (22.1 mg, 36.6%).

LC/MS: m/z 575.4 (M+H), r.t: 1.66 min.

Example 13

5-(3-{[ethyl(methyl)amino]methyl}phenyl)-3-[1-(ethylsulfonyl)-4-piperidinyl]-1H-indole-7-carboxamide

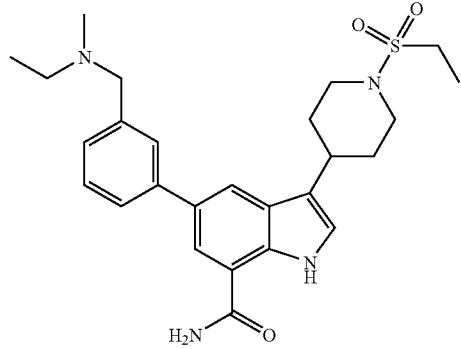

Following the general procedure of example 1, 3-[1-(ethylsulfonyl)-4-piperidinyl]-5-(3-formylphenyl)-1H-indole-7-carboxamide (50.0 mg, 0.112 mmol), N-methylethanamine (50.7 mg, 0.86 mmol) and NaBH(OAc)$_3$ (58.0 mg, 0.303 mmol) were reacted to give the title compound (11.5 mg, 21%).

LC/MS: m/z 483.4 (M+H), r.t: 1.57 min.

Example 14

5-[3-(aminomethyl)phenyl]-3-[1-(ethylsulfonyl)-4-piperidinyl]-1H-indole-7-carboxamide

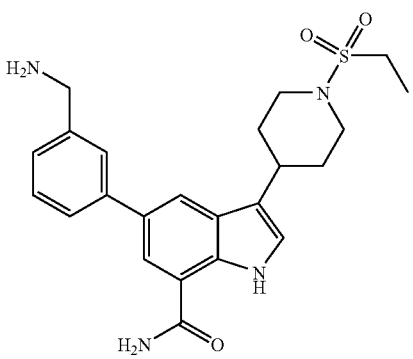

To a solution of 5-bromo-3-[1-(ethylsulfonyl)-4-piperidinyl]-1H-indole-7-carboxamide (30.0 mg, 0.072 mmol), Cs$_2$CO$_3$ (95 mg, 0.290 mmol) and 1-[3-(4,4,5,5-tetramethyl-1,3,2-dioxaborolan-2-yl)phenyl]methanamine (82 mg, 0.350 mmol) in dioxane/H$_2$O (2 mL/0.7 mL) was bubbled argon for 5 minutes prior to addition of Pd(PPh$_3$)$_4$ (7.5 mg, 0.0072 mmol). The reaction mixture was heated in a microwave reactor (Smith synthesizer) for 20 minutes at 160° C. The solvent was evaporated, and the residue was partitioned between ethyl acetate and water. The organic layer was washed with brine (10 mL), dried over MgSO$_4$, filtered, concentrated, and purified by reverse phase HPLC method A (water/CH$_3$CN, 0.1% TFA 10-90%) to give the title compound (2.7 mg, 8.5%).

LC/MS: m/z 441.4 (M+H), r.t: 1.54 min.

Example 15

5-{3-[(cyclopentylamino)methyl]phenyl}-3-[1-(ethylsulfonyl)-4-piperidinyl]-1H-indole-7-carboxamide

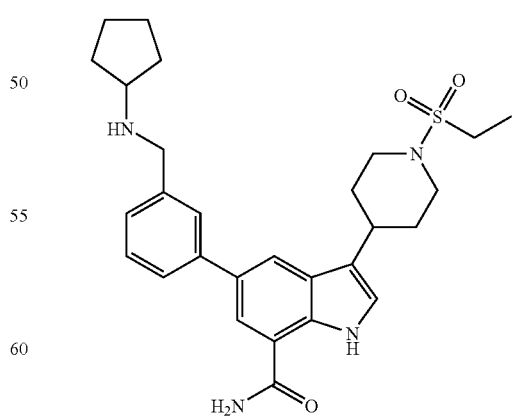

Following the general procedure of example 5, 3-[1-(ethylsulfonyl)-4-piperidinyl]-5-(3-formylphenyl)-1H-indole-7-carboxamide (45 mg, 0.101 mmol), cyclopentylamine (90 uL, 0.090 mmol) and NaBH(OAc)₃ (197 mg, 0.93 mmol) were reacted to give the title compound (33.0 mg, 64%).
LC/MS: m/z 509.4 (M+H), r.t: 1.64 min.

Example 16

5-[3-({[(3,4-dihydroxyphenyl)methyl]amino}methyl)phenyl]-3-[1-(ethylsulfonyl)-4-piperidinyl]-1H-indole-7-carboxamide

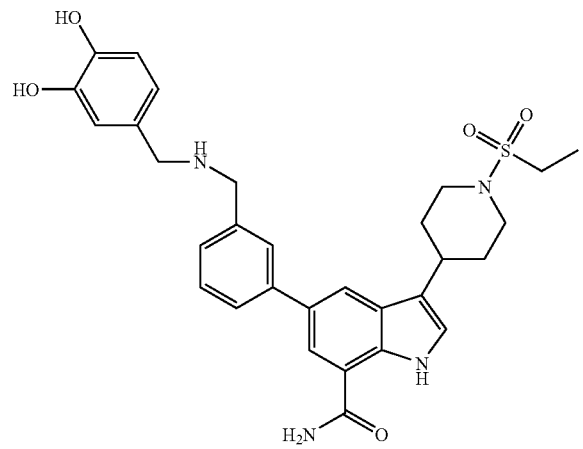

To a solution of 3-[1-(ethylsulfonyl)-4-piperidinyl]-5-(3-formylphenyl)-1H-indole-7-carboxamide (50 mg, 0.114 mmol) in dichloroethane (2 mL) was added 4-(aminomethyl)-1,2-benzenediol (12.1 mg, 0.087 mmol). The reaction solution was stirred at ambient temperature for 10 min prior to addition of NaBH(OAc)₃ (58 mg, 0.261 mmol). The resulting mixture was shaken overnight at ambient temperature after which time the solvent was removed under reduced pressure. The crude product was purified by reverse phase HPLC (water/CH₃CN, 0.1% TFA 10-90%) to give the title compound (7.4 mg, 12%).
LC/MS: m/z 563.2 (M+H), r.t: 1.67 min.

Example 17

3-[1-(ethylsulfonyl)-4-piperidinyl]-5-(3-{[(3-thienylmethyl)amino]methyl}phenyl)-1H-indole-7-carboxamide

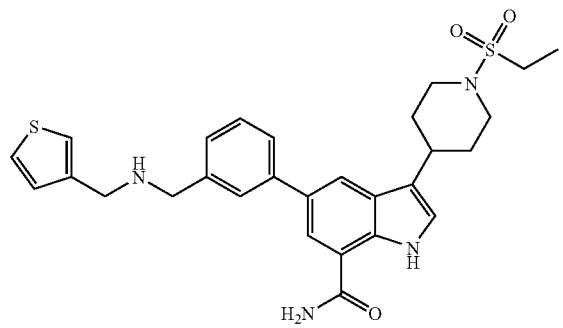

Following the general procedure of example 16, 3-[1-(ethylsulfonyl)-4-piperidinyl]-5-(3-formylphenyl)-1H-indole-7-carboxamide (50 mg, 0.114 mmol), 1-(3-thienyl)methanamine (9.83 mg, 0.087 mmol) and NaBH(OAc)₃ (58 mg, 0.261 mmol) were reacted to give the title compound (4.7 mg, 7.8%).
LC/MS: m/z 537.2 (M+H), r.t: 1.62 min.

Example 18

3-[1-(ethylsulfonyl)-4-piperidinyl]-5-[3-({[(1R)-1-(hydroxymethyl)-2-methylpropyl]amino}methyl)phenyl]-1H-indole-7-carboxamide

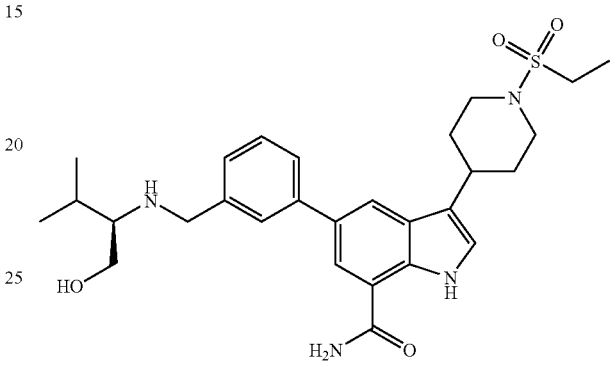

Following the general procedure of example 16, 3-[1-(ethylsulfonyl)-4-piperidinyl]-5-(3-formylphenyl)-1H-indole-7-carboxamide (50 mg, 0.114 mmol), (2R)-2-amino-3-methyl-1-butanol (10.2 mg, 0.087 mmol) and NaBH(OAc)₃ (58 mg, 0.261 mmol) were reacted to give the title compound (14.9 mg, 25%).
LC/MS: m/z 527.6 (M+H), r.t: 1.48 min.

Example 19

3-[1-(ethylsulfonyl)-4-piperidinyl]-5-(3-{[(2-hydroxy-1-methylethyl)amino]methyl}phenyl)-1H-indole-7-carboxamide

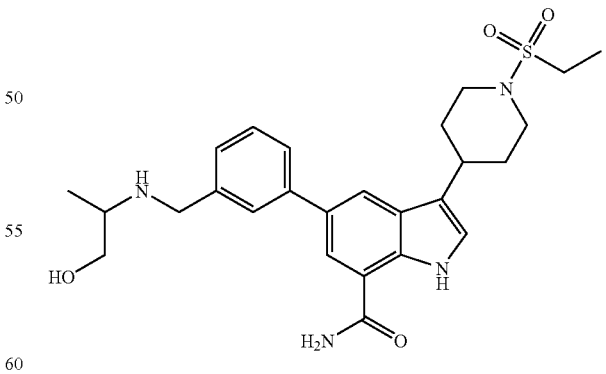

Following the general procedure of example 16, 3-[1-(ethylsulfonyl)-4-piperidinyl]-5-(3-formylphenyl)-1H-indole-7-carboxamide (50 mg, 0.114 mmol), 2-amino-1-propanol (6.5 mg, 0.087 mmol) and NaBH(OAc)₃ (58 mg, 0.261 mmol) were reacted to give the title compound (3.4 mg, 6.0%).
LC/MS: m/z 499.6 (M+H), r.t: 1.46 min.

Example 20

3-[1-(ethylsulfonyl)-4-piperidinyl]-5-(3-{[(trans-4-hydroxycyclohexyl)amino]methyl}phenyl)-1H-indole-7-carboxamide

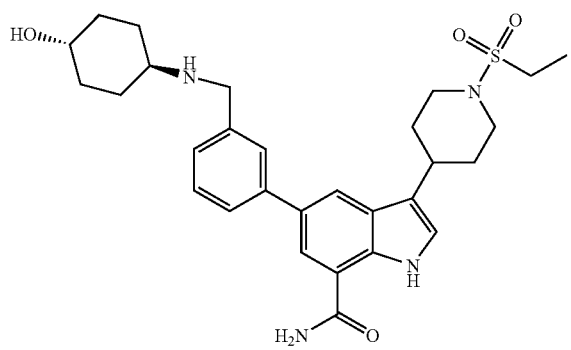

Following the general procedure of example 16, 3-[1-(ethylsulfonyl)-4-piperidinyl]-5-(3-formylphenyl)-1H-indole-7-carboxamide (50 mg, 0.114 mmol), trans-4-aminocyclohexanol (10 mg, 0.087 mmol) and NaBH(OAc)₃ (58 mg, 0.261 mmol) were reacted to give the title compound (6.0 mg, 9.8%).

LC/MS: m/z 539.2 (M+H), r.t: 1.54 min.

Example 21

3-[1-(ethylsulfonyl)-4-piperidinyl]-5-{3-[({[1-(1-piperidinyl)cyclohexyl]methyl}amino)methyl]phenyl}-1H-indole-7-carboxamide

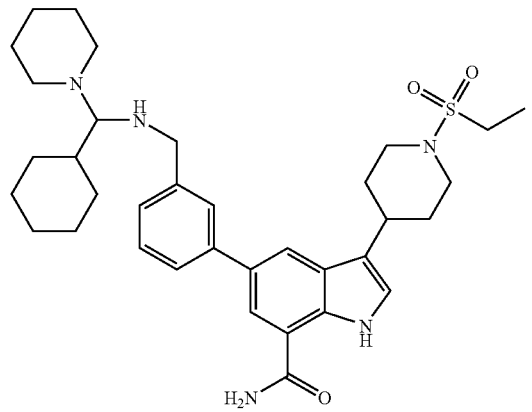

Following the general procedure of example 16, 3-[1-(ethylsulfonyl)-4-piperidinyl]-5-(3-formylphenyl)-1H-indole-7-carboxamide (50 mg, 0.114 mmol), 1-[1-(1-piperidinyl)cyclohexyl]methanamine (17 mg, 0.087 mmol) and NaBH(OAc)₃ (58 mg, 0.261 mmol) were reacted to give the title compound (18.7 mg, 27%).

LC/MS: m/z 620.6 (M+H), r.t: 1.6 min.

Example 22

3-[1-(ethylsulfonyl)-4-piperidinyl]-5-[3-({[(2S)-2-hydroxypropyl]amino}methyl)phenyl]-1H-indole-7-carboxamide

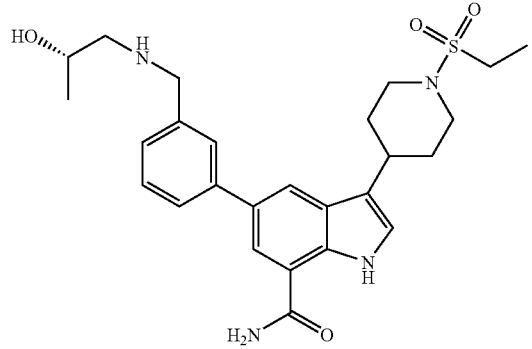

Following the general procedure of example 16, 3-[1-(ethylsulfonyl)-4-piperidinyl]-5-(3-formylphenyl)-1H-indole-7-carboxamide (50 mg, 0.114 mmol), (2S)-1-amino-2-propanol (6.5 mg, 0.087 mmol) and NaBH(OAc)₃ (58 mg, 0.261 mmol) were reacted to give the title compound (13.1 mg, 23%).

LC/MS: m/z 499.6 (M+H), r.t: 1.46 min.

Example 23

5-{3-[(ethylamino)methyl]phenyl}-3-[1-(ethylsulfonyl)-4-piperidinyl]-1H-indole-7-carboxamide

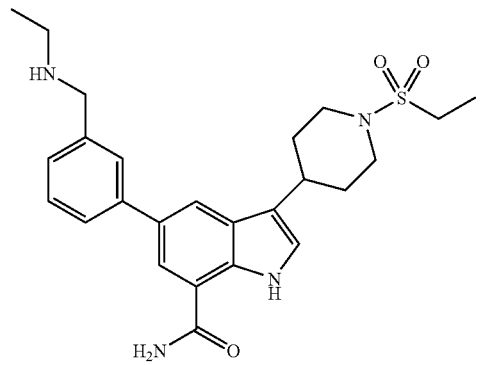

To a solution of 3-[1-(ethylsulfonyl)-4-piperidinyl]-5-(3-formylphenyl)-1H-indole-7-carboxamide (20 mg, 0.045 mmol) in dichloromethane (0.5 mL) and methanol (0.5 mL) was added ethylamine (130 uL, 0.27 mmol). This mixture was stirred for 1 h at room temperature, and then sodium borohydride (10 mg, 0.27 mmol) was added. The reaction was stirred at ambient temperature overnight, and the solvent was removed under reduced pressure. The crude product was purified by reverse phase HPLC (water/CH₃CN, 0.1% TFA 10-90%) to give the title compound (13.2 mg, 63%).

LC/MS: m/z 469.4 (M+H), r.t: 1.54 min.

Example 24

3-[1-(ethylsulfonyl)-4-piperidinyl]-5-{3-[(propylamino)methyl]phenyl}-1H-indole-7-carboxamide

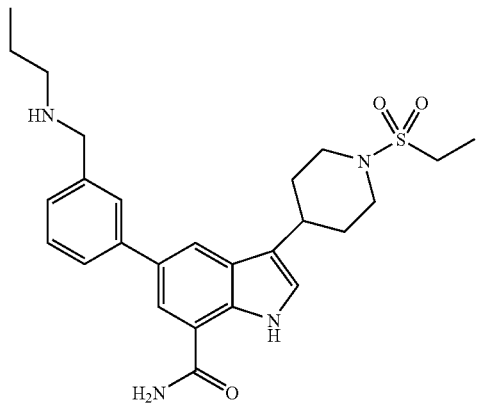

To a solution of 3-[1-(ethylsulfonyl)-4-piperidinyl]-5-(3-formylphenyl)-1H-indole-7-carboxamide (20 mg, 0.046 mmol) in dichloromethane (0.7 mL) and methanol (0.7 mL) was added propylamine (22 uL, 0.27 mmol) and 1 drop of acetic acid. This mixture was stirred for 1 h at room temperature and then sodium borohydride (10 mg, 0.27 mmol) was added. The reaction was stirred overnight at ambient temperature, and the solvent was removed under reduced pressure. The crude product was purified by reverse phase HPLC (water/CH$_3$CN, 0.1% TFA 10-90%) to give the title compound (22.1 mg, 99%).

LC/MS: m/z 483.2 (M+H), r.t: 1.58 min.

Example 25

3-[1-(ethylsulfonyl)-4-piperidinyl]-5-(3-{[(1-methylethyl)amino]methyl}phenyl)-1H-indole-7-carboxamide

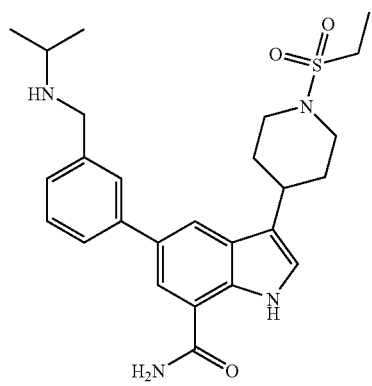

Following the general procedure of example 24, 3-[1-(ethylsulfonyl)-4-piperidinyl]-5-(3-formylphenyl)-1H-indole-7-carboxamide (20 mg, 0.045 mmol), isopropylamine (23 uL, 0.27 mmol) and NaBH$_4$ (10 mg, 0.27 mmol) were reacted to give the title compound (11.5 mg, 53%).

LC/MS: m/z 483.2 (M+H), r.t: 1.52 min.

Example 26

5-(3-{[(1-ethylpropyl)amino]methyl}phenyl)-3-[1-(ethylsulfonyl)-4-piperidinyl]-1H-indole-7-carboxamide

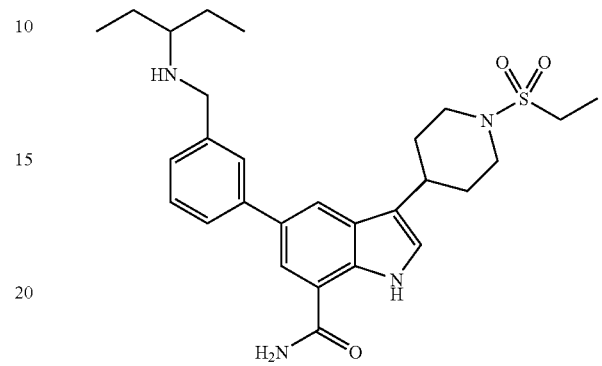

Following the general procedure of example 1, 3-[1-(ethylsulfonyl)-4-piperidinyl]-5-(3-formylphenyl)-1H-indole-7-carboxamide (20 mg, 0.045 mmol), 3-pentanamide (32 uL, 0.27 mmol) and NaBH$_4$ (10 mg, 0.27 mmol) were reacted to give the title compound (18.5 mg, 80%).

LC/MS: m/z 511.4 (M+H), r.t: 1.66 min.

Example 27

3-[1-(ethylsulfonyl)-4-piperidinyl]-5-[4-(1-piperidinylmethyl)phenyl]-1H-indole-7-carboxamide

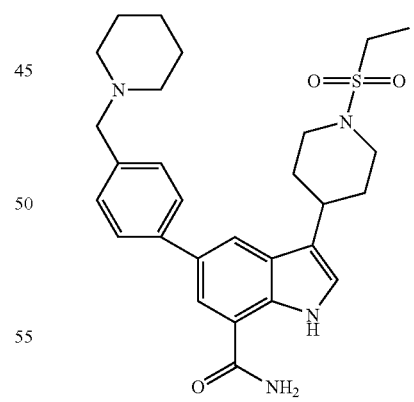

Following the general procedure of example 1, 3-[1-(ethylsulfonyl)-4-piperidinyl]-5-(3-formylphenyl)-1H-indole-7-carboxamide (40 mg, 0.09 mmol), piperidine (0.009 mL, 0.09 mmol) and NaBH(OAc)$_3$ (58 mg, 0.27 mmol) were reacted to give the title compound (8 mg, 17.5%).

LC/MS: m/z 509.4 (M+H), r.t: 1.71 min.

Example 28

3-[1-(ethylsulfonyl)-4-piperidinyl]-5-{3-[(methy-lamino)methyl]phenyl}-1H-indole-7-carboxamide

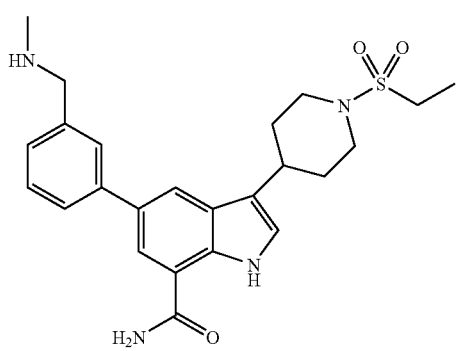

Following the general procedure of example 24, 3-[1-(ethylsulfonyl)-4-piperidinyl]-5-(3-formylphenyl)-1H-indole-7-carboxamide (20 mg, 0.045 mmol), methylamine (130 uL, 0.27 mmol) and NaBH₄ (10 mg, 0.27 mmol) were reacted to give title compound (17.0 mg, 83%).

LC/MS: m/z 455.2 (M+H), r.t: 1.48 min.

Example 29

3-[1-(ethylsulfonyl)-4-piperidinyl]-5-[4-(4-morpholinylmethyl)phenyl]-1H-indole-7-carboxamide

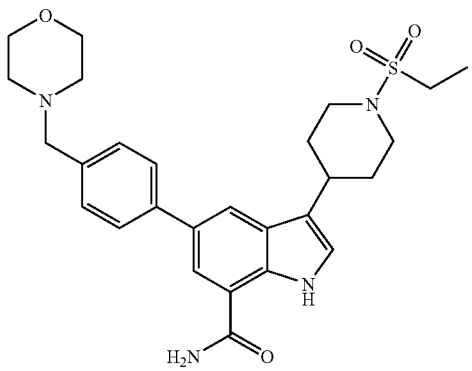

Following the general procedure of example 1, 3-[1-(ethylsulfonyl)-4-piperidinyl]-5-(4-formylphenyl)-1H-indole-7-carboxamide (50 mg, 0.114 mmol), morpholine (18 uL, 0.206 mmol) and NaBH(OAc)₃ (290 mg, 1.37 mmol) were reacted to give the title compound (2.1 mg, 13%).

LC/MS: m/z 511.4 (M+H), r.t: 1.63 min.

Example 30

5-[4-(aminomethyl)phenyl]-3-[1-(ethylsulfonyl)-4-piperidinyl]-1H-indole-7-carboxamide

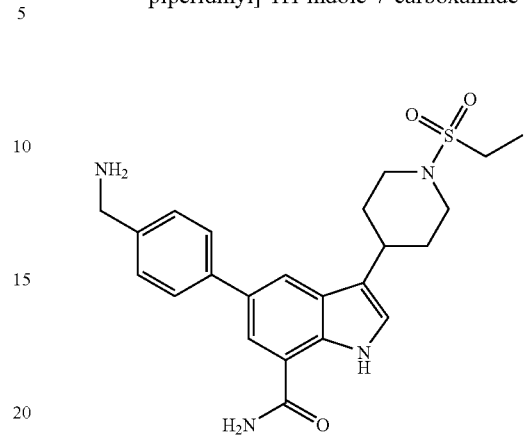

To a solution of 5-bromo-3-[1-(ethylsulfonyl)-4-piperidinyl]-1H-indole-7-carboxamide (30.0 mg, 0.072 mmol), Cs₂CO₃ (95 mg, 0.290 mmol) and [4-(aminomethyl)phenyl boronic acid (55 mg, 0.290 mmol) in dioxane/H₂O (1.5 mL/0.5 mL) was bubbled argon for 5 minutes prior to addition of Pd(PPh₃)₄ (7.5 mg, 0.0072 mmol). The reaction mixture was heated in a microwave reactor (Smith synthesizer) for 20 minutes at 160° C. The solvent was evaporated, and the residue was partitioned between ethyl acetate and water. The organic layer was washed with brine (10 mL), dried over MgSO₄, filtered, concentrated, and purified by reverse phase HPLC (water/CH₃CN, 0.1% TFA 10-90%) to give the title compound (9.8 mg, 31%).

LC/MS: m/z 424.4 (M-NH2), r.t: 1.48 min.

Example 31

5-{3-[(cyclopropylamino)methyl]phenyl}-3-[1-(ethylsulfonyl)-4-piperidinyl]-1H-indole-7-carboxamide

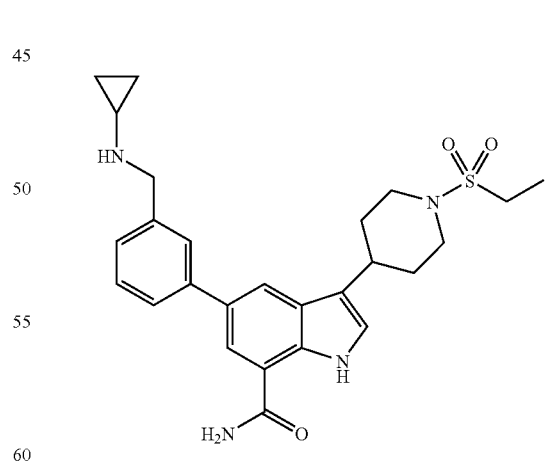

To a solution of 3-[1-(ethylsulfonyl)-4-piperidinyl]-5-(3-formylphenyl)-1H-indole-7-carboxamide (50 mg, 0.113 mmol) in DCM (2 mL) was added cyclopropanamine (19.3 mg, 0.339 mmol). The reaction solution was stirred at ambient temperature for 30 min prior to addition of HOAc (1 drop) and NaBH(OAc)₃ (75 mg, 0.545 mmol). The resulting mixture was stirred overnight at ambient temperature after which time the solvent was removed under reduced pressure. The crude product was purified by reverse phase HPLC (water/CH₃CN, 0.1% TFA 10-90%) to give the title compound (18.2 mg, 34%).

LC/MS: m/z 481.2 (M+H), r.t: 1.52 min.

Example 32

5-{3-[(cyclobutylamino)methyl]phenyl}-3-[1-(ethylsulfonyl)-4-piperidinyl]-1H-indole-7-carboxamide

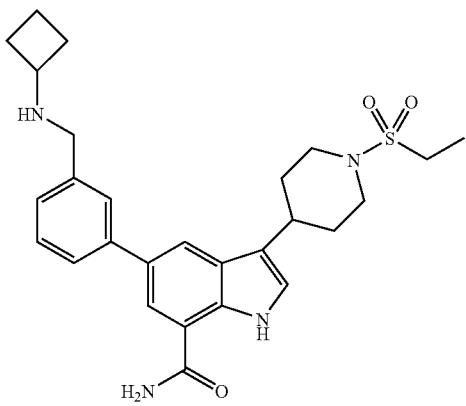

Following the general procedure of example 31, 3-[1-(ethylsulfonyl)-4-piperidinyl]-5-(3-formylphenyl)-1H-indole-7-carboxamide (50 mg, 0.113 mmol), cyclobutanamine (24.1 mg, 0.339 mmol) and NaBH(OAc)₃ (75 mg, 0.545 mmol) were reacted to give the title compound (19.3 mg, 35%).

LC/MS: m/z 495.6 (M+H), r.t: 1.55 min.

Example 33

3-[1-(ethylsulfonyl)-4-piperidinyl]-5-{3-[(2-methylpropyl)amino]-2,3-dihydro-1H-inden-5-yl}-1H-indole-7-carboxamide trifluoroacetate

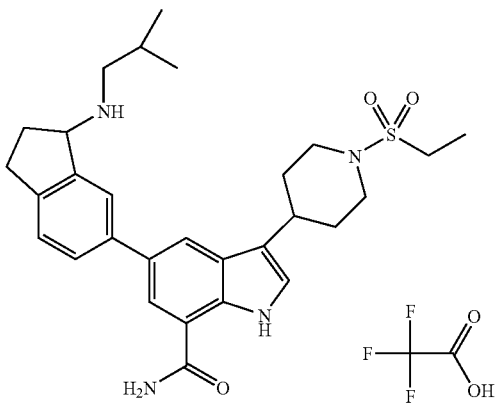

To a solution of 3-[1-(ethylsulfonyl)-4-piperidinyl]-5-(4,4,5,5-tetramethyl-1,3,2-dioxaborolan-2-yl)-1H-indole-7-carboxamide (200 mg, 0.434 mmol) in dioxane (3.0 mL) and H₂O (1.0 mL) was added 6-bromo-2,3-dihydro-1H-inden-1-one (274 mg, 1.30 mmol), and potassium carbonate (360 mg, 2.60 mmol) in a microwave tube. The reaction mixture was degassed for 5 min before the addition of tetrakis (triphenylphosphine) palladium (0) (50 mg, 0.043 mmol). The reaction was then heated in the microwave for 30 min at 160° C. The reaction was then filtered and the solid was dissolved in EtOAc and H₂O. The organic layer was separated and concentrated. The crude residue was purified by Gilson Preparatory HPLC to yield 3-[1-(ethylsulfonyl)-4-piperidinyl]-5-(3-oxo-2,3-dihydro-1H-inden-5-yl)-1H-indole-7-carboxamide.

To a solution of 3-[1-(ethylsulfonyl)-4-piperidinyl]-5-(3-oxo-2,3-dihydro-1H-inden-5-yl)-1H-indole-7-carboxamide (45 mg, 0.097 mmol) in EtOH (2 mL) and acetic acid (200 μL) was added 2-methyl-1-propanamine (170 μL, 1.93 mmol) and sodium cyanoborohydride (20 mg, 0.291 mmol). The resulting mixture was reacted in a CEM microwave tube at 150° C. for 40 min. It was then purified by Gilson Preparatory HPLC to give 4.5 mg of the title compound (8.9%).

LC/MS=m/z 523.4 [M+H] Ret. Time: 1.72

Example 34

3-[1-(ethylsulfonyl)-4-piperidinyl]-5-{8-[(2-methylpropyl)amino]-5,6,7,8-tetrahydro-2-naphthalenyl}-1H-indole-7-carboxamide trifluoroacetate

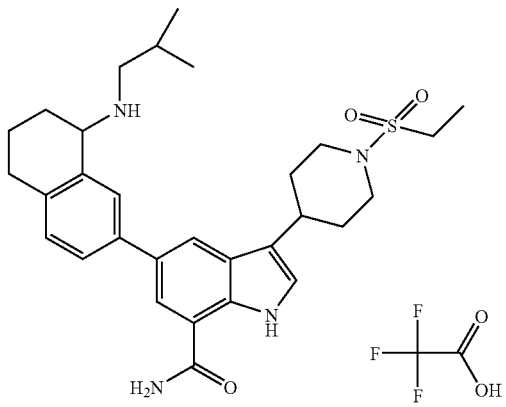

To a solution of 3-[1-(ethylsulfonyl)-4-piperidinyl]-5-(4,4,5,5-tetramethyl-1,3,2-dioxaborolan-2-yl)-1H-indole-7-carboxamide (200 mg, 0.434 mmol) in dioxane (3.0 mL) and H₂O (1.0 mL) was added 7-bromo-3,4-dihydro-1(2H)-naphthalenone (292 mg, 1.30 mmol), and potassium carbonate (360 mg, 2.60 mmol) in a microwave tube. The reaction mixture was degassed for 5 min before the addition of tetrakis (triphenylphosphine) palladium (0) (50 mg, 0.043 mmol). The reaction was then heated in the microwave for 30 min at 160° C. The reaction was then filtered and the solid was dissolved in EtOAc and H₂O. The organic layer was separated and concentrated. The crude residue was purified by Gilson Preparatory HPLC to yield 3-[1-(ethylsulfonyl)-4-piperidinyl]-5-(8-oxo-5,6,7,8-tetrahydro-2-naphthalenyl)-1H-indole-7-carboxamide.

To a solution of 3-[1-(ethylsulfonyl)-4-piperidinyl]-5-(8-oxo-5,6,7,8-tetrahydro-2-naphthalenyl)-1H-indole-7-carboxamide (40 mg, 0.08 mmol) in EtOH (2 mL) and acetic acid (0.2 mL) was added 2-methyl-1-propanamine (140 μL, 1.6 mmol) and sodium cyanoborohydride (15 mg, 0.24 mmol). The resulting mixture was reacted in a CEM microwave tube at 150° C. for 40 min. It was then purified by Gilson Preparatory HPLC to give 3.2 mg of the title compound (7.5%).

LC/MS=m/z 537.4 [M+H] Ret. Time: 1.71

Example 35

5-(5-{[(2-cyanoethyl)amino]methyl}-2-fluorophenyl)-3-[1-(ethylsulfonyl)-4-piperidinyl]-1H-indole-7-carboxamide trifluoroacetate

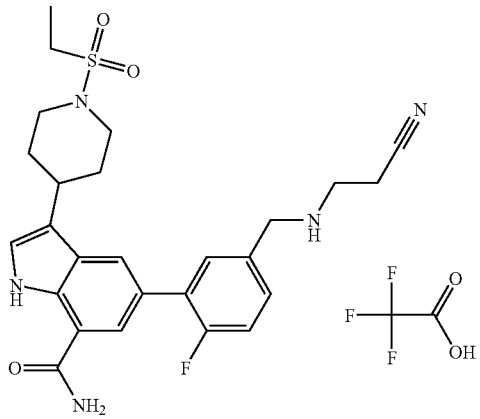

To a solution of 3-[1-(ethylsulfonyl)-4-piperidinyl]-5-(4,4,5,5-tetramethyl-1,3,2-dioxaborolan-2-yl)-1H-indole-7-carboxamide (200 mg, 0.434 mmol) in dioxane (3.0 mL) and H₂O (1.0 mL) was added 3-bromo-4-fluorobenzaldehyde (264 mg, 1.30 mmol), and K₂CO₃ (360 mg, 2.60 mmol) in microwave tube. The reaction mixture was degassed for 5 min before addition of tetrakis(triphenylphosphine) palladium (0) (48 mg, 0.043 mmol). The reaction was heated in a microwave for 30 min at 160° C. The organic layer was separated and concentrated. The residue was dissolved in MeOH until solid precipitated to yield 3-[1-(ethylsulfonyl)-4-piperidinyl]-5-(2-fluoro-5-formylphenyl)-1H-indole-7-carboxamide.

To a solution of 3-[1-(ethylsulfonyl)-4-piperidinyl]-5-(2-fluoro-5-formylphenyl)-1H-indole-7-carboxamide (40 mg, 0.087 mmol) in dichloromethane (2 mL) and methanol (1 mL) was added 3-aminopropanenitrile (53 μL, 0.524 mmol), and 1 drop of acetic acid. The reaction mixture was stirred at room temperature for 48 h. Sodium borohydride (20 mg, 0.524 mmol) was then added and reacted for 30 min at room temperature. Purified by Gilson Preparatory HPLC to give 14.4 mg of the title compound (32.4%).

LC/MS=m/z 512.2 [M+H] Ret. Time: 1.45

Example 36

3-[1-(ethylsulfonyl)-4-piperidinyl]-5-(2-fluoro-5-{[(2,2,2-trifluoroethyl)amino]methyl}phenyl)-1H-indole-7-carboxamide trifluoroacetate

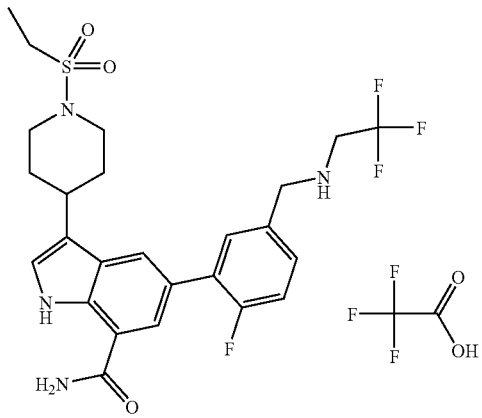

To a solution of 3-[1-(ethylsulfonyl)-4-piperidinyl]-5-(2-fluoro-5-formylphenyl)-1H-indole-7-carboxamide (20 mg, 0.04 mmol) in dichloromethane (4 mL) and methanol (2 mL) was added 2 drops of acetic acid and 2,2,2-trifluoroethanamine (23 μL, 0.26 mmol). The resulting mixture was stirred overnight. All solvent was evaporated and dissolved in dimethyl sulfoxide (1 mL). Purified by Gilson Preparatory HPLC to give 5.2 mg of the title compound (24.0%).

LC/MS=m/z 541.4 [M+H] Ret. Time. 1.67

Example 37

3-[1-(ethylsulfonyl)-4-piperidinyl]-5-(1,2,3,4-tetrahydro-7-isoquinolinyl)-1H-indole-7-carboxamide trifluoroacetate

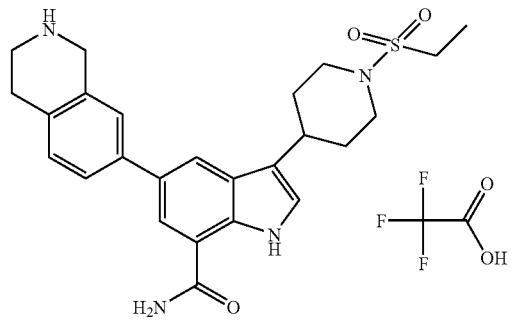

To a solution of 3-[1-(ethylsulfonyl)-4-piperidinyl]-5-(4,4,5,5-tetramethyl-1,3,2-dioxaborolan-2-yl)-1H-indole-7-carboxamide (60 mg, 0.13 mmol) in dioxane (2 mL) and water (1 mL) was added 7-bromo-1,2,3,4-tetrahydroisoquinoline (97 mg, 0.39 mmol) and potassium carbonate (108 mg, 0.78 mmol). This mixture was degassed for 5 min before the addition of tetrakis(triphenylphosphine)palladium(0) (15 mg, 0.013 mmol). The resulting mixture was reacted in a CEM microwave tube at 160° C. for 30 min. The organic layers were separated and concentrated. The resulting residue was dissolved in dimethyl sulfoxide (1 mL) and purified by Gilson Preparatory HPLC to give 3.5 mg of the title compound (5.7%).

LC/MS=m/z 467.2 [M+H] Ret. Time. 1.48

Example 38

3-[1-(ethylsulfonyl)-4-piperidinyl]-5-(3-{[(2,2,2-trifluoroethyl)amino]methyl}phenyl)-1H-indole-7-carboxamide trifluoroacetate

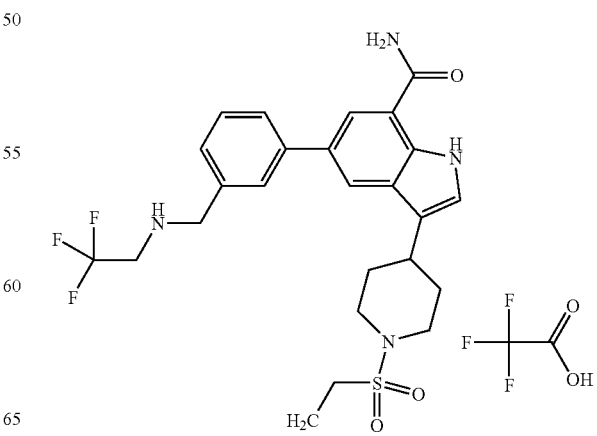

To a solution of 5-bromo-3-[1-(ethylsulfonyl)-4-piperidinyl]-1H-indole-7-carboxamide (200 mg, 0.483 mmol) in dioxane (3.0 mL) and H$_2$O (1.0 mL) was added (3-formylphenyl)boronic acid (317 mg, 1.93 mmol), and Cs$_2$CO$_3$ (315 mg, 0.97 mmol) in a microwave tube. The reaction mixture was degassed for 5 min before addition of tetrakis(triphenylphosphine) palladium (0) (48 mg, 0.043 mmol). The reaction was heated in a microwave for 30 min at 160° C. The organic layer was separated and concentrated. The residue was dissolved in MeOH until solid precipitated to yield 3-[1-(ethylsulfonyl)-4-piperidinyl]-5-(3-formylphenyl)-1H-indole-7-carboxamide.

To a solution of 3-[1-(ethylsulfonyl)-4-piperidinyl]-5-(3-formylphenyl)-1H-indole-7-carboxamide (40 mg, 0.09 mmol) and 2,2,2-trifluoroethylamine (78 µL, 0.55 mmol) in dichloromethane (2 mL) and methanol (1 mL) was added 2 drops of acetic acid. The mixture was then stirred overnight. Sodium borohydride (20.8 mg, 0.55 mmol) was then added and the mixture was stirred for 30 min. The resulting mixture was concentrated and dissolved in dimethyl sulfoxide followed by purification by Gilson Preparatory HPLC to give 29.4 mg of the title compound (62.5%).

LC/MS=m/z 523.2 [M+H] Ret. Time. 1.66

Example 39

5-(3-{[(2-amino-2-oxoethyl)(methyl)amino]methyl}phenyl)-3-[1-(ethylsulfonyl)-4-piperidinyl]-1H-indole-7-carboxamide trifluoroacetate

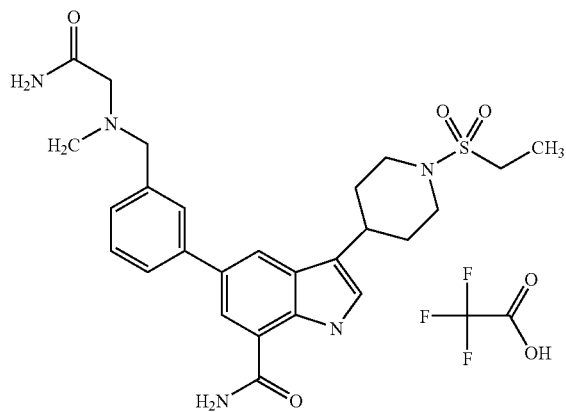

To a solution 3-[1-(ethylsulfonyl)-4-piperidinyl]-5-(3-formylphenyl)-1H-indole-7-carboxamide (44 mg, 0.1 mmol) and N$^2$-methylglycinamide (76 mg, 0.6 mmol) in dichloromethane (3 mL) and methanol (1.5 mL) was added 3 drops of acetic acid. The mixture was stirred overnight. Sodium triacetoxyborohydride (134 mg, 0.6 mmol) was then added and stirred overnight. The resulting reaction was quenched with sodium biocarbonate (2 mL) and brine (2 mL). Organic layer was then collected and concentrated. The resulting residue was then purified by Gilson Preparatory HPLC to give 13 mg of the title compound (25.4%).

LC/MS=m/z 512.6 [M+H] Ret. Time. 1.20

Example 40

3-[1-(ethylsulfonyl)-4-piperidinyl]-5-(2-{[(2,2,2-trifluoroethyl)amino]methyl}-1,3-thiazol-4-yl)-1H-indole-7-carboxamide trifluoroacetate

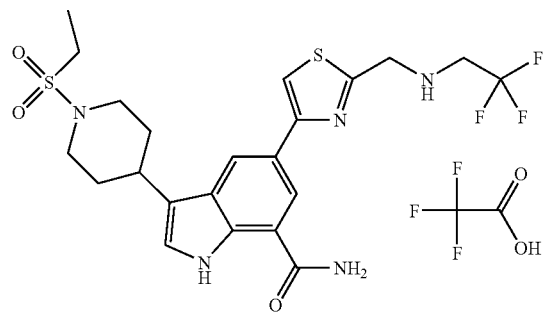

To a solution of 4-bromo-1,3-thiazole-2-carbaldehyde (192 mg, 1.0 mmol) in DCM (4.0 mL) was added acetic acid (3 drops) and 2,2,2-trifluoroethanamine (120 µL, 1.5 mmol). The reaction was stirred overnight. Sodium triacetoxyborohydride (335 mg, 1.5 mmol) was then added and reaction was stirred for 6 h. It was then quenched with sodium bicarbonate to yield 3-[1-(ethylsulfonyl)-4-piperidinyl]-5-(4,4,5,5-tetramethyl-1,3,2-dioxaborolan-2-yl)-1H-indole-7-carboxamide.

To a solution of 3-[1-(ethylsulfonyl)-4-piperidinyl]-5-(4,4,5,5-tetramethyl-1,3,2-dioxaborolan-2-yl)-1H-indole-7-carboxamide (46 mg, 0.1 mmol) in dioxane (2 mL) and water (0.7 mL) was added N-[(4-bromo-1,3-thiazol-2-yl)methyl]-2,2,2-trifluoroethanamine (30 mg, 0.11 mmol) and potassium carbonate (83 mg, 0.6 mmol). The resulting mixture was degassed for 5 min before the addition of tetrakis(triphenylphosphine)palladium(0) (11 mg, 0.01 mmol). The mixture was reacted in a CEM microwave tube at 160° C. for 20 min. Organic layers were separated and concentrated. The resulting residue was purified by Gilson Preparatory HPLC to give 25 mg of the title compound (47.2%).

LC/MS=m/z 530.2 [M+H] Ret. Time. 1.94

Example 41

5-(3-cyano-5-{[(2,2,2-trifluoroethyl)amino]methyl}phenyl)-3-[1-(ethylsulfonyl)-4-piperidinyl]-1H-indole-7-carboxamide trifluoroacetate

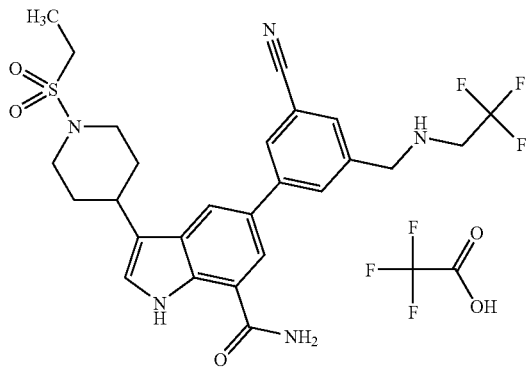

To a solution of 3-[1-(ethylsulfonyl)-4-piperidinyl]-5-(4,4,5,5-tetramethyl-1,3,2-dioxaborolan-2-yl)-1H-indole-7-carboxamide (46 mg, 0.1 mmol) in dioxane (2.0 mL, 0.7 mL) was added 3-bromo-5-formylbenzonitrile (68 mg, 0.3 mmol) and $K_2CO_3$ (83 mg, 0.6 mmol) in a microwave tube. The reaction mixture was degassed for 5 min before addition of tetrakis(triphenylphosphine) palladium (0) (11 mg, 0.01 mmol). The reaction was heated in a microwave for 20 min at 160° C. It was then purified by Gilson Preparatory HPLC to give 5-(3-cyano-5-formylphenyl)-3-[1-(ethylsulfonyl)-4-piperidinyl]-1H-indole-7-carboxamide.

To a solution of 5-(3-cyano-5-formylphenyl)-3-[1-(ethylsulfonyl)-4-piperidinyl]-1H-indole-7-carboxamide (52 mg, 0.11 mmol) in dichloromethane (3 mL) and methanol (1 mL) was added 20 drops of acetic acid and 2,2,2-trifluoroethanamine (53 μL, 0.66 mmol). The mixture was stirred for 48 h followed by addition of sodium triacetoxyborohydride (140 mg, 0.66 mmol). The mixture was then stirred for 48 h. The resulting reaction was quenched with sodium biocarbonate and brine was added. The organic layer was separated and purified by Gilson Preparatory HPLC to give 3.6 mg of the title compound (6.0%).

LC/MS=m/z 548.2 [M+H] Ret. Time. 1.88

Example 42

3-[1-(ethylsulfonyl)-4-piperidinyl]-5-(5-{[methyl(1-methyl-4-piperidinyl)amino]methyl}-3-thienyl)-1H-indole-7-carboxamide trifluoroacetate

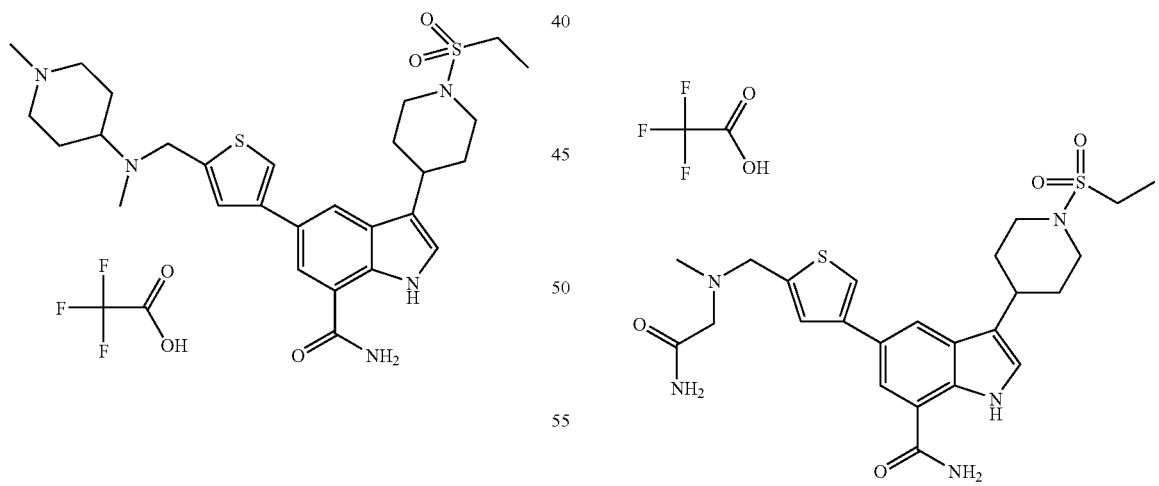

To a solution of 3-[1-(ethylsulfonyl)-4-piperidinyl]-5-(5-formyl-3-thienyl)-1H-indole-7-carboxamide (50 mg, 0.11 mmol) in dimethyl sulfoxide (2 mL) was added N,1-dimethyl-4-piperidinamine (128.22 mg, 1.0 mmol), 2 drops of acetic acid and reacted overnight. Sodium triacetoxyborohydride (212 mg, 1 mmol) was then added and reacted overnight at room temperature. It was then purified by Gilson Preparatory HPLC to give 8 mg of the title compound (13.0%).

LC/MS=m/z 558.4 [M+H] Ret. Time: 1.32 min

Example 43

5-(5-{[(2-cyanoethyl)(methyl)amino]methyl}-3-thienyl)-3-[1-(ethylsulfonyl)-4-piperidinyl]-1H-indole-7-carboxamide trifluoroacetate

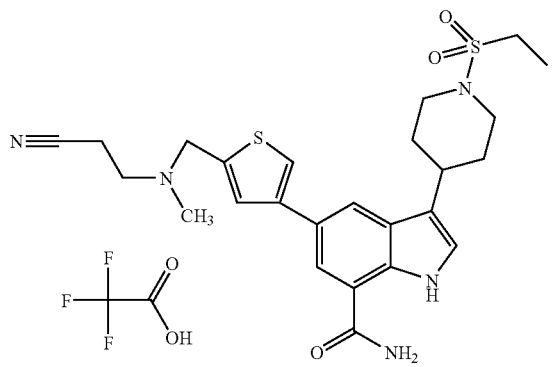

The title compound was prepared according to the general procedure for 3-[1-(ethylsulfonyl)-4-piperidinyl]-5-(5-{[methyl(1-methyl-4-piperidinyl)amino]methyl}-3-thienyl)-1H-indole-7-carboxamide trifluoroacetate, substituting 3-(methylamino)propanenitrile (84.12 mg, 1.0 mmol) for N,1-dimethyl-4-piperidinamine to afford 24 mg of the title compound (42.5%).

LC/MS=m/z 514.4 [M+H] Ret. Time: 1.55 min

Example 44

5-(5-{[(2-amino-2-oxoethyl)(methyl)amino]methyl}-3-thienyl)-3-[1-(ethylsulfonyl)-4-piperidinyl]-1H-indole-7-carboxamide trifluoroacetate The title compound was prepared according to the general procedure for 3-[1-(ethylsulfonyl)-4-piperidinyl]-5-(5-{[methyl(1-methyl-4-piperidinyl)amino]methyl}-3-thienyl)-1H-indole-7-carboxamide trifluoroacetate, substituting $N^2$-methylglycinamide (88.11 mg, 1.0 mmol) for N,1-dimethyl-4-piperidinamine to afford 19 mg of the title compound (33.3%).

LC/MS=m/z 518.2 [M+H] Ret. Time: 1.43 min

Example 45

3-[1-(ethylsulfonyl)-4-piperidinyl]-5-[5-({methyl[2-(phenylsulfonyl)ethyl]amino}methyl)-3-thienyl]-1H-indole-7-carboxamide trifluoroacetate

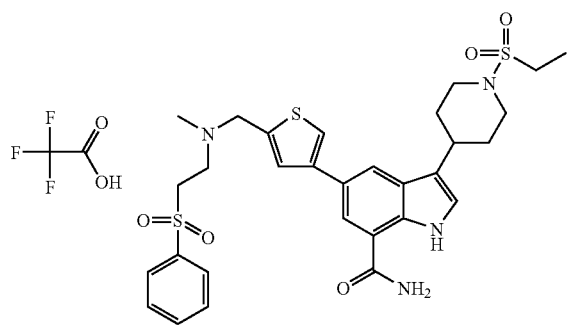

The title compound was prepared according to the general procedure for 3-[1-(ethylsulfonyl)-4-piperidinyl]-5-(5-{[methyl(1-methyl-4-piperidinyl)amino]methyl}-3-thienyl)-1H-indole-7-carboxamide trifluoroacetate, substituting N-methyl-2-(phenylsulfonyl)ethanamine (199.27 mg, 1.0 mmol) for N,1-dimethyl-4-piperidinamine to afford 30 mg of the title compound (47.3%).

LC/MS=m/z 629.4 [M+H] Ret. Time: 1.57 min

Example 46

3-[1-(ethylsulfonyl)-4-piperidinyl]-5-{5-[(2-phenyl-1-pyrrolidinyl)methyl]-3-thienyl}-1H-indole-7-carboxamide

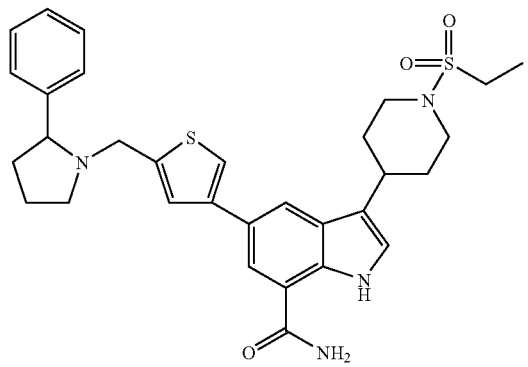

To a solution of 3-[1-(ethylsulfonyl)-4-piperidinyl]-5-(5-formyl-3-thienyl)-1H-indole-7-carboxamide (50 mg, 0.11 mmol) in DMSO (2.0 mL) was added 2-phenylpyrrolidine (147 mg, 1.0 mmol). The reaction mixture was then reacted in a microwave at 120° C. for 10 min. Sodium triacetoxyborohydride (220 mg, 1.0 mmol) was then added and the reaction was reacted at room temperature overnight. It was then purified by Gilson Preparatory HPLC to give 14.0 mg of the title compound (22%).

LC/MS=m/z 577.2 [M+H] Ret. Time: 1.65 min.

Example 47

3-[1-(ethylsulfonyl)-4-piperidinyl]-5-(5-{[2-(1-piperidinylmethyl)-1-pyrrolidinyl]methyl}-3-thienyl)-1H-indole-7-carboxamide

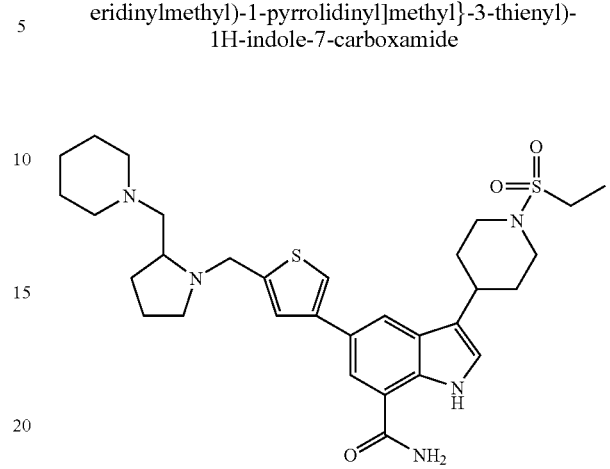

The title compound was prepared according to the general procedure for 3-[1-(ethylsulfonyl)-4-piperidinyl]-5-{5-[(2-phenyl-1-pyrrolidinyl)methyl]-3-thienyl}-1H-indole-7-carboxamide, substituting 1-(2-pyrrolidinylmethyl)piperidine (168.3 mg, 1.0 mmol) for 2-phenylpyrrolidine to afford 21 mg of the title compound (32%).

LC/MS=m/z 598.4 [M+H] Ret. Time: 1.34

Example 48

5-(5-{[(2R)-2-(aminocarbonyl)-1-pyrrolidinyl]methyl}-3-thienyl)-3-[1-(ethylsulfonyl)-4-piperidinyl]-1H-indole-7-carboxamide

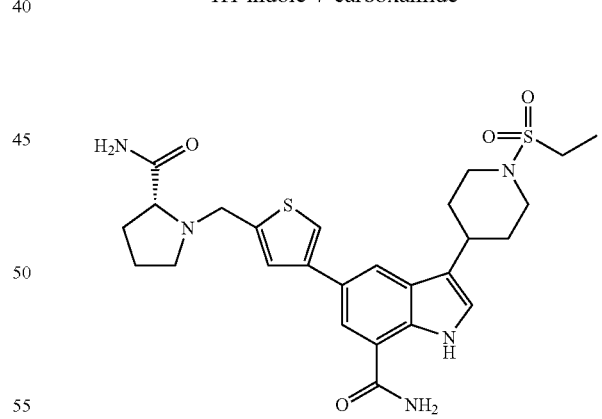

The title compound was prepared according to the general procedure for 3-[1-(ethylsulfonyl)-4-piperidinyl]-5-{5-[(2-phenyl-1-pyrrolidinyl)methyl]-3-thienyl}-1H-indole-7-carboxamide, substituting D-prolinamide (114 mg, 1.0 mmol) for 2-phenylpyrrolidine to afford 14 mg of the title compound (23%).

LC/MS=m/z 544.2 [M+H] Ret. Time: 1.39

Example 49

5-(5-{[(3S)-3-(dimethylamino)-1-pyrrolidinyl]methyl}-3-thienyl)-3-[1-(ethylsulfonyl)-4-piperidinyl]-1H-indole-7-carboxamide

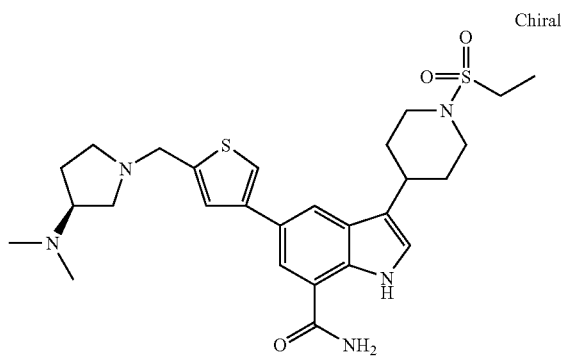

The title compound was prepared according to the general procedure for 3-[1-(ethylsulfonyl)-4-piperidinyl]-5-{5-[(2-phenyl-1-pyrrolidinyl)methyl]-3-thienyl}-1H-indole-7-carboxamide, substituting (2R)—N,N-dimethyl-2-pyrrolidinamine (114 mg, 1.0 mmol) for 2-phenylpyrrolidine to afford 11 mg of the title compound (18%).

LC/MS=m/z 544.2 [M+H] Ret. Time: 1.36

Example 50

5-(1-{2-[4-(dimethylamino)-1-piperidinyl]ethyl}-1H-pyrazol-4-yl)-3-[1-(ethylsulfonyl)-4-piperidinyl]-1H-indole-7-carboxamide trifluoroacetate

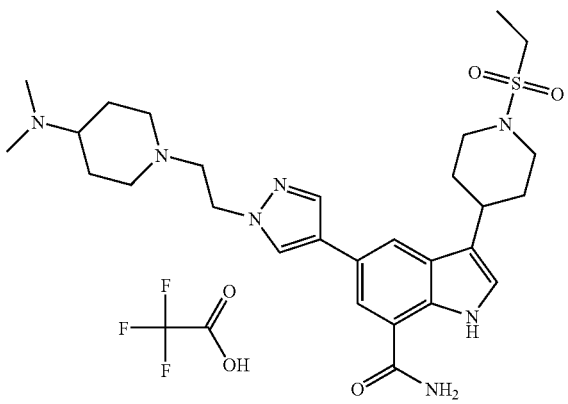

To a solution of 3-[1-(ethylsulfonyl)-4-piperidinyl]-5-(4,4,5,5-tetramethyl-1,3,2-dioxaborolan-2-yl)-1H-indole-7-carboxamide (40 mg, 0.090 mmol) in dioxane (750 μL) and H$_2$O (250 μL) was added sodium carbonate (53 mg, 0.50 mmol), and 4-bromo-1-(2-chloroethyl)-1H-pyrazole (26 mg, 0.126 mmol). The reaction mixture was flushed under Argon for 10 min before addition of tetrakis(triphenylphosphine)palladium (0) (5 mg, 0.004 mmol). The reaction was heated in a microwave at 120° C. for 20 min. It was then diluted with EtOAc (10 mL), filtered thru celite, followed by an aqueous work-up. The compound was purified by Gilson Preparatory HPLC to give 10 mg of 5-[1-(2-chloroethyl)-1H-pyrazol-4-yl]-3-[1-(ethylsulfonyl)-4-piperidinyl]-1H-indole-7-carboxamide (24%).

To a solution of 5-[1-(2-chloroethyl)-1H-pyrazol-4-yl]-3-[1-(ethylsulfonyl)-4-piperidinyl]-1H-indole-7-carboxamide (33 mg, 0.071 mmol) in tetrahydrofuran (500 uL) was added N,N-dimethyl-4-piperidinamine (100 μL, 0.71 mmol) and Sodium Iodide (5 mg, 0.018 mmol). The resulting mixture was reacted in a microwave tube at 130° C. for 2 h. Performed aqueous wash with EtOAc and water, isolated organic layers and removed all solvent. It was then purified by Gilson Preparatory HPLC to give 7.0 mg of the title compound (14.7%).

LC/MS=m/z 556 [M+H] Ret. Time: 1.23 min.

Example 51

5-[3-[(dimethylamino)methyl]-4,5-bis(methyloxy)phenyl]-3-[1-(ethylsulfonyl)-4-piperidinyl]-1H-indole-7-carboxamide

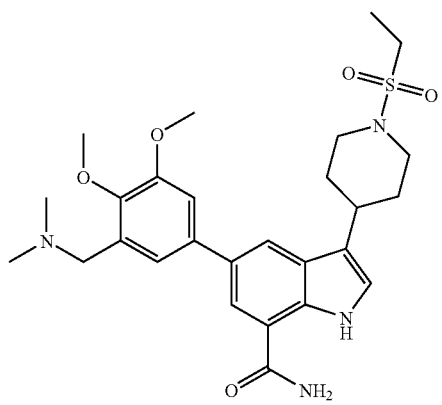

To a solution of 3-[1-(ethylsulfonyl)-4-piperidinyl]-5-(4,4,5,5-tetramethyl-1,3,2-dioxaborolan-2-yl)-1H-indole-7-carboxamide (500 mg, 1.09 mmol) in dioxane (9.0 mL) and H$_2$O (3.0 mL) was added sodium carbonate (690 mg, 6.51 mmol), and 5-bromo-2,3-bis(methyloxy)benzaldehyde (7.95 mg, 3.25 mmol). The reaction mixture was flushed under Argon for 10 min before addition of tetrakis(triphenylphosphine) palladium (0) (63 mg, 0.054 mmol). The reaction was then heated in a microwave at 120° C. for 30 min. All solvent was then concentrated and an aqueous wash was performed with EtOAc and H$_2$O. The desired compound then precipitated and was filtered to give 322 mg of 3-[1-(ethylsulfonyl)-4-piperidinyl]-5-[3-formyl-4,5-bis(methyloxy)phenyl]-1H-indole-7-carboxamide (59%).

To a solution of 3-[1-(ethylsulfonyl)-4-piperidinyl]-5-[3-formyl-4,5-bis(methyloxy)phenyl]-1H-indole-7-carboxamide (30 mg, 0.06 mmol) in methanol (2 mL), zinc chloride (5 mg, 0.03 mmol), sodium cyanoborohydride (5 mg, 0.06 mmol) and dimethylamine (100 μL, 0.30 mmol). The mixture was stirred at room temperature for 2 h then reacted in the microwave at 100° C. for 30 min. The resulting mixture was purified by Gilson Preparatory HPLC to give 11 mg of the title compound (34.7%).

LC/MS=m/z 529 [M+H] Ret. Time: 1.67 min.

Example 52

5-[3,4-bis(methyloxy)-5-(4-morpholinylmethyl)phenyl]-3-[1-(ethylsulfonyl)-4-piperidinyl]-1H-indole-7-carboxamide

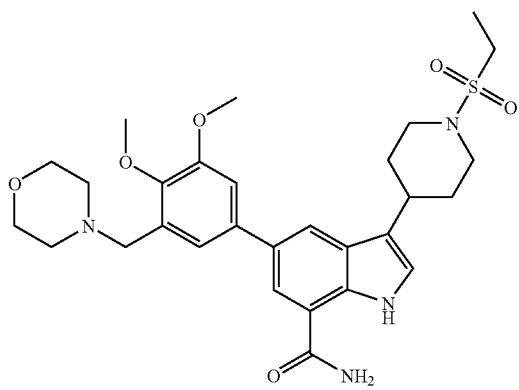

The title compound was prepared according to the general procedure of 5-[3-[(dimethylamino)methyl]-4,5-bis(methyloxy)phenyl]-3-[1-(ethylsulfonyl)-4-piperidinyl]-1H-indole-7-carboxamide, substituting morpholine (20 μL, 0.30 mmol) for dimethylamine to afford 8.0 mg of the title compound (23.4%).

LC/MS=m/z 571 [M+H] Ret. Time: 1.59 min.

Example 53

3-[1-(ethylsulfonyl)-4-piperidinyl]-5-[3-{[(1-methylethyl)amino]methyl}-4,5-bis(methyloxy)phenyl]-1H-indole-7-carboxamide

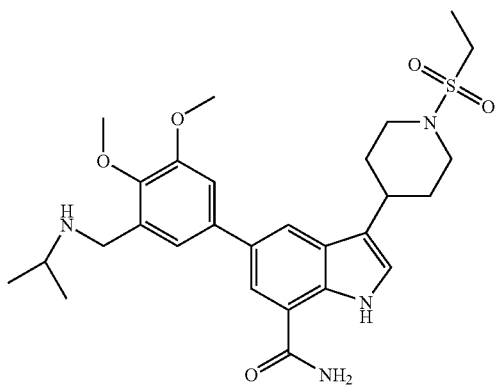

The title compound was prepared according to the general procedure of 5-[3-[(dimethylamino)methyl]-4,5-bis(methyloxy)phenyl]-3-[1-(ethylsulfonyl)-4-piperidinyl]-1H-indole-7-carboxamide, substituting 2-propanamine (20 μL, 0.30 mmol) for dimethylamine to afford 15 mg of the title compound (46.1%).

LC/MS=m/z 543 [M+H] Ret. Time: 1.59 min.

Example 54

3-[1-(ethylsulfonyl)-4-piperidinyl]-5-[3-{[(1-methylethyl)amino]methyl}-4,5-bis(methyloxy)phenyl]-1H-indole-7-carboxamide

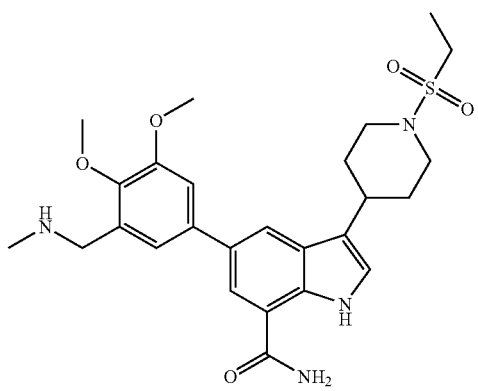

The title compound was prepared according to the general procedure of 5-[3-[(dimethylamino)methyl]-4,5-bis(methyloxy)phenyl]-3-[1-(ethylsulfonyl)-4-piperidinyl]-1H-indole-7-carboxamide, substituting 40 wt. % methylamine (50 μL, 0.30 mmol) for dimethylamine to afford 6 mg of the title compound (19.4%).

LC/MS=m/z 515 [M+H] Ret. Time: 1.46 min.

Example 55

5-[3-{[(2,2-dimethylpropyl)amino]methyl}-4,5-bis(methyloxy)phenyl]-3-[1-(ethylsulfonyl)-4-piperidinyl]-1H-indole-7-carboxamide

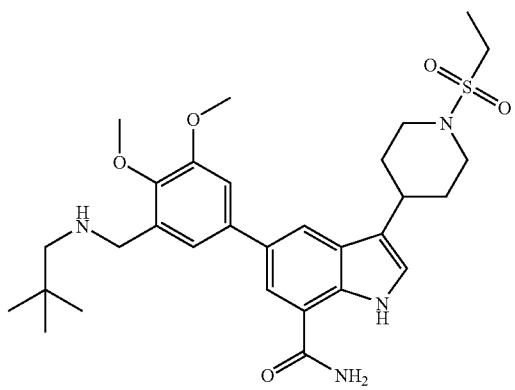

The title compound was prepared according to the general procedure of 5-[3-[(dimethylamino)methyl]-4,5-bis(methyloxy)phenyl]-3-[1-(ethylsulfonyl)-4-piperidinyl]-1H-indole-7-carboxamide, substituting (2,2-dimethylpropyl)amine (20 μL, 0.30 mmol) for dimethylamine to afford 10 mg of the title compound (29.2%).

LC/MS=m/z 571 [M+H] Ret. Time: 1.75 min.

Example 56

3-[1-(ethylsulfonyl)-4-piperidinyl]-5-[3-{[(2-hydroxyethyl)(methyl)amino]methyl}-4,5-bis(methyloxy)phenyl]-1H-indole-7-carboxamide

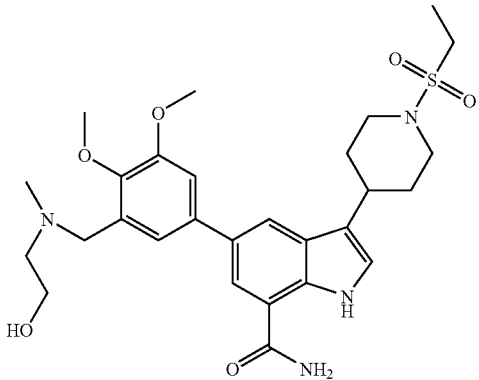

The title compound was prepared according to the general procedure of 5-[3-[(dimethylamino)methyl]-4,5-bis(methyloxy)phenyl]-3-[1-(ethylsulfonyl)-4-piperidinyl]-1H-indole-7-carboxamide, substituting 2-(methylamino)ethanol (20 µL, 0.30 mmol) for dimethylamine to afford 10 mg of the title compound (29.8%).

LC/MS=m/z 559 [M+H] Ret. Time: 1.54 min.

Example 57

5-[3,4-bis(methyloxy)-5-(1-pyrrolidinylmethyl)phenyl]-3-[1-(ethylsulfonyl)-4-piperidinyl]-1H-indole-7-carboxamide

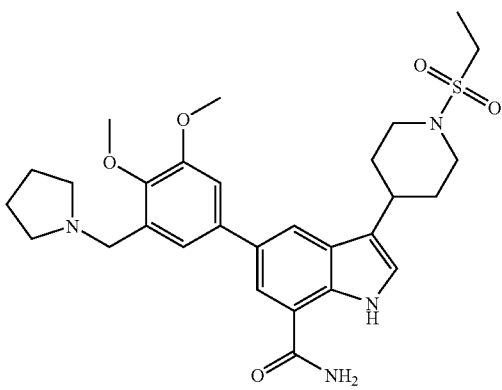

The title compound was prepared according to the general procedure of 5-[3-[(dimethylamino)methyl]-4,5-bis(methyloxy)phenyl]-3-[1-(ethylsulfonyl)-4-piperidinyl]-1H-indole-7-carboxamide, substituting pyrrolidine (50 µL, 0.30 mmol) for dimethylamine to afford 13 mg of the title compound (39.1%).

LC/MS=m/z 555 [M+H] Ret. Time: 1.61 min.

Example 58

5-{4-[(dimethylamino)methyl]-2,3-dihydro-1-benzofuran-6-yl}-3-[1-(ethylsulfonyl)-4-piperidinyl]-1H-indole-7-carboxamide

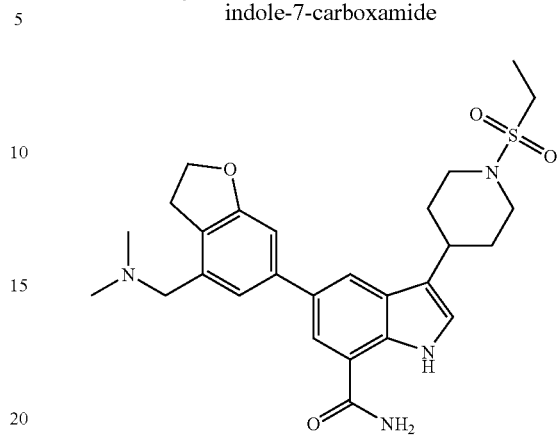

To a solution of 5-bromo-3-[1-(ethylsulfonyl)-4-piperidinyl]-1H-indole-7-carboxamide (113 mg, 0.274 mmol) in dioxane (9.0 mL) and H$_2$O (3.0 mL) was added sodium carbonate (174 mg, 1.64 mmol), and 6-(4,4,5,5-tetramethyl-1,3,2-dioxaborolan-2-yl)-2,3-dihydro-1-benzofuran-4-carbaldehyde (150 mg, 0.547 mmol). The reaction mixture was flushed under Argon for 10 min before addition of tetrakis(triphenylphosphine)palladium (0) (16 mg, 0.014 mmol). The reaction was heated in a microwave at 120° C. for 30 min. All solvent was then concentrated and purified by flash chromatography using DCM and MeOH to give 120 mg of 3-[1-(ethylsulfonyl)-4-piperidinyl]-5-(4-formyl-2,3-dihydro-1-benzofuran-6-yl)-1H-indole-7-carboxamide (91%).

To a solution of 3-[1-(ethylsulfonyl)-4-piperidinyl]-5-(4-formyl-2,3-dihydro-1-benzofuran-6-yl)-1H-indole-7-carboxamide (20 mg, 0.042 mmol) in methanol (2 mL) was added dimethylamine (3 µL 0.050 mmol), zinc chloride (3 mg, 0.021 mmol) and sodium cyanoborohydride (4 mg, 0.062 mmol). This mixture was reacted in the microwave at 100° C. for 1 h and then removed all solvent. The residue was washed with EtOAc and water. All solvent was removed and purified by Gilson Preparatory HPLC to give 6.0 mg of the title compound (19.6%).

LC/MS=m/z 525 [M+H] Ret. Time: 1.56 min.

Example 59

3-[1-(ethylsulfonyl)-4-piperidinyl]-5-(4-{[(1-methylethyl)amino]methyl}-2,3-dihydro-1-benzofuran-6-yl)-1H-indole-7-carboxamide

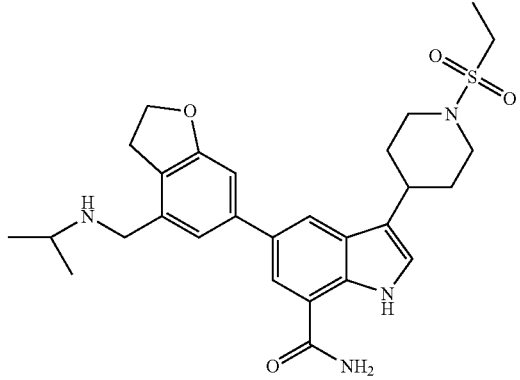

The title compound was prepared according to the general procedure of 5-{4-[(dimethylamino)methyl]-2,3-dihydro-1-benzofuran-6-yl}-3-[1-(ethylsulfonyl)-4-piperidinyl]-1H-indole-7-carboxamide, substituting 2-propanamine (3 mg 0.050 mmol) for dimethylamine to afford 9.0 mg of the title compound (28.6%).

LC/MS=m/z 511 [M+H] Ret. Time: 1.58 min.

Example 60

3-[1-(ethylsulfonyl)-4-piperidinyl]-5-[4-(4-morpholinylmethyl)-2,3-dihydro-1-benzofuran-6-yl]-1H-indole-7-carboxamide

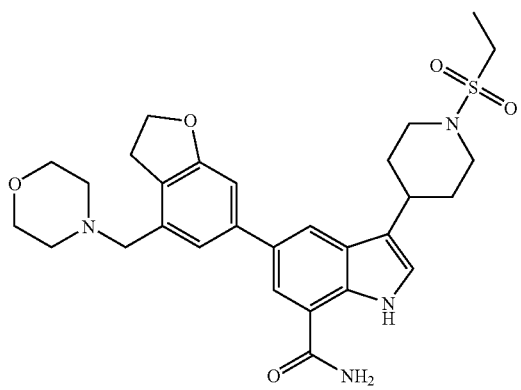

The title compound was prepared according to the general procedure of 5-{4-[(dimethylamino)methyl]-2,3-dihydro-1-benzofuran-6-yl}-3-[1-(ethylsulfonyl)-4-piperidinyl]-1H-indole-7-carboxamide, substituting 2,2-dimethyl-1-propanamine (4 mg, 0.050 mmol) for dimethylamine to afford 8.0 mg of the title compound (24.1%).

LC/MS=m/z 554 [M+H] Ret. Time: 1.71 min.

Example 61

3-[1-(ethylsulfonyl)-4-piperidinyl]-5-[5-({[1-methyl-2-(methyloxy)ethyl]amino}methyl)-2-thienyl]-1H-indole-7-carboxamide

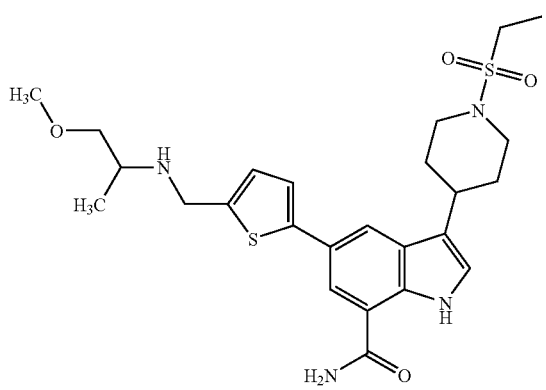

[5-({[1-methyl-2-(methyloxy)ethyl]amino}methyl)-2-thienyl]boronic acid (60 mg, 0.262 mmol) was transferred to a CEM microwave tube with methanol. The methanol was evaporated under a stream of $N_2$. To this was added 5-bromo-3-[1-(ethylsulfonyl)-4-piperidinyl]-1H-indole-7-carboxamide (80 mg, 0.19 mmol), potassium carbonate (160 mg, 1.16 mmol), tetrakis(triphenylphosphine)palladium(0) (5 mg, 0.004 mmol), dioxane (1.5 mL), and water (0.5 mL). The vial was capped and reacted in a CEM microwave at 150° C. for 30 min. This solution was loaded onto a 2 g SCX SPE cartridge primed with 3 mL of methanol. The cartridge was then sequentially eluted with water (3 mL), methanol (9 mL), and 2M $NH_3$ in MeOH (6 mL). The $NH_3$ in MeOH fractions were dried under a stream of $N_2$ at 40° C. The crude product was taken up in dimethyl sulfoxide (1 mL) and purified on an Agilent MDAP with UV (230 nm) and MS detection. The desired fractions were passed thru two sequential 500 mg Pharmasil CHQAX cartridge primed with 1 mL of methanol and 1 mL of water. The solvents were evaporated under a stream of $N_2$ at 60° C. to give 34.7 mg of the title compound (34%).

LC/MS=m/z 430 [M+H] Ret. Time: 1.32 min.

Example 62

5-(5-{[(2-cyanoethyl)amino]methyl}-3-pyridinyl)-3-[1-(ethylsulfonyl)-4-piperidinyl]-1H-indole-7-carboxamide

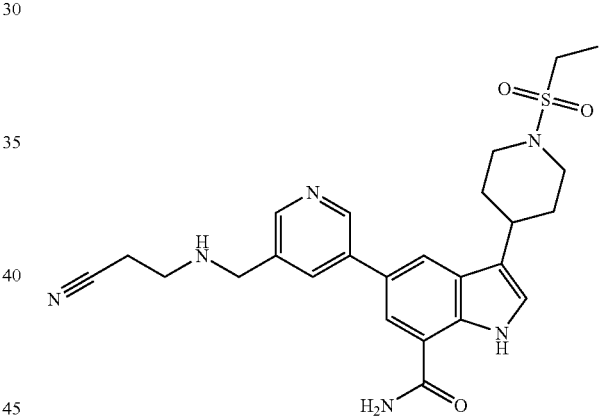

To 5-bromo-3-[1-(ethylsulfonyl)-4-piperidinyl]-1H-indole-7-carboxamide (30 mg, 0.072 mmol) was added 3-({[5-(4,4,5,5-tetramethyl-1,3,2-dioxaborolan-2-yl)-3-pyridinyl]methyl}amino)propanenitrile (24.8 mg, 0.086 mmol). To this mixture was added dioxane (0.75 mL), followed by a solution of potassium carbonate (60 mg, 0.434 mmol) in water (0.25 mL) and SK-CC02-A (4.4 mg, 0.007 mmol). The vials were capped and reacted in a CEM microwave at 150° C. for 30 min. The reaction was loaded onto a 2 g SCX SPE cartridge primed with 3 mL of methanol. The cartridge was then sequentially eluted with water (3 mL), methanol (9 mL), and 2M $NH_3$ in MeOH (6 mL). The $NH_3$ in MeOH fractions were dried under a stream of $N_2$ at 40° C. The crude product was purified on the Agilent MDAP with UV (230 nm) and MS detection. The desired fractions were passed thru a 5 g CHQAX cartridge primed with 4 mL of methanol and 4 mL of water. The solvents were evaporated under a stream of $N_2$ at 65° C. to give 6.2 mg of the title compound (17.4%).

LC/MS=m/z 495 [M+H] Ret. Time: 1.29 min.

Example 63

3-[1-(ethylsulfonyl)-4-piperidinyl]-5-(5-{[(2,2,2-trifluoroethyl)amino]methyl}-3-pyridinyl)-1H-indole-7-carboxamide

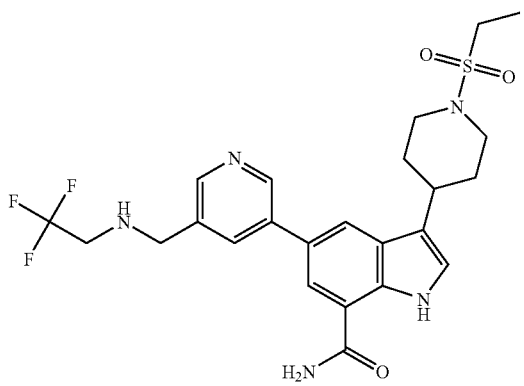

The title compound was prepared according to the general procedure of 5-(5-{[(2-cyanoethyl)amino]methyl}-3-pyridinyl)-3-[1-(ethylsulfonyl)-4-piperidinyl]-1H-indole-7-carboxamide, substituting 2,2,2-trifluoro-N-{[5-(4,4,5,5-tetramethyl-1,3,2-dioxaborolan-2-yl)-3-pyridinyl]methyl}ethanamine (24.3 mg, 0.077 mmol) for 3-({[5-(4,4,5,5-tetramethyl-1,3,2-dioxaborolan-2-yl)-3-pyridinyl]methyl}amino)propanenitrile to afford 8.3 mg of the title compound (22.0%).

LC/MS=m/z 524 [M+H] Ret. Time: 1.55 min.

Example 64

5-{3-[(dimethylamino)methyl]phenyl}-3-[1-(ethylsulfonyl)-4-piperidinyl]-1H-indole-7-carboxamide

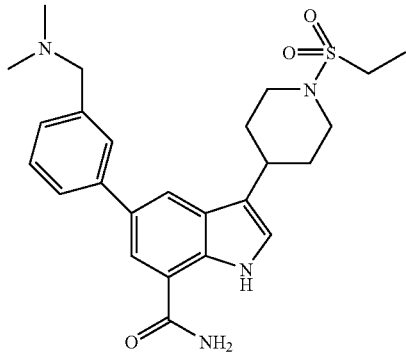

To a solution of 3-[1-(ethylsulfonyl)-4-piperidinyl]-5-(3-formylphenyl)-1H-indole-7-carboxamide (45 mg, 0.10 mmol) in DMSO (2 mL) was added 2 M dimethylamine in THF (500 μL, 1.0 mmol). The reaction mixture was stirred at room temperature for 5 h before addition of sodium triacetoxyborohydride (220 mg, 1.04 mmol). The reaction was then stirred overnight. Compound was purified by Gilson Preparatory HPLC to give 9.0 mg of the title compound (19.2%).

LC/MS=m/z 469 [M+H] Ret. Time: 1.55 min

Example 65

5-(5-{[ethyl(methyl)amino]methyl}-3-thienyl)-3-[1-(ethylsulfonyl)-4-piperidinyl]-1H-indole-7-carboxamide trifluoroacetate

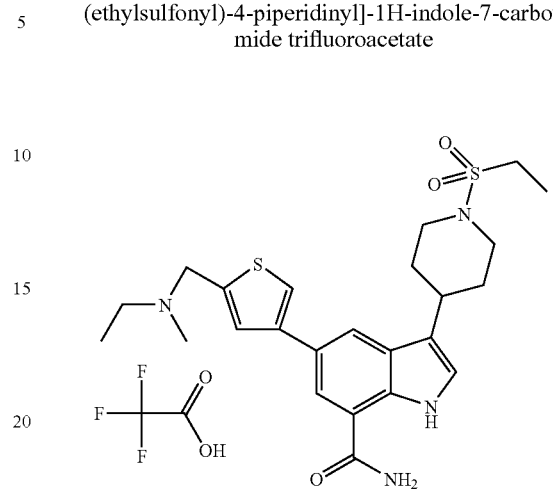

To a solution of 3-[1-(ethylsulfonyl)-4-piperidinyl]-5-(5-formyl-3-thienyl)-1H-indole-7-carboxamide (50 mg, 0.11 mmol) in dimethyl sulfoxide (2 mL) was added N-methylethanamine (59.1 mg, 1.0 mmol), 2 drops of acetic acid and reacted overnight. Sodium triacetoxyborohydride (212 mg, 1 mmol) was then added and reacted overnight at room temperature. It was then purified by Gilson Preparatory HPLC to give 20.0 mg of the title compound (33.2%).

LC/MS=m/z 489 [M+H] Ret. Time: 1.50 min

Example 66

5-(5-{[[2-(diethylamino)ethyl](methyl)amino]methyl}-3-thienyl)-3-[1-(ethylsulfonyl)-4-piperidinyl]-1H-indole-7-carboxamide trifluoroacetate

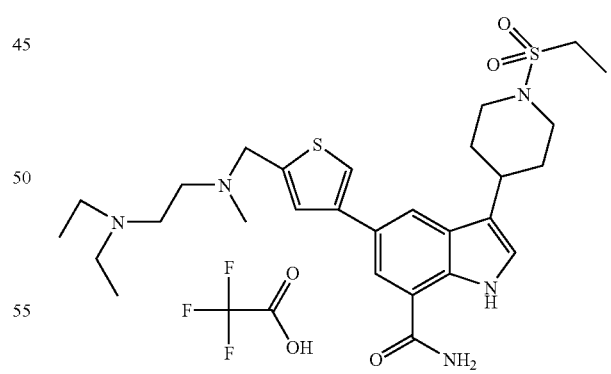

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting N,N-diethyl-N'-methyl-1,2-ethanediamine (130 mg, 1.0 mmol) for N-methylethanamine to afford 30.0 mg of the title compound (44.5%).

LC/MS=m/z 560 [M+H] Ret. Time: 1.41 min.

Example 67

5-(5-{[butyl(methyl)amino]methyl}-3-thienyl)-3-[1-(ethylsulfonyl)-4-piperidinyl]-1H-indole-7-carboxamide trifluoroacetate

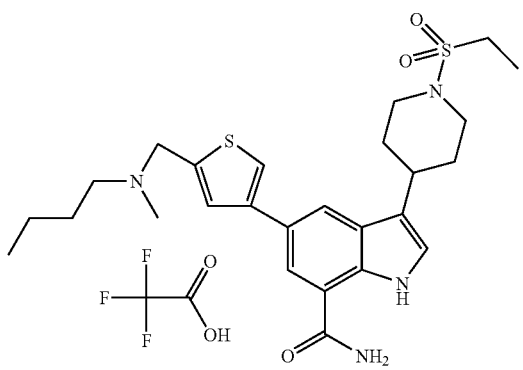

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting butyl(methyl)amine (87 mg, 1.0 mmol) for N-methylethanamine to afford 10 mg of the title compound (15.8%).

LC/MS=m/z 517 [M+H] Ret. Time: 1.61 min.

Example 68

3-[1-(ethylsulfonyl)-4-piperidinyl]-5-(5-{[methyl(propyl)amino]methyl}-3-thienyl)-1H-indole-7-carboxamide trifluoroacetate

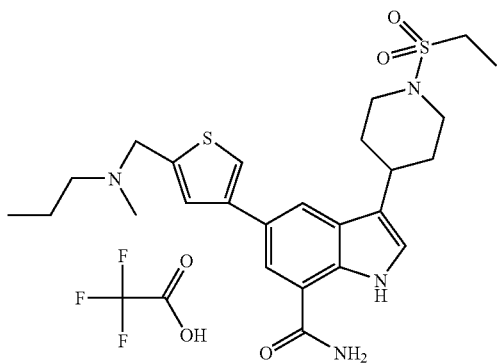

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting methyl(propyl)amine (73 mg, 1.0 mmol) for N-methylethanamine to afford 20.0 mg of the title compound (32.4%).

LC/MS=m/z 503 [M+H] Ret. Time: 1.54 min.

Example 69

5-(5-{[[2-(dimethylamino)ethyl](methyl)amino]methyl}-3-thienyl)-3-[1-(ethylsulfonyl)-4-piperidinyl]-1H-indole-7-carboxamide trifluoroacetate

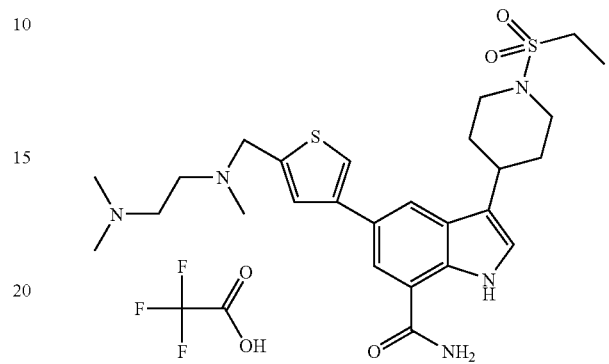

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting [2-(dimethylamino)ethyl]methylamine (102 mg, 1.0 mmol) for N-methylethanamine to afford 26.0 mg of the title compound (40.3%).

LC/MS=m/z 532 [M+H] Ret. Time: 1.48 min.

Example 70

5-(5-{[[3-(dimethylamino)propyl](methyl)amino]methyl}-3-thienyl)-3-[1-(ethylsulfonyl)-4-piperidinyl]-1H-indole-7-carboxamide trifluoroacetate

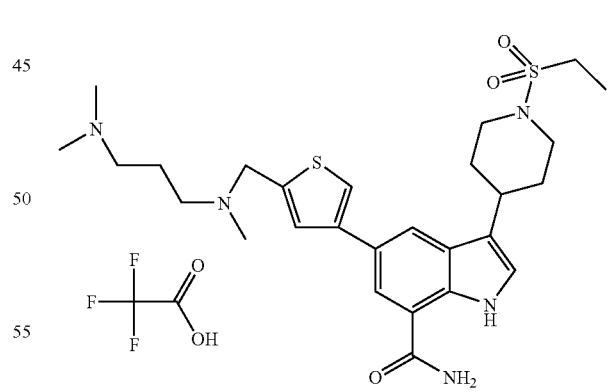

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting [3-(dimethylamino)propyl]methylamine (116 mg, 1.0 mmol) for N-methylethanamine to afford 21.0 mg of the title compound (31.8%).

LC/MS=m/z 546 [M+H] Ret. Time: 1.49 min.

Example 71

5-(5-{[cyclopentyl(methyl)amino]methyl}-3-thienyl)-3-[1-(ethylsulfonyl)-4-piperidinyl]-1H-indole-7-carboxamide trifluoroacetate

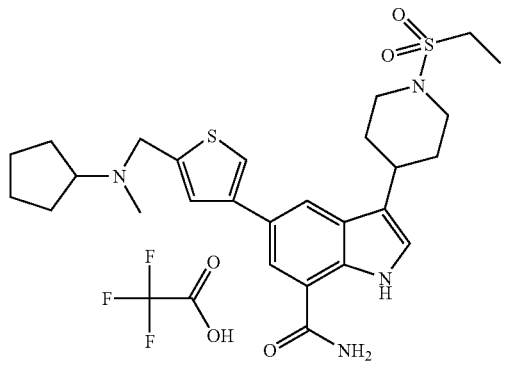

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting cyclopentyl(methyl)amine (99 mg, 1.0 mmol) for N-methylethanamine to afford 5.0 mg of the title compound (7.78%).

LC/MS=m/z 529 [M+H] Ret. Time: 1.65 min.

Example 72

3-[1-(ethylsulfonyl)-4-piperidinyl]-5-(5-{[methyl(pentyl)amino]methyl}-3-thienyl)-1H-indole-7-carboxamide trifluoroacetate

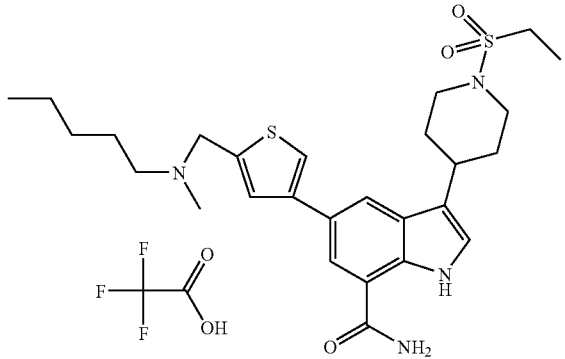

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting methyl(pentyl)amine (101 mg, 1.0 mmol) for N-methylethanamine to afford 19.0 mg of the title compound (29.5%).

LC/MS=m/z 531 [M+H] Ret. Time: 161 min.

Example 73

3-[1-(ethylsulfonyl)-4-piperidinyl]-5-(5-{[methyl(2-methylpropyl)amino]methyl}-3-thienyl)-1H-indole-7-carboxamide trifluoroacetate

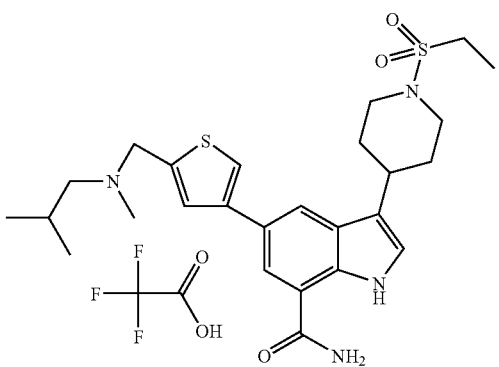

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting methyl(2-methylpropyl)amine (87 mg, 1.0 mmol) for N-methylethanamine to afford 3.0 mg of the title compound (4.8%).

LC/MS=m/z 517 [M+H] Ret. Time: 1.61 min.

Example 74

3-[1-(ethylsulfonyl)-4-piperidinyl]-5-(5-{[methyl(phenylmethyl)amino]methyl}-3-thienyl)-1H-indole-7-carboxamide trifluoroacetate

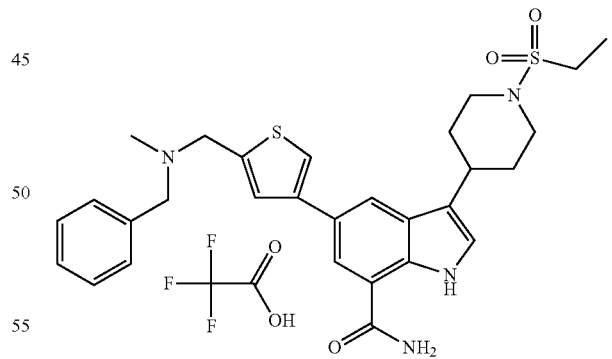

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting methyl(phenylmethyl)amine (121 mg, 1.0 mmol) for N-methylethanamine to afford 15 mg of the title compound (22.6%).

LC/MS=m/z 551 [M+H] Ret. Time: 1.67 min.

Example 75

3-[1-(ethylsulfonyl)-4-piperidinyl]-5-(5-{[(2-hydroxyethyl)(methyl)amino]methyl}-3-thienyl)-1H-indole-7-carboxamide trifluoroacetate

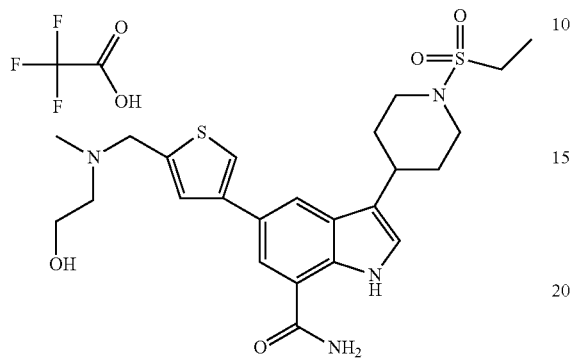

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting 2-(methylamino)ethanol (75 mg, 1.0 mmol) for N-methylethanamine to afford 27.0 mg of the title compound (43.6%).

LC/MS=m/z 505 [M+H] Ret. Time: 1.46 min.

Example 76

3-[1-(ethylsulfonyl)-4-piperidinyl]-5-[5-({methyl[2-(2-pyridinyl)ethyl]amino}methyl)-3-thienyl]-1H-indole-7-carboxamide trifluoroacetate

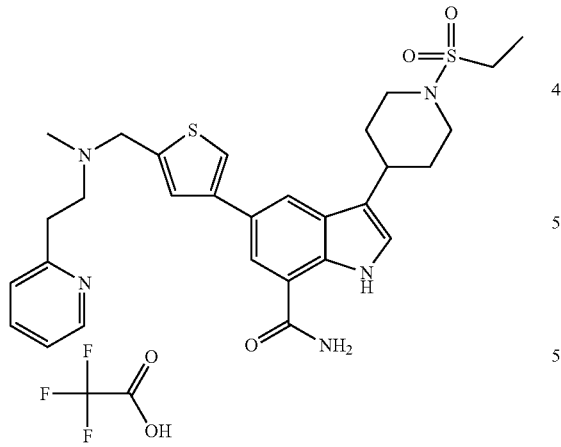

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting methyl[2-(2-pyridinyl)ethyl]amine (75 mg, 1.0 mmol) for N-methylethanamine to afford 5.0 mg of the title compound (7.36%).

LC/MS=m/z 566 [M+H] Ret. Time: 1.59 min.

Example 77

3-[1-(ethylsulfonyl)-4-piperidinyl]-5-(5-{[(2-furanylmethyl)(methyl)amino]methyl}-3-thienyl)-1H-indole-7-carboxamide trifluoroacetate

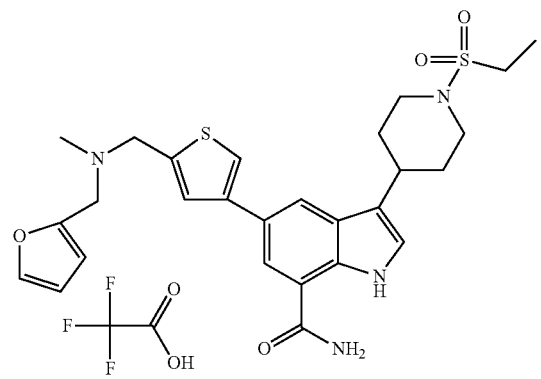

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting 1-(2-furanyl)-N-methylmethanamine (111 mg, 1.0 mmol) for N-methylethanamine to afford 19.0 mg of the title compound (29.0%).

LC/MS=m/z 541 [M+H] Ret. Time: 1.59 min.

Example 78

3-[1-(ethylsulfonyl)-4-piperidinyl]-5-(5-{[methyl(4-pyridinylmethyl)amino]methyl}-3-thienyl)-1H-indole-7-carboxamide trifluoroacetate

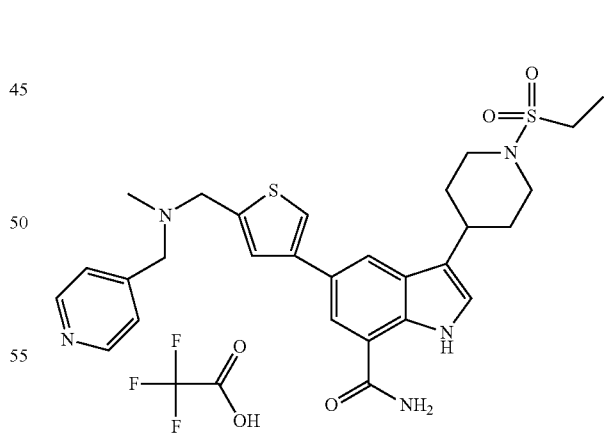

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting methyl(4-pyridinylmethyl)amine (122 mg, 1.0 mmol) for N-methylethanamine to afford 31.0 mg of the title compound (46.6%).

LC/MS=m/z 552 [M+H] Ret. Time: 1.37 min.

Example 79

3-[1-(ethylsulfonyl)-4-piperidinyl]-5-{5-[(methyl{[1-(1-methylethyl)-3-pyrrolidinyl]methyl}amino)methyl]-3-thienyl}-1H-indole-7-carboxamide trifluoroacetate

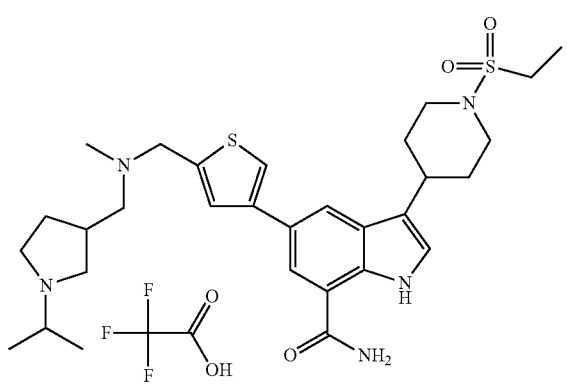

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting methyl{[1-(1-methylethyl)-3-pyrrolidinyl]methyl}amine (156 mg, 1.0 mmol) for N-methylethanamine to afford 21.0 mg of the title compound (30.0%).

LC/MS=m/z 586 [M+H] Ret. Time: 1.43 min.

Example 80

3-[1-(ethylsulfonyl)-4-piperidinyl]-5-(5-{[methyl(2-thienylmethyl)amino]methyl}-3-thienyl)-1H-indole-7-carboxamide trifluoroacetate

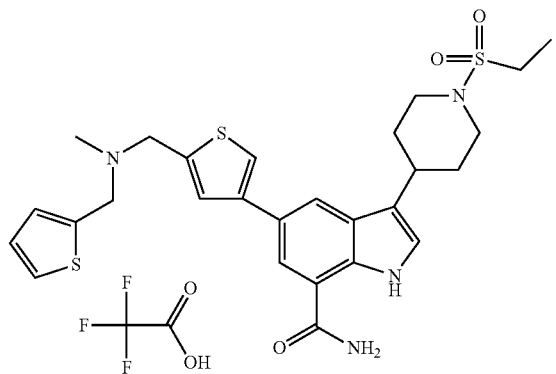

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting methyl(2-thienylmethyl)amine (127 mg, 1.0 mmol) for N-methylethanamine to afford 26.0 mg of the title compound (38.8%).

LC/MS=m/z 557 [M+H] Ret. Time: 1.72 min.

Example 81

3-[1-(ethylsulfonyl)-4-piperidinyl]-5-[5-({methyl[1-(2-thienyl)ethyl]amino}methyl)-3-thienyl]-1H-indole-7-carboxamide trifluoroacetate

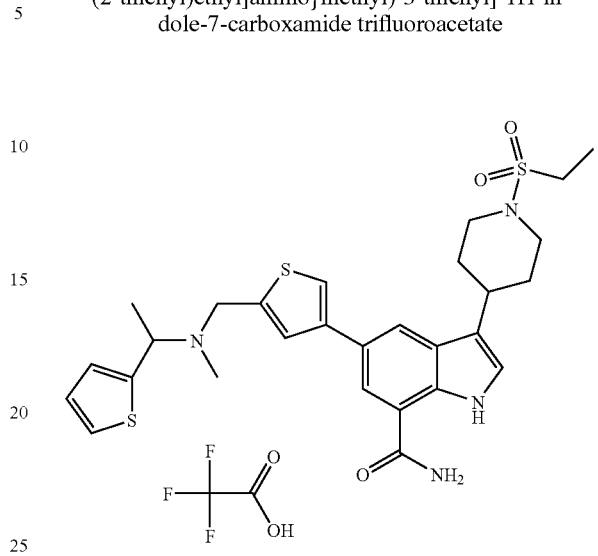

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting methyl[1-(2-thienyl)ethyl]amine (141 mg, 1.0 mmol) for N-methylethanamine to afford 6.0 mg of the title compound (8.76%).

LC/MS=m/z 571 [M+H] Ret. Time: 1.78 min.

Example 82

3-[1-(ethylsulfonyl)-4-piperidinyl]-5-(5-{[methyl(3-thienylmethyl)amino]methyl}-1'-3-thienyl)-1H-indole-7-carboxamide trifluoroacetate

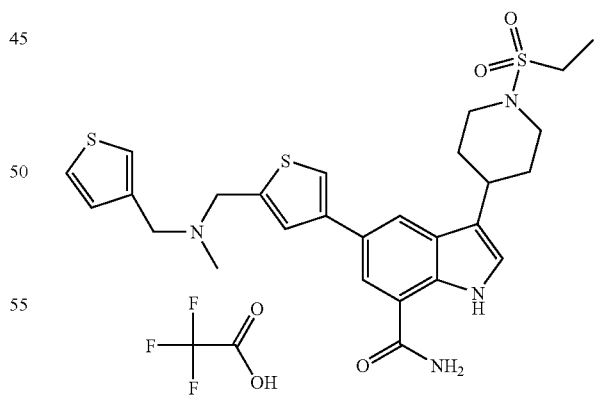

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting methyl(3-thienylmethyl)amine (127 mg, 1.0 mmol) for N-methylethanamine to afford 7.0 mg of the title compound (10.4%).

LC/MS=m/z 557 [M+H] Ret. Time: 1.78 min.

Example 83

3-[1-(ethylsulfonyl)-4-piperidinyl]-5-(5-{[methyl(tetrahydro-2H-pyran-4-ylmethyl)amino]methyl}-3-thienyl)-1H-indole-7-carboxamide trifluoroacetate

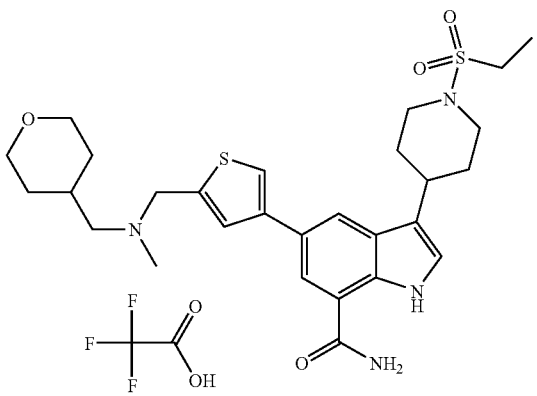

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting methyl(tetrahydro-2H-pyran-4-ylmethyl)amine (129 mg, 1.0 mmol) for N-methylethanamine to afford 11.0 mg of the title compound (16.4%).

LC/MS=m/z 559 [M+H] Ret. Time: 1.63 min.

Example 84

3-[1-(ethylsulfonyl)-4-piperidinyl]-5-(5-{[methyl(3-pyridinylmethyl)amino]methyl}-3-thienyl)-1H-indole-7-carboxamide trifluoroacetate

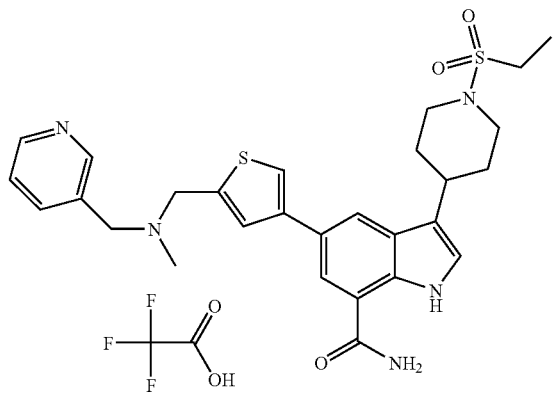

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting methyl(3-pyridinylmethyl)amine (122 mg, 1.0 mmol) for N-methylethanamine to afford 9.5 mg of the title compound (14.3%).

LC/MS=m/z 552 [M+H] Ret. Time: 1.56 min.

Example 85

3-[1-(ethylsulfonyl)-4-piperidinyl]-5-(5-{[methyl(4-pyrimidinylmethyl)amino]methyl}-3-thienyl)-1H-indole-7-carboxamide trifluoroacetate

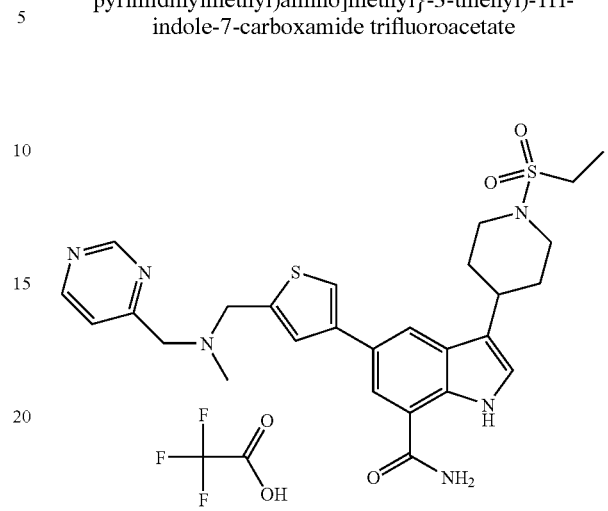

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide trifluoroacetate, substituting methyl(4-pyrimidinylmethyl)amine (123 mg, 1.0 mmol) for N-methylethanamine to afford 4.0 mg of the title compound (6.0%).

LC/MS=m/z 555 [M+H] Ret. Time: 1.65 min.

Example 86

3-[1-(ethylsulfonyl)-4-piperidinyl]-5-[5-({methyl[2-(methyloxy)ethyl]amino}methyl)-3-thienyl]-1H-indole-7-carboxamide trifluoroacetate

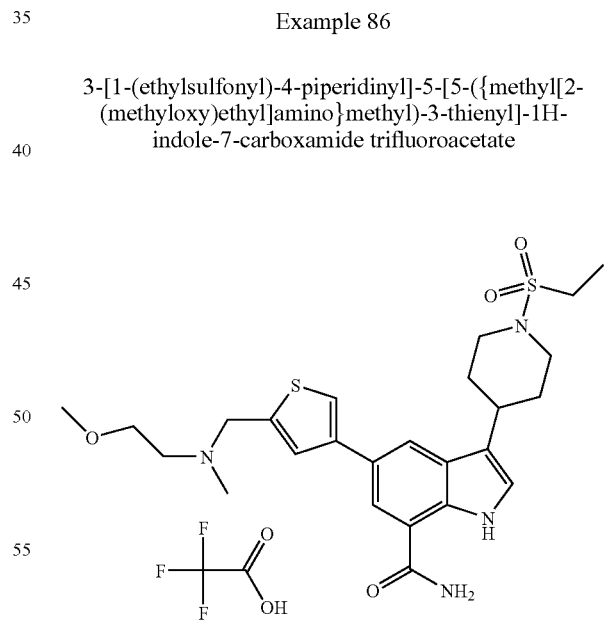

To a solution of 3-[1-(ethylsulfonyl)-4-piperidinyl]-5-(5-formyl-3-thienyl)-1H-indole-7-carboxamide (884 mg, 1.98 mmol) in dimethyl sulfoxide (5 mL) was added methyl[2-(methyloxy)ethyl]amine (1.86 g, 21 mmol) and HOAc (2 mL, 35 mmol). The reaction was stirred overnight at room temperature, and sodium triacetoxyborohydride (212 mg, 1 mmol) was added. Stirring continued for 1 hr. and CHCl₃ (50 mL) was added. The mixture was filtered, the CHCl₃ was

Example 87

5-{3-[(dimethylamino)methyl]phenyl}-3-[1-(ethyl-sulfonyl)-4-piperidinyl]-1H-indole-7-carboxamide trifluoroacetate

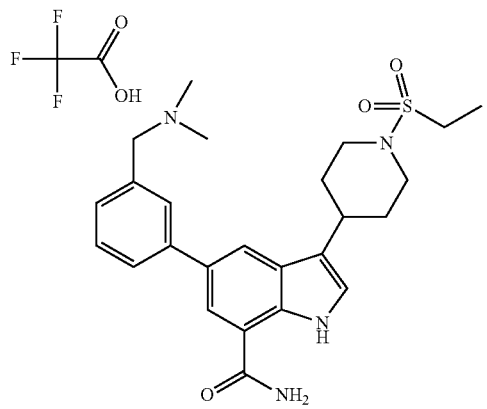

To a solution of 3-[1-(ethylsulfonyl)-4-piperidinyl]-5-(3-formylphenyl)-1H-indole-7-carboxamide (45 mg, 0.1 mmol) in DMSO (2 mL) was added 2 M methylamine in THF (500 µL, 1.0 mmol) and stirred at room temperature for 5 h. To the mixture, was then added sodium triacetoxyborohydride (220 mg, 1.0 mmol) and stirred overnight. It was then purified by Gilson Preparatory HPLC to give 9.0 mg of the title compound (15.4%).

LC/MS=m/z 469 [M+H] Ret. Time: 1.55 min.

Example 88

3-[1-(ethylsulfonyl)-4-piperidinyl]-5-(5-{[methyl(1-methylethyl)amino]methyl}-3-thienyl)-1H-indole-7-carboxamide trifluoroacetate

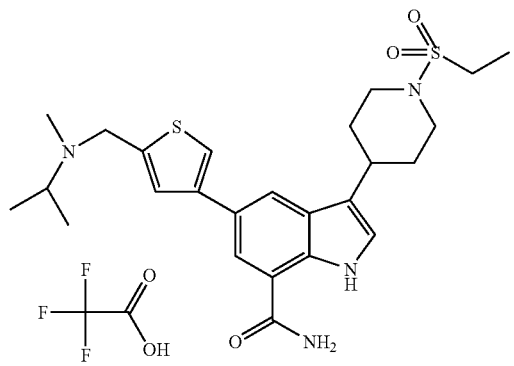

To a solution of 3-[1-(ethylsulfonyl)-4-piperidinyl]-5-(5-formyl-3-thienyl)-1H-indole-7-carboxamide (46.0 mg, 0.1 mmol) in DMSO (2.0 mL) was added N-methyl-2-propan-amine (73.1 mg, 1.0 mmol). The reaction mixture was then reacted in a microwave at 160° C. for 10 min. Sodium triacetoxyborohydride (220 mg, 1.0 mmol) was then added and the reaction was reacted at room temperature overnight. It was then purified by Gilson Preparatory HPLC to give 24.0 mg of the title compound (44.2%).

LC/MS=m/z 543 [M+H] Ret. Time: 1.70 min.

Example 89

3-[1-(ethylsulfonyl)-4-piperidinyl]-5-{5-[(2-propyl-1-pyrrolidinyl)methyl]-3-thienyl}-1H-indole-7-carboxamide

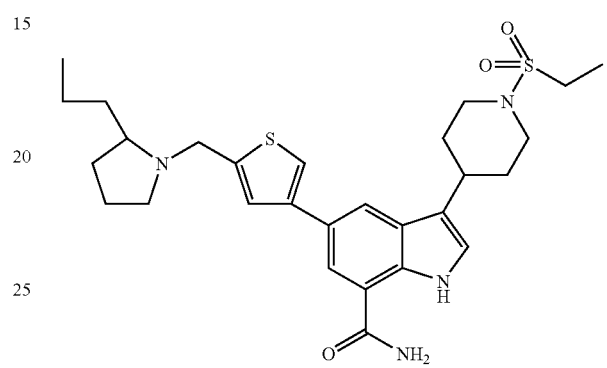

To a solution of 3-[1-(ethylsulfonyl)-4-piperidinyl]-5-(5-formyl-3-thienyl)-1H-indole-7-carboxamide (50 mg, 0.11 mmol) in DMSO (2.0 mL) was added 2-propylpyrrolidine (113 mg, 1.0 mmol). The reaction mixture was then reacted in a microwave at 120° C. for 10 min. Sodium triacetoxyborohydride (220 mg, 1.0 mmol) was then added and the reaction was reacted at room temperature overnight. It was then purified by Gilson Preparatory HPLC to give 21.0 mg of the title compound (38.7%).

LC/MS=m/z 543 [M+H] Ret. Time: 1.70 min.

Example 90

3-[1-(ethylsulfonyl)-4-piperidinyl]-5-(5-{[2-(3-py-ridinyl)-1-pyrrolidinyl]methyl}-3-thienyl)-1H-in-dole-7-carboxamide

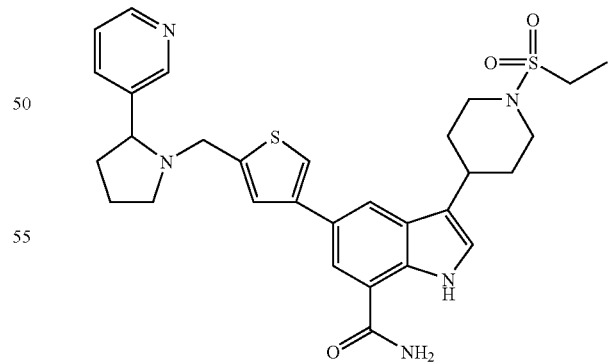

The title compound was prepared according to the general procedure of 3-[1-(ethylsulfonyl)-4-piperidinyl]-5-{5-[(2-propyl-1-pyrrolidinyl)methyl]-3-thienyl}-1H-indole-7-carboxamide, substituting 3-(2-pyrrolidinyl)pyridine (148 mg, 1.0 mmol) for 2-propylpyrrolidine to afford 13.0 mg of the title compound (22.5%).

LC/MS=m/z 578 [M+H] Ret. Time: 1.52 min.

Example 91

5-(5-{[2-(1,1-dimethylethyl)-1-pyrrolidinyl]methyl}-3-thienyl)-3-[1-(ethylsulfonyl)-4-piperidinyl]-1H-indole-7-carboxamide trifluoroacetate

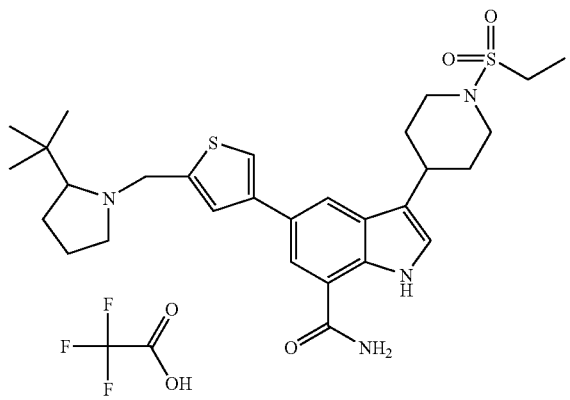

The title compound was prepared according to the general procedure of 3-[1-(ethylsulfonyl)-4-piperidinyl]-5-{5-[(2-propyl-1-pyrrolidinyl)methyl]-3-thienyl}-1H-indole-7-carboxamide, substituting 2-(1,1-dimethylethyl)pyrrolidine (127 mg, 1.0 mmol) for 2-propylpyrrolidine to afford 11.0 mg of the title compound (16.4%).

LC/MS=m/z 557 [M+H] Ret. Time: 1.65 min.

Example 92

5-{5-[(2-ethyl-1-pyrrolidinyl)methyl]-3-thienyl}-3-[1-(ethylsulfonyl)-4-piperidinyl]-1H-indole-7-carboxamide

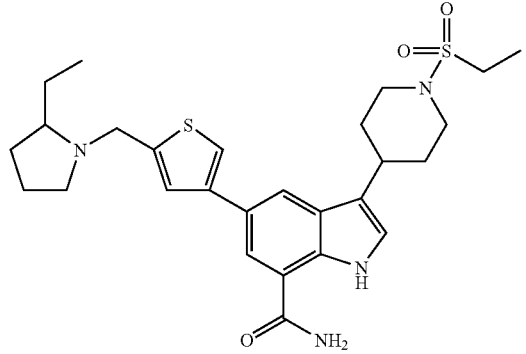

The title compound was prepared according to the general procedure of 3-[1-(ethylsulfonyl)-4-piperidinyl]-5-{5-[(2-propyl-1-pyrrolidinyl)methyl]-3-thienyl}-1H-indole-7-carboxamide, substituting 2-ethylpyrrolidine (99.0 mg, 1.0 mmol) for 2-propylpyrrolidine to afford 15.0 mg of the title compound (28.4%).

LC/MS=m/z 529 [M+H] Ret. Time: 1.66 min.

Example 93

3-[1-(ethylsulfonyl)-4-piperidinyl]-5-(5-{[2-(2-methylpropyl)-1-pyrrolidinyl]methyl}-3-thienyl)-1H-indole-7-carboxamide trifluoroacetate

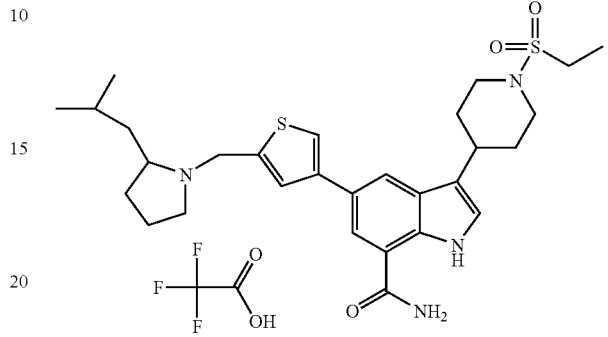

The title compound was prepared according to the general procedure of 3-[1-(ethylsulfonyl)-4-piperidinyl]-5-{5-[(2-propyl-1-pyrrolidinyl)methyl]-3-thienyl}-1H-indole-7-carboxamide, substituting 2-(2-methylpropyl)pyrrolidine (127 mg, 1.0 mmol) for 2-propylpyrrolidine to afford 7.0 mg of the title compound (10.4%).

LC/MS=m/z 557 [M+H] Ret. Time: 1.74 min.

Example 94

3-[1-(ethylsulfonyl)-4-piperidinyl]-5-(5-{[2-(1-methylethyl)-1-pyrrolidinyl]methyl}-3-thienyl)-1H-indole-7-carboxamide

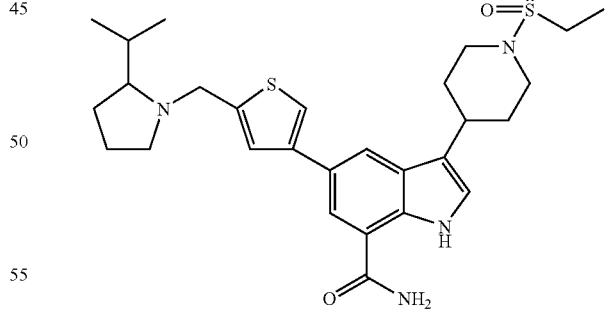

The title compound was prepared according to the general procedure of 3-[1-(ethylsulfonyl)-4-piperidinyl]-5-{5-[(2-propyl-1-pyrrolidinyl)methyl]-3-thienyl}-1H-indole-7-carboxamide, substituting 2-(1-methylethyl)pyrrolidine (113 mg, 1.0 mmol) for 2-propylpyrrolidine to afford 16.0 mg of the title compound (29.5%).

LC/MS=m/z 543 [M+H] Ret. Time: 1.61 min.

Example 95

3-[1-(ethylsulfonyl)-4-piperidinyl]-5-[5-({(2S)-2-[(methyloxy)methyl]-1-pyrrolidinyl}methyl)-3-thienyl]-1H-indole-7-carboxamide

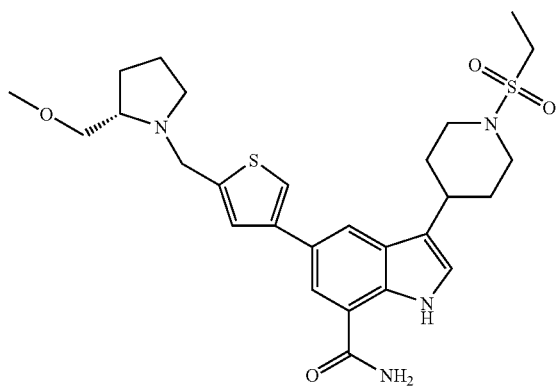

The title compound was prepared according to the general procedure of 3-[1-(ethylsulfonyl)-4-piperidinyl]-5-{5-[(2-propyl-1-pyrrolidinyl)methyl]-3-thienyl}-1H-indole-7-carboxamide, substituting (2S)-2-[(methyloxy)methyl]pyrrolidine (115 mg, 1.0 mmol) for 2-propylpyrrolidine to afford 22.0 mg of the title compound (40.4%).

LC/MS=m/z 544 [M+H] Ret. Time: 1.44 min.

Example 96

5-(5-{[cyclohexyl(methyl)amino]methyl}-3-thienyl)-3-[1-(ethylsulfonyl)-4-piperidinyl]-1H-indole-7-carboxamide

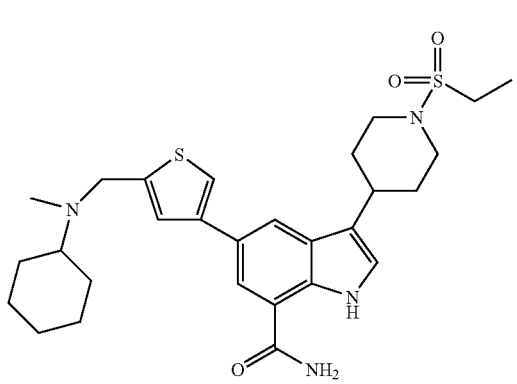

The title compound was prepared according to the general procedure of 3-[1-(ethylsulfonyl)-4-piperidinyl]-5-{5-[(2-propyl-1-pyrrolidinyl)methyl]-3-thienyl}-1H-indole-7-carboxamide, substituting cyclohexyl(methyl)amine (113 mg, 1.0 mmol) for 2-propylpyrrolidine to afford 15.0 mg of the title compound (27.6%).

LC/MS=m/z 543 [M+H] Ret. Time: 1.64 min.

Example 97

3-[1-(ethylsulfonyl)-4-piperidinyl]-5-(5-{[2-(2-methylpropyl)-1-pyrrolidinyl]methyl}-3-thienyl)-1H-indole-7-carboxamide

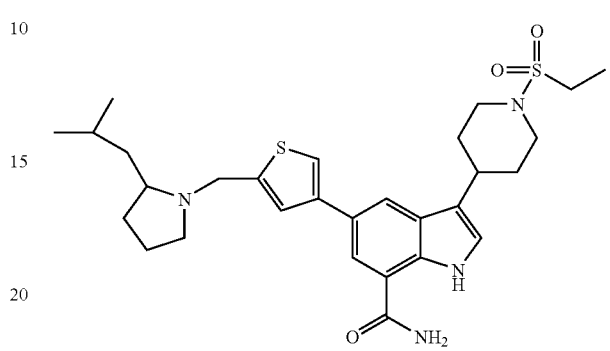

The title compound was prepared according to the general procedure of 3-[1-(ethylsulfonyl)-4-piperidinyl]-5-{5-[(2-propyl-1-pyrrolidinyl)methyl]-3-thienyl}-1H-indole-7-carboxamide, substituting 2-(2-methylpropyl)pyrrolidine (127 mg, 1.0 mmol) for 2-propylpyrrolidine to afford 12.0 mg of the title compound (21.6%).

LC/MS=m/z 557 [M+H] Ret. Time: 1.74 min.

Example 98

5-(5-{[ethyl(methyl)amino]methyl}-3-thienyl)-3-[1-(ethylsulfonyl)-4-piperidinyl]-1H-indole-7-carboxamide

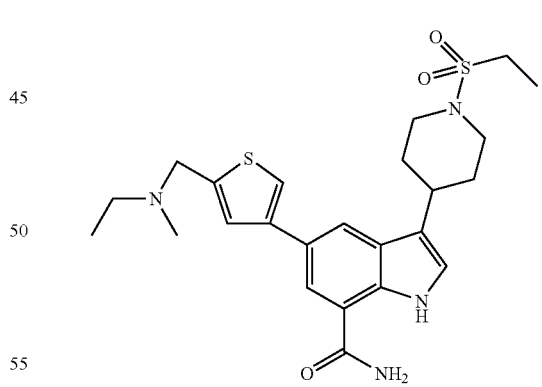

To a solution of 3-[1-(ethylsulfonyl)-4-piperidinyl]-5-(5-formyl-3-thienyl)-1H-indole-7-carboxamide (50 mg, 0.11 mmol) in DMSO (2.0 mL) was added 2 drops of acetic acid, ethyl(methyl)amine (59 mg, 1.0 mmol), and stirred at room temperature for 5 h. To this was then added sodium triacetoxyborohydride (212 mg, 1.0 mmol) and reacted overnight. It was then purified by Gilson Preparatory HPLC to give 30.0 mg of the title compound (61.4%).

LC/MS=m/z 489 [M+H] Ret. Time: 1.50 min.

Example 99

3-[1-(ethylsulfonyl)-4-piperidinyl]-5-(5-{[methyl(propyl)amino]methyl}-3-thienyl)-1H-indole-7-carboxamide

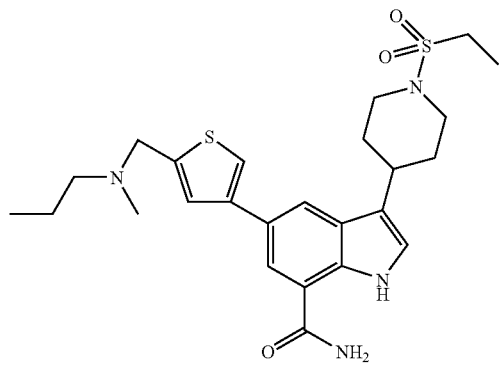

The title compound was prepared according to the general procedure of 5-(5-{[ethyl(methyl)amino]methyl}-3-thienyl)-3-[1-(ethylsulfonyl)-4-piperidinyl]-1H-indole-7-carboxamide, substituting methyl(propyl)amine (73 mg, 1.0 mmol) for 2-propylpyrrolidine to afford 32.0 mg of the title compound (63.7%).

LC/MS=m/z 503 [M+H] Ret. Time: 1.54 min.

Example 100

3-{1-[(1-methylethyl)sulfonyl]-4-piperidinyl}-5-(5-{[methyl(propyl)amino]methyl}-3-thienyl)-1H-indole-7-carboxamide trifluoroacetate

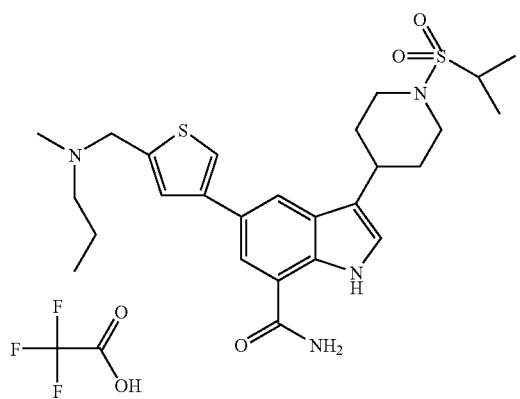

To a solution of 5-(5-formyl-3-thienyl)-3-{1-[(1-methylethyl)sulfonyl]-4-piperidinyl}-1H-indole-7-carboxamide (46 mg, 0.10 mmol) in DMSO (2.0 mL) was added 2 drops of acetic acid, methyl(propyl)amine (73 mg, 1.0 mmol), and stirred at room temperature for 5 h. To this was then added sodium triacetoxyborohydride (212 mg, 1.0 mmol) and reacted overnight. It was then purified by Gilson Preparatory HPLC to give 25.0 mg of the title compound (39.6%).

LC/MS=m/z 517 [M+H] Ret. Time: 1.61 min.

Example 101

5-(5-{[ethyl(methyl)amino]methyl}-3-thienyl)-3-{1-[(1-methylethyl)sulfonyl]-4-piperidinyl}-1H-indole-7-carboxamide

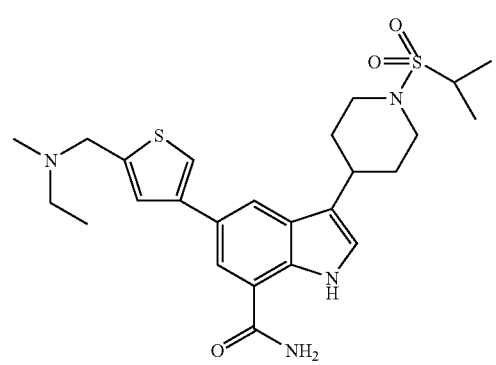

The title compound was prepared according to the general procedure of 3-{1-[(1-methylethyl)sulfonyl]-4-piperidinyl}-5-(5-{[methyl(propyl)amino]methyl}-3-thienyl)-1H-indole-7-carboxamide trifluoroacetate, substituting ethyl(methyl)amine (59 mg, 1.0 mmol) for methyl(propyl)amine to afford 8.0 mg of the title compound (15.9%).

LC/MS=m/z 503 [M+H] Ret. Time: 1.59 min.

Example 102

3-{1-[(1-methylethyl)sulfonyl]-4-piperidinyl}-5-[5-({methyl[2-(methyloxy)ethyl]amino}methyl)-3-thienyl]-1H-indole-7-carboxamide

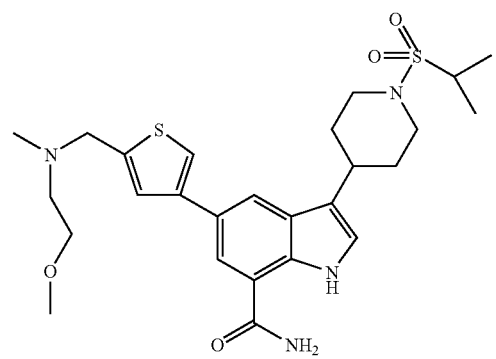

The title compound was prepared according to the general procedure of 3-{1-[(1-methylethyl)sulfonyl]-4-piperidinyl}-5-(5-{[methyl(propyl)amino]methyl}-3-thienyl)-1H-indole-7-carboxamide trifluoroacetate, substituting methyl[2-(methyloxy)ethyl]amine (89 mg, 1.0 mmol) for methyl(propyl)amine to afford 37.0 mg of the title compound (69.4%).

LC/MS=m/z 533 [M+H] Ret. Time: 1.58 min.

Example 103

3-[1-(ethylsulfonyl)-4-piperidinyl]-5-{5-[(methylamino)methyl]-2-thienyl}-1H-indole-7-carboxamide

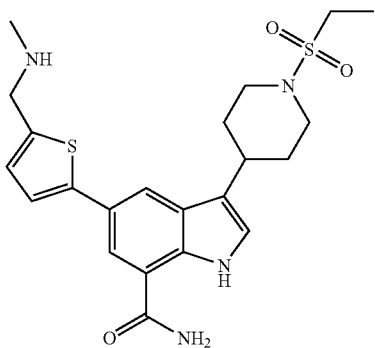

To a solution of 3-[1-(ethylsulfonyl)-4-piperidinyl]-5-(5-formyl-2-thienyl)-1H-indole-7-carboxamide (35 mg, 0.078 mmol) in DMSO (1.0 mL) was added acetic acid (3 drops), 2 M methylamine in THF (0.24 mL, 0.471 mmol), and reacted for 3 h. Sodium triacetoxyborohydride (100 mg, 0.471 mmol) was then added and reaction was stirred overnight. All solvent was removed in vacuo and purified by Gilson Preparatory HPLC. The impure desired fraction was concentrated under reduced pressure and loaded onto a 500 mg SCX SPE cartridge primed with 10 mL of methanol. The cartridge was then sequentially eluted with 2M $NH_3$ in MeOH (10 mL×2). The $NH_3$ in MeOH fractions were concentrated to give 7.3 mg of the title compound (20%).

LC/MS=m/z 459.6 [M+H] Ret. Time: 1.25 min.

Example 104

3-[1-(ethylsulfonyl)-4-piperidinyl]-5-{5-[(2-methyl-1-pyrrolidinyl)methyl]-3-thienyl}-1H-indole-7-carboxamide trifluoroacetate

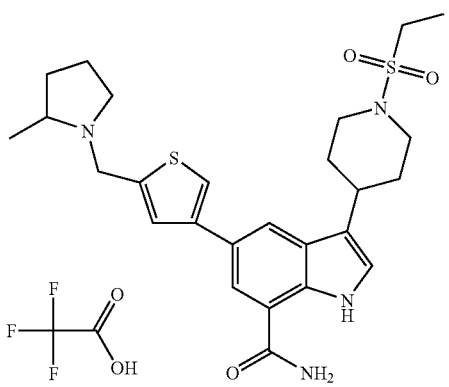

To a solution of 3-[1-(ethylsulfonyl)-4-piperidinyl]-5-(5-formyl-2-thienyl)-1H-indole-7-carboxamide (50 mg, 0.112 mmol) in DMSO (3.0 mL) was added acetic acid (3 drops), 2-methylpyrrolidine (0.12 mL, 1.12 mmol) and reacted for 4 h. Sodium triacetoxyborohydride (238 mg, 1.12 mmol) was then added and the reaction was stirred overnight. The reaction mixture was purified by reverse phase Gilson Preparatory HPLC to give 17 mg of the title compound (30%).

LCMS: 515.4 (M+H), Rt 1.60 min

Example 105

3-[1-(ethylsulfonyl)-4-piperidinyl]-5-(5-{[(2-methylpropyl)amino]methyl}-3-thienyl)-1H-indole-7-carboxamide trifluoroacetate

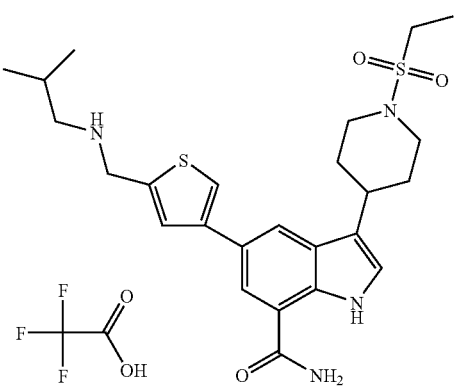

To a solution of 3-[1-(ethylsulfonyl)-4-piperidinyl]-5-(5-formyl-3-thienyl)-1H-indole-7-carboxamide (50 mg, 0.112 mmol) in DMSO (2.0 mL) was added acetic acid (4 drops), (2-methylpropyl)amine (0.17 mL, 1.68 mmol), and sodium triacetoxyborohydride (356 mg, 1.68 mmol) were reacted. The reaction mixture was purified by reverse phase Gilson Preparatory HPLC to give 15 mg of the title compound (27%).

LCMS: 503.4 (M+H), Rt 1.60 min

Example 106

3-[1-(ethylsulfonyl)-4-piperidinyl]-5-{5-[(propylamino)methyl]-3-thienyl}-1H-indole-7-carboxamide trifluoroacetate

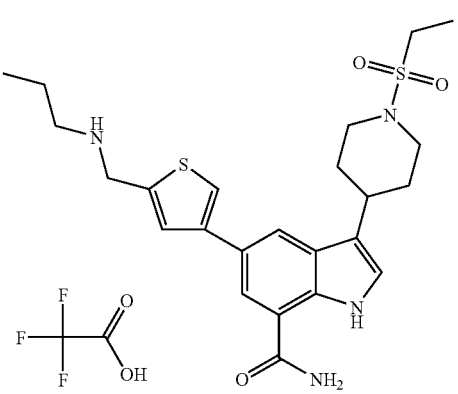

To a solution of 3-[1-(ethylsulfonyl)-4-piperidinyl]-5-(5-formyl-3-thienyl)-1H-indole-7-carboxamide (50 mg, 0.112 mmol) in DMSO (2.0 mL) was added acetic acid (3 drops), (2-methylpropyl)amine (0.17 mL, 1.68 mmol), and sodium triacetoxyborohydride (356 mg, 1.68 mmol) were reacted. The reaction mixture was purified by reverse phase Gilson Preparatory HPLC to give 15 mg of the title compound (27%).
LCMS: 489 (M+H), Rt 1.61 min

Example 107

5-{5-[(diethylamino)methyl]-3-thienyl}-3-[1-(ethylsulfonyl)-4-piperidinyl]-1H-indole-7-carboxamide trifluoroacetate

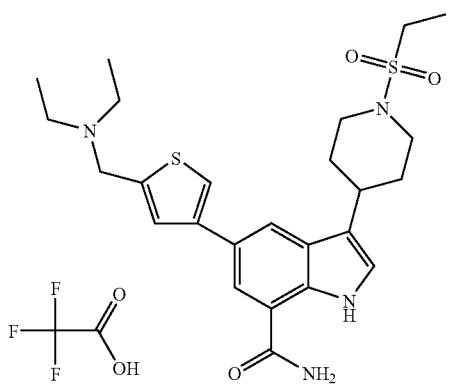

To a solution of 3-[1-(ethylsulfonyl)-4-piperidinyl]-5-(5-formyl-3-thienyl)-1H-indole-7-carboxamide (50 mg, 0.11 mmol) in DMSO (2.0 mL), was added acetic acid (3 drops), diethylamine (0.12 mL, 1.12 mmol) and stirred for 4 h at room temperature. Sodium triacetoxyborohydride (238 mg, 1.12 mmol) was then added and the reaction was stirred overnight. The reaction mixture was purified by reverse phase Gilson Preparatory HPLC to give 7.0 mg of the title compound (13%).
LCMS: 501.4 (M+H), Rt 1.51 min

Example 108

5-(5-{[(2R,5R)-2,5-dimethyl-1-pyrrolidinyl]methyl}-3-thienyl)-3-[1-(ethylsulfonyl)-4-piperidinyl]-1H-indole-7-carboxamide trifluoroacetate

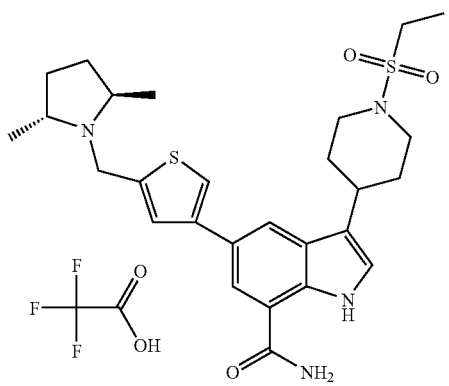

To a solution of 3-[1-(ethylsulfonyl)-4-piperidinyl]-5-(5-formyl-3-thienyl)-1H-indole-7-carboxamide (50 mg, 0.112 mmol) in DMSO (2.0 mL), was added acetic acid (3 drops), (2R,5R)-2,5-dimethylpyrrolidine (151 mg, 1.123 mmol), and reacted for 4 h. Sodium triacetoxyborohydride (238 mg, 1.123 mmol) was then added. The reaction mixture was purified by reverse phase Gilson Preparatory HPLC to give 27 mg of the title compound (46%).
LCMS: 529.4 (M+H), Rt 1.64 min

Example 109

5-{5-[(cyclopropylamino)methyl]-3-thienyl}-3-[1-(ethylsulfonyl)-4-piperidinyl]-1H-indole-7-carboxamide trifluoroacetate

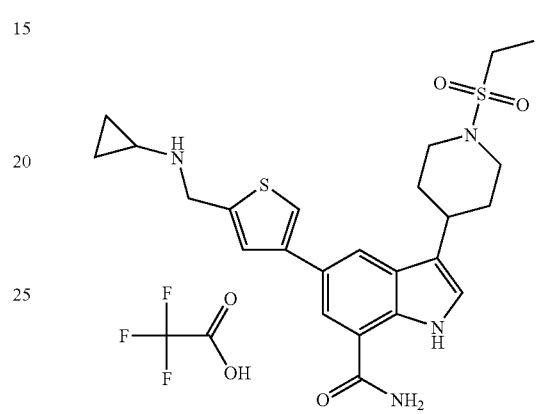

To a solution of 3-[1-(ethylsulfonyl)-4-piperidinyl]-5-(5-formyl-3-thienyl)-1H-indole-7-carboxamide (50 mg, 0.11 mmol) in DMSO (2.0 mL), was added acetic acid (5 drops), and cyclopropylamine (0.12 mL, 1.68 mmol) and reacted for 6 h. Sodium triacetoxyborohydride (356 mg, 1.68 mmol) was then added and the reaction was stirred overnight. The reaction mixture was purified by reverse phase Gilson Preparatory HPLC to give 8.0 mg of the title compound (10%).
LCMS: 487.2 (M+H), Rt 1.64 min and 1.68 min

Example 110

5-{5-[(cyclobutylamino)methyl]-3-thienyl}-3-[1-(ethylsulfonyl)-4-piperidinyl]-1H-indole-7-carboxamide trifluoroacetate

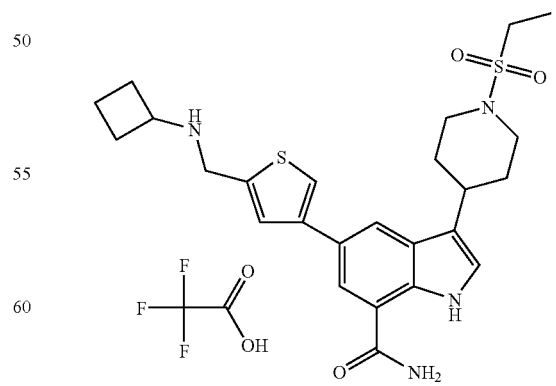

To a solution of 3-[1-(ethylsulfonyl)-4-piperidinyl]-5-(5-formyl-3-thienyl)-1H-indole-7-carboxamide (50 mg, 0.11 mmol) in DMSO (2.0 mL), was added acetic acid (4 drops), and cyclobutylamine (0.15 mL, 1.68 mmol) and reacted for 4 h. Sodium triacetoxyborohydride (356 mg, 1.68 mmol) was then added and the reaction was stirred overnight. The reaction mixture was purified by reverse phase Gilson Preparatory HPLC to give 5.0 mg of the title compound (10%).

LCMS: 501.4 (M+H), Rt 1.51 min

Example 111

5-{5-[(dimethylamino)methyl]-3-thienyl}-3-[1-(ethylsulfonyl)-4-piperidinyl]-1H-indole-7-carboxamide trifluoroacetate

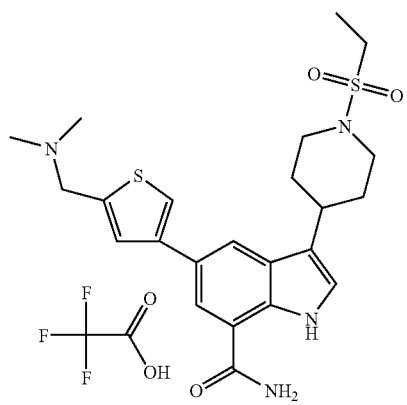

To a solution of 3-[1-(ethylsulfonyl)-4-piperidinyl]-5-(4-formyl-2-thienyl)-1H-indole-7-carboxamide (300 mg, 0.67 mmol) in DMSO (4 mL), was added a solution of 2 M dimethylamine in THF (3.36 mL, 6.7 mmol). The reaction was stirred at room temperature for 7 h, and sodium triacetoxyborohydride (1.42 g, 6.7 mmol) was added. Stirring continued overnight at room temperature. The reaction mixture was purified by reverse phase Gilson Prepatory HPLC to give the title compound (205 mg, 64%).

LCMS: 475.2 (M+H), Rt 1.51 min

Example 112

5-(5-{[(cyclopentylmethyl)amino]methyl}-3-thienyl)-3-[1-(ethylsulfonyl)-4-piperidinyl]-1H-indole-7-carboxamide trifluoroacetate

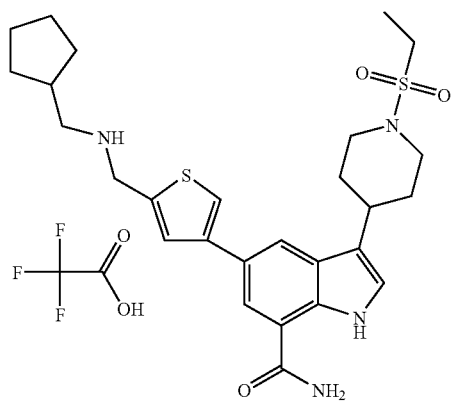

To a solution of 3-[1-(ethylsulfonyl)-4-piperidinyl]-5-(5-formyl-3-thienyl)-1H-indole-7-carboxamide (50 mg, 0.112 mmol) in DMSO (2.0 mL), acetic acid (3 drops), (cyclopentylmethyl)amine (112 mg, 1.123 mmol), and was reacted for 4 h. Sodium triacetoxyborohydride (238 mg, 1.123 mmol) was then added and the reaction was stirred overnight. The reaction mixture was purified by reverse phase Gilson Preparatory HPLC to give 8.0 mg of the title compound (14%).

LCMS: 529.4 (M+H), Rt 1.61 min and 1.64 min

Example 113

5-[5-({[(1R)-1,2-dimethylpropyl]amino}methyl)-3-thienyl]-3-[1-(ethylsulfonyl)-4-piperidinyl]-1H-indole-7-carboxamide trifluoroacetate

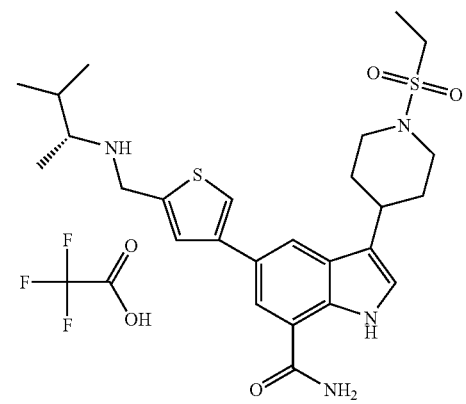

To a solution of 3-[1-(ethylsulfonyl)-4-piperidinyl]-5-(5-formyl-3-thienyl)-1H-indole-7-carboxamide (50 mg, 0.112 mmol) in DMSO (2.0 mL), was added acetic acid (3 drops), (2R)-3-methyl-2-butanamine (98 mg, 1.123 mmol), and reacted for 4 h. Sodium triacetoxyborohydride (238 mg, 1.123 mmol) was then added and the reaction was stirred overnight. The reaction mixture was purified by reverse phase Gilson Preparatory HPLC to give 5.0 mg of the title compound (10%).

LCMS: 517.2 (M+H), Rt 1.65 min

Example 114

5-{5-[(cyclopentylamino)methyl]-3-thienyl}-3-[1-(ethylsulfonyl)-4-piperidinyl]-1H-indole-7-carboxamide trifluoroacetate

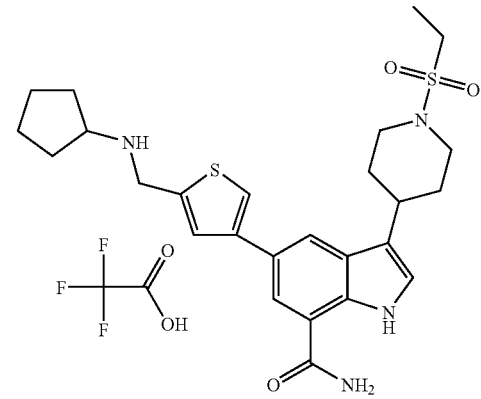

To a solution of 3-[1-(ethylsulfonyl)-4-piperidinyl]-5-(5-formyl-3-thienyl)-1H-indole-7-carboxamide (50 mg, 0.112 mmol) in DMSO (2.0 mL), was added acetic acid (3 drops), cyclopentanamine (0.11 mL, 1.123 mmol), and reacted for 4 h. Sodium triacetoxyborohydride (238 mg, 1.123 mmol) was then added and the reaction was reacted overnight. The reaction mixture was purified by reverse phase Gilson Preparatory HPLC to give 5.0 mg of the title compound (6.0%).
LCMS: 515.6 (M+H), Rt 1.38 min Example 115

5-(5-{[(cyclopropylmethyl)amino]methyl}-3-thienyl)-3-[1-(ethylsulfonyl)-4-piperidinyl]-1H-indole-7-carboxamide trifluoroacetate

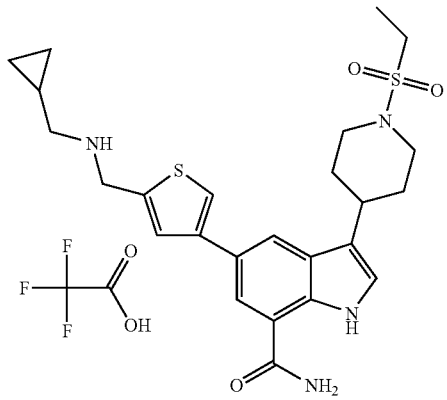

To a solution of 3-[1-(ethylsulfonyl)-4-piperidinyl]-5-(5-formyl-3-thienyl)-1H-indole-7-carboxamide (50 mg, 0.112 mmol) in DMSO (2.0 mL), acetic acid (3 drops), 1-cyclopropylmethanamine (0.10 mL, 1.123 mmol), and was reacted for 6 h. Sodium triacetoxyborohydride (238 mg, 1.123 mmol) was then added and the reaction was stirred overnight. The reaction mixture was purified by reverse phase Gilson Preparatory HPLC to give 5.0 mg of the title compound (10%).
LCMS: 501.4 (M+H), Rt 1.53 min Example 116

5-[5-({[(1S)-1,2-dimethylpropyl]amino}methyl)-3-thienyl]-3-[1-(ethylsulfonyl)-4-piperidinyl]-1H-indole-7-carboxamide trifluoroacetate

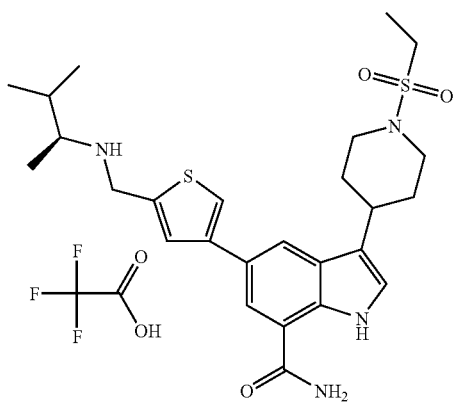

To a solution of 3-[1-(ethylsulfonyl)-4-piperidinyl]-5-(5-formyl-3-thienyl)-1H-indole-7-carboxamide (50 mg, 0.112 mmol) in DMSO (2.0 mL), acetic acid (3 drops), (2S)-3-methyl-2-butanamine (98 mg, 1.123 mmol), and was reacted for 6 h. Sodium triacetoxyborohydride (238 mg, 1.123 mmol) was then added and the reaction was stirred overnight. The reaction mixture was purified by reverse phase Gilson Preparatory HPLC to give 8.0 mg of the title compound (15%).
LCMS: 517.2 (M+H), Rt 1.65 min Example 117

5-(5-{[(2,2-dimethylpropyl)amino]methyl}-3-thienyl)-3-[1-(ethylsulfonyl)-4-piperidinyl]-1H-indole-7-carboxamide trifluoroacetate

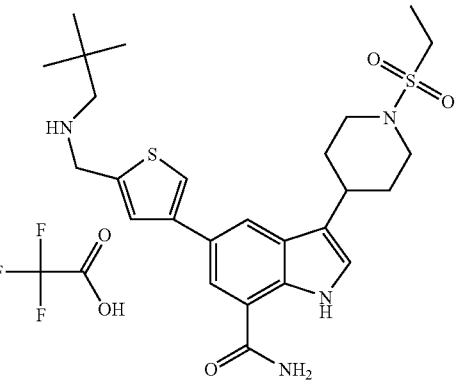

To a solution of 3-[1-(ethylsulfonyl)-4-piperidinyl]-5-(5-formyl-3-thienyl)-1H-indole-7-carboxamide (50 mg, 0.112 mmol) in DMSO (2.0 mL), was added acetic acid (3 drops), (2,2-dimethylpropyl)amine (0.13 mL, 1.123 mmol), and reacted for 6 h. Sodium triacetoxyborohydride (238 mg, 1.123 mmol) was then added and stirred overnight. The reaction mixture was purified by reverse phase Gilson Preparatory HPLC to give 4.0 mg of the title compound (7%).
LCMS: 517.2 (M+H), Rt 1.68 min and 1.71 min Example 118

3-[1-(ethylsulfonyl)-4-piperidinyl]-5-(5-{[(phenylmethyl)amino]methyl}-3-thienyl)-1H-indole-7-carboxamide trifluoroacetate

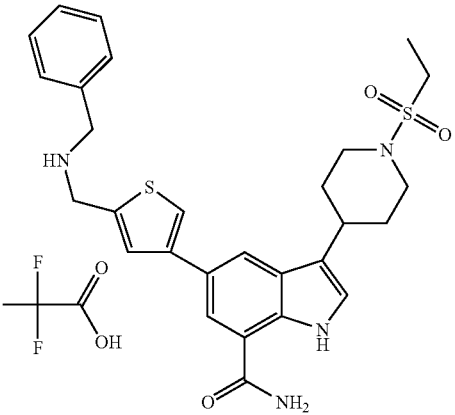

To a solution of 3-[1-(ethylsulfonyl)-4-piperidinyl]-5-(5-formyl-3-thienyl)-1H-indole-7-carboxamide (50 mg, 0.112 mmol) in DMSO (2.0 mL), was added acetic acid (5 drops), (phenylmethyl)amine (0.14 mL, 1.123 mmol), and reacted for 6 h. Sodium triacetoxyborohydride (238 mg, 1.123 mmol) was then added and stirred overnight. The reaction mixture was purified by reverse phase Gilson Preparatory HPLC to give 5.0 mg of the title compound (8%).

LCMS: 537.2 (M+H), Rt 1.68 min

Example 119

3-[1-(ethylsulfonyl)-4-piperidinyl]-5-[5-({[(2S)-tetrahydro-2-furanylmethyl]amino}methyl)-3-thienyl]-1H-indole-7-carboxamide trifluoroacetate

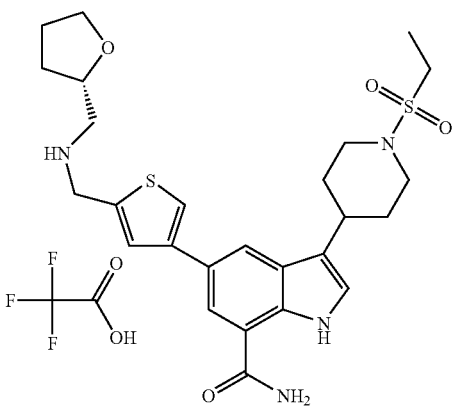

To a solution of 3-[1-(ethylsulfonyl)-4-piperidinyl]-5-(5-formyl-3-thienyl)-1H-indole-7-carboxamide (50 mg, 0.112 mmol) in dichloromethane (3.0 mL) and methanol (1.5 mL), acetic acid (5 drops), 1-[(2S)-tetrahydro-2-furanyl]methanamine (0.12 mL, 1.123 mmol), and reacted for 6 h. Sodium triacetoxyborohydride (238 mg, 1.123 mmol) was then added and the reaction mixture was stirred at room temperature overnight. The reaction mixture was purified by reverse phase Gilson Preparatory HPLC to give 23 mg of the title compound (8%).

LCMS: 531.4 (M+H), Rt 1.58 min

Example 120

3-[1-(ethylsulfonyl)-4-piperidinyl]-5-(5-{[(tetrahydro-2H-pyran-4-ylmethyl)amino]methyl}-3-thienyl)-1H-indole-7-carboxamide trifluoroacetate

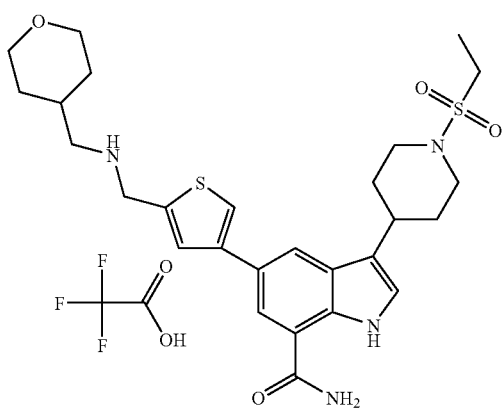

To a solution of 3-[1-(ethylsulfonyl)-4-piperidinyl]-5-(5-formyl-3-thienyl)-1H-indole-7-carboxamide (50 mg, 0.112 mmol) in DMSO (2.0 mL), acetic acid (5 drops), and (tetrahydro-2H-pyran-4-ylmethyl)amine (130 mg, 1.123 mmol), and reacted for 6 h. Sodium triacetoxyborohydride (238 mg, 1.123 mmol) was then added and the reaction was stirred overnight. The reaction mixture was purified by reverse phase Gilson Preparatory HPLC to give 7.0 mg of the title compound (11%).

LCMS: 545.4 (M+H), Rt 1.52 min

Example 121

5-{5-[(butylamino)methyl]-3-thienyl}-3-[1-(ethylsulfonyl)-4-piperidinyl]-1H-indole-7-carboxamide trifluoroacetate

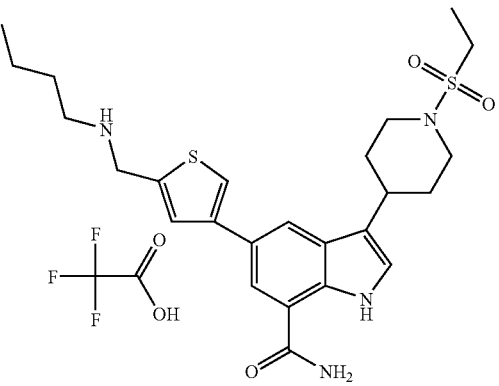

To a solution of 3-[1-(ethylsulfonyl)-4-piperidinyl]-5-(5-formyl-3-thienyl)-1H-indole-7-carboxamide (50 mg, 0.112 mmol) in dichloromethane (3.0 mL) and methanol (1.5 mL), was added 5 drops of acetic acid, butylamine (0.11 mL, 1.123 mmol) and reacted for 6 h. Sodium borohydride (43 mg, 1.123 mmol) was then added and stirred at room temperature overnight. All solvent was removed in vacuo and dissolved in DMSO (1.0 mL). It was then purified by reverse phase Gilson Preparatory HPLC to give 5.0 mg of the title compound (10%).

LCMS: 503.4 (M+H), Rt 1.63 min

Example 122

3-[1-(ethylsulfonyl)-4-piperidinyl]-5-[5-({[(2R)-tetrahydro-2-furanylmethyl]amino}methyl)-3-thienyl]-1H-indole-7-carboxamide trifluoroacetate

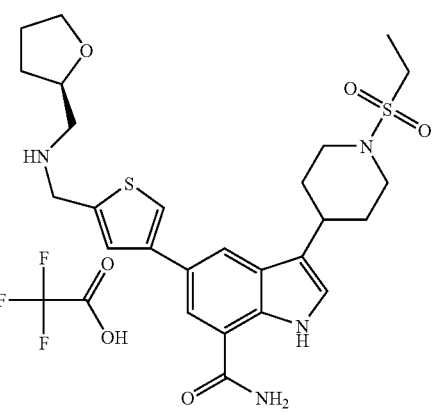

To a solution of 3-[1-(ethylsulfonyl)-4-piperidinyl]-5-(5-formyl-3-thienyl)-1H-indole-7-carboxamide (50 mg, 0.112 mmol) in DMSO (2.0 mL), was added acetic acid (5 drops), 1-[(2R)-tetrahydro-2-furanyl]methanamine (130 mg, 1.123 mmol), and the reaction mixture was reacted for 6 h. Sodium triacetoxyborohydride (238 mg, 1.123 mmol) was then added and the reaction was stirred overnight. Additional 1-[(2R)-tetrahydro-2-furanyl]methanamine (130 mg, 1.123 mmol) was then added followed by sodium triacetoxyborohydride after 6 h. The reaction mixture was purified by reverse phase Gilson Preparatory HPLC to give 5.0 mg of the title compound (8.0%).

LCMS: 531.4 (M+H), Rt 1.50 min

Example 123

3-[1-(ethylsulfonyl)-4-piperidinyl]-5-[5-({(2S)-2-[(methyloxy)methyl]-1-pyrrolidinyl}methyl)-3-thienyl]-1H-indole-7-carboxamide trifluoroacetate

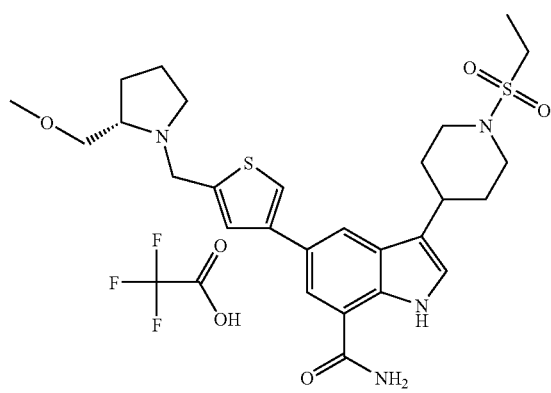

To a solution of 3-[1-(ethylsulfonyl)-4-piperidinyl]-5-(5-formyl-3-thienyl)-1H-indole-7-carboxamide (50 mg, 0.112 mmol) in dichloromethane (3.0 mL) and methanol (1.5 mL), was added 5 drops of acetic acid, (2S)-2-[(methyloxy)methyl]pyrrolidine (129 mg, 1.123 mmol) and reacted at room temperature for 6 h. Sodium borohydride (43 mg, 1.123 mmol) was than added and the reaction was stirred at room temperature overnight. The reaction mixture was purified by reverse phase Gilson Preparatory HPLC to give 8.0 mg of the title compound the (13%).

LCMS: 545.2 (M+H), Rt 1.62 min and 1.66 min.

Example 124

3-[1-(ethylsulfonyl)-4-piperidinyl]-5-[5-({(2R)-2-[(methyloxy)methyl]-1-pyrrolidinyl}methyl)-3-thienyl]-1H-indole-7-carboxamide trifluoroacetate

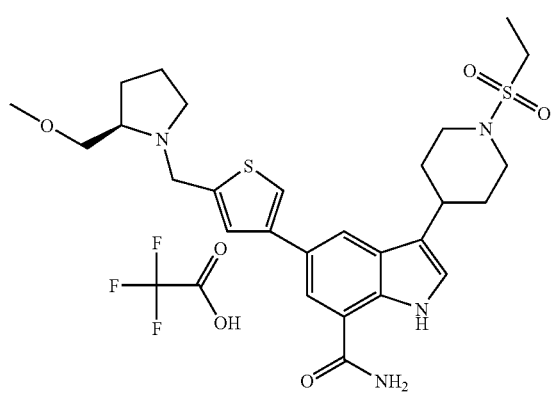

To a solution of 3-[1-(ethylsulfonyl)-4-piperidinyl]-5-(5-formyl-3-thienyl)-1H-indole-7-carboxamide (50 mg, 0.112 mmol) in dichloromethane (3.0 mL) and methanol (1.5 mL), was added acetic acid (5 drops), (2R)-2-[(methyloxy)methyl]pyrrolidine (129 mg, 1.123 mmol) and stirred at room temperature for 6 h. Sodium borohydride (43 mg, 1.123 mmol) was then added and the reaction was stirred at room temperature overnight. The mixture was purified by reverse phase Gilson Preparatory HPLC to give 5.0 mg of the title compound (13%).

LCMS: 545.2 (M+H), Rt 1.62 min and 1.66 min.

Example 125

3-[1-(ethylsulfonyl)-4-piperidinyl]-5-{4-[2-(methylamino)ethyl]phenyl}-1H-indole-7-carboxamide

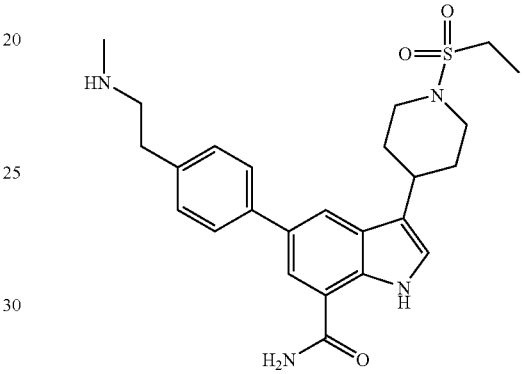

To a solution of 5-bromo-3-[1-(ethylsulfonyl)-4-piperidinyl]-1H-indole-7-carboxamide (200 mg, 0.48 mmol) in dioxane and H$_2$O was added was added [4-(cyanomethyl)phenyl]boronic acid (232 mg, 0.144 mmol), potassium carbonate (400 mg, 2.88 mmol), and tetrakis(triphenylphosphine)palladium (0) (30 mg, 0.048 mmol). The solution was stirred and heated in the microwave at 160° C. for 40 min. The reaction was diluted with EtOAc and H$_2$O and filtered to obtain a yellow crystal as desired product. The solution was washed with brine and H$_2$O and then EtOAc was concentrated. To the reside was added MeOH which precipitated the desired product and then washed again with MeOH to give 5-[4-(cyanomethyl)phenyl]-3-[1-(ethylsulfonyl)-4-piperidinyl]-1H-indole-7-carboxamide.

To 5-[4-(cyanomethyl)phenyl]-3-[1-(ethylsulfonyl)-4-piperidinyl]-1H-indole-7-carboxamide (78 mg, 0.173 mmol) in DCM was added 1.5 M diisobutylaluminum hydride solution in toluene (240 mL, 0.346 mmol) at 0° C. The reaction was stirred at 0° C. for 20 min. The reaction was then quenched with saturated KNa tartrate solution. The bi-layer was filtered, and the solid was the desired product. Additionally, the organic layer was concentrated to give the desired compound, 3-[1-(ethylsulfonyl)-4-piperidinyl]-5-[4-(2-oxoethyl)phenyl]-1H-indole-7-carboxamide, which was taken on without further purification.

To a solution of 3-[1-(ethylsulfonyl)-4-piperidinyl]-5-[4-(2-oxoethyl)phenyl]-1H-indole-7-carboxamide (50 mg, 0.11 mmol) in methanol (5 mL) and methylene chloride (5 mL) at room temperature was added 2 M methylamine in tetrahydrofuran (0.4 mL) followed by 1 drop of acetic acid. The reaction was stirred at room temperature for 2 h followed by an addition of sodium triacetoxyborohydride (200 mg, 0.94 mmol). This reaction was stirred overnight. It was then purified by flash chromatography to give 10 mg of the title compound (19.4%).

LC/MS=m/z 469.4 [M+H] Ret. Time: 1.63 min.

Example 126

3-[1-(ethylsulfonyl)-4-piperidinyl]-5-{4-[2-(propylamino)ethyl]phenyl}-1H-indole-7-carboxamide

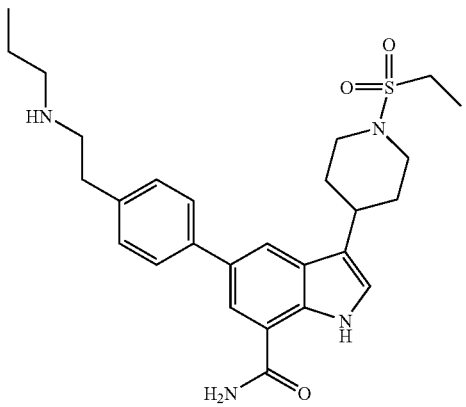

The title compound was prepared according to the general procedure of 3-[1-(ethylsulfonyl)-4-piperidinyl]-5-{4-[2-(methylamino)ethyl]phenyl}-1H-indole-7-carboxamide, substituting 2 M propylamine in tetrahydrofuran (0.4 mL) for methylamine to afford 15 mg of the title compound (27.5%).

LC/MS=m/z 497.6 [M+H] Ret. Time: 1.63 min.

Example 127

5-{4-[2-(ethylamino)ethyl]phenyl}-3-[1-(ethylsulfonyl)-4-piperidinyl]-1H-indole-7-carboxamide

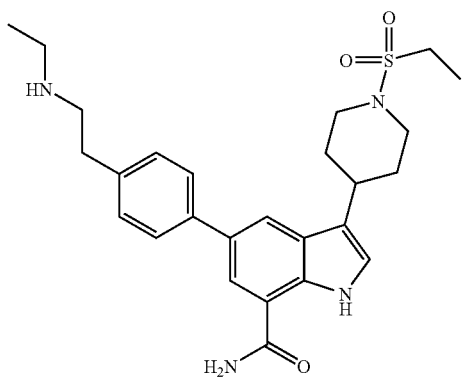

To a solution of 3-[1-(ethylsulfonyl)-4-piperidinyl]-5-[4-(2-oxoethyl)phenyl]-1H-indole-7-carboxamide (50 mg, 0.11 mmol) in methanol (5 mL) and methylene chloride (5 mL) at room temperature was added 2 M ethylamine in tetrahydrofuran (0.4 mL), followed by 1 drop of acetic acid. The reaction was stirred at room temperature for 2 h followed by an addition of sodium triacetoxyborohydride (200 mg, 0.94 mmol). This reaction was stirred overnight. It was then purified by flash chromatography to give 15 mg of the title compound (28.3%).

LC/MS=m/z 483.2 [M+H] Ret. Time: 1.57 min.

Example 128

5-{4-[({[1-(1,1-dimethylethyl)-3-methyl-1H-pyrazol-5-yl]carbonyl}amino)methyl]phenyl}-3-[1-(ethylsulfonyl)-4-piperidinyl]-1H-indole-7-carboxamide trifluoroacetate

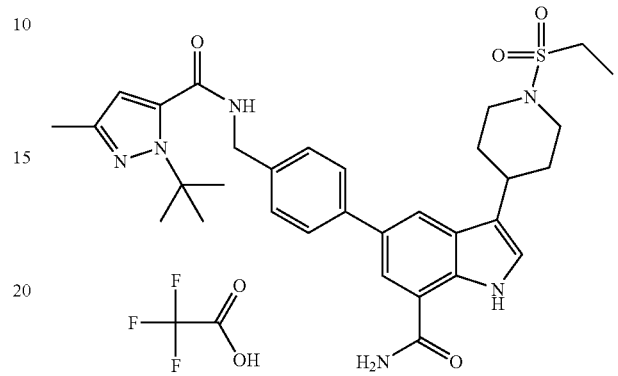

To a solution of [4-(aminomethyl)phenyl]boronic acid (145 mg, 0.966 mmol) in DMF (2 mL) was added 1-(1,1-dimethylethyl)-3-methyl-1H-pyrazole-5-carbonyl chloride (290 mg, 1.45 mmol) and triethylamine (403 µL, 2.90 mmol). The reaction was stirred for 2 h. It was then quenched and partitioned between EtOAc and H₂O and the organic layer was concentrated to give {4-[({[1-(1,1-dimethylethyl)-3-methyl-1H-pyrazol-5-yl]carbonyl}amino)methyl]phenyl}boronic acid.

To a solution of 5-bromo-3-[1-(ethylsulfonyl)-4-piperidinyl]-1H-indole-7-carboxamide (50 mg, 0.120 mmol) in dioxane (1 mL) and water (0.4 mL) was added potassium carbonate (74 mg, 0.484 mmol) and {4-[({[1-(1,1-dimethylethyl)-3-methyl-1H-pyrazol-5-yl]carbonyl}amino)methyl]phenyl}boronic acid (153 mg, 0.483 mmol). The reaction mixture was stirred and bubbled with argon for 5 min. before the addition of chloro(di-2-norbornylphosphino)(2-dimethylaminomethylferrocen-1-yl)palladium (II) (7 mg, 0.012 mmol). The reaction was stirred for 10 min then heated to 150° C. The reaction was evaporated and purified by Gilson Preparatory HPLC to give 5 mg of the title compound (5.8%).

LC/MS=m/z 605.4 [M+H] Ret. Time: 2.14 min.

Example 129

3-[1-(ethylsulfonyl)-4-piperidinyl]-5-(4-{[(4-pyridinylcarbonyl)amino]methyl}phenyl)-1H-indole-7-carboxamide

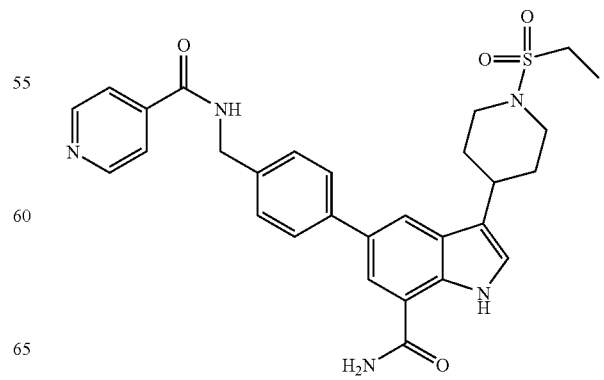

The title compound was prepared according to the general procedure of 5-{4-[({[1-(1,1-dimethylethyl)-3-methyl-1H-pyrazol-5-yl]carbonyl}amino)methyl]phenyl}-3-[1-(ethyl-sulfonyl)-4-piperidinyl]-1H-indole-7-carboxamide trifluoroacetate, substituting (4-{[(4-pyridinylcarbonyl)amino]methyl}phenyl)boronic acid (124 mg, 0.480 mmol) for {4-[({[1-(1,1-dimethylethyl)-3-methyl-1H-pyrazol-5-yl]carbonyl}amino)methyl]phenyl}boronic acid to afford 30 mg of the title compound (45.8%).

LC/MS=m/z 537 [M+H] Ret. Time: 2.04 min.

Example 130

5-(4-{[(cyclopentylcarbonyl)amino]methyl}phenyl)-3-[1-(ethylsulfonyl)-4-piperidinyl]-1H-indole-7-carboxamide

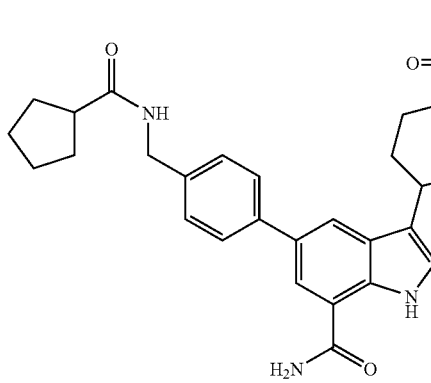

The title compound was prepared according to the general procedure of 5-{4-[({[1-(1,1-dimethylethyl)-3-methyl-1H-pyrazol-5-yl]carbonyl}amino)methyl]phenyl}-3-[1-(ethyl-sulfonyl)-4-piperidinyl]-1H-indole-7-carboxamide trifluoroacetate, substituting (4-{[(cyclopentylcarbonyl)amino]methyl}phenyl)boronic acid (119 mg, 0.480 mmol) for {4-[({[1-(1,1-dimethylethyl)-3-methyl-1H-pyrazol-5-yl]carbonyl}amino)methyl]phenyl}boronic acid to afford 30 mg of the title compound (47%).

LC/MS=m/z 537 [M+H] Ret. Time: 2.04 min.

Example 131

3-[1-(ethylsulfonyl)-4-piperidinyl]-5-(4-{[(2-furanyl-carbonyl)amino]methyl}phenyl)-1H-indole-7-carboxamide

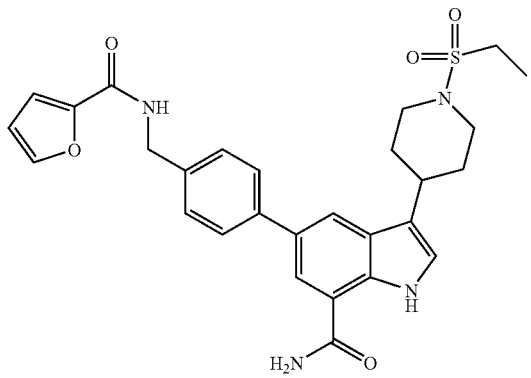

The title compound was prepared according to the general procedure of 5-{4-[({[1-(1,1-dimethylethyl)-3-methyl-1H-pyrazol-5-yl]carbonyl}amino)methyl]phenyl}-3-[1-(ethyl-sulfonyl)-4-piperidinyl]-1H-indole-7-carboxamide trifluoroacetate, substituting (4-{[(2-furanylcarbonyl)amino]methyl}phenyl)boronic acid (118 mg, 0.480 mmol) for {4-[({[1-(1,1-dimethylethyl)-3-methyl-1H-pyrazol-5-yl]carbonyl}amino)methyl]phenyl}boronic acid to afford 16 mg of the title compound (25%).

LC/MS=m/z 535.5 [M+H] Ret. Time: 1.99 min.

Example 132

5-(4-{2-[(cyclobutylcarbonyl)amino]ethyl}phenyl)-3-[1-(ethylsulfonyl)-4-piperidinyl]-1H-indole-7-carboxamide

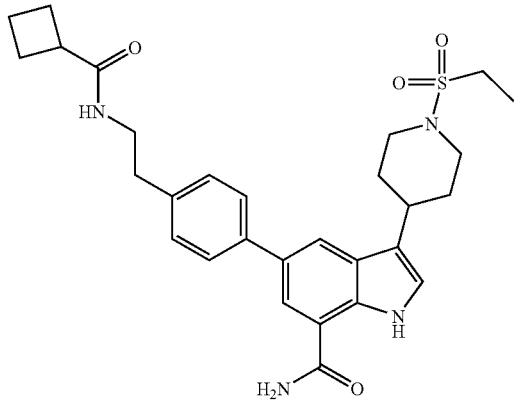

The title compound was prepared according to the general procedure of 5-{4-[2-(acetylamino)ethyl]phenyl}-3-[1-(ethylsulfonyl)-4-piperidinyl]-1H-indole-7-carboxamide, substituting N-[2-(4-bromophenyl)ethyl]cyclobutanecarboxamide (100 mg, 0.324 mmol) for N-[2-(4-bromophenyl)ethyl]acetamide. Purified by flash chromatography to afford 28 mg of the title compound (48.3%).

LC/MS=m/z 537.2 [M+H] Ret. Time: 1.99 min.

Example 133

5-(4-{2-[(cyclohexylcarbonyl)amino]ethyl}phenyl)-3-[1-(ethylsulfonyl)-4-piperidinyl]-1H-indole-7-carboxamide

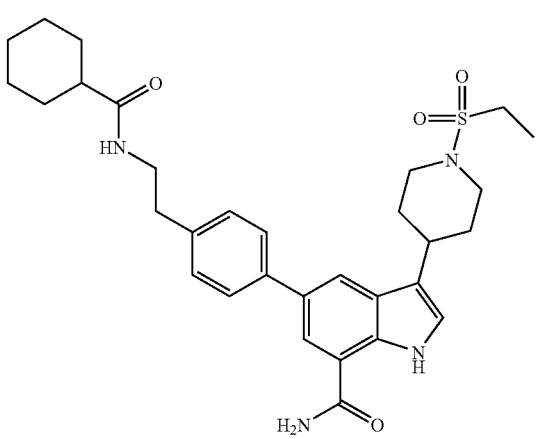

The title compound was prepared according to the general procedure of 5-{4-[2-(acetylamino)ethyl]phenyl}-3-[1-(ethylsulfonyl)-4-piperidinyl]-1H-indole-7-carboxamide, substituting N-[2-(4-bromophenyl)ethyl]cyclohexanecarboxamide (100 mg, 0.324 mmol) for N-[2-(4-bromophenyl)ethyl] acetamide. Purified by flash chromatography to afford 32 mg of the title compound (52.5%).

LC/MS=m/z 565.4 [M+H] Ret. Time: 2.14 min.

Example 134

5-(3-{2-[(cyclohexylcarbonyl)amino]ethyl}phenyl)-3-[1-(ethylsulfonyl)-4-piperidinyl]-1H-indole-7-carboxamide

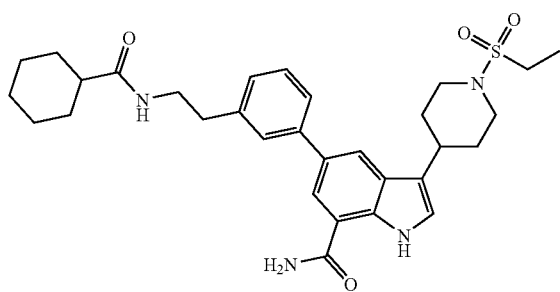

The title compound was prepared according to the general procedure of 5-{4-[2-(acetylamino)ethyl]phenyl}-3-[1-(ethylsulfonyl)-4-piperidinyl]-1H-indole-7-carboxamide, substituting N-[2-(3-bromophenyl)ethyl]cyclohexanecarboxamide (100 mg, 0.324 mmol) for N-[2-(4-bromophenyl)ethyl] acetamide. The concentrated reaction mixture was purified by Gilson Preparatory HPLC followed by re-purification by flash chromatography to give the title compound.

LC/MS=m/z 565.2 [M+H] Ret. Time: 2.16 min.

Example 135

3-[1-(ethylsulfonyl)-4-piperidinyl]-5-[6-(1-piperazinyl)-3-pyridinyl]-1H-indole-7-carboxamide trifluoroacetate

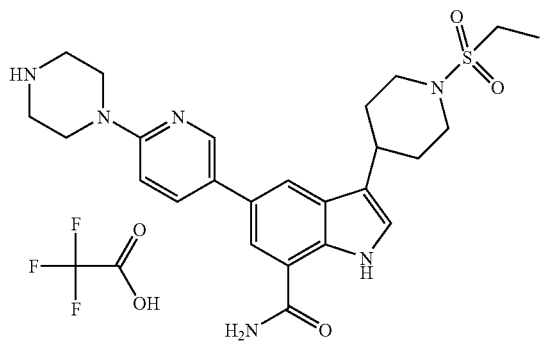

To a solution of 5-bromo-3-[1-(ethylsulfonyl)-4-piperidinyl]-1H-indole-7-carboxamide (100 mg, 0.241 mmol) in dioxane (1.0 mL) and H₂O (0.8 mL) was added cesium carbonate (314 mg, 0.964 mmol), and [6-(4-{[(1,1-dimethylethyl)oxy]carbonyl}-1-piperazinyl)-3-pyridinyl]boronic acid (297 mg, 0.964 mmol). The reaction mixture was stirred before addition of tetrakis(triphenylphosphine)palladium(0) (28 mg, 0.024 mmol). The reaction was heated in a microwave at 160° C. for 20 min. Mixture was concentrated and taken up in EtOAc (10 mL) and H₂O (5.0 mL). Compound was purified by Gilson Preparatory HPLC to give 129 mg of 1,1-dimethylethyl 4-(5-{7-(aminocarbonyl)-3-[1-(ethylsulfonyl)-4-piperidinyl]-1H-indol-5-yl}-2-pyridinyl)-1-piperazinecarboxylate and 3-[1-(ethylsulfonyl)-4-piperidinyl]-5-[6-(1-piperazinyl)-3-pyridinyl]-1H-indole-7-carboxamide (44%).

To a solution of 1,1-dimethylethyl 4-(5-{7-(aminocarbonyl)-3-[1-(ethylsulfonyl)-4-piperidinyl]-1H-indol-5-yl}-2-pyridinyl)-1-piperazinecarboxylate (130 mg, 0.218 mmol) in methanol (0.3 mL) was added 4 M HCl in dioxane (0.3 mL). The reaction was heated at 50° C. and stirred for 3 h. Reaction mixture was concentrated and neutralized on a SCX cartridge primed with CH₂Cl₂, followed by MeOH and collection with ammonia in MeOH. 20 mg of desired fraction was concentrated and purified using MDAP HPLC to give 9.4 mg of the title compound (7%).

LC/MS=m/z 497.2 [M+H] Ret. Time: 1.45 min

Example 136

5-[6-(4-ethyl-1-piperazinyl)-3-pyridinyl]-3-[1-(ethylsulfonyl)-4-piperidinyl]-1H-indole-7-carboxamide trifluoroacetate

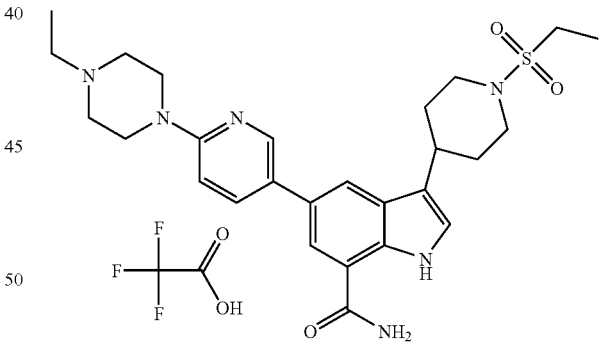

To a solution of 3-[1-(ethylsulfonyl)-4-piperidinyl]-5-[6-(1-piperazinyl)-3-pyridinyl]-1H-indole-7-carboxamide (40 mg, 0.081 mmol) in dichloromethane was added acetaldehyde (7 mg, 0.162 mmol) and sodium triacetoxyborohydride (100 mg, 0.472 mmol). The reaction was stirred overnight at room temperature. Reaction mixture was then concentrated and dissolved in EtOAc and H₂O. Salts were filtered and organic layer was concentrated and purified by Gilson Preparatory HPLC to give 39 mg of the title compound (92%).

LC/MS=m/z 525.6 [M+H] Ret. Time: 1.44 min

Example 137

3-[1-(ethylsulfonyl)-4-piperidinyl]-5-[4-(1-piperidinylmethyl)phenyl]-1H-indole-7-carboxamide trifluoroacetate

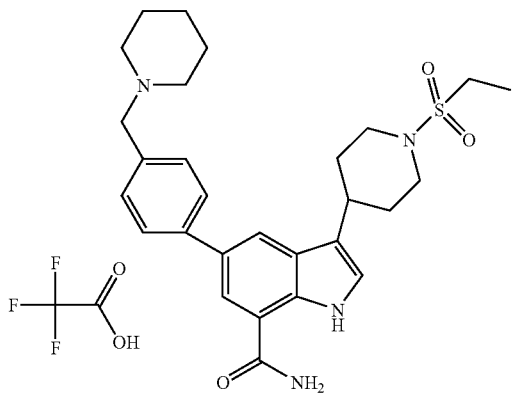

To a solution of 3-[1-(ethylsulfonyl)-4-piperidinyl]-5-(4-formylphenyl)-1H-indole-7-carboxamide (40 mg, 0.09 mmol) in dichloromethane was added piperidine (9 μL, 0.09 mmol). The reaction was stirred for 1 h before addition of sodium triacetoxyborohydride (58 mg, 0.27 mmol). The reaction mixture was stirred overnight at room temperature. Mixture was then concentrated and purified by Gilson Preparatory HPLC to give 8.0 mg of the title compound (14%).
LC/MS=m/z 509.4 [M+H] Ret. Time: 1.71 min

Example 138

3-[1-(ethylsulfonyl)-4-piperidinyl]-5-[3-(1-piperidinylmethyl)phenyl]-1H-indole-7-carboxamide trifluoroacetate

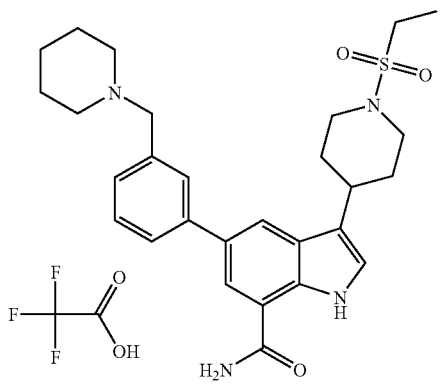

To a solution of 3-[1-(ethylsulfonyl)-4-piperidinyl]-5-(3-formylphenyl)-1H-indole-7-carboxamide (50 mg, 0.114 mmol) in dichloromethane (2 mL) and acetic acid (1 drop) was added piperidine (46 μL, 0.456 mmol). The reaction was stirred for 2 h at room temperature before the addition of sodium triacetoxyborohydride (75 mg, 0.342 mmol). The reaction was then stirred an additional 3 h. The mixture was then purified by Gilson Preparatory HPLC to give 36 mg of the title compound (61%).
LC/MS=m/z 509.4 [M+H] Ret. Time: 1.80 min

Example 139

3-[1-(ethylsulfonyl)-4-piperidinyl]-5-{4-[(methylamino)methyl]phenyl}-1H-indole-7-carboxamide trifluoroacetate

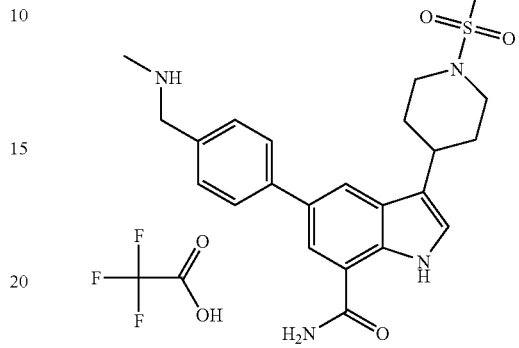

To a solution of 3-[1-(ethylsulfonyl)-4-piperidinyl]-5-(4-formylphenyl)-1H-indole-7-carboxamide (20 mg, 0.045 mmol) in dichloromethane (12 mL), Methanol (2 mL) and acetic acid was added methylamine in THF (20 μL, 0.54 mmol). The reaction mixture was stirred at room temperature for 2 h before addition of sodium triacetoxyborohydride (10.3 mg, 0.270 mmol). The mixture was then stirred for another 3 h before the mixture was concentrated and purified by Gilson Preparatory HPLC to give 6 mg of the title compound (10%).
LC/MS=m/z 454.6 [M+H] Ret. Time: 1.23 min

Example 140

3-[1-(ethylsulfonyl)-4-piperidinyl]-5-(4-{[(1-methylethyl)amino]methyl}phenyl)-1H-indole-7-carboxamide

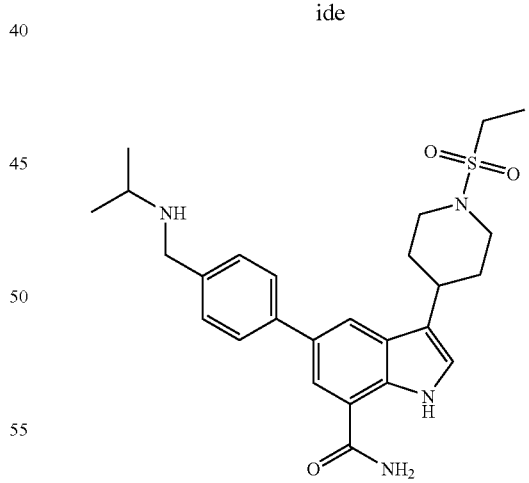

To a solution of 3-[1-(ethylsulfonyl)-4-piperidinyl]-5-(4-formylphenyl)-1H-indole-7-carboxamide (40 mg, 0.09 mmol) in DMSO (900 μL) and acetic acid (2 drops) was added 2-propanamine (93 μL, 1.08 mmol). After 2 h, sodium triacetoxyborohydride (172 mg, 0.81 mmol) was added. Reaction mixture was stirred overnight. Compound was purified by Gilson Preparatory HPLC to afford 30 mg of the title compound (69%).
LC/MS=m/z 483.2 [M+H] Ret. Time: 1.56 min

Example 141

3-[1-(ethylsulfonyl)-4-piperidinyl]-5-{4-[(propylamino)methyl]phenyl}-1H-indole-7-carboxamide trifluoroacetate

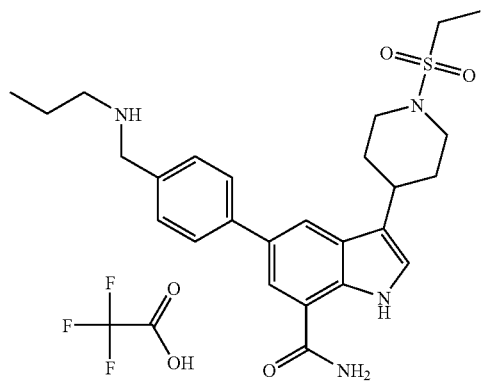

To a solution of 3-[1-(ethylsulfonyl)-4-piperidinyl]-5-(4-formylphenyl)-1H-indole-7-carboxamide (20 mg, 0.045 mmol) in DMSO (900 μL) and acetic acid (2 drops) was added propylamine (45 μL, 1.08 mmol). After 2 h, sodium triacetoxyborohydride (172 mg, 0.81 mmol) was added. Reaction mixture was stirred overnight. Compound was purified by Gilson Preparatory HPLC to afford 21.1 mg of the title compound (74%).

LC/MS=m/z 483.2 [M+H] Ret. Time: 1.54 min.

Example 142

5-(4-{[(1-ethylpropyl)amino]methyl}phenyl)-3-[1-(ethylsulfonyl)-4-piperidinyl]-1H-indole-7-carboxamide

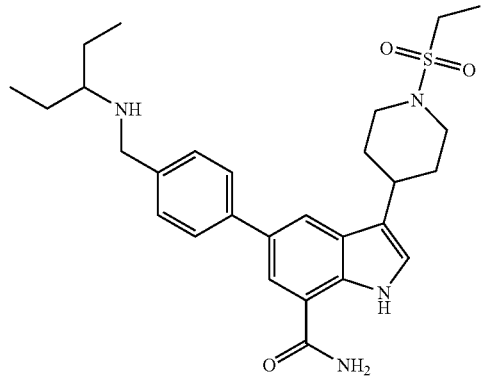

To a solution of 3-[1-(ethylsulfonyl)-4-piperidinyl]-5-(4-formylphenyl)-1H-indole-7-carboxamide (40 mg, 0.09 mmol) in DMSO (900 μL) and acetic acid (2 drops) was added 3-pentanamine (108 μL, 1.08 mmol). After 2 h, sodium triacetoxyborohydride (172 mg, 0.81 mmol) was added. Reaction mixture was stirred overnight. Compound was purified by Gilson Preparatory HPLC to afford 34.5 mg of the title compound (74%).

LC/MS=m/z 511.4 [M+H] Ret. Time: 1.69 min

Example 143

5-{4-[(cyclopentylamino)methyl]phenyl}-3-[1-(ethylsulfonyl)-4-piperidinyl]-1H-indole-7-carboxamide trifluoroacetate

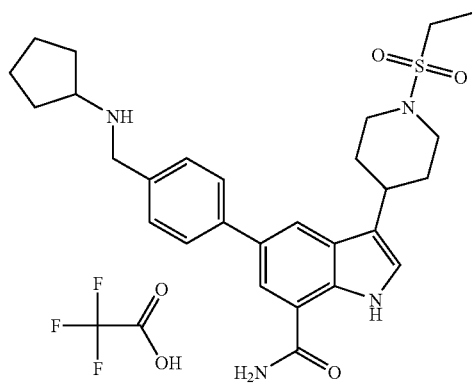

To a solution of 3-[1-(ethylsulfonyl)-4-piperidinyl]-5-(4-formylphenyl)-1H-indole-7-carboxamide (40 mg, 0.09 mmol) in DMSO (900 μL) and acetic acid (2 drops) was added cyclopentylamine (108 μL, 1.08 mmol). After 2 h, sodium triacetoxyborohydride (172 mg, 0.81 mmol) was added. Reaction mixture was stirred overnight. Compound was purified by Gilson Preparatory HPLC to afford 11.1 mg of the title compound (20%).

LC/MS=m/z 509.4 [M+H] Ret. Time: 1.66 min.

Example 144

5-{4-[(cyclobutylamino)methyl]phenyl}-3-[1-(ethylsulfonyl)-4-piperidinyl]-1H-indole-7-carboxamide

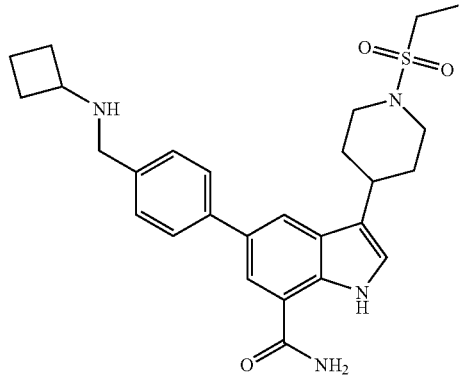

To a solution of 3-[1-(ethylsulfonyl)-4-piperidinyl]-5-(4-formylphenyl)-1H-indole-7-carboxamide (40 mg, 0.091 mmol) in DMSO (900 μL) and acetic acid (2 drops) was added cyclobutylamine (94 μL, 1.08 mmol). After 2 h, sodium triacetoxyborohydride (120 mg, 1.10 mmol) was added. Reaction mixture was stirred overnight. Compound was purified by Gilson Preparatory HPLC to afford 26.3 mg of the title compound (59%).

LC/MS=m/z 495.4 [M+H] Ret. Time: 1.37 min

Example 145

5-{4-[(ethylamino)methyl]phenyl}-3-[1-(ethylsulfonyl)-4-piperidinyl]-1H-indole-7-carboxamide

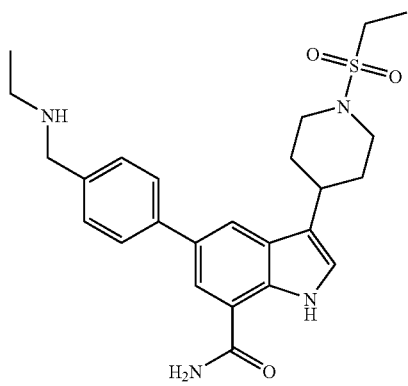

To a solution of 3-[1-(ethylsulfonyl)-4-piperidinyl]-5-(4-formylphenyl)-1H-indole-7-carboxamide (20 mg, 0.046 mmol) in DMSO and acetic acid was added ethylamine (32 µL, 0.547 mmol). After 2 h, sodium triacetoxyborohydride (120 mg, 1.10 mmol) was added. Reaction mixture was stirred overnight. Compound was purified by Gilson Preparatory HPLC to afford 11.5 mg of the title compound (55%).

LC/MS=m/z 469.4 [M+H] Ret. Time: 1.52 min.

Example 146

5-{4-[(dimethylamino)methyl]phenyl}-3-[1-(ethylsulfonyl)-4-piperidinyl]-1H-indole-7-carboxamide

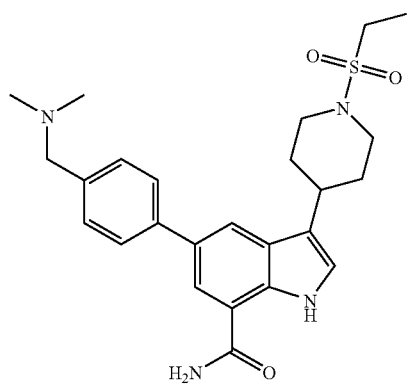

To a solution of 3-[1-(ethylsulfonyl)-4-piperidinyl]-5-(4-formylphenyl)-1H-indole-7-carboxamide (50 mg, 0.114 mmol) in DMSO (3 mL) and acetic acid was added N-dimethylamine (170 µL, 0.342 mmol). After 2 h, sodium triacetoxyborohydride (290 mg, 1.36 mmol) was added. Reaction mixture was stirred overnight. Compound was purified by Gilson Preparatory HPLC to afford 28.9 mg of the title compound (54%).

LC/MS=m/z 469.4 [M+H] Ret. Time: 1.52 min.

Example 147

5-{4-[(diethylamino)methyl]phenyl}-3-[1-(ethylsulfonyl)-4-piperidinyl]-1H-indole-7-carboxamide

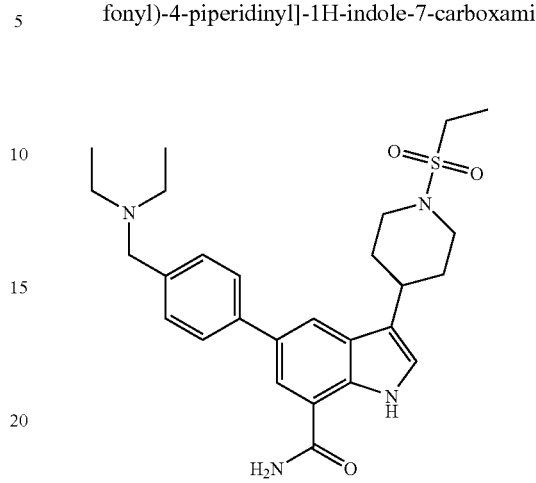

To a solution of 3-[1-(ethylsulfonyl)-4-piperidinyl]-5-(4-formylphenyl)-1H-indole-7-carboxamide (50 mg, 0.114 mmol) in DMSO (3 mL) and acetic acid was added diethylamine (36 µL, 0.342 mmol). After 2 h, sodium triacetoxyborohydride (290 mg, 1.36 mmol) was added. Reaction mixture was stirred overnight. Compound was purified by Gilson Preparatory HPLC to afford 37.6 mg of the title compound (67%).

LC/MS=m/z 497.6 [M+H] Ret. Time: 1.52 min.

Example 148

3-[1-(ethylsulfonyl)-4-piperidinyl]-5-[4-(4-morpholinylmethyl)phenyl]-1H-indole-7-carboxamide

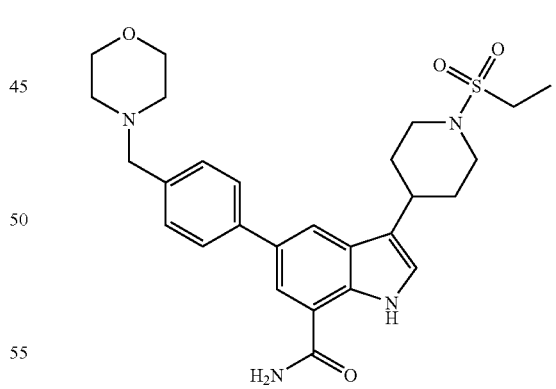

To a solution of 3-[1-(ethylsulfonyl)-4-piperidinyl]-5-(4-formylphenyl)-1H-indole-7-carboxamide (50 mg, 0.114 mmol) in DMSO (3 mL) and acetic acid was added morpholine (30 µL, 0.342 mmol). After 2 h, sodium triacetoxyborohydride (290 mg, 1.36 mmol) was added. Reaction mixture was stirred overnight. Compound was purified by Gilson Preparatory HPLC to afford 40.3 mg of the title compound (70%).

LC/MS=m/z 511.4 [M+H] Ret. Time: 1.53 min

Example 149

3-[1-(ethylsulfonyl)-4-piperidinyl]-5-[4-(1-pyrrolidinylmethyl)phenyl]-1H-indole-7-carboxamide trifluoroacetate

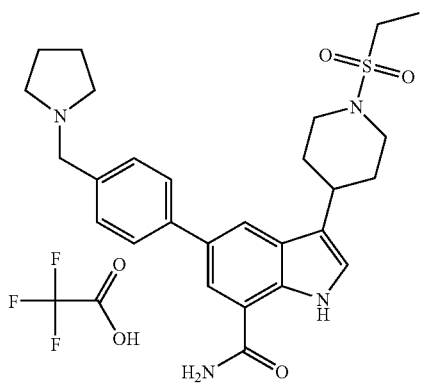

To a solution of 3-[1-(ethylsulfonyl)-4-piperidinyl]-5-(4-formylphenyl)-1H-indole-7-carboxamide (50 mg, 0.114 mmol) in DMSO (3 mL) and acetic acid was added cyclopentylamine (28 µL, 0.342 mmol). After 2 h, sodium triacetoxyborohydride (290 mg, 1.36 mmol) was added. Reaction mixture was stirred overnight. Compound was purified by Gilson Preparatory HPLC to afford 20.1 mg of the title compound (36%).

LC/MS=m/z 495.4 [M+H] Ret. Time: 1.58 min

Example 150

3-[1-(ethylsulfonyl)-4-piperidinyl]-5-[4-({[(1S)-2-hydroxy-1-methylethyl]amino}methyl)phenyl]-1H-indole-7-carboxamide trifluoroacetate

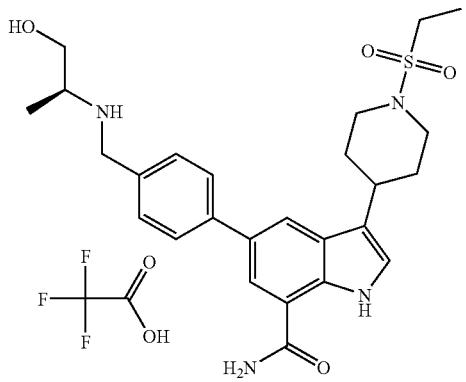

To a solution of 3-[1-(ethylsulfonyl)-4-piperidinyl]-5-(4-formylphenyl)-1H-indole-7-carboxamide (50 mg, 0.114 mmol) in DMSO (3 mL) and acetic acid was added (2S)-2-amino-1-propanol (56 µL, 0.745 mmol). After 2 h, sodium triacetoxyborohydride (290 mg, 1.36 mmol) was added. Reaction mixture was stirred overnight. Compound was purified by Gilson Preparatory HPLC to afford 25.9 mg of the title compound (15%).

LC/MS=m/z 499.6 [M+H] Ret. Time: 1.54 min

Example 151

3-[1-(ethylsulfonyl)-4-piperidinyl]-5-[4-({[(1R)-2-hydroxy-1-methylethyl]amino}methyl)phenyl]-1H-indole-7-carboxamide trifluoroacetate

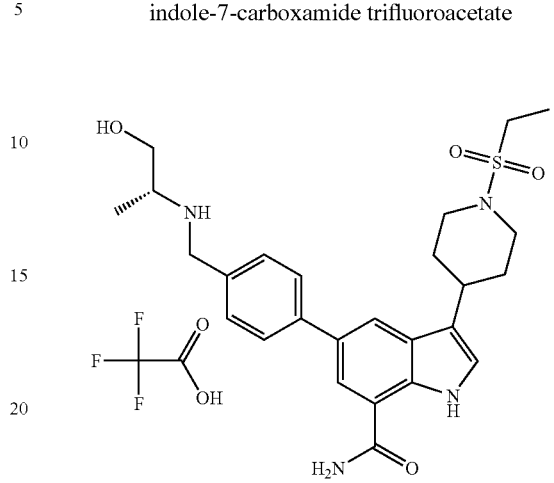

To a solution of 3-[1-(ethylsulfonyl)-4-piperidinyl]-5-(4-formylphenyl)-1H-indole-7-carboxamide (50 mg, 0.114 mmol) in DMSO (3 mL) and acetic acid was added (2R)-2-amino-1-propanol (56 µL, 0.745 mmol). After 2 h, sodium triacetoxyborohydride (290 mg, 1.36 mmol) was added. Reaction mixture was stirred overnight. Compound was purified by Gilson Preparatory HPLC to afford 29.6 mg of the title compound (53%).

LC/MS=m/z 499.6 [M+H] Ret. Time: 1.47 min

Example 152

3-[1-(ethylsulfonyl)-4-piperidinyl]-5-[4-({[(2R)-2-hydroxypropyl]amino}methyl)phenyl]-1H-indole-7-carboxamide trifluoroacetate

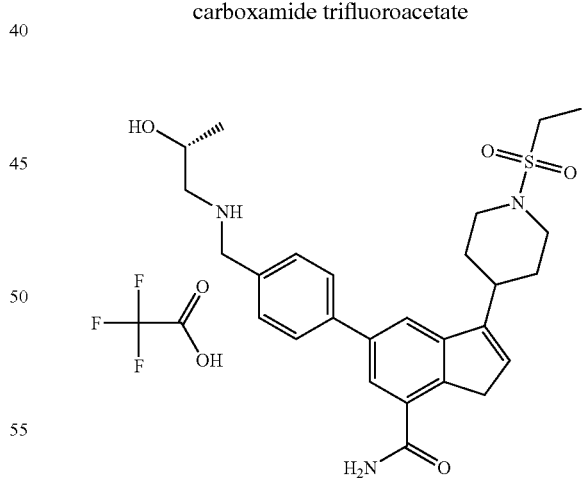

To a solution of 3-[1-(ethylsulfonyl)-4-piperidinyl]-5-(4-formylphenyl)-1H-indole-7-carboxamide (50 mg, 0.114 mmol) in DMSO (3 mL) and acetic acid was added (2R)-1-amino-2-propanol (56 µL, 0.745 mmol). After 2 h, sodium triacetoxyborohydride (290 mg, 1.36 mmol) was added. Reaction mixture was stirred overnight. Compound was purified by Gilson Preparatory HPLC to afford 14.7 mg of the title compound (26%).

LC/MS=m/z 499.6 [M+H] Ret. Time: 1.46 min.

Example 153

3-[1-(ethylsulfonyl)-4-piperidinyl]-5-[4-({[2-hydroxy-1-(hydroxymethyl)ethyl]amino}methyl)phenyl]-1H-indole-7-carboxamide trifluoroacetate

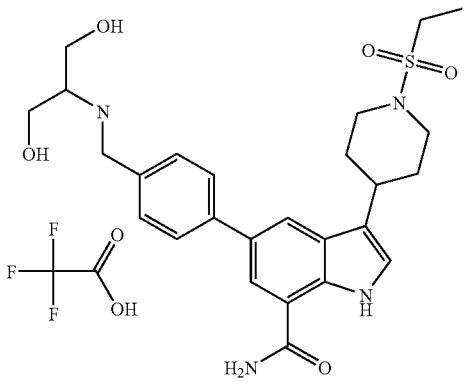

To a solution of 3-[1-(ethylsulfonyl)-4-piperidinyl]-5-(4-formylphenyl)-1H-indole-7-carboxamide (40 mg, 0.091 mmol) in DMSO was added 2-amino-1,3-propanediol (50 mg, 0.55 mmol) and acetic acid (1 drop). After 2 h, sodium triacetoxyborohydride (232 mg, 1.10 mmol) was added. Reaction mixture was stirred overnight. Compound was purified by Gilson Preparatory HPLC to afford 15.9 mg of the title compound (28%).

LC/MS=m/z 515.4 [M+H] Ret. Time: 1.45 min.

Example 154

3-[1-(ethylsulfonyl)-4-piperidinyl]-5-(3-{[(1-methylbutyl)amino]methyl}phenyl)-1H-indole-7-carboxamide trifluoroacetate

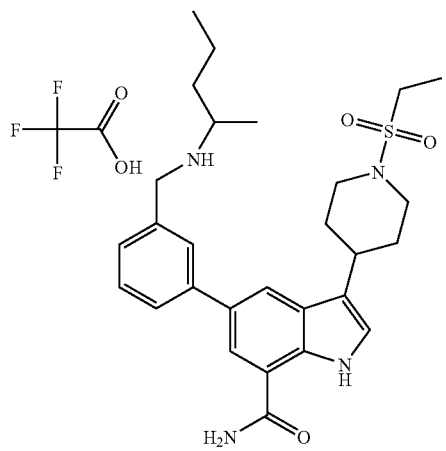

To a solution of 3-[1-(ethylsulfonyl)-4-piperidinyl]-5-(3-formylphenyl)-1H-indole-7-carboxamide (50 mg, 0.114 mmol) in DMSO (3.0 mL) was added 1-2-pentanamine (324 μL, 2.74 mmol) and acetic acid (1 drop). After 2 h, sodium triacetoxyborohydride (290 mg, 1.10 mmol) was added. Reaction mixture was stirred overnight. Compound was then filtered and concentrated. It was then purified by Gilson Preparatory HPLC to afford 9.5 mg of the title compound (13%).

LC/MS=m/z 511.4 [M+H] Ret. Time: 1.66 min

Example 155

3-[1-(ethylsulfonyl)-4-piperidinyl]-5-[3-({[(1R)-1-methylpropyl]amino}methyl)phenyl]-1H-indole-7-carboxamide trifluoroacetate

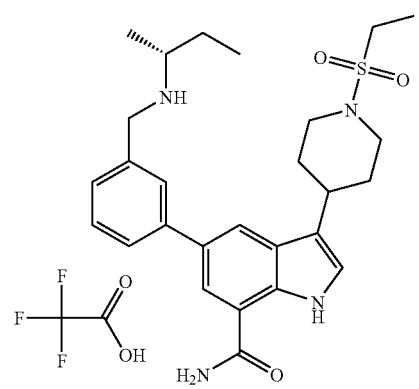

To a solution of 3-[1-(ethylsulfonyl)-4-piperidinyl]-5-(3-formylphenyl)-1H-indole-7-carboxamide (50 mg, 0.114 mmol) in DMSO (2.0 mL) was added (2R)-2-butanamine (69 μL, 0.684 mmol) and acetic acid (1 drop). After 2 h, sodium triacetoxyborohydride (0.435 mg, 2.05 mmol) was added. Reaction mixture was stirred overnight. Compound was then filtered and concentrated. It was then purified by Gilson Preparatory HPLC to afford 18.6 mg of the title compound (33%).

LC/MS=m/z 497.6 [M+H] Ret. Time: 1.70 min

Example 156

3-[1-(ethylsulfonyl)-4-piperidinyl]-5-(3-{[(2-methylpropyl)amino]methyl}phenyl)-1H-indole-7-carboxamide

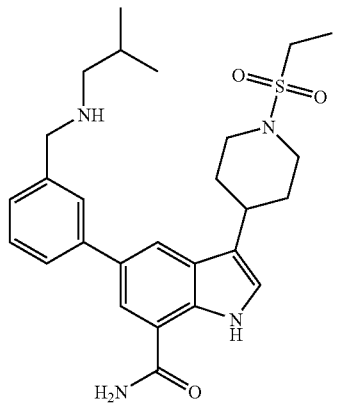

To a solution of 3-[1-(ethylsulfonyl)-4-piperidinyl]-5-(3-formylphenyl)-1H-indole-7-carboxamide (50 mg, 0.114 mmol) in DCM (1.5 mL), MeOH (1.5 mL), and acetic acid (4 drops) was added 2-methyl-1-propanamine (137 μL, 1.37 mmol) and stirred at room temperature. After 2 h, sodium borohydride (23 mg, 0.684 mmol) was added and the reaction mixture was purified by SCX cartridge to give 47.8 mg of the title compound (85%).
LC/MS=m/z 497.2 [M+H] Ret. Time: 1.69 min Example 157

3-[1-(ethylsulfonyl)-4-piperidinyl]-5-[3-({[(1S)-1-methylpropyl]amino}methyl)phenyl]-1H-indole-7-carboxamide acetate

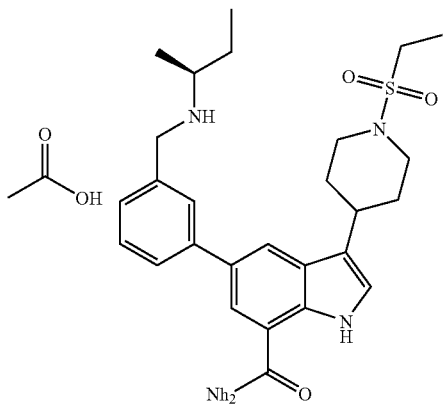

The title compound was prepared according to the general procedure of 3-[1-(ethylsulfonyl)-4-piperidinyl]-5-(3-{[(2-methylpropyl)amino]methyl}phenyl)-1H-indole-7-carboxamide, substituting (2S)-2-butanamine (138 μL, 1.37 mmol) for 2-methyl-1-propanamine to afford 43.2 mg of the title compound (76%).
LC/MS=m/z 497.4 [M+H] Ret. Time: 1.84 min Example 158

5-(4-{[(cyclopropylcarbonyl)amino]methyl}phenyl)-3-[1-(ethylsulfonyl)-4-piperidinyl]-1H-indole-7-carboxamide

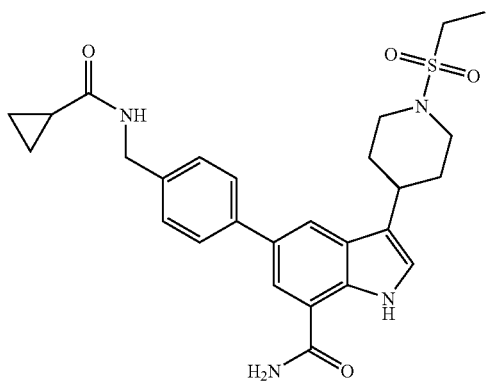

The title compound was prepared according to the general procedure of 5-{4-[(acetylamino)methyl]phenyl}-3-[1-(ethylsulfonyl)-4-piperidinyl]-1H-indole-7-carboxamide substituting cyclopropanecarbonyl chloride (14 μL, 1.37 mmol) for acetyl chloride. Compound was purified by Gilson Preparatory HPLC to afford 19.1 mg of the title compound (28%).
LC/MS=m/z 509.2 [M+H] Ret. Time: 1.86 min Example 159

5-(4-{[(cyclobutylcarbonyl)amino]methyl}phenyl)-3-[1-(ethylsulfonyl)-4-piperidinyl]-1H-indole-7-carboxamide

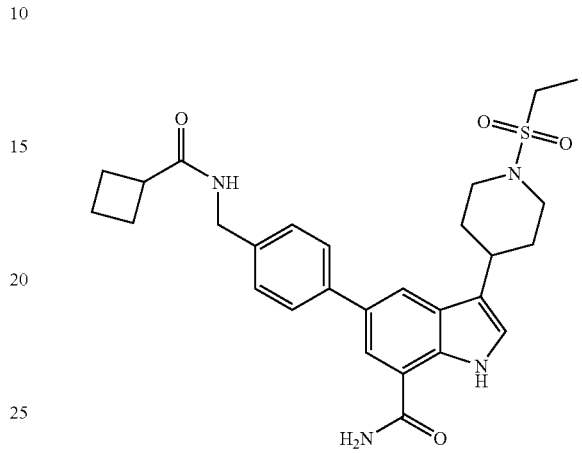

The title compound was prepared according to the general procedure of 5-{4-[(acetylamino)methyl]phenyl}-3-[1-(ethylsulfonyl)-4-piperidinyl]-1H-indole-7-carboxamide substituting cyclobutanecarbonyl chloride (17 μL, 1.37 mmol) for acetyl chloride. Compound was purified by Gilson Preparatory HPLC to afford 20.2 mg of the title compound (28%).
LC/MS=m/z 523.2 [M+H] Ret. Time: 1.94 min Example 160

3-[1-(ethylsulfonyl)-4-piperidinyl]-5-(4-{[(2-thienylacetyl)amino]methyl}phenyl)-1H-indole-7-carboxamide

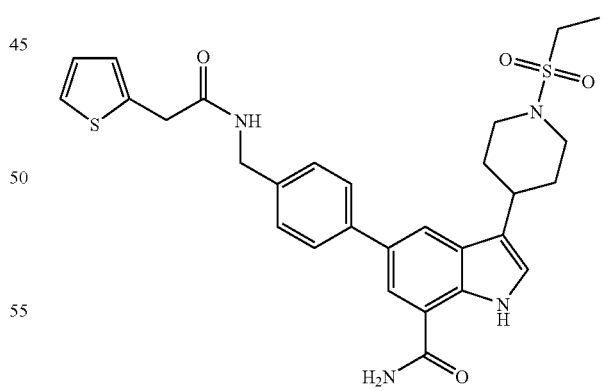

The title compound was prepared according to the general procedure of 5-{4-[(acetylamino)methyl]phenyl}-3-[1-(ethylsulfonyl)-4-piperidinyl]-1H-indole-7-carboxamide substituting (3Z)-3-(methylthio)-3,5-hexadienoyl chloride (18 μL, 1.37 mmol) for acetyl chloride. Compound was purified by Gilson Preparatory HPLC to afford 13.5 mg of the title compound (18%).
LC/MS=m/z 565.2 [M+H] Ret. Time: 1.98 min

Example 161

5-[4-({[(1S)-1,2-dimethylpropyl]amino}methyl)phenyl]-3-[1-(ethylsulfonyl)-4-piperidinyl]-1H-indole-7-carboxamide trifluoroacetate

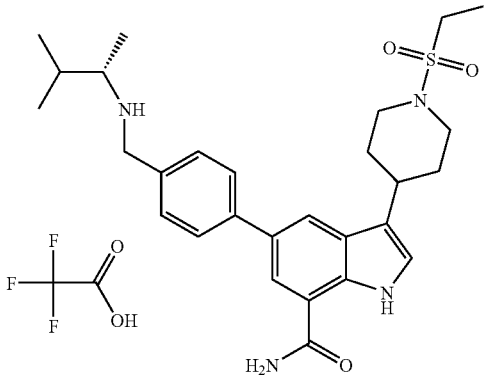

To a solution of 3-[1-(ethylsulfonyl)-4-piperidinyl]-5-(3-formylphenyl)-1H-indole-7-carboxamide (40 mg, 0.091 mmol) in DCM (1.5 mL), MeOH (1.5 mL) and acetic acid was added (2S)-3-methyl-2-butanamine (128 μL, 1.10 mmol) and stirred at room temperature for 2 h. Sodium borohydride (19 mg, 0.546 mmol) was then added and stirred for 48 h. Compound was then purified by Gilson Preparatory HPLC to give 5.8 mg of the title compound (12%).
LC/MS=m/z 511.2 [M+H] Ret. Time: 1.76 min To a solution of 5-bromo-3-[1-(ethylsulfonyl)-4-piperidinyl]-1H-indole-7-carboxamide (50 mg, 0.121 mmol) in dioxane (1 mL) and H₂O (0.4 mL) was added potassium carbonate (74 mg, 0.484 mmol), and (4{[(methylsulfonyl)amino]methyl}phenyl)boronic acid (110 mg, 0.50 mmol). The reaction mixture was stirred and bubbled thru with Argon for 5 min before addition of chloro(di-2-norbornylphosphino)(2-dimethylaminomethylferrocen-1-yl)palladium (II) (7 mg, 0.012 mmol). The reaction was then stirred and heated for 10 min in a microwave at 160° C. The mixture was concentrated and purified by Gilson Preparatory HPLC to afford 34.3 mg of the title compound (55%).
LC/MS=m/z 519.4 [M+H] Ret. Time: 1.77 min

Example 162

5-[3-({[(1R)-1,2-dimethylpropyl]amino}methyl)phenyl]-3-[1-(ethylsulfonyl)-4-piperidinyl]-1H-indole-7-carboxamide trifluoroacetate

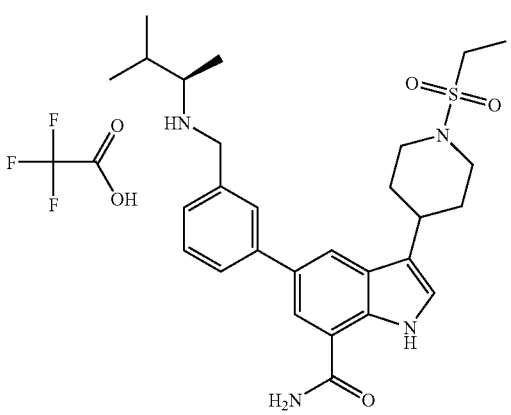

To a solution of 3-[1-(ethylsulfonyl)-4-piperidinyl]-5-(3-formylphenyl)-1H-indole-7-carboxamide (50 mg, 0.114 mmol) in DCM (1.5 mL), MeOH (1.5 mL) and acetic acid was added (2R)-3-methyl-2-butanamine (160 μL, 1.37 mmol) and stirred at room temperature for 2 h. Sodium borohydride (19 mg, 0.546 mmol) was then added and stirred for 48 h. Compound was then purified by Gilson Preparatory HPLC to give 50 mg of the title compound (86%).
LC/MS=m/z 511.4 [M+H] Ret. Time: 1.65 min

Example 163

5-(6-amino-2-pyridinyl)-3-[1-(ethylsulfonyl)-4-piperidinyl]-1H-indole-7-carboxamide trifluoroacetate

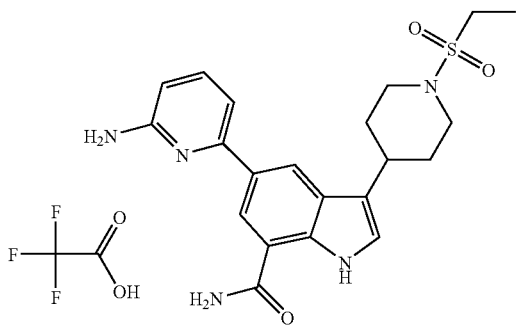

To a solution of 3-[1-(ethylsulfonyl)-4-piperidinyl]-5-(4,4,5,5-tetramethyl-1,3,2-dioxaborolan-2-yl)-1H-indole-7-carboxamide (83 mg, 0.18 mmol) in dioxane (5 mL) was added 6-bromo-2-pyridinamine (93 mg, 0.54 mmol), potassium carbonate (149 mg, 1.08 mmol) in H₂O (1.5 mL) and chloro(di-2-norbornylphosphino)(2-dimethylaminomethylferrocen-1-yl)palladium (II) (19 mg, 0.031 mmol). The reaction was heated in the microwave at 150° C. for 20 min. The reaction mixture was then concentrated and an aqueous extraction was performed. Organic layer was then concentrated and purified on a Mass Directed Auto Prep HPLC to give 22.3 mg of the title compound (29%).
LC/MS=m/z 428.6 [M+H] Ret. Time: 1.34 min

Example 164

3-[1-(ethylsulfonyl)-4-piperidinyl]-5-[3-(1H-pyrazol-1-yl)phenyl]-1H-indole-7-carboxamide

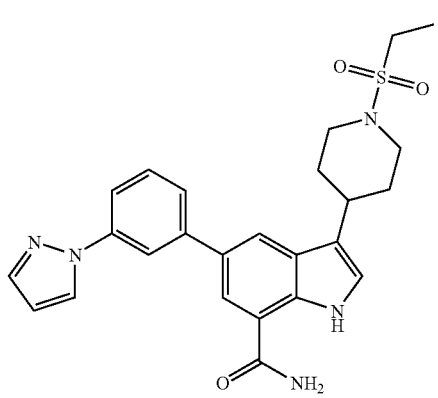

To 5-bromo-3-[1-(ethylsulfonyl)-4-piperidinyl]-1H-indole-7-carboxamide (20 mg, 0.048 mmol) was added [3-(1H-pyrazol-1-yl)phenyl]boronic acid (36 mg, 0.193 mmol), dioxane (2.8 mL) and a solution of potassium carbonate (20 mg) in water (1.2 mL). To this mixture was added chloro-2-(dimethylaminomethyl)-ferrocen-1-yl-(dinorbornylphosphine)palladium(II) (3 mg, 0.005 mmol). The resulting mixture was reacted in a CEM microwave for 10 min at 160° C. then concentrated under a stream of nitrogen (greenhouse) at 80° C. The crude product was partitioned between water (2 mL) and CH$_2$CL$_2$ (2 mL). The layers were separated with a hydrophobic frit, and the aqueous layer was extracted with CH$_2$CL$_2$ (2×2 mL). The organic layers were pooled and concentrated under a stream of nitrogen at 80° C. Dimethyl sulfoxide (0.8 mL) was added to residue, which was sonicated for 10 sec. filtered through a cotton plug, and then filtered through a 0.2 μm filter. The crude product was purified on an Agilent MDAP using a Zorbax Eclipse XDB 610 21.2×50 mm column to afford 2.3 mg of the title compound (10%).

LC/MS=m/z 478.2 [M+H] Ret. Time: 2.05 min.

Example 165

5-[4-(dimethylamino)phenyl]-3-[1-(ethylsulfonyl)-4-piperidinyl]-1H-indole-7-carboxamide

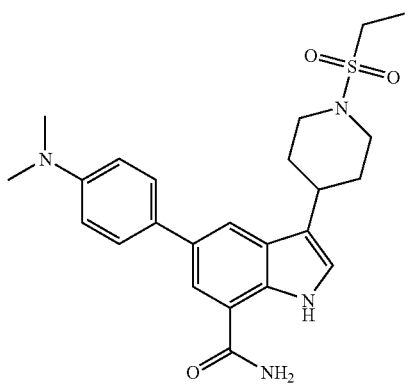

To a CEM microwave tube was added 5-bromo-3-[1-(ethylsulfonyl)-4-piperidinyl]-1H-indole-7-carboxamide (40 mg, 0.097 mmol), dioxane (2.8 mL) and a solution of potassium carbonate (40 mg, 0.289 mmol) in water (1.2 mL). To this mixture was added [4-(dimethylamino)phenyl]boronic acid (65 mg, 0.386 mmol) and chloro-2-(dimethylaminomethyl)-ferrocen-1-yl-(dinorbornylphosphine)palladium(II) (1 mg, 0.002 mmol). The vial was capped and the reaction was reacted in a CEM microwave for 10 min at 160° C. The reaction was concentrated under a stream of nitrogen at 80° C. The crude product was taken up in dimethyl sulfoxide (1 mL) and purified through a 1 g silica SPE cartridge eluting with dimethyl sulfoxide (4 mL). The dimethyl sulfoxide was concentrated in a Genevac at 65° C. for 3 h, and the residue was reconstituted in dimethyl sulfoxide (1 mL) and filtered through an acrodisc. The solution of crude product was then purified on the Agilent MDAP (UV 214 selection). The purified product was passed through a polymer-bound carbonate SPE cartridge to afford 2.7 mg of the title compound (6.2%).

LC/MS=m/z 455.2 [M+H] Ret. Time: 1.71 min.

Example 166

5-(3-aminophenyl)-3-[1-(ethylsulfonyl)-4-piperidinyl]-1H-indole-7-carboxamide

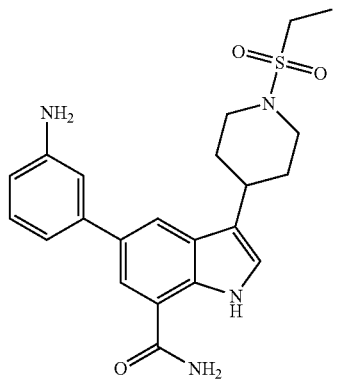

To a CEM microwave tube was added 5-bromo-3-[1-(ethylsulfonyl)-4-piperidinyl]-1H-indole-7-carboxamide (40 mg, 0.0965 mmol), potassium carbonate (80 mg, 0.578 mmol) and (3-aminophenyl)boronic acid sulfate (145 mg, 0.386 mmol). The mixture was taken up in water (1.2 mL) and dioxane (2.8 mL), and chloro-2-(dimethylaminomethyl)-ferrocen-1-yl-(dinorbornylphosphine)palladium(II) (1 mg, 0.002 mmol) was added. The mixture was then reacted in a CEM microwave for 10 min at 150° C. Ethyl acetate (2 mL) was added and the layers were separated. The aqueous layer was washed with ethyl acetate (1×2 mL). The organic layers were pooled, concentrated under a stream of nitrogen, and taken up in dimethyl sulfoxide (0.89 mL) and trifluoroacetic acid (0.15 mL). This solution of crude product was purified on an Agilent MDAP eluting with a linear gradient of 30% CH$_3$CN/H$_2$O (0.1% TFA) to 70% CH$_3$CN/H$_2$O (0.1% TFA) at 20 mL/min over 9 min. To the HPLC fraction containing product was added a solution of saturated K$_2$CO$_3$ (1 mL), a 1 M solution of sodium hydroxide (1 mL), and ethyl acetate (2 mL). The layers were separated and the aqueous layer was extracted with ethyl acetate (2×2 mL). The organic layers were pooled, filtered through a plug of magnesium sulfate, and concentrated under a stream of nitrogen to give 14.9 mg of the title compound (36%).

LC/MS=m/z 427.2 [M+H] Ret. Time: 1.39 min.

Example 167

3-[1-(ethylsulfonyl)-4-piperidinyl]-5-{5-[(2-methyl-1-pyrrolidinyl)methyl]-2-thienyl}-1H-indole-7-carboxamide

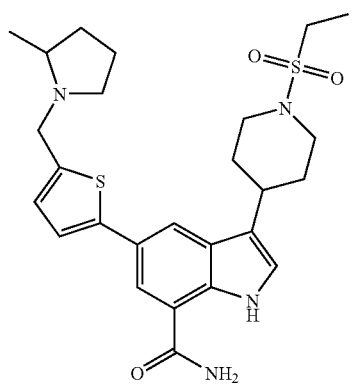

The {5-[(2-methyl-1-pyrrolidinyl)methyl]-2-thienyl}boronic acid used to prepare 3-[1-(ethylsulfonyl)-4-piperidinyl]-5-{5-[(2-methyl-1-pyrrolidinyl)methyl]-2-thienyl}-1H-indole-7-carboxamide was prepared in three separate batches using the procedures shown below:

Batch 1: NaBH(OAc)$_3$ (271 mg, 1.28 mmol), HOAc (0.07 mL), and 2-Methylpyrrolidine (0.043 mL, 0.42 mmol) were added to a solution of (5-formyl-2-thienyl)boronic acid (100 mg, 0.64 mmol) in CH$_2$Cl$_2$ (4 mL) in a 2-dram vial. The vial was capped and the reaction was stirred at room temperature for 15 h. The reaction mixture was loaded directly onto a 2 g SCX cartridge (pre-equilibrated with MeOH), eluting in sequence with MeOH (12 mL) and a 2 M solution of NH$_3$/MeOH (8 mL). The fractions containing the boronic acid crude product were concentrated under a stream of N$_2$ and dried under high vacuum to give 45 mg of crude product. The crude product was taken up in saturated NaHCO$_3$ (2 mL) and extracted with EtOAc (3×2 mL) to give 6.6 mg of crude {5-[(2-methyl-1-pyrrolidinyl)methyl]-2-thienyl}boronic acid.

Batch 2: NaBH(OAc)$_3$ (271 mg, 1.28 mmol), HOAc (0.07 mL), and 2-Methylpyrrolidine (0.043 mL, 0.42 mmol) were added to a solution of (5-formyl-2-thienyl)boronic acid (100 mg, 0.64 mmol) in 1:1 CH$_2$Cl$_2$/MeOH (4 mL) in a 2-dram vial. The vial was capped and the reaction was stirred at room temperature for 15 h. The reaction mixture was loaded directly onto a 2 g SCX cartridge (pre-equilibrated with MeOH), eluting in sequence with MeOH (12 mL) and a 2 M solution of NH$_3$/MeOH (8 mL). The fractions containing the boronic acid crude product were concentrated under a stream of N$_2$ and dried under high vacuum to give 45 mg of crude product. The crude product was taken up in saturated NaHCO$_3$ (2 mL) and extracted with EtOAc (3×2 mL) to give 5 mg of crude {5-[(2-methyl-1-pyrrolidinyl)methyl]-2-thienyl}boronic acid.

Batch 3: 2-Methylpyrrolidine (0.033 mL, 0.32 mmol) was added to a solution of (5-formyl-2-thienyl)boronic acid (50 mg, 0.32 mmol) in MeOH (1 mL) in a 2-dram vial. The vial was capped and the reaction was stirred at room temperature for 2 h. NaCNBH$_3$ (40 mg, 0.64 mol) was added, and stirring continued for 19 h. The reaction mixture was loaded directly onto a 2 g SCX cartridge (pre-equilibrated with MeOH), eluting in sequence with MeOH (12 mL) and a 2 M solution of NH$_3$/MeOH (9 mL). The fractions containing the boronic acid crude product were concentrated under a stream of N$_2$ and dried under high vacuum to give 45 mg of crude product. The crude product was taken up in saturated NaHCO$_3$ (2 mL) and extracted with EtOAc (3×2 mL) to give 7.8 mg of crude {5-[(2-methyl-1-pyrrolidinyl)methyl]-2-thienyl}boronic acid. The crude boronic acid from the above three reactions were pooled and carried on for the preparation of 3-[1-(ethylsulfonyl)-4-piperidinyl]-5-{5-[(2-methyl-1-pyrrolidinyl)methyl]-2-thienyl}-1H-indole-7-carboxamide (final weight after pooling the three batches of {5-[(2-methyl-1-pyrrolidinyl)methyl]-2-thienyl}boronic acid was 19 mg).

A solution of 5-bromo-3-[1-(ethylsulfonyl)-4-piperidinyl]-1H-indole-7-carboxamide (36 mg, 0.0862 mmol), {5-[(2-methyl-1-pyrrolidinyl)methyl]-2-thienyl}boronic acid (19 mg, 0.0862 mmol) and potassium carbonate (71 mg, 0.517 mmol) was combined in a CEM microwave tube. To this mixture was added water (0.25 mL), dioxane (0.75 mL) and tetrakis(triphenylphosphine)palladium(0) (10 mg, 0.009 mmol). The vial was capped and reacted in a CEM microwave for 20 min at 150° C. To this reaction was added tetrakis(triphenylphosphine)palladium(0) (10 mg, 0.009 mmol) and reacted in a microwave for 20 min at 150° C. Additional tetrakis(triphenylphosphine)palladium(0) (10 mg, 0.009 mmol) was added, and the reaction was heated in the CEM microwave for an additional 20 min at 150° C. The reaction mixture was filtered through a 2 g SCX cartridge (pre-equilibrated with 3 mL H$_2$O), eluting in sequence with water (3 mL), MeOH (9 mL), and a 2 M solution of NH$_3$/MeOH (9 mL). The fraction containing crude product solution was concentrated under a stream of nitrogen, and the residue was taken up in DMSO (3 mL). This DMSO solution of crude product was purified as three separate injections (1 mL each) on the Agilent MDAP (Zorbax Eclipse XDB-C18 column: 21.2×50 mm) eluting at 20 mL per min for 1 min with 10% CH$_3$CN/H$_2$O (0.1% TFA) then a linear gradient of 10% CH$_3$CN/H$_2$O (0.1% TFA) to 95% CH$_3$CN/H$_2$O (0.1% TFA) over 8 min and holding at the final concentration for 30 sec. The two fractions containing product were filtered through a 500 mg Pharmasil CHQAX column (polymer bound ammonium hydroxide; United Chemical Technologies) to remove TFA (2 columns used per fraction) and concentrated under a stream of nitrogen at 40° C. to give 13 mg of the title compound (29.3%).

LC/MS=m/z 515.6 [M+H] Ret. Time: 1.62 min.

Example 168

5-{5-[(ethylamino)methyl]-2-thienyl}-3-[1-(ethylsulfonyl)-4-piperidinyl]-1H-indole-7-carboxamide

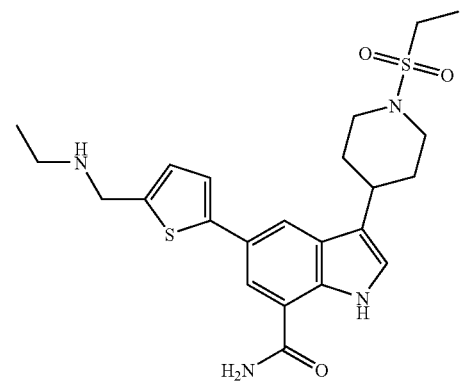

The {5-[(ethylamino)methyl]-2-thienyl}boronic acid used to prepare 5-{5-[(ethylamino)methyl]-2-thienyl}-3-[1-(ethylsulfonyl)-4-piperidinyl]-1H-indole-7-carboxamide was prepared as follows: A 2 M solution of ethylamine in THF (0.16 mL, 0.32 mmol) was added to a solution of (5-formyl-2-thienyl)boronic acid (50 mg, 0.32 mmol) in MeOH (1 mL) in a 2-dram vial. The vial was capped and the reaction was stirred at room temperature for 2 h. NaCNBH$_3$ (40 mg, 0.64 mmol) was added, and stirring continued for 17 h. The reaction mixture was filtered through a 2 g SCX cartridge (pre-equilibrated with 3 mL MeOH), eluting in sequence with MeOH (6 mL) and a 2 M solution of NH$_3$/MeOH (9 mL). The NH$_3$/MeOH fraction was concentrated under a stream of nitrogen to give 47 mg of crude {5-[(ethylamino)methyl]-2-thienyl}boronic acid.

To a CEM microwave tube containing {5-[(ethylamino)methyl]-2-thienyl}boronic acid (47 mg, 0.254 mmol) was added 5-bromo-3-[1-(ethylsulfonyl)-4-piperidinyl]-1H-indole-7-carboxamide (80 mg, 0.193 mmol), potassium carbonate (160 mg, 1.16 mmol), dioxane (1.5 mL), H$_2$O (0.5 mL) and tetrakis(triphenylphosphine)palladium(0) (5 mg, 0.004 mmol). The reaction was heated in a CEM microwave for 30 min at 150° C. (This run was aborted prior to 30 min due to excessive pressure build-up). The reaction mixture was filtered through a 2 g SCX cartridge (pre-equilibrated with 3 mL MeOH), eluting in sequence with H$_2$O (3 mL), MeOH (9 mL) and a 2 M solution of NH$_3$/MeOH (6 mL). The NH$_3$/MeOH fraction was dried under a stream of nitrogen at 40° C., and the crude product was taken up in dimethyl sulfoxide (1 mL) and purified on an Agilent MDAP (Zorbax Eclipse XDB-C18 column: 21.2×50 mm) eluting at 20 mL per min for 1 min with 10% CH$_3$CN/H$_2$O (0.1% TFA) then a linear gradient of 10% CH$_3$CN/H$_2$O (0.1% TFA) to 95% CH$_3$CN/H$_2$O (0.1% TFA) over 8 min and holding at the final concentration for 30 sec. The fractions containing product were filtered through a 500 mg Pharmasil CHQAX column (polymer bound ammonium hydroxide; United Chemical Technologies) to remove TFA (2 columns used per fraction) and concentrated under a stream of nitrogen at 60° C. to give 8.8 mg of the title compound (10%).

LC/MS=m/z 429.8 [M+H] Ret. Time: 1.25 min.

Example 169

3-[1-(ethylsulfonyl)-4-piperidinyl]-5-(5-{[(1-methylethyl)amino]methyl}-2-thienyl)-1H-indole-7-carboxamide

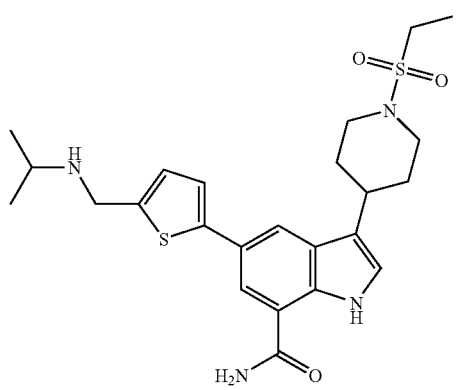

Following the general procedure of 5-{5-[(ethylamino)methyl]-2-thienyl}-3-[1-(ethylsulfonyl)-4-piperidinyl]-1H-indole-7-carboxamide, (5-formyl-2-thienyl)boronic acid (50 mg, 0.32 mmol), isopropylamine (0.027 mL, 0.32 mmol), and NaCNBH$_3$ (40 mg, 0.64 mmol) were reacted to give 41 mg of crude (5-{[(1-methylethyl)amino]methyl}-2-thienyl)boronic acid. The crude (5-{[(1-methylethyl)amino]methyl}-2-thienyl)boronic acid was then reacted with 5-bromo-3-[1-(ethylsulfonyl)-4-piperidinyl]-1H-indole-7-carboxamide (80 mg, 0.193 mmol), potassium carbonate (160 mg, 1.16 mmol), and tetrakis(triphenylphosphine)palladium(0) (5 mg, 0.004 mmol) to give 74 mg of the title compound (37%).

LC/MS=m/z 430.2 [M+H] Ret. Time: 1.29 min.

Example 170

5-{5-[(cyclopropylamino)methyl]-2-thienyl}-3-[1-(ethylsulfonyl)-4-piperidinyl]-1H-indole-7-carboxamide

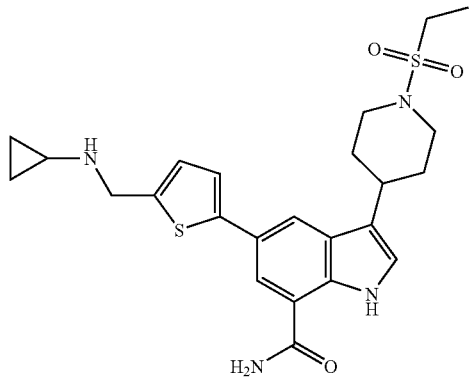

Following the general procedure of 5-{5-[(ethylamino)methyl]-2-thienyl}-3-[1-(ethylsulfonyl)-4-piperidinyl]-1H-indole-7-carboxamide, (5-formyl-2-thienyl)boronic acid (50 mg, 0.32 mmol), cyclopropylamine (0.022 mL, 0.32 mmol), and NaCNBH$_3$ (40 mg, 0.64 mmol) were reacted to give 63 mg of crude {5-[(cyclopropylamino)methyl]-2-thienyl}boronic acid. The crude {5-[(cyclopropylamino)methyl]-2-thienyl}boronic acid was then reacted with 5-bromo-3-[1-(ethylsulfonyl)-4-piperidinyl]-1H-indole-7-carboxamide (80 mg, 0.193 mmol), potassium carbonate (160 mg, 1.16 mmol), and tetrakis(triphenylphosphine)palladium(0) (5 mg, 0.004 mmol) to give impure title compound. The impure title compound was purified again with the Agilent MDAP and isolated as the free base according to the procedure shown in Example 5 to give 6.8 mg of the title compound (7.2%).

LC/MS=m/z 430.2 [M+H] Ret. Time: 1.62 min.

Example 171

5-(5-{[(2,2-dimethylpropyl)amino]methyl}-2-thienyl)-3-[1-(ethylsulfonyl)-4-piperidinyl]-1H-indole-7-carboxamide

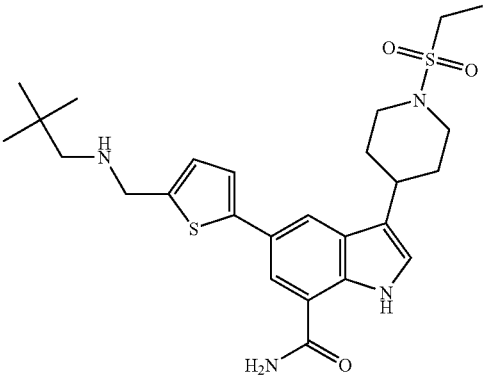

Following the general procedure of 5-{5-[(ethylamino)methyl]-2-thienyl}-3-[1-(ethylsulfonyl)-4-piperidinyl]-1H-indole-7-carboxamide, (5-formyl-2-thienyl)boronic acid (50 mg, 0.32 mmol), (2,2-dimethylpropyl)amine (0.037 mL, 0.32 mmol), and NaCNBH$_3$ (40 mg, 0.64 mmol) were reacted to give 73 mg of crude (5-{[(2,2-dimethylpropyl)amino]methyl}-2-thienyl)boronic acid. The crude (5-{[(2,2-dimethylpropyl)amino]methyl}-2-thienyl)boronic acid was then reacted with 5-bromo-3-[1-(ethylsulfonyl)-4-piperidinyl]-1H-indole-7-carboxamide (80 mg, 0.193 mmol), potassium carbonate (160 mg, 1.16 mmol), and tetrakis(triphenylphosphine)palladium(0) (5 mg, 0.004 mmol) to give 21 mg of the title compound (21%).

LC/MS=m/z 430.2 [M+H] Ret. Time: 1.45 min.

Example 172

5-(5-{[(cyclopropylmethyl)amino]methyl}-2-thienyl)-3-[1-(ethylsulfonyl)-4-piperidinyl]-1H-indole-7-carboxamide

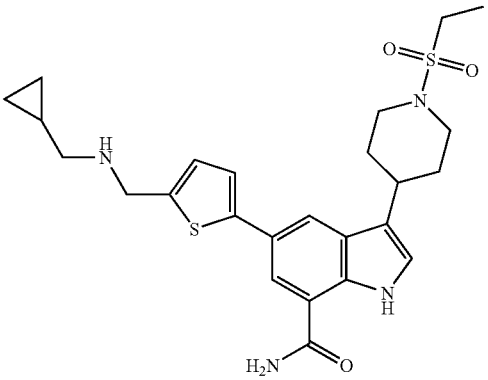

Following the general procedure of 5-{5-[(ethylamino)methyl]-2-thienyl}-3-[1-(ethylsulfonyl)-4-piperidinyl]-1H-indole-7-carboxamide, (5-formyl-2-thienyl)boronic acid (50 mg, 0.32 mmol), (cyclopropylmethyl)amine (0.027 mL, 0.32 mmol), and NaCNBH₃ (40 mg, 0.64 mmol) were reacted to give 73 mg of crude (5-{[(cyclopropylmethyl)amino]methyl}-2-thienyl)boronic acid. The crude (5-{[(cyclopropylmethyl)amino]methyl}-2-thienyl)boronic acid was then reacted with 5-bromo-3-[1-(ethylsulfonyl)-4-piperidinyl]-1H-indole-7-carboxamide (80 mg, 0.193 mmol), potassium carbonate (160 mg, 1.16 mmol), and tetrakis(triphenylphosphine)palladium(0) (5 mg, 0.004 mmol) to give 19.1 mg of the title compound (20%).
LC/MS=m/z 430.2 [M+H] Ret. Time: 1.33 min.

Example 173

5-(5-{[(cyclopropylmethyl)amino]methyl}-3-pyridinyl)-3-[1-(ethylsulfonyl)-4-piperidinyl]-1H-indole-7-carboxamide

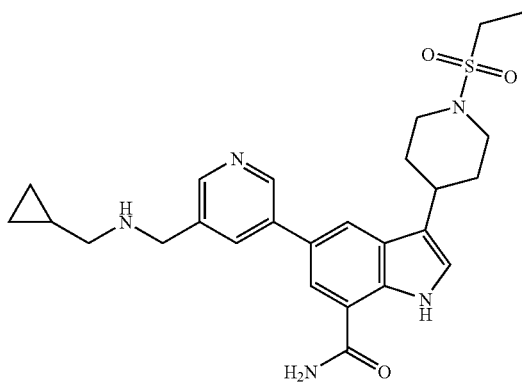

The (cyclopropylmethyl){[5-(4,4,5,5-tetramethyl-1,3,2-dioxaborolan-2-yl)-3-pyridinyl]methyl}amine used to prepare 5-(5-{[(cyclopropylmethyl)amino]methyl}-3-pyridinyl)-3-[1-(ethylsulfonyl)-4-piperidinyl]-1H-indole-7-carboxamide was prepared as follows: (Cyclopropylmethyl)amine (0.011 mL, 0.129 mmol) was added to a solution of 5-(4,4,5,5-tetramethyl-1,3,2-dioxaborolan-2-yl)-3-pyridinecarbaldehyde (30 mg, 0.129 mmol) in MeOH (1 mL) in a 2-dram vial. The vial was capped and the reaction was stirred at room temperature for 17 h. NaCNBH₃ (16 mg, 0.258 mmol) was added, and stirring continued for 30 h. The reaction mixture was filtered through a 2 g SCX cartridge (pre-equilibrated with 3 mL MeOH), eluting in sequence with MeOH (6 mL) and a 2 M solution of NH₃/MeOH (9 mL). The NH₃/MeOH fraction was concentrated under a stream of nitrogen to give 21 mg of crude (cyclopropylmethyl){[5-(4,4,5,5-tetramethyl-1,3,2-dioxaborolan-2-yl)-3-pyridinyl]methyl}amine.

To a CEM microwave tube containing (cyclopropylmethyl){[5-(4,4,5,5-tetramethyl-1,3,2-dioxaborolan-2-yl)-3-pyridinyl]methyl}amine (21 mg, 0.0725 mmol) was added 5-bromo-3-[1-(ethylsulfonyl)-4-piperidinyl]-1H-indole-7-carboxamide (30 mg, 0.0723 mmol), dioxane (0.75 mL), a solution of potassium carbonate (60 mg, 0.434 mmol) in H₂O (0.25 mL), and chloro-2-(dimethylaminomethyl)-ferrocen-1-yl-(dinorbornylphosphine)palladium(II) (4.4 mg, 0.00723 mmol). The reaction was heated in a CEM microwave for 30 min at 150° C. The reaction mixture was filtered through a 2 g SCX cartridge (pre-equilibrated with 3 mL MeOH), eluting in sequence with H₂O (3 mL), MeOH (6 mL) and a 2 M solution of NH₃/MeOH (9 mL). The NH₃/MeOH fraction was dried under a stream of nitrogen at 40° C. and purified on an Agilent MDAP (Zorbax Eclipse XDB-C18 column: 21.2× 50 mm) eluting at 20 mL per min for 1 min with 10% CH₃CN/H₂O (0.1% TFA) then a linear gradient of 10% CH₃CN/H₂O (0.1% TFA) to 95% CH₃CN/H₂O (0.1% TFA) over 8 min and holding at the final concentration for 30 sec. The fractions containing product were filtered through a 2 g Pharmasil CHQAX column (polymer bound ammonium hydroxide; United Chemical Technologies) to remove TFA and concentrated under a stream of nitrogen at 65° C. to give impure title compound, which was repurified on the Agilent MDAP as shown above to give 25 mg of the title compound (70%).
LC/MS=m/z 496.6 [M+H] Ret. Time: 1.35 min.

Example 174

3-[1-(ethylsulfonyl)-4-piperidinyl]-5-[5-({[2-(methyloxy)ethyl]amino}methyl)-3-pyridinyl]-1H-indole-7-carboxamide

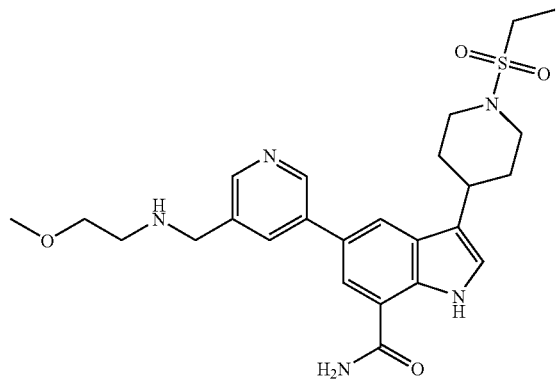

Following the general procedure of 5-(5-{[(cyclopropylmethyl)amino]methyl}-3-pyridinyl)-3-[1-(ethylsulfonyl)-4-piperidinyl]-1H-indole-7-carboxamide, 5-(4,4,5,5-tetramethyl-1,3,2-dioxaborolan-2-yl)-3-pyridinecarbaldehyde (30 mg, 0.129 mmol), [2-(methyloxy)ethyl]amine (0.011 mL, 0.129 mmol), and NaCNBH₃ (16 mg, 0.258 mmol) were reacted to give 19 mg of crude [2-(methyloxy)ethyl]{[5-(4,4,5,5-tetramethyl-1,3,2-dioxaborolan-2-yl)-3-pyridinyl]methyl}amine. The crude [2-(methyloxy)ethyl]{[5-(4,4,5,5-tetramethyl-1,3,2-dioxaborolan-2-yl)-3-pyridinyl]methyl}amine was then reacted with 5-bromo-3-[1-(ethylsulfonyl)-4-piperidinyl]-1H-indole-7-carboxamide (30 mg, 0.0723 mmol), potassium carbonate (60 mg, 0.434 mmol), and chloro-2-(dimethylaminomethyl)-ferrocen-1-yl-(dinorbornylphosphine)palladium(II) (4.4 mg, 0.00723 mmol) to give 15 mg of the title compound (46%).
LC/MS=m/z 500.6 [M+H] Ret. Time: 1.52 min.

Example 175

3-[1-(ethylsulfonyl)-4-piperidinyl]-5-[5-({[3-(methyloxy)propyl]amino}methyl)-3-pyridinyl]-1H-indole-7-carboxamide

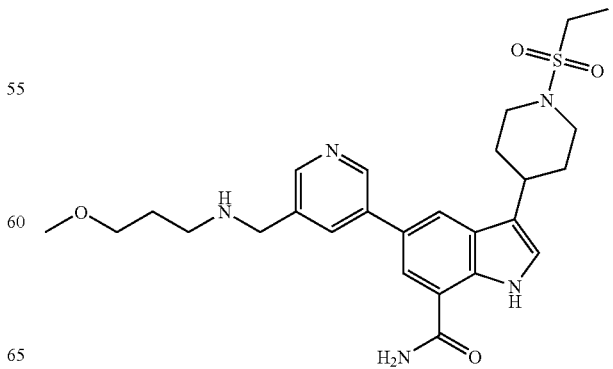

Following the general procedure of 5-(5-{[(cyclopropylmethyl)amino]methyl}-3-pyridinyl)-3-[1-(ethylsulfonyl)-4-piperidinyl]-1H-indole-7-carboxamide, 5-(4,4,5,5-tetramethyl-1,3,2-dioxaborolan-2-yl)-3-pyridinecarbaldehyde (30 mg, 0.129 mmol), [3-(methyloxy)propyl]amine (0.013 mL, 0.129 mmol), and NaCNBH₃ (16 mg, 0.258 mmol) were reacted to give 22 mg of crude [3-(methyloxy)propyl]{[5-(4,4,5,5-tetramethyl-1,3,2-dioxaborolan-2-yl)-3-pyridinyl]methyl}amine. The crude [3-(methyloxy)propyl]{[5-(4,4,5,5-tetramethyl-1,3,2-dioxaborolan-2-yl)-3-pyridinyl]methyl}amine was then reacted with 5-bromo-3-[1-(ethylsulfonyl)-4-piperidinyl]-1H-indole-7-carboxamide (30 mg, 0.0723 mmol), potassium carbonate (60 mg, 0.434 mmol), and chloro-2-(dimethylaminomethyl)-ferrocen-1-yl-(dinorbornylphosphine)palladium(II) (4.4 mg, 0.00723 mmol) to give 31 mg of the title compound (83%).

LC/MS=m/z 514.4 [M+H] Ret. Time: 1.46 min.

Example 176

3-[1-(ethylsulfonyl)-4-piperidinyl]-5-[5-(4-morpholinylmethyl)-3-pyridinyl]-1H-indole-7-carboxamide

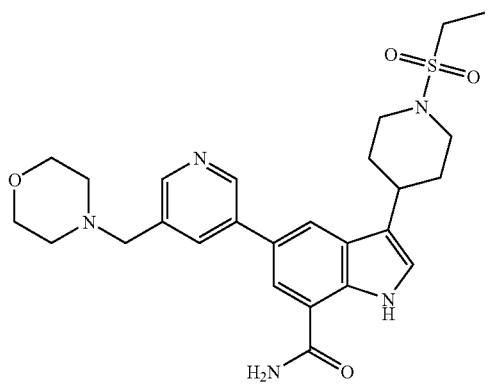

Following the general procedure of 5-(5-{[(cyclopropylmethyl)amino]methyl}-3-pyridinyl)-3-[1-(ethylsulfonyl)-4-piperidinyl]-1H-indole-7-carboxamide, 5-(4,4,5,5-tetramethyl-1,3,2-dioxaborolan-2-yl)-3-pyridinecarbaldehyde (30 mg, 0.129 mmol), morpholine (0.011 mL, 0.129 mmol), and NaCNBH₃ (16 mg, 0.258 mmol) were reacted to give 28 mg of crude 4-{[5-(4,4,5,5-tetramethyl-1,3,2-dioxaborolan-2-yl)-3-pyridinyl]methyl}morpholine. The crude 4-{[5-(4,4,5,5-tetramethyl-1,3,2-dioxaborolan-2-yl)-3-pyridinyl]methyl}morpholine was then reacted with 5-bromo-3-[1-(ethylsulfonyl)-4-piperidinyl]-1H-indole-7-carboxamide (30 mg, 0.0723 mmol), potassium carbonate (60 mg, 0.434 mmol), and chloro-2-(dimethylaminomethyl)-ferrocen-1-yl-(dinorbornylphosphine)palladium(II) (4.4 mg, 0.00723 mmol) to give 15.8 mg of the title compound (43%).

LC/MS=m/z 512.2 [M+H] Ret. Time: 1.38 min.

Example 177

5-{5-[(ethylamino)methyl]-3-pyridinyl}-3-[1-(ethylsulfonyl)-4-piperidinyl]-1H-indole-7-carboxamide

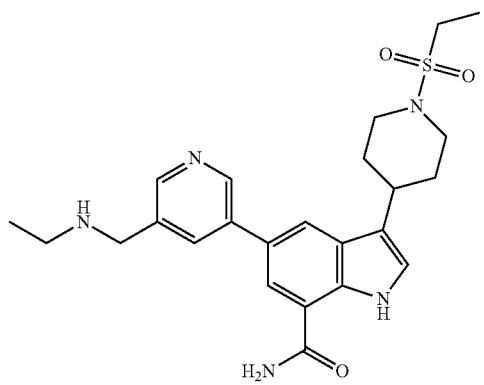

Following the general procedure of 5-(5-{[(cyclopropylmethyl)amino]methyl}-3-pyridinyl)-3-[1-(ethylsulfonyl)-4-piperidinyl]-1H-indole-7-carboxamide, 5-(4,4,5,5-tetramethyl-1,3,2-dioxaborolan-2-yl)-3-pyridinecarbaldehyde (30 mg, 0.129 mmol), a 2 M solution of ethylamine in THF (0.065 mL, 0.129 mmol), and NaCNBH₃ (16 mg, 0.258 mmol) were reacted to give 19 mg of crude ethyl{[5-(4,4,5,5-tetramethyl-1,3,2-dioxaborolan-2-yl)-3-pyridinyl]methyl}amine. The crude ethyl{[5-(4,4,5,5-tetramethyl-1,3,2-dioxaborolan-2-yl)-3-pyridinyl]methyl}amine was then reacted with 5-bromo-3-[1-(ethylsulfonyl)-4-piperidinyl]-1H-indole-7-carboxamide (30 mg, 0.0723 mmol), potassium carbonate (60 mg, 0.434 mmol), and chloro-2-(dimethylaminomethyl)-ferrocen-1-yl-(dinorbornylphosphine)palladium(II) (4.4 mg, 0.00723 mmol) to give 12.3 mg of the title compound (36%).

LC/MS=m/z 470.4 [M+H] Ret. Time: 1.44 min.

Example 178

5-{5-[(dimethylamino)methyl]-3-pyridinyl}-3-[1-(ethylsulfonyl)-4-piperidinyl]-1H-indole-7-carboxamide

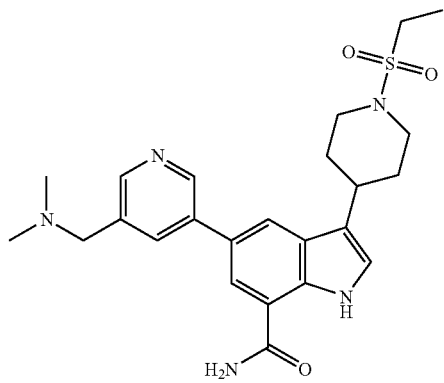

Following the general procedure of 5-(5-{[(cyclopropylmethyl)amino]methyl}-3-pyridinyl)-3-[1-(ethylsulfonyl)-4-piperidinyl]-1H-indole-7-carboxamide, 5-(4,4,5,5-tetramethyl-1,3,2-dioxaborolan-2-yl)-3-pyridinecarbaldehyde (30 mg, 0.129 mmol), a 2 M solution of dimethylamine in THF (0.065 mL, 0.129 mmol), and NaCNBH₃ (16 mg, 0.258 mmol) were reacted to give 23 mg of crude dimethyl{[5-(4,4,5,5-tetramethyl-1,3,2-dioxaborolan-2-yl)-3-pyridinyl]methyl}amine. The crude dimethyl{[5-(4,4,5,5-tetramethyl-1,3,2-dioxaborolan-2-yl)-3-pyridinyl]methyl}amine was then reacted with 5-bromo-3-[1-(ethylsulfonyl)-4-piperidinyl]-1H-indole-7-carboxamide (30 mg, 0.0723 mmol), potassium carbonate (60 mg, 0.434 mmol), and chloro-2-(dimethylaminomethyl)-ferrocen-1-yl-(dinorbornylphosphine)palladium(II) (4.4 mg, 0.00723 mmol) to give 5.4 mg of the title compound (16%).

LC/MS=m/z 470.6 [M+H] Ret. Time: 1.35 min.

Example 179

3-[1-(ethylsulfonyl)-4-piperidinyl]-5-{5-[(2-methyl-1-pyrrolidinyl)methyl]-3-pyridinyl}-1H-indole-7-carboxamide

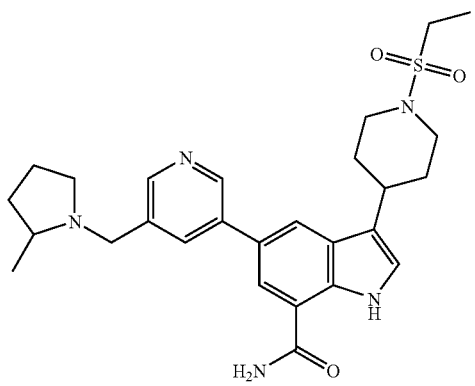

Following the general procedure of 5-(5-{[(cyclopropylmethyl)amino]methyl}-3-pyridinyl)-3-[1-(ethylsulfonyl)-4-piperidinyl]-1H-indole-7-carboxamide, 5-(4,4,5,5-tetramethyl-1,3,2-dioxaborolan-2-yl)-3-pyridinecarbaldehyde (30 mg, 0.129 mmol), 2-methylpyrrolidine (0.013 mL, 0.129 mmol), and NaCNBH₃ (16 mg, 0.258 mmol) were reacted to give 25 mg of crude 3-[(2-methyl-1-pyrrolidinyl)methyl]-5-(4,4,5,5-tetramethyl-1,3,2-dioxaborolan-2-yl)pyridine. The crude 3-[(2-methyl-1-pyrrolidinyl)methyl]-5-(4,4,5,5-tetramethyl-1,3,2-dioxaborolan-2-yl)pyridine was then reacted with 5-bromo-3-[1-(ethylsulfonyl)-4-piperidinyl]-1H-indole-7-carboxamide (30 mg, 0.0723 mmol), potassium carbonate (60 mg, 0.434 mmol), and chloro-2-(dimethylaminomethyl)-ferrocen-1-yl-(dinorbornylphosphine)palladium(II) (4.4 mg, 0.00723 mmol) to give 6 mg of the title compound (16%).

LC/MS=m/z 512.6 [M+H] Ret. Time: 1.67 min.

Example 180

3-[1-(ethylsulfonyl)-4-piperidinyl]-5-(5-{[(2-methylpropyl)amino]methyl}-3-pyridinyl)-1H-indole-7-carboxamide

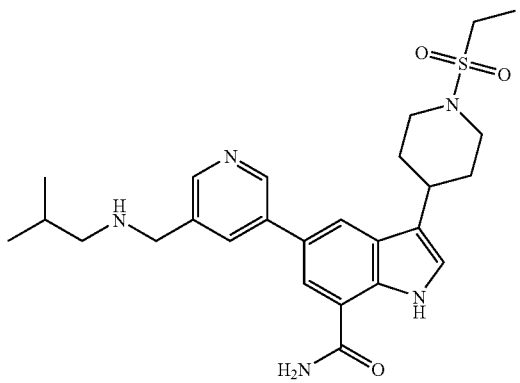

Following the general procedure of 5-(5-{[(cyclopropylmethyl)amino]methyl}-3-pyridinyl)-3-[1-(ethylsulfonyl)-4-piperidinyl]-1H-indole-7-carboxamide, 5-(4,4,5,5-tetramethyl-1,3,2-dioxaborolan-2-yl)-3-pyridinecarbaldehyde (30 mg, 0.129 mmol), isobutylamine (0.013 mL, 0.129 mmol), and NaCNBH₃ (16 mg, 0.258 mmol) were reacted to give 21 mg of crude (2-methylpropyl){[5-(4,4,5,5-tetramethyl-1,3,2-dioxaborolan-2-yl)-3-pyridinyl]methyl}amine. The crude (2-methylpropyl){[5-(4,4,5,5-tetramethyl-1,3,2-dioxaborolan-2-yl)-3-pyridinyl]methyl}amine was then reacted with 5-bromo-3-[1-(ethylsulfonyl)-4-piperidinyl]-1H-indole-7-carboxamide (30 mg, 0.0723 mmol), potassium carbonate (60 mg, 0.434 mmol), and chloro-2-(dimethylaminomethyl)-ferrocen-1-yl-(dinorbornylphosphine)palladium(II) (4.4 mg, 0.00723 mmol) to give 12.5 mg of the title compound (35%).

LC/MS=m/z 498.2 [M+H] Ret. Time: 1.38 min.

Example 181

5-(5-{[(2,2-dimethylpropyl)amino]methyl}-3-pyridinyl)-3-[1-(ethylsulfonyl)-4-piperidinyl]-1H-indole-7-carboxamide

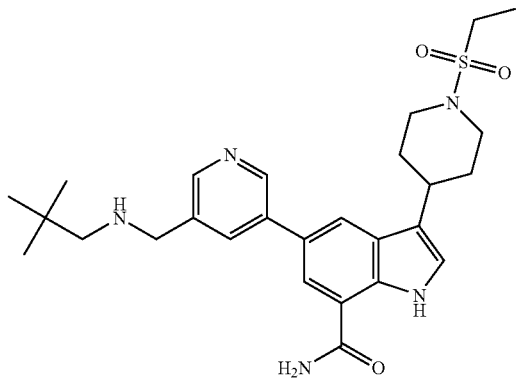

Following the general procedure of 5-(5-{[(cyclopropylmethyl)amino]methyl}-3-pyridinyl)-3-[1-(ethylsulfonyl)-4-piperidinyl]-1H-indole-7-carboxamide, 5-(4,4,5,5-tetramethyl-1,3,2-dioxaborolan-2-yl)-3-pyridinecarbaldehyde (30 mg, 0.129 mmol), (2,2-dimethylpropyl)amine (0.015 mL, 0.129 mmol), and NaCNBH₃ (16 mg, 0.258 mmol) were reacted to give 25 mg of crude (2,2-dimethylpropyl){[5-(4,4,5,5-tetramethyl-1,3,2-dioxaborolan-2-yl)-3-pyridinyl]methyl}amine. The crude (2,2-dimethylpropyl){[5-(4,4,5,5-tetramethyl-1,3,2-dioxaborolan-2-yl)-3-pyridinyl]methyl}amine was then reacted with 5-bromo-3-[1-(ethylsulfonyl)-4-piperidinyl]-1H-indole-7-carboxamide (30 mg, 0.0723 mmol), potassium carbonate (60 mg, 0.434 mmol), and chloro-2-(dimethylaminomethyl)-ferrocen-1-yl-(dinorbornylphosphine)palladium(II) (4.4 mg, 0.00723 mmol) to give 12.7 mg of the title compound (34%).

LC/MS=m/z 512.4 [M+H] Ret. Time: 1.51 min.

Example 182

3-[1-(ethylsulfonyl)-4-piperidinyl]-5-(5-{[(2-methylbutyl)amino]methyl}-2-thienyl)-1H-indole-7-carboxamide

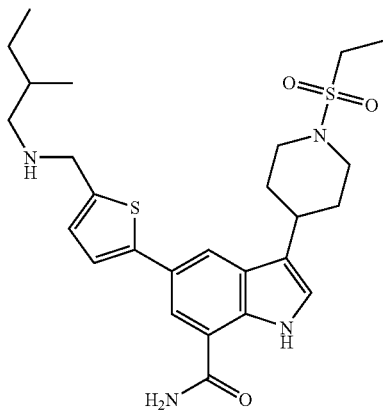

The {5-[(ethylamino)methyl]-2-thienyl}boronic acid used to prepare 3-[1-(ethylsulfonyl)-4-piperidinyl]-5-(5-{[(2-methylbutyl)amino]methyl}-2-thienyl)-1H-indole-7-carboxamide was prepared as follows: A solution of (5-formyl-2-thienyl)boronic acid (50 mg, 0.32 mmol) in MeOH (0.5 mL) and a solution of NaCNBH$_3$ (40 mg, 0.64 mmol) in MeOH (0.5 mL) were added to (2-methylbutyl)amine (28 mg, 0.32 mmol) in a 2-dram vial. The vial was capped and the reaction was stirred at room temperature for 20 h. The reaction mixture was filtered through a 2 g SCX cartridge (pre-equilibrated with 3 mL MeOH), eluting in sequence with MeOH (6 mL) and a 2 M solution of NH$_3$/MeOH (9 mL). The NH$_3$/MeOH fraction was concentrated under a stream of nitrogen to give 43 mg of crude (5-{[(2-methylbutyl)amino]methyl}-2-thienyl)boronic acid.

To a CEM microwave tube containing the crude (5-{[(2-methylbutyl)amino]methyl}-2-thienyl)boronic acid (43 mg, 0.188 mmol) was added 5-bromo-3-[1-(ethylsulfonyl)-4-piperidinyl]-1H-indole-7-carboxamide (65 mg, 0.157 mmol), K$_2$CO$_3$ (130 mg, 0.942 mmol), dioxane (1.5 mL), H$_2$O (0.5 mL) and tetrakis(triphenylphosphine)palladium(0) (4 mg, 0.003 mmol). The reaction was heated in a CEM microwave for 30 min at 150° C. The reaction mixture was filtered through a 2 g SCX cartridge (pre-equilibrated with 3 mL MeOH), eluting in sequence with H$_2$O (3 mL), MeOH (9 mL) and a 2 M solution of NH$_3$/MeOH (6 mL). The NH$_3$/MeOH fraction was dried under a stream of nitrogen at 40° C., and the crude product was taken up in dimethyl sulfoxide (1 mL) and purified on an Agilent MDAP (Zorbax Eclipse XDB-C18 column: 21.2×50 mm) eluting at 20 mL per min for 1 min with 10% CH$_3$CN/H$_2$O (0.1% TFA) then a linear gradient of 10% CH$_3$CN/H$_2$O (0.1% TFA) to 95% CH$_3$CN/H$_2$O (0.1% TFA) over 8 min and holding at the final concentration for 30 sec. The fractions containing product were filtered through a 2 g Pharmasil CHQAX column (polymer bound ammonium hydroxide; United Chemical Technologies) to remove TFA and concentrated under a stream of nitrogen at 50° C. to give 16.2 mg of the title compound (17%).

LC/MS=m/z 430.4 [M+H] Ret. Time: 1.75 min.

Example 183

5-[5-({[(1R)-1,2-dimethylpropyl]amino}methyl)-2-thienyl]-3-[1-(ethylsulfonyl)-4-piperidinyl]-1H-indole-7-carboxamide

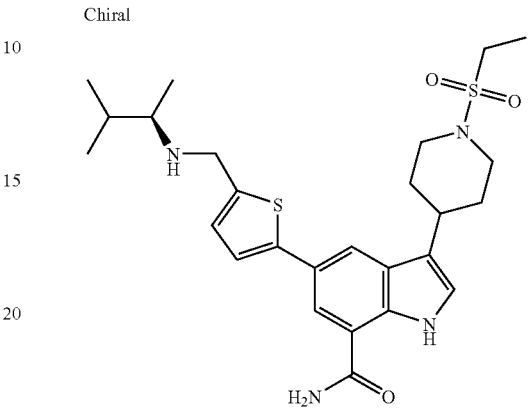

Chiral

Following the general procedure of 3-[1-(ethylsulfonyl)-4-piperidinyl]-5-(5-{[(2-methylbutyl)amino]methyl}-2-thienyl)-1H-indole-7-carboxamide, (5-formyl-2-thienyl)boronic acid (50 mg, 0.32 mmol), [(1R)-1,2-dimethylpropyl]amine (28 mg, 0.32 mmol), and NaCNBH$_3$ (40 mg, 0.64 mmol) were reacted to give 30 mg of crude [5-({[(1R)-1,2-dimethylpropyl]amino}methyl)-2-thienyl]boronic acid. The crude [5-({[(1R)-1,2-dimethylpropyl]amino}methyl)-2-thienyl]boronic acid was then reacted with 5-bromo-3-[1-(ethylsulfonyl)-4-piperidinyl]-1H-indole-7-carboxamide (65 mg, 0.157 mmol), K$_2$CO$_3$ (130 mg, 0.942 mmol), and tetrakis(triphenylphosphine)palladium(0) (4 mg, 0.003 mmol) to give 20.5 mg of the title compound (30%).

LC/MS=m/z 430.4 [M+H] Ret. Time: 1.75 min.

Example 184

3-[1-(ethylsulfonyl)-4-piperidinyl]-5-{5-[(pentylamino)methyl]-2-thienyl}-1H-indole-7-carboxamide

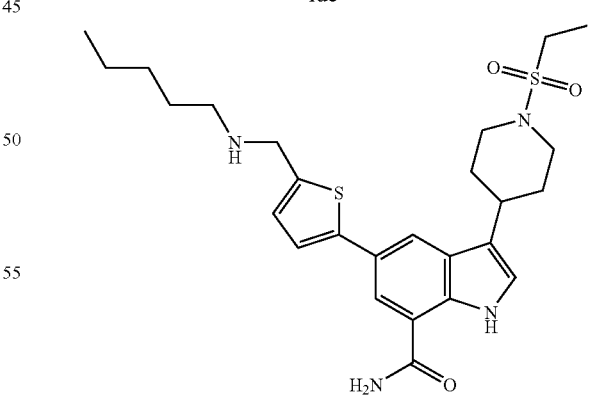

Following the general procedure of 3-[1-(ethylsulfonyl)-4-piperidinyl]-5-(5-{[(2-methylbutyl)amino]methyl}-2-thienyl)-1H-indole-7-carboxamide, (5-formyl-2-thienyl)boronic acid (50 mg, 0.32 mmol), pentylamine (29 mg, 0.32 mmol), and NaCNBH$_3$ (40 mg, 0.64 mmol) were reacted to give 45 mg of crude {5-[(pentylamino)methyl]-2-thienyl}boronic acid. The crude {5-[(pentylamino)methyl]-2-thienyl}boronic acid was then reacted with 5-bromo-3-[1-(ethylsulfonyl)-4-piperidinyl]-1H-indole-7-carboxamide (65 mg, 0.157 mmol), K₂CO₃ (130 mg, 0.942 mmol), and tetrakis(triphenylphosphine)palladium(0) (4 mg, 0.003 mmol) to give 20.7 mg of the title compound (20%).

LC/MS=m/z 430.6 [M+H] Ret. Time: 1.75 min.

Example 185

3-[1-(ethylsulfonyl)-4-piperidinyl]-5-[5-({[(2S)-2-methylbutyl]amino}methyl)-2-thienyl]-1H-indole-7-carboxamide

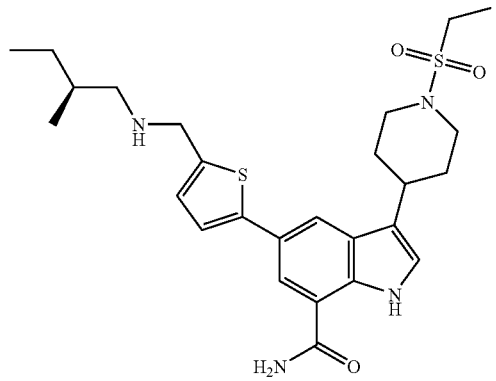

Following the general procedure of 3-[1-(ethylsulfonyl)-4-piperidinyl]-5-(5-{[(2-methylbutyl)amino]methyl}-2-thienyl)-1H-indole-7-carboxamide, (5-formyl-2-thienyl)boronic acid (50 mg, 0.32 mmol), [(2S)-2-methylbutyl]amine (28 mg, 0.32 mmol), and NaCNBH₃ (40 mg, 0.64 mmol) were reacted to give 43 mg of crude [5-({[(2S)-2-methylbutyl]amino}methyl)-2-thienyl]boronic acid. The crude [5-({[(2S)-2-methylbutyl]amino}methyl)-2-thienyl]boronic acid was then reacted with 5-bromo-3-[1-(ethylsulfonyl)-4-piperidinyl]-1H-indole-7-carboxamide (65 mg, 0.157 mmol), K₂CO₃ (130 mg, 0.942 mmol), and tetrakis(triphenylphosphine)palladium(0) (4 mg, 0.003 mmol) to give 37.6 mg of the title compound (39%).

LC/MS=m/z 430 [M+H] Ret. Time: 1.67 min.

Example 186

3-[1-(ethylsulfonyl)-4-piperidinyl]-5-(5-{[(1-methylbutyl)amino]methyl}-2-thienyl)-1H-indole-7-carboxamide

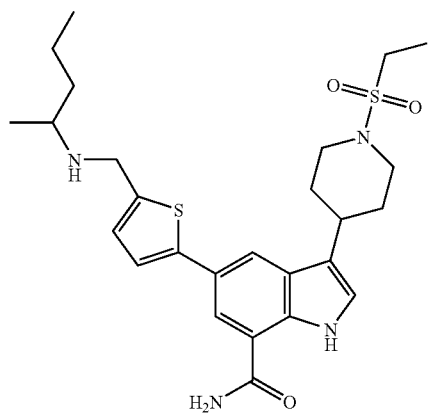

Following the general procedure of 3-[1-(ethylsulfonyl)-4-piperidinyl]-5-(5-{[(2-methylbutyl)amino]methyl}-2-thienyl)-1H-indole-7-carboxamide, (5-formyl-2-thienyl)boronic acid (50 mg, 0.32 mmol), (1-methylbutyl)amine (29 mg, 0.32 mmol), and NaCNBH₃ (40 mg, 0.64 mmol) were reacted to give 43 mg of crude (5-{[(1-methylbutyl)amino]methyl}-2-thienyl)boronic acid. The crude (5-{[(1-methylbutyl)amino]methyl}-2-thienyl)boronic acid was then reacted with 5-bromo-3-[1-(ethylsulfonyl)-4-piperidinyl]-1H-indole-7-carboxamide (65 mg, 0.157 mmol), K₂CO₃ (130 mg, 0.942 mmol), and tetrakis(triphenylphosphine)palladium(0) (4 mg, 0.003 mmol) to give 35.2 mg of the title compound (60%).

LC/MS=m/z 430 [M+H] Ret. Time: 1.62 min.

Example 187

5-{5-[(butylamino)methyl]-2-thienyl}-3-[1-(ethylsulfonyl)-4-piperidinyl]-1H-indole-7-carboxamide

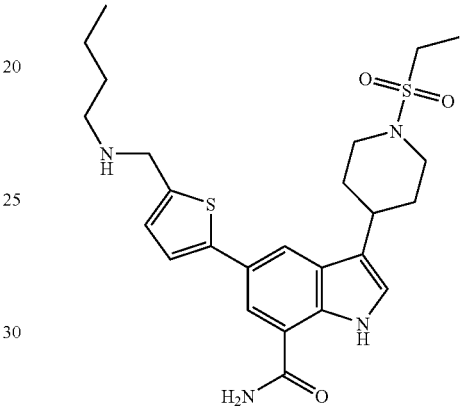

Following the general procedure of 3-[1-(ethylsulfonyl)-4-piperidinyl]-5-(5-{[(2-methylbutyl)amino]methyl}-2-thienyl)-1H-indole-7-carboxamide, (5-formyl-2-thienyl)boronic acid (50 mg, 0.32 mmol), butylamine (24 mg, 0.32 mmol), and NaCNBH₃ (40 mg, 0.64 mmol) were reacted to give 49 mg of crude {5-[(butylamino)methyl]-2-thienyl}boronic acid. The crude {5-[(butylamino)methyl]-2-thienyl}boronic acid was then reacted with 5-bromo-3-[1-(ethylsulfonyl)-4-piperidinyl]-1H-indole-7-carboxamide (65 mg, 0.157 mmol), K₂CO₃ (130 mg, 0.942 mmol), and tetrakis(triphenylphosphine)palladium(0) (4 mg, 0.003 mmol) to give 27.2 mg of the title compound (24%).

LC/MS=m/z 430 [M+H] Ret. Time: 1.56 min.

Example 188

3-[1-(ethylsulfonyl)-4-piperidinyl]-5-[5-({[2-(methyloxy)ethyl]amino}methyl)-2-thienyl]-1H-indole-7-carboxamide

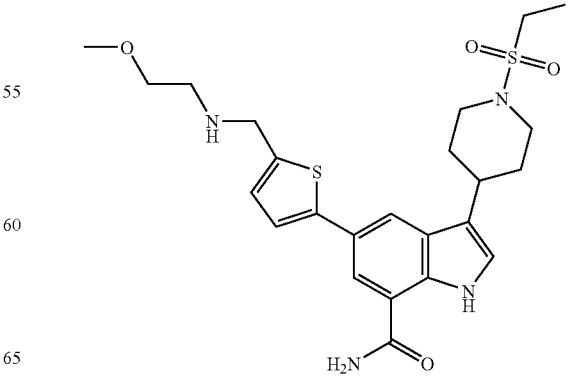

Following the general procedure of 3-[1-(ethylsulfonyl)-4-piperidinyl]-5-(5-{[(2-methylbutyl)amino]methyl}-2-thienyl)-1H-indole-7-carboxamide, (5-formyl-2-thienyl)boronic acid (50 mg, 0.32 mmol), [2-(methyloxy)ethyl]amine (24 mg, 0.32 mmol), and NaCNBH₃ (40 mg, 0.64 mmol) were reacted to give 42 mg of crude [5-({[2-(methyloxy)ethyl]amino}methyl)-2-thienyl]boronic acid. The crude [5-({[2-(methyloxy)ethyl]amino}methyl)-2-thienyl]boronic acid was then reacted with 5-bromo-3-[1-(ethylsulfonyl)-4-piperidinyl]-1H-indole-7-carboxamide (65 mg, 0.157 mmol), K₂CO₃ (130 mg, 0.942 mmol), and tetrakis(triphenylphosphine)palladium(0) (4 mg, 0.003 mmol) to give impure title compound. The impure title compound was repurified using the HPLC and ammonium hydroxide SPE workup shown in preparation of 3-[1-(ethylsulfonyl)-4-piperidinyl]-5-(5-{[(2-methylbutyl)amino]methyl}-2-thienyl)-1H-indole-7-carboxamide to give 15 mg of the title compound (15%).

LC/MS=m/z 430.2 [M+H] Ret. Time: 1.33 min.

Example 189

5-{5-[(cyclopentylamino)methyl]-2-thienyl}-3-[1-(ethylsulfonyl)-4-piperidinyl]-1H-indole-7-carboxamide

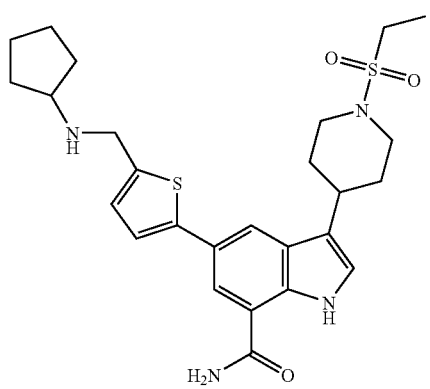

Following the general procedure of 3-[1-(ethylsulfonyl)-4-piperidinyl]-5-(5-{[(2-methylbutyl)amino]methyl}-2-thienyl)-1H-indole-7-carboxamide, (5-formyl-2-thienyl)boronic acid (50 mg, 0.32 mmol), cyclopentylamine (28 mg, 0.32 mmol), and NaCNBH₃ (40 mg, 0.64 mmol) were reacted to give 48 mg of crude {5-[(cyclopentylamino)methyl]-2-thienyl}boronic acid. The crude {5-[(cyclopentylamino)methyl]-2-thienyl}boronic acid was then reacted with 5-bromo-3-[1-(ethylsulfonyl)-4-piperidinyl]-1H-indole-7-carboxamide (65 mg, 0.157 mmol), K₂CO₃ (130 mg, 0.942 mmol), and tetrakis(triphenylphosphine)palladium(0) (4 mg, 0.003 mmol) to give 93.5 mg of the title compound (85%).

LC/MS=m/z 430.4 [M+H] Ret. Time: 1.64 min.

Example 190

3-[1-(ethylsulfonyl)-4-piperidinyl]-5-(5-{[(3-methylbutyl)amino]methyl}-2-thienyl)-1H-indole-7-carboxamide

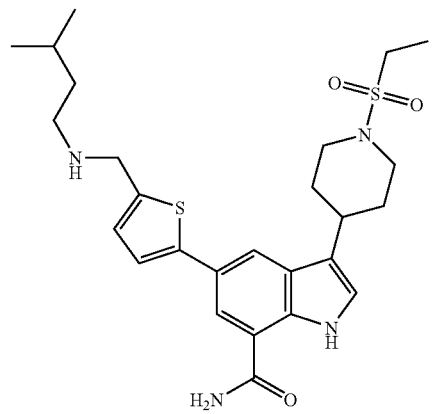

Following the general procedure of 3-[1-(ethylsulfonyl)-4-piperidinyl]-5-(5-{[(2-methylbutyl)amino]methyl}-2-thienyl)-1H-indole-7-carboxamide, (5-formyl-2-thienyl)boronic acid (50 mg, 0.32 mmol), (3-methylbutyl)amine (28 mg, 0.32 mmol), and NaCNBH₃ (40 mg, 0.64 mmol) were reacted to give 46 mg of crude (5-{[(3-methylbutyl)amino]methyl}-2-thienyl)boronic acid. The crude (5-{[(3-methylbutyl)amino]methyl}-2-thienyl)boronic acid was then reacted with 5-bromo-3-[1-(ethylsulfonyl)-4-piperidinyl]-1H-indole-7-carboxamide (65 mg, 0.157 mmol), K₂CO₃ (130 mg, 0.942 mmol), and tetrakis(triphenylphosphine)palladium(0) (4 mg, 0.003 mmol) to give 38.3 mg of the title compound (37%).

LC/MS=m/z 430.4 [M+H] Ret. Time: 1.75 min.

Example 191

3-[1-(ethylsulfonyl)-4-piperidinyl]-5-(5-{[(1-methylethyl)amino]methyl}-3-pyridinyl)-1H-indole-7-carboxamide

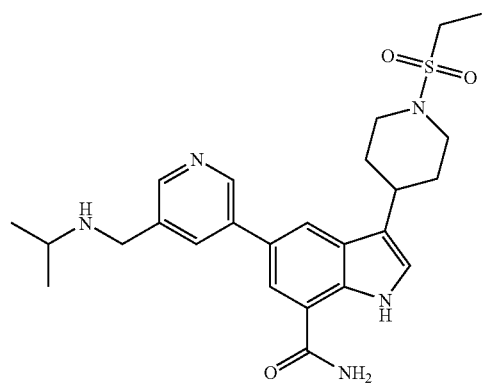

The (cyclopropylmethyl){[5-(4,4,5,5-tetramethyl-1,3,2-dioxaborolan-2-yl)-3-pyridinyl]methyl}amine used to prepare 3-[1-(ethylsulfonyl)-4-piperidinyl]-5-(5-{[(1-methylethyl)amino]methyl}-3-pyridinyl)-1H-indole-7-carboxamide was prepared as follows: isopropylamine (0.011 mL, 0.129 mmol) was added to a solution of 5-(4,4,5,5-tetramethyl-1,3,2-dioxaborolan-2-yl)-3-pyridinecarbaldehyde (30 mg, 0.129 mmol) in MeOH (1 mL) in a 2-dram vial. NaCNBH$_3$ (16 mg, 0.258 mmol) was then added, the vial was capped and the reaction was stirred at room temperature for 24 h. The reaction mixture was filtered through a 2 g SCX cartridge (pre-equilibrated with 3 mL MeOH), eluting in sequence with MeOH (6 mL) and a 2 M solution of NH$_3$/MeOH (9 mL). The NH$_3$/MeOH fraction was concentrated under a stream of nitrogen to give 22 mg of crude (1-methylethyl){[5-(4,4,5,5-tetramethyl-1,3,2-dioxaborolan-2-yl)-3-pyridinyl]methyl}amine.

To a CEM microwave tube containing (1-methylethyl){[5-(4,4,5,5-tetramethyl-1,3,2-dioxaborolan-2-yl)-3-pyridinyl]methyl}amine (22 mg, 0.080 mmol) was added 5-bromo-3-[1-(ethylsulfonyl)-4-piperidinyl]-1H-indole-7-carboxamide (50 mg, 0.121 mmol), K$_2$CO$_3$ (100 mg, 0.724 mmol), dioxane (1.5 mL), H$_2$O (0.5 mL), and chloro-2-(dimethylaminomethyl)-ferrocen-1-yl-(dinorbornylphosphine)palladium(II) (7.3 mg, 0.012 mmol). The reaction was heated in a CEM microwave for 30 min at 150° C. The reaction mixture was filtered through a 2 g SCX cartridge (pre-equilibrated with 3 mL MeOH), eluting in sequence with H$_2$O (3 mL), MeOH (6 mL) and a 2 M solution of NH$_3$/MeOH (9 mL). The NH$_3$/MeOH fraction was dried under a stream of nitrogen at 50° C. and purified on an Agilent MDAP (Zorbax Eclipse XDB-C18 column: 21.2×100 mm) eluting at 20 mL per min for 1 min with 10% CH$_3$CN/H$_2$O (0.1% TFA) then a linear gradient of 10% CH$_3$CN/H$_2$O (0.1% TFA) to 95% CH$_3$CN/H$_2$O (0.1% TFA) over 8 min and holding at the final concentration for 30 sec. The fractions containing product were filtered through a 2 g Pharmasil CHQAX column (polymer bound ammonium hydroxide; United Chemical Technologies) to remove TFA and concentrated under a stream of nitrogen at 50° C. to give 27.2 mg of the title compound (70%).

LC/MS=m/z 484 [M+H] Ret. Time: 1.25 min.

Example 192

5-(5-{[(2-ethylbutyl)amino]methyl}-2-thienyl)-3-[1-(ethylsulfonyl)-4-piperidinyl]-1H-indole-7-carboxamide

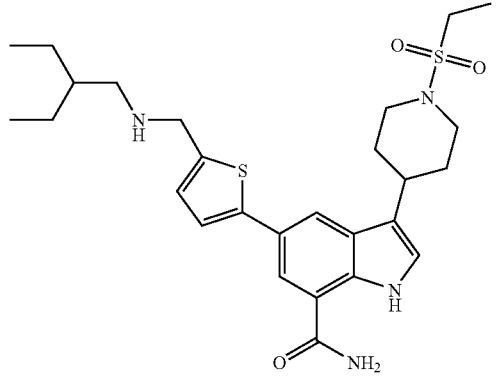

The {5-[(ethylamino)methyl]-2-thienyl}boronic acid used to prepare 5-(5-{[(2-ethylbutyl)amino]methyl}-2-thienyl)-3-[1-(ethylsulfonyl)-4-piperidinyl]-1H-indole-7-carboxamide was prepared as follows: A solution of (5-formyl-2-thienyl)boronic acid (50 mg, 0.32 mmol) in MeOH (0.5 mL) and a solution of NaCNBH$_3$ (40 mg, 0.64 mmol) in MeOH (0.5 mL) were added to (2-ethylbutyl)amine (32 mg, 0.32 mmol) in a 2-dram vial. The vial was capped and the reaction was stirred at room temperature for 20 h. The reaction mixture was filtered through a 2 g SCX cartridge (pre-equilibrated with 3 mL MeOH), eluting in sequence with MeOH (6 mL) and a 2 M solution of NH$_3$/MeOH (9 mL). The NH$_3$/MeOH fraction was concentrated under a stream of nitrogen to give 48 mg of crude (5-{[(2-ethylbutyl)amino]methyl}-2-thienyl)boronic acid.

To a CEM microwave tube containing the crude (5-{[(2-ethylbutyl)amino]methyl}-2-thienyl)boronic acid (48 mg, 0.199 mmol) was added a solution of 5-bromo-3-[1-(ethylsulfonyl)-4-piperidinyl]-1H-indole-7-carboxamide (65 mg, 0.157 mmol) in dioxane (1.75 mL), a solution of K$_2$CO$_3$ (130 mg, 0.942 mmol) in H$_2$O (0.25 mL), and tetrakis(triphenylphosphine)palladium(0) (9 mg, 0.0079 mmol). The reaction was heated in a CEM microwave for 30 min at 150° C. The reaction mixture was filtered through a 2 g SCX cartridge (pre-equilibrated with 3 mL MeOH), eluting in sequence with MeOH (3 mL) and a 2 M solution of NH$_3$/MeOH (9 mL). The NH$_3$/MeOH fraction was dried under a stream of nitrogen at 50° C., and the crude product was taken up in dimethyl sulfoxide (1.1 mL) and purified on an Agilent MDAP (Zorbax Eclipse XDB-C18 column: 21.2×100 mm) eluting at 20 mL per min for 1 min with 10% CH$_3$CN/H$_2$O (0.1% TFA) then a linear gradient of 10% CH$_3$CN/H$_2$O (0.1% TFA) to 95% CH$_3$CN/H$_2$O (0.1% TFA) over 8 min and holding at the final concentration for 30 sec. The fractions containing product were filtered through a 2 g Pharmasil CHQAX column (polymer bound ammonium hydroxide; United Chemical Technologies) to remove TFA and concentrated under a stream of nitrogen at 50° C. to give impure title compound. The impure title compound was repurified on an Agilent MDAP and free based with the ammonium hydroxide column as shown above to give 8.5 mg of the title compound (10%).

LC/MS=m/z 430 [M+H] Ret. Time: 1.72 min.

Example 193

5-[5-({[3-(ethyloxy)propyl]amino}methyl)-2-thienyl]-3-[1-(ethylsulfonyl)-4-piperidinyl]-1H-indole-7-carboxamide

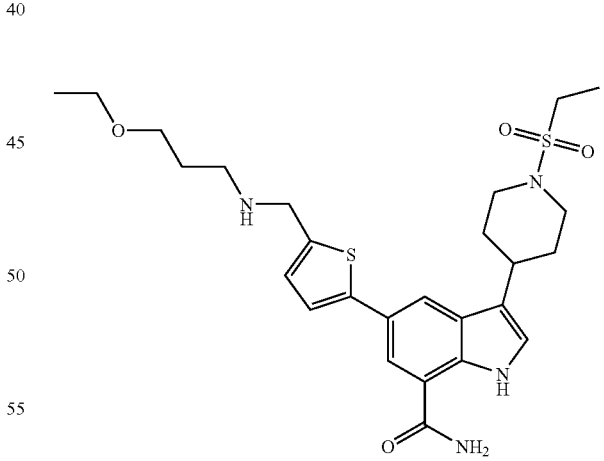

Following the general procedure of 5-(5-{[(2-ethylbutyl)amino]methyl}-2-thienyl)-3-[1-(ethylsulfonyl)-4-piperidinyl]-1H-indole-7-carboxamide, (5-formyl-2-thienyl)boronic acid (50 mg, 0.32 mmol), [3-(ethyloxy)propyl]amine (34 mg, 0.32 mmol), and NaCNBH$_3$ (40 mg, 0.64 mmol) were reacted to give 30 mg of crude [5-({[3-(ethyloxy)propyl]amino}methyl)-2-thienyl]boronic acid. The crude [5-({[3-(ethyloxy)propyl]amino}methyl)-2-thienyl]boronic acid was then reacted with 5-bromo-3-[1-(ethylsulfonyl)-4-piperidinyl]-1H-indole-7-carboxamide (65 mg, 0.157 mmol), K₂CO₃ (130 mg, 0.942 mmol), and tetrakis(triphenylphosphine)palladium(0) (9 mg, 0.0079 mmol) to give 8.1 mg of the title compound (10%).
LC/MS=m/z 430 [M+H] Ret. Time: 1.62 min.

Example 194

3-[1-(ethylsulfonyl)-4-piperidinyl]-5-[5-({[3-(methyloxy)propyl]amino}methyl)-2-thienyl]-1H-indole-7-carboxamide

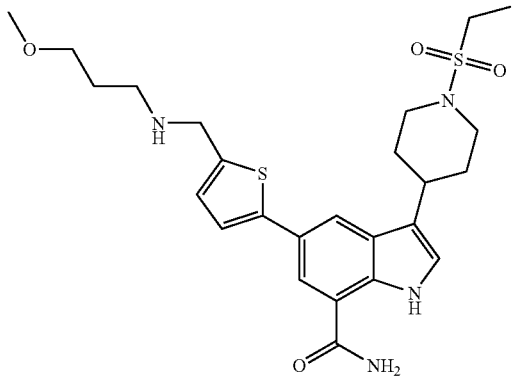

Following the general procedure of 5-(5-{[(2-ethylbutyl)amino]methyl}-2-thienyl)-3-[1-(ethylsulfonyl)-4-piperidinyl]-1H-indole-7-carboxamide, (5-formyl-2-thienyl)boronic acid (50 mg, 0.32 mmol), [3-(methyloxy)propyl]amine (29 mg, 0.32 mmol), and NaCNBH₃ (40 mg, 0.64 mmol) were reacted to give 30 mg of crude [5-({[3-(methyloxy)propyl]amino}methyl)-2-thienyl]boronic acid. The crude [5-({[3-(methyloxy)propyl]amino}methyl)-2-thienyl]boronic acid was then reacted with 5-bromo-3-[1-(ethylsulfonyl)-4-piperidinyl]-1H-indole-7-carboxamide (65 mg, 0.157 mmol), K₂CO₃ (130 mg, 0.942 mmol), and tetrakis(triphenylphosphine)palladium(0) (9 mg, 0.0079 mmol). The crude product was purified once on an Agilent MDAP using the procedure shown in preparation of 5-(5-{[(2-ethylbutyl)amino]methyl}-2-thienyl)-3-[1-(ethylsulfonyl)-4-piperidinyl]-1H-indole-7-carboxamide to give 7.6 mg of the title compound (9%).
LC/MS=m/z 430 [M+H] Ret. Time: 1.50 min.

Example 195

5-(5-{[(cyclohexylmethyl)amino]methyl}-2-thienyl)-3-[1-(ethylsulfonyl)-4-piperidinyl]-1H-indole-7-carboxamide

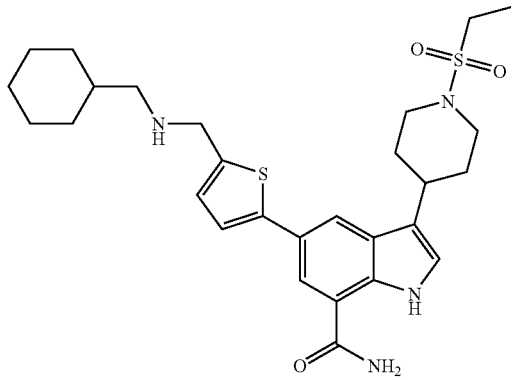

Following the general procedure of 5-(5-{[(2-ethylbutyl)amino]methyl}-2-thienyl)-3-[1-(ethylsulfonyl)-4-piperidinyl]-1H-indole-7-carboxamide, (5-formyl-2-thienyl)boronic acid (50 mg, 0.32 mmol), (cyclohexylmethyl)amine (37 mg, 0.32 mmol), and NaCNBH₃ (40 mg, 0.64 mmol) were reacted to give 30 mg of crude (5-{[(cyclohexylmethyl)amino]methyl}-2-thienyl)boronic acid. The crude (5-{[(cyclohexylmethyl)amino]methyl}-2-thienyl)boronic acid was then reacted with 5-bromo-3-[1-(ethylsulfonyl)-4-piperidinyl]-1H-indole-7-carboxamide (65 mg, 0.157 mmol), K₂CO₃ (130 mg, 0.942 mmol), and tetrakis(triphenylphosphine)palladium(0) (9 mg, 0.0079 mmol). The crude product was purified once on an Agilent MDAP using the procedure shown in preparation of 5-(5-{[(2-ethylbutyl)amino]methyl}-2-thienyl)-3-[1-(ethylsulfonyl)-4-piperidinyl]-1H-indole-7-carboxamide. The purified product was washed with a 20:4:1 mixture of hexanes/EtOAc/MeOH (2.5 mL), taken up in EtOAc (2 mL) and washed with saturated K₂CO₃ (1 mL). The organic layer was concentrated to give 4.7 mg of the title compound (6%).
LC/MS=m/z 430 [M+H] Ret. Time: 1.82 min.

Example 196

3-[1-(ethylsulfonyl)-4-piperidinyl]-5-{5-[({3-[(1-methylethyl)oxy]propyl}amino)methyl]-2-thienyl}-1H-indole-7-carboxamide

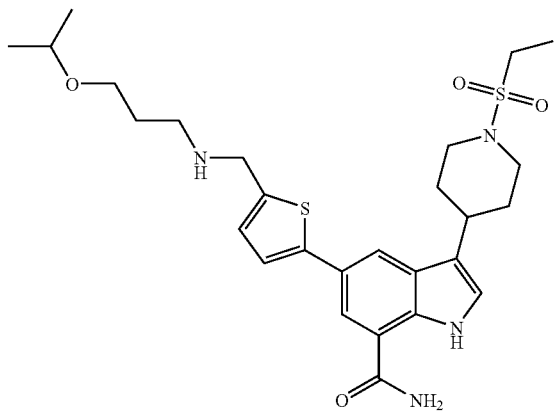

Following the general procedure of 5-(5-{[(2-ethylbutyl)amino]methyl}-2-thienyl)-3-[1-(ethylsulfonyl)-4-piperidinyl]-1H-indole-7-carboxamide, (5-formyl-2-thienyl)boronic acid (50 mg, 0.32 mmol), {3-[(1-methylethyl)oxy]propyl}amine (38 mg, 0.32 mmol), and NaCNBH₃ (40 mg, 0.64 mmol) were reacted to give 30 mg of crude {5-[({3-[(1-methylethyl)oxy]propyl}amino)methyl]-2-thienyl}boronic acid. The crude {5-[({3-[(1-methylethyl)oxy]propyl}amino)methyl]-2-thienyl}boronic acid was then reacted with 5-bromo-3-[1-(ethylsulfonyl)-4-piperidinyl]-1H-indole-7-carboxamide (65 mg, 0.157 mmol), K₂CO₃ (130 mg, 0.942 mmol), and tetrakis(triphenylphosphine)palladium(0) (9 mg, 0.0079 mmol). After purification on an Agilent MDAP twice as shown in preparation of 5-(5-{[(2-ethylbutyl)amino]methyl}-2-thienyl)-3-[1-(ethylsulfonyl)-4-piperidinyl]-1H-indole-7-carboxamide, the impure title compound was washed with a 20:4:1 mixture of hexanes/EtOAc/MeOH (2.5 mL) to give 7.6 mg of the title compound (9%).
LC/MS=m/z 430 [M+H] Ret. Time: 1.62 min.

Example 197

5-[5-({[2-(ethyloxy)ethyl]amino}methyl)-2-thienyl]-3-[1-(ethylsulfonyl)-4-piperidinyl]-1H-indole-7-carboxamide

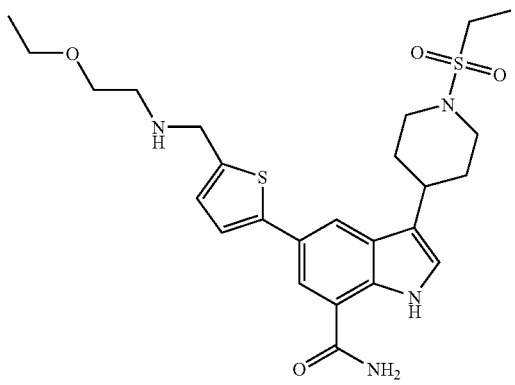

Following the general procedure of 5-(5-{[(2-ethylbutyl)amino]methyl}-2-thienyl)-3-[1-(ethylsulfonyl)-4-piperidinyl]-1H-indole-7-carboxamide, (5-formyl-2-thienyl)boronic acid (50 mg, 0.32 mmol), [2-(ethyloxy)ethyl]amine (30 mg, 0.32 mmol), and $NaCNBH_3$ (40 mg, 0.64 mmol) were reacted to give 30 mg of crude [5-({[2-(ethyloxy)ethyl]amino}methyl)-2-thienyl]boronic acid. The crude [5-({[2-(ethyloxy)ethyl]amino}methyl)-2-thienyl]boronic acid was then reacted with 5-bromo-3-[1-(ethylsulfonyl)-4-piperidinyl]-1H-indole-7-carboxamide (65 mg, 0.157 mmol), $K_2CO_3$ (130 mg, 0.942 mmol), and tetrakis(triphenylphosphine)palladium(0) (9 mg, 0.0079 mmol). The crude product was purified once on an Agilent MDAP using the procedure shown for preparation of 5-(5-{[(2-ethylbutyl)amino]methyl}-2-thienyl)-3-[1-(ethylsulfonyl)-4-piperidinyl]-1H-indole-7-carboxamide to give 6 mg of the title compound (7%).

LC/MS=m/z 430 [M+H] Ret. Time: 1.66 min.

Example 198

3-[1-(ethylsulfonyl)-4-piperidinyl]-5-[5-({[3-(propyloxy)propyl]amino}methyl)-2-thienyl]-1H-indole-7-carboxamide

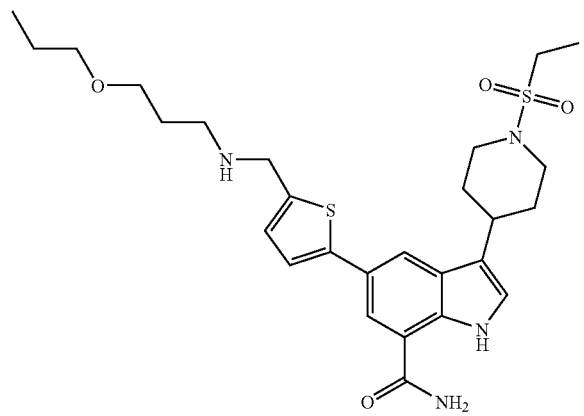

Following the general procedure of 5-(5-{[(2-ethylbutyl)amino]methyl}-2-thienyl)-3-[1-(ethylsulfonyl)-4-piperidinyl]-1H-indole-7-carboxamide, (5-formyl-2-thienyl)boronic acid (50 mg, 0.32 mmol), [3-(propyloxy)propyl]amine (38 mg, 0.32 mmol), and $NaCNBH_3$ (40 mg, 0.64 mmol) were reacted to give 30 mg of crude [5-({[3-(propyloxy)propyl]amino}methyl)-2-thienyl]boronic acid. The crude [5-({[3-(propyloxy)propyl]amino}methyl)-2-thienyl]boronic acid was then reacted with 5-bromo-3-[1-(ethylsulfonyl)-4-piperidinyl]-1H-indole-7-carboxamide (65 mg, 0.157 mmol), $K_2CO_3$ (130 mg, 0.942 mmol), and tetrakis(triphenylphosphine)palladium(0) (9 mg, 0.0079 mmol). The crude product was purified twice on an Agilent MDAP using the procedure shown in preparation of 5-(5-{[(2-ethylbutyl)amino]methyl}-2-thienyl)-3-[1-(ethylsulfonyl)-4-piperidinyl]-1H-indole-7-carboxamide. The purified product was washed with a 20:4:1 mixture of hexanes/EtOAc/MeOH (2.5 mL), taken up in EtOAc (2 mL) and washed with saturated $K_2CO_3$ (1 mL). The organic layer was concentrated to give to give 1.4 mg of the title compound (2%).

LC/MS=m/z 430 [M+H] Ret. Time: 1.66 min.

Example 199

5-(5-{[(3,3-dimethylbutyl)amino]methyl}-2-thienyl)-3-[1-(ethylsulfonyl)-4-piperidinyl]-1H-indole-7-carboxamide

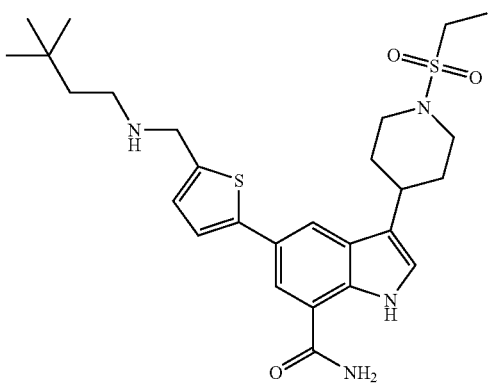

Following the general procedure of 5-(5-{[(2-ethylbutyl)amino]methyl}-2-thienyl)-3-[1-(ethylsulfonyl)-4-piperidinyl]-1H-indole-7-carboxamide, (5-formyl-2-thienyl)boronic acid (50 mg, 0.32 mmol), (3,3-dimethylbutyl)amine (32 mg, 0.32 mmol), and $NaCNBH_3$ (40 mg, 0.64 mmol) were reacted to give 30 mg of crude (5-{[(3,3-dimethylbutyl)amino]methyl}-2-thienyl)boronic acid. The crude (5-{[(3,3-dimethylbutyl)amino]methyl}-2-thienyl)boronic acid was then reacted with 5-bromo-3-[1-(ethylsulfonyl)-4-piperidinyl]-1H-indole-7-carboxamide (65 mg, 0.157 mmol), $K_2CO_3$ (130 mg, 0.942 mmol), and tetrakis(triphenylphosphine)palladium(0) (9 mg, 0.0079 mmol) to give 4.5 mg of the title compound (5%).

LC/MS=m/z 430 [M+H] Ret. Time: 1.79 min.

Example 200

3-[1-(ethylsulfonyl)-4-piperidinyl]-5-[5-({[(1S)-1,2,2-trimethylpropyl]amino}methyl)-2-thienyl]-1H-indole-7-carboxamide

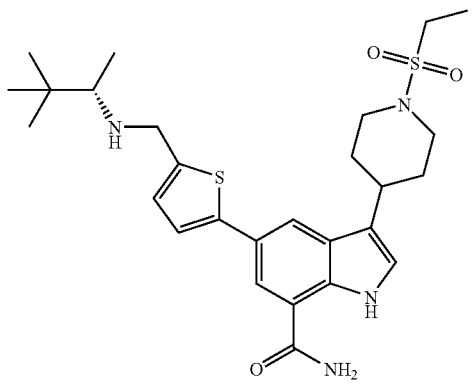

Following the general procedure of 5-(5-{[(2-ethylbutyl)amino]methyl}-2-thienyl)-3-[1-(ethylsulfonyl)-4-piperidinyl]-1H-indole-7-carboxamide, (5-formyl-2-thienyl)boronic acid (50 mg, 0.32 mmol), [(1S)-1,2,2-trimethylpropyl]amine (32 mg, 0.32 mmol), and NaCNBH$_3$ (40 mg, 0.64 mmol) were reacted to give 30 mg of crude [5-({[(1S)-1,2,2-trimethylpropyl]amino}methyl)-2-thienyl]boronic acid. The crude [5-({[(1S)-1,2,2-trimethylpropyl]amino}methyl)-2-thienyl]boronic acid was then reacted with 5-bromo-3-[1-(ethylsulfonyl)-4-piperidinyl]-1H-indole-7-carboxamide (65 mg, 0.157 mmol), K$_2$CO$_3$ (130 mg, 0.942 mmol), and tetrakis(triphenylphosphine)palladium(0) (9 mg, 0.0079 mmol) to give 10.3 mg of the title compound (12%).

LC/MS=m/z 430 [M+H] Ret. Time: 1.62 min.

Example 201

3-[1-(ethylsulfonyl)-4-piperidinyl]-5-{5-[(hexylamino)methyl]-2-thienyl}-1H-indole-7-carboxamide

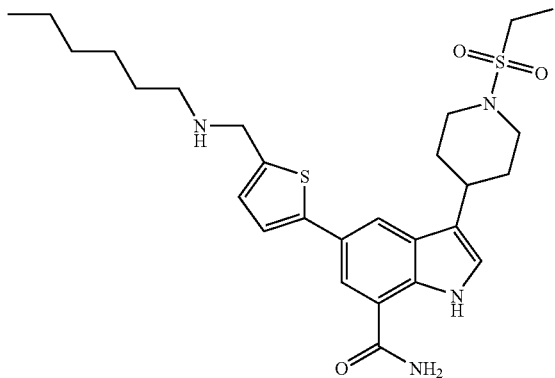

Following the general procedure of 5-(5-{[(2-ethylbutyl)amino]methyl}-2-thienyl)-3-[1-(ethylsulfonyl)-4-piperidinyl]-1H-indole-7-carboxamide, (5-formyl-2-thienyl)boronic acid (50 mg, 0.32 mmol), hexylamine (33 mg, 0.32 mmol), and NaCNBH$_3$ (40 mg, 0.64 mmol) were reacted to give 30 mg of crude {5-[(hexylamino)methyl]-2-thienyl}boronic acid. The crude {5-[(hexylamino)methyl]-2-thienyl}boronic acid was then reacted with 5-bromo-3-[1-(ethylsulfonyl)-4-piperidinyl]-1H-indole-7-carboxamide (65 mg, 0.157 mmol), K$_2$CO$_3$ (130 mg, 0.942 mmol), and tetrakis(triphenylphosphine)palladium(0) (9 mg, 0.0079 mmol). The crude product was purified once on an Agilent MDAP using the procedure shown in preparation of 5-(5-{[(2-ethylbutyl)amino]methyl}-2-thienyl)-3-[1-(ethylsulfonyl)-4-piperidinyl]-1H-indole-7-carboxamide to give 13 mg of the title compound (16%).

LC/MS=m/z 430.6 [M+H] Ret. Time: 1.92 min.

Example 202

5-[2-(dimethylamino)-4-pyridinyl]-3-[1-(ethylsulfonyl)-4-piperidinyl]-1H-indole-7-carboxamide trifluoroacetate

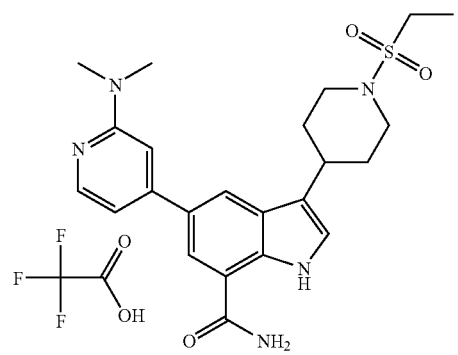

To 3-[1-(ethylsulfonyl)-4-piperidinyl]-5-(2-fluoro-4-pyridinyl)-1H-indole-7-carboxamide (40 mg, 0.093 mmol) was added dimethylamine (1 mL, 0.015 mmol) and DMF (0.3 mL). The resulting mixture was reacted in a microwave for 1 h at 180° C. All solvent was evaporated and the mixture was then purified by Gilson Preparatory HPLC to give 18.2 mg of the title compound (34.4%).

LC/MS=m/z 456.2 [M+H] Ret. Time: 1.54 min.

Example 203

5-{6-[ethyl(methyl)amino]-3-pyridinyl}-3-[1-(ethylsulfonyl)-4-piperidinyl]-1H-indole-7-carboxamide trifluoroacetate

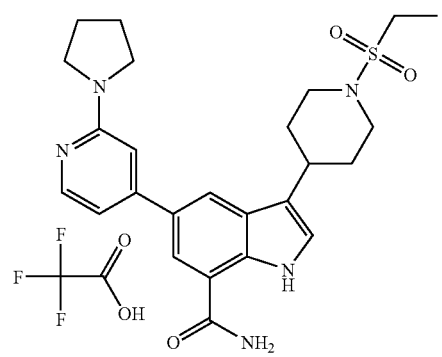

The title compound was prepared according to the general procedure of 5-[2-(dimethylamino)-4-pyridinyl]-3-[1-(ethylsulfonyl)-4-piperidinyl]-1H-indole-7-carboxamide trifluoroacetate, substituting pyrrolidine (1 mL) for dimethylamine to afford 48.9 mg of the title compound (27.1%).

LC/MS=m/z 482.2 [M+H] Ret. Time: 1.62 min.

Example 204

3-[1-(ethylsulfonyl)-4-piperidinyl]-5-[2-(4-morpholinyl)-4-pyridinyl]-1H-indole-7-carboxamide trifluoroacetate

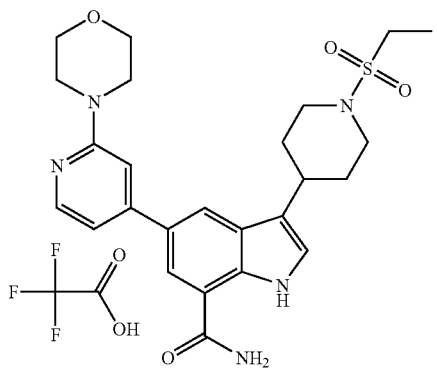

The title compound was prepared according to the general procedure of 5-[2-(dimethylamino)-4-pyridinyl]-3-[1-(ethylsulfonyl)-4-piperidinyl]-1H-indole-7-carboxamide trifluoroacetate, substituting morpholine (1 mL) for dimethylamine to afford 12 mg of the title compound (21.1%).

LC/MS=m/z 498.6 [M+H] Ret. Time: 1.47 min.

Example 205

3-[1-(ethylsulfonyl)-4-piperidinyl]-5-{2-[(2-methylpropyl)amino]-4-pyridinyl}-1H-indole-7-carboxamide trifluoroacetate

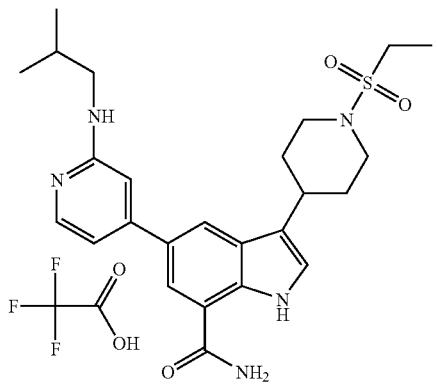

The title compound was prepared according to the general procedure of 5-[2-(dimethylamino)-4-pyridinyl]-3-[1-(ethylsulfonyl)-4-piperidinyl]-1H-indole-7-carboxamide trifluoroacetate, substituting 2-methyl-1-propanamine (1 mL) for dimethylamine to afford 11.1 mg of the title compound (20%).

LC/MS=m/z 484.2 [M+H] Ret. Time: 1.68 min.

Example 206

5-{2-[(2,2-dimethylpropyl)amino]-4-pyridinyl}-3-[1-(ethylsulfonyl)-4-piperidinyl]-1H-indole-7-carboxamide trifluoroacetate

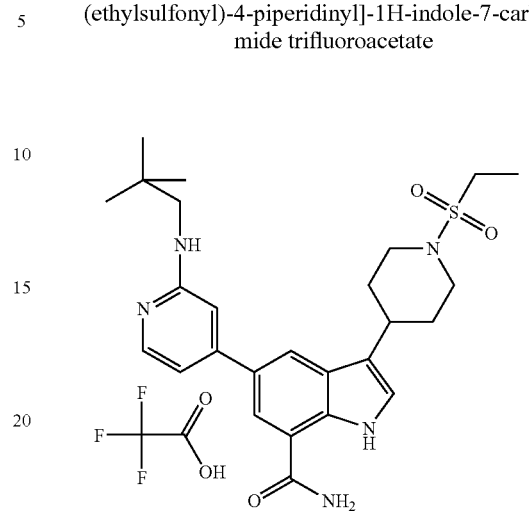

The title compound was prepared according to the general procedure of 5-[2-(dimethylamino)-4-pyridinyl]-3-[1-(ethylsulfonyl)-4-piperidinyl]-1H-indole-7-carboxamide trifluoroacetate, substituting 2,2-dimethyl-1-propanamine (1 mL) for dimethylamine to afford 9 mg of the title compound (15.8%).

LC/MS=m/z 498.6 [M+H] Ret. Time: 1.75 min.

Example 207

3-[1-(ethylsulfonyl)-4-piperidinyl]-5-[2-(propylamino)-4-pyridinyl]-1H-indole-7-carboxamide trifluoroacetate

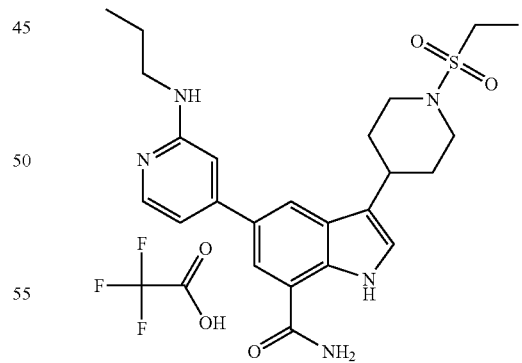

The title compound was prepared according to the general procedure of 5-[2-(dimethylamino)-4-pyridinyl]-3-[1-(ethylsulfonyl)-4-piperidinyl]-1H-indole-7-carboxamide trifluoroacetate, substituting propylamine (1 mL) for dimethylamine to afford 18.2 mg of the title compound (33.5%).

LC/MS=m/z 470.4 [M+H] Ret. Time: 1.57 min.

Example 208

3-[1-(ethylsulfonyl)-4-piperidinyl]-5-{4-[(methylamino)methyl]-2-thienyl}-1H-indole-7-carboxamide trifluoroacetate

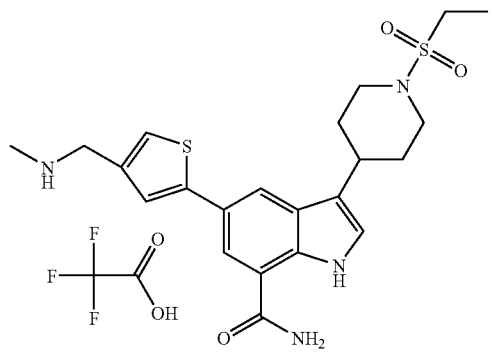

To a solution of 3-[1-(ethylsulfonyl)-4-piperidinyl]-5-(4-formyl-2-thienyl)-1H-indole-7-carboxamide (45 mg, 0.1 mmol) in methylene chloride (2 mL) and methanol (1 mL) was added 2 M methylamine (0.5 mL). The reaction mixture was stirred at room temperature for 5 h followed by an addition of sodium tetrahydridoborate (37.83 mg, 1 mmol). The resulting mixture was stirred at room temperature overnight. The solvent was concentrated and purified using Gilson Preparatory HPLC to give 16.8 mg of the title compound (29.2%).

LC/MS=m/z 461.6 [M+H] Ret. Time: 1.40 min.

Example 209

3-[1-(ethylsulfonyl)-4-piperidinyl]-5-[4-(1-pyrrolidinylmethyl)-2-thienyl]-1H-indole-7-carboxamide trifluoroacetate

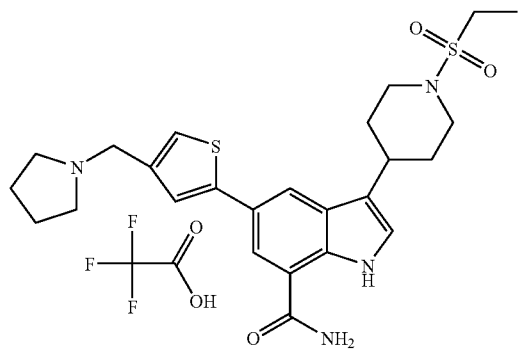

The title compound was prepared according to the general procedure of 3-[1-(ethylsulfonyl)-4-piperidinyl]-5-{4-[(methylamino)methyl]-2-thienyl}-1H-indole-7-carboxamide trifluoroacetate, substituting pyrrolidine (0.083 mL) for 2 M methylamine to afford 14.8 mg of the title compound (24.1%).

LC/MS=m/z 470.4 [M+H] Ret. Time: 1.57 min.

Example 210

3-[1-(ethylsulfonyl)-4-piperidinyl]-5-(4-{[(2-methylpropyl)amino]methyl}-2-thienyl)-1H-indole-7-carboxamide trifluoroacetate

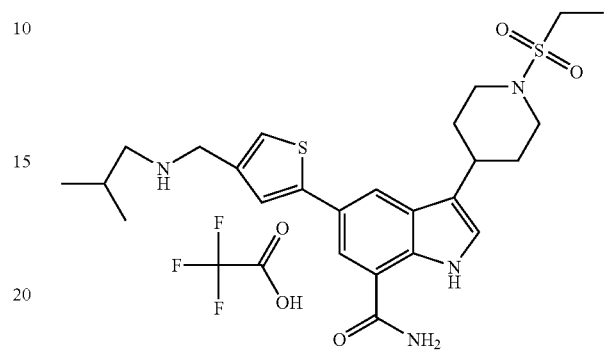

The title compound was prepared according to the general procedure of 3-[1-(ethylsulfonyl)-4-piperidinyl]-5-{4-[(methylamino)methyl]-2-thienyl}-1H-indole-7-carboxamide trifluoroacetate, substituting 2-methyl-1-propanamine (0.1 mL) for 2 M methylamine to afford 15.4 mg of the title compound (25%).

LC/MS=m/z 503.2 [M+H] Ret. Time: 1.42 min.

Example 211

5-{4-[(dimethylamino)methyl]-2-thienyl}-3-[1-(ethylsulfonyl)-4-piperidinyl]-1H-indole-7-carboxamide trifluoroacetate

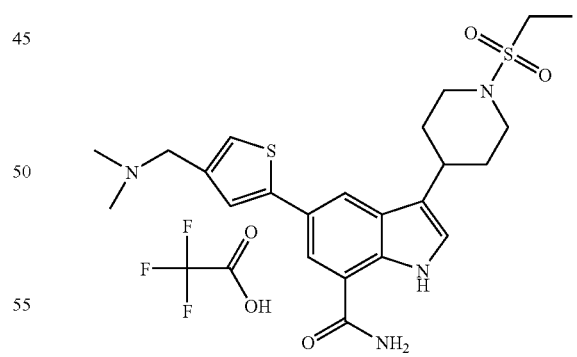

The title compound was prepared according to the general procedure of 3-[1-(ethylsulfonyl)-4-piperidinyl]-5-{4-[(methylamino)methyl]-2-thienyl}-1H-indole-7-carboxamide trifluoroacetate, substituting dimethylamine (0.5 mL) for 2 M methylamine to afford 9 mg of the title compound (15.3%).

LC/MS=m/z 475.2 [M+H] Ret. Time: 1.27 min.

Example 212

3-[1-(ethylsulfonyl)-4-piperidinyl]-5-{5-[(1S)-1-(1-pyrrolidinyl)ethyl]-3-thienyl}-1H-indole-7-carboxamide

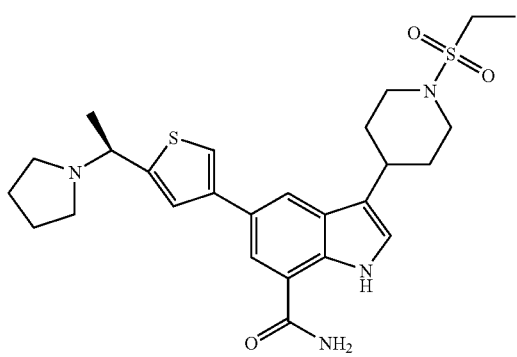

To 5-(5-acetyl-3-thienyl)-3-[1-(ethylsulfonyl)-4-piperidinyl]-1H-indole-7-carboxamide (10 mg, 0.02 mmol) was added sodium cyanoborohydride (7.5 mg, 0.12 mmol) and pyrrolidine (0.03 mL, 0.30 mmol). The resulting mixture was reacted in a microwave for 40 min at 150° C. All the solvent was evaporated and the crude product was partitioned between ethyl acetate (1.5 mL) and 1 M sodium hydroxide (0.2 mL). The reaction was purified by SFC to give the title compound as 100% chirally pure.

LC/MS=m/z 515.4 [M+H] Ret. Time: 1.54 min.

Example 213

3-[1-(ethylsulfonyl)-4-piperidinyl]-5-{5-[(1R)-1-(1-pyrrolidinyl)ethyl]-3-thienyl}-1H-indole-7-carboxamide

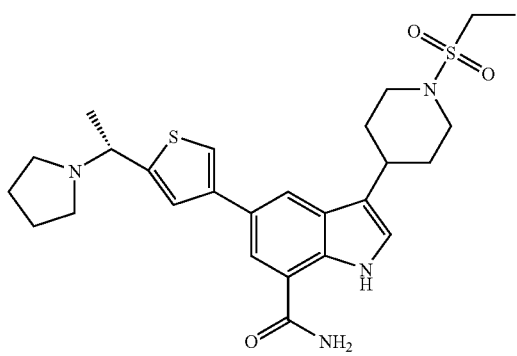

To 5-(5-acetyl-3-thienyl)-3-[1-(ethylsulfonyl)-4-piperidinyl]-1H-indole-7-carboxamide (10 mg, 0.02 mmol) was added sodium cyanoborohydride (7.5 mg, 0.12 mmol) and pyrrolidine (0.03 mL, 0.30 mmol). The resulting mixture was reacted in a microwave for 40 min at 150° C. All the solvent was evaporated and the crude product was partitioned between ethyl acetate (1.5 mL) and 1 M sodium hydroxide (0.2 mL). The reaction was purified by SFC to give the title compound as 100% chirally pure.

LC/MS=m/z 515.4 [M+H] Ret. Time: 1.54 min.

Example 214

3-[1-(ethylsulfonyl)-4-piperidinyl]-5-[4-({[3-(methyloxy)propyl]amino}methyl)-2-thienyl]-1H-indole-7-carboxamide trifluoroacetate

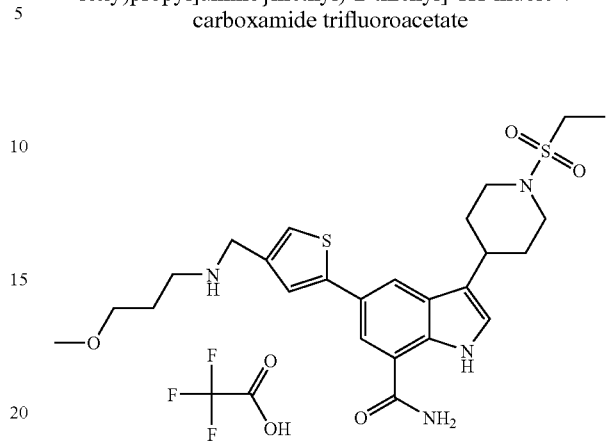

To a solution of 5-[(1Z)-1-(ethenylthio)-4-oxo-1-buten-1-yl]-3-[1-(ethylsulfonyl)-4-piperidinyl]-1H-indole-7-carboxamide (45 mg, 0.1 mmol) in methylene chloride (2 mL) and methanol (1 mL) was added 3 drops of acetic acid and 3-(methyloxy)-1-propanamine (89.14 mg, 1 mmol). The resulting mixture was stirred for 6 h followed by an addition of sodium borohydride (37.83 mg, 1 mmol). The reaction was stirred at room temperature overnight. The solvent was evaporated and the mixture was then purified by Gilson Preparatory HPLC to give 23.7 mg of the title compound (37.5%).

LC/MS=m/z 519.4 [M+H] Ret. Time: 1.69 min.

Example 215

3-[1-(ethylsulfonyl)-4-piperidinyl]-5-[4-({(2S)-2-[(methyloxy)methyl]-1-pyrrolidinyl}methyl)-2-thienyl]-1H-indole-7-carboxamide trifluoroacetate

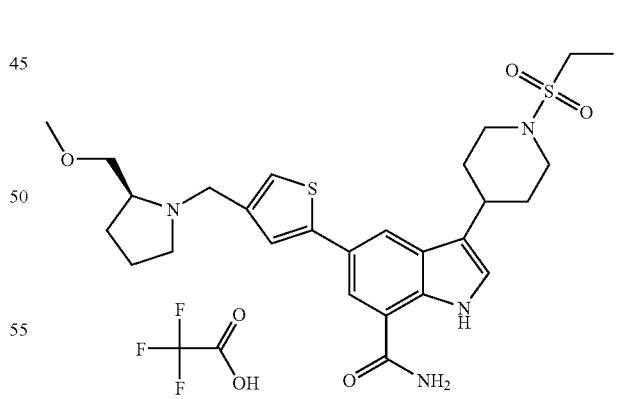

The title compound was prepared according to the general procedure of 3-[1-(ethylsulfonyl)-4-piperidinyl]-5-[4-({[3-(methyloxy)propyl]amino}methyl)-2-thienyl]-1H-indole-7-carboxamide trifluoroacetate, substituting (2S)-2-[(methyloxy)methyl]pyrrolidine (115.18 mg, 1 mmol) for 3-(methyloxy)-1-propanamine to afford 3 mg of the title compound (4.6%).

LC/MS=m/z 545.2 [M+H] Ret. Time: 1.78 min.

Example 216

5-(4-{[(2R,5R)-2,5-dimethyl-1-pyrrolidinyl]methyl}-2-thienyl)-3-[1-(ethylsulfonyl)-4-piperidinyl]-1H-indole-7-carboxamide trifluoroacetate

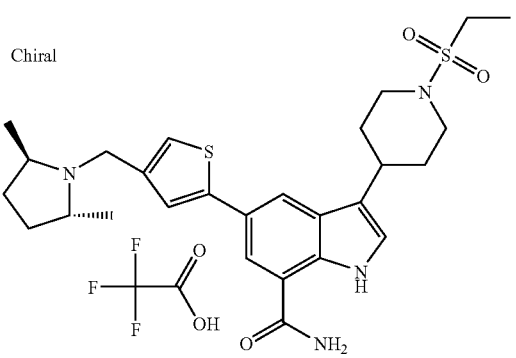

The title compound was prepared according to the general procedure of 3-[1-(ethylsulfonyl)-4-piperidinyl]-5-[4-({[3-(methyloxy)propyl]amino}methyl)-2-thienyl]-1H-indole-7-carboxamide trifluoroacetate
(64.3 mg, 1 mmol) for 3-(methyloxy)-1-propanamine to afford 6.4 mg of the title compound (10%).
LC/MS=m/z 529.4 [M+H] Ret. Time: 1.69 min.

Example 217

3-[1-(ethylsulfonyl)-4-piperidinyl]-5-(5-{[(2S)-2-methyl-1-pyrrolidinyl]methyl}-3-thienyl)-1H-indole-7-carboxamide

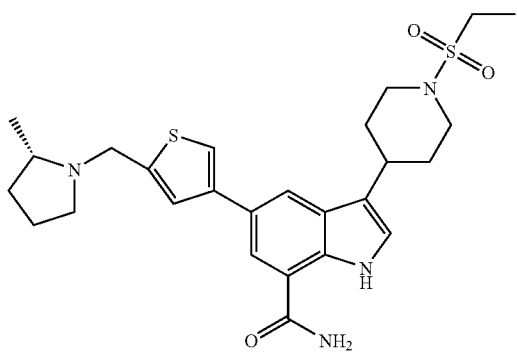

To a solution of 3-[1-(ethylsulfonyl)-4-piperidinyl]-5-(5-formyl-3-thienyl)-1H-indole-7-carboxamide (600 mg, 1.348 mmol) in dimethyl sulfoxide (10 mL) was added of 20 drops of acetic acid and (2S)-1,2-dimethylpyrrolidine (1.37 mL, 13.483 mmol). The resulting mixture was stirred at room temperature for 6 h followed by an addition of sodium triacetoxyborohydride (2.858 g, 13.483 mmol). The reaction was stirred at room temperature overnight then purified by SFC. This compound was separated by RTP CASS Group. The fraction of enantiomer #1 is 99.7% chirally pure to give 119.9 mg of the title compound (17.3%).
LC/MS=m/z 515.4 [M+H] Ret. Time: 1.56 min.

Example 218

3-[1-(ethylsulfonyl)-4-piperidinyl]-5-(5-{[(2R)-2-methyl-1-pyrrolidinyl]methyl}-1'-3-thienyl)-1H-indole-7-carboxamide

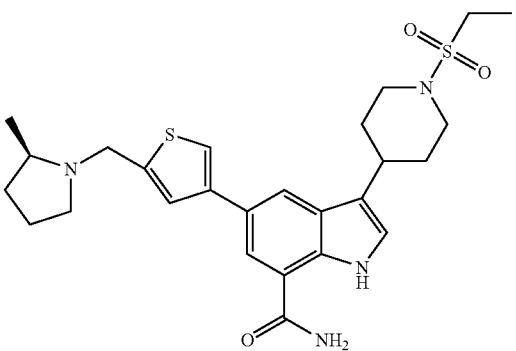

To a solution of 3-[1-(ethylsulfonyl)-4-piperidinyl]-5-(5-formyl-3-thienyl)-1H-indole-7-carboxamide (600 mg, 1.35 mmol) in dimethyl sulfoxide (10 mL) was added of 20 drops of acetic acid and 2-methylpyrrolidine (1.37 mL, 13.5 mmol). The resulting mixture was stirred at room temperature for 6 h followed by an addition of sodium triacetoxyborohydride (2.86 g, 13.5 mmol). The reaction was stirred at room temperature overnight then purified by Gilson Preparatory HPLC. This compound was then separated to give the title compound as 98.6% chirally pure.
LC/MS=m/z 515.4 [M+H] Ret. Time: 1.56 min.

Example 219

3-[1-(ethylsulfonyl)-4-piperidinyl]-5-{5-[1-(1-pyrrolidinyl)propyl]-3-thienyl}-1H-indole-7-carboxamide trifluoroacetate

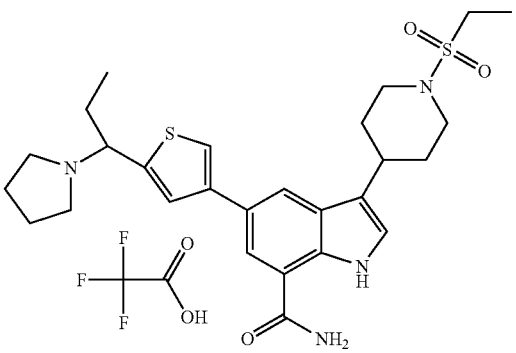

To a solution of 3-[1-(ethylsulfonyl)-4-piperidinyl]-5-(4,4,5,5-tetramethyl-1,3,2-dioxaborolan-2-yl)-1H-indole-7-carboxamide (250 mg, 0.541 mmol) in dioxane (4.5 mL) and H$_2$O (1.5 mL) was added 1-(4-bromo-2-thienyl)-1-propanone (356 mg, 1.62 mmol), potassium carbonate (447 mg, 3.24 mmol), and tetrakis(triphenylphosphine)palladium(0) (64 mg, 0.055 mmol). The reaction was run in the microwave at 150° C. for 20 min. An aqueous work-up was performed using EtOAc and H$_2$O followed by addition of MeOH (20 mL) to the crude product.

The desired product precipitated and was filtered to give 110 mg of 3-[1-(ethylsulfonyl)-4-piperidinyl]-5-(5-propanoyl-3-thienyl)-1H-indole-7-carboxamide (43%).

To 3-[1-(ethylsulfonyl)-4-piperidinyl]-5-(5-propanoyl-3-thienyl)-1H-indole-7-carboxamide (60 mg, 0.13 mmol) was added sodium cyanoborohydride (49.2 mg, 0.78 mmol), pyrrolidine (0.2 mL, 1.95 mmol), ethanol (3 mL) and acetic acid (0.4 mL). The resulting mixture was reacted in a microwave for 30 min at 150° C. All solvent was evaporated and the mixture was then purified by Gilson Preparatory HPLC to give 12 mg of the title compound (14.4%).

LC/MS=m/z 529.4 [M+H] Ret. Time: 1.65 min.

Example 220

5-{5-[(dimethylamino)methyl]-3-thienyl}-3-{1-[(1-methylethyl)sulfonyl]-4-piperidinyl}-1H-indole-7-carboxamide trifluoroacetate

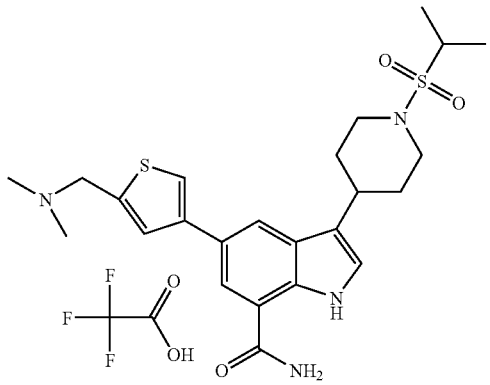

To a solution of 3-[1-(ethylsulfonyl)-4-piperidinyl]-5-(5-formyl-3-thienyl)-1H-indole-7-carboxamide (50 mg, 0.11 mmol) in dimethyl sulfoxide (2 mL) was added 3 drops of acetic acid and trimethylamine (0.55 mL, 1.1 mmol). The resulting mixture was stirred at room temperature for 6 h followed by an addition of sodium triacetoxyborohydride (233 mg, 1 mmol). This was then stirred at room temperature overnight then purified by Gilson Preparatory HPLC to give 29.4 mg of the title compound (44.3%).

LC/MS=m/z 489.4 [M+H] Ret. Time: 1.32 min.

Example 221

5-[5-(aminomethyl)-3-thienyl]-3-[1-(ethylsulfonyl)-4-piperidinyl]-1H-indole-7-carboxamide trifluoroacetate

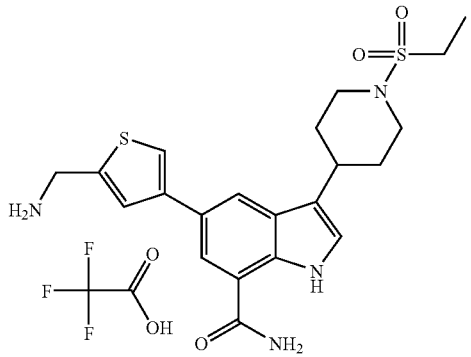

To a solution of 3-[1-(ethylsulfonyl)-4-piperidinyl]-5-(5-formyl-3-thienyl)-1H-indole-7-carboxamide (50 mg, 0.11 mmol) in methylene chloride (2 mL) and methanol (1 mL) was added ammonium acetate (84.7 mg, 1.1 mmol) and sodium cyanoborohydride (4.84 mg, 0.077 mmol). The resulting mixture was stirred at room temperature overnight. All solvent was evaporated and the mixture was then purified by Gilson Preparatory HPLC to give 1.8 mg of the title compound (2.9%).

LC/MS=m/z 447.2 [M+H] Ret. Time: 1.53 min.

Example 222

3-[1-(ethylsulfonyl)-4-piperidinyl]-5-(5-{2-[(2-methylpropyl)amino]ethyl}-3-thienyl)-1H-indole-7-carboxamide trifluoroacetate

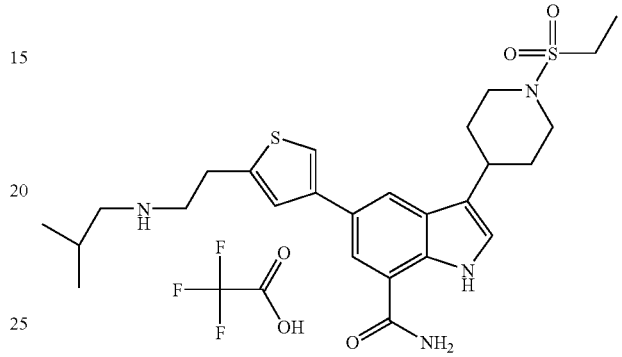

To a solution of [2-(4-bromo-2-thienyl)ethyl]amine (100 mg, 0.48 mmol) in DCM (2.0 mL) and MeOH (1.0 mL) was added acetic acid (3 drops) and 2-methylpropanal (105 mg, 1.44 mmol). The reaction was stirred overnight at room temperature before addition of Sodium borohydride (53.3 mg, 1.44 mmol). Reaction run for 1 h and then treated with EtOAc and brine. Organic layers were then dried and concentrated to give 80 mg of [2-(4-bromo-2-thienyl)ethyl](1-methylethyl)amine (64%).

To a solution of 3-[1-(ethylsulfonyl)-4-piperidinyl]-5-(4,4,5,5-tetramethyl-1,3,2-dioxaborolan-2-yl)-1H-indole-7-carboxamide (139 mg, 0.3 mmol) in dioxane (3 mL) and water (1 mL) was added [2-(4-bromo-2-thienyl)ethyl](1-methylethyl)amine (50 mg, 0.2 mmol), potassium carbonate (82.8 mg, 0.6 mmol) and tetrakis(triphenylphosphine)palladium(0) (22 mg, 0.019 mmol). The resulting mixture was reacted in a microwave for 20 min at 150° C. All solvent was evaporated and the mixture was then purified by Gilson Preparatory HPLC to give 18 mg of the title compound (9.5%).

LC/MS=m/z 517.2 [M+H] Ret. Time: 1.68 min.

Example 223

5-{5-[2-(dimethylamino)ethyl]-3-thienyl}-3-[1-(ethylsulfonyl)-4-piperidinyl]-1H-indole-7-carboxamide trifluoroacetate

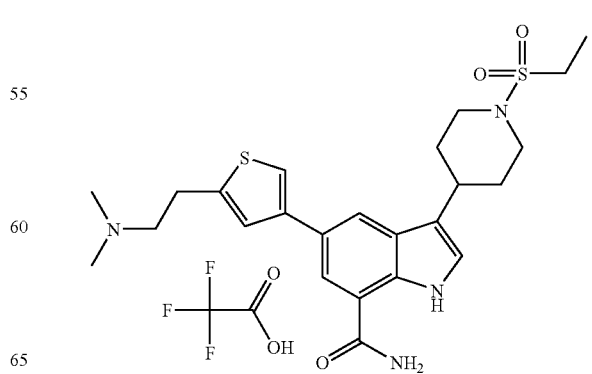

To a solution of [2-(4-bromo-2-thienyl)ethyl]amine (100 mg, 0.48 mmol) in DCM (2.0 mL) and MeOH (1.0 mL) was added acetic acid (3 drops) and formaldehyde, 37% in H₂O (105 mg, 1.44 mmol). The reaction was stirred overnight at room temperature before addition of Sodium borohydride (53.3 mg, 1.44 mmol). Reaction run for 1 h and then treated with EtOAc and brine. Organic layers were then dried and concentrated to give 50 mg of 2-(4-bromo-2-thienyl)-N,N-dimethylethanamine (44%).

To a solution of 3-[1-(ethylsulfonyl)-4-piperidinyl]-5-(4,4,5,5-tetramethyl-1,3,2-dioxaborolan-2-yl)-1H-indole-7-carboxamide (139 mg, 0.345 mmol) in dioxane (3 mL) and water (1 mL) was added 2-(4-bromo-2-thienyl)-N,N-dimethylethanamine (50 mg, 0.23 mmol), potassium carbonate (82.8 mg, 0.69 mmol) and tetrakis(triphenylphosphine)palladium(0) (22 mg, 0.019 mmol). The resulting mixture was reacted in a microwave for 20 min at 150° C. All solvent was evaporated and the mixture was then purified by Gilson Preparatory HPLC to give 12 mg of the title compound (5.8%).

LC/MS=m/z 489.2 [M+H] Ret. Time: 1.54 min.

Example 224

3-[1-(ethylsulfonyl)-4-piperidinyl]-5-[6-(1-pyrrolidinyl)-3-pyridinyl]-1H-indole-7-carboxamide trifluoroacetate

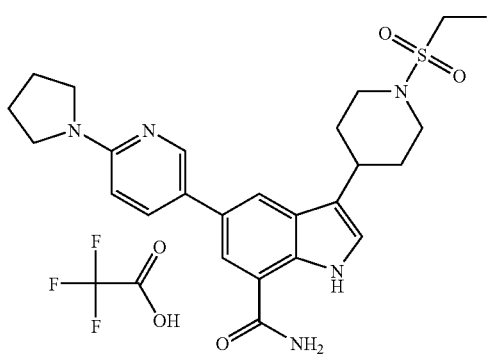

To a solution of 5-bromo-3-[1-(ethylsulfonyl)-4-piperidinyl]-1H-indole-7-carboxamide (110 mg, 0.27 mmol) in dioxane (2.0 mL) and H₂O (0.7 mL) was added (6-fluoro-3-pyridinyl)boronic acid (151 mg, 1.08 mmol), potassium carbonate (298 mg, 2.16 mmol), and tetrakis(triphenylphosphine)palladium(0) (31 mg, 0.026 mmol). The reaction was run in the microwave for 20 min at 150° C. The reaction was then treated with EtOAc and brine and purified by flash chromatography to give 50 mg of 3-[1-(ethylsulfonyl)-4-piperidinyl]-5-(6-fluoro-3-pyridinyl)-1H-indole-7-carboxamide (43%).

To 3-[1-(ethylsulfonyl)-4-piperidinyl]-5-(6-fluoro-3-pyridinyl)-1H-indole-7-carboxamide (25 mg, 0.058 mmol) was added pyrrolidine (3 mL). The resulting mixture was reacted in a microwave for 30 min at 100° C. All extra pyrrolidine was evaporated and it was then purified by Gilson Preparatory HPLC to give 25 mg of the title compound (72.4%).

LC/MS=m/z 482.2 [M+H] Ret. Time: 1.67 min.

Example 225

5-{6-[ethyl(methyl)amino]-3-pyridinyl}-3-[1-(ethylsulfonyl)-4-piperidinyl]-1H-indole-7-carboxamide trifluoroacetate

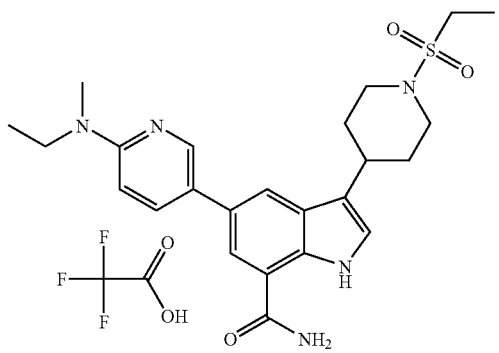

To a solution of 5-bromo-3-[1-(ethylsulfonyl)-4-piperidinyl]-1H-indole-7-carboxamide (110 mg, 0.27 mmol) in dioxane (2.0 mL) and H₂O (0.7 mL) was added (6-fluoro-3-pyridinyl)boronic acid (151 mg, 1.08 mmol), potassium carbonate (298 mg, 2.16 mmol), and tetrakis(triphenylphosphine)palladium(0) (31 mg, 0.026 mmol). The reaction was run in the microwave for 20 min at 150° C. The reaction was then treated with EtOAc and brine and purified by flash chromatography to give 50 mg of 3-[1-(ethylsulfonyl)-4-piperidinyl]-5-(6-fluoro-3-pyridinyl)-1H-indole-7-carboxamide (43%).

To 3-[1-(ethylsulfonyl)-4-piperidinyl]-5-(6-fluoro-3-pyridinyl)-1H-indole-7-carboxamide (40 mg, 0.093 mmol) was added dimethylamine (1 mL) and DMF (0.3 mL). The resulting mixture was reacted in a microwave for 1 h at 200° C. The resulting mixture was washed with water. Ethyl acetate was added and the organic layer was evaporated and purified by Gilson Preparatory HPLC to afford 34.4 mg of the title compound (63.4%).

LC/MS=m/z 470 [M+H] Ret. Time: 1.50 min.

Example 226

5-[6-(dimethylamino)-3-pyridinyl]-3-[1-(ethylsulfonyl)-4-piperidinyl]-1H-indole-7-carboxamide trifluoroacetate

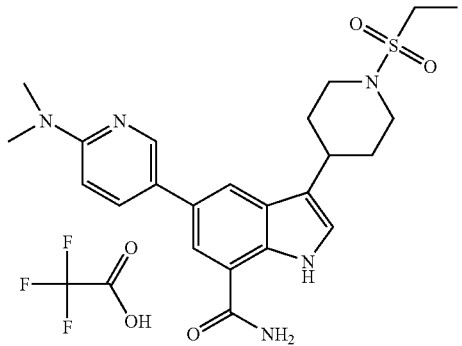

To a solution of 5-bromo-3-[1-(ethylsulfonyl)-4-piperidinyl]-1H-indole-7-carboxamide (110 mg, 0.27 mmol) in dioxane (2.0 mL) and H₂O (0.7 mL) was added (6-fluoro-3-pyridinyl)boronic acid (151 mg, 1.08 mmol), potassium carbonate (298 mg, 2.16 mmol), and tetrakis(triphenylphosphine)palladium(0) (31 mg, 0.026 mmol). The reaction was run in the microwave for 20 min at 150° C. The reaction was then treated with EtOAc and brine and purified by flash chromatography to give 50 mg of 3-[1-(ethylsulfonyl)-4-piperidinyl]-5-(6-fluoro-3-pyridinyl)-1H-indole-7-carboxamide (43%).

To 3-[1-(ethylsulfonyl)-4-piperidinyl]-5-(6-fluoro-3-pyridinyl)-1H-indole-7-carboxamide (50 mg, 0.116 mmol) was added dimethylamine (1 mL) and DMF (0.3 mL). The resulting mixture was reacted in a microwave for 1 h at 200° C. the purified by Gilson Preparatory HPLC to afford 8.4 mg of the title compound (12.7%).

LC/MS=m/z 456.2 [M+H] Ret. Time: 1.39 min.

Example 227

3-[1-(ethylsulfonyl)-4-piperidinyl]-5-[6-(propylamino)-3-pyridinyl]-1H-indole-7-carboxamide trifluoroacetate

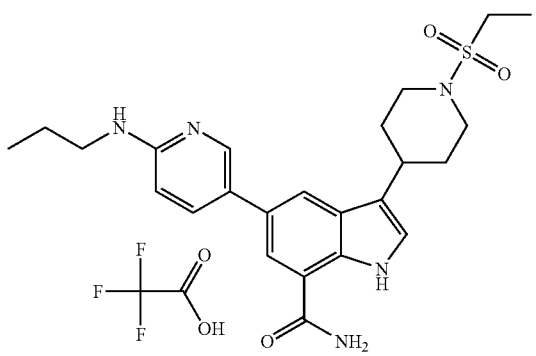

To a solution of 5-bromo-3-[1-(ethylsulfonyl)-4-piperidinyl]-1H-indole-7-carboxamide (110 mg, 0.27 mmol) in dioxane (2.0 mL) and H₂O (0.7 mL) was added (6-fluoro-3-pyridinyl)boronic acid (151 mg, 1.08 mmol), potassium carbonate (298 mg, 2.16 mmol), and tetrakis(triphenylphosphine)palladium(0) (31 mg, 0.026 mmol). The reaction was run in the microwave for 20 min at 150° C. The reaction was then treated with EtOAc and brine and purified by flash chromatography to give 50 mg of 3-[1-(ethylsulfonyl)-4-piperidinyl]-5-(6-fluoro-3-pyridinyl)-1H-indole-7-carboxamide (43%).

To 3-[1-(ethylsulfonyl)-4-piperidinyl]-5-(6-fluoro-3-pyridinyl)-1H-indole-7-carboxamide (50 mg, 0.116 mmol) was added propylamine (1 mL) and DMF (0.3 mL). The resulting mixture was reacted in a microwave for 5 h at 200° C. was purified by Gilson Preparatory HPLC to afford 24.5 mg of the title compound (36.2%).

LC/MS=m/z 470.2 [M+H] Ret. Time: 1.49 min.

Example 228

3-[1-(ethylsulfonyl)-4-piperidinyl]-5-{6-[(1-methylethyl)amino]-3-pyridinyl}-1H-indole-7-carboxamide trifluoroacetate

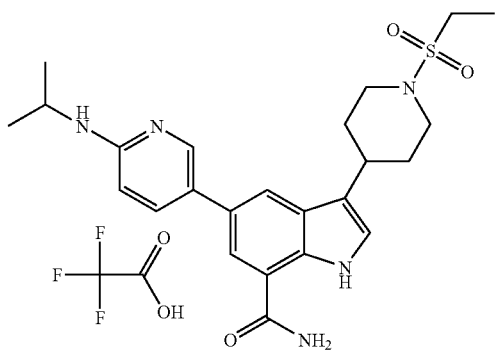

The title compound was prepared according to the general procedure of 5-{6-[ethyl(methyl)amino]-3-pyridinyl}-3-[1-(ethylsulfonyl)-4-piperidinyl]-1H-indole-7-carboxamide trifluoroacetate, substituting 2-propanamine (64.3 mg, 1 mmol) for dimethylamine to afford 9.8 mg of the title compound (14.5%).

LC/MS=m/z 470.4 [M+H] Ret. Time: 1.52 min.

Example 229

3-[1-(ethylsulfonyl)-4-piperidinyl]-5-[6-(4-morpholinyl)-3-pyridinyl]-1H-indole-7-carboxamide

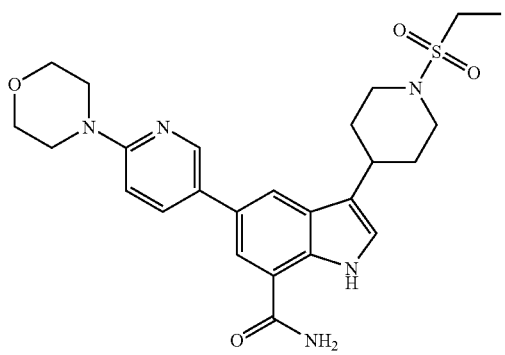

The title compound was prepared according to the general procedure of 5-{6-[ethyl(methyl)amino]-3-pyridinyl}-3-[1-(ethylsulfonyl)-4-piperidinyl]-1H-indole-7-carboxamide trifluoroacetate, substituting morpholine (1 mL) for dimethylamine to afford 40.1 mg of the title compound (69.5%).

LC/MS=m/z 498.6 [M+H] Ret. Time: 1.44 min.

Example 230

3-[1-(ethylsulfonyl)-4-piperidinyl]-5-{5-[(methylamino)methyl]-3-thienyl}-1H-indole-7-carboxamide trifluoroacetate

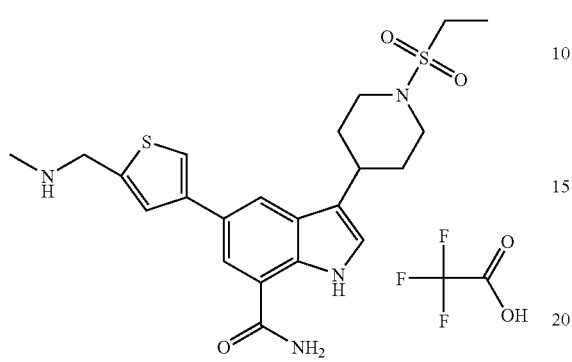

To a solution of 3-[1-(ethylsulfonyl)-4-piperidinyl]-5-(5-formyl-3-thienyl)-1H-indole-7-carboxamide (20 mg, 0.045 mmol) in methanol (1.5 mL) and methylene chloride (1.5 mL) was added methylamine (0.13 mL). The resulting mixture was stirred at room temperature for 2 h followed by the addition of sodium tetrahydridoborate (9.18 mg, 0.27 mmol). This was stirred at room temperature for 1 h. All solvent was evaporated and it was then purified by Gilson Preparatory HPLC to give 12.4 mg of the title compound (48%).

LC/MS=m/z 461.4 [M+H] Ret. Time: 1.48 min.

Example 231

3-[1-(ethylsulfonyl)-4-piperidinyl]-5-(5-{[(1-methylethyl)amino]methyl}-3-thienyl)-1H-indole-7-carboxamide trifluoroacetate

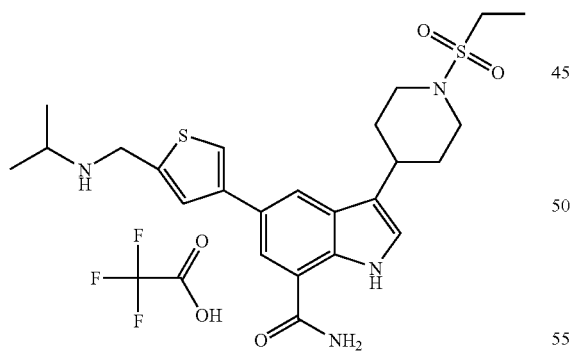

To a solution of 3-[1-(ethylsulfonyl)-4-piperidinyl]-5-(5-formyl-3-thienyl)-1H-indole-7-carboxamide (30 mg, 0.067 mmol) in methanol (0.5 mL) and methylene chloride (1 mL) was added 2-propanamine (23.8 mg, 0.402 mmol). The resulting mixture was stirred for 2.5 h followed by an addition of sodium tetrahydridoborate (15.2 mg, 0.402 mmol). The reaction was stirred at room temperature for 1 h. All solvent was evaporated and it was then purified by Gilson Preparatory HPLC to give 19.5 mg of the title compound (48.3%).

LC/MS=m/z 489.2 [M+H] Ret. Time: 1.54 min.

Example 232

3-[1-(ethylsulfonyl)-4-piperidinyl]-5-[5-(1-pyrrolidinylmethyl)-3-thienyl]-1H-indole-7-carboxamide trifluoroacetate

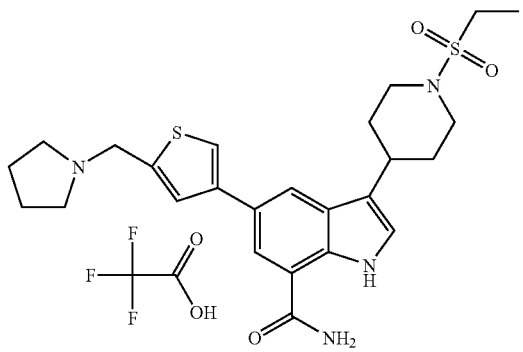

To a solution of 3-[1-(ethylsulfonyl)-4-piperidinyl]-5-(5-formyl-3-thienyl)-1H-indole-7-carboxamide (30 mg, 0.067 mmol) in methanol (0.5 mL) and methylene chloride (1 mL) was added pyrrolidine (85 mg, 1.195 mmol). The resulting mixture was stirred for 1.5 h followed by an addition of sodium triacetoxyborohydride (85 mg, 0.402 mmol). The reaction was stirred at room temperature for 2 h. All solvent was evaporated and it was then purified by Gilson Preparatory HPLC to give 22.5 mg of the title compound (54.6%).

LC/MS=m/z 501.4 [M+H] Ret. Time: 1.52 min.

Example 233

5-{5-[(ethylamino)methyl]-3-thienyl}-3-[1-(ethylsulfonyl)-4-piperidinyl]-1H-indole-7-carboxamide trifluoroacetate

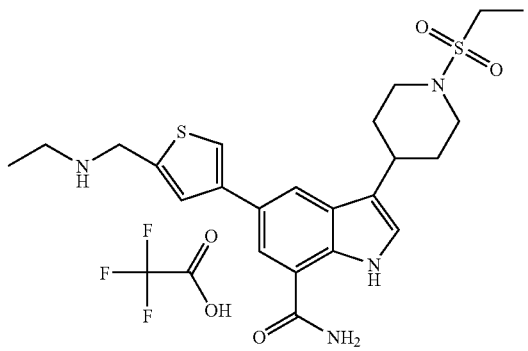

To a solution of 3-[1-(ethylsulfonyl)-4-piperidinyl]-5-(5-formyl-3-thienyl)-1H-indole-7-carboxamide (30 mg, 0.067 mmol) in methanol (3 mL), methylene chloride (3 mL) was added ethylamine (0.2 mL, 0.402 mmol). After 2 h sodium tetrahydridoborate (27 mg, 0.402 mmol) was added and the mixture was allowed to rest 1 h. All solvent was evaporated and it was then purified by Gilson Preparatory HPLC to give 15 mg of the title compound (38%).

LC/MS=m/z 475.4 [M+H] Ret. Time: 1.52 min.

Example 234

3-[1-(ethylsulfonyl)-4-piperidinyl]-5-[5-({[(1R)-2-hydroxy-1-methylethyl]amino}methyl)-3-thienyl]-1H-indole-7-carboxamide trifluoroacetate (salt)

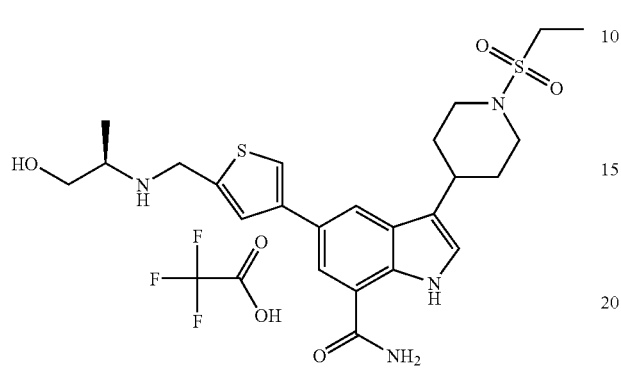

The title compound was prepared according to the general procedure of 5-{5-[(ethylamino)methyl]-3-thienyl}-3-[1-(ethylsulfonyl)-4-piperidinyl]-1H-indole-7-carboxamide trifluoroacetate, substituting (2R)-2-amino-1-propanol (0.031 mL, 0.402 mmol) for ethylamine to afford 16.2 mg of the title compound (39.1%).

LC/MS=m/z 505.4 [M+H] Ret. Time: 1.42 min.

Example 235

3-[1-(ethylsulfonyl)-4-piperidinyl]-5-[5-(1-piperidinylmethyl)-3-thienyl]-1H-indole-7-carboxamide trifluoroacetate

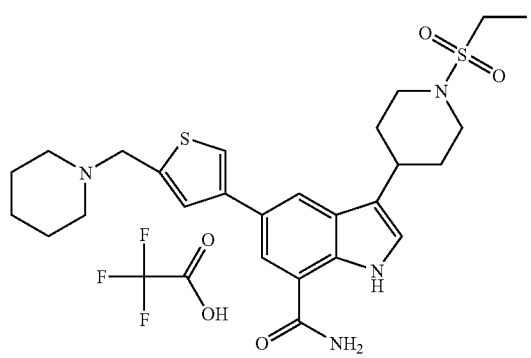

To a solution of 3-[1-(ethylsulfonyl)-4-piperidinyl]-5-(5-formyl-3-thienyl)-1H-indole-7-carboxamide (30 mg, 0.067 mmol) in dimethyl sulfoxide (2 mL) was added piperidine (70 mg, 0.670 mmol). The resulting mixture was allowed to rest for 2 h then sodium triacetoxyborohydride (142 mg, 0.670 mmol) was added. This mixture was stirred at room temperature overnight then purified by Gilson Preparatory HPLC to give 16.2 mg of the title compound (38.5%).

LC/MS=m/z 514.8 [M+H] Ret. Time: 1.37 min.

Example 236

3-[1-(ethylsulfonyl)-4-piperidinyl]-5-[5-(4-morpholinylmethyl)-3-thienyl]-1H-indole-7-carboxamide trifluoroacetate

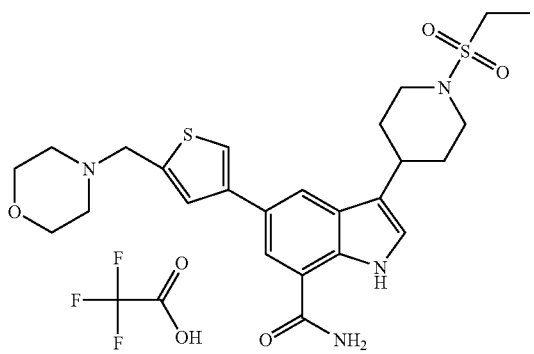

The title compound was prepared according to the general procedure of 3-[1-(ethylsulfonyl)-4-piperidinyl]-5-[5-(1-pyrrolidinylmethyl)-3-thienyl]-1H-indole-7-carboxamide trifluoroacetate, substituting morpholine (70 mg, 0.670 mmol) for piperidine to afford 6.3 mg of the title compound (14.9%).

LC/MS=m/z 517 [M+H] Ret. Time: 1.54 min.

Example 237

3-[1-(ethylsulfonyl)-4-piperidinyl]-5-{5-[(methylamino)methyl]-3-furanyl}-1H-indole-7-carboxamide trifluoroacetate

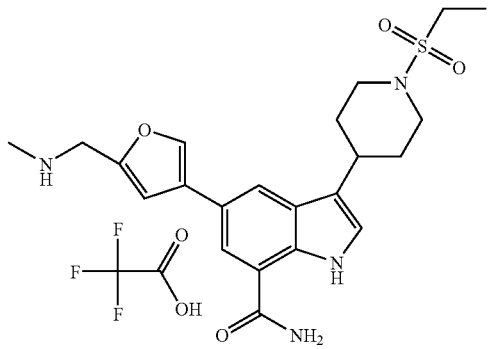

To a solution of 3-[1-(ethylsulfonyl)-4-piperidinyl]-5-(4,4,5,5-tetramethyl-1,3,2-dioxaborolan-2-yl)-1H-indole-7-carboxamide (50 mg, 0.11 mmol) in dioxane (3.0 mL) and H$_2$O (1.0 mL) was added 4-bromo-2-furancarbaldehyde (58 mg, 0.33 mmol), potassium carbonate (89.8 mg, 0.66 mmol), and tetrakis(triphenylphosphine)palladium(0) (14 mg, 0.012 mmol). The reaction was heated in the microwave for 20 min at 150° C. to give 58 mg of 3-[1-(ethylsulfonyl)-4-piperidinyl]-5-(5-formyl-3-furanyl)-1H-indole-7-carboxamide.

To a solution of 3-[1-(ethylsulfonyl)-4-piperidinyl]-5-(5-formyl-3-furanyl)-1H-indole-7-carboxamide (20.6 mg, 0.05 mmol) in DMSO (0.5 mL) was added methylamine (0.24 mL, 0.5 mmol) in 2 M tetrahydrofuran. The resulting mixture was reacted for 6 h followed by an addition of sodium triacetoxyborohydride was added. This was then purified by Gilson Preparatory HPLC to afford 5.5 mg of the title compound (32.8%).

LC/MS=m/z 459.4 [M+H] Ret. Time: 1.42 min.

Example 238

3-[1-(ethylsulfonyl)-4-piperidinyl]-5-{5-[1-(1-pyrrolidinyl)ethyl]-3-thienyl}-1H-indole-7-carboxamide trifluoroacetate

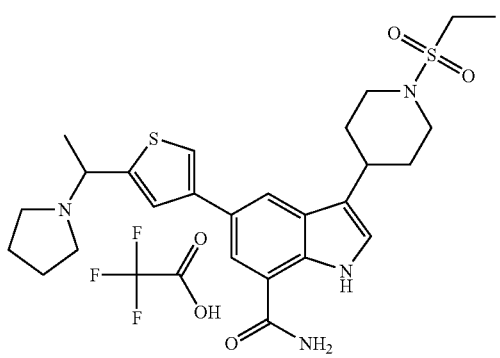

To a solution of 3-[1-(ethylsulfonyl)-4-piperidinyl]-5-(4,4,5,5-tetramethyl-1,3,2-dioxaborolan-2-yl)-1H-indole-7-carboxamide (300 mg, 0.65 mmol) in dioxane (9 mL) and H₂O (3 mL) was added 1-(4-bromo-2-thienyl)ethanone (400 mg, 1.95 mmol), potassium carbonate (538 mg, 3.90 mmol), and tetrakis(triphenylphosphine)palladium(0) (70 mg, 0.060 mmol). The reaction was run in the microwave at 150° C. for 20 min. An aqueous work-up was performed using EtOAc and H₂O followed by addition of MeOH (3 mL) to the crude product. The desired product precipitated and was filtered to give 230 mg of 3-[1-(ethylsulfonyl)-4-piperidinyl]-5-(5-propanoyl-3-thienyl)-1H-indole-7-carboxamide (77%).

To a solution of 5-(5-acetyl-3-thienyl)-3-[1-(ethylsulfonyl)-4-piperidinyl]-1H-indole-7-carboxamide (50 mg, 0.11 mmol) in DMF (0.8 mL) and acetic acid (0.2 mL) was added pyrrolidine (30.92 mg, 0.44 mmol) and N,N-dimethylformamide (30 mg, 0.44 mmol). The reaction mixture was reacted in a microwave for 20 min at 150° C. The results were then purified twice by Gilson Preparatory HPLC to give 3.7 mg of the title compound (5.3%).

LC/MS=m/z 515.4 [M+H] Ret. Time: 1.62 min.

Example 239

3-[1-(ethylsulfonyl)-4-piperidinyl]-5-[5-(1-pyrrolidinylmethyl)-2-thienyl]-1H-indole-7-carboxamide trifluoroacetate

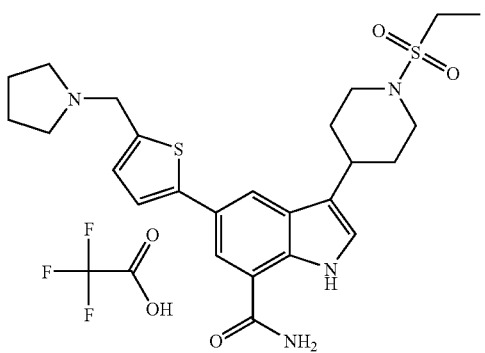

To 3-[1-(ethylsulfonyl)-4-piperidinyl]-5-(5-formyl-2-thienyl)-1H-indole-7-carboxamide (40 mg, 0.09 mmol) in dimethyl sulfoxide (0.5 mL) was added 2M pyrrolidine (0.074 mL, 0.90 mmol). The resulting mixture was allowed to rest for 6 h followed by an addition of sodium triacetoxyborohydride (233 mg, 9.90 mmol). This was then allowed to rest for 2 h then purified by Gilson Preparatory HPLC to give 6.5 mg of the title compound (11.7%).

LC/MS=m/z 515.4 [M+H] Ret. Time: 1.62 min.

Example 240

5-{5-[(dimethylamino)methyl]-2-thienyl}-3-[1-(ethylsulfonyl)-4-piperidinyl]-1H-indole-7-carboxamide trifluoroacetate

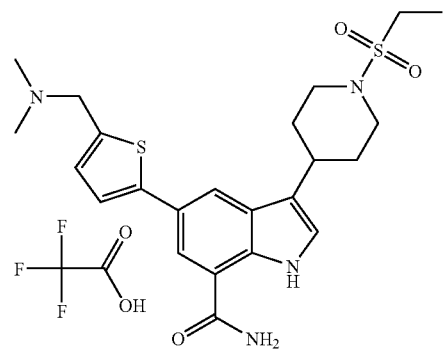

To 3-[1-(ethylsulfonyl)-4-piperidinyl]-5-(5-formyl-2-thienyl)-1H-indole-7-carboxamide (35 mg, 0.09 mmol) in dimethyl sulfoxide (0.5 mL) was added 2M dimethylamine (0.4 mL, 0.90 mmol). The resulting mixture was allowed to rest for 6 h followed by an addition of sodium triacetoxyborohydride (233 mg, 9.90 mmol). This was then allowed to rest for 2 h then purified by Gilson Preparatory HPLC to give 17.8 mg of the title compound (33.6%).

LC/MS=m/z 475.2 [M+H] Ret. Time: 1.53 min.

Example 241

3-[1-(ethylsulfonyl)-4-piperidinyl]-5-{5-[(propylamino)methyl]-2-thienyl}-1H-indole-7-carboxamide trifluoroacetate

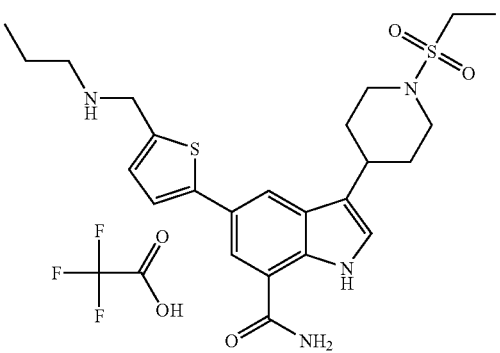

The title compound was prepared according to the general procedure of 5-{5-[(dimethylamino)methyl]-2-thienyl}-3-

[1-(ethylsulfonyl)-4-piperidinyl]-1H-indole-7-carboxamide trifluoroacetate, substituting propylamine (0.064 mL, 0.90 mmol) for 2M dimethylamine to afford 8.9 mg of the title compound (16.4%).

LC/MS=m/z 487.2 [M+H] Ret. Time: 1.80 min.

Example 242

5-{5-[(diethylamino)methyl]-2-thienyl}-3-[1-(ethylsulfonyl)-4-piperidinyl]-1H-indole-7-carboxamide trifluoroacetate

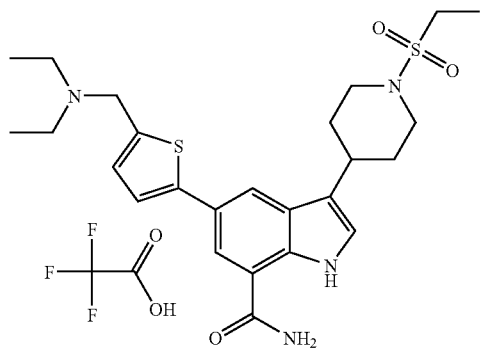

The title compound was prepared according to the general procedure of 5-{5-[(dimethylamino)methyl]-2-thienyl}-3-[1-(ethylsulfonyl)-4-piperidinyl]-1H-indole-7-carboxamide trifluoroacetate, substituting diethylamine (0.081 mL, 0.90 mmol) for 2M dimethylamine to afford 16.6 mg of the title compound (29.9%).

LC/MS=m/z 502.0 [M+H] Ret. Time: 1.71 min.

Example 243

3-[1-(ethylsulfonyl)-4-piperidinyl]-5-(5-{[(2-methylpropyl)amino]methyl}-2-thienyl)-1H-indole-7-carboxamide trifluoroacetate

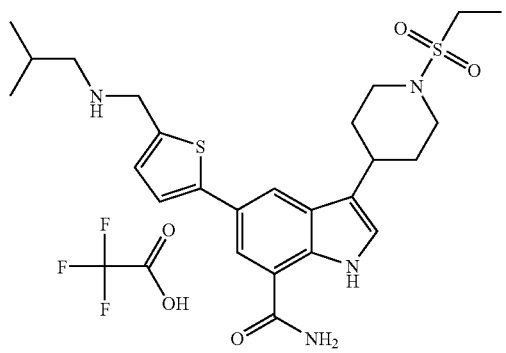

To 3-[1-(ethylsulfonyl)-4-piperidinyl]-5-(5-formyl-2-thienyl)-1H-indole-7-carboxamide (30 mg, 0.09 mmol) in dimethyl sulfoxide (0.5 mL) was added 2-methyl-1-propanamine (0.068 mL, 0.90 mmol). The resulting mixture was allowed to rest for 6 h followed by an addition of sodium triacetoxyborohydride (233 mg, 9.90 mmol). This was then allowed to rest for 2 h then purified by Gilson Preparatory HPLC to give 2.7 mg of the title compound (4.9%).

LC/MS=m/z 501.4 [M+H] Ret. Time: 1.79 min.

Example 244

5-(5-{[(2,2-dimethylpropyl)amino]methyl}-3-furanyl)-3-[1-(ethylsulfonyl)-4-piperidinyl]-1H-indole-7-carboxamide trifluoroacetate

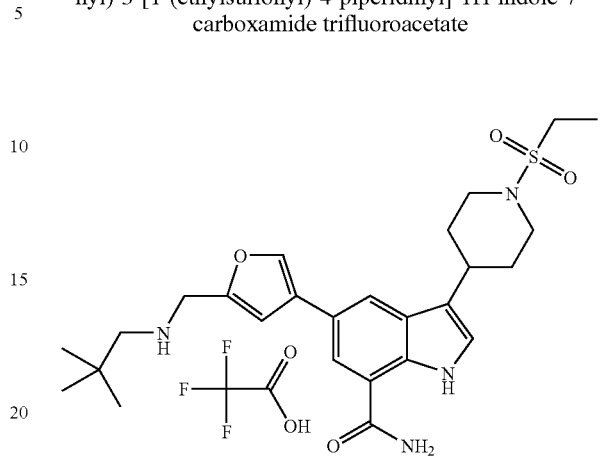

To a solution of 3-[1-(ethylsulfonyl)-4-piperidinyl]-5-(4,4,5,5-tetramethyl-1,3,2-dioxaborolan-2-yl)-1H-indole-7-carboxamide (50 mg, 0.11 mmol) in dioxane (3.0 mL) and $H_2O$ (1.0 mL) was added 4-bromo-2-furancarbaldehyde (58 mg, 0.33 mmol), potassium carbonate (89.8 mg, 0.66 mmol), and tetrakis(triphenylphosphine)palladium(0) (14 mg, 0.012 mmol). The reaction was heated in the microwave for 20 min at 150° C. to give 58 mg of 3-[1-(ethylsulfonyl)-4-piperidinyl]-5-(5-formyl-3-furanyl)-1H-indole-7-carboxamide.

To 3-[1-(ethylsulfonyl)-4-piperidinyl]-5-(5-formyl-3-furanyl)-1H-indole-7-carboxamide (60 mg, 0.14 mmol) was added 2,2-dimethyl-1-propanamine (60 mg, 0.14 mmol) in dimethyl sulfoxide (0.5 mL) was added 2,2-dimethyl-1-propanamine (122 mg, 1.40 mmol). The resulting mixture was allowed to rest for 6 h followed by an addition of sodium triacetoxyborohydride (233 mg, 9.90 mmol). This was then allowed to rest for 2 h then purified by Gilson Preparatory HPLC to give 23.8 mg of the title compound (27.7%).

LC/MS=m/z 501.1 [M+H] Ret. Time: 1.67 min.

Example 245

3-[1-(ethylsulfonyl)-4-piperidinyl]-5-(5-{[(2-methylpropyl)amino]methyl}-3-furanyl)-1H-indole-7-carboxamide trifluoroacetate

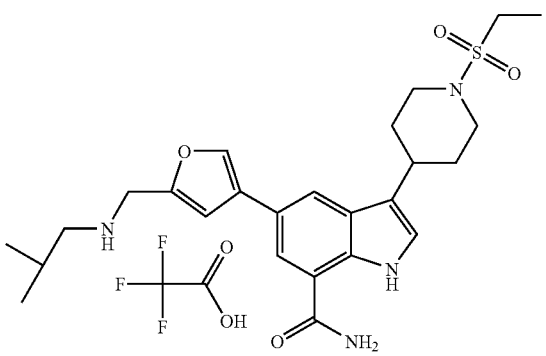

The title compound was prepared according to the general procedure of 5-(5-{[(2,2-dimethylpropyl)amino]methyl}-3-furanyl)-3-[1-(ethylsulfonyl)-4-piperidinyl]-1H-indole-7-carboxamide trifluoroacetate, substituting 2-methyl-1-propanamine (102.4 mg, 1.4 mmol) for 2,2-dimethyl-1-propanamine to afford 31.7 mg of the title compound (37.7%).

LC/MS=m/z 487.2 [M+H] Ret. Time: 1.44 min.

Example 246

5-(5-{[(cyclopentylmethyl)amino]methyl}-3-furanyl)-3-[1-(ethylsulfonyl)-4-piperidinyl]-1H-indole-7-carboxamide trifluoroacetate

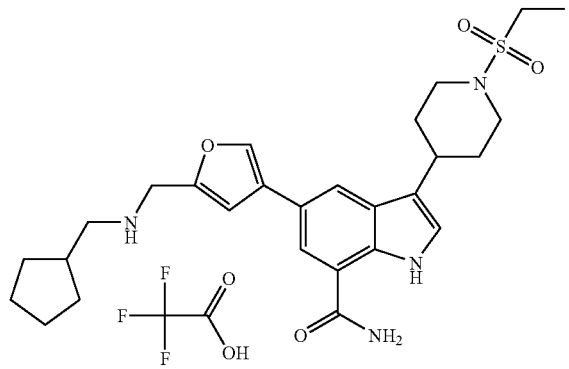

The title compound was prepared according to the general procedure of 5-(5-{[(2,2-dimethylpropyl)amino]methyl}-3-furanyl)-3-[1-(ethylsulfonyl)-4-piperidinyl]-1H-indole-7-carboxamide trifluoroacetate, substituting 1-cyclopentyl-methanamine (137 mg, 1.4 mmol) for 2,2-dimethyl-1-propanamine to afford 22 mg of the title compound (25.1%).

LC/MS=m/z 513.4 [M+H] Ret. Time: 1.59 min.

Example 247

3-[1-(ethylsulfonyl)-4-piperidinyl]-5-[5-(1-pyrrolidinylmethyl)-3-furanyl]-1H-indole-7-carboxamide trifluoroacetate

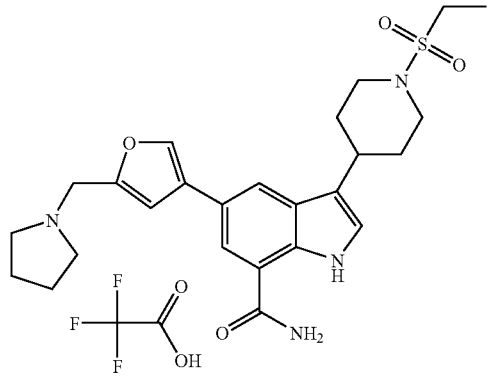

The title compound was prepared according to the general procedure of 5-(5-{[(2,2-dimethylpropyl)amino]methyl}-3-furanyl)-3-[1-(ethylsulfonyl)-4-piperidinyl]-1H-indole-7-carboxamide trifluoroacetate, substituting pyrrolidine (99.6 mg, 1.4 mmol) for 2,2-dimethyl-1-propanamine to afford 6 mg of the title compound (7.2%).

LC/MS=m/z 485.2 [M+H] Ret. Time: 1.50 min.

Example 248

5-{5-[(diethylamino)methyl]-3-furanyl}-3-[1-(ethylsulfonyl)-4-piperidinyl]-1H-indole-7-carboxamide trifluoroacetate

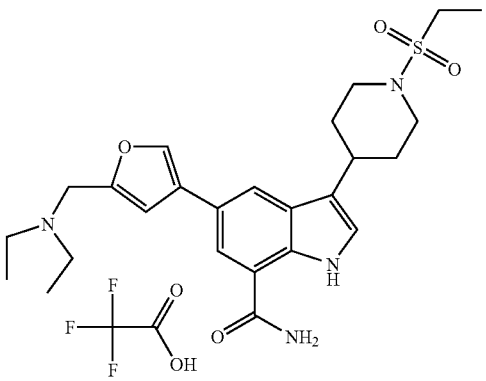

The title compound was prepared according to the general procedure of 5-(5-{[(2,2-dimethylpropyl)amino]methyl}-3-furanyl)-3-[1-(ethylsulfonyl)-4-piperidinyl]-1H-indole-7-carboxamide trifluoroacetate, substituting 2M diethylamine (102.4 mg, 1.4 mmol) for 2,2-dimethyl-1-propanamine to afford 10.1 mg of the title compound (12%).

LC/MS=m/z 487.4 [M+H] Ret. Time: 1.50 min.

Example 249

3-[1-(ethylsulfonyl)-4-piperidinyl]-5-[5-(1-pyrrolidinylmethyl)-1,3-thiazol-2-yl]-1H-indole-7-carboxamide trifluoroacetate

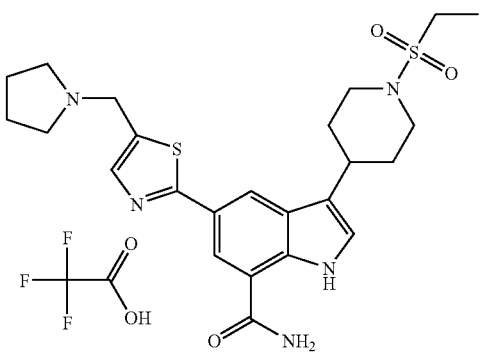

To a solution of 3-[1-(ethylsulfonyl)-4-piperidinyl]-5-(4,4,5,5-tetramethyl-1,3,2-dioxaborolan-2-yl)-1H-indole-7-carboxamide (500 mg, 1.1 mmol) in dioxane (12 mL) and H₂O (4 mL) was added 2-bromo-1,3-thiazole-5-carbaldehyde (634 mg, 3.3 mmol), potassium carbonate (898 mg, 8.8 mmol) and tetrakis(triphenylphosphine)palladium(0) (210 mg, 0.181 mmol). Reaction was run in the microwave at 150° C. for 20 min. Aqueous work-up performed to give crude product. The reaction was then repeated in the microwave at 150° C. for 30 min to give 3-[1-(ethylsulfonyl)-4-piperidinyl]-5-(5-formyl-1,3-thiazol-2-yl)-1H-indole-7-carboxamide.

To a solution of 3-[1-(ethylsulfonyl)-4-piperidinyl]-5-(5-formyl-1,3-thiazol-2-yl)-1H-indole-7-carboxamide (25 mg, 0.06 mmol) in dimethyl sulfoxide (1 mL) was added pyrrolidine (0.05 mL, 0.60 mmol). The resulting mixture was stirred at room temperature for 6 h followed by an addition of sodium triacetoxyborohydride (160 mg, 0.60 mmol). The resulting mixture was stirred overnight then purified by Gilson Preparatory HPLC to give 6.3 mg of the title compound (17.1%).

LC/MS=m/z 502.2 [M+H] Ret. Time: 1.35 min.

Example 250

3-[1-(ethylsulfonyl)-4-piperidinyl]-5-{5-[2-methyl-1-(1-pyrrolidinyl)propyl]-3-thienyl}-1H-indole-7-carboxamide trifluoroacetate

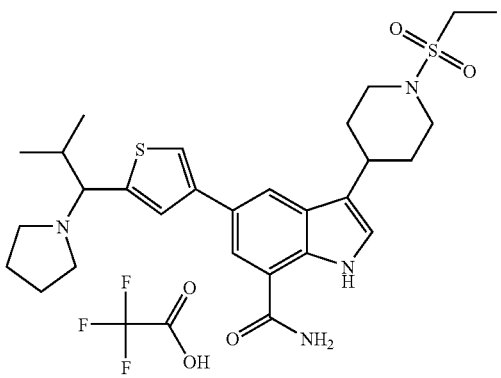

To a solution of 3-[1-(ethylsulfonyl)-4-piperidinyl]-5-(4,4,5,5-tetramethyl-1,3,2-dioxaborolan-2-yl)-1H-indole-7-carboxamide (50 mg, 0.11 mmol) in dioxane (3 mL) and H₂O (1 mL) was added potassium carbonate (89.8 mg, 0.66 mmol), 1-(4-bromo-2-thienyl)-2-methyl-1-propanone (87 mg, 0.33 mmol) and tetrakis(triphenylphosphine)palladium(0) (14 mg, 0.012 mmol). The reaction was run in a microwave for 20 min at 150° C. followed by an aqueous work-up with EtOAd and H₂O. The reaction was then concentrated and treated with 1 N NaOH and extracted with EtOAc. The compound was purified by flash chromatography using DCM and MeOH to give 3-[1-(ethylsulfonyl)-4-piperidinyl]-5-[5-(2-methylpropanoyl)-3-thienyl]-1H-indole-7-carboxamide.

To a solution of 3-[1-(ethylsulfonyl)-4-piperidinyl]-5-[5-(2-methylpropanoyl)-3-thienyl]-1H-indole-7-carboxamide (40 mg, 0.02 mmol) in EtOH (1.5 mL) and acetic acid (0.2 mL) was added sodium cyanoborohydride (7.5 mg, 0.12 mmol) and pyrrolidine (0.03 mL, 0.3 mmol). The resulting mixture was reacted in a microwave for 40 min at 150° C. All solvent was then evaporated, and basified in sodium hydroxide and extracted with ethyl acetate. This was then purified by Gilson Preparatory HPLC to give 13 mg of the title compound.

LC/MS=m/z 543.4 [M+H] Ret. Time: 1.71 min.

Example 251

3-[1-(ethylsulfonyl)-4-piperidinyl]-5-[4-(1-pyrrolidinylmethyl)-1,3-thiazol-2-yl]-1H-indole-7-carboxamide trifluoroacetate

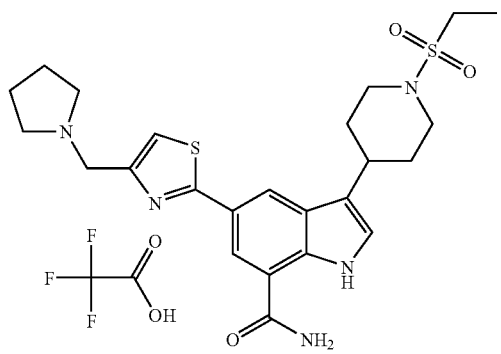

To a solution of 3-[1-(ethylsulfonyl)-4-piperidinyl]-5-(2-formyl-1,3-thiazol-4-yl)-1H-indole-7-carboxamide (42 mg, 0.094 mmol) in DMSO (2 mL) was added pyrrolidine (0.08 mL, 0.940 mmol). The resulting mixture was stirred at room temperature for 6 h followed by an addition of sodium triacetoxyborohydride. This mixture was stirred at room temperature overnight then purified by Gilson Preparatory HPLC to give 15.1 mg of the title compound (26.1%).

LC/MS=m/z 502.4 [M+H] Ret. Time: 1.54 min.

Example 252

5-{1-[2-(dimethylamino)ethyl]-1H-pyrazol-4-yl}-3-[1-(ethylsulfonyl)-4-piperidinyl]-1H-indole-7-carboxamide

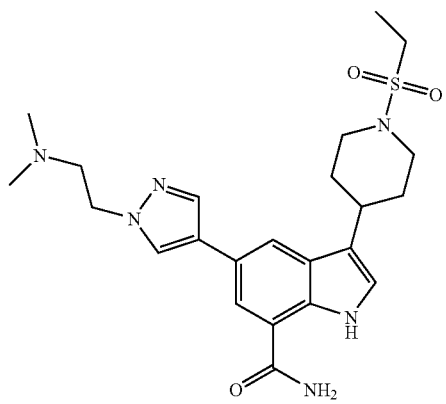

A solution of 3-[1-(ethylsulfonyl)-4-piperidinyl]-5-(4,4,5,5-tetramethyl-1,3,2-dioxaborolan-2-yl)-1H-indole-7-carboxamide (40 mg, 0.084 mmol), [2-(4-bromo-1H-pyrazol-1-yl)ethyl]dimethylamine (27 mg, 0.126 mmol) and sodium carbonate (53 mg, 0.5 mmol) was suspended in dioxane (750 µL) and water (250 µL). This was flushed with argon for 10 min before the addition of tetrakis(triphenylphosphine)palladium(0) (5 mg, 0.004 mmol). The resulting mixture was reacted in a microwave for 20 min at 120° C. then diluted with EtOAc (10 mL). The mixture was filtered through Celite and an aqueous wash was performed. It was then purified by Gilson Preparatory HPLC to give 6 mg of the title compound (15%).

LC/MS=m/z 473.4 [M+H] Ret. Time: 1.48 min.

Example 253

3-[1-(ethylsulfonyl)-4-piperidinyl]-5-{1-[2-(1-pyrrolidinyl)ethyl]-1H-pyrazol-4-yl}-1H-indole-7-carboxamide trifluoroacetate

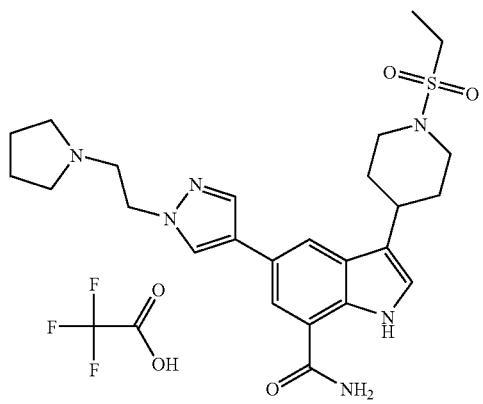

To a solution of 3-[1-(ethylsulfonyl)-4-piperidinyl]-5-(4,4,5,5-tetramethyl-1,3,2-dioxaborolan-2-yl)-1H-indole-7-carboxamide (40 mg, 0.090 mmol) in dioxane (750 µL) and H₂O (250 µL) was added sodium carbonate (53 mg, 0.50 mmol), and 4-bromo-1-(2-chloroethyl)-1H-pyrazole (26 mg, 0.126 mmol). The reaction mixture was flushed under Argon for 10 min before addition of tetrakis(triphenylphosphine)palladium (0) (5 mg, 0.004 mmol). The reaction was heated in a microwave at 120° C. for 20 min. It was then diluted with EtOAc (10 mL), filtered thru celite, followed by an aqueous work-up. The compound was purified by Gilson Preparatory HPLC to give 10 mg of 5-[1-(2-chloroethyl)-1H-pyrazol-4-yl]-3-[1-(ethylsulfonyl)-4-piperidinyl]-1H-indole-7-carboxamide (24%).

To a solution of 5-[1-(2-chloroethyl)-1H-pyrazol-4-yl]-3-[1-(ethylsulfonyl)-4-piperidinyl]-1H-indole-7-carboxamide (33 mg, 0.071 mmol), pyrrolidine (60 µL, 0.710 mmol) and sodium iodide (5 mg, 0.018 mmol) was added tetrahydrofuran (500 µL). This mixture was reacted in a microwave for 2 h at 130° C. and given an aqueous wash with EtOAc and water. Organic layer was then isolated and all solvent was removed. It was then purified by Gilson Preparatory HPLC to give 11 mg of the title compound (25%).

LC/MS=m/z 499.6 [M+H] Ret. Time: 1.34 min.

Example 254

3-[1-(ethylsulfonyl)-4-piperidinyl]-5-{1-[2-(4-morpholinyl)ethyl]-1H-pyrazol-4-yl}-1H-indole-7-carboxamide trifluoroacetate

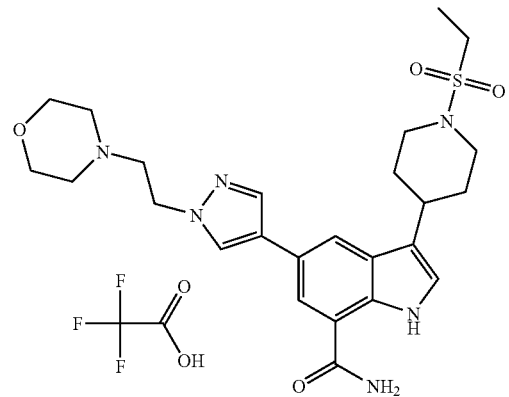

The title compound was prepared according to the general procedure of 3-[1-(ethylsulfonyl)-4-piperidinyl]-5-{1-[2-(1-pyrrolidinyl)ethyl]-1H-pyrazol-4-yl}-1H-indole-7-carboxamide trifluoroacetate, substituting morpholine (70 µL, 0.71 mmol) for the pyrrolidine to afford 15 mg of the title compound (34%).

LC/MS=m/z 515.4 [M+H] Ret. Time: 1.46 min.

Example 255

3-[1-(ethylsulfonyl)-4-piperidinyl]-5-(1-{2-[(2-hydroxyethyl)amino]ethyl}-1H-pyrazol-4-yl)-1H-indole-7-carboxamide trifluoroacetate

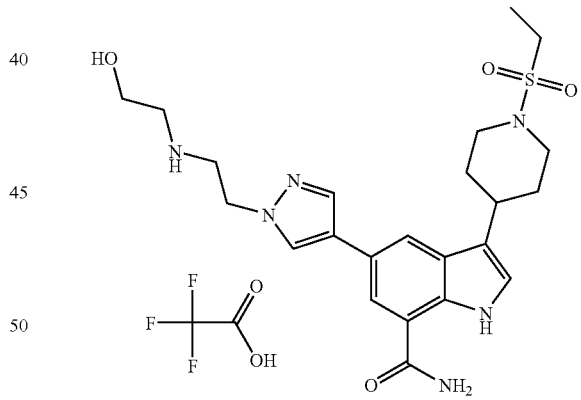

To a solution of 3-[1-(ethylsulfonyl)-4-piperidinyl]-5-(4,4,5,5-tetramethyl-1,3,2-dioxaborolan-2-yl)-1H-indole-7-carboxamide (40 mg, 0.090 mmol) in dioxane (750 µL) and H₂O (250 µL) was added sodium carbonate (53 mg, 0.50 mmol), and 4-bromo-1-(2-chloroethyl)-1H-pyrazole (26 mg, 0.126 mmol). The reaction mixture was flushed under Argon for 10 min before addition of tetrakis(triphenylphosphine)palladium (0) (5 mg, 0.004 mmol). The reaction was heated in a microwave at 120° C. for 20 min. It was then diluted with EtOAc (10 mL), filtered thru celite, followed by an aqueous work-up. The compound was purified by Gilson Preparatory HPLC to give 10 mg of 5-[1-(2-chloroethyl)-1H-pyrazol-4-yl]-3-[1-(ethylsulfonyl)-4-piperidinyl]-1H-indole-7-carboxamide (24%).

A solution of 5-[1-(2-chloroethyl)-1H-pyrazol-4-yl]-3-[1-(ethylsulfonyl)-4-piperidinyl]-1H-indole-7-carboxamide (20 mg, 0.043 mmol), 2-aminoethanol (26 mg, 0.43 mmol) and sodium iodide (5 mg, 0.022 mmol) in tetrahydrofuran (1 mL) was reacted in a microwave for 2 h at 130° C. The tetrahydrofuran was then removed and the mixture was given an aqueous was of EtOAc and water. The organic layer was then separated and all solvent was removed. The mixture was then purified by Gilson Preparatory HPLC to give 8 mg of the title compound (31%).

LC/MS=m/z 489.2 [M+H] Ret. Time: 1.40 min.

Example 256

5-{1-[2-(butylamino)ethyl]-1H-pyrazol-4-yl}-3-[1-(ethylsulfonyl)-4-piperidinyl]-1H-indole-7-carboxamide trifluoroacetate

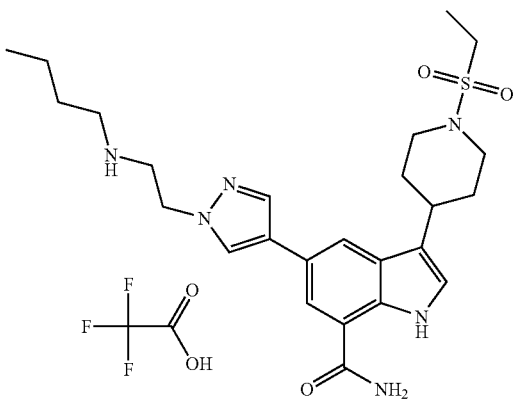

The title compound was prepared according to the general procedure of 3-[1-(ethylsulfonyl)-4-piperidinyl]-5-(1-{2-[(2-hydroxyethyl)amino]ethyl}-1H-pyrazol-4-yl)-1H-indole-7-carboxamide trifluoroacetate, substituting 1-butanamine (31 mg, 0.43 mmol) for the 2-aminoethanol to afford 7 mg of the title compound (26%).

LC/MS=m/z 499.4 [M+H] Ret. Time: 1.39 min.

Example 257

5-{1-[2-(cyclobutylamino)ethyl]-1H-pyrazol-4-yl}-3-[1-(ethylsulfonyl)-4-piperidinyl]-1H-indole-7-carboxamide trifluoroacetate

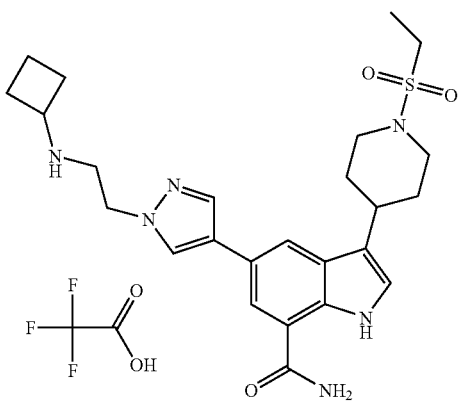

The title compound was prepared according to the general procedure of 3-[1-(ethylsulfonyl)-4-piperidinyl]-5-(1-{2-[(2-hydroxyethyl)amino]ethyl}-1H-pyrazol-4-yl)-1H-indole-7-carboxamide trifluoroacetate, substituting cyclobutanamine (31 mg, 0.43 mmol) for the 2-aminoethanol to afford 10 mg of the title compound (38%).

LC/MS=m/z 501.4 [M+H] Ret. Time: 1.48 min.

Example 258

5-[1-(2-{[2-(diethylamino)ethyl]amino}ethyl)-1H-pyrazol-4-yl]-3-[1-(ethylsulfonyl)-4-piperidinyl]-1H-indole-7-carboxamide trifluoroacetate

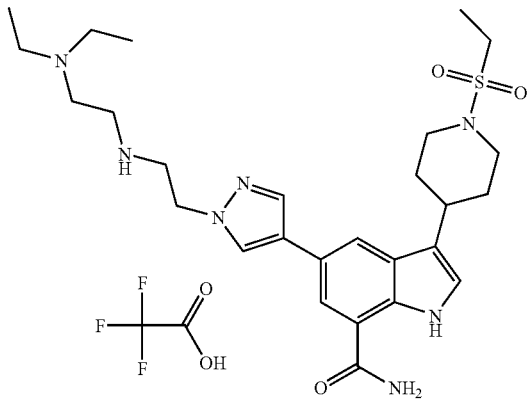

The title compound was prepared according to the general procedure of 3-[1-(ethylsulfonyl)-4-piperidinyl]-5-(1-{2-[(2-hydroxyethyl)amino]ethyl}-1H-pyrazol-4-yl)-1H-indole-7-carboxamide trifluoroacetate, substituting N,N-diethyl-1,2-ethanediamine (50 mg, 0.43 mmol) for the 2-aminoethanol to afford 12 mg of the title compound (42%).

LC/MS=m/z 545.2 [M+H] Ret. Time: 1.25 min.

Example 259

3-[1-(ethylsulfonyl)-4-piperidinyl]-5-(1-{2-[(1-methylethyl)amino]ethyl}-1H-pyrazol-4-yl)-1H-indole-7-carboxamide trifluoroacetate

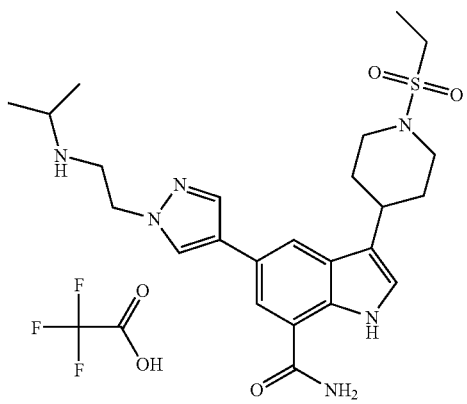

The title compound was prepared according to the general procedure of 3-[1-(ethylsulfonyl)-4-piperidinyl]-5-(1-{2-[(2-hydroxyethyl)amino]ethyl}-1H-pyrazol-4-yl)-1H-indole-7-carboxamide trifluoroacetate, substituting 2-propanamine (25 mg, 0.43 mmol) for the 2-aminoethanol to afford 9 mg of the title compound (35%).

LC/MS=m/z 487.2 [M+H] Ret. Time: 1.47 min.

Example 260

3-[1-(ethylsulfonyl)-4-piperidinyl]-5-(1-{2-[(2-methylpropyl)amino]ethyl}-1H-pyrazol-4-yl)-1H-indole-7-carboxamide trifluoroacetate

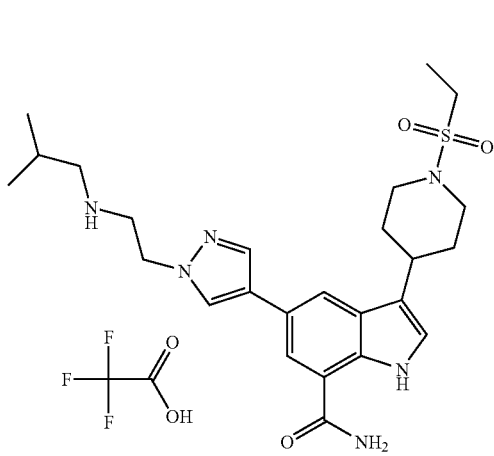

The title compound was prepared according to the general procedure of 3-[1-(ethylsulfonyl)-4-piperidinyl]-5-(1-{2-[(2-hydroxyethyl)amino]ethyl}-1H-pyrazol-4-yl)-1H-indole-7-carboxamide trifluoroacetate, substituting 2-methyl-1-propanamine (31 mg, 0.43 mmol) for the 2-aminoethanol to afford 8 mg of the title compound (30%).

LC/MS=m/z 501.2 [M+H] Ret. Time: 1.45 min.

Example 261

5-(1-{2-[(cyclopentylmethyl)amino]ethyl}-1H-pyrazol-4-yl)-3-[1-(ethylsulfonyl)-4-piperidinyl]-1H-indole-7-carboxamide trifluoroacetate

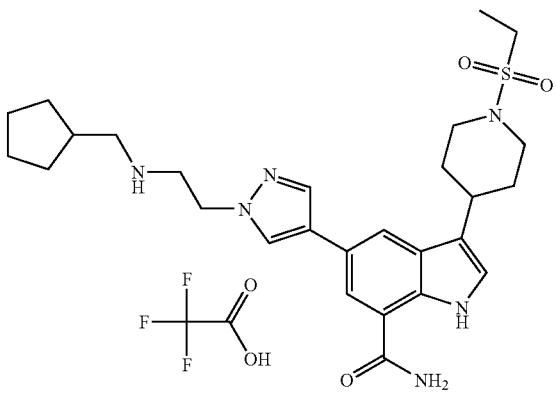

The title compound was prepared according to the general procedure of 3-[1-(ethylsulfonyl)-4-piperidinyl]-5-(1-{2-[(2-hydroxyethyl)amino]ethyl}-1H-pyrazol-4-yl)-1H-indole-7-carboxamide trifluoroacetate, substituting cyclopentanamine (37 mg, 0.43 mmol) for the 2-aminoethanol to afford 11 mg of the title compound (40%).

LC/MS=m/z 513.4 [M+H] Ret. Time: 1.47 min.

Example 262

3-[1-(ethylsulfonyl)-4-piperidinyl]-5-[4-(methyloxy)-3-(1-pyrrolidinylmethyl)phenyl]-1H-indole-7-carboxamide trifluoroacetate

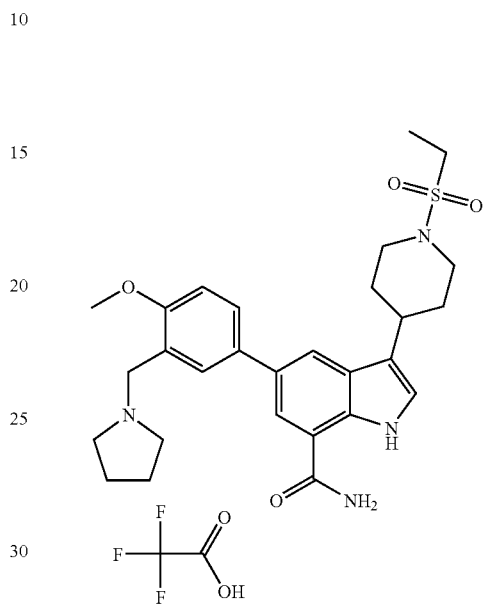

To a solution of 2-(methyloxy)-5-(4,4,5,5-tetramethyl-1,3,2-dioxaborolan-2-yl)benzaldehyde (610 mg, 2.33 mmol) in dioxane (19 mL) and H$_2$O (6.3 mL), was added 5-bromo-3-[1-(ethylsulfonyl)-4-piperidinyl]-1H-indole-7-carboxamide (963 mg, 2.33 mmol), and sodium carbonate (1.48 g, 13.9 mmol). After flushing with Agron for 10 min, tetrakis(triphenylphosphine)palladium(0) (134 mg, 0.166 mmol) was added. The reaction was heated in the microwave 120° C. for 120 min. Compound was purified by flash chromatography using DCM and MeOH to give 632 mg of 3-[1-(ethylsulfonyl)-4-piperidinyl]-5-[3-formyl-4-(methyloxy)phenyl]-1H-indole-7-carboxamide (58%).

A solution of 3-[1-(ethylsulfonyl)-4-piperidinyl]-5-[3-formyl-4-(methyloxy)phenyl]-1H-indole-7-carboxamide (50 mg, 0.107 mmol), pyrrolidine (45 μL, 0.214 mmol), zinc chloride (10 mg, 0.054 mmol) and sodium cyanoborohydride (7 mg, 0.107 mmol) in methanol (5 mL) was stirred at room temperature for 2 h. To this mixture was added 0.1 normal solution of sodium hydroxide in water (2 mL). The methanol was then evaporated. The aqueous phase was extracted with EtOAc (5 mL) three times. The organic phase was then washed with brine (5 mL) twice. All solvent was then removed. The mixture was purified by Gilson Preparatory HPLC to give 9 mg of the title compound (13%).

LC/MS=m/z 525.6 [M+H] Ret. Time: 1.67 min.

Example 263

5-[3-[(dimethylamino)methyl]-4-(methyloxy)phenyl]-3-[1-(ethylsulfonyl)-4-piperidinyl]-1H-indole-7-carboxamide trifluoroacetate

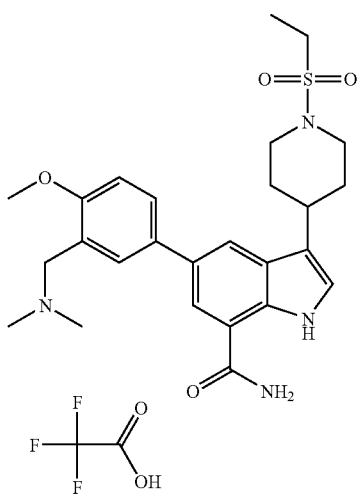

To a solution of 2-(methyloxy)-5-(4,4,5,5-tetramethyl-1,3,2-dioxaborolan-2-yl)benzaldehyde (610 mg, 2.33 mmol) in dioxane (19 mL) and H₂O (6.3 mL), was added 5-bromo-3-[1-(ethylsulfonyl)-4-piperidinyl]-1H-indole-7-carboxamide (963 mg, 2.33 mmol), and sodium carbonate (1.48 g, 13.9 mmol). After flushing with Agron for 10 min, tetrakis(triphenylphosphine)palladium(0) (134 mg, 0.166 mmol) was added. The reaction was heated in the microwave 120° C. for 120 min. Compound was purified by flash chromatography using DCM and MeOH to give 632 mg of 3-[1-(ethylsulfonyl)-4-piperidinyl]-5-[3-formyl-4-(methyloxy)phenyl]-1H-indole-7-carboxamide (58%).

A solution of 3-[1-(ethylsulfonyl)-4-piperidinyl]-5-[3-formyl-4-(methyloxy)phenyl]-1H-indole-7-carboxamide (50 mg, 0.214 mmol), dimethylamine (107 µL, 0.214 mmol), zinc chloride (10 mg, 0.054 mmol) and sodium cyanoborohydride (7 mg, 0.107 mmol) in methanol (5 mL) was stirred at room temperature for 2 h. To this mixture was added 0.1 normal solution of sodium hydroxide in water (2 mL). The methanol was then evaporated. The aqueous phase was extracted with EtOAc (5 mL) three times. The organic phase was then washed with brine (5 mL) twice. All solvent was then removed. The mixture was purified by Gilson Preparatory HPLC to give 4 mg of the title compound (6.1%).

LC/MS=m/z 499.4 [M+H] Ret. Time: 1.56 min.

Example 264

3-[1-(ethylsulfonyl)-4-piperidinyl]-5-[4-(methyloxy)-3-(4-morpholinylmethyl)phenyl]-1H-indole-7-carboxamide trifluoroacetate

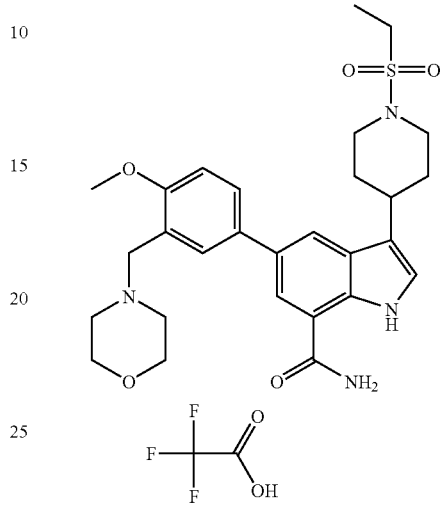

The title compound was prepared according to the general procedure of 5-[3-[(dimethylamino)methyl]-4-(methyloxy)phenyl]-3-[1-(ethylsulfonyl)-4-piperidinyl]-1H-indole-7-carboxamide trifluoroacetate, substituting morpholine (20 µL, 0.214 mmol) for the dimethylamine to afford 12 mg of the title compound (17%).

LC/MS=m/z 541.6 [M+H] Ret. Time: 1.69 min.

Example 265

3-[1-(ethylsulfonyl)-4-piperidinyl]-5-[3-{[(1-methylethyl)amino]methyl}-4-(methyloxy)phenyl]-1H-indole-7-carboxamide trifluoroacetate

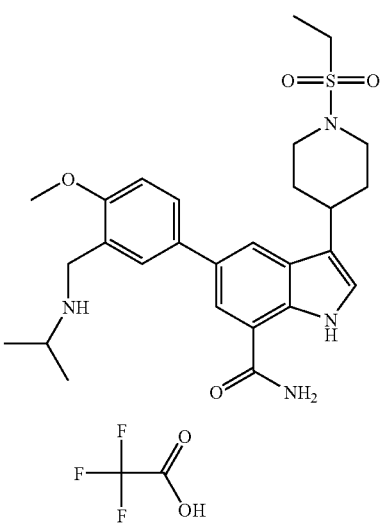

The title compound was prepared according to the general procedure of 5-[3-[(dimethylamino)methyl]-4-(methyloxy)phenyl]-3-[1-(ethylsulfonyl)-4-piperidinyl]-1H-indole-7-carboxamide trifluoroacetate, substituting 2-propanamine (15 μL, 0.214 mmol) for the dimethylamine to afford 16 mg of the title compound (24%).

LC/MS=m/z 513.2 [M+H] Ret. Time: 1.62 min.

Example 266

3-[1-(ethylsulfonyl)-4-piperidinyl]-5-[3-[(methylamino)methyl]-4-(methyloxy)phenyl]-1H-indole-7-carboxamide trifluoroacetate

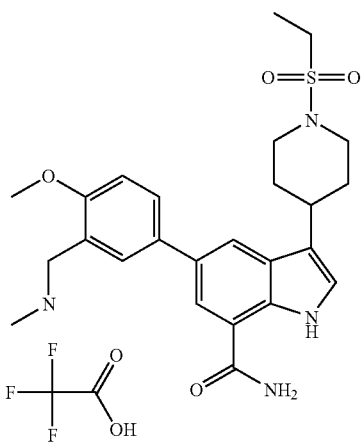

The title compound was prepared according to the general procedure of 5-[3-[(dimethylamino)methyl]-4-(methyloxy)phenyl]-3-[1-(ethylsulfonyl)-4-piperidinyl]-1H-indole-7-carboxamide trifluoroacetate, substituting methylamine (50 μL, 0.214 mmol) for the dimethylamine to afford 10 mg of the title compound (16%).

LC/MS=m/z 485.2 [M+H] Ret. Time: 1.57 min.

Example 267

5-[3-{[(2,2-dimethylpropyl)amino]methyl}-4-(methyloxy)phenyl]-3-[1-(ethylsulfonyl)-4-piperidinyl]-1H-indole-7-carboxamide trifluoroacetate

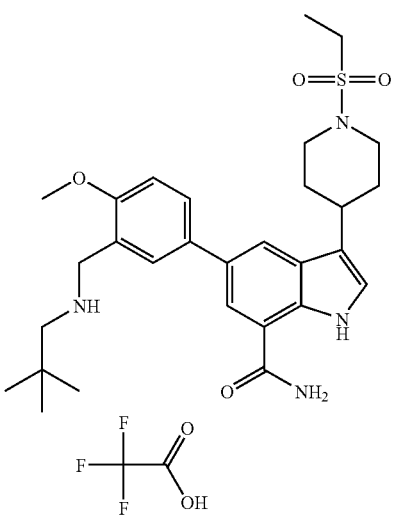

The title compound was prepared according to the general procedure of 5-[3-[(dimethylamino)methyl]-4-(methyloxy)phenyl]-3-[1-(ethylsulfonyl)-4-piperidinyl]-1H-indole-7-carboxamide trifluoroacetate, substituting 2,2-dimethyl-1-propanamine (20 μL, 0.214 mmol) for the dimethylamine to afford 11 mg of the title compound (16%).

LC/MS=m/z 541.2 [M+H] Ret. Time: 1.77 min.

Example 268

3-[1-(ethylsulfonyl)-4-piperidinyl]-5-(1-{2-[(2-hydroxyethyl)(methyl)amino]ethyl}-1H-pyrazol-4-yl)-1H-indole-7-carboxamide

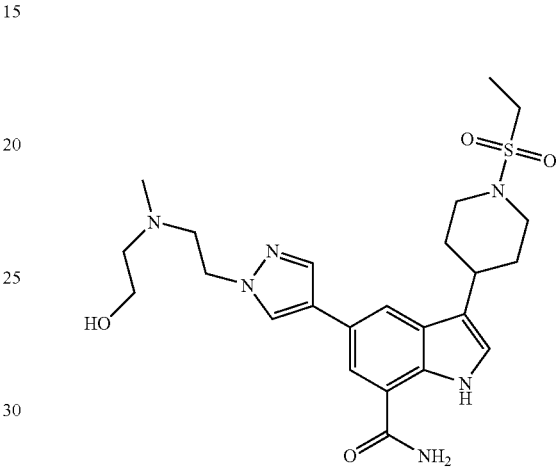

A solution of 5-[1-(2-chloroethyl)-1H-pyrazol-4-yl]-3-[1-(ethylsulfonyl)-4-piperidinyl]-1H-indole-7-carboxamide (30 mg, 0.065 mmol), 2-(methylamino)ethanol (500 μL, 6.5 mmol) and sodium iodide (3 mg, 0.016 mmol) in tetrahydrofuran (1 mL) was reacted in a microwave for 2 h at 130° C. An aqueous work-up was performed on the resulting mixture. This was then purified by Gilson Preparatory HPLC to give 9 mg of the title compound (17%).

LC/MS=m/z 503.2 [M+H] Ret. Time: 1.40 min.

Example 269

3-[1-(ethylsulfonyl)-4-piperidinyl]-5-{4-fluoro-3-[(methylamino)methyl]phenyl}-1H-indole-7-carboxamide trifluoroacetate

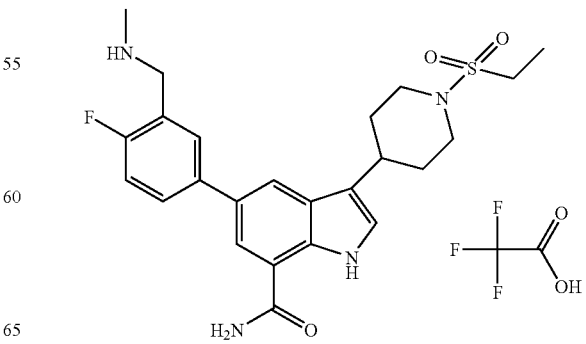

To a solution of 3-[1-(ethylsulfonyl)-4-piperidinyl]-5-(4-fluoro-3-formylphenyl)-1H-indole-7-carboxamide (16.0 mg, 0.035 mmol) in dichloromethane (1 mL) and methanol (1 mL) was added 2M methylamine in THF (105 μL, 0.21 mmol) and 1 drop of acetic acid. This mixture was stirred for 3 h. Sodium tetrahydridoborate (8.4 mg, 0.21 mmol) was added and the mixture was stirred for 1 h. The resulting mixture was concentrated and dissolved in dimethyl sulfoxide (1.5 mL). It was then purified by Gilson Preparatory HPLC to give 6.4 mg of the title compound (31.2%).

LC/MS=m/z 473.4 [M+H] Ret. Time: 1.50 min.

Example 270

5-{3,5-bis[(methylamino)methyl]phenyl}-3-[1-(ethylsulfonyl)-4-piperidinyl]-1H-indole-7-carboxamide trifluoroacetate

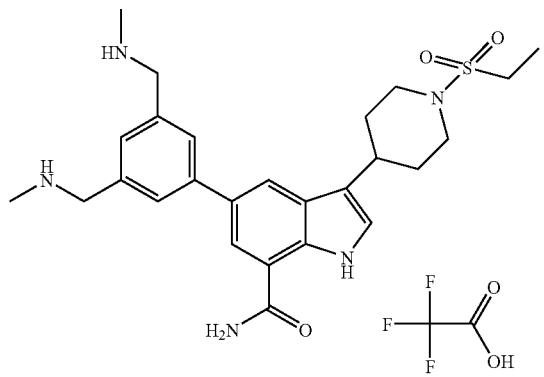

To a solution of 5-(3,5-diformylphenyl)-3-[1-(ethylsulfonyl)-4-piperidinyl]-1H-indole-7-carboxamide (10 mg, 0.2 mmol) in dichloromethane (1 mL) and methanol (1 mL) was added methylamine (64 μL, 0.128 mmol) and 1 drop of acetic acid. The resulting mixture was stirred for 3 h at room temperature then sodium tetrahydridoborate (5.1 mg, 0.128 mmol) was added. This was stirred for 1 h then concentrated and purified by Gilson Preparatory HPLC to give 3 mg of the title compound (23.4%).

LC/MS=m/z 498.6 [M+H] Ret. Time: 1.17 min.

Example 271

5-{3-[(ethylamino)methyl]-4-fluorophenyl}-3-[1-(ethylsulfonyl)-4-piperidinyl]-1H-indole-7-carboxamide trifluoroacetate

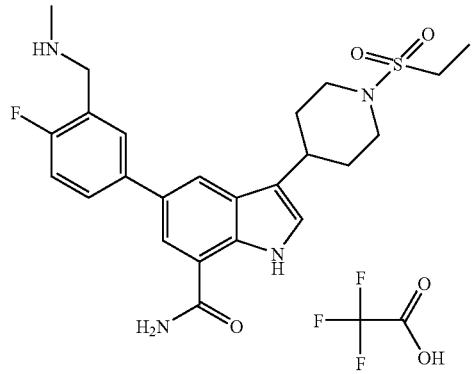

To a solution of 3-[1-(ethylsulfonyl)-4-piperidinyl]-5-(4-fluoro-3-formylphenyl)-1H-indole-7-carboxamide (35 mg, 0.076 mmol) in dichloromethane (1 mL) and methanol (1 mL) was added 2 M ethylamine (230 μL, 0.46 mmol) and 1 drop of acetic acid. The mixture was stirred for 1 h at room temperature then tetrahydrofuran (1 mL) was added. The mixture was stirred for 30 min followed by the addition of sodium tetrahydridoborate (17.5 mg, 0.46 mmol). The resulting mixture was stirred for an additional 1 h, concentrated and purified by Gilson Preparatory HPLC to give 20 mg of the title compound (43.8%).

LC/MS=m/z 487.4 [M+H] Ret. Time: 1.46 min.

Example 272

3-[1-(ethylsulfonyl)-4-piperidinyl]-5-[4-fluoro-3-({[2-hydroxy-1-(hydroxymethyl)ethyl]amino}methyl)phenyl]-1H-indole-7-carboxamide trifluoroacetate (salt)

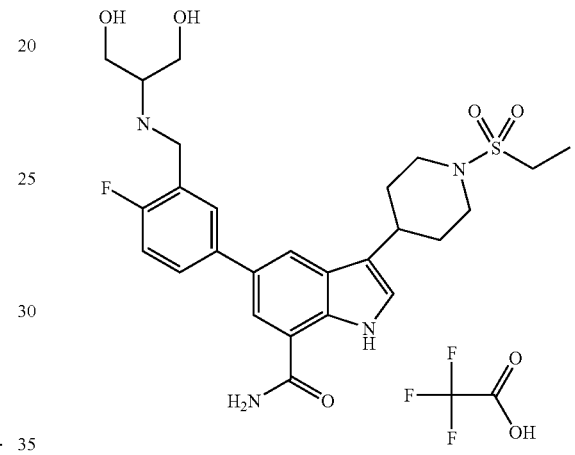

The title compound was prepared according to the general procedure of 5-{3-[(ethylamino)methyl]-4-fluorophenyl}-3-[1-(ethylsulfonyl)-4-piperidinyl]-1H-indole-7-carboxamide trifluoroacetate, substituting 2-amino-1,3-propanediol (42 mg, 0.46 mmol) for ethylamine to afford 21 mg of the title compound (42.7%).

LC/MS=m/z 533.2 [M+H] Ret. Time: 1.39 min.

Example 273

3-[1-(ethylsulfonyl)-4-piperidinyl]-5-[4-fluoro-3-({[(1S)-2-hydroxy-1-methylethyl]amino}methyl)phenyl]-1H-indole-7-carboxamide trifluoroacetate (salt)

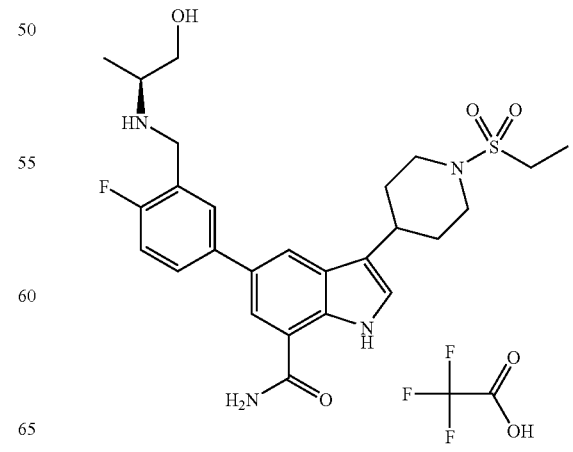

The title compound was prepared according to the general procedure of 5-{3-[(ethylamino)methyl]-4-fluorophenyl}-3-[1-(ethylsulfonyl)-4-piperidinyl]-1H-indole-7-carboxamide trifluoroacetate, substituting (2S)-2-amino-1-propanol (37 mg, 0.46 mmol) for ethylamine to afford 26 mg of the title compound (54.2%).

LC/MS=m/z 517.2 [M+H] Ret. Time: 1.44

Example 274

5-{3-[(cyclopropylamino)methyl]-4-fluorophenyl}-3-[1-(ethylsulfonyl)-4-piperidinyl]-1H-indole-7-carboxamide trifluoroacetate

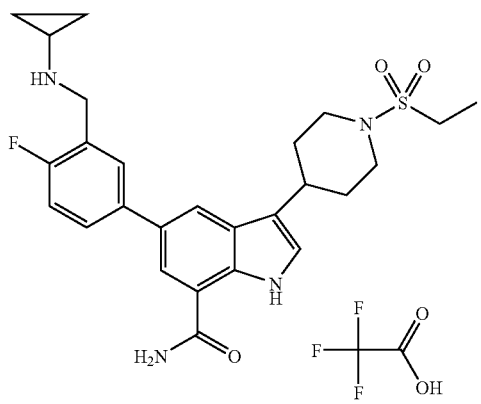

The title compound was prepared according to the general procedure of 5-{3-[(ethylamino)methyl]-4-fluorophenyl}-3-[1-(ethylsulfonyl)-4-piperidinyl]-1H-indole-7-carboxamide trifluoroacetate, substituting cyclopropylamine (32 mg, 0.46 mmol) for ethylamine to afford 23 mg of the title compound (49.4%).

LC/MS=m/z 499.6 [M+H] Ret. Time: 1.75 min.

Example 275

5-{3-[(cyclobutylamino)methyl]-4-fluorophenyl}-3-[1-(ethylsulfonyl)-4-piperidinyl]-1H-indole-7-carboxamide trifluoroacetate

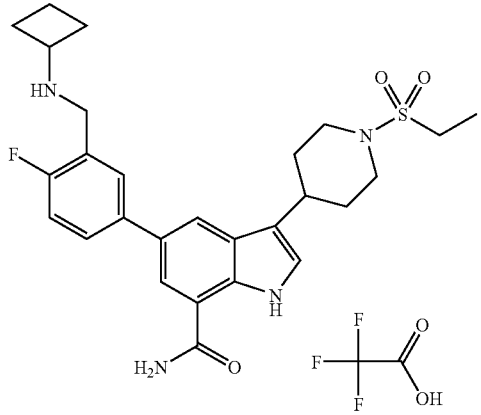

The title compound was prepared according to the general procedure of 5-{3-[(ethylamino)methyl]-4-fluorophenyl}-3-[1-(ethylsulfonyl)-4-piperidinyl]-1H-indole-7-carboxamide trifluoroacetate, substituting cyclobutanamine (39 mg, 0.46 mmol) for ethylamine to afford 20 mg of the title compound (42%).

LC/MS=m/z 513.2 [M+H] Ret. Time: 1.58 min.

Example 276

3-[1-(ethylsulfonyl)-4-piperidinyl]-5-[3-(1-pyrrolidinylmethyl)phenyl]-1H-indole-7-carboxamide trifluoroacetate

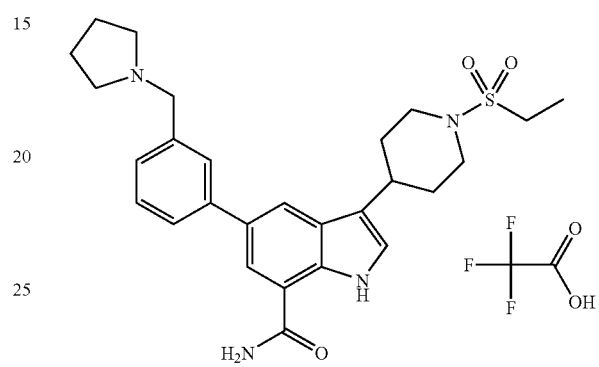

To a solution of 3-[1-(ethylsulfonyl)-4-piperidinyl]-5-(3-formylphenyl)-1H-indole-7-carboxamide (33 mg 0.74 mmol) in dichloromethane (0.5 mL) and methanol (0.5 mL) was added pyrrolidine (32 mg, 0.444 mmol) and 1 drop of acetic acid. The mixture was stirred for 2 min then sodium tetrahydridoborate (17.8 mg, 0.444 mmol) was added. This was then stirred overnight then concentrated and by Gilson Preparatory HPLC to give 9.7 mg of the title compound (21.5%)

LC/MS=m/z 495.4 [M+H] Ret. Time: 1.67 min.

Example 277

5-{3,5-bis[(ethylamino)methyl]phenyl}-3-[1-(ethylsulfonyl)-4-piperidinyl]-1H-indole-7-carboxamide trifluoroacetate

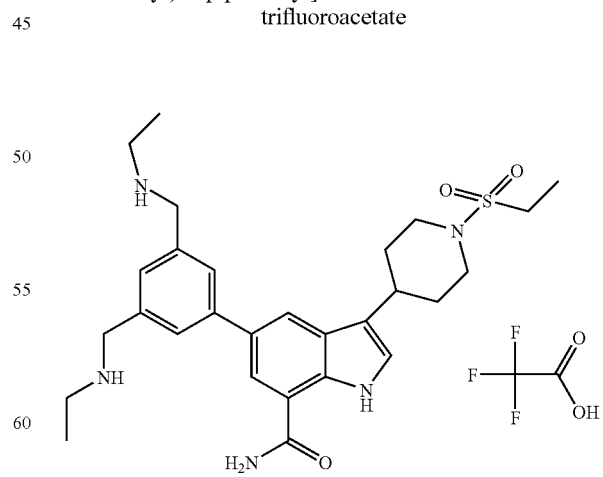

To a solution of 5-(3,5-diformylphenyl)-3-[1-(ethylsulfonyl)-4-piperidinyl]-1H-indole-7-carboxamide (27 mg, 0.058 mmol) in dichloromethane (1.5 mL) and methanol (1.5 mL) was added ethylamine (31.4 mg, 0.696 mmol) and 1 drop of acetic acid. The resulting mixture was stirred for 2 h then sodium tetrahydridoborate (13.2 mg, 0.348 mmol) was added. This was stirred for another 50 min then purified by Gilson Preparatory HPLC to give 20 mg of the title compound (53.9%).

LC/MS=m/z 526.6 [M+H] Ret. Time: 1.41 min.

Example 278

5-{3,5-bis[(dimethylamino)methyl]phenyl}-3-[1-(ethylsulfonyl)-4-piperidinyl]-1H-indole-7-carboxamide trifluoroacetate

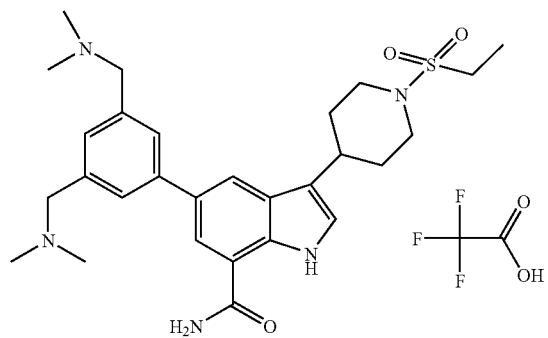

To a solution of 3-[1-(ethylsulfonyl)-4-piperidinyl]-5-(3-formyl-5-mercaptophenyl)-1H-indole-7-carboxamide (34 mg, 0.058 mmol) in dichloromethane (1.5 mL) and methanol (1.5 mL) was added dimethylamine (31.4 mg, 0.696 mmol) and a drop of acetic acid. The resulting mixture was stirred for 2 h at room temperature then sodium tetrahydridoborate (13.2 mg, 0.348 mmol) was added. This was stirred for another 30 min then purified by Gilson Preparatory HPLC to give 11 mg of the title compound (29.6%).

LC/MS=m/z 526.6 [M+H] Ret. Time: 1.27 min.

Example 279

3-[1-(ethylsulfonyl)-4-piperidinyl]-5-[3-(2-piperidinyl)phenyl]-1H-indole-7-carboxamide trifluoroacetate

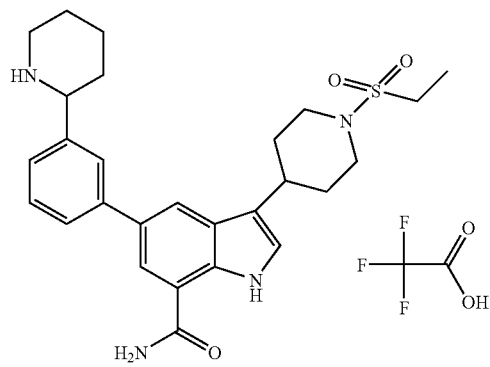

To a solution of 3-[1-(ethylsulfonyl)-4-piperidinyl]-5-(4,4,5,5-tetramethyl-1,3,2-dioxaborolan-2-yl)-1H-indole-7-carboxamide (46 mg, 0.1 mmol) in dioxane (2 mL) and H₂O (0.7 mL) was added 2-(3-chlorophenyl)piperidine (46 mg, 0.2 mmol). Potassium carbonate (55 mg, 0.4 mmol) and, after being degassed for 5 min, tetrakis(triphenylphosphine)palladium(0) (5 mg, 0.5 mmol) was added. The resulting mixture was reacted in a 300 W CEM microwave for 30 min at 160° C. then the solids were filtered off. The solvent was evaporated and the solution was purified by Gilson Preparatory HPLC to give 13.2 mg of the title compound (21.7%).

LC/MS=m/z 495.4 [M+H] Ret. Time: 1.76

Example 280

5-{3-[1-(ethylamino)ethyl]phenyl}-3-[1-(ethylsulfonyl)-4-piperidinyl]-1H-indole-7-carboxamide trifluoroacetate

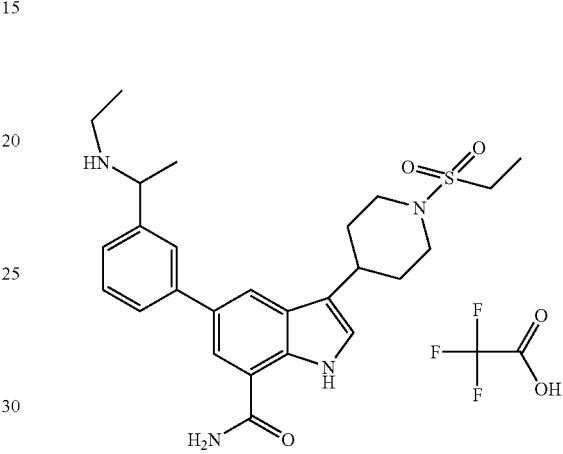

A solution of 5-(3-acetylphenyl)-3-[1-(ethylsulfonyl)-4-piperidinyl]-1H-indole-7-carboxamide (50 mg, 0.11 mmol), ethylamine (19.9 mg, 0.441 mmol) and sodium cyanoborohydride (30 mg, 0.441 mmol) in N,N-dimethylformamide (0.8 mL) and acetic acid (0.2 mL) was reacted in a microwave for 20 min at 150° C. The reaction was purified by Gilson Preparatory HPLC to give 20.6 mg of the title compound (39%).

LC/MS=m/z 483.2 [M+H] Ret. Time: 1.67

Example 281

5-{3-[1-(dimethylamino)ethyl]phenyl}-3-[1-(ethylsulfonyl)-4-piperidinyl]-1H-indole-7-carboxamide trifluoroacetate

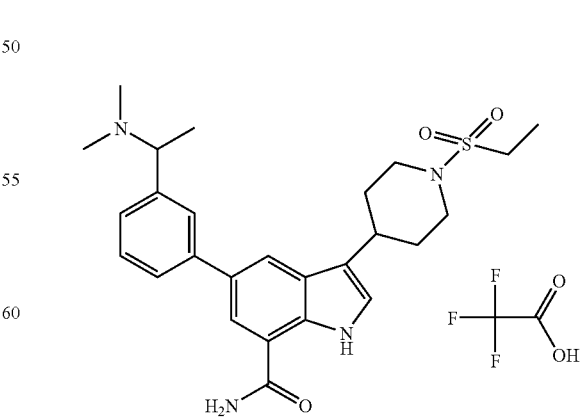

5-(3-acetylphenyl)-3-[1-(ethylsulfonyl)-4-piperidinyl]-1H-indole-7-carboxamide (50 mg, 0.11 mmol), dimethylamine (220 μL, 0.44 mmol) and sodium cyanoborohydride (30 mg, 0.44 mmol) were dissolved in N,N-dimethylformamide (400 μL) and acetic acid (100 μL). The resulting mixture was reacted in a Smith 150 W microwave for 20 min. at 150° C. The reaction was purified by Gilson Preparatory HPLC to give 14.6 mg of the title compound (22.2%).
LC/MS=m/z 483.2 [M+H] Ret. Time: 1.63

Example 282

3-[1-(ethylsulfonyl)-4-piperidinyl]-5-{3-fluoro-5-[(methylamino)methyl]phenyl}-1H-indole-7-carboxamide trifluoroacetate

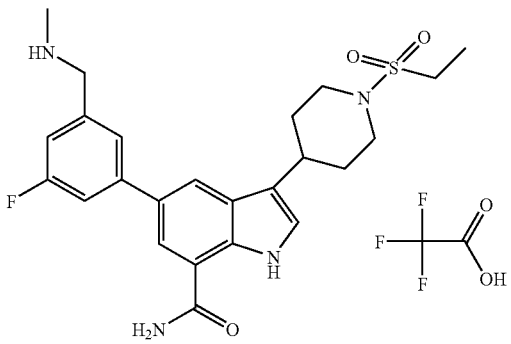

To a solution of 3-[1-(ethylsulfonyl)-4-piperidinyl]-5-(3-fluoro-5-formylphenyl)-1H-indole-7-carboxamide (32 mg, 0.07 mmol) in dichloromethane (1.5 mL) and methanol (1.5 mL) was added 2 M methylamine in THF (210 μl, 0.42 mmol) and 1 drop of acetic acid. The resulting mixture was stirred for 3 h at room temperature then sodium tetrahydridoborate (15 mg, 0.42 mmol) was added. This mixture was stirred for 1 hour then concentrated and purified by Gilson Preparatory HPLC to give 30 mg of the title compound (73.1%).
LC/MS=m/z 473.6 [M+H] Ret. Time: 1.73 min.

Example 283

5-{3-[(ethylamino)methyl]-5-fluorophenyl}-3-[1-(ethylsulfonyl)-4-piperidinyl]-1H-indole-7-carboxamide trifluoroacetate

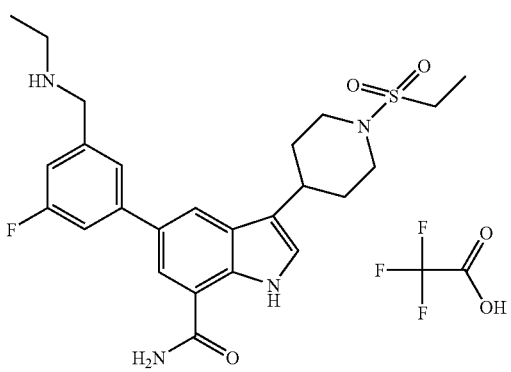

The title compound was prepared according to the general procedure of 3-[1-(ethylsulfonyl)-4-piperidinyl]-5-{3-fluoro-5-[(methylamino)methyl]phenyl}-1H-indole-7-carboxamide trifluoroacetate, substituting 2 M ethanamine in THF (210 ul, 0.42 mmol) for methanamine to afford 6.5 mg of the title compound (15.5%).
LC/MS=m/z 487.4 [M+H] Ret. Time: 1.64 min.

Example 284

3-[1-(ethylsulfonyl)-4-piperidinyl]-5-{3-fluoro-5-[(propylamino)methyl]phenyl}-1H-indole-7-carboxamide trifluoroacetate

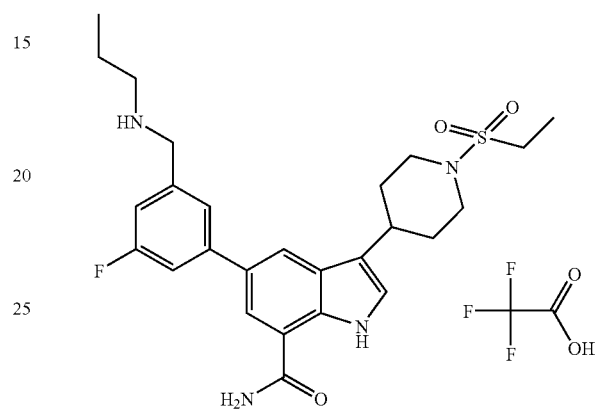

The title compound was prepared according to the general procedure of 3-[1-(ethylsulfonyl)-4-piperidinyl]-5-{3-fluoro-5-[(methylamino)methyl]phenyl}-1H-indole-7-carboxamide trifluoroacetate, substituting propylamine (21 mg, 0.42 mmol) for methanamine to afford 31 mg of the title compound (72%).
LC/MS=m/z 501.4 [M+H] Ret. Time: 1.54

Example 285

3-[1-(ethylsulfonyl)-4-piperidinyl]-5-(3-fluoro-5-{[(1-methylethyl)amino]methyl}phenyl)-1H-indole-7-carboxamide trifluoroacetate

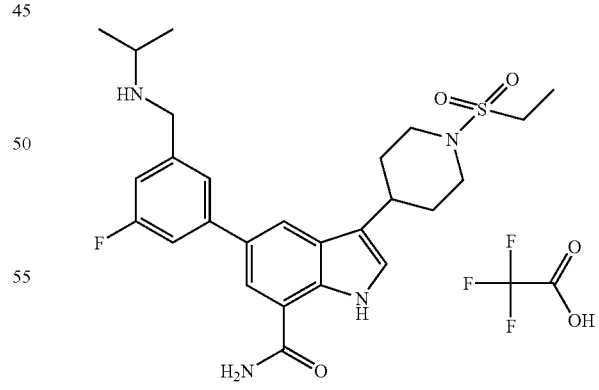

The title compound was prepared according to the general procedure of 3-[1-(ethylsulfonyl)-4-piperidinyl]-5-{3-fluoro-5-[(methylamino)methyl]phenyl}-1H-indole-7-carboxamide trifluoroacetate, substituting 2-propanamine (21 mg, 0.42 mmol) for methanamine to afford 28.5 mg of the title compound (66.2%).
LC/MS=m/z 501.4 [M+H] Ret. Time: 1.53 min.

Example 286

3-[1-(ethylsulfonyl)-4-piperidinyl]-5-(3-fluoro-5-{[(2-methylpropyl)amino]methyl}phenyl)-1H-indole-7-carboxamide trifluoroacetate

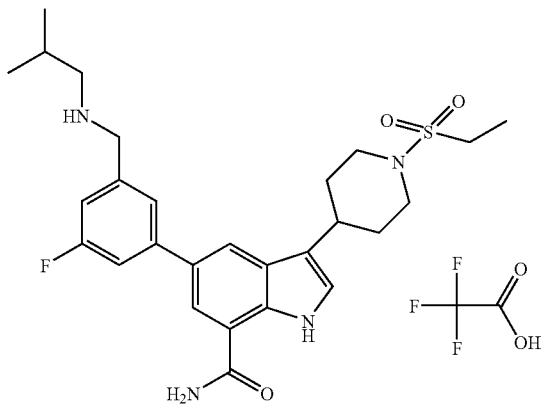

The title compound was prepared according to the general procedure of 3-[1-(ethylsulfonyl)-4-piperidinyl]-5-{3-fluoro-5-[(methylamino)methyl]phenyl}-1H-indole-7-carboxamide trifluoroacetate, substituting 2-methyl-1-propanamine (21 mg, 0.42 mmol) for methanamine to afford 10 mg of the title compound (22.7%).

LC/MS=m/z 515.4 [M+H] Ret. Time: 1.72 min.

Example 287

5-{3-[(cyclobutylamino)methyl]-5-fluorophenyl}-3-[1-(ethylsulfonyl)-4-piperidinyl]-1H-indole-7-carboxamide trifluoroacetate

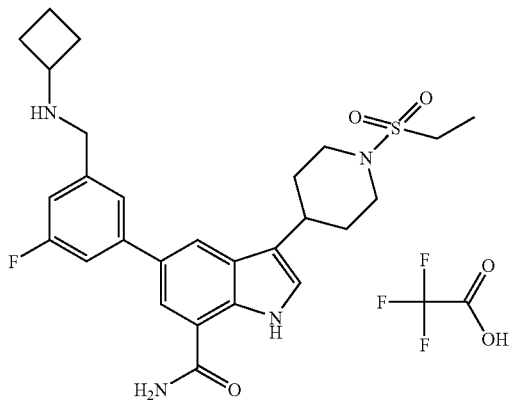

The title compound was prepared according to the general procedure of 3-[1-(ethylsulfonyl)-4-piperidinyl]-5-{3-fluoro-5-[(methylamino)methyl]phenyl}-1H-indole-7-carboxamide trifluoroacetate, substituting cyclobutylamine (21.5 mg, 0.42 mmol) for methanamine to afford 33 mg of the title compound (75.2%).

LC/MS=m/z 513.2 [M+H] Ret. Time: 1.50 min.

Example 288

5-{3-[(dimethylamino)methyl]-5-fluorophenyl}-3-[1-(ethylsulfonyl)-4-piperidinyl]-1H-indole-7-carboxamide trifluoroacetate

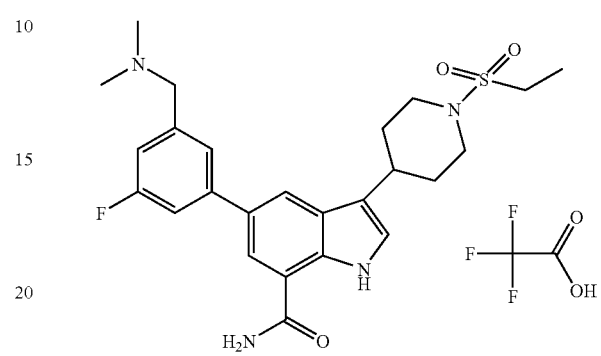

The title compound was prepared according to the general procedure of 3-[1-(ethylsulfonyl)-4-piperidinyl]-5-{3-fluoro-5-[(methylamino)methyl]phenyl}-1H-indole-7-carboxamide trifluoroacetate, substituting 2M dimethylamine in THF (210 ul, 0.42 mmol) for methanamine to afford 33.7 mg of the title compound (80.2%).

LC/MS=m/z 487.2 [M+H] Ret. Time: 1.43 min.

Example 289

3-[1-(ethylsulfonyl)-4-piperidinyl]-5-[3-fluoro-5-(1-pyrrolidinylmethyl)phenyl]-1H-indole-7-carboxamide trifluoroacetate

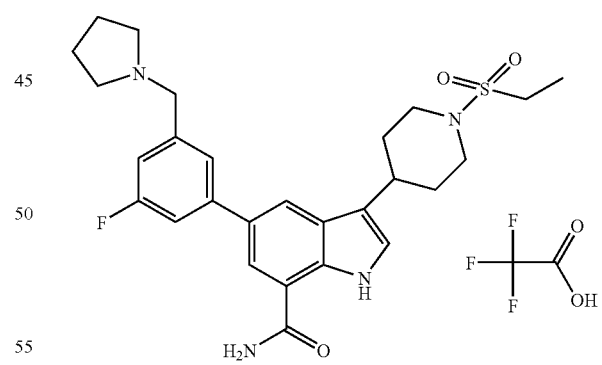

The title compound was prepared according to the general procedure of 3-[1-(ethylsulfonyl)-4-piperidinyl]-5-{3-fluoro-5-[(methylamino)methyl]phenyl}-1H-indole-7-carboxamide trifluoroacetate, substituting pyrrolidine (20.4 mg, 0.42 mmol) for methanamine to afford 18 mg of the title compound (41%).

LC/MS=m/z 513.4 [M+H] Ret. Time: 1.63 min.

Example 290

3-[1-(ethylsulfonyl)-4-piperidinyl]-5-[3-fluoro-5-(4-morpholinylmethyl)phenyl]-1H-indole-7-carboxamide trifluoroacetate

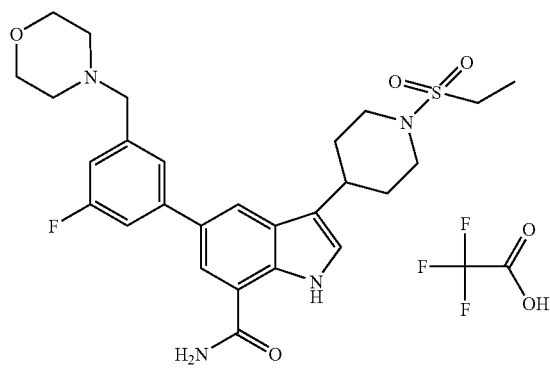

The title compound was prepared according to the general procedure of 3-[1-(ethylsulfonyl)-4-piperidinyl]-5-{3-fluoro-5-[(methylamino)methyl]phenyl}-1H-indole-7-carboxamide trifluoroacetate, substituting morpholine (22 mg, 0.42 mmol) for methanamine to afford 22.9 mg of the title compound (50.9%).

LC/MS=m/z 529.4 [M+H] Ret. Time: 1.47 min.

Example 291

3-[1-(ethylsulfonyl)-4-piperidinyl]-5-[3-fluoro-5-(1-piperidinylmethyl)phenyl]-1H-indole-7-carboxamide trifluoroacetate

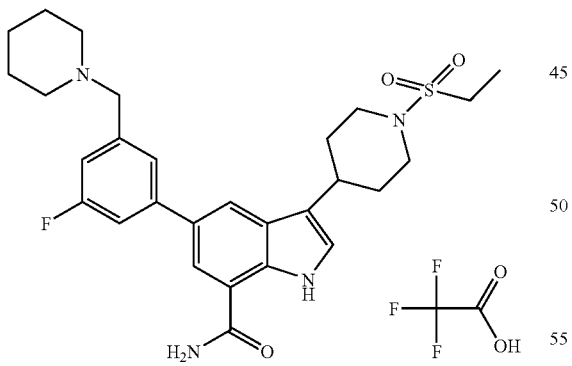

The title compound was prepared according to the general procedure of 3-[1-(ethylsulfonyl)-4-piperidinyl]-5-{3-fluoro-5-[(methylamino)methyl]phenyl}-1H-indole-7-carboxamide trifluoroacetate, substituting piperidine (22 mg, 0.42 mmol) for methanamine to afford 13.4 mg of the title compound (29.9%).

LC/MS=m/z 527.6 [M+H] Ret. Time: 1.62

Example 292

3-[1-(ethylsulfonyl)-4-piperidinyl]-5-{3-[1-(methylamino)ethyl]phenyl}-1H-indole-7-carboxamide trifluoroacetate

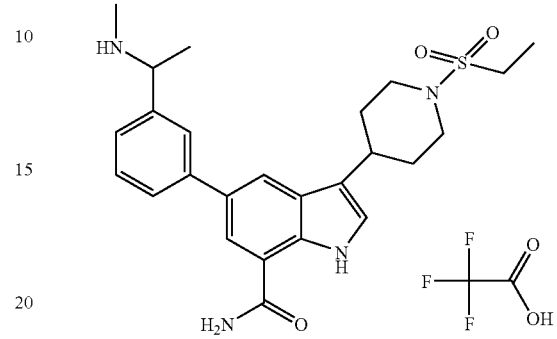

To a solution of 5-(3-acetylphenyl)-3-[1-(ethylsulfonyl)-4-piperidinyl]-1H-indole-7-carboxamide (20 mg, 0.044 mmol) in ethanol was added methylamine hydrochloride salt and 1 drop of concentrated hydrochloride. The mixture was reacted in a CEM microwave at 100° C. for 10 min then sodium tetrahydridoborate was added. The resulting mixture was reacted in a CEM microwave at 50° C. for 5 min then all solvent was evaporated. It was again dissolved in dimethyl sulfoxide then purified by Gilson Preparatory HPLC to afford 16.5 mg of the title compound (64.4%).

LC/MS=m/z 469.4 [M+H] Ret. Time: 1.45 min.

Example 293

3-[1-(ethylsulfonyl)-4-piperidinyl]-5-(3-{1-[(1-methylethyl)amino]ethyl}phenyl)-1H-indole-7-carboxamide trifluoroacetate

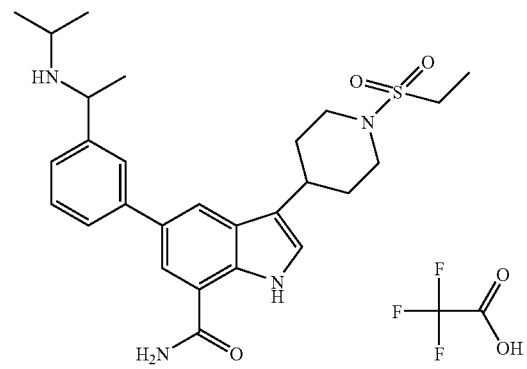

To a solution of 5-(3-acetylphenyl)-3-[1-(ethylsulfonyl)-4-piperidinyl]-1H-indole-7-carboxamide (20 mg, 0.044 mmol), in N,N-dimethylformamide (0.8 mL) and acetic acid (0.2 mL) was added 2-propanamine (75 µL, 0.88 mmol) and sodium cyanoborohydride (6 mg, 0.09 mmol). The resulting mixture was reacted in a Smith microwave at 70° C. for 1 h. The solid was filtered off and then purified by Gilson Preparatory HPLC to afford 19.4 mg of the title compound (72.2%).

LC/MS=m/z 497.4 [M+H] Ret. Time: 1.44 min.

Example 294

3-[1-(ethylsulfonyl)-4-piperidinyl]-5-(3-{1-[(2-methylpropyl)amino]ethyl}phenyl)-1H-indole-7-carboxamide trifluoroacetate

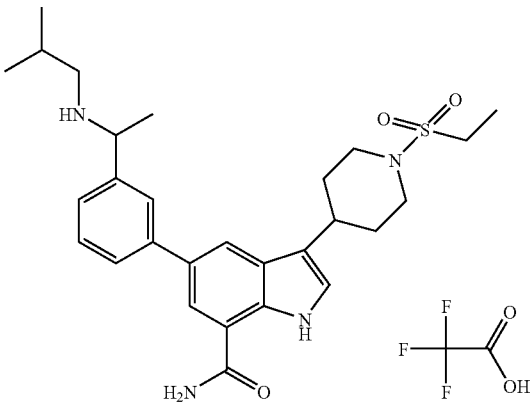

To a solution of 5-(3-acetylphenyl)-3-[1-(ethylsulfonyl)-4-piperidinyl]-1H-indole-7-carboxamide (30 mg, 0.066 mmol), in ethanol (1.2 mL) and acetic acid (0.3 mL) was added (2-methylpropyl)amine (101 mg, 1.98 mmol) and sodium cyanoborohydride (13.5 mg, 0.198 mmol). The resulting mixture was reacted in a Smith microwave at 70° C. for 1 h. All solvent was evaporated and dimethyl sulfoxide was used to dissolve the solid. It was then purified by Gilson Preparatory HPLC to afford 22.7 mg of the title compound (55.1%).

LC/MS=m/z 511.2 [M+H] Ret. Time: 1.52 min.

Example 295

5-{3-[1-(cyclobutylamino)ethyl]phenyl}-3-[1-(ethylsulfonyl)-4-piperidinyl]-1H-indole-7-carboxamide trifluoroacetate

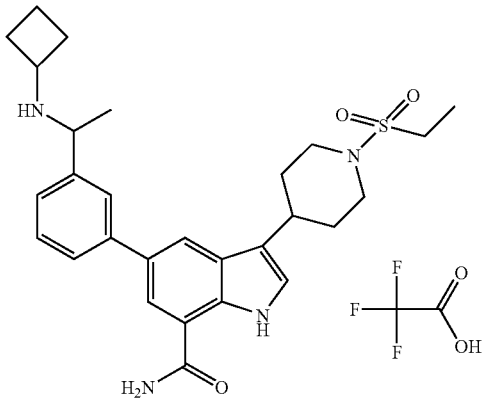

The title compound was prepared according to the general procedure of 3-[1-(ethylsulfonyl)-4-piperidinyl]-5-(3-{1-[(2-methylpropyl)amino]ethyl}phenyl)-1H-indole-7-carboxamide trifluoroacetate, substituting cyclobutylamine (101 mg, 1.98 mmol) for (2-methylpropyl)amine to afford 29.1 mg of the title compound (70.8%).

LC/MS=m/z 509.4 [M+H] Ret. Time: 1.52 min.

Example 296

3-[1-(ethylsulfonyl)-4-piperidinyl]-5-{3-[1-(1-pyrrolidinyl)ethyl]phenyl}-1H-indole-7-carboxamide trifluoroacetate

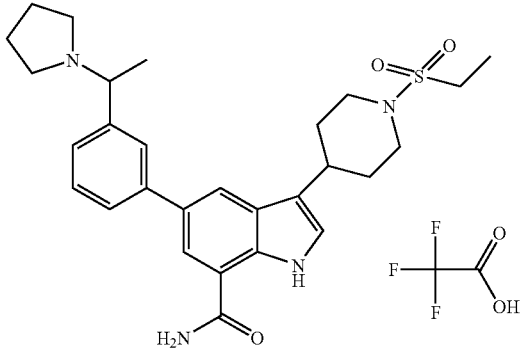

The title compound was prepared according to the general procedure of 3-[1-(ethylsulfonyl)-4-piperidinyl]-5-(3-{1-[(2-methylpropyl)amino]ethyl}phenyl)-1H-indole-7-carboxamide trifluoroacetate, substituting pyrrolidine (101 mg, 1.98 mmol) for (2-methylpropyl)amine to afford 29.2 mg of the title compound (71%).

LC/MS=m/z 509.4 [M+H] Ret. Time: 1.49 min.

Example 297

3-[1-(ethylsulfonyl)-4-piperidinyl]-5-[3-(3-thiomorpholinyl)phenyl]-1H-indole-7-carboxamide trifluoroacetate

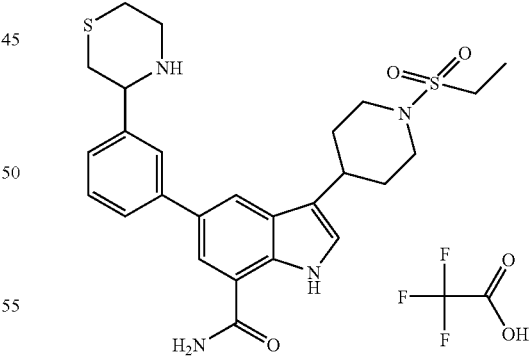

To a solution of 3-[1-(ethylsulfonyl)-4-piperidinyl]-5-(4,4,5,5-tetramethyl-1,3,2-dioxaborolan-2-yl)-1H-indole-7-carboxamide (60 mg, 0.13 mmol) in dioxane (1.5 mL) and water (0.5 mL) was added 3-(3-chlorophenyl)thiomorpholine (84 mg, 0.39 mmol) and potassium carbonate (107.6 mg, 0.78 mmol). This mixture was degassed for 5 min then tetrakis (triphenylphosphine)palladium(0) (14.0 mg, 0.013 mmol) was added. The resulting mixture was reacted in a microwave for 30 min at 160° C. The solid was filtered off and all solvents were evaporated. The resulting solution was re-dissolved in dichloromethane and separator was used to remove water. The mixture was concentrated to give organic solvent and then purified by Gilson Preparatory HPLC to give 7.4 mg of the title compound (11%).

LC/MS=m/z 513.4 [M+H] Ret. Time: 1.54

Example 298

3-[1-(ethylsulfonyl)-4-piperidinyl]-5-[5-(2-piperazinyl)-2-thienyl]-1H-indole-7-carboxamide trifluoroacetate

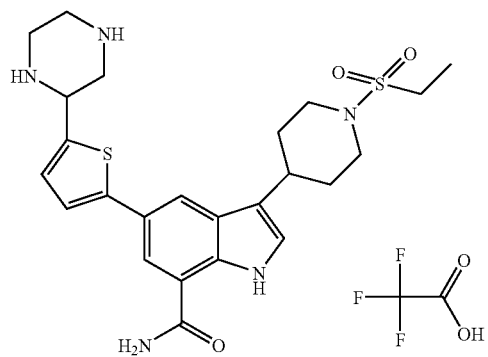

To a solution of 3-[1-(ethylsulfonyl)-4-piperidinyl]-5-(4,4,5,5-tetramethyl-1,3,2-dioxaborolan-2-yl)-1H-indole-7-carboxamide (60 mg, 0.13 mmol) in dioxane (1.5 mL) and water (0.5 mL) was added 2-(5-bromo-2-thienyl)piperazine (102 mg, 0.39 mmol) and potassium carbonate (108 mg, 0.78 mmol). This mixture was degassed for 5 min then tetrakis(triphenylphosphine)palladium(0) (15.0 mg, 0.013 mmol) was added. The resulting mixture was reacted in a microwave for 30 min at 160° C. The solid was filtered off and all solvents were evaporated. The resulting solution was re-dissolved in dichloromethane and separator was used to remove water. The mixture was concentrated to give organic solvent and then purified by Gilson Preparatory HPLC to give 29.1 mg of the title compound (36.4%).

LC/MS=m/z 502.4 [M+H] Ret. Time: 1.31

Example 299

3-[1-(ethylsulfonyl)-4-piperidinyl]-5-[4-(2-piperazinyl)phenyl]-1H-indole-7-carboxamide trifluoroacetate

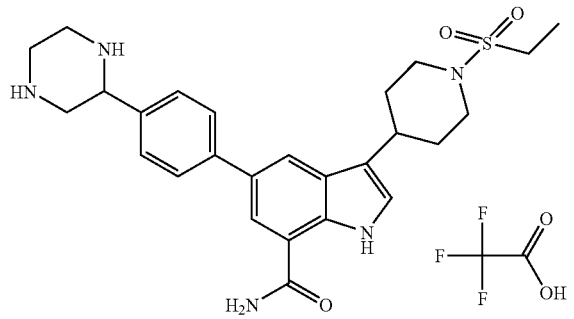

The title compound was prepared according to the general procedure of 3-[1-(ethylsulfonyl)-4-piperidinyl]-5-[5-(2-piperazinyl)-2-thienyl]-1H-indole-7-carboxamide trifluoroacetate, substituting 2-(4-bromophenyl)piperazine (94 mg, 0.39 mmol) for 2-(5-bromo-2-thienyl)piperazine to afford 20.5 mg of the title compound (25.9%).

LC/MS=m/z 496.4 [M+H] Ret. Time: 1.25

Example 300

3-[1-(ethylsulfonyl)-4-piperidinyl]-5-[3-(2-piperazinyl)phenyl]-1H-indole-7-carboxamide trifluoroacetate

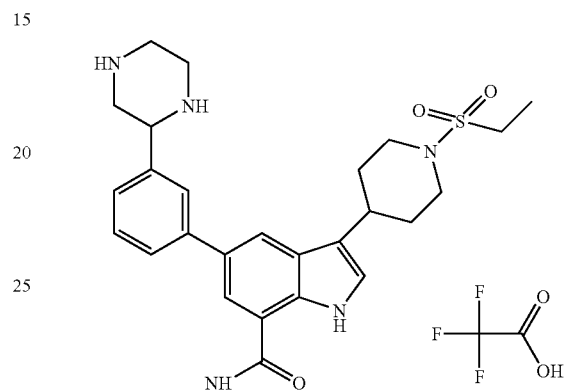

To a solution of 3-[1-(ethylsulfonyl)-4-piperidinyl]-5-(4,4,5,5-tetramethyl-1,3,2-dioxaborolan-2-yl)-1H-indole-7-carboxamide (60 mg, 0.13 mmol) in dioxane (1.5 mL) and water (0.5 mL) was added 2-(3-chlorophenyl)piperazine (63.7 mg, 0.325 mmol) and potassium carbonate (90 mg, 0.650 mmol). This mixture was degassed for 5 min then tetrakis(triphenylphosphine)palladium(0) (12 mg, 0.011 mmol) was added. The resulting mixture was reacted in a microwave for 30 min at 160° C. The solid was filtered off and all solvents were evaporated. The resulting solution was re-dissolved in dichloromethane and separator was used to remove water. The mixture was concentrated to give organic solvent and then purified by Gilson Preparatory HPLC to give 21.7 mg of the title compound (27.4%).

LC/MS=m/z 496.4 [M+H] Ret. Time: 1.28 min.

Example 301

3-[1-(ethylsulfonyl)-4-piperidinyl]-5-[6-(4-morpholinyl)-3-pyridazinyl]-1H-indole-7-carboxamide trifluoroacetate

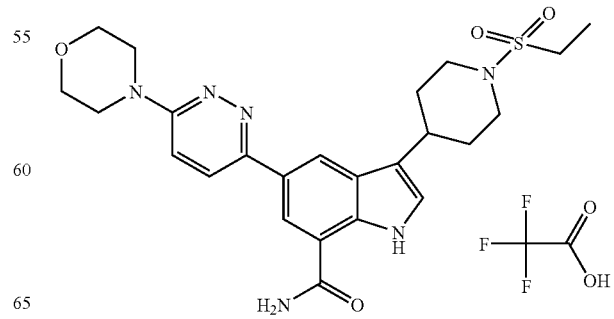

The title compound was prepared according to the general procedure of 3-[1-(ethylsulfonyl)-4-piperidinyl]-5-[3-(2-piperazinyl)phenyl]-1H-indole-7-carboxamide trifluoroacetate, substituting 4-(6-chloro-3-pyridazinyl)morpholine (65 mg, 0.325 mmol) for 2-(3-chlorophenyl)piperazine to afford 3.1 mg of the title compound (3.9%).

LC/MS=m/z 499.6 [M+H] Ret. Time: 1.57 min.

Example 302

3-[1-(ethylsulfonyl)-4-piperidinyl]-5-[6-(1-pyrrolidinyl)-3-pyridazinyl]-1H-indole-7-carboxamide trifluoroacetate

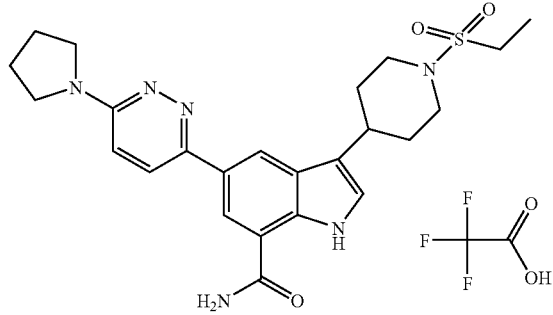

The title compound was prepared according to the general procedure of 3-[1-(ethylsulfonyl)-4-piperidinyl]-5-[3-(2-piperazinyl)phenyl]-1H-indole-7-carboxamide trifluoroacetate, substituting 3-chloro-6-(1-pyrrolidinyl)pyridazine (60 mg, 0.325 mmol) for 2-(3-chlorophenyl)piperazine to afford 4.1 mg of the title compound (5.3%).

LC/MS=m/z 483.2 [M+H] Ret. Time: 1.44 min.

Example 303

3-[1-(ethylsulfonyl)-4-piperidinyl]-5-{2-[(methylamino)methyl]phenyl}-1H-indole-7-carboxamide trifluoroacetate

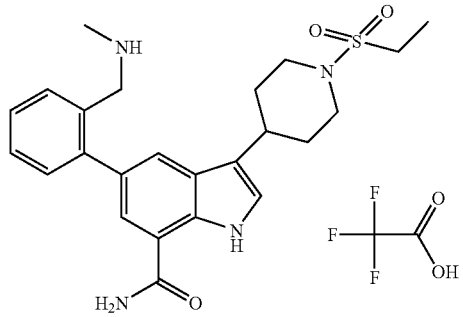

The title compound was prepared according to the general procedure of 3-[1-(ethylsulfonyl)-4-piperidinyl]-5-[3-(2-piperazinyl)phenyl]-1H-indole-7-carboxamide trifluoroacetate, substituting 1-(2-bromophenyl)-N-methylmethanamine (65 mg, 0.325 mmol) for 2-(3-chlorophenyl)piperazine to afford 14.6 mg of the title compound (19.8%).

LC/MS=m/z 455.0 [M+H] Ret. Time: 1.57 min.

Example 304

3-[1-(ethylsulfonyl)-4-piperidinyl]-5-(3-{[(2-thienylmethyl)amino]methyl}phenyl)-1H-indole-7-carboxamide trifluoroacetate

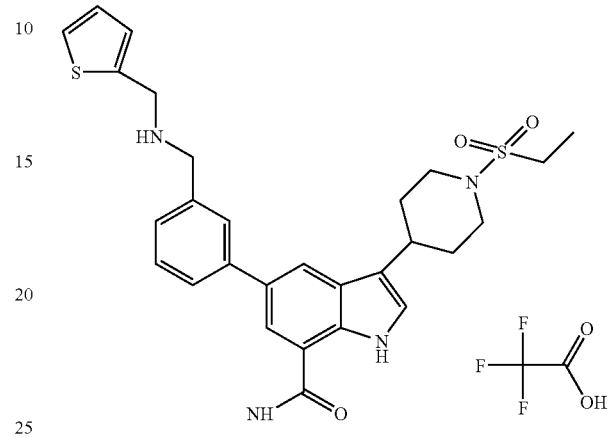

To a solution of 3-[1-(ethylsulfonyl)-4-piperidinyl]-5-(3-formylphenyl)-1H-indole-7-carboxamide (44 mg, 0.1 mmol) in dichloromethane (2 mL) and methanol (2 mL) was added 1-(2-thienyl)methanamine (33.6 mg, 0.6 mmol) and 1 drop of acetic acid. This mixture was stirred for 2 h then sodium tetrahydridoborate (22.8 mg, 0.6 mmol) was added. The resulting mixture was stirred for 1 h. It was then concentrated and again dissolved in dimethyl sulfoxide (3 mL). It was then purified by Gilson Preparatory HPLC to give 41.7 mg of the title compound (74.5%).

LC/MS=m/z 537.2 [M+H] Ret. Time: 1.81 min.

Example 305

3-[1-(ethylsulfonyl)-4-piperidinyl]-5-[3-({[(5-methyl-2-furanyl)methyl]amino}methyl)phenyl]-1H-indole-7-carboxamide trifluoroacetate

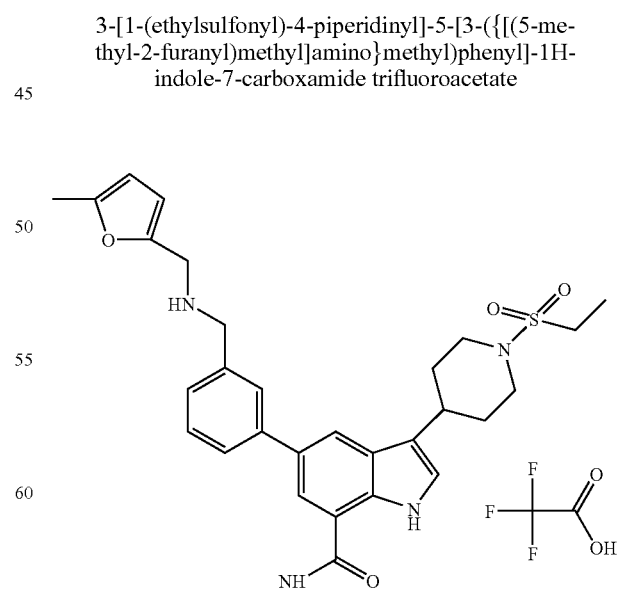

The title compound was prepared according to the general procedure of 3-[1-(ethylsulfonyl)-4-piperidinyl]-5-(3-{[(2- thienylmethyl)amino]methyl}phenyl)-1H-indole-7-carboxamide trifluoroacetate, substituting 1-(5-methyl-2-furanyl)methanamine (32 mg, 0.6 mmol) for 1-(2-thienyl)methanamine to afford 29.3 mg of the title compound (54.7%).

LC/MS=m/z 535.2 [M+H] Ret. Time: 1.74 min.

Example 306

3-[1-(ethylsulfonyl)-4-piperidinyl]-5-[3-({[(2R)-tetrahydro-2-furanylmethyl]amino}methyl)phenyl]-1H-indole-7-carboxamide trifluoroacetate

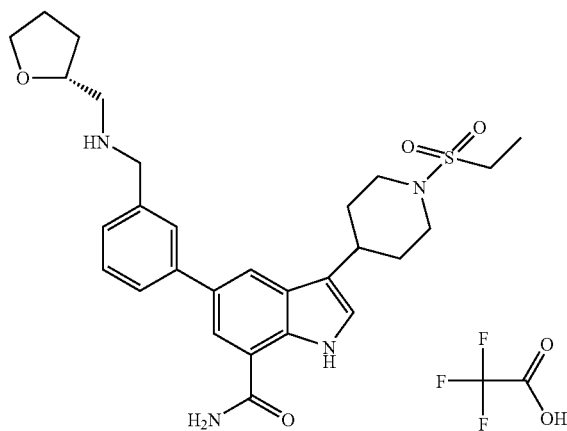

The title compound was prepared according to the general procedure of 3-[1-(ethylsulfonyl)-4-piperidinyl]-5-(3-{[(2-thienylmethyl)amino]methyl}phenyl)-1H-indole-7-carboxamide trifluoroacetate, substituting 1-[(2R)-tetrahydro-2-furanyl]methanamine (31.5 mg, 0.6 mmol) for 1-(2-thienyl)methanamine to afford 36.9 mg of the title compound (70.3%).

LC/MS=m/z 525.6 [M+H] Ret. Time: 1.63 min.

Example 307

3-[1-(ethylsulfonyl)-4-piperidinyl]-5-[3-({[(2S)-tetrahydro-2-furanylmethyl]amino}methyl)phenyl]-1H-indole-7-carboxamide trifluoroacetate

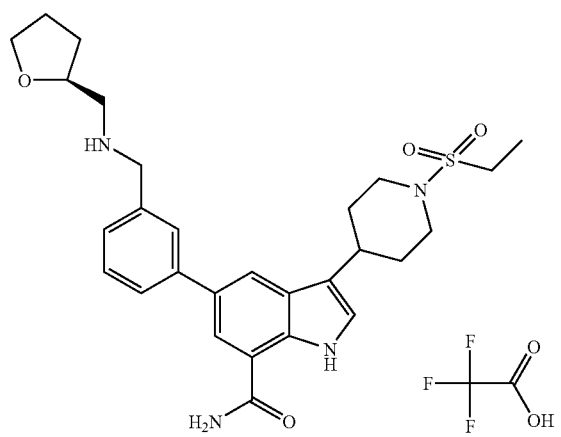

The title compound was prepared according to the general procedure of 3-[1-(ethylsulfonyl)-4-piperidinyl]-5-(3-{[(2-thienylmethyl)amino]methyl}phenyl)-1H-indole-7-carboxamide trifluoroacetate, substituting 1-[(2S)-tetrahydro-2-furanyl]methanamine (31.5 mg, 0.6 mmol) for 1-(2-thienyl)methanamine to afford 39.2 mg of the title compound (74.7%).

LC/MS=m/z 525.6 [M+H] Ret. Time: 1.61 min.

Example 308

5-(3-{[(2,2-dimethylpropyl)amino]methyl}phenyl)-3-[1-(ethylsulfonyl)-4-piperidinyl]-1H-indole-7-carboxamide trifluoroacetate

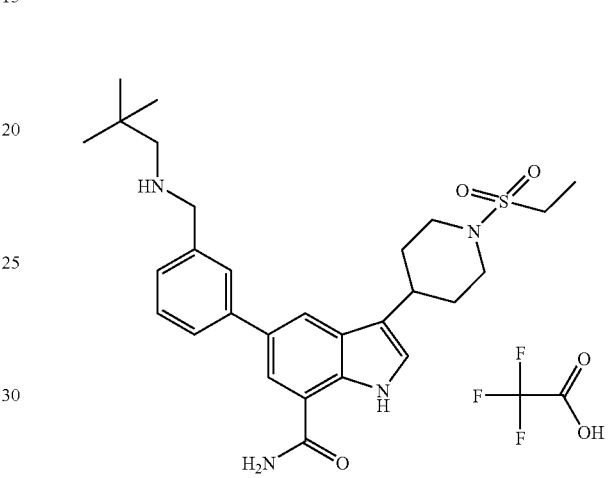

The title compound was prepared according to the general procedure of 3-[1-(ethylsulfonyl)-4-piperidinyl]-5-(3-{[(2-thienylmethyl)amino]methyl}phenyl)-1H-indole-7-carboxamide trifluoroacetate, substituting 2,2-dimethyl-1-propanamine (30.6 mg, 0.6 mmol) for 1-(2-thienyl)methanamine to afford 30.4 mg of the title compound (59.5%).

LC/MS=m/z 511.4 [M+H] Ret. Time: 1.69 min.

Example 309

3-[1-(ethylsulfonyl)-4-piperidinyl]-5-(3-{[(2-methylbutyl)amino]methyl}phenyl)-1H-indole-7-carboxamide

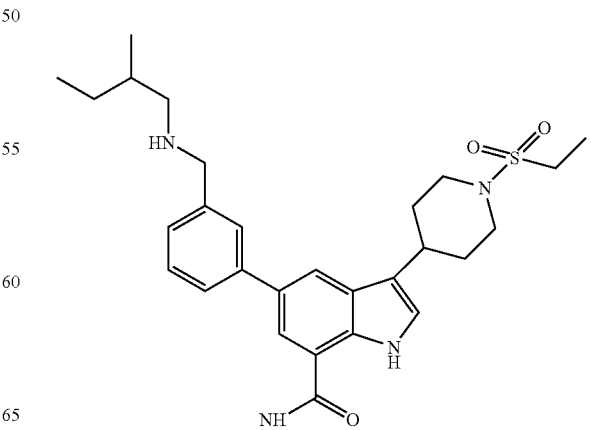

To a solution of 3-[1-(ethylsulfonyl)-4-piperidinyl]-5-(3-formylphenyl)-1H-indole-7-carboxamide (44 mg, 0.1 mmol) in dichloromethane (2 mL) and methanol (1 mL) was added 2-methyl-1-butanamine (52 mg, 0.6 mmol) and 1 drop of acetic acid. This mixture was stirred for 2 h then sodium tetrahydridoborate (22.8 mg, 0.6 mmol) was added. The resulting mixture was stirred for 1 h. It was then concentrated and again dissolved in dimethyl sulfoxide (3 mL). It was then purified by Gilson Preparatory HPLC to give 28.4 mg of the title compound (55.6%).

LC/MS=m/z 511.4 [M+H] Ret. Time: 1.71

Example 310

3-[1-(ethylsulfonyl)-4-piperidinyl]-5-[3-({[(2S)-2-methylbutyl]amino}methyl)phenyl]-1H-indole-7-carboxamide

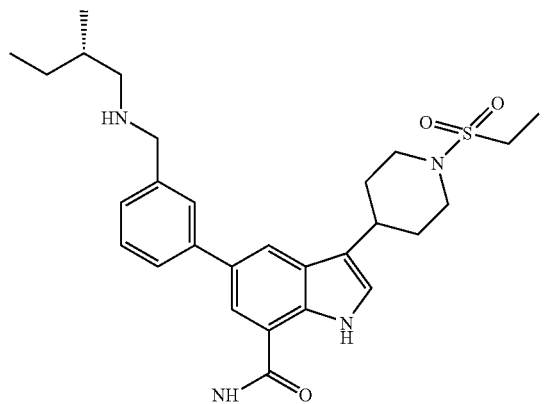

The title compound was prepared according to the general procedure of 3-[1-(ethylsulfonyl)-4-piperidinyl]-5-(3-{[(2-methylbutyl)amino]methyl}phenyl)-1H-indole-7-carboxamide, substituting (2S)-2-methyl-1-butanamine (52 mg, 0.6 mmol) for 2-methyl-1-butanamine to afford 30 mg of the title compound (58.7%).

LC/MS=m/z 511.4 [M+H] Ret. Time: 1.68

Example 311

3-[1-(ethylsulfonyl)-4-piperidinyl]-5-[3-({[(1R)-1,2,2-trimethylpropyl]amino}methyl)phenyl]-1H-indole-7-carboxamide

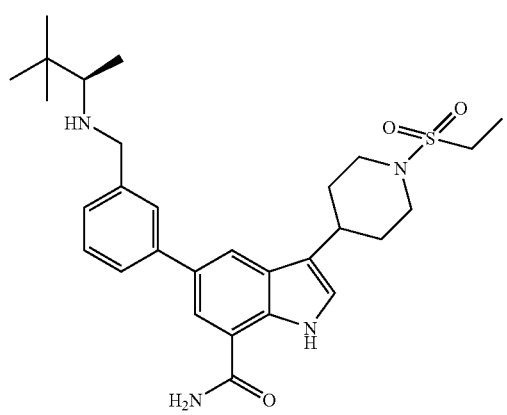

The title compound was prepared according to the general procedure of 3-[1-(ethylsulfonyl)-4-piperidinyl]-5-(3-{[(2-methylbutyl)amino]methyl}phenyl)-1H-indole-7-carboxamide, substituting (2R)-3,3-dimethyl-2-butanamine (60 mg, 0.6 mmol) for 2-methyl-1-butanamine to afford 24.5 mg of the title compound (46.7%).

LC/MS=m/z 525.6 [M+H] Ret. Time: 1.67

Example 312

3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate

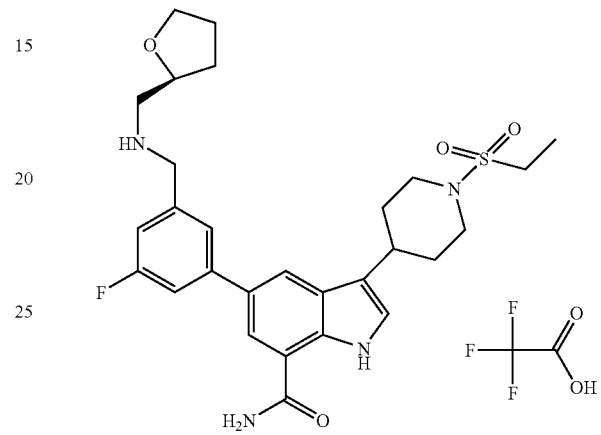

To a solution of 3-[1-(ethylsulfonyl)-4-piperidinyl]-5-(3-fluoro-5-formylphenyl)-1H-indole-7-carboxamide (40 mg, 0.087 mmol) in dichloromethane (2 mL) and methane (1 mL) was added 1-[(2S)-tetrahydro-2-furanyl]methanamine (53 mg, 0.525 mmol) and 2 drops of acetic acid. The resulting mixture was stirred for 2 h at room temperature followed by an addition of sodium tetrahydridoborate (20 mg, 0.525 mmol). This mixture was stirred for 30 min then concentrated and purified by Gilson Preparatory HPLC to give 26.6 mg of the title compound (46.6%).

LC/MS=m/z 543.4 [M+H] Ret. Time: 1.60 min.

Example 313

3-[1-(ethylsulfonyl)-4-piperidinyl]-5-[3-fluoro-5-({[(2R)-tetrahydro-2-furanylmethyl]amino}methyl)phenyl]-1H-indole-7-carboxamide trifluoroacetate

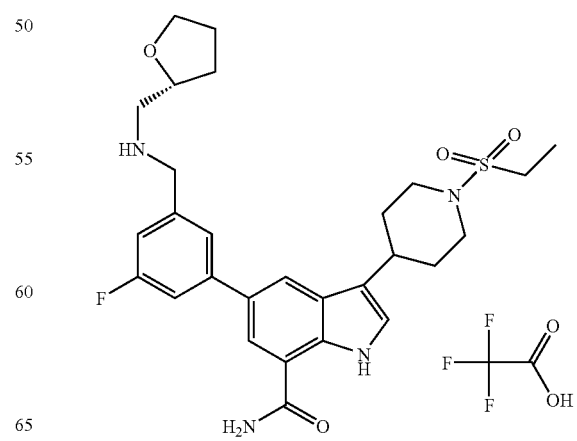

The title compound was prepared according to the general procedure of 3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate, substituting 1-[(2R)-tetrahydro-2-furanyl]methanamine (53 mg, 0.525 mmol) for 1-[(2S)-tetrahydro-2-furanyl]methanamine to afford 27.1 mg of the title compound (47.4%).

LC/MS=m/z 543.4 [M+H] Ret. Time: 1.58 min.

Example 314

5-[3-({[(1S)-1,2-dimethylpropyl]amino}methyl)-5-fluorophenyl]-3-[1-(ethylsulfonyl)-4-piperidinyl]-1H-indole-7-carboxamide

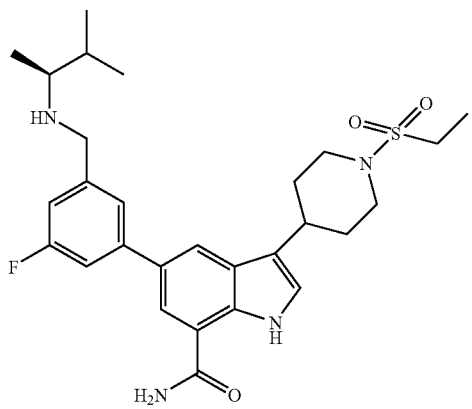

The title compound was prepared according to the general procedure of 3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate, substituting (2S)-3-methyl-2-butanamine (45 mg, 0.525 mmol) for 1-[(2S)-tetrahydro-2-furanyl]methanamine to afford 19.3 mg of the title compound (42%).

LC/MS=m/z 529.6 [M+H] Ret. Time: 1.65

Example 315

5-[3-({[(1R)-1,2-dimethylpropyl]amino}methyl)-5-fluorophenyl]-3-[1-(ethylsulfonyl)-4-piperidinyl]-1H-indole-7-carboxamide trifluoroacetate

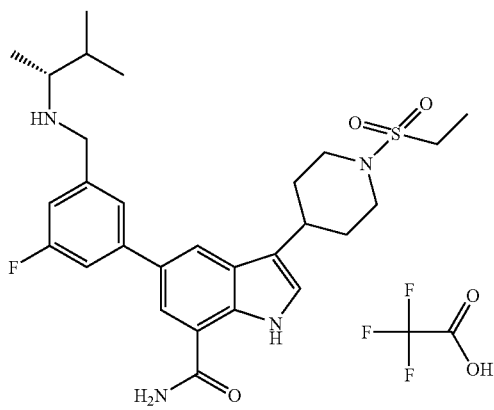

The title compound was prepared according to the general procedure of 3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate, substituting (2R)-3-methyl-2-butanamine (45 mg, 0.525 mmol) for 1-[(2S)-tetrahydro-2-furanyl]methanamine to afford 19.5 mg of the title compound (34.9%).

LC/MS=m/z 529.4 [M+H] Ret. Time: 1.82 min.

Example 316

3-[1-(ethylsulfonyl)-4-piperidinyl]-5-(3-fluoro-5-{[(1-methylpropyl)amino]methyl}phenyl)-1H-indole-7-carboxamide trifluoroacetate

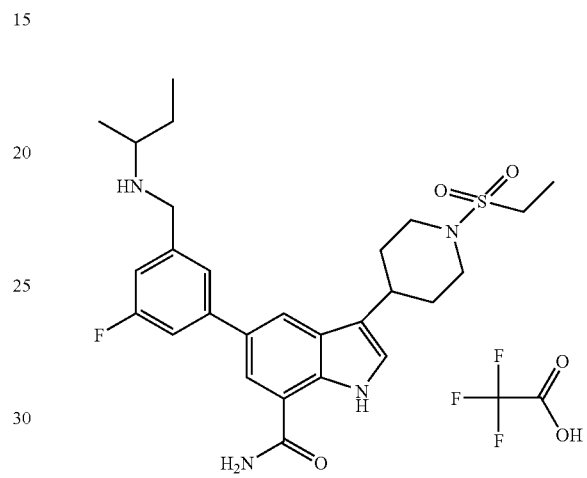

The title compound was prepared according to the general procedure of 3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate, substituting 2-butanamine (37 mg, 0.525 mmol) for 1-[(2S)-tetrahydro-2-furanyl]methanamine to afford 27.7 mg of the title compound (50.6%).

LC/MS=m/z 515.4 [M+H] Ret. Time: 1.63 min.

Example 317

3-[1-(ethylsulfonyl)-4-piperidinyl]-5-[3-fluoro-5-({[(1S)-1,2,2-trimethylpropyl]amino}methyl)phenyl]-1H-indole-7-carboxamide trifluoroacetate

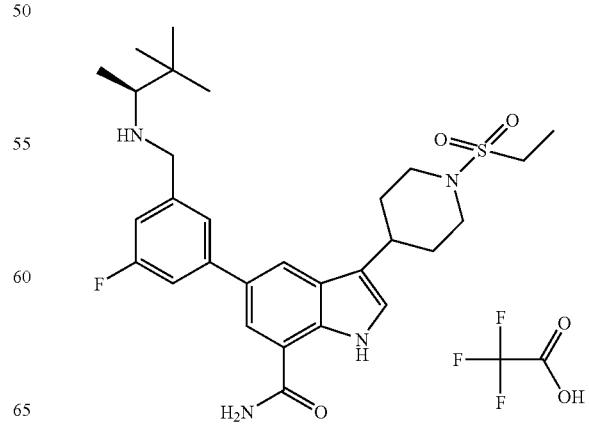

The title compound was prepared according to the general procedure of 3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate, substituting (2S)-3,3-dimethyl-2-butanamine (52 mg, 0.525 mmol) for 1-[(2S)-tetrahydro-2-furanyl]methanamine to afford 19.8 mg of the title compound (34.7%).

LC/MS=m/z 543.4 [M+H] Ret. Time: 1.78 min.

Example 318

3-[1-(ethylsulfonyl)-4-piperidinyl]-5-[3-fluoro-5-({[(2S)-2-methylbutyl]amino}methyl)phenyl]-1H-indole-7-carboxamide trifluoroacetate

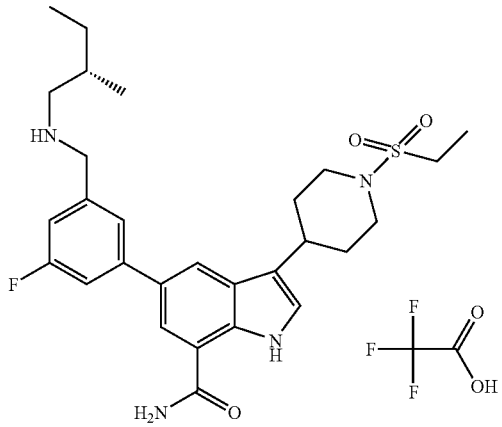

The title compound was prepared according to the general procedure of 3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate, substituting (2S)-2-methyl-1-butanamine (45 mg, 0.525 mmol) for 1-[(2S)-tetrahydro-2-furanyl]methanamine to afford 23.3 mg of the title compound (41.7%).

LC/MS=m/z 529.4 [M+H] Ret. Time: 1.62 min.

Example 319

3-[1-(ethylsulfonyl)-4-piperidinyl]-5-(3-fluoro-5-{[(2-methylbutyl)amino]methyl}phenyl)-1H-indole-7-carboxamide trifluoroacetate

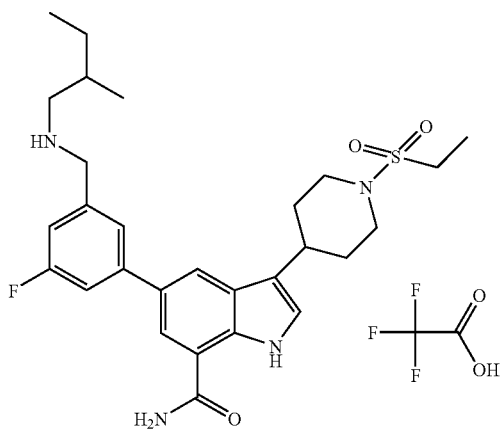

The title compound was prepared according to the general procedure of 3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate, substituting 2-methyl-1-butanamine (45 mg, 0.525 mmol) for 1-[(2S)-tetrahydro-2-furanyl]methanamine to afford 30.5 mg of the title compound (54.5%).

LC/MS=m/z 529.4 [M+H] Ret. Time: 1.73 min.

Example 320

3-[1-(ethylsulfonyl)-4-piperidinyl]-5-[3-fluoro-5-({[(1R)-1,2,2-trimethylpropyl]amino}methyl)phenyl]-1H-indole-7-carboxamide trifluoroacetate

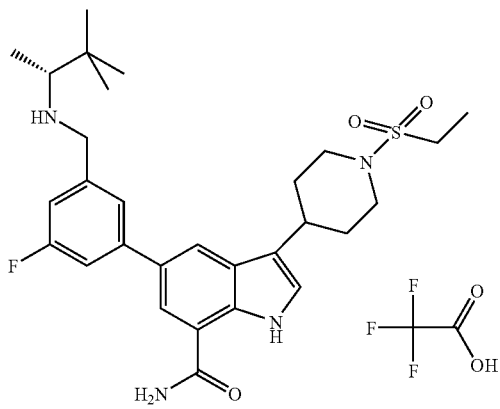

The title compound was prepared according to the general procedure of 3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate, substituting (2R)-3,3-dimethyl-2-butanamine (52 mg, 0.525 mmol) for 1-[(2S)-tetrahydro-2-furanyl]methanamine to afford 24.9 mg of the title compound (43.6%).

LC/MS=m/z 543.4 [M+H] Ret. Time: 1.73 min.

Example 321

5-(3-{[(2,2-dimethylpropyl)amino]methyl}-5-fluorophenyl)-3-[1-(ethylsulfonyl)-4-piperidinyl]-1H-indole-7-carboxamide trifluoroacetate

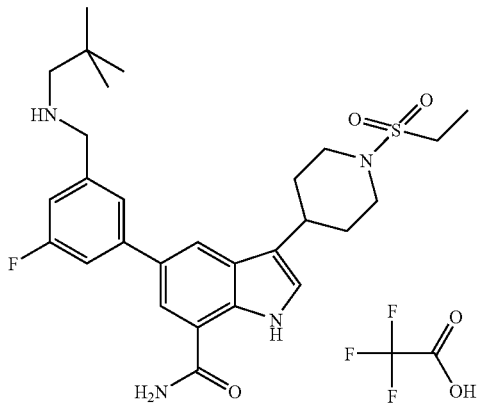

The title compound was prepared according to the general procedure of 3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate, substituting 2,2-dimethyl-1-propanamine (45 mg, 0.525 mmol) for 1-[(2S)-tetrahydro-2-furanyl]methanamine to afford 14 mg of the title compound (25%).

LC/MS=m/z 529.4 [M+H] Ret. Time: 1.79 min.

Example 322

5-(3-{[(cyclopropylmethyl)amino]methyl}-5-fluorophenyl)-3-[1-(ethylsulfonyl)-4-piperidinyl]-1H-indole-7-carboxamide trifluoroacetate

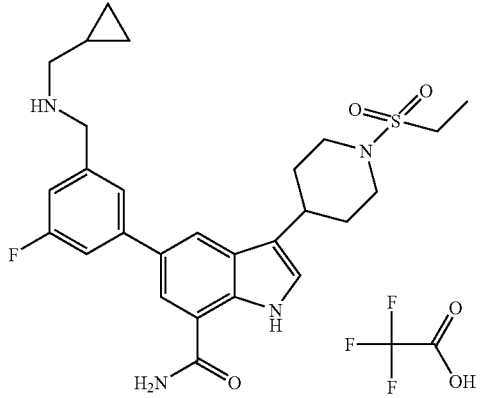

The title compound was prepared according to the general procedure of 3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate, substituting 1-cyclopropylmethanamine (37 mg, 0.525 mmol) for 1-[(2S)-tetrahydro-2-furanyl]methanamine to afford 21.1 mg of the title compound (38.7%).

LC/MS=m/z 513.4 [M+H] Ret. Time: 1.69 min.

Example 323

5-(3-{[(cyclopentylmethyl)amino]methyl}-5-fluorophenyl)-3-[1-(ethylsulfonyl)-4-piperidinyl]-1H-indole-7-carboxamide trifluoroacetate

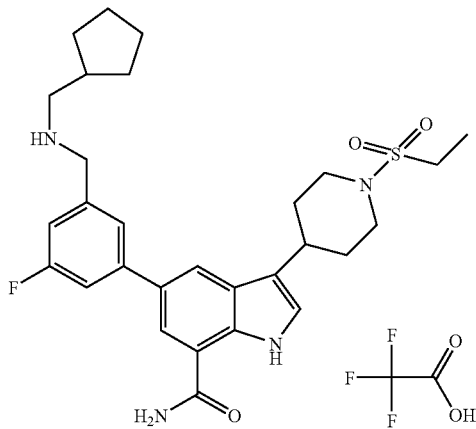

The title compound was prepared according to the general procedure of 3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate, substituting 1-cyclopentylmethanamine (52 mg, 0.525 mmol) for 1-[(2S)-tetrahydro-2-furanyl]methanamine to afford 21.6 mg of the title compound (37.9%).

LC/MS=m/z 541.4 [M+H] Ret. Time: 1.82 min.

Example 324

3-[1-(ethylsulfonyl)-4-piperidinyl]-5-(3-fluoro-5-{[(tetrahydro-2H-pyran-4-ylmethyl)amino]methyl}phenyl)-1H-indole-7-carboxamide trifluoroacetate

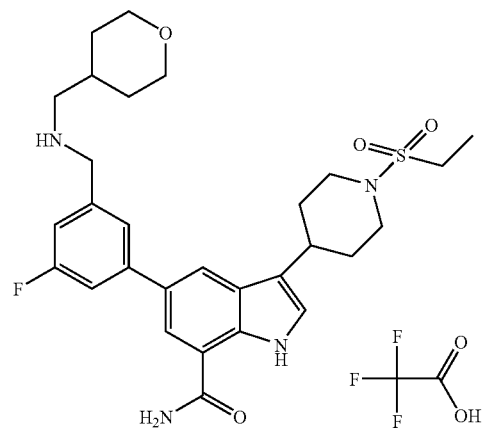

The title compound was prepared according to the general procedure of 3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate, substituting 1-(tetrahydro-2H-pyran-4-yl)methanamine (60 mg, 0.525 mmol) for 1-[(2S)-tetrahydro-2-furanyl]methanamine to afford 40.1 mg of the title compound (68.7%).

LC/MS=m/z 557.4 [M+H] Ret. Time: 1.54 min.

Example 325

3-[1-(ethylsulfonyl)-4-piperidinyl]-5-(3-fluoro-5-{[(2-thienylmethyl)amino]methyl}phenyl)-1H-indole-7-carboxamide trifluoroacetate

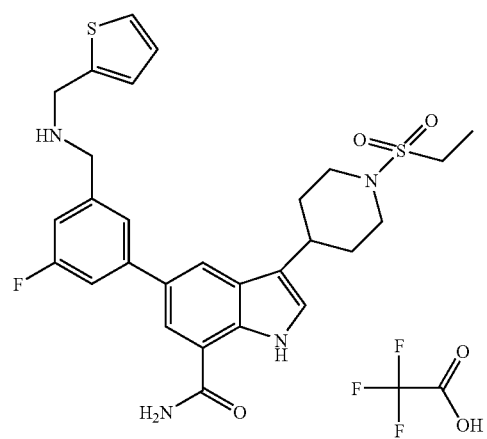

The title compound was prepared according to the general procedure of 3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate, substituting 1-(2-thienyl)methanamine (59 mg, 0.525 mmol) for 1-[(2S)-tetrahydro-2-furanyl]methanamine to afford 24.4 mg of the title compound (41.9%).

LC/MS=m/z 555.4 [M+H] Ret. Time: 1.67 min.

Example 326

3-[1-(ethylsulfonyl)-4-piperidinyl]-5-[3-fluoro-5-({[2-(methyloxy)ethyl]amino}methyl)phenyl]-1H-indole-7-carboxamide trifluoroacetate

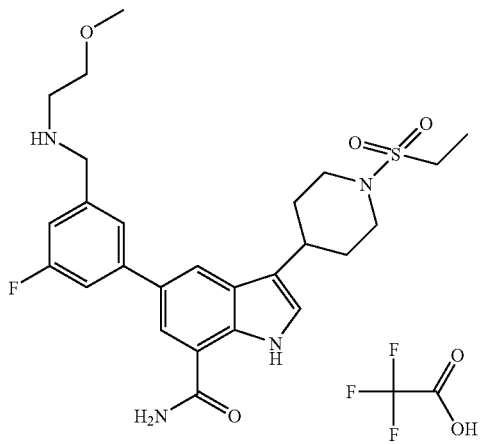

The title compound was prepared according to the general procedure of 3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate, substituting 2-(methyloxy)ethanamine (39 mg, 0.525 mmol) for 1-[(2S)-tetrahydro-2-furanyl]methanamine to afford 31 mg of the title compound (56.5%).

LC/MS=m/z 517.2 [M+H] Ret. Time: 1.52 min.

Example 327

3-[1-(ethylsulfonyl)-4-piperidinyl]-5-[3-fluoro-5-({[3-(methyloxy)propyl]amino}methyl)phenyl]-1H-indole-7-carboxamide trifluoroacetate

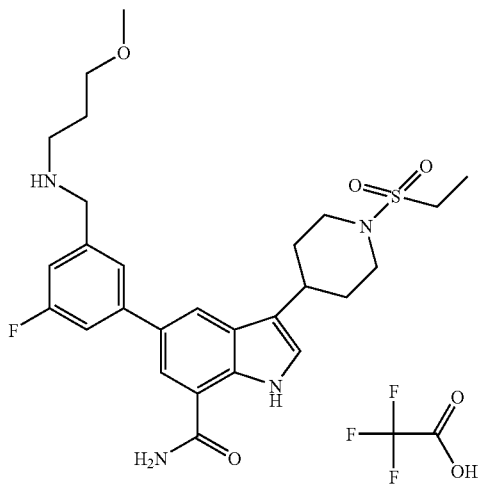

The title compound was prepared according to the general procedure of 3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate, substituting 3-(methyloxy)-1-propanamine (46 mg, 0.525 mmol) for 1-[(2S)-tetrahydro-2-furanyl]methanamine to afford 27.3 mg of the title compound (48.7%).

LC/MS=m/z 531.4 [M+H] Ret. Time: 1.54 min.

Example 328

3-[1-(ethylsulfonyl)-4-piperidinyl]-5-(3-fluoro-5-{[(2-furanylmethyl)amino]methyl}phenyl)-1H-indole-7-carboxamide trifluoroacetate

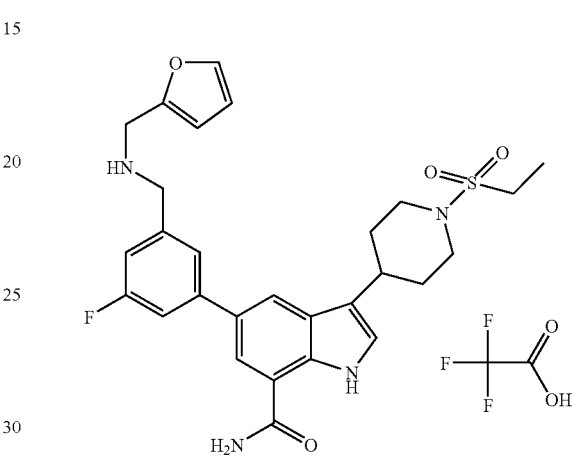

The title compound was prepared according to the general procedure of 3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate, substituting 1-(2-furanyl)methanamine (50 mg, 0.525 mmol) for 1-[(2S)-tetrahydro-2-furanyl]methanamine to afford 24.8 mg of the title compound (43.7%).

LC/MS=m/z 539.4 [M+H] Ret. Time: 1.63 min.

Example 329

3-[1-(ethylsulfonyl)-4-piperidinyl]-5-(3-fluoro-5-{[(3-methylbutyl)amino]methyl}phenyl)-1H-indole-7-carboxamide trifluoroacetate

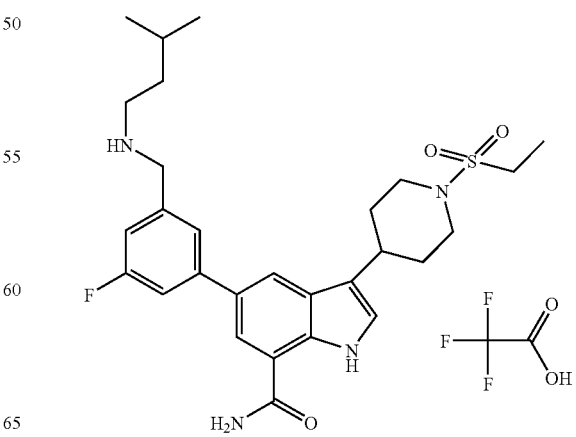

The title compound was prepared according to the general procedure of 3-[1-(ethylsulfonyl)-4-piperidinyl]-5-[3-

The title compound was prepared according to the general procedure of 3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate, substituting 3-methyl-1-butanamine (45 mg, 0.525 mmol) for 1-[(2S)-tetrahydro-2-furanyl]methanamine to afford 27.6 mg of the title compound (49.4%).

LC/MS=m/z 529.4 [M+H] Ret. Time: 1.67 min.

Example 330

3-[1-(ethylsulfonyl)-4-piperidinyl]-5-[3-fluoro-5-({[(5-methyl-2-furanyl)methyl]amino}methyl)phenyl]-1H-indole-7-carboxamide trifluoroacetate

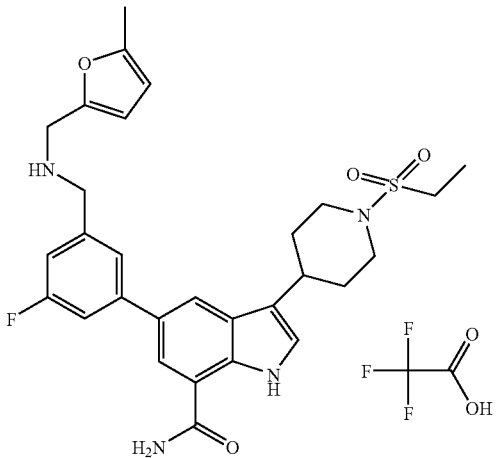

The title compound was prepared according to the general procedure of 3-[1-(ethylsulfonyl)-4-piperidinyl]-5-[3-fluoro-5-({[(2S)-tetrahydro-2-furanylmethyl]amino}methyl)phenyl]-1H-indole-7-carboxamide trifluoroacetate, substituting 1-(5-methyl-2-furanyl)methanamine (58 mg, 0.525 mmol) for 1-[(2S)-tetrahydro-2-furanyl]methanamine to afford 28.3 mg of the title compound (48.8%).

LC/MS=m/z 553.6 [M+H] Ret. Time: 1.78 min.

Example 331

3-[1-(ethylsulfonyl)-4-piperidinyl]-5-(3-{[(2-methylpropyl)amino]methyl}phenyl)-1H-indole-7-carboxamide trifluoroacetate

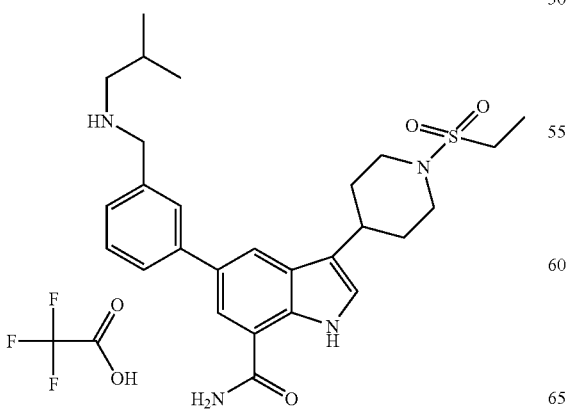

To a solution of 3-[1-(ethylsulfonyl)-4-piperidinyl]-5-(3-formylphenyl)-1H-indole-7-carboxamide (50 mg, 0.114 mmol) in dichloromethane (2 mL) and methanol (1 mL) was added 2-methyl-1-propanamine (70 μL, 0.683 mmol) and 2 drops of acetic acid. This mixture was stirred for 2 h at room temperature and then sodium tetrahydridoborate (26 mg, 0.683 mmol) was added. After 30 min the mixture was concentrated and was dissolved in dimethyl sulfoxide (2 mL) and purified by Gilson Preparatory HPLC to give 19.8 mg of the title compound (61%).

LC/MS=m/z 497.4 [M+H] Ret. Time: 1.57

Example 332

3-[1-(ethylsulfonyl)-4-piperidinyl]-5-[3-(2-pyrrolidinyl)phenyl]-1H-indole-7-carboxamide trifluoroacetate

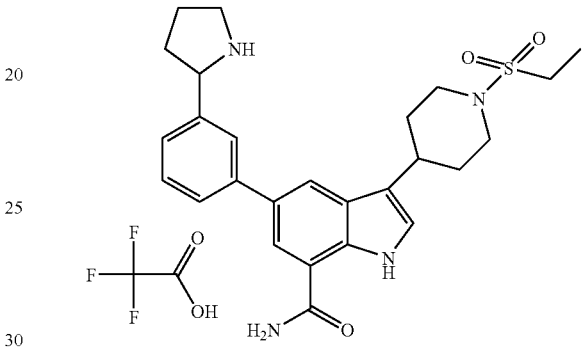

A solution of 3-[1-(ethylsulfonyl)-4-piperidinyl]-5-(4,4,5,5-tetramethyl-1,3,2-dioxaborolan-2-yl)-1H-indole-7-carboxamide (70 mg, 0.151 mmol), 2-(3-iodophenyl)pyrrolidine (70 mg, 0.456 mmol) in potassium carbonate (126 mg, 0.910 mmol) in dioxane (2 mL) and water (1 mL) was degassed for 5 min and tetrakis(triphenylphosphine)palladium(0) (17 mg, 0.015 mmol) was added. The mixture was reacted in a CEM microwave for 20 min at 160° C. The organic layers were then separated and concentrated. This was then dissolved in dimethyl sulfoxide (1 mL) and purified by Gilson Preparatory HPLC to give 48 mg of the title compound (59.5%).

LC/MS=m/z 481.0 [M+H] Ret. Time: 1.47

Example 333

3-[1-(ethylsulfonyl)-4-piperidinyl]-5-{2-fluoro-5-[(methylamino)methyl]phenyl}-1H-indole-7-carboxamide trifluoroacetate

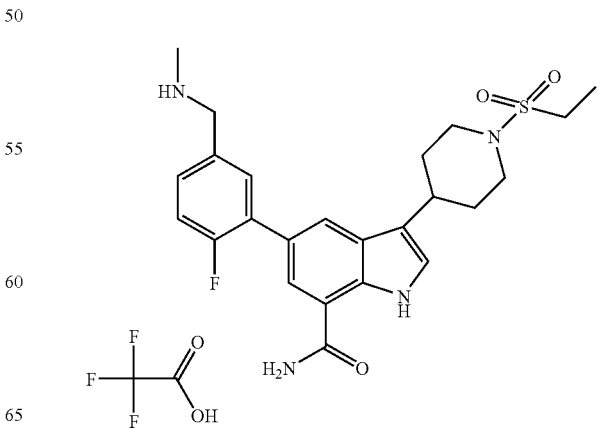

To a solution of 3-[1-(ethylsulfonyl)-4-piperidinyl]-5-(2-fluoro-5-formylphenyl)-1H-indole-7-carboxamide (40 mg, 0.087 mmol) in dichloromethane (2 mL) and methanol (1 mL) was added methanamine (262 μL, 0.524 mmol) and 1 drop of acetic acid. After being stirred for 2 h at room temperature, sodium tetrahydridoborate (20 mg, 0.524 mmol) was added and allowed to stand for 30 min. The mixture was then purified by Gilson Preparatory HPLC to give 12.3 mg of the title compound (58.6%).
LC/MS=m/z 473.4 [M+H] Ret. Time: 1.55.

Example 334

3-[1-(ethylsulfonyl)-4-piperidinyl]-5-{2-fluoro-5-[(propylamino)methyl]phenyl}-1H-indole-7-carboxamide trifluoroacetate

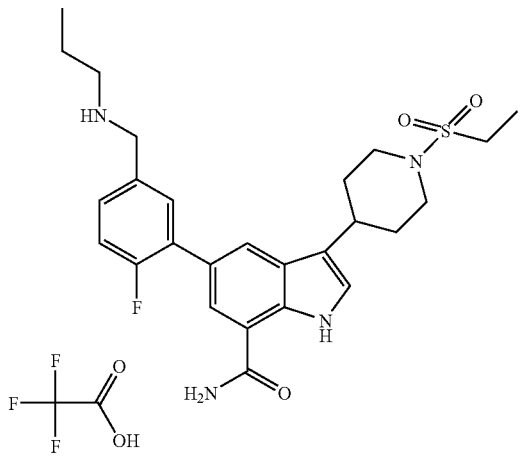

The title compound was prepared according to the general procedure of 3-[1-(ethylsulfonyl)-4-piperidinyl]-5-{2-fluoro-5-[(methylamino)methyl]phenyl}-1H-indole-7-carboxamide trifluoroacetate, substituting propylamine (44 μL, 0.524 mmol) for methanamine to afford 15.4 mg of the title compound (61.5%).
LC/MS=m/z 501.4[M+H] Ret. Time: 1.55

Example 335

3-[1-(ethylsulfonyl)-4-piperidinyl]-5-(2-fluoro-5-{[(2-methylpropyl)amino]methyl}phenyl)-1H-indole-7-carboxamide trifluoroacetate

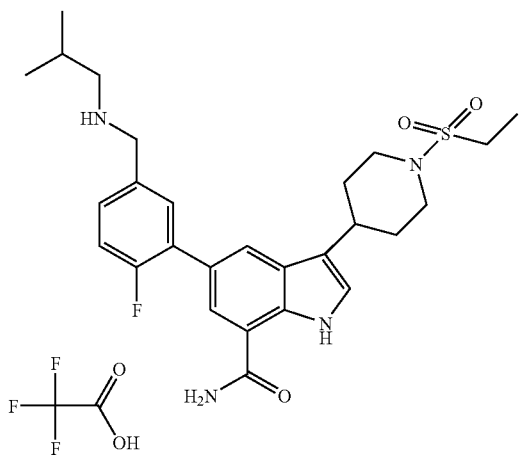

The title compound was prepared according to the general procedure of 3-[1-(ethylsulfonyl)-4-piperidinyl]-5-{2-fluoro-5-[(methylamino)methyl]phenyl}-1H-indole-7-carboxamide trifluoroacetate, substituting 2-methyl-1-propanamine (53 μL, 0.524 mmol) for methanamine to afford 15 mg of the title compound (62.9%)
LC/MS=m/z 515.4 [M+H] Ret. Time: 1.55

Example 336

5-(5-{[(2,2-dimethylpropyl)amino]methyl}-2-fluorophenyl)-3-[1-(ethylsulfonyl)-4-piperidinyl]-1H-indole-7-carboxamide trifluoroacetate

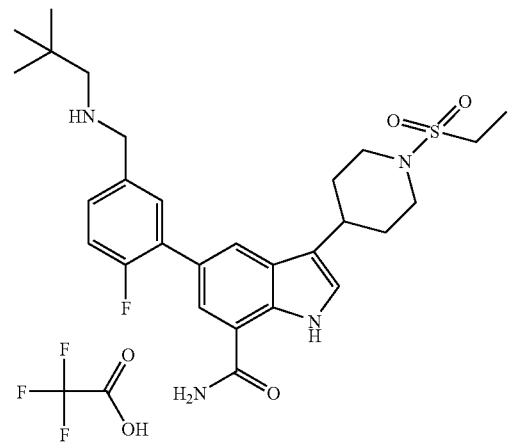

The title compound was prepared according to the general procedure of 3-[1-(ethylsulfonyl)-4-piperidinyl]-5-{2-fluoro-5-[(methylamino)methyl]phenyl}-1H-indole-7-carboxamide trifluoroacetate, substituting 2,2-dimethyl-1-propanamine (46 μL, 0.524 mmol) for methanamine to afford 14.3 mg of the title compound (64.3%).
LC/MS=m/z 530.2[M+H] Ret. Time: 1.59

Example 337

5-[5-({[(1S)-1,2-dimethylpropyl]amino}methyl)-2-fluorophenyl]-3-[1-(ethylsulfonyl)-4-piperidinyl]-1H-indole-7-carboxamide trifluoroacetate

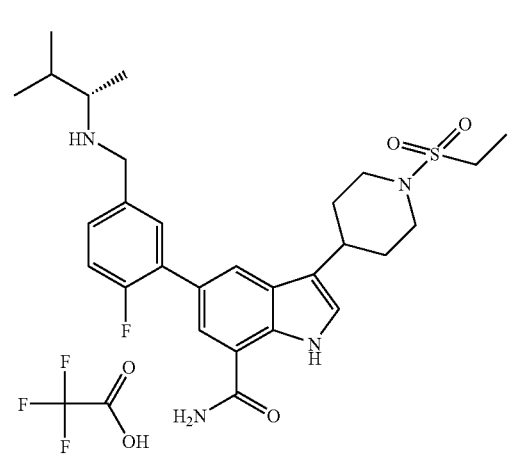

The title compound was prepared according to the general procedure of 3-[1-(ethylsulfonyl)-4-piperidinyl]-5-{2-fluoro-5-[(methylamino)methyl]phenyl}-1H-indole-7-carboxamide trifluoroacetate, substituting (2S)-3-methyl-2-butanamine (46 µL, 0.524 mmol) for methanamine to afford 17.3 mg of the title compound (64.3%)

LC/MS=m/z 529.4 [M+H] Ret. Time: 1.69

Example 338

5-[5-({[(1R)-1,2-dimethylpropyl]amino}methyl)-2-fluorophenyl]-3-[1-(ethylsulfonyl)-4-piperidinyl]-1H-indole-7-carboxamide trifluoroacetate

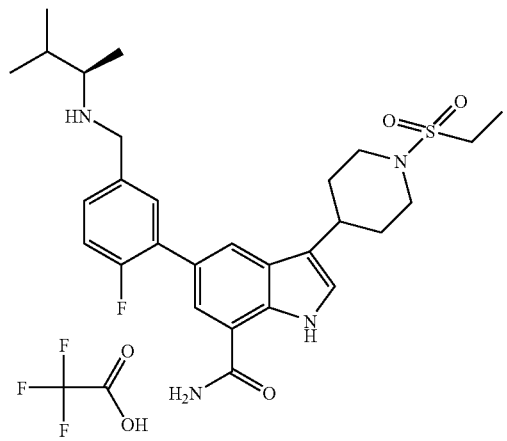

The title compound was prepared according to the general procedure of 3-[1-(ethylsulfonyl)-4-piperidinyl]-5-{2-fluoro-5-[(methylamino)methyl]phenyl}-1H-indole-7-carboxamide trifluoroacetate, substituting (2R)-3-methyl-2-butanamine (46 µL, 0.524 mmol) for methanamine to afford 15 mg of the title compound (64.3%).

LC/MS=m/z 529.4 [M+H] Ret. Time: 1.70

Example 339

5-(5-{[(cyclopropylmethyl)amino]methyl}-2-fluorophenyl)-3-[1-(ethylsulfonyl)-4-piperidinyl]-1H-indole-7-carboxamide trifluoroacetate

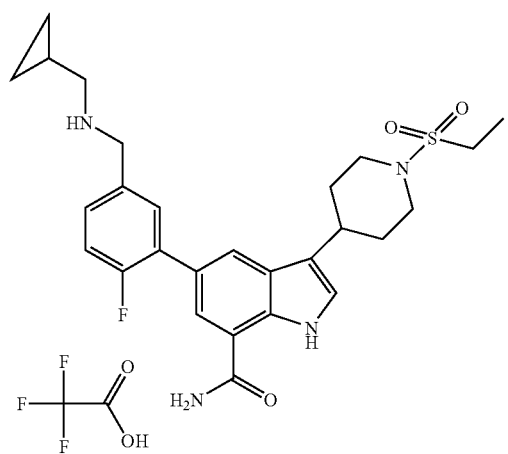

The title compound was prepared according to the general procedure of 3-[1-(ethylsulfonyl)-4-piperidinyl]-5-{2-fluoro-5-[(methylamino)methyl]phenyl}-1H-indole-7-carboxamide trifluoroacetate, substituting 2-methyl-1-butanamine (38 µL, 0.524 mmol) for methanamine to afford 16.2 mg of the title compound (62.7%).

LC/MS=m/z 513.4 [M+H] Ret. Time: 1.57

Example 340

3-[1-(ethylsulfonyl)-4-piperidinyl]-5-[2-fluoro-5-(1-pyrrolidinylmethyl)phenyl]-1H-indole-7-carboxamide trifluoroacetate

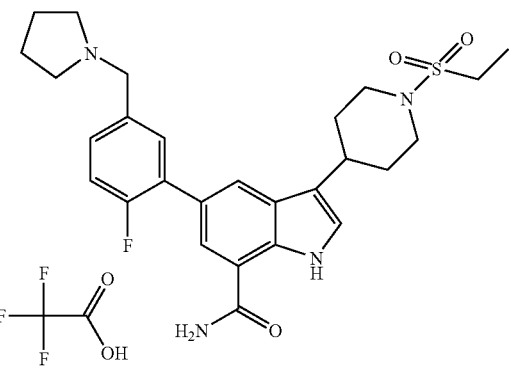

The title compound was prepared according to the general procedure of 3-[1-(ethylsulfonyl)-4-piperidinyl]-5-{2-fluoro-5-[(methylamino)methyl]phenyl}-1H-indole-7-carboxamide trifluoroacetate, substituting pyrrolidine (44 µL, 0.524 mmol) for methanamine to afford 10 mg of the title compound (62.7%).

LC/MS=m/z 513.4 [M+H] Ret. Time: 1.62

Example 341

3-[1-(ethylsulfonyl)-4-piperidinyl]-5-[2-fluoro-5-(4-morpholinylmethyl)phenyl]-1H-indole-7-carboxamide trifluoroacetate

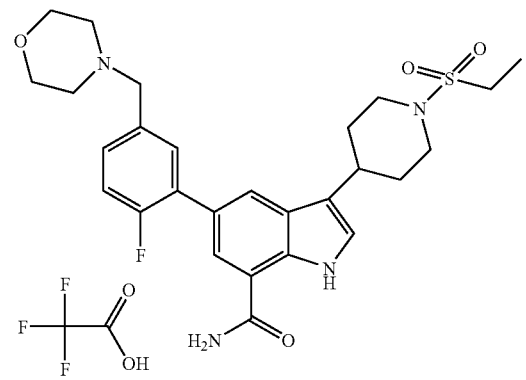

The title compound was prepared according to the general procedure of 3-[1-(ethylsulfonyl)-4-piperidinyl]-5-{2-fluoro-5-[(methylamino)methyl]phenyl}-1H-indole-7-carboxamide trifluoroacetate, substituting morpholine (45 μL, 0.524 mmol) for methanamine to afford 15 mg of the title compound (64.3%)
LC/MS=m/z 529.4 [M+H] Ret. Time: 1.52

Example 342

3-[1-(ethylsulfonyl)-4-piperidinyl]-5-[2-fluoro-5-({[2-(methyloxy)ethyl]amino}methyl)phenyl]-1H-indole-7-carboxamide trifluoroacetate

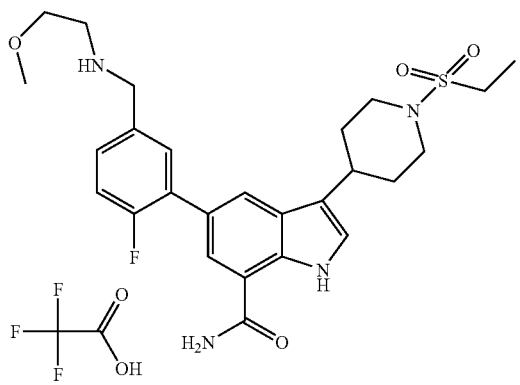

To a solution of 3-[1-(ethylsulfonyl)-4-piperidinyl]-5-(2-fluoro-5-formylphenyl)-1H-indole-7-carboxamide (40 mg, 0.087 mmol) in dichloromethane (2 mL) and methanol (1 mL) was added 2-(methyloxy)ethanamine (54 μL, 0.524 mmol) and 1 drop of acetic acid. After being stirred over the weekend at room temperature, sodium tetrahydridoborate (20 mg, 0.524 mmol) was added and allowed to stand for 30 min. The mixture was then purified by Gilson Preparatory HPLC to afford 11.4 mg of the title compound (63%).
LC/MS=m/z 517.2 [M+H] Ret. Time: 1.57

Example 343

3-[1-(ethylsulfonyl)-4-piperidinyl]-5-[2-fluoro-5-({[3-(methyloxy)propyl]amino}methyl)phenyl]-1H-indole-7-carboxamide trifluoroacetate

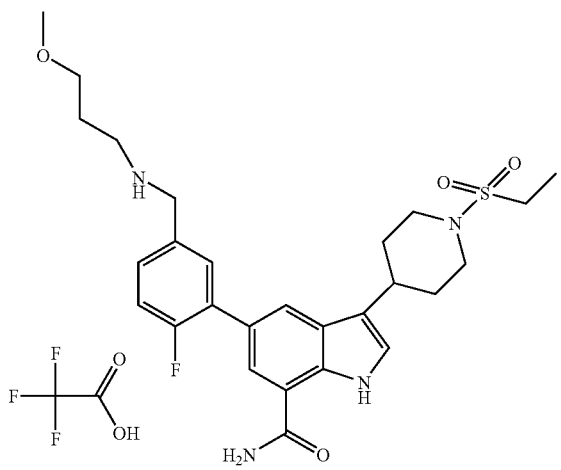

The title compound was prepared according to the general procedure of 3-[1-(ethylsulfonyl)-4-piperidinyl]-5-[2-fluoro-5-({[2-(methyloxy)ethyl]amino}methyl)phenyl]-1H-indole-7-carboxamide trifluoroacetate, substituting 3-(methyloxy)-1-propanamine (53 μL, 0.524 mmol) for 2-(methyloxy)ethanamine to afford 15 mg of the title compound (64.5%)
LC/MS=m/z 531.4 [M+H] Ret. Time: 1.60

Example 344

3-[1-(ethylsulfonyl)-4-piperidinyl]-5-[3-(1-methyl-2-pyrrolidinyl)phenyl]-1H-indole-7-carboxamide trifluoroacetate

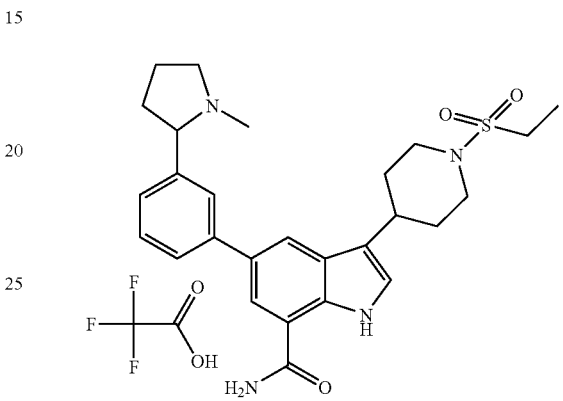

To a solution of 3-[1-(ethylsulfonyl)-4-piperidinyl]-5-[3-(2-pyrrolidinyl)phenyl]-1H-indole-7-carboxamide (20 mg, 0.04 mmol), formaldehyde (9.5 mL, 0.125 mmol) and sodium triacetoxyborohydride in dichloromethane (2 mL) was added 2 drops of acetic acid. The resulting mixture was stirred overnight at room temperature. All solvent was evaporated and the result was re-dissolved in dimethyl sulfoxide (1 mL). The mixture was then separated twice by Gilson Preparatory HPLC to afford 8.9 mg of the title compound (60.9%).
LC/MS=m/z 495.4 [M+H] Ret. Time: 1.54

Example 345

3-[1-(ethylsulfonyl)-4-piperidinyl]-5-(3-{2-[(2-methylpropyl)amino]ethyl}phenyl)-1H-indole-7-carboxamide trifluoroacetate

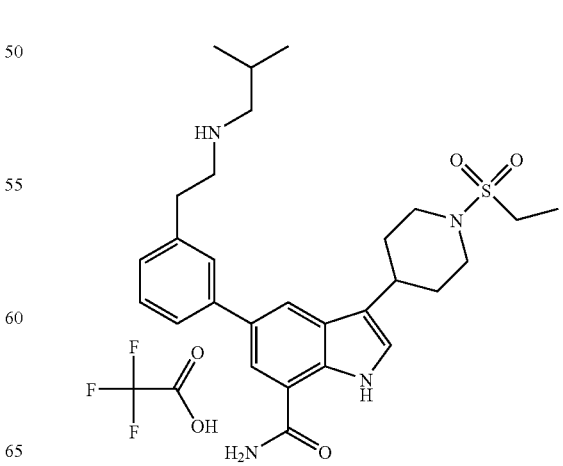

To a solution of 3-[1-(ethylsulfonyl)-4-piperidinyl]-5-(4,4,5,5-tetramethyl-1,3,2-dioxaborolan-2-yl)-1H-indole-7-carboxamide (60 mg, 0.13 mmol), [2-(3-bromophenyl)ethyl](2-methylpropyl)amine (100 mg, 0.39 mmol) and potassium carbonate (108 mg, 0.780 mmol) in dioxide (2 mL) and water (0.7 mL). The resulting mixture was degassed for 5 min then tetrakis(triphenylphosphine)palladium(0) (14 mg, 0.013 mmol) was added. This was reacted in a CEM microwave for 20 min at 160° C. The reaction was then purified using Gilson Preparatory HPLC to afford 44 mg of the title compound (62.5%).

LC/MS=m/z 511.2 [M+H] Ret. Time: 1.79

Example 346

5-{3-[2-(ethylamino)ethyl]phenyl}-3-[1-(ethylsulfonyl)-4-piperidinyl]-1H-indole-7-carboxamide trifluoroacetate

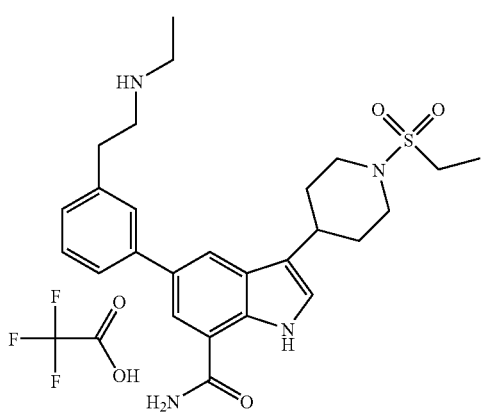

A solution of 3-[1-(ethylsulfonyl)-4-piperidinyl]-5-(4,4,5,5-tetramethyl-1,3,2-dioxaborolan-2-yl)-1H-indole-7-carboxamide (40.4 mg, 0.09 mmol), 2-(3-bromophenyl)-N-ethylethanamine (60 mg, 0.263 mmol) and potassium carbonate (72 mg, 0.526 mmol) in dioxane (2 mL) and water (0.7 mL) was degassed for 5 min. To this was added tetrakis(triphenylphosphine)palladium(0) (11 mg, 0.009 mmol). The resulting mixture was reacted in a CEM microwave for 20 min at 160° C. The reaction was then purified using Gilson Preparatory HPLC to afford 38.6 mg of the title compound (59.7%).

LC/MS=m/z 482.8 [M+H] Ret. Time: 1.54

Example 347

3-[1-(ethylsulfonyl)-4-piperidinyl]-5-{3-[2-(propylamino)ethyl]phenyl}-1H-indole-7-carboxamide trifluoroacetate

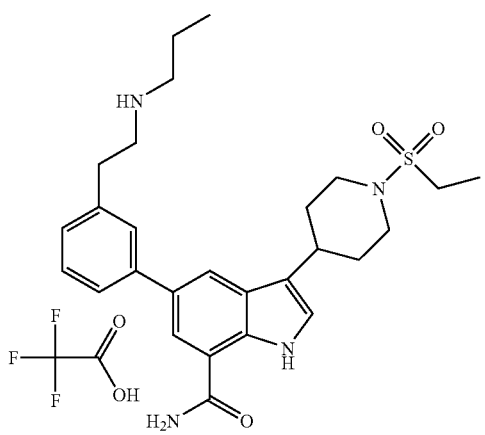

A solution of 3-[1-(ethylsulfonyl)-4-piperidinyl]-5-(4,4,5,5-tetramethyl-1,3,2-dioxaborolan-2-yl)-1H-indole-7-carboxamide (25 mg, 0.055 mmol), potassium carbonate (46 mg, 0.33 mmol) and [2-(3-bromophenyl)ethyl]propylamine (40 mg, 0.165 mmol) in dioxane (2 mL) and water (0.7 mL) was degassed for 5 min then tetrakis(triphenylphosphine)palladium(0) (7 mg, 0.006 mmol) was added. The resulting mixture was reacted in a CEM microwave for 20 min at 160° C. The reaction was then separated using Gilson Preparatory HPLC to afford 17.6 mg of the title compound (61%).

LC/MS=m/z 497.4 [M+H] Ret. Time: 1.97

Example 348

5-{3-[2-(dimethylamino)ethyl]phenyl}-3-[1-(ethylsulfonyl)-4-piperidinyl]-1H-indole-7-carboxamide trifluoroacetate

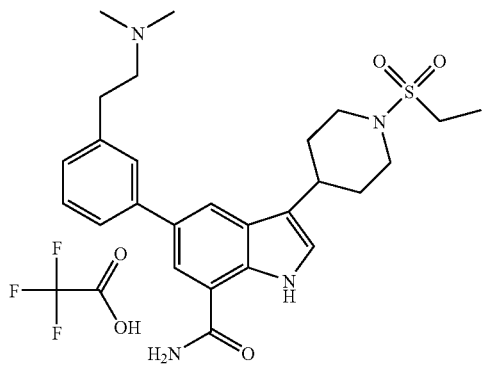

A solution of 3-[1-(ethylsulfonyl)-4-piperidinyl]-5-(4,4,5,5-tetramethyl-1,3,2-dioxaborolan-2-yl)-1H-indole-7-carboxamide (60 mg, 0.13 mmol), potassium carbonate (108 mg, 0.78 mmol) and 2-(3-bromophenyl)-N,N-dimethylethanamine (90 mg, 0.39 mmol) in dioxane (2 mL) and water (0.7 mL) was degassed for 5 min then tetrakis(triphenylphosphine)palladium(0) (15 mg, 0.013 mmol) was added. The resulting mixture was reacted in a CEM microwave for 20 min at 160° C. The reaction was then separated using Gilson Preparatory HPLC to afford 30 mg of the title compound (59.7%).

LC/MS=m/z 483.2 [M+H] Ret. Time: 1.60

Example 349

5-{3-[2-(dipropylamino)ethyl]phenyl}-3-[1-(ethylsulfonyl)-4-piperidinyl]-1H-indole-7-carboxamide trifluoroacetate

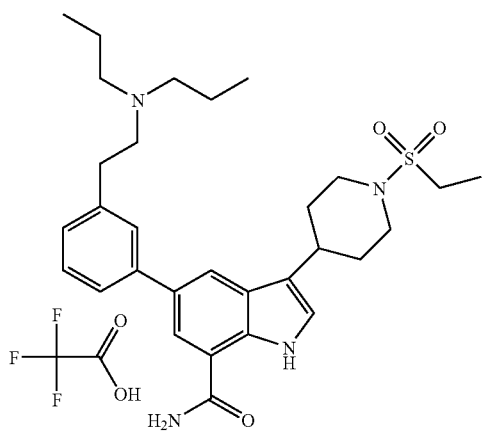

A solution of 3-[1-(ethylsulfonyl)-4-piperidinyl]-5-(4,4,5,5-tetramethyl-1,3,2-dioxaborolan-2-yl)-1H-indole-7-carboxamide (66 mg, 0.14 mmol), potassium carbonate (120 mg, 0.86 mmol) and (2-phenylethyl)dipropylamine (120 mg, 0.43 mmol) in dioxane (2 mL) and water (0.7 mL) was degassed for 5 min then tetrakis(triphenylphosphine)palladium(0) (15 mg, 0.014 mmol) was added. The resulting mixture was reacted in a CEM microwave for 20 min at 160° C. The reaction was then separated using Gilson Preparatory HPLC to afford 9 mg of the title compound (65.3%).

LC/MS=m/z 455.0 [M+H] Ret. Time: 1.55

Example 350

5-[3-({[2-(3,5-dimethyl-1H-pyrazol-1-yl)ethyl]amino}methyl)phenyl]-3-[1-(ethylsulfonyl)-4-piperidinyl]-1H-indole-7-carboxamide trifluoroacetate

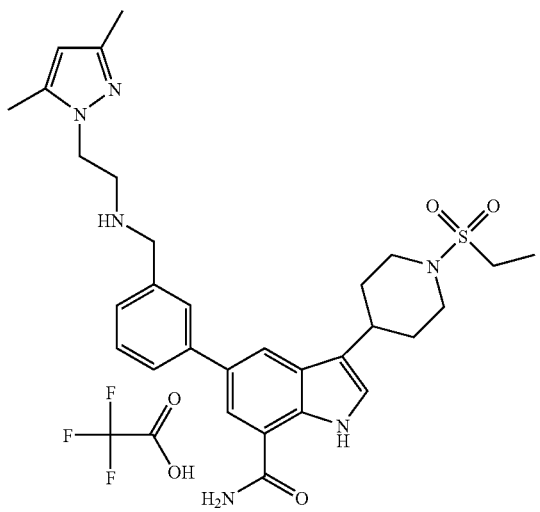

To a solution of 3-[1-(ethylsulfonyl)-4-piperidinyl]-5-(3-formylphenyl)-1H-indole-7-carboxamide (44 mg, 0.1 mmol), 2-(3,5-dimethyl-1H-pyrazol-1-yl)ethanamine (105 mg, 0.6 mmol) in dichloromethane (3 mL) and methanol (1.5 mL) was added 3 drops of acetic acid. The resulting mixture was stirred overnight then sodium triacetoxyborohydride (134 mg, 0.6 mmol) was added. This mixture was stirred overnight. The resulting mixture was quenched with sodium bicarbonate (2 mL) and brine (2 mL) and organic layer was collected and concentrated. The reaction was then separated using Gilson Preparatory HPLC to afford 26 mg of the title compound (67.7%)

LC/MS=m/z 563.2 [M+H] Ret. Time: 1.51

Example 351

3-[1-(ethylsulfonyl)-4-piperidinyl]-5-[2-(4-morpholinylmethyl)-1,3-thiazol-4-yl]-1H-indole-7-carboxamide trifluoroacetate

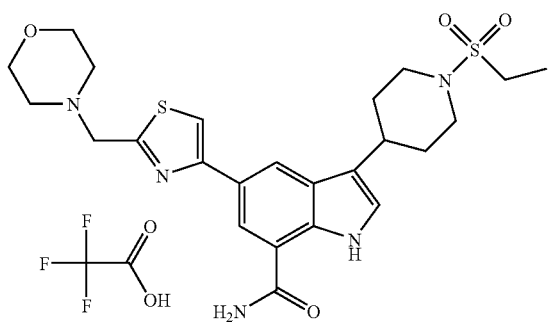

To a solution of 4-bromo-1,3-thiazole-2-carbaldehyde (192 mg, 1.0 mmol) in DCM (4.0 mL) was added morpholine (130 ul, 1.5 mmol) and 3 drops of AcOH. The mixture was stirred for 12 hr and then Na(OAc)3BH (0.335 g, 1.5 mmol) was added. After 6 hr. the mixture was quenched with Sat. NaHCO3 (4.0 mL) and brine (3.0 mL). The organic layer was separated and concentrated to give 200 mg of 4-[(4-bromo-1,3-thiazol-2-yl)methyl]morpholine (76%).

A solution of 3-[1-(ethylsulfonyl)-4-piperidinyl]-5-(4,4,5,5-tetramethyl-1,3,2-dioxaborolan-2-yl)-1H-indole-7-carboxamide (46 mg, 0.1 mmol), 4-[(4-bromo-1,3-thiazol-2-yl)methyl]morpholine (79 mg, 0.3 mmol) and potassium carbonate (83 mg, 0.6 mmol) in dioxane (2 mL) and water (0.7 mL) was degassed for 5 min then triacetoxyborohydride (11 mg, 0.1 mmol) was added. This mixture was reacted in a CEM microwave for 20 min at 160° C. The organic layer was collected and concentrated. The residue was re-dissolved with dimethyl sulfoxide (1 mL) and was then purified using Gilson Preparatory HPLC to afford 26.6 mg of the title compound (63.2%)

LC/MS=m/z 518.2 [M+H] Ret. Time: 1.49

Example 352

3-[1-(ethylsulfonyl)-4-piperidinyl]-5-(2-{[(2-methylpropyl)amino]methyl}-1,3-thiazol-4-yl)-1H-indole-7-carboxamide trifluoroacetate

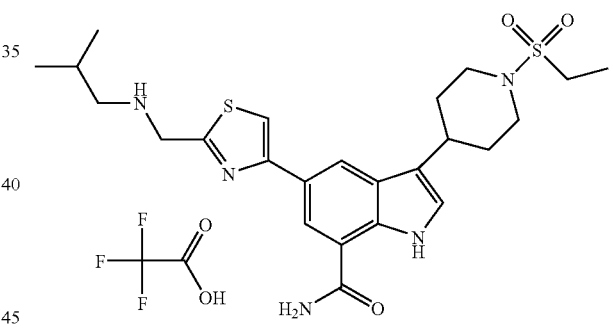

To a solution of 4-bromo-1,3-thiazole-2-carbaldehyde (192 mg, 1.0 mmol) in DCM (4.0 mL) was added iso-propyl amine (152 ul, 1.5 mmol) and 3 drops of AcOH. The mixture was stirred for 12 hr and then Na(OAc)3BH (0.335 g, 1.5 mmol) was added. After 6 hr. the mixture was quenched with Sat. NaHCO3 (4.0 mL) and brine (3.0 mL). The organic layer was separated and concentrated to give 145 mg of the title compound (58%).

To a solution of 3-[1-(ethylsulfonyl)-4-piperidinyl]-5-(4,4,5,5-tetramethyl-1,3,2-dioxaborolan-2-yl)-1H-indole-7-carbaldehyde (46 mg, 0.1 mmol), 2-methyl-1-propanamine (70 mg, 0.3 mmol) and potassium carbonate (83 mg, 0.6 mmol) in dioxane (2 mL) and water (0.7 mL) was added triacetoxyborohydride (11 mg, 0.01 mmol). This solution was degassed for 5 min then reacted in a CEM microwave for 20 min at 160° C. The organic layer was separated and concentrated. It was then purified using Gilson Preparatory HPLC to afford 24 mg of the title compound (61.8%)

LC/MS=m/z 504.2 [M+H] Ret. Time: 1.43

Example 353

3-[1-(ethylsulfonyl)-4-piperidinyl]-5-[2-(1-pyrrolidinylmethyl)-1,3-thiazol-4-yl]-1H-indole-7-carboxamide

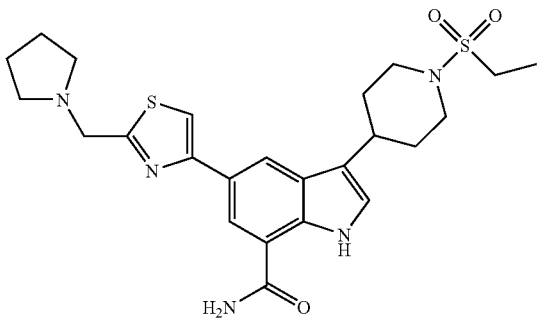

To a solution of 4-bromo-1,3-thiazole-2-carbaldehyde (192 mg, 1.0 mmol) in DCM (4.0 mL) was added pyrrolidine (124 ul, 1.5 mmol) and 3 drops of AcOH. The mixture was stirred for 12 hr and then Na(OAc)3BH (0.335 g, 1.5 mmol) was added. After 6 hr, the mixture was quenched with Sat. NaHCO3 (4.0 mL) and brine (3.0 mL). The organic layer was separated and concentrated to give 200 mg of the title compound (82%).

The title compound was prepared according to the general procedure of 3-[1-(ethylsulfonyl)-4-piperidinyl]-5-(2-{[(2-methylpropyl)amino]methyl}-1,3-thiazol-4-yl)-1H-indole-7-carboxamide trifluoroacetate, substituting pyrrolidine (74 mg, 0.3 mmol) for 2-methyl-1-propanamine to afford 6.3 mg of the title compound (50%)

LC/MS=m/z 500.4 [M+H] Ret. Time: 1.22

Example 354

3-[1-(ethylsulfonyl)-4-piperidinyl]-5-[2-(1-piperidinylmethyl)-1,3-thiazol-4-yl]-1H-indole-7-carboxamide

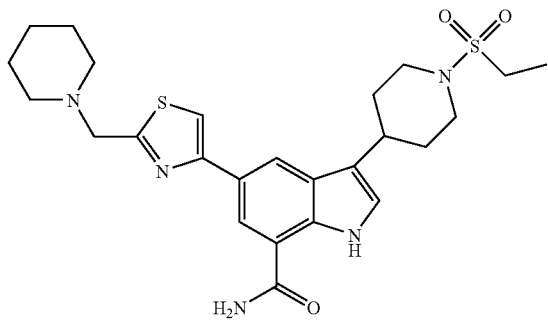

To a solution of 4-bromo-1,3-thiazole-2-carbaldehyde (192 mg, 1.0 mmol) in DCM (4.0 mL) was added piperidine (150 ul, 1.5 mmol) and 3 drops of AcOH. The mixture was stirred for 12 hr and then Na(OAc)3BH (0.335 g, 1.5 mmol) was added. After 6 hr. the mixture was quenched with Sat. NaHCO3 (4.0 mL) and brine (3.0 mL). The organic layer was separated and concentrated to give 166 mg of the title compound (64%).

The title compound was prepared according to the general procedure of 3-[1-(ethylsulfonyl)-4-piperidinyl]-5-(2-{[(2-methylpropyl)amino]methyl}-1,3-thiazol-4-yl)-1H-indole-7-carboxamide trifluoroacetate, substituting piperidine (78 mg, 0.3 mmol) for 2-methyl-1-propanamine to afford 15.5 mg of the title compound (51.6%).

LC/MS=m/z 517.4 [M+H] Ret. Time: 1.29

Example 355

5-{2-[(dimethylamino)methyl]-1,3-thiazol-4-yl}-3-[1-(ethylsulfonyl)-4-piperidinyl]-1H-indole-7-carboxamide trifluoroacetate

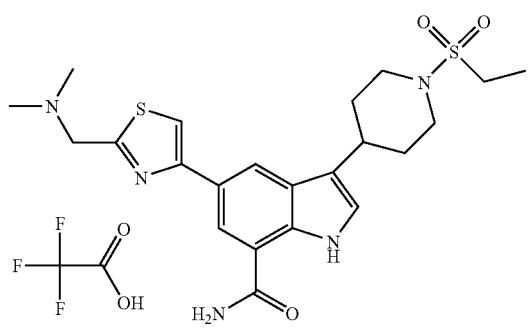

To a solution of 4-bromo-1,3-thiazole-2-carbaldehyde (192 mg, 1.0 mmol) in DCM (4.0 mL) was added dimethyl amine (2.0M, 3.0 mL) and 3 drops of AcOH. The mixture was stirred for 48 hr and then Na(OAc)3BH (1.33 g, 6.0 mmol) was added. After 12 hr. the mixture was quenched with Sat. NaHCO3 (4.0 mL) and brine (3.0 mL) and separator was used to get the DCM organic layer. The organic layer was concentrated to give 90 mg of desired product (40%).

To a solution of 3-[1-(ethylsulfonyl)-4-piperidinyl]-5-(4,4,5,5-tetramethyl-1,3,2-dioxaborolan-2-yl)-1H-indole-7-carboxamide (46 mg, 0.1 mmol), dimethylamine (69 mg, 0.3 mmol) and potassium carbonate (83 mg, 0.6 mmol) in dioxane (2 mL) and water (0.7 mL) was added triacetoxyborohydride (12 mg, 0.01 mmol). This mixture was degassed for 5 min. The mixture was then reacted in a microwave for 20 min at 160° C. The organic layers were separated and concentrated. It was then purified using Gilson Preparatory HPLC to afford 23 mg of the title compound (59%)

LC/MS=m/z 474.4 [M+H] Ret. Time: 1.20

Example 356

5-(2-{[ethyl(methyl)amino]methyl}-1,3-thiazol-4-yl)-3-[1-(ethylsulfonyl)-4-piperidinyl]-1H-indole-7-carboxamide trifluoroacetate

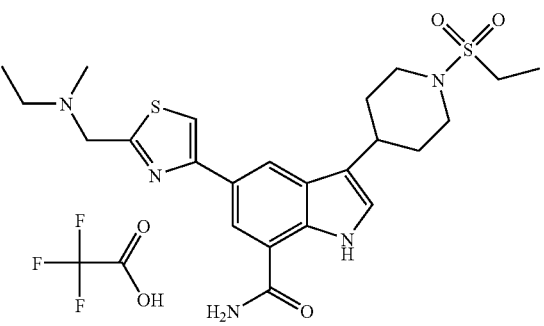

To a solution of 4-bromo-1,3-thiazole-2-carbaldehyde (192 mg, 1.0 mmol) in DCM (4.0 mL) was added N-methylethanamine (470 ul, 6.0 mmol) and 3 drops of AcOH. The mixture was stirred for 48 hr and then Na(OAc)3BH (1.33 g, 6.0 mmol) was added. After 12 hr. the mixture was quenched with Sat. NaHCO3 (4.0 mL) and brine (3.0 mL) and separator was used to get the DCM organic layer. The organic layer was concentrated to give 160 mg of the title compound (68%).

The title compound was prepared according to the general procedure of 5-{2-[(dimethylamino)methyl]-1,3-thiazol-4-yl}-3-[1-(ethylsulfonyl)-4-piperidinyl]-1H-indole-7-carboxamide trifluoroacetate, substituting ethyl(methyl)amine (73 mg, 0.3 mmol) for dimethylamine to afford 25 mg of the title compound (60.4%).

LC/MS=m/z 490.4 [M+H] Ret. Time: 1.25

Example 357

5-(3-cyano-5-{[(2-methylpropyl)amino]methyl}phenyl)-3-[1-(ethylsulfonyl)-4-piperidinyl]-1H-indole-7-carboxamide trifluoroacetate

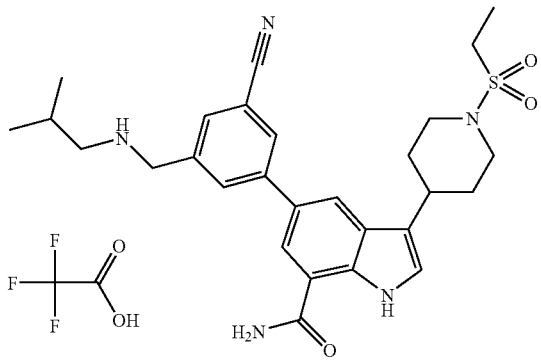

To a solution of 3-formylbenzonitrile (1.0 g, 7.6 mmol) in TFA (4.0 mL) at 0° C. under argon atmosphere was added concentrated $H_2SO_4$ (6.0 mL) dropwise followed by addition of NBS in small portion. The mixture was warmed to room temperature slowly and then stirred for 12 h under argon atmosphere. Upon reaction completion, the mixture was poured into ice-$H_2O$ (80 mL), $PdCl_2$ (117 mg, 0.658 mmol) and the solid was collected and dried over vacuum overnight to give 1.50 g of 3-bromo-5-formylbenzamide (86%).

LC/MS=m/z 228.2 [M+H] Ret. Time: 1.37

To a solution of 3-bromo-5-formylbenzamide (1.5 g, 6.58 mmol) in $H_2O$ (50.0 mL) and MeCN (50.0 mL) was added $PdCl_2$ (117 mg, 0.658 mmol). The mixture was stirred for 72 h at room temperature and another portion of $H_2O$ (100 mL) and MeCN (100 mL) was added followed with addition of $PdCl_2$ (100 mg, 0.56 mol). The mixture was stirred for another 12 hr and concentrated. The residue was dissolved in EtOAc (200 mL), washed with brine (3×50.0 mL), dried over Na2SO4 and concentrated, and then was purified by chromatography (10% EtOAc in hexanes) to give 550 mg of 3-bromo-5-formylbenzonitrile (40%).

To a solution of 3-[1-(ethylsulfonyl)-4-piperidinyl]-5-(4,4,5,5-tetramethyl-1,3,2-dioxaborolan-2-yl)-1H-indole-7-carboxamide (46 mg, 0.1 mmol) in dioxane (2.0 mL) and $H_2O$ (0.7 mL) was added 3-bromo-5-formylbenzonitrile (68 mg, 0.3 mmol), and potassium carbonate (83 mg, 0.6 mmol). The mixture was degassed for 5 min before addition of tetrakis(triphenylphosphine) palladium (0) (12 mg, 0.01 mmol). The mixture was reacted in the microwave at 160° C. for 20 min. The compound was purified by Gilson Preparatory HPLC to give 5-(3-cyano-5-formylphenyl)-3-[1-(ethylsulfonyl)-4-piperidinyl]-1H-indole-7-carboxamide.

To a solution of 5-(3-cyano-5-formylphenyl)-3-[1-(ethylsulfonyl)-4-piperidinyl]-1H-indole-7-carboxamide (47 mg, 0.1 mmol) in dichloromethane (3 mL) and methanol (1 mL) was added a few drops of acetic acid and methyl(2-methylpropyl)amine (64 μL, 0.6 mmol). This mixture was stirred overnight followed by an addition of 20 drops of acetic acid and sodium triacetoxyborohydride (0.6 mmol). The reaction was mixed for 4 h followed by an addition of methyl (2-methylpropyl) amine (64 μL, 0.6 mmol) and sodium triacetoxyborohydride (0.6 mmol). The mixture was stirred overnight then quenched with sodium biocarbonate and brine. The organic layer was separated by SOX cartridge and concentrated. It was then separated using Gilson Preparatory HPLC to afford 10.3 mg of the title compound (63.6%).

LC/MS=m/z 522.4 [M+H] Ret. Time: 1.65

Example 358

5-{3-cyano-5-[(dimethylamino)methyl]phenyl}-3-[1-(ethylsulfonyl)-4-piperidinyl]-1H-indole-7-carboxamide trifluoroacetate

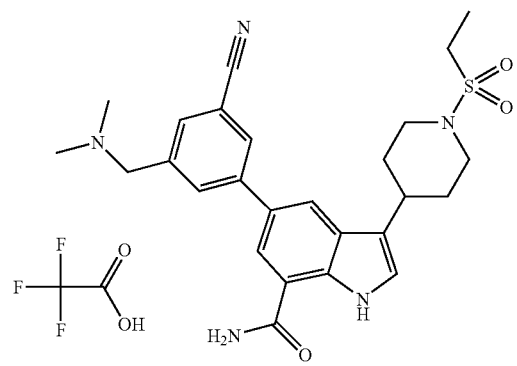

The title compound was prepared according to the general procedure of 5-(3-cyano-5-{[(2-methylpropyl)amino]methyl}phenyl)-3-[1-(ethylsulfonyl)-4-piperidinyl]-1H-indole-7-carboxamide trifluoroacetate, substituting trimethylamine (300 μL, 0.3 mmol) for methyl(2-methylpropyl)amine to afford 10.5 mg of the title compound (61%).

LC/MS=m/z 494.4 [M+H] Ret. Time: 1.48

Example 359

3-[1-(ethylsulfonyl)-4-piperidinyl]-5-[3-(4-morpholinylmethyl)phenyl]-1H-indole-7-carboxamide trifluoroacetate

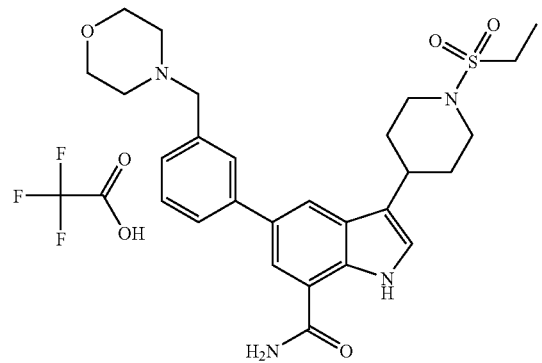

To a solution of 3-[1-(ethylsulfonyl)-4-piperidinyl]-5-(3-formylphenyl)-1H-indole-7-carboxamide (80 mg, 0.181 mmol) in DCM was added morpholine (50 μL, 0.545 mmol). The reaction was stirred at room temperature for 30 min before the addition of sodium triacetoxyborohydride (120 mg, 0.545 mmol). The reaction was run at room temperature overnight and then concentrated. Compound was purified by Gilson Preparatory HPLC to afford 28.6 mg of the title compound (25%).

LC/MS=m/z 511.4 [M+H] Ret. Time: 1.48 min

Example 360

3-[1-(ethylsulfonyl)-4-piperidinyl]-5-[3-({[(4-fluorophenyl)carbonyl]amino}methyl)phenyl]-1H-indole-7-carboxamide trifluoroacetate

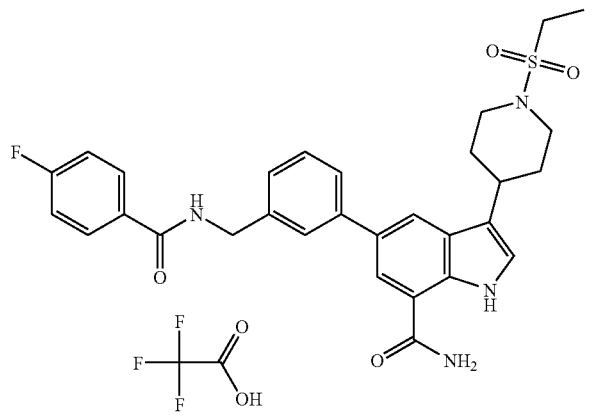

The title compound was prepared according to the general procedure of 5-{3-[(acetylamino)methyl]phenyl}-3-[1-(ethylsulfonyl)-4-piperidinyl]-1H-indole-7-carboxamide substituting 4-fluoro-N-{[3-(4,4,5,5-tetramethyl-1,3,2-dioxaborolan-2-yl)phenyl]methyl}benzamide (125 mg, 0.352 mmol) for N-{[3-(4,4,5,5-tetramethyl-1,3,2-dioxaborolan-2-yl)phenyl]methyl}acetamide. Compound was purified by Gilson Preparatory HPLC to give 18.3 mg of the title compound (27%).

LC/MS=m/z 563.1 [M+H] Ret. Time: 2.07 min

Example 361

3-[1-(ethylsulfonyl)-4-piperidinyl]-5-(3-{[(2-furanylcarbonyl)amino]methyl}phenyl)-1H-indole-7-carboxamide trifluoroacetate

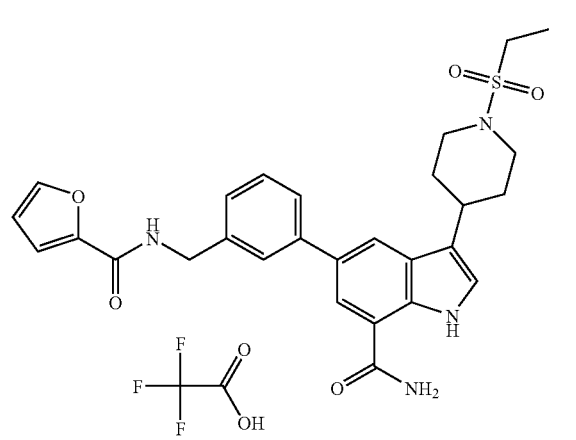

The title compound was prepared according to the general procedure of 5-{3-[(acetylamino)methyl]phenyl}-3-[1-(ethylsulfonyl)-4-piperidinyl]-1H-indole-7-carboxamide substituting N-{[3-(4,4,5,5-tetramethyl-1,3,2-dioxaborolan-2-yl)phenyl]methyl}-2-furancarboxamide (115 mg, 0.352 mmol) for N-{[3-(4,4,5,5-tetramethyl-1,3,2-dioxaborolan-2-yl)phenyl]methyl}acetamide. Compound was purified by Gilson Preparatory HPLC to give 8.1 mg of the title compound (12%).

LC/MS=m/z 535 [M+H] Ret. Time: 1.89 min

Example 362

5-(3-{[(cyclopentylcarbonyl)amino]methyl}phenyl)-3-[1-(ethylsulfonyl)-4-piperidinyl]-1H-indole-7-carboxamide trifluoroacetate

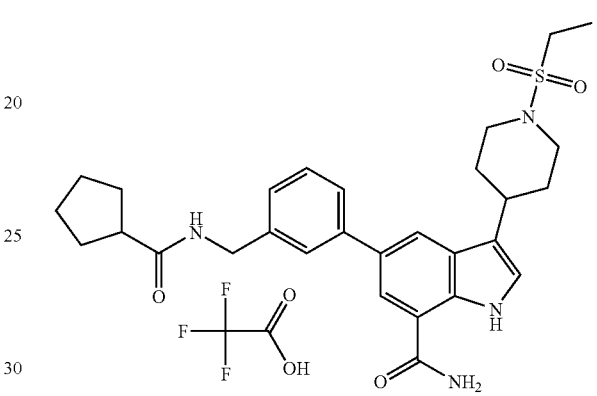

The title compound was prepared according to the general procedure of 5-{3-[(acetylamino)methyl]phenyl}-3-[1-(ethylsulfonyl)-4-piperidinyl]-1H-indole-7-carboxamide substituting N-{[3-(4,4,5,5-tetramethyl-1,3,2-dioxaborolan-2-yl)phenyl]methyl}cyclopentanecarboxamide (116 mg, 0.352 mmol) for N-{[3-(4,4,5,5-tetramethyl-1,3,2-dioxaborolan-2-yl)phenyl]methyl}acetamide. Compound was purified by Gilson Preparatory HPLC to give 9.2 mg of the title compound (14%).

LC/MS=m/z 535 [M+H] Ret. Time: 1.89 min

Example 363

5-(3-{[(1-benzothien-2-ylcarbonyl)amino]methyl}phenyl)-3-[1-(ethylsulfonyl)-4-piperidinyl]-1H-indole-7-carboxamide

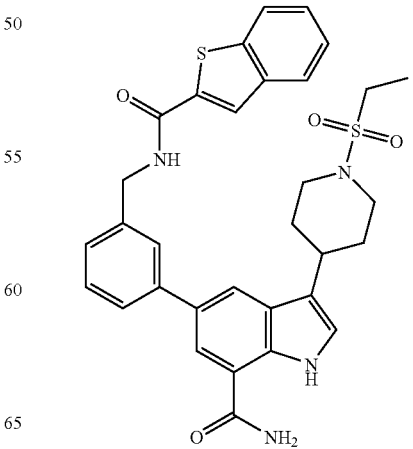

The title compound was prepared according to the general procedure of 3-[1-(ethylsulfonyl)-4-piperidinyl]-5-{3-[(pentanoylamino)methyl]phenyl}-1H-indole-7-carboxamide substituting N-{[3-(4,4,5,5-tetramethyl-1,3,2-dioxaborolan-2-yl)phenyl]methyl}-1-benzothiophene-2-carboxamide (57 mg, 0.144 mmol) for N-{[3-(4,4,5,5-tetramethyl-1,3,2-dioxaborolan-2-yl)phenyl]methyl}pentanamide. Compound was purified by Gilson Preparatory HPLC to give the title compound.

LC/MS=m/z 601.2 [M+H] Ret. Time: 2.18 min

Example 364

5-[3-({[(1-acetyl-4-piperidinyl)carbonyl]amino}methyl)phenyl]-3-[1-(ethylsulfonyl)-4-piperidinyl]-1H-indole-7-carboxamide

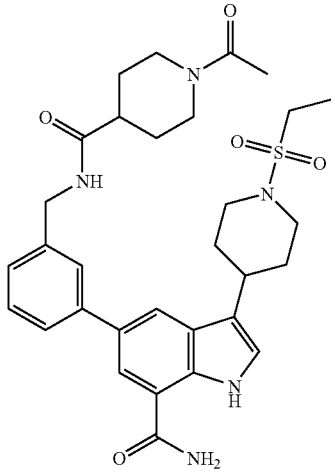

The title compound was prepared according to the general procedure of 3-[1-(ethylsulfonyl)-4-piperidinyl]-5-{3-[(pentanoylamino)methyl]phenyl}-1H-indole-7-carboxamide substituting 1-acetyl-N-{[3-(4,4,5,5-tetramethyl-1,3,2-dioxaborolan-2-yl)phenyl]methyl}-4-piperidinecarboxamide (56 mg, 0.144 mmol) for N-{[3-(4,4,5,5-tetramethyl-1,3,2-dioxaborolan-2-yl)phenyl]methyl}pentanamide. Compound was purified by Gilson Preparatory HPLC to give the title compound.

LC/MS=m/z 594.4 [M+H] Ret. Time: 1.87 min

Example 365

3-[1-(ethylsulfonyl)-4-piperidinyl]-5-[3-({[(1-methyl-1H-pyrrol-2-yl)carbonyl]amino}methyl)phenyl]-1H-indole-7-carboxamide

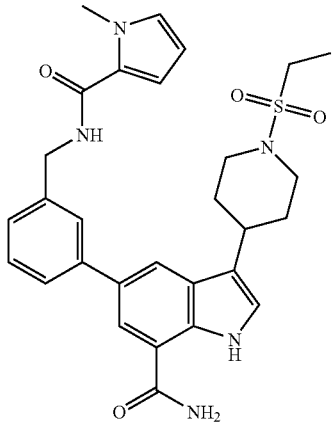

The title compound was prepared according to the general procedure of 3-[1-(ethylsulfonyl)-4-piperidinyl]-5-{3-[(pentanoylamino)methyl]phenyl}-1H-indole-7-carboxamide substituting 1-methyl-N-{[3-(4,4,5,5-tetramethyl-1,3,2-dioxaborolan-2-yl)phenyl]methyl}-1H-pyrrole-2-carboxamide (49 mg, 0.144 mmol) for N-{[3-(4,4,5,5-tetramethyl-1,3,2-dioxaborolan-2-yl)phenyl]methyl}pentanamide. Compound was purified by Gilson Preparatory HPLC to give the title compound.

LC/MS=m/z 548.4 [M+H] Ret. Time: 2.02 min

Example 366

3-[1-(ethylsulfonyl)-4-piperidinyl]-5-(3-{[(2-thienylacetyl)amino]methyl}phenyl)-1H-indole-7-carboxamide

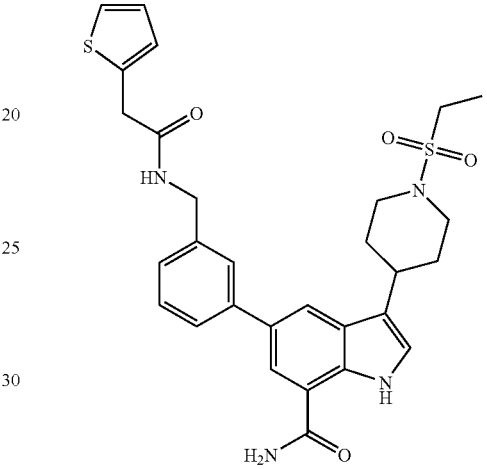

The title compound was prepared according to the general procedure of 3-[1-(ethylsulfonyl)-4-piperidinyl]-5-{3-[(pentanoylamino)methyl]phenyl}-1H-indole-7-carboxamide substituting N-{[3-(4,4,5,5-tetramethyl-1,3,2-dioxaborolan-2-yl)phenyl]methyl}-2-(2-thienyl)acetamide (51 mg, 0.144 mmol) for N-{[3-(4,4,5,5-tetramethyl-1,3,2-dioxaborolan-2-yl)phenyl]methyl}pentanamide. Compound was purified by Mass Directed Auto Prep HPLC to give 10.3 mg of the title compound (18.2%).

LC/MS=m/z 565.2 [M+H] Ret. Time: 1.95 min

Example 367

5-(3-{[(cyclobutylcarbonyl)amino]methyl}phenyl)-3-[1-(ethylsulfonyl)-4-piperidinyl]-1H-indole-7-carboxamide

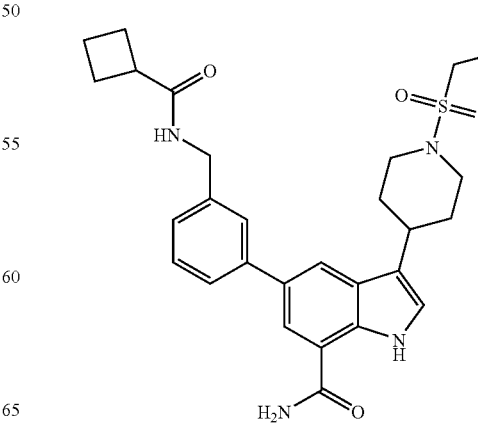

The title compound was prepared according to the general procedure of 3-[1-(ethylsulfonyl)-4-piperidinyl]-5-{3-[(pentanoylamino)methyl]phenyl}-1H-indole-7-carboxamide substituting N-{[3-(4,4,5,5-tetramethyl-1,3,2-dioxaborolan-2-yl)phenyl]methyl}cyclobutanecarboxamide (45 mg, 0.144 mmol) for N-{[3-(4,4,5,5-tetramethyl-1,3,2-dioxaborolan-2-yl)phenyl]methyl}pentanamide. Compound was purified by Mass Directed Auto Prep HPLC to give 4.3 mg of the title compound (8%).

LC/MS=m/z 523.4 [M+H] Ret. Time: 1.90 min

Example 368

5-(3-{[(cyclopropylcarbonyl)amino]methyl}phenyl)-3-[1-(ethylsulfonyl)-4-piperidinyl]-1H-indole-7-carboxamide

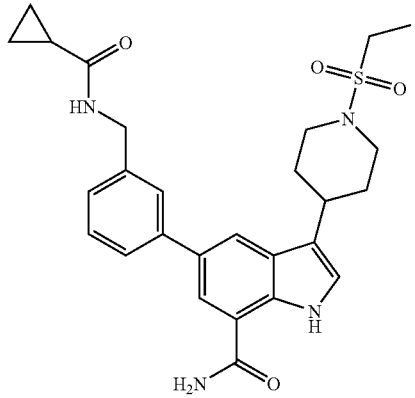

The title compound was prepared according to the general procedure of 3-[1-(ethylsulfonyl)-4-piperidinyl]-5-{3-[(pentanoylamino)methyl]phenyl}-1H-indole-7-carboxamide substituting N-{[3-(4,4,5,5-tetramethyl-1,3,2-dioxaborolan-2-yl)phenyl]methyl}cyclopropanecarboxamide (43 mg, 0.144 mmol) for N-{[3-(4,4,5,5-tetramethyl-1,3,2-dioxaborolan-2-yl)phenyl]methyl}pentanamide. Compound was purified by Mass Directed Auto Prep HPLC to give 5.5 mg of the title compound (11%).

LC/MS=m/z 509.2 [M+H] Ret. Time: 1.85 min

Examples 369

5-(3-{[(cyclopropylsulfonyl)amino]methyl}phenyl)-3-[1-(ethylsulfonyl)-4-piperidinyl]-1H-indole-7-carboxamide

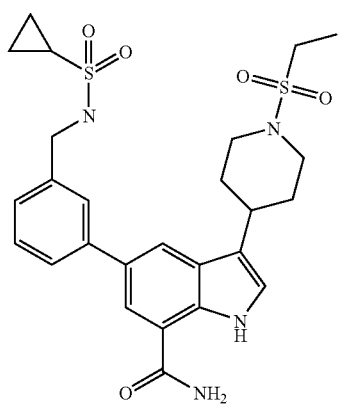

To a solution of 5-[3-(aminomethyl)phenyl]-3-[1-(ethylsulfonyl)-4-piperidinyl]-1H-indole-7-carboxamide (35 mg, 0.079 mmol) in DMF (1.0 mL) and DCM (1.0 mL) was added cyclopropanesulfonyl chloride (11 mg, 0.079 mmol) and DIEA (14 µL, 0.079 mmol). Reaction was stirred at room temperature overnight. Compound was purified by Gilson Preparatory HPLC to give 7.2 mg the title compound (17%).

LC/MS=m/z 545.4 [M+H] Ret. Time: 1.94 min

Example 370

5-[3-({[(2,5-dichlorophenyl)sulfonyl]amino}methyl)phenyl]-3-[1-(ethylsulfonyl)-4-piperidinyl]-1H-indole-7-carboxamide

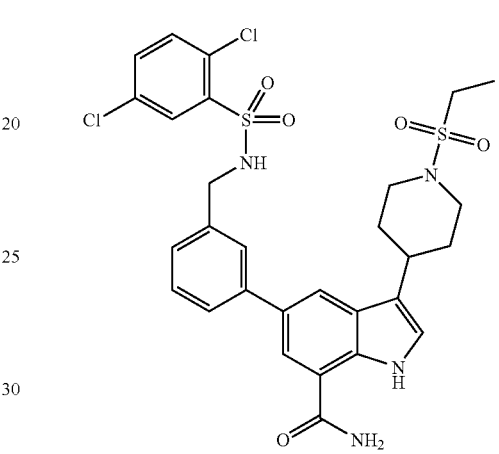

To a solution of 5-[3-(aminomethyl)phenyl]-3-[1-(ethylsulfonyl)-4-piperidinyl]-1H-indole-7-carboxamide (40 mg, 0.096 mmol) in DMF (1.0 mL) and DCM (1.0 mL) was added 2,5-dichlorobenzenesulfonyl chloride (86 mg, 0.352 mmol) and DIEA (62 µL, 0.352 mmol). Reaction was stirred at room temperature for 6 h. Reaction mixture was then concentrated and purified by Gilson Preparatory HPLC to give 6.6 mg the title compound (11%).

LC/MS=m/z 649.2 [M+H] Ret. Time: 2.25 min

Example 371

5-[3-({[(4-bromophenyl)sulfonyl]amino}methyl)phenyl]-3-[1-(ethylsulfonyl)-4-piperidinyl]-1H-indole-7-carboxamide

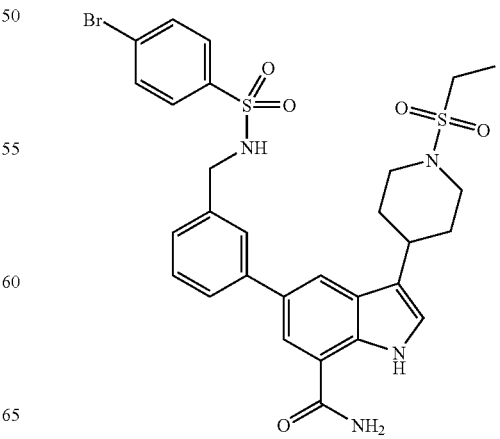

The title compound was prepared according to the general procedure of 5-[3-({[(2,5-dichlorophenyl)sulfonyl]amino}methyl)phenyl]-3-[1-(ethylsulfonyl)-4-piperidinyl]-1H-indole-7-carboxamide substituting 4-bromobenzenesulfonyl chloride (90 mg, 0.352 mmol) for 2,5-dichlorobenzenesulfonyl chloride. Reaction mixture was then concentrated and purified by Gilson Preparatory HPLC to give 19.4 mg the title compound (31%).

LC/MS=m/z 659.4 [M+H] Ret. Time: 2.20 min

Example 372

5-[3-({[(4-chlorophenyl)sulfonyl]amino}methyl)phenyl]-3-[1-(ethylsulfonyl)-4-piperidinyl]-1H-indole-7-carboxamide

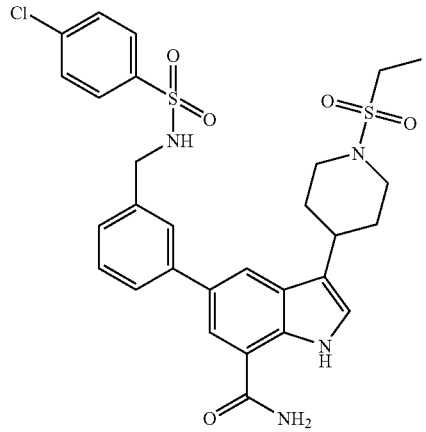

The title compound was prepared according to the general procedure of 5-[3-({[(2,5-dichlorophenyl)sulfonyl]amino}methyl)phenyl]-3-[1-(ethylsulfonyl)-4-piperidinyl]-1H-indole-7-carboxamide substituting (2E,4E)-5-chloro-2,4,6-heptatriene-2-sulfonyl chloride (80 mg, 0.352 mmol) for 2,5-dichlorobenzenesulfonyl chloride. Reaction mixture was then concentrated and purified by Gilson Preparatory HPLC to give 7.5 mg the title compound (13%).

LC/MS=m/z 615.2 [M] Ret. Time: 2.19 min

Example 373

3-[1-(ethylsulfonyl)-4-piperidinyl]-5-[3-({[(3-fluorophenyl)sulfonyl]amino}methyl)phenyl]-1H-indole-7-carboxamide

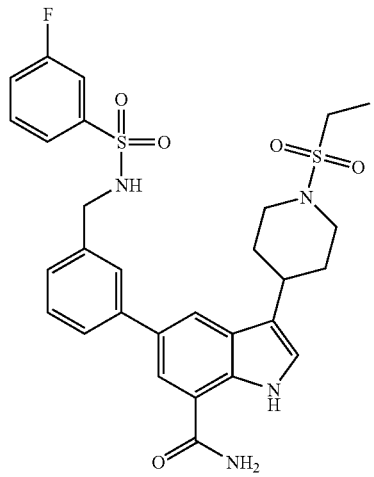

The title compound was prepared according to the general procedure of 5-[3-({[(2,5-dichlorophenyl)sulfonyl]amino}methyl)phenyl]-3-[1-(ethylsulfonyl)-4-piperidinyl]-1H-indole-7-carboxamide substituting 3-fluorobenzenesulfonyl chloride (69 mg, 0.352 mmol) for 2,5-dichlorobenzenesulfonyl chloride. Reaction mixture was then concentrated and purified by Gilson Preparatory HPLC to give 7.3 mg the title compound (13%).

LC/MS=m/z 599.2 [M+H] Ret. Time: 2.15 min

Example 374

5-[3-({[(2-chlorophenyl)sulfonyl]amino}methyl)phenyl]-3-[1-(ethylsulfonyl)-4-piperidinyl]-1H-indole-7-carboxamide

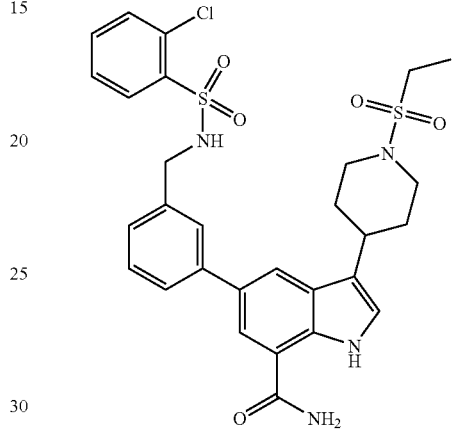

The title compound was prepared according to the general procedure of 5-[3-({[(2,5-dichlorophenyl)sulfonyl]amino}methyl)phenyl]-3-[1-(ethylsulfonyl)-4-piperidinyl]-1H-indole-7-carboxamide substituting 2-chlorobenzenesulfonyl chloride (74 mg, 0.352 mmol) for 2,5-dichlorobenzenesulfonyl chloride. Reaction mixture was then concentrated and purified by Gilson Preparatory HPLC to give 17.3 mg the title compound (29%).

LC/MS=m/z 615.2 [M] Ret. Time: 2.15 min

Example 375

5-[3-({[(2,5-dichloro-3-thienyl)sulfonyl]amino}methyl)phenyl]-3-[1-(ethylsulfonyl)-4-piperidinyl]-1H-indole-7-carboxamide

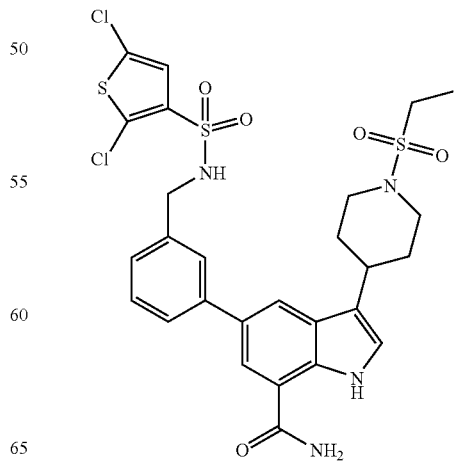

The title compound was prepared according to the general procedure of 5-[3-({[(2,5-dichlorophenyl)sulfonyl]amino}methyl)phenyl]-3-[1-(ethylsulfonyl)-4-piperidinyl]-1H-indole-7-carboxamide substituting 2,5-dichloro-3-thiophenesulfonyl chloride (86 mg, 0.352 mmol) for 2,5-dichlorobenzenesulfonyl chloride. Reaction mixture was then concentrated and purified by Gilson Preparatory HPLC to give 16.7 mg the title compound (27%).
LC/MS=m/z 655.2 [M] Ret. Time: 2.24 min Example 376

5-[3-({[(2-chloro-6-methylphenyl)sulfonyl]amino}methyl)phenyl]-3-[1-(ethylsulfonyl)-4-piperidinyl]-1H-indole-7-carboxamide

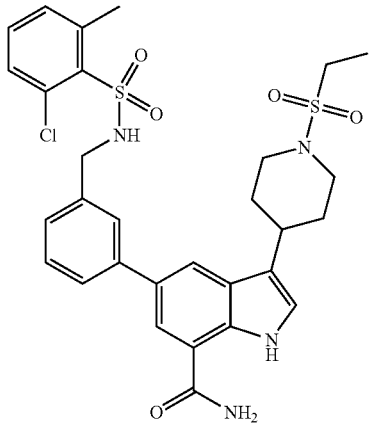

The title compound was prepared according to the general procedure of 5-[3-({[(2,5-dichlorophenyl)sulfonyl]amino}methyl)phenyl]-3-[1-(ethylsulfonyl)-4-piperidinyl]-1H-indole-7-carboxamide substituting 2-chloro-6-methyl-benzenesulfonyl chloride (86 mg, 0.352 mmol) for 2,5-dichlorobenzenesulfonyl chloride. Reaction mixture was then concentrated and purified by Gilson Preparatory HPLC to give 17.9 mg the title compound (30%).
LC/MS=m/z 629.4 [M] Ret. Time: 2.19 min Example 377

3-[1-(ethylsulfonyl)-4-piperidinyl]-5-[3-({[(5-fluoro-2-methylphenyl)sulfonyl]amino}methyl)phenyl]-1H-indole-7-carboxamide

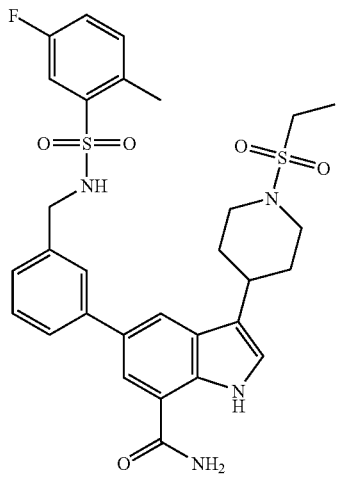

The title compound was prepared according to the general procedure of 5-[3-({[(2,5-dichlorophenyl)sulfonyl]amino}methyl)phenyl]-3-[1-(ethylsulfonyl)-4-piperidinyl]-1H-indole-7-carboxamide substituting 5-fluoro-2-methyl-benzenesulfonyl chloride (86 mg, 0.352 mmol) for 2,5-dichlorobenzenesulfonyl chloride. Reaction mixture was then concentrated and purified by Gilson Preparatory HPLC to give the title compound.
LC/MS=m/z 613.2 [M+H] Ret. Time: 2.18 min Example 378

5-[3-({[(1,2-dimethyl-1H-imidazol-4-yl)sulfonyl]amino}methyl)phenyl]-3-[1-(ethylsulfonyl)-4-piperidinyl]-1H-indole-7-carboxamide

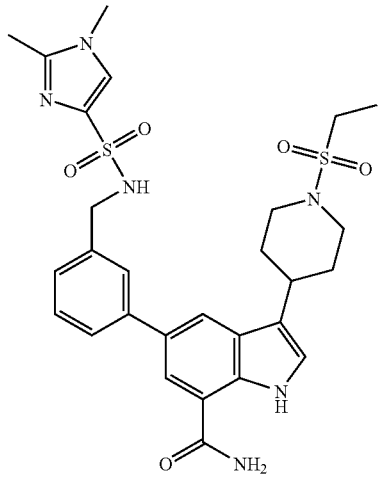

The title compound was prepared according to the general procedure of 5-[3-({[(2,5-dichlorophenyl)sulfonyl]amino}methyl)phenyl]-3-[1-(ethylsulfonyl)-4-piperidinyl]-1H-indole-7-carboxamide substituting 1,2-dimethyl-1H-imidazole-4-sulfonyl chloride (69 mg, 0.352 mmol) for 2,5-dichlorobenzenesulfonyl chloride. Reaction mixture was then concentrated and purified by Gilson Preparatory HPLC to give 1.9 mg the title compound (3.3%).
LC/MS=m/z 599.2 [M+H] Ret. Time: 1.76 min Example 379

3-[1-(ethylsulfonyl)-4-piperidinyl]-5-(3-{[(phenylsulfonyl)amino]methyl}phenyl)-1H-indole-7-carboxamide

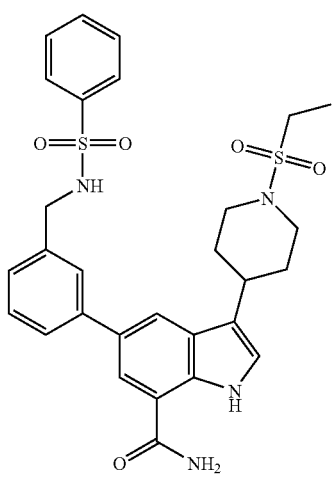

The title compound was prepared according to the general procedure of 5-[3-({[(2,5-dichlorophenyl)sulfonyl]amino}methyl)phenyl]-3-[1-(ethylsulfonyl)-4-piperidinyl]-1H-indole-7-carboxamide substituting benzenesulfonyl chloride (62 mg, 0.352 mmol) for 2,5-dichlorobenzenesulfonyl chloride. Reaction mixture was then concentrated and purified by Gilson Preparatory HPLC to give 13.4 mg the title compound (24%).

LC/MS=m/z 581.6 [M+H] Ret. Time: 2.10 min

Example 380

3-[1-(ethylsulfonyl)-4-piperidinyl]-5-[3-({[(4-fluorophenyl)sulfonyl]amino}methyl)phenyl]-1H-indole-7-carboxamide

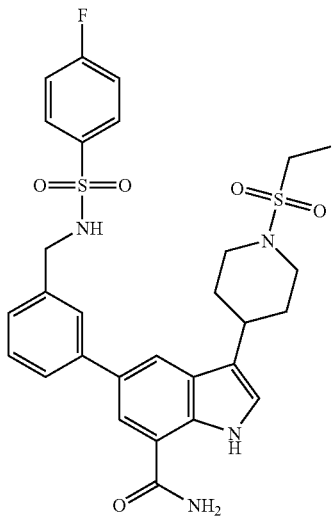

The title compound was prepared according to the general procedure of 5-[3-({[(2,5-dichlorophenyl)sulfonyl]amino}methyl)phenyl]-3-[1-(ethylsulfonyl)-4-piperidinyl]-1H-indole-7-carboxamide substituting 4-fluorobenzenesulfonyl chloride (69 mg, 0.352 mmol) for 2,5-dichlorobenzenesulfonyl chloride. Reaction mixture was then concentrated and purified by Gilson Preparatory HPLC to give 11.5 mg the title compound (20%).

LC/MS=m/z 599.2 [M+H] Ret. Time: 2.10 min

Example 381

5-[3-({[(4-bromo-2-ethylphenyl)sulfonyl]amino}methyl)phenyl]-3-[1-(ethylsulfonyl)-4-piperidinyl]-1H-indole-7-carboxamide

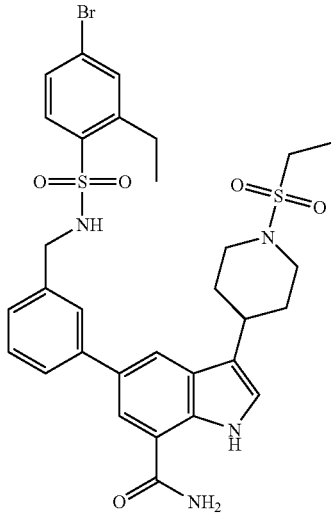

The title compound was prepared according to the general procedure of 5-[3-({[(2,5-dichlorophenyl)sulfonyl]amino}methyl)phenyl]-3-[1-(ethylsulfonyl)-4-piperidinyl]-1H-indole-7-carboxamide substituting 4-bromo-2-ethylbenzenesulfonyl chloride (100 mg, 0.352 mmol) for 2,5-dichlorobenzenesulfonyl chloride. Reaction mixture was then concentrated and purified by Gilson Preparatory HPLC to give 2.7 mg the title compound (4%).

LC/MS=m/z 687.6 [M] Ret. Time: 2.38 min

Example 382

5-(3-{[(1-benzothien-3-ylsulfonyl)amino]methyl}phenyl)-3-[1-(ethylsulfonyl)-4-piperidinyl]-1H-indole-7-carboxamide

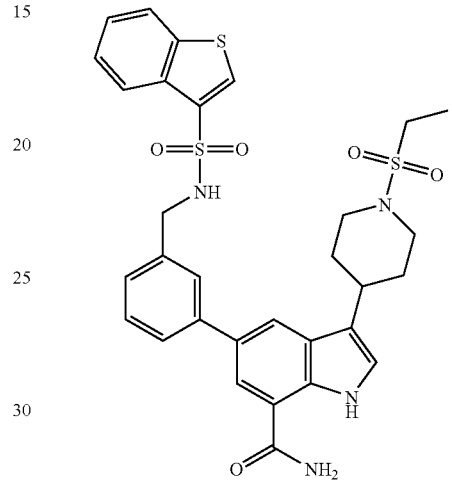

The title compound was prepared according to the general procedure of 5-[3-({[(2,5-dichlorophenyl)sulfonyl]amino}methyl)phenyl]-3-[1-(ethylsulfonyl)-4-piperidinyl]-1H-indole-7-carboxamide substituting 1-benzothiophene-3-sulfonyl chloride (82 mg, 0.352 mmol) for 2,5-dichlorobenzenesulfonyl chloride. Reaction mixture was then concentrated and purified by Gilson Preparatory HPLC to give 3.9 mg the title compound (6%).

LC/MS=m/z 637.4 [M+H] Ret. Time: 2.19 min

Example 383

5-{3-[({[4-(1,1-dimethylethyl)phenyl]sulfonyl}amino)methyl]phenyl}-3-[1-(ethylsulfonyl)-4-piperidinyl]-1H-indole-7-carboxamide

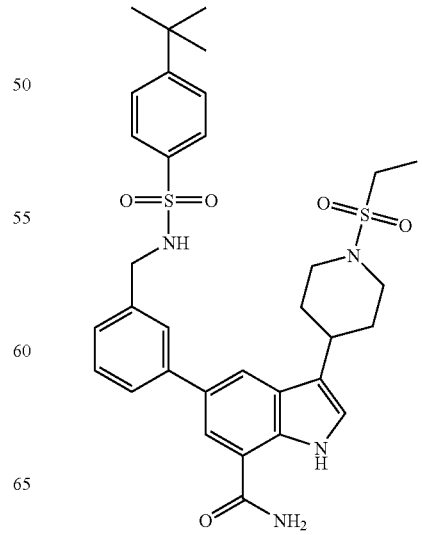

The title compound was prepared according to the general procedure of 5-[3-({[(2,5-dichlorophenyl)sulfonyl]amino}methyl)phenyl]-3-[1-(ethylsulfonyl)-4-piperidinyl]-1H-indole-7-carboxamide substituting 4-(1,1-dimethylethyl)benzenesulfonyl chloride (82 mg, 0.352 mmol) for 2,5-dichlorobenzenesulfonyl chloride. Reaction mixture was then concentrated and purified by Gilson Preparatory HPLC to give 15.6 mg the title compound (26%).
LC/MS=m/z 637.4 [M+H] Ret. Time: 2.35 min

Example 384

5-[3-({[(3,4-difluorophenyl)sulfonyl]amino}methyl)phenyl]-3-[1-(ethylsulfonyl)-4-piperidinyl]-1H-indole-7-carboxamide

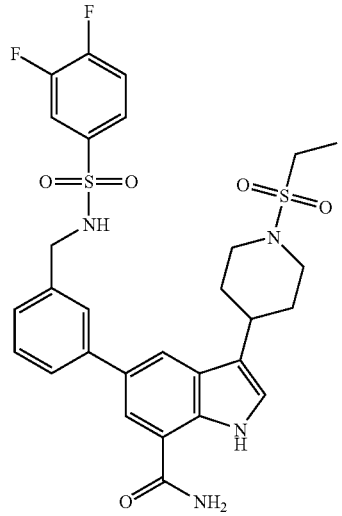

The title compound was prepared according to the general procedure of 5-[3-({[(2,5-dichlorophenyl)sulfonyl]amino}methyl)phenyl]-3-[1-(ethylsulfonyl)-4-piperidinyl]-1H-indole-7-carboxamide substituting 3,4-difluorobenzenesulfonyl chloride (75 mg, 0.352 mmol) for 2,5-dichlorobenzenesulfonyl chloride. Reaction mixture was then concentrated and purified by Gilson Preparatory HPLC to give the title compound.
LC/MS=m/z 617.2 [M+H] Ret. Time: 2.16 min

Example 385

5-(3-{[(2,1,3-benzoxadiazol-4-ylsulfonyl)amino]methyl}phenyl)-3-[1-(ethylsulfonyl)-4-piperidinyl]-1H-indole-7-carboxamide

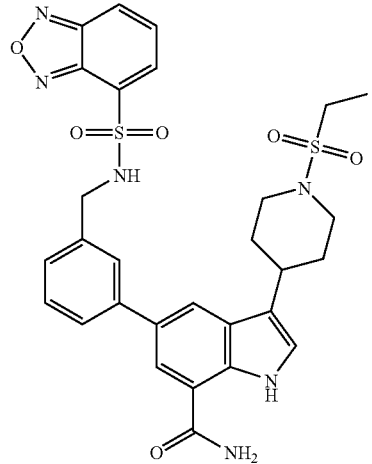

The title compound was prepared according to the general procedure of 5-[3-({[(2,5-dichlorophenyl)sulfonyl]amino}methyl)phenyl]-3-[1-(ethylsulfonyl)-4-piperidinyl]-1H-indole-7-carboxamide substituting 2,1,3-benzoxadiazole-4-sulfonyl chloride (77 mg, 0.352 mmol) for 2,5-dichlorobenzenesulfonyl chloride. Reaction mixture was then concentrated and purified by Gilson Preparatory HPLC to give the title compound.
LC/MS=m/z 623.4 [M+H] Ret. Time: 2.10 min

Example 386

3-[1-(ethylsulfonyl)-4-piperidinyl]-5-(3-{[(tetrahydro-3-furanylcarbonyl)amino]methyl}phenyl)-1H-indole-7-carboxamide

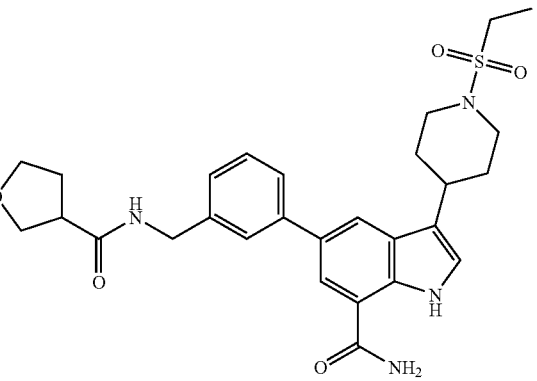

To a solution of tetrahydro-3-furancarboxylic acid (17 mg, 0.144 mmol) in DCM (2.0 mL) was added pyridine (3 drops) and oxalyl chloride (18 mg, 0.144 mmol). Reaction mixture was stirred overnight at room temperature. To the mixture was then added 5-[3-(aminomethyl)phenyl]-3-[1-(ethylsulfonyl)-4-piperidinyl]-1H-indole-7-carboxamide (40 mg, 0.096 mmol) in DMF (1.0 mL) and DIEA (33 µL, 0.192 mmol). Reaction mixture was stirred at room temperature overnight. Reaction mixture was concentrated under nitrogen and purified by Gilson Preparatory HPLC to give 5.3 mg the title compound (10%).
LC/MS=m/z 539.2 [M+H] Ret. Time: 1.80 min

Example 387

5-{4-[(cyclopentylsulfonyl)amino]phenyl}-3-[1-(ethylsulfonyl)-4-piperidinyl]-1H-indole-7-carboxamide trifluoroacetate

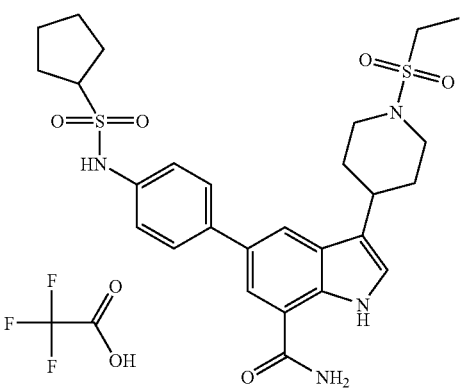

To 5-bromo-3-[1-(ethylsulfonyl)-4-piperidinyl]-1H-indole-7-carboxamide (20 mg, 0.048 mmol) was added chloro(di-2-norbornylphosphino)(2-dimethylaminomethylferrocen-1-yl)palladium (II) (10 mg, 0.016 mmol), potassium carbonate (13.4 mg, 0.097 mmol), and N-[4-(4,4,5,5-tetramethyl-1,3,2-dioxaborolan-2-yl)phenyl]cyclopentanesulfonamide (34 mg, 0.097 mmol) in dioxane (3 mL) and H$_2$O (1 mL). The reactin mixture was heated in a microwave at 160° C. for 10 min. The reaction mixture was concentrated under nitrogen and purified by Gilson Preparatory HPLC to give 8.6 mg the title compound (32%).

LC/MS=m/z 559.2[M+H] Ret. Time: 2.00 min

Example 388

3-[1-(ethylsulfonyl)-4-piperidinyl]-5-[4-(4-methyl-2-oxo-1-piperazinyl)phenyl]-1H-indole-7-carboxamide

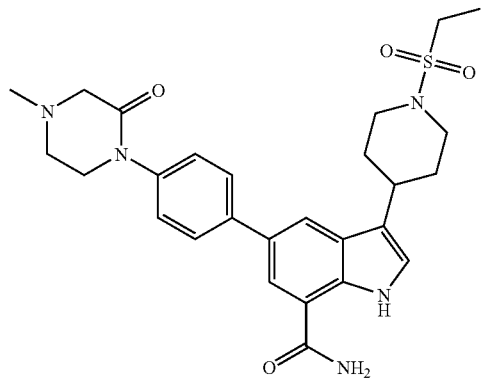

To 5-bromo-3-[1-(ethylsulfonyl)-4-piperidinyl]-1H-indole-7-carboxamide (20 mg, 0.048 mmol) was added 4-methyl-1-[4-(4,4,5,5-tetramethyl-1,3,2-dioxaborolan-2-yl)phenyl]-2-piperazinone (31 mg, 0.097 mmol) in dioxane (3.0 mL) and H$_2$O (1.0 mL), potassium carbonate (13 mg, 0.097 mmol) and chloro(di-2-norbornylphosphino)(2-dimethylaminomethylferrocen-1-yl)palladium (II) (10 mg, 0.016 mmol). The reaction mixture was reacted in a microwave at 160° C. for 10 min. The reaction mixture was heated in a microwave at 160° C. for 10 min. The reaction mixture was concentrated under Nitrogen and purified by Gilson Preparatory HPLC. The desired fraction in CH$_3$CN and H$_2$O was treated with saturated potassium carbonate to neutralize salts and then concentrated to give 1.9 mg the title compound (8%).

LC/MS=m/z 524.6 [M+H] Ret. Time: 1.49 min

Example 389

5-[6-(4-acetyl-1-piperazinyl)-3-pyridinyl]-3-[1-(ethylsulfonyl)-4-piperidinyl]-1H-indole-7-carboxamide trifluoroacetate

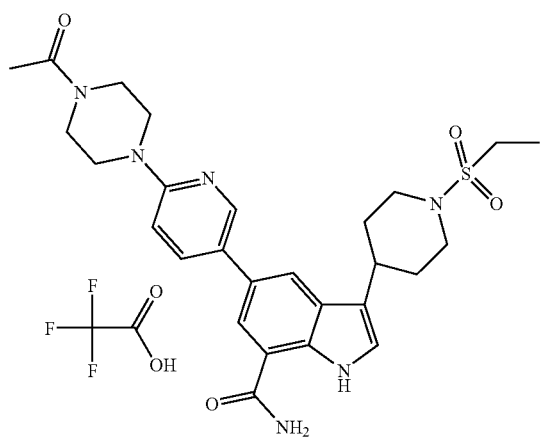

To a solution of 3-[1-(ethylsulfonyl)-4-piperidinyl]-5-[6-(1-piperazinyl)-3-pyridinyl]-1H-indole-7-carboxamide (40 mg, 0.080 mmol) in dichloromethane at 0° C., was added acetyl chloride (7 μL, 0.096 mmol) and DIEA (11.6 μL, 0.12 mmol). Reaction mixture was reacted for 0.5 h from 0° C. to room temperature and then quenched with H$_2$O. Compound was purified by MDAP HPLC to give 7 mg of the title compound (40%).

LC/MS=m/z 539.4 [M+H] Ret. Time: 1.27 min

Example 390

3-[1-(ethylsulfonyl)-4-piperidinyl]-5-(4-{[(methyloxy)amino]methyl}phenyl)-1H-indole-7-carboxamide

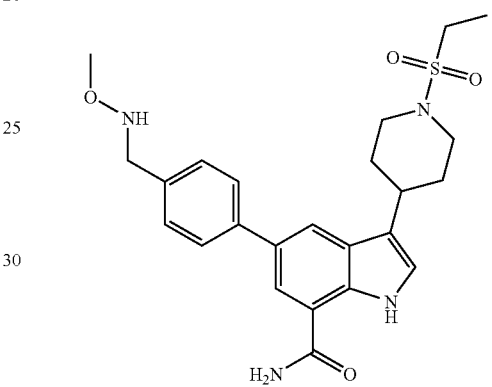

To a solution of 3-[1-(ethylsulfonyl)-4-piperidinyl]-5-(4-formylphenyl)-1H-indole-7-carboxamide (50 mg, 0.114 mmol) in DCM (1.5 mL) and MeOH (1.5 mL) was added O-methylhydroxylamine (114 mg, 1.71 mmol). The reaction was stirred overnight. The solvent was then concentrated and purified by Gilson Preparatory HPLC to give 38 mg of 3-[1-(ethylsulfonyl)-4-piperidinyl]-5-(4-{[(methyloxy)imino]methyl}phenyl)-1H-indole-7-carboxamide (76%).

To a solution of 3-[1-(ethylsulfonyl)-4-piperidinyl]-5-(4-{[(methyloxy)imino]methyl}phenyl)-1H-indole-7-carboxamide (21.5 mg, 0.046 mmol) in DCM (3.0 mL) and MeOH (3.0 mL) was added drops of HCl in 1,4-dioxane to maintain pH=4 at 0° C. Sodium cyanoborohydride (29 mg, 0.46 mmol) was then added and stirred overnight at room temperature. Additional HCl in 1,4-dioxane was added to maintain pH=4 in addition to sodium cyanoborohydride (45 mg, 0.72 mmol). Reaction mixture then stirred over 48 h. Additional HCl in 1,4-dioxane was added to maintain pH=4 at 0° C. and stirred till room temperature was achieved. Mixture was quenched with H$_2$O. DCM was then added for aqueous work-up and mixture was concentrated. The reside was then take up in DCM and purified on the SCX SPE cartridge to afford 15.2 mg of the title compound (70%).

LC/MS=m/z 471.6 [M+H] Ret. Time: 1.67 min

Example 391

3-[1-(ethylsulfonyl)-4-piperidinyl]-5-(3-{[(methyloxy)amino]methyl}phenyl)-1H-indole-7-carboxamide

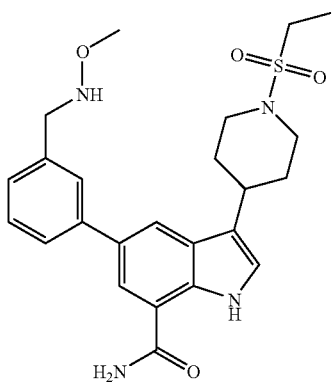

To a solution of 3-[1-(ethylsulfonyl)-4-piperidinyl]-5-(3-formylphenyl)-1H-indole-7-carboxamide (50 mg, 0.114 mmol) in DMSO (3.0 mL) was added O-methylhydroxylamine (57 mg, 0.684 mmol). The reaction was stirred overnight. Additional O-methylhydroxylamine (0.342 mmol) was added to the reaction mixture and stirred for 48 h. The solvent was then concentrated and purified by Gilson Preparatory HPLC to give 29.8 mg of 3-[1-(ethylsulfonyl)-4-piperidinyl]-5-(3-{[(methyloxy)imino]methyl}phenyl)-1H-indole-7-carboxamide (56%).

To a solution of 3-[1-(ethylsulfonyl)-4-piperidinyl]-5-(3-{[(methyloxy)imino]methyl}phenyl)-1H-indole-7-carboxamide (58 mg, 0.123 mmol) in DCM (3.0 mL) and MeOH (3.0 mL) was added HCl in 1,4-dioxane to maintain pH=4 at 0° C. Sodium cyanoborohydride (176 mg, 3.69 mmol) was then added and stirred overnight for 48 h. The compound was purified by Gilson Preparatory HPLC to give 20.0 mg of the title compound (89%).

LC/MS=m/z 471.6 [M+H] Ret. Time: 1.75 min

Example 392

3-[1-(ethylsulfonyl)-4-piperidinyl]-5-(5-{[4-(1-pyrrolidinyl)-1-piperidinyl]methyl}-3-thienyl)-1H-indole-7-carboxamide trifluoroacetate

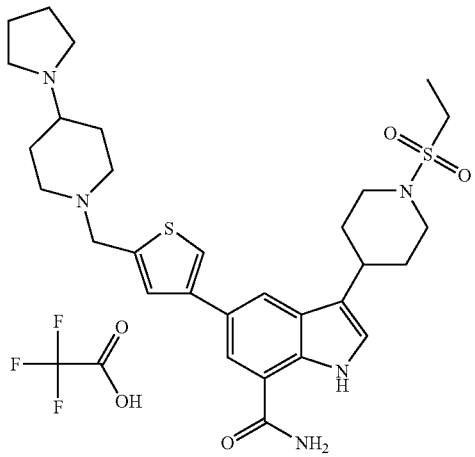

To a solution of 3-[1-(ethylsulfonyl)-4-piperidinyl]-5-(5-formyl-3-thienyl)-1H-indole-7-carboxamide (50 mg, 0.112 mmol) in DMSO (2.0 mL) was added 4-(1-pyrrolidinyl)piperidine (173 mg, 1.12 mmol) and acetic acid (5 drops). After 6 h, sodium triacetoxyborohydride (238 mg, 1.12 mmol) was added and the reaction was stirred overnight. The reaction mixture was purified by Gilson Preparatory HPLC to give 17.0 mg of the title compound (26%).

LC/MS=m/z 584.4 [M+H] Ret. Time: 1.38 min

Example 393

3-[1-(ethylsulfonyl)-4-piperidinyl]-5-(5-{[(2S)-2-(trifluoromethyl)-1-pyrrolidinyl]methyl}-3-thienyl)-1H-indole-7-carboxamide trifluoroacetate

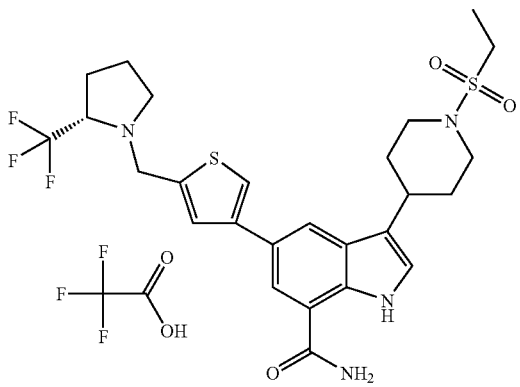

To a solution of 3-[1-(ethylsulfonyl)-4-piperidinyl]-5-(5-formyl-3-thienyl)-1H-indole-7-carboxamide (50 mg, 0.112 mmol) in DCM (3.0 mL) and MeOH (1.5 mL) was added (2S)-2-(trifluoromethyl)pyrrolidine (156 mg, 1.12 mmol) and acetic acid (5 drops). After 6 h of stirring at room temperature, sodium borohydride (43 mg, 1.12 mmol) was added and the reaction was stirred overnight at room temperature. The reaction mixture was purified by Gilson Preparatory HPLC to give 5.0 mg of the title compound (8%).

LC/MS=m/z 569.4 [M+H] Ret. Time: 2.37 min

Example 394

5-(5-{[(2R)-2-(hydroxymethyl)-1-pyrrolidinyl]methyl}-3-thienyl)-3-{1-[(1-methylethyl)sulfonyl]-4-piperidinyl}-1H-indole-7-carboxamide

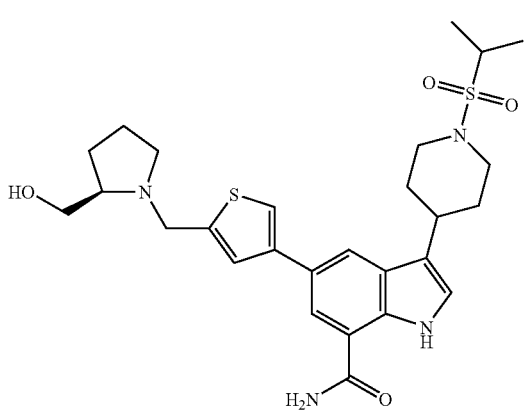

To a solution of 5-(5-formyl-3-thienyl)-3-{1-[(1-methylethyl)sulfonyl]-4-piperidinyl}-1H-indole-7-carboxamide (25 mg, 0.054 mmol) in DMSO (2 mL) was added (2R)-2-pyrrolidinylmethanol (101.15 mg, 1 mmol) and 2 drops of acetic acid. The resulting mixture was stirred at room temperature for 4 h followed by an addition of sodium triacetoxyborohydride (212 mg, 0.54 mmol). The mixture was reacted overnight. It was then purified by Gilson Preparatory HPLC to give 20.5 mg of the title compound (69.7%).

LC/MS=m/z 546 [M+H] Ret. Time: 1.47 min.

Example 395

5-(5-{[(3S)-3-hydroxy-1-pyrrolidinyl]methyl}-3-thienyl)-3-{1-[(1-methylethyl)sulfonyl]-4-piperidinyl}-1H-indole-7-carboxamide

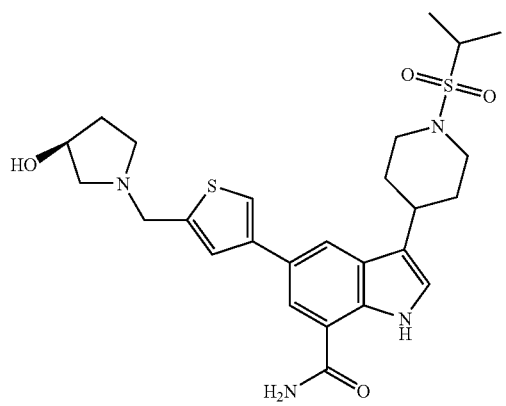

The title compound was prepared according to the general procedure of 5-(5-{[(2R)-2-(hydroxymethyl)-1-pyrrolidinyl]methyl}-3-thienyl)-3-{1-[(1-methylethyl)sulfonyl]-4-piperidinyl}-1H-indole-7-carboxamide, substituting (3S)-3-pyrrolidinol (90.13 mg, 1.20 mmol) for (2R)-2-pyrrolidinylmethanol to afford 12.8 mg of the title compound (53.1%).

LC/MS=m/z 532 [M+H] Ret. Time: 1.45 min.

Example 396

5-(5-{[cyclopentyl(methyl)amino]methyl}-3-thienyl)-3-{1-[(1-methylethyl)sulfonyl]-4-piperidinyl}-1H-indole-7-carboxamide

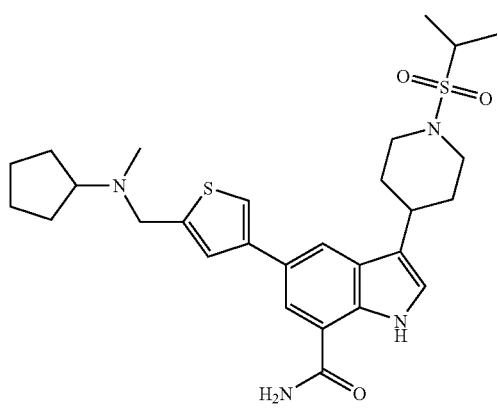

The title compound was prepared according to the general procedure of 5-(5-{[(2R)-2-(hydroxymethyl)-1-pyrrolidinyl]methyl}-3-thienyl)-3-{1-[(1-methylethyl)sulfonyl]-4-piperidinyl}-1H-indole-7-carboxamide, substituting N-methylcyclopentanamine (90.13 mg, 1.20 mmol) for (2R)-2-pyrrolidinylmethanol to afford 10 mg of the title compound (54.3%)

LC/MS=m/z 544.2 [M+H] Ret. Time: 1.65 min.

Example 397

5-(5-{[(2-hydroxyethyl)(methyl)amino]methyl}-3-thienyl)-3-{1-[(1-methylethyl)sulfonyl]-4-piperidinyl}-1H-indole-7-carboxamide

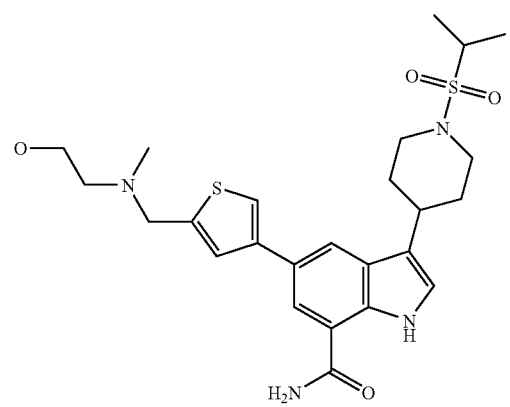

The title compound was prepared according to the general procedure of 5-(5-{[(2R)-2-(hydroxymethyl)-1-pyrrolidinyl]methyl}-3-thienyl)-3-{1-[(1-methylethyl)sulfonyl]-4-piperidinyl}-1H-indole-7-carboxamide, substituting 2-(methylamino)ethanol (90.13 mg, 1.20 mmol) for (2R)-2-pyrrolidinylmethanol to afford 8 mg of the title compound (51.9%), LC/MS=m/z 520 [M+H] Ret. Time: 1.44 min.

Example 398

5-(5-{[(2-amino-2-oxoethyl)(methyl)amino]methyl}-3-thienyl)-3-{1-[(1-methylethyl)sulfonyl]-4-piperidinyl}-1H-indole-7-carboxamide

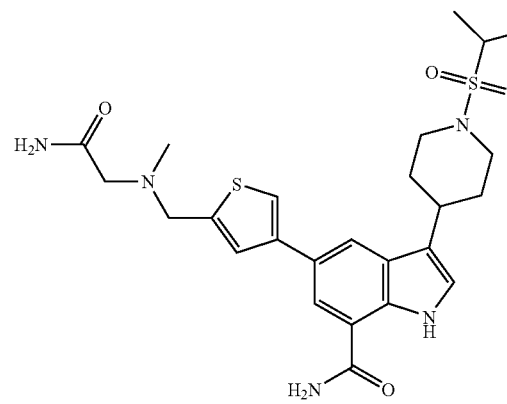

The title compound was prepared according to the general procedure of 5-(5-{[(2R)-2-(hydroxymethyl)-1-pyrrolidinyl]methyl}-3-thienyl)-3-{1-[(1-methylethyl)sulfonyl]-4-piperidinyl}-1H-indole-7-carboxamide, substituting N2-methylglycinamide (90.13 mg, 1.200 mmol) for (2R)-2-pyrrolidinylmethanol to afford 15 mg of the title compound (53.2%).

LC/MS=m/z 520 [M+H] Ret. Time: 1.44 min.

Example 399

3-[1-(ethylsulfonyl)-4-piperidinyl]-5-(5-{[methyl(2-propen-1-yl)amino]methyl}-3-thienyl)-1H-indole-7-carboxamide

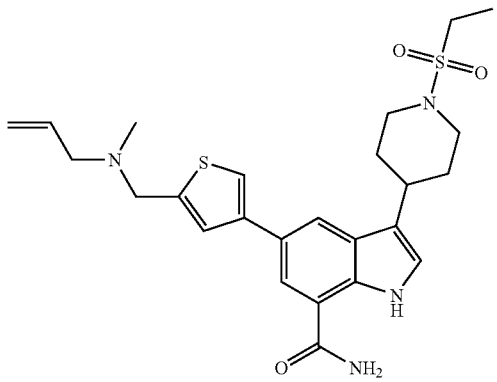

Allylamine (0.034 mL, 0.449 mmol) and HOAc (0.026 mL, 0.449 mmol) were added to a solution of 3-[1-(ethylsulfonyl)-4-piperidinyl]-5-(5-formyl-3-thienyl)-1H-indole-7-carboxamide (20 mg, 0.0449 mmol) in DMSO (0.5 mL) in a 1-dram vial. NaBH(OAc)$_3$ (95 mg, 0.449 mmol) was then added, the vial was capped and the reaction was stirred at room temperature for 15 h. NaCNBH$_3$ (28 mg, 0.449 mmol) and MeOH were added, and the reaction was stirred for an additional 4 h. An aqueous solution of 37 wt % formaldehyde (0.069 mL, 0.898 mmol) was added, and the reaction was stirred for an additional 1 h. The reaction mixture was filtered through a 2 g SCX cartridge (pre-equilibrated with 3 mL MeOH), eluting in sequence with MeOH (3 mL) and a 2 M solution of NH$_3$/MeOH (9 mL). The NH$_3$/MeOH fraction was concentrated under a stream of nitrogen at 50° C., and the residue was dissolved in DMSO (1 mL) and purified on a Gilson HPLC (Xbridge Prep C18 column: 19×100 mm) eluting at 20 mL per min with a linear gradient running from 10% CH$_3$CN/H$_2$O (0.1% NH$_4$OH) to 70% CH$_3$CN/H$_2$O (0.1% NH$_4$OH) over 15 min. The fractions containing the title compound were concentrated under a stream of nitrogen at 50° C. to give 5.2 mg of the title compound (23%).

LC/MS=m/z 501.4 [M+H] Ret. Time: 1.48 min.

Example 400

5-(5-{[[(3,5-dimethyl-1H-pyrazol-4-yl)methyl](methyl)amino]methyl}-3-thienyl)-3-[1-(ethylsulfonyl)-4-piperidinyl]-1H-indole-7-carboxamide

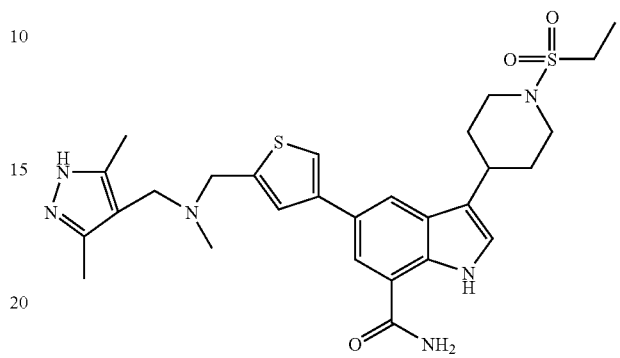

To a solution of 3-[1-(ethylsulfonyl)-4-piperidinyl]-5-(5-formyl-3-thienyl)-1H-indole-7-carboxamide (45 mg, 100 μmol) in dimethyl sulfoxide (1.0 mL) was added 1-(3,5-dimethyl-1H-pyrazol-4-yl)-N-methylmethanamine (320 μmol) and 2 to 3 drops of glacial acetic acid. The resulting mixture is agitated overnight. After 18 h, sodium triacetoxyborohydride (200 mg, 1000 μmol) is added. This mixture is agitated for 1.5 h followed by purification by Gilson Preparatory HPLC to give 6.24 mg of the title compound (11.0%).

LC/MS=m/z 569.3 [M+H] Ret. Time: 1.42 min.

Example 401

5-(5-{[(cyanomethyl)(methyl)amino]methyl}-3-thienyl)-3-[1-(ethylsulfonyl)-4-piperidinyl]-1H-indole-7-carboxamide

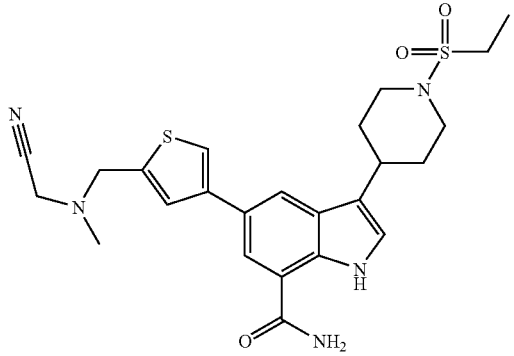

The title compound was prepared according to the general procedure of 5-(5-{[[(3,5-dimethyl-1H-pyrazol-4-yl)methyl](methyl)amino]methyl}-3-thienyl)-3-[1-(ethylsulfonyl)-4-piperidinyl]-1H-indole-7-carboxamide, substituting (methylamino)acetonitrile (320 μmol) for 1-(3,5-dimethyl-1H-pyrazol-4-yl)-N-methylmethanamine to afford 6.36 mg of the title compound (12.7%).

LC/MS=m/z 430 [M+H] Ret. Time: 1.70 min.

Example 402

3-[1-(ethylsulfonyl)-4-piperidinyl]-5-(5-{[methyl(1-methylpropyl)amino]methyl}-3-thienyl)-1H-indole-7-carboxamide

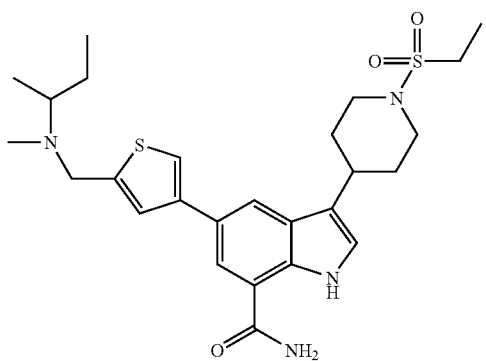

To a solution of 3-[1-(ethylsulfonyl)-4-piperidinyl]-5-(5-formyl-3-thienyl)-1H-indole-7-carboxamide (45 mg, 0.1 mmol) in dimethyl sulfoxide (1 mL) was added 2-butanamine (1 mmol), 1 to 2 drops of acetic acid and sodium triacetoxyborohydride (211 mg, 1 mmol). The resulting mixture was capped and stirred for 18 h followed by an addition of sodium cyanoborohydride (62 mg, 1 mmol) in methanol (0.5 mL). This was stirred for 3 h followed by an addition of formaldehyde, 37% in water, (1.5 mL). This was purified through SCX (2 g) cartridge eluting with methanol followed by $NH_3$ in methanol. Further purification was performed by Gilson Preparatory HPLC. XBridge C18 Column (P/N 186002978) using a gradient of 10% acetonitrile to 70% acetonitrile in water with 0.1% $NH_4OH$ to give 14.4 mg of the title compound (27.9%).

LC/MS=m/z 517.3 [M+H] Ret. Time: 1.58 min.

Example 403

5-(5-{[[2-(ethyloxy)ethyl](methyl)amino]methyl}-3-thienyl)-3-[1-(ethylsulfonyl)-4-piperidinyl]-1H-indole-7-carboxamide

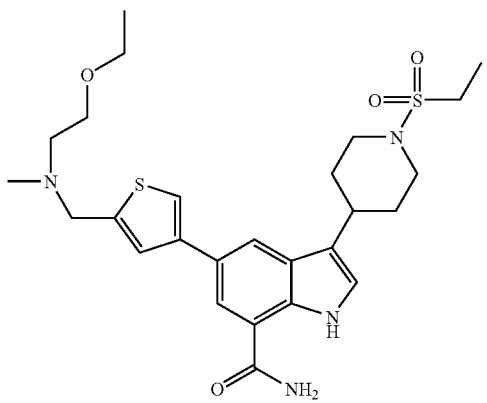

The title compound was prepared according to the general procedure of 3-[1-(ethylsulfonyl)-4-piperidinyl]-5-(5-{[methyl(1-methylpropyl)amino]methyl}-3-thienyl)-1H-indole-7-carboxamide, substituting 2-(ethyloxy)ethanamine (1 mmol) for added 2-butanamine to afford 6.1 mg of the title compound (11.5%).

LC/MS=m/z 533.2 [M+H] Ret. Time: 1.57 min.

Example 404

5-(5-{[cyclobutyl(methyl)amino]methyl}-3-thienyl)-3-[1-(ethylsulfonyl)-4-piperidinyl]-1H-indole-7-carboxamide trifluoroacetate

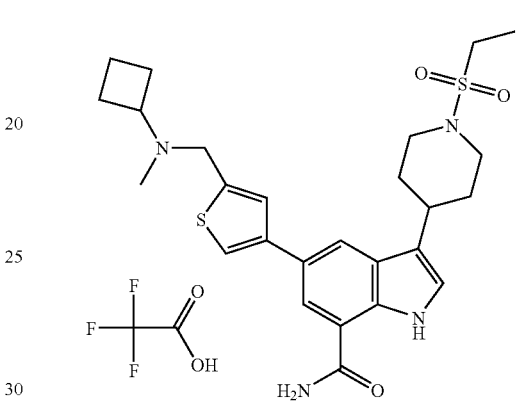

The title compound was prepared according to the general procedure of 3-[1-(ethylsulfonyl)-4-piperidinyl]-5-(5-{[methyl(1-methylpropyl)amino]methyl}-3-thienyl)-1H-indole-7-carboxamide, substituting cyclobutylamine (1 mmol) for added 2-butanamine to afford 3.7 mg of the title compound (5.9%).

LC/MS=m/z 515.3 [M+H] Ret. Time: 1.64 min.

Example 405

3-[1-(ethylsulfonyl)-4-piperidinyl]-5-[5-({2-[(methyloxy)methyl]-1-pyrrolidinyl}methyl)-3-thienyl]-1H-indole-7-carboxamide trifluoroacetate

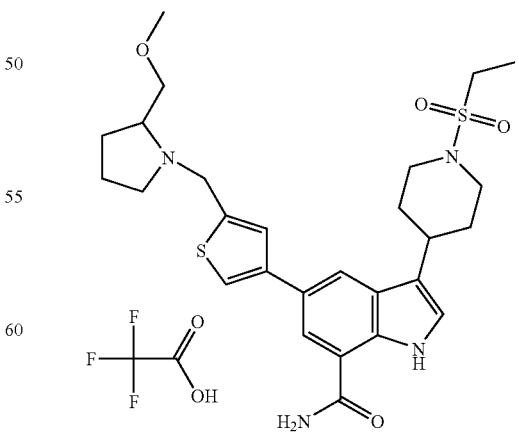

The title compound was prepared according to the general procedure of 3-[1-(ethylsulfonyl)-4-piperidinyl]-5-(5-{[methyl(1-methylpropyl)amino]methyl}-3-thienyl)-1H-indole-7-carboxamide, substituting 2-[(methyloxy)methyl]pyrrolidine (1 mmol) for added 2-butanamine to afford 5 mg of the title compound (7.6%).

LC/MS=m/z 545.3 [M+H] Ret. Time: 1.65 min.

Example 406

5-(5-{[(1,1-dimethylethyl)(methyl)amino]methyl}-3-thienyl)-3-[1-(ethylsulfonyl)-4-piperidinyl]-1H-indole-7-carboxamide trifluoroacetate

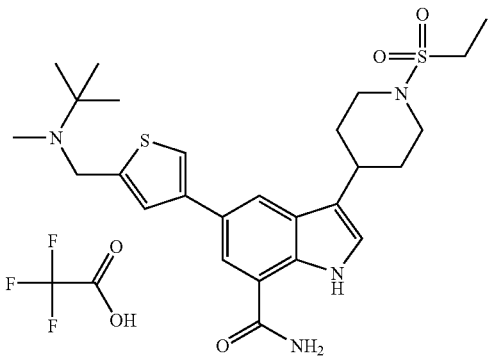

The title compound was prepared according to the general procedure of 3-[1-(ethylsulfonyl)-4-piperidinyl]-5-(5-{[methyl(1-methylpropyl)amino]methyl}-3-thienyl)-1H-indole-7-carboxamide, substituting 2-methyl-2-propanamine (1 mmol) for added 2-butanamine to afford 10.9 mg of the title compound (17.3%).

LC/MS=m/z 517.3 [M+H] Ret. Time: 1.61 min.

Example 407

3-[1-(ethylsulfonyl)-4-piperidinyl]-5-(5-{[3-(trifluoromethyl)-1-piperidinyl]methyl}-3-thienyl)-1H-indole-7-carboxamide trifluoroacetate

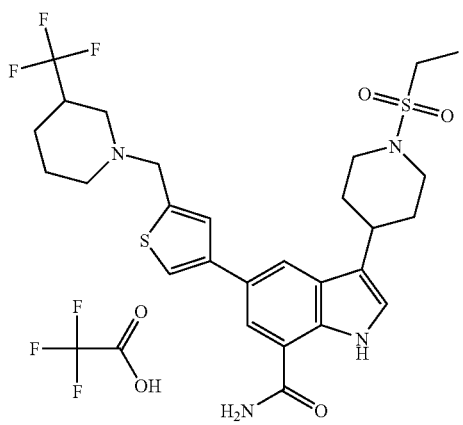

The title compound was prepared according to the general procedure of 3-[1-(ethylsulfonyl)-4-piperidinyl]-5-(5-{[methyl(1-methylpropyl)amino]methyl}-3-thienyl)-1H-indole-7-carboxamide, substituting 3-(trifluoromethyl)piperidine (1 mmol) for added 2-butanamine to afford 5.4 mg of the title compound (7.8%).

LC/MS=m/z 583.3 [M+H] Ret. Time: 1.73 min.

Example 408

3-[1-(ethylsulfonyl)-4-piperidinyl]-5-(5-{[[(1S)-2-hydroxy-1-methylethyl](methyl)amino]methyl}-3-thienyl)-1H-indole-7-carboxamide trifluoroacetate

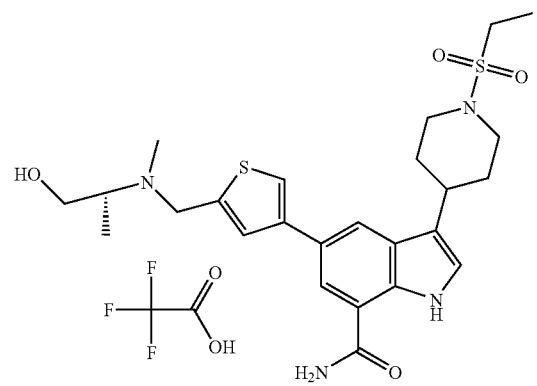

To a vial containing (2R)-2-amino-1-propanol (90.13 mg, 1.2 mmol) was added a solution of 3-[1-(ethylsulfonyl)-4-piperidinyl]-5-(5-formyl-3-thienyl)-1H-indole-7-carboxamide (30 mg, 0.067 mmol) in DMSO (300 µL) and acetic acid (50 µL). The resulting mixture was shaken for 5 min followed by an addition of sodium triacetoxyborohydride (250 mg, 1.20 mmol) in DMSO (800 µL). The mixture was shaken overnight. Sodium cyanoborohydride (79 mg, 1.20 mmol) in methanol (300 µL) was then added and stirred for 48 h. This was followed by an addition of formaldehyde (100 µL). The reaction was then stirred for 1 h followed by a 2 g SCX crude cartridge separation. The solids were then filtered off, solution was concentrated and purification was repeated on a 5 g SCX cartridge eluting with ammonia in MeOH. The ammonia in MeOH fraction collection was concentrated and separated using Gilson Preparatory HPLC to afford 18.6 mg of the title compound (43.9%).

LC/MS=m/z 519.3 [M+H] Ret. Time: 1.49 min.

Example 409

5-(5-{[(cyclopropylmethyl)(methyl)amino]methyl}-3-thienyl)-3-[1-(ethylsulfonyl)-4-piperidinyl]-1H-indole-7-carboxamide trifluoroacetate

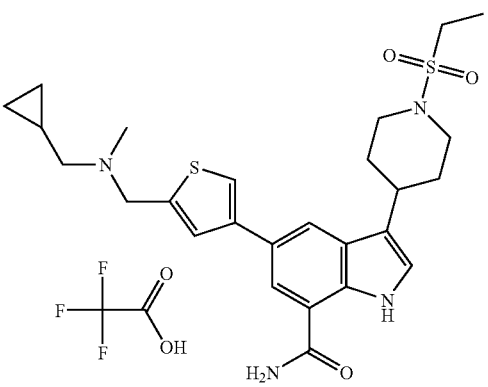

The title compound was prepared according to the general procedure of 3-[1-(ethylsulfonyl)-4-piperidinyl]-5-(5-{[[(1S)-2-hydroxy-1-methylethyl](methyl)amino]methyl}-3-thienyl)-1H-indole-7-carboxamide trifluoroacetate (salt), substituting (cyclopropylmethyl)amine (1.20 mmol) for (2R)-2-amino-1-propanol to afford 6.2 mg of the title compound (14.7%).

LC/MS=m/z 515.3 [M+H] Ret. Time: 1.61 min.

Example 410

5-(5-{[[2-(acetylamino)ethyl](methyl)amino]methyl}-3-thienyl)-3-[1-(ethylsulfonyl)-4-piperidinyl]-1H-indole-7-carboxamide trifluoroacetate

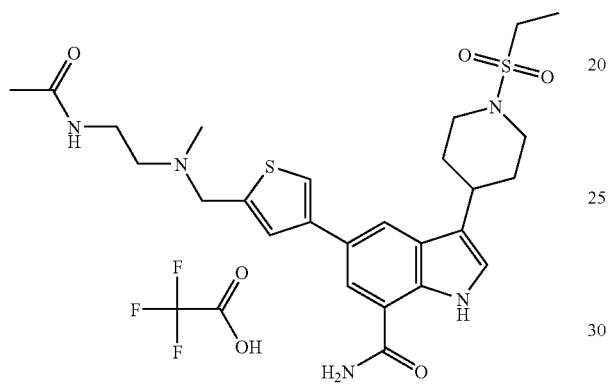

The title compound was prepared according to the general procedure of 3-[1-(ethylsulfonyl)-4-piperidinyl]-5-(5-{[[(1S)-2-hydroxy-1-methylethyl](methyl)amino]methyl}-3-thienyl)-1H-indole-7-carboxamide trifluoroacetate (salt), substituting N-(2-aminoethyl)acetamide (1.20 mmol) for (2R)-2-amino-1-propanol to afford 13.6 mg of the title compound (30.8%)

LC/MS=m/z 546.2 [M+H] Ret. Time: 1.47 min.

Example 411

3-[1-(ethylsulfonyl)-4-piperidinyl]-5-(5-{[[(1R,2R)-2-hydroxycyclopentyl](methyl)amino]methyl}-3-thienyl)-1H-indole-7-carboxamide trifluoroacetate

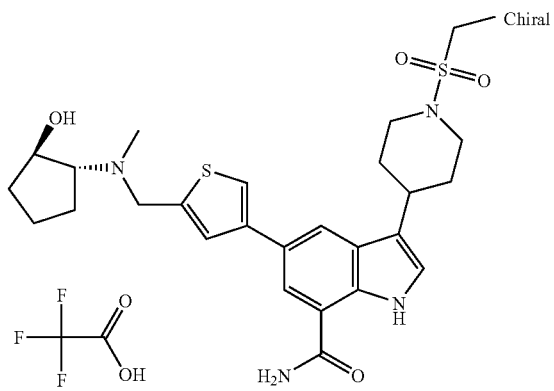

The title compound was prepared according to the general procedure of 3-[1-(ethylsulfonyl)-4-piperidinyl]-5-(5-{[[(1S)-2-hydroxy-1-methylethyl](methyl)amino]methyl}-3-thienyl)-1H-indole-7-carboxamide trifluoroacetate (salt), substituting (1R,2R)-2-aminocyclopentanol (1.20 mmol) for (2R)-2-amino-1-propanol to afford 9.6 mg of the title compound (21.8%)

LC/MS=m/z 545.3 [M+H] Ret. Time: 1.54 min.

Example 412

5-{5-[(1,1-dimethylpropyl)(methyl)amino]methyl}-3-thienyl)-3-[1-(ethylsulfonyl)-4-piperidinyl]-1H-indole-7-carboxamide trifluoroacetate

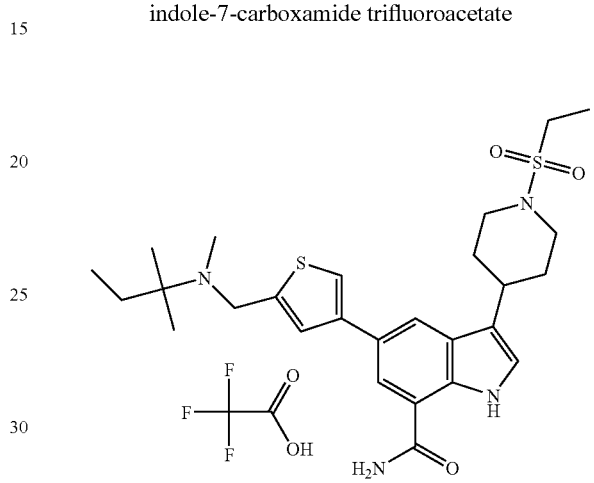

The title compound was prepared according to the general procedure of 3-[1-(ethylsulfonyl)-4-piperidinyl]-5-(5-{[[(1S)-2-hydroxy-1-methylethyl](methyl)amino]methyl}-3-thienyl)-1H-indole-7-carboxamide trifluoroacetate (salt), substituting (1,1-dimethylpropyl)amine (1.20 mmol) for (2R)-2-amino-1-propanol to afford 13.1 mg of the title compound (30.3%)

LC/MS=m/z 531.3 [M+H] Ret. Time: 1.65 min.

Example 413

3-[1-(ethylsulfonyl)-4-piperidinyl]-5-(5-{[[(2S)-2-hydroxypropyl](methyl)amino]methyl}-3-thienyl)-1H-indole-7-carboxamide trifluoroacetate

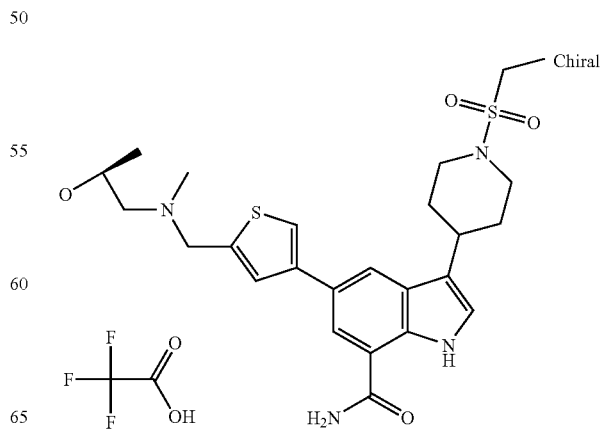

The title compound was prepared according to the general procedure of 3-[1-(ethylsulfonyl)-4-piperidinyl]-5-(5-{[[(1S)-2-hydroxy-1-methylethyl](methyl)amino]methyl}-3-thienyl)-1H-indole-7-carboxamide trifluoroacetate (salt), substituting (2S)-1-amino-2-propanol (1.20 mmol) for (2R)-2-amino-1-propanol to afford 15.3 mg of the title compound (36.1%)

LC/MS=m/z 519.3 [M+H] Ret. Time: 1.49 min.

Example 414

3-[1-(ethylsulfonyl)-4-piperidinyl]-5-[5-({methyl[(2R)-tetrahydro-2-furanylmethyl]amino}methyl)-3-thienyl]-1H-indole-7-carboxamide trifluoroacetate

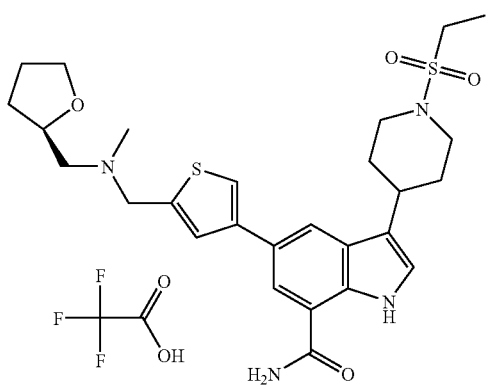

The title compound was prepared according to the general procedure of 3-[1-(ethylsulfonyl)-4-piperidinyl]-5-(5-{[[(1S)-2-hydroxy-1-methylethyl](methyl)amino]methyl}-3-thienyl)-1H-indole-7-carboxamide trifluoroacetate (salt), substituting [(2R)-tetrahydro-2-furanylmethyl]amine (1.20 mmol) for (2R)-2-amino-1-propanol to afford 15.5 mg of the title compound (35.1%)

LC/MS=m/z 545.3 [M+H] Ret. Time: 1.58 min.

Example 415

3-[1-(ethylsulfonyl)-4-piperidinyl]-5-(5-{[{2-[(2-hydroxyethyl)oxy]ethyl}(methyl)amino]methyl}-3-thienyl)-1H-indole-7-carboxamide trifluoroacetate

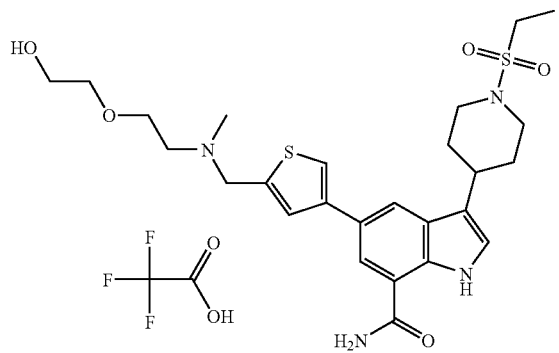

The title compound was prepared according to the general procedure of 3-[1-(ethylsulfonyl)-4-piperidinyl]-5-(5-{[[(1S)-2-hydroxy-1-methylethyl](methyl)amino]methyl}-3-thienyl)-1H-indole-7-carboxamide trifluoroacetate (salt), substituting 2-[(2-aminoethyl)oxy]ethanol (1.20 mmol) for (2R)-2-amino-1-propanol to afford 17.2 mg of the title compound (38.7%).

LC/MS=m/z 549.5 [M+H] Ret. Time: 1.48 min.

Example 416

3-[1-(ethylsulfonyl)-4-piperidinyl]-5-[5-(1-{methyl[2-(methyloxy)ethyl]amino}ethyl)-3-thienyl]-1H-indole-7-carboxamide trifluoroacetate

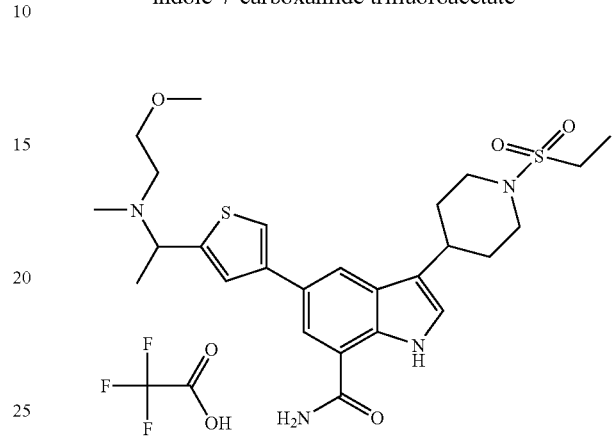

To a solution of 5-(5-acetyl-3-thienyl)-3-[1-(ethylsulfonyl)-4-piperidinyl]-1H-indole-7-carboxamide (46 mg, 0.1 mmol) in EtOH (2.0 mL) and AcOH (0.2 mL) was added methyl[2-(methyloxy)ethyl]amine (200 µL, 2.0 mmol) and sodium cyanoborohydride (50 mg, 0.8 mmol). The mixture was reacted in the microwave at 120° C. for 2 h. Additional methyl[2-(methyloxy)ethyl]amine (100 µL, 1.0 mmol) and sodium cyanoborohydride (25 mg, 0.4 mmol) was added and reacted for another 3 h in the microwave at 120° C. for 2 h. This was then followed by another addition of methyl[2-(methyloxy)ethyl]amine (100 µL, 2.0 mmol) and sodium cyanoborohydride (25 mg, 0.4 mmol) and reacted for another 3 h in the microwave at 120° C. for 2 h.

All solvent was concentrated and purified by Gilson Preparatory HPLC to afford 20 mg of the title compound (38%).

LC/MS=m/z 533.2 [M+H] Ret. Time: 1.46 min.

Example 417

3-[1-(ethylsulfonyl)-4-piperidinyl]-5-(5-{1-[methyl(propyl)amino]ethyl}-3-thienyl)-1H-indole-7-carboxamide trifluoroacetate

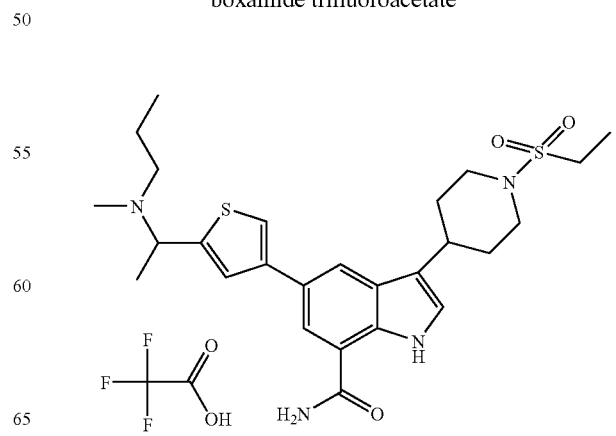

To a solution of 5-(5-acetyl-3-thienyl)-3-[1-(ethylsulfonyl)-4-piperidinyl]-1H-indole-7-carboxamide (46 mg, 0.1 mmol) in EtOH (2.0 mL) and AcOH (0.2 mL) was added N-methyl-1-propanamine (200 µL, 2.0 mmol) and sodium cyanoborohydride (50 mg, 0.8 mmol). The mixture was reacted in the microwave at 120° C. for 120 min. Additional N-methyl-1-propanamine (100 µL, 1.0 mmol) and sodium cyanoborohydride (25 mg, 0.4 mmol) was added and reacted for another 3 h in the microwave at 120° C. for 120 min. All solvent was concentrated, dissolved in DMSO and solids were filtered. It was then purified by Gilson Preparatory HPLC to afford 18 mg of the title compound (35%).

LC/MS=m/z 517.2 [M+H] Ret. Time: 1.52 min.

Example 418

5-(2,3-dihydro-1H-isoindol-5-yl)-3-[1-(ethylsulfonyl)-4-piperidinyl]-1H-indole-7-carboxamide

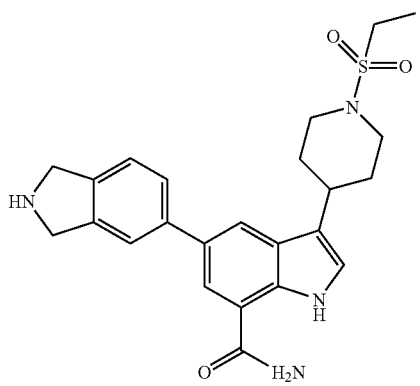

To a solution of 3-[1-(ethylsulfonyl)-4-piperidinyl]-5-(4,4,5,5-tetramethyl-1,3,2-dioxaborolan-2-yl)-1H-indole-7-carboxamide (150 mg, 0.325 mmol) in dioxane (0.75 mL) and water (0.25 mL), was added 5-bromo-2,3-dihydro-1H-isoindole hydrochloride (130 mg, 0.651 mmol), and cesium carbonate (636 mg, 1.952 mmol). The reaction mixture was kept under argon for 10 min before addition of tetrakis(triphenylphosphine)palladium(0) (19 mg, 0.016 mmol). The resultant mixture was heated in a microwave for 20 min at 150° C. Mixture was then purified by HPLC to give 11 mg of the title compound.

LC/MS=m/z 453 [M+H] Ret. Time: 1.33 min.

Example 419

5-(2-ethyl-2,3-dihydro-1H-isoindol-5-yl)-3-[1-(ethylsulfonyl)-4-piperidinyl]-1H-indole-7-carboxamide

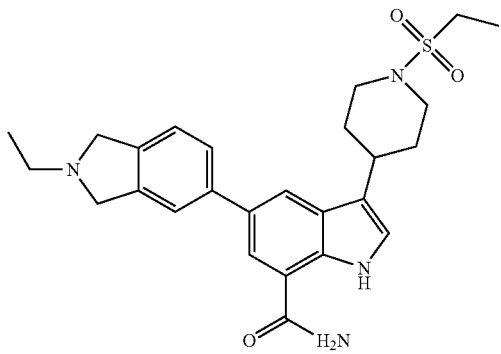

To a solution of 5-(2,3-dihydro-1H-isoindol-5-yl)-3-[1-(ethylsulfonyl)-4-piperidinyl]-1H-indole-7-carboxamide (20 mg, 0.044 mmol) in MeOH (1 mL), was added acetaldehyde (6 mg, 0.133 mmol), sodium cyanoborohydride (6 mg, 0.088 mmol) and zinc chloride (6 mg, 0.044 mmol). The resultant mixture was heated in a microwave for 30 min at 100° C. Mixture was then concentrated, filtered and purified by Gilson Preparatory HPLC to give 8.2 mg of the title compound.

LC/MS=m/z 481 [M+H] Ret. Time: 1.40 min.

Example 420

3-[1-(ethylsulfonyl)-4-piperidinyl]-5-[2-(1-methylethyl)-2,3-dihydro-1H-isoindol-5-yl]-1H-indole-7-carboxamide

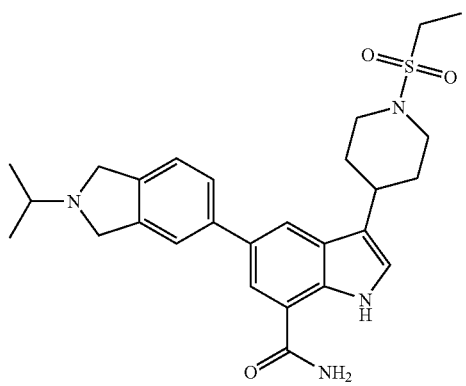

To a solution of 5-(2,3-dihydro-1H-isoindol-5-yl)-3-[1-(ethylsulfonyl)-4-piperidinyl]-1H-indole-7-carboxamide (30 mg, 0.066 mmol) in MeOH (0.5 mL), was added 2-propanone (12 mg, 0.198 mmol), sodium cyanoborohydride (8 mg, 0.133 mmol) and zinc chloride (9 mg, 0.066 mmol). The resultant mixture was heated in a microwave for 30 min at 100° C. Mixture was then concentrated, filtered and purified by Gilson Preparatory HPLC to give 0.8 mg of the title compound.

LC/MS=m/z 495.5 [M+H] Ret. Time: 1.56 min.

Example 421

5-[2-(1,2-dimethylpropyl)-2,3-dihydro-1H-isoindol-5-yl]-3-[1-(ethylsulfonyl)-4-piperidinyl]-1H-indole-7-carboxamide

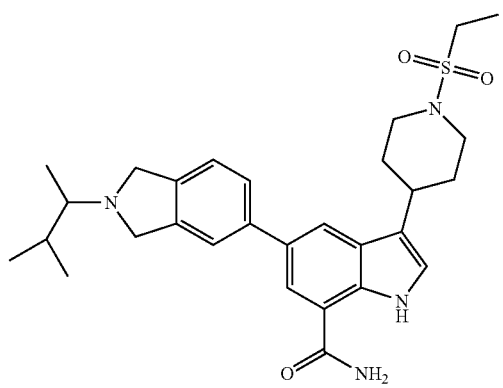

The title compound was prepared according to the general procedure of 3-[1-(ethylsulfonyl)-4-piperidinyl]-5-[2-(1-methylethyl)-2,3-dihydro-1H-isoindol-5-yl]-1H-indole-7-carboxamide, substituting 3-methyl-2-butanone (17 mg, 0.198 mmol) for 2-propanone to afford 14.6 mg of the title compound.

LC/MS=m/z 523 [M+H] Ret. Time: 1.55 min.

Example 422

3-[1-(ethylsulfonyl)-4-piperidinyl]-5-[2-(1-methylpropyl)-2,3-dihydro-1H-isoindol-5-yl]-1H-indole-7-carboxamide

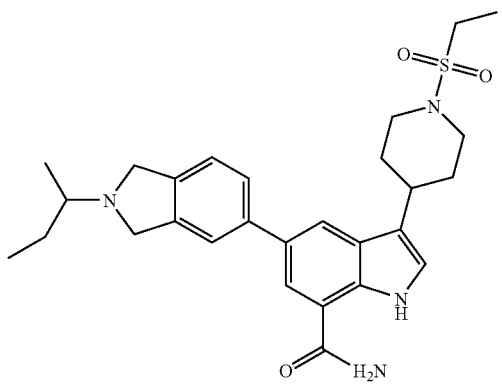

The title compound was prepared according to the general procedure of 3-[1-(ethylsulfonyl)-4-piperidinyl]-5-[2-(1-methylethyl)-2,3-dihydro-1H-isoindol-5-yl]-1H-indole-7-carboxamide, substituting 2-butanone (14 mg, 0.198 mmol) for 2-propanone to afford 14.6 mg of the title compound.

LC/MS=m/z 509 [M+H] Ret. Time: 1.48 min.

Example 423

5-[2-(1-ethylpropyl)-2,3-dihydro-1H-isoindol-5-yl]-3-[1-(ethylsulfonyl)-4-piperidinyl]-1H-indole-7-carboxamide

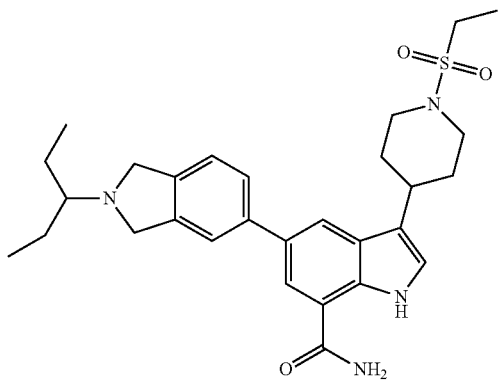

The title compound was prepared according to the general procedure of 3-[1-(ethylsulfonyl)-4-piperidinyl]-5-[2-(1-methylethyl)-2,3-dihydro-1H-isoindol-5-yl]-1H-indole-7-carboxamide, substituting 3-pentanone (17 mg, 0.198 mmol) for 2-propanone to afford 13.8 mg of the title compound.

LC/MS=m/z 523 [M+H] Ret. Time: 1.58 min.

Example 424

5-(2-cyclopentyl-2,3-dihydro-1H-isoindol-5-yl)-3-[1-(ethylsulfonyl)-4-piperidinyl]-1H-indole-7-carboxamide

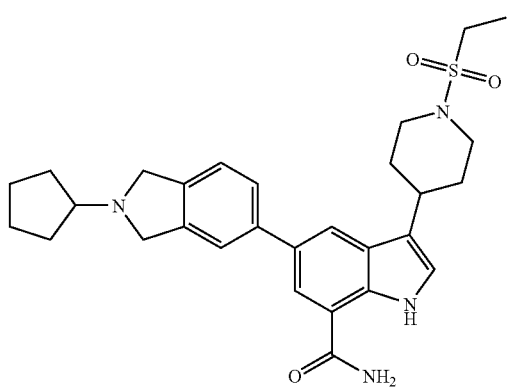

The title compound was prepared according to the general procedure of 3-[1-(ethylsulfonyl)-4-piperidinyl]-5-[2-(1-methylethyl)-2,3-dihydro-1H-isoindol-5-yl]-1H-indole-7-carboxamide, substituting cyclopentanone (17 mg, 0.198 mmol) for 2-propanone to afford 4.8 mg of the title compound.

LC/MS=m/z 521 [M+H] Ret. Time: 1.54 min.

Example 425

5-[2-(cyclopropylmethyl)-2,3-dihydro-1H-isoindol-5-yl]-3-[1-(ethylsulfonyl)-4-piperidinyl]-1H-indole-7-carboxamide

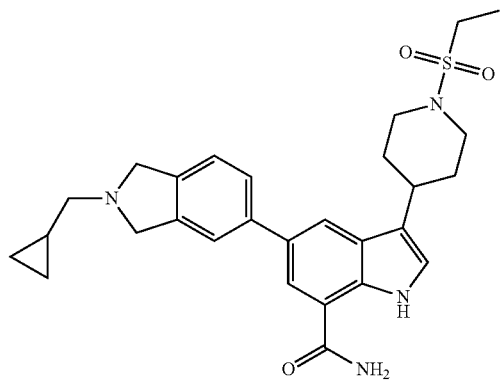

The title compound was prepared according to the general procedure of 3-[1-(ethylsulfonyl)-4-piperidinyl]-5-[2-(1-methylethyl)-2,3-dihydro-1H-isoindol-5-yl]-1H-indole-7-carboxamide, substituting cyclopropanecarbaldehyde (14 mg, 0.198 mmol) for 2-propanone to afford 10.8 mg of the title compound.
LC/MS=m/z 507 [M+H] Ret. Time: 1.47 min.

Example 426

5-[2-(2,2-dimethylpropyl)-2,3-dihydro-1H-isoindol-5-yl]-3-[1-(ethylsulfonyl)-4-piperidinyl]-1H-indole-7-carboxamide

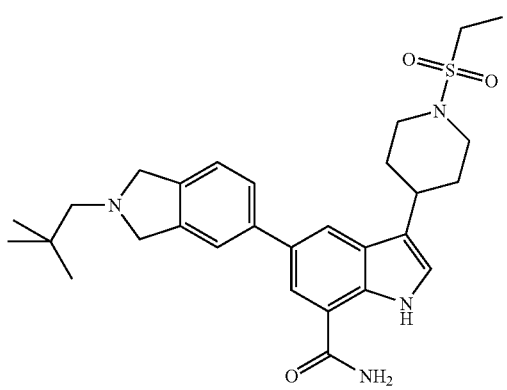

The title compound was prepared according to the general procedure of 3-[1-(ethylsulfonyl)-4-piperidinyl]-5-[2-(1-methylethyl)-2,3-dihydro-1H-isoindol-5-yl]-1H-indole-7-carboxamide, substituting 2,2-dimethylpropanal (17 mg, 0.198 mmol) for 2-propanone to afford 12.7 mg of the title compound.
LC/MS=m/z 523 [M+H] Ret. Time: 1.60 min.

Example 427

3-[1-(ethylsulfonyl)-4-piperidinyl]-5-(2-methyl-2,3-dihydro-1H-isoindol-5-yl)-1H-indole-7-carboxamide

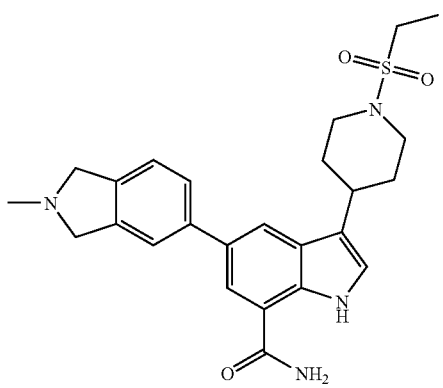

The title compound was prepared according to the general procedure of 3-[1-(ethylsulfonyl)-4-piperidinyl]-5-[2-(1-methylethyl)-2,3-dihydro-1H-isoindol-5-yl]-1H-indole-7-carboxamide, substituting formaldehyde (6 mg, 0.198 mmol) for 2-propanone to afford 1.2 mg of the title compound.
LC/MS=m/z 467 [M+H] Ret. Time: 1.37 min.

Example 428

3-[1-(ethylsulfonyl)-4-piperidinyl]-5-(2-{[(phenylsulfonyl)amino]carbonyl}-2,3-dihydro-1H-isoindol-5-yl)-1H-indole-7-carboxamide

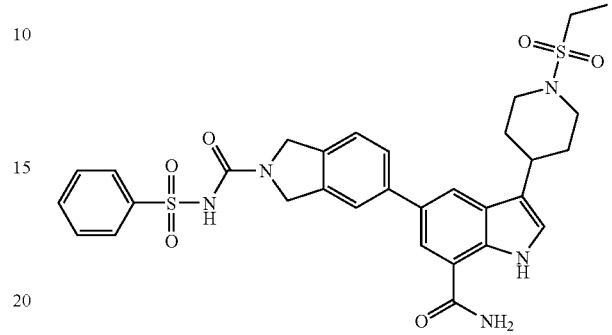

To a solution of 5-(2,3-dihydro-1H-isoindol-5-yl)-3-[1-(ethylsulfonyl)-4-piperidinyl]-1H-indole-7-carboxamide (30 mg, 0.066 mmol) in DMSO (1.0 mL), was added benzenesulfonyl isocyanate (15 mg, 0.079 mmol). The resultant mixture was stirred overnight at room temperature. Mixture purified by Gilson Preparatory HPLC to give 15.5 mg of the title compound.
LC/MS=m/z 637 [M+H] Ret. Time: 1.94 min.

Example 429

5-(5-{[(2R)-2-(aminocarbonyl)-1-pyrrolidinyl]methyl}-3-thienyl)-3-[1-[(1-methylethyl)sulfonyl]-4-piperidinyl]-1H-indole-7-carboxamide

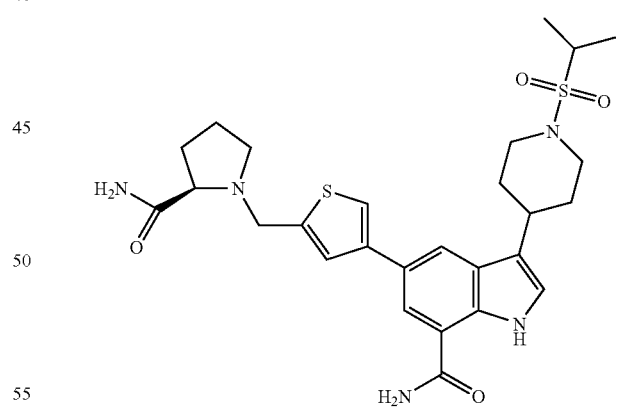

To a solution of 5-(5-formyl-3-thienyl)-3-{1-[(1-methylethyl)sulfonyl]-4-piperidinyl}-1H-indole-7-carboxamide (25 mg, 0.054 mmol) in DMSO (2 mL) was added D-prolinamide (114 mg, 1 mmol) and 2 drops of acetic acid. The resulting mixture was stirred at room temperature for 4 h followed by an addition of sodium triacetoxyborohydride (212 mg, 1.0 mmol). The mixture was reacted overnight. It was then purified by Gilson Preparatory HPLC to give 20.4 mg of the title compound.
LC/MS=m/z 557 [M+H] Ret. Time: 1.56 min.

Example 430

3-[1-(ethylsulfonyl)-4-piperidinyl]-5-(5-{[[2-(ethylthio)ethyl](methyl)amino]methyl}-3-thienyl)-1H-indole-7-carboxamide

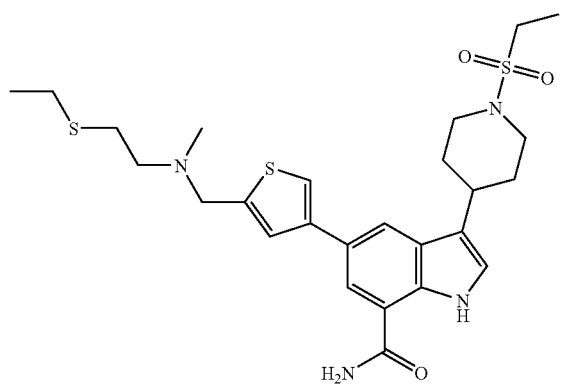

To a solution of 5-(5-formyl-3-thienyl)-3-{1-[(1-methylethyl)sulfonyl]-4-piperidinyl}-1H-indole-7-carboxamide (40 mg, 0.09 mmol) in DMSO (2 mL) was added [2-(ethylthio)ethyl]amine (105 mg, 1 mmol), acetic acid (50 μL), and sodium triacetoxyborohydride (212 mg, 1.0 mmol). The resulting mixture was stirred overnight. To the mixture was added sodium cyanoborohydride (80 mg, 1.2 mmol) and stirred overnight followed by addition of formaldehyde (100 μL, 1.2 mmol). The mixture was then stirred for an additional 3 h. It was then purified by Gilson Preparatory HPLC to give 7.0 mg of the title compound.

LC/MS=m/z 550 [M+H] Ret. Time: 1.68 min.

Example 431

3-[1-(ethylsulfonyl)-4-piperidinyl]-5-(5-{[{2-[(2-hydroxyethyl)thio]ethyl}(methyl)amino]methyl}-3-thienyl)-1H-indole-7-carboxamide

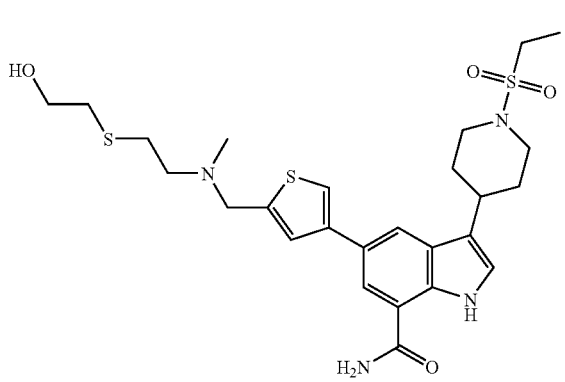

The title compound was prepared according to the general procedure of 3-[1-(ethylsulfonyl)-4-piperidinyl]-5-(5-{[[2-(ethylthio)ethyl](methyl)amino]methyl}-3-thienyl)-1H-indole-7-carboxamide substituting 2-[(2-aminoethyl)thio]ethanol (121 mg, 1.0 mmol) for [2-(ethylthio)ethyl]amine to afford 16.0 mg of the title compound.

LC/MS=m/z 566 [M+H] Ret. Time: 1.52 min.

Example 432

3-[1-(ethylsulfonyl)-4-piperidinyl]-5-(5-{[[2-hydroxy-1-(hydroxymethyl)ethyl](methyl)amino]methyl}-3-thienyl)-1H-indole-7-carboxamide

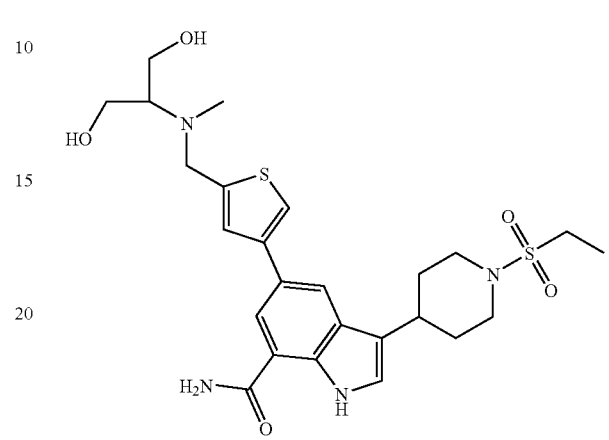

The title compound was prepared according to the general procedure of 3-[1-(ethylsulfonyl)-4-piperidinyl]-5-(5-{[[2-(ethylthio)ethyl](methyl)amino]methyl}-3-thienyl)-1H-indole-7-carboxamide substituting 2-amino-1,3-propanediol (91 mg, 1.0 mmol) for [2-(ethylthio)ethyl]amine to afford 15.0 mg of the title compound.

LC/MS=m/z 535 [M+H] Ret. Time: 1.44 min.

Example 433 ethyl[(4-{7-(aminocarbonyl)-3-[1-(ethylsulfonyl)-4-piperidinyl]-1H-indol-5-yl}-2-thienyl)methyl]methylcarbamate

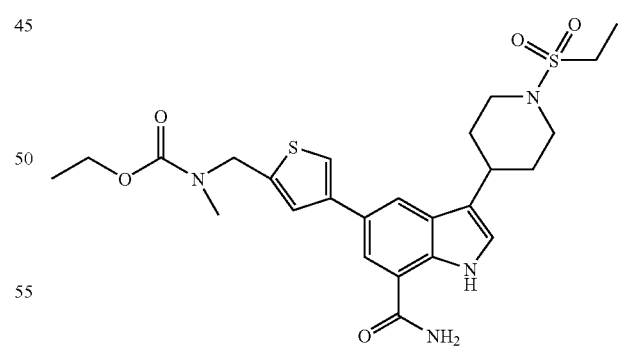

To a solution of 3-[1-(ethylsulfonyl)-4-piperidinyl]-5-{5-[(methylamino)methyl]-3-thienyl}-1H-indole-7-carboxamide (50 mg, 0.11 mmol) in DMF (1.0 mL) at 0° C. was added triethylamine (0.06 mL, 0.44 mmol), and ethyl chloridocarbonate (0.021 mL, 0.22 mmol). The resultant mixture was reacted for 30 min followed by purification on Gilson Preparatory HLPC to afford 31.4 mg of the title compound (53.5%).

LC/MS=m/z 533.2 [M+H] Ret. Time: 2.06 min.

Example 434 ethyl N-[(4-[7-(aminocarbonyl)-3-[1-(ethylsulfonyl)-4-piperidinyl]-1H-indol-5-yl]-2-thienyl)methyl]-N-methylglycinate

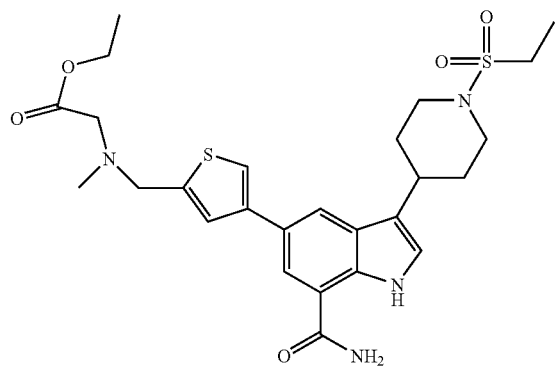

To a solution of 3-[1-(ethylsulfonyl)-4-piperidinyl]-5-(5-formyl-3-thienyl)-1H-indole-7-carboxamide (45 mg, 100 μmol) in dimethyl sulfoxide (1.0 mL) was added ethyl N-methylglycinate (320 μmol) and 2 to 3 drops of glacial acetic acid. The resulting mixture is agitated overnight. After 18 h, sodium triacetoxyborohydride (200 mg, 1000 μmol) is added. This mixture is agitated for 1.5 h followed by purification by Gilson Preparatory HPLC to give 16.5 mg of the title compound (30.0%).

LC/MS=m/z 547.1 [M+H] Ret. Time: 1.55 min.

Example 435

3-[1-(ethylsulfonyl)-4-piperidinyl]-5-(5-{[[(1S)-2-hydroxy-1-methylethyl](methyl)amino]methyl}-3-thienyl)-1H-indole-7-carboxamide trifluoroacetate (salt)

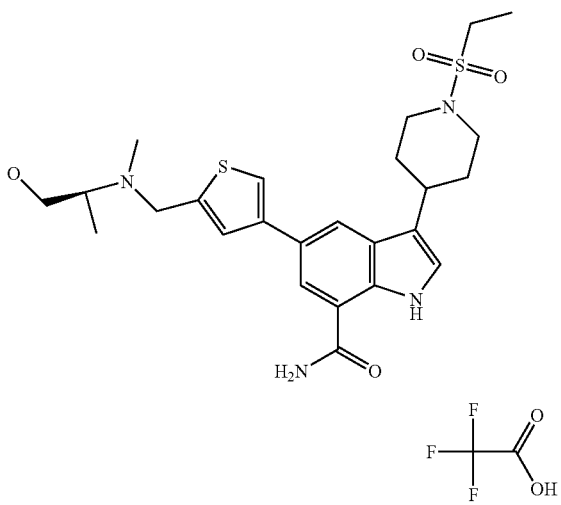

To a vial containing (2S)-2-amino-1-propanol (91 mg, 1.2 mmol) was added a solution of 3-[1-(ethylsulfonyl)-4-piperidinyl]-5-(5-formyl-3-thienyl)-1H-indole-7-carboxamide (30 mg, 0.067 mmol) in DMSO (300 μL) and acetic acid (50 μL). The resulting mixture was shaken for 5 min followed by an addition of sodium triacetoxyborohydride (250 mg, 1.20 mmol) in DMSO (800 μL). The mixture was shaken overnight. Sodium cyanoborohydride (79 mg, 1.20 mmol) in methanol (300 μL) was then added and stirred for 48 h. This was followed by an addition of formaldehyde (100 μL). The reaction was then stirred for 1 h followed by a 2 g SCX cartridge separation. The solids were then filtered off, solution was concentrated and purification was repeated on a 5 g SCX cartridge eluting with ammonia in MeOH. The ammonia in MeOH fraction collection was concentrated and separated using Gilson Preparatory HPLC to afford 18.7 mg of the title compound.

LC/MS=m/z 519.3 [M+H] Ret. Time: 1.49 min.

Example 436

5-(5-{[(1,1-dioxidotetrahydro-3-thienyl)(methyl)amino]methyl}-3-thienyl)-3-[1-(ethylsulfonyl)-4-piperidinyl]-1H-indole-7-carboxamide trifluoroacetate

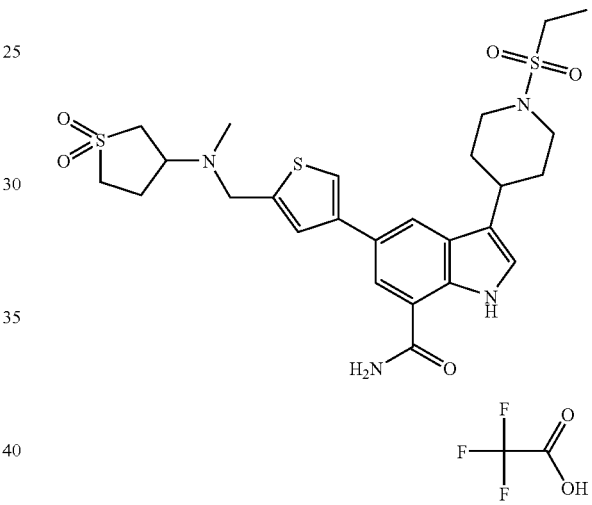

The title compound was prepared according to the general procedure of 3-[1-(ethylsulfonyl)-4-piperidinyl]-5-(5-{[[(1S)-2-hydroxy-1-methylethyl](methyl)amino]methyl}-3-thienyl)-1H-indole-7-carboxamide trifluoroacetate, substituting (1,1-dioxidotetrahydro-3-thienyl)amine (1.20 mmol) for (2S)-2-amino-1-propanol to afford 9.3 mg of the title compound.

LC/MS=m/z 579 [M+H] Ret. Time: 1.54 min.

Biological Data

IKK2 Assay

Recombinant human IKKβ (residues 1-737) was expressed in baculovirus as a C-terminal GST-tagged fusion protein, and its activity was assessed using a time-resolved fluorescence resonance energy transfer (TR-FRET) assay. Briefly, IKK2 (0.5 nM-5 nM final) diluted in assay buffer (50 mM HEPES, 10 mM $MgCl_2$, 1 mM CHAPS pH 7.4 with 1 mM DTT and 0.01% w/v BSA) was added to wells containing various concentrations of compound or DMSO vehicle (1.7% final). The reaction was initiated by the addition of GST-IB substrate (25 nM final)/ATP (1 μM final), in a total volume of 6 μl. The reaction was incubated for 15 minutes at room temperature, then terminated by the addition of 3 μl of detection reagent in buffer containing 50 mM EDTA (100 mM HEPES pH 7.4, 150 mM NaCl, 50 mM EDTA and 0.01% w/v BSA) containing antiphosphoserine-IB-32/36 monoclonal antibody 12C2 (Cell Signalling Technology, Beverly Mass., USA) labelled with W-1024 europium chelate (Wallac OY, Turku, Finland), and an APC-labelled anti-GST antibody (Prozyme, San Leandro, Calif., USA) was added and the reaction was further incubated for 60 minutes at room temperature. The degree of phosphorylation of GST-IB was measured using a BMG Rubystar plate reader (BMG Labtech, Aylesbury, UK) as a ratio of specific 665 nm energy transfer signal to reference europium 620 nm signal.

Results

The compounds of Examples 1-31, 33, 35-51, 53-58, 60-97, 100-116, 118-121, 123-137, 139-163, 165-172, 174-197, 199-220, 222-242, 244-276, 279-330, 332-358, 360-385, 387-402, 404-419, 421-426, and 428-436 were tested for activity against IKK2 and these Examples were found to be inhibitors of IKK2. These compounds had a $pIC_{50}$ of 5.0 or greater. Examples 277 and 278 were also tested for activity against IKK2 and these two compounds were found to have a $pIC_{50}$ of less than 5.0.

Monocyte Assay

Effect of IKK-β inhibition on human monocyte stimulated cytokine production was assessed as follows: Monocytes were isolated from heparinized whole blood by Ficoll gradient, followed by purification of CD14+ cells using MACS magnetic cell separation beads. Isolated monocytes were then adhered to 96-well culture plates at $1 \times 10^6$ cells/mL in RPMI 1640 10% FBS (JRH Biosciences, Lenexa Kans.) for 2 h. Test compounds are added to the wells 30 minutes prior to stimulation with a final vehicle concentration of 0.1% DMSO. Monocytes were activated by the addition of 200 ng/mL endotoxin (LPS; *E. coli* serotype 026:B6)(Sigma, St. Louis, Mo.) and incubated for 24 hrs at 37 C. Cell-free supernates were analyzed by ELISA for TNF-α using Pharmingen matched pair Abs. Viability of the cells was determined by 10% trypan blue exclusion.

Results

Certain Examples of this invention were tested in the monocyte assay. Examples 1-3, 5-13, 16-23, 25-31, 33, 37, 38, 42-44, 61, 62, 64-69, 71-73, 75-78, 82, 83 86-89, 92, 95, 96, 100-117, 119-121, 123-127, 129-131, 139, 141, 144, 151, 154-157, 160-164, 166-167, 168-172, 182, 191, 208-220, 222, 223, 227, 230-248, 250, 251, 269, 271, 273-276, 279-83, 285-90, 292-298, 304-327, 329, 332-337, 342-344, 346, 348, 353, 356-358, 361, 364, 366-373, 376, 380, 383, 394-397, 399-404, 406, 408, 409, 412, 416-419, 432, 434, and 453 were found to have an IC50 of 1.5 µM or less in the monocyte assay.

Examples 4, 15, 24, 34-36, 50, 70, 118, 128, 132-134, 136, 137, 140, 143, 146-148, 153, 158, 159, 165, 168, 192-194, 196, 197, 200-207, 224, 249, 253-262, 270, 272, 299-303, 330, 338-341, 360, 362, 363, 365, 374, 375, 377-379, 381, 383, 385, 388-390, 392, and 393 were found to have an IC50 greater than 1 µM.

Examples 39, 40, 45-49, 58-60, 63, 74, 79-81, 84, 85, 90, 91, 94, 97, 173-181, 184-190, 195, 198, 328, 345, 347, 349-353, 345, 355, 429-431, 433, and 436 showed 0-60% inhibition at 300 nM.

We claim:
1. 3-[1-(ethylsulfonyl)-4-piperidinyl]-5-[2-(1-methylethyl)-2,3-dihydro-1H-isoindol-5-yl]-1H-indole-7-carboxamide of formula (I);

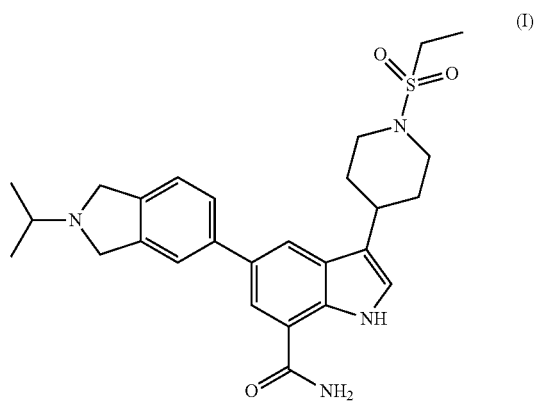

or a pharmaceutically acceptable salt thereof.
2. 3-[1-(ethylsulfonyl)-4-piperidinyl]-5-[2-(1-methylethyl)-2,3-dihydro-1H-isoindol-5-yl]-1H-indole-7-carboxamide of formula (I)

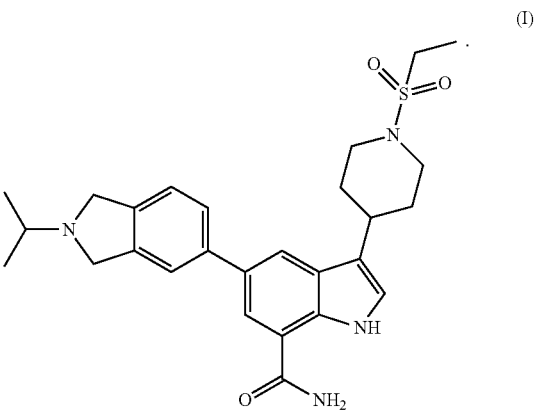

3. A pharmaceutical composition comprising (a) 3-[1-(ethylsulfonyl)-4-piperidinyl]-5-[2-(1-methylethyl)-2,3-dihydro-1H-isoindol-5-yl]-1H-indole-7-carboxamide or a pharmaceutically acceptable salt thereof, and (b) one or more pharmaceutically acceptable excipients.
4. A pharmaceutical composition according to claim 3, which further comprises one or more additional pharmaceutically active compounds.
5. A method of treating a disorder mediated by inappropriate IKK2 activity comprising administering a safe and effective amount of 3-[1 (ethylsulfonyl)-4-piperidinyl]-5-[2-(1-methylethyl)-2,3-dihydro-1H-isoindol-5-yl]-1H-indole-7-carboxamide, or a pharmaceutically acceptable salt thereof to a patient in need thereof, wherein the disorder mediated by inappropriate IKK2 activity is asthma or COPD.
6. The method of claim 5, wherein the disorder mediated by inappropriate IKK2 activity is asthma.
7. The method of claim 5, wherein the disorder mediated by inappropriate IKK2 activity is COPD.

* * * * *